(12) United States Patent
Lee et al.

(10) Patent No.: US 10,573,838 B2
(45) Date of Patent: Feb. 25, 2020

(54) ORGANIC ELECTRIC ELEMENT COMPRISING COMPOUND FOR ORGANIC ELECTRIC ELEMENT AND ELECTRONIC DEVICE THEREOF

(71) Applicants: DUK SAN NEOLUX CO., LTD., Cheonan-si, Chungcheongnam-do (KR); SAMSUNG DISPLAY CO., LTD., Yongin-si, Gyeonggi-do (KR)

(72) Inventors: Bumsung Lee, Hwaseong-si (KR); Sun-Hee Lee, Hwaseong-si (KR); Soung Yun Mun, Cheonan-si (KR); Junghwan Park, Hwaseong-si (KR); Daesung Kim, Yongin-si (KR); Jung Cheol Park, Suwon-si (KR); Jung Wook Lee, Gunsan-si (KR); Mikyung Kim, Yongin-si (KR); Kwanhee Lee, Yongin-si (KR)

(73) Assignees: DUK SAN NEOLUX CO., LTD., Cheonan-si, Chungcheon (KR); SAMSUNG DISPLAY CO., LTD., Yongin-si, Gyeonggi-do (KR)

( * ) Notice: Subject to any disclaimer, the term of this patent is extended or adjusted under 35 U.S.C. 154(b) by 148 days.

(21) Appl. No.: 15/743,535

(22) PCT Filed: Jul. 5, 2016

(86) PCT No.: PCT/KR2016/007269
§ 371 (c)(1),
(2) Date: Jan. 10, 2018

(87) PCT Pub. No.: WO2017/010726
PCT Pub. Date: Jan. 19, 2017

(65) Prior Publication Data
US 2018/0205032 A1    Jul. 19, 2018

(30) Foreign Application Priority Data

Jul. 10, 2015 (KR) ........................ 10-2015-0098090

(51) Int. Cl.
*H01L 51/50* (2006.01)
*C09K 11/06* (2006.01)
(Continued)

(52) U.S. Cl.
CPC .......... *H01L 51/5024* (2013.01); *C09K 11/06* (2013.01); *H01L 51/0005* (2013.01);
(Continued)

(58) Field of Classification Search
None
See application file for complete search history.

(56) References Cited

FOREIGN PATENT DOCUMENTS

| KR | 10-2013-0050237 A | 5/2013 |
| KR | 10-2014-0069199 A | 6/2014 |

(Continued)

OTHER PUBLICATIONS

Machine English translation of Park et al. (KR 10-2013-0050237). Jul. 31, 2019.*
Extended European Search Report, dated Mar. 7, 2019, 5 pages.

*Primary Examiner* — Jay Yang
(74) *Attorney, Agent, or Firm* — Vorys, Sater, Seymour & Pease LLP; Mih Suhn Koh

(57) ABSTRACT

The present invention provides an organic electric element in which a first electrode, a second electrode, and an organic material layer are sequentially stacked, wherein the organic material layer comprises a hole transport layer, an emission-auxiliary layer and a light emitting layer, at least one of the hole transport layer and the emission-auxiliary layer comprises the compound represented by Formula 1, and the light emitting layer comprises the compound represented by
(Continued)

Formula 2. According to the present invention, the driving voltage of an organic electronic device can be lowered, and the luminous efficiency, color purity and life time of an organic electronic device can be improved.

14 Claims, 1 Drawing Sheet

(51) Int. Cl.
*H01L 51/00* (2006.01)
*H01L 51/52* (2006.01)

(52) U.S. Cl.
CPC ...... *H01L 51/0072* (2013.01); *H01L 51/0073* (2013.01); *H01L 51/0074* (2013.01); *H01L 51/5056* (2013.01); *H01L 51/5072* (2013.01); *H01L 51/5092* (2013.01); *H01L 51/5096* (2013.01); *H01L 51/5212* (2013.01); *H01L 51/5221* (2013.01); *C09K 2211/1029* (2013.01); *C09K 2211/1048* (2013.01); *C09K 2211/1051* (2013.01)

(56) References Cited

FOREIGN PATENT DOCUMENTS

| | | |
|---|---|---|
| KR | 10-2014-0145887 | 12/2014 |
| KR | 10-1493482 B1 | 2/2015 |
| KR | 10-2015-0023174 | 3/2015 |
| WO | 2014/042405 A1 | 3/2014 |
| WO | 2014/092362 A1 | 6/2014 |

\* cited by examiner

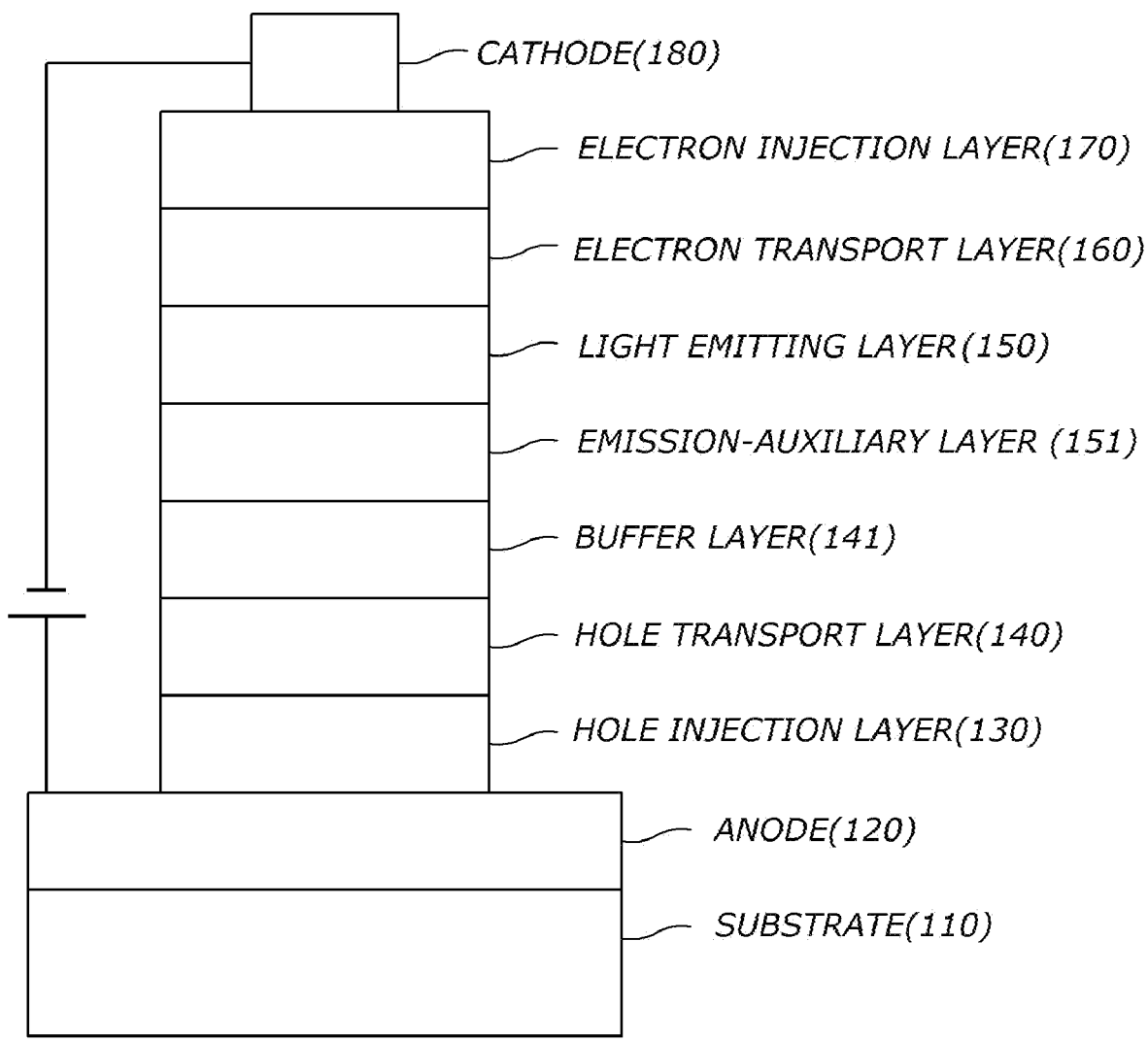

ORGANIC ELECTRIC ELEMENT COMPRISING COMPOUND FOR ORGANIC ELECTRIC ELEMENT AND ELECTRONIC DEVICE THEREOF

CROSS-REFERENCE TO RELATED APPLICATION

This patent application claims priority from and the benefit under 35 U.S.C. 119(a) of Korean Patent Application No. 10-2015-0098090, filed on Jul. 10, 2015, which is hereby incorporated by reference for all purposes as if fully set forth herein. Further, this application claims the benefit of priority in countries other than U.S.A, which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and the situation is such that efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

In order to solve the problem of luminescence in the hole transport layer in recent organic electroluminescent devices, an emission-auxiliary layer must be present between the hole transport layer and the light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton. However, it mainly has a low T1 value since a material used in a hole transporting layer should have a low HOMO value. Due to this, excitons generated from a light emitting layer are transported to the hole transporting layer, resulting in a charge unbalance in the light emitting layer. Thus, light emission occurs in the hole transporting layer or at an interface of the hole transporting layer so that the organic electroluminescent device is reduced in color purity, efficiency, and lifespan.

In addition, when a material having a rapid hole mobility is used to make a low driving voltage, the efficiency tends to decrease. This is because, in a general organic electroluminescent device, hole mobility is faster than electron mobility, which leads to charge unbalance in the light emitting layer, resulting in reduction in efficiency and lifetime.

Therefore, the emission-auxiliary layer should be formed of a material having hole mobility, lei h electron block (I), and wide band gap so as to have a proper driving voltage capable of solving the problems of the hole transport layer.

These requirements are not met by the structural properties of the core of the emission-auxiliary layer material alone, but are achieved when the properties of the material, such as core and sub-substituent, are all properly combined. Therefore, in order to improve the efficiency and lifetime of an organic electric device, it is strongly required to develop materials of the emission-auxiliary layer having a high T1 value and a wide band gap.

That is, in order to allow an organic electric element to fully exhibit the excellent features, it should be preceded that the materials consisting an organic material layer of the element, for example, a hole injection material, a hole transport material, a light emitting material, an electron transport material, an electron injection material, an emission-auxiliary layer material or the like, are supported by a stable and efficient material. However, such a stable and efficient material of organic material layer for an organic electric element has not yet been fully developed. Accordingly, there is a continuous need to develop new materials for an organic material layer, particularly, it is strongly required to develop materials of the emission-auxiliary layer and/or materials of the hole transport layer and the light emitting layer.

SUMMARY

Object, Technical Solution and Effects of the Invention

In order to solve one or more of the above-mentioned problems in prior art, an aspect of the present invention is to provide a compound having high luminous efficiency, low driving voltage, and high heat-resistance, improving color purity and lifetime of the element, an organic electric element comprising the same, and an electronic device thereof.

In accordance with an aspect of the present invention, the present invention provides an organic electric element comprising a first electrode, a second electrode, and an organic material layer formed between the first electrode and the second electrode comprising at least one of a hole transport layer, an emission-auxiliary layer, and a light emitting layer, wherein the hole transport layer or the emission-auxiliary layer comprise the compound represented by the following formula 1 and the light emitting layer comprises the compound represented by the following formula 2.

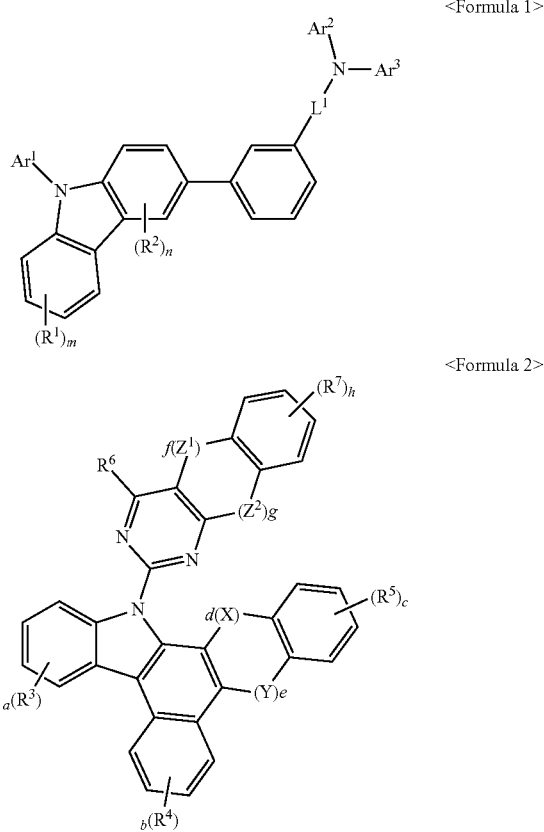

<Formula 1>

<Formula 2>

In another aspect of the present invention, the present invention provides an electronic device comprising the compound represented by the following formulas.

By using the compound according to embodiments of the present invention, high luminous efficiency, low driving voltage and high heat-resistance of the element can be achieved, and color purity and life span of the element can be improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine(F), chlorine(Cl), bromine(Br), or iodine(I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below, "substituted fluorenyl group" or "substituted fluorenylene group" means, functional group which at least any one of R, R' and R" is a functional group other than hydrogen, and fluorenyl group" or "fluorenylene group" comprises spiro compound which is formed by linking R and R' together with the carbon bonded to them.

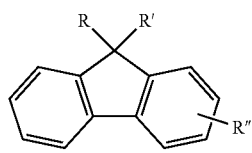

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the following compound.

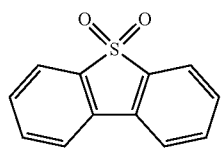 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula:

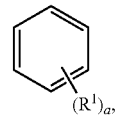

wherein, when a is an integer of zero, the substituent $R^1$ is absent. That is, when a is 0, it means that hydrogen is bonded to all the carbons forming the benzene ring, and chemical formulas or compounds can be represented by omitting the indication of hydrogen bonded to the carbon. In addition, when a is an integer of 1, the sole $R^1$ is bonded to any one of the carbon atoms constituting the benzene ring, when a is an integer of 2 or 3, for example, the substituent $R^1$s may be bonded as follows, when a is an integer from 4 to 6, the substituent $R^1$s may be bonded to the carbon of the benzene ring in a similar manner, and the substituents $R^1$s may be the same and different when a is an integer of 2 or more.

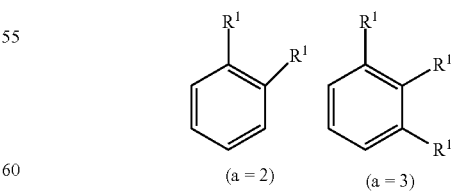

FIGURE illustrates an organic electric element according to an embodiment of the present invention.

Referring to FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, an electron transport auxiliary layer, a buffer layer 141, etc., the electron transport layer 160 or the like may serve as the hole blocking layer, and a hole transport layer 140 and an electron transport layer 160 may be formed of at least one or more layers.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a material of a hole injection layer 130, a hole transport layer 140, an emission-auxiliary layer 151, an electron transport auxiliary layer, an electron transport layer 160, or an electron injection layer 170, as a host or a dopant material of a light emitting layer 150, or as a material of a capping layer. For example, the inventive compound may be used as material of the light emitting layer 150, the hole transport layer 140, and/or the emission-auxiliary layer 151.

On the other hand, even if the core is the same core, the band gap, the electrical characteristics, the interface characteristics, and the like may be different depending on which substituent is bonded at which position. Therefore, it is necessary to study the selection of the core and the combination of the sub-substituent. Specially, long life span and high efficiency can be simultaneously achieved when the optimal combination of energy levels and T1 values, inherent material properties (mobility, interfacial properties, etc.), and the like among the respective layers of an organic material layer is achieved.

As already described above, generally, in order to solve the emission problem in a hole transport layer of an organic electroluminescent element, it is preferable that an emission-auxiliary layer is formed between the hole transport layer and a light emitting layer, and it is necessary to develop different material of an emission-auxiliary layers according to respective light emitting layers (R, G, B). On the other hand, in the case of an emission-auxiliary layer, it is necessary to grasp the correlation between a hole transport layer and a light emitting layer (host). Therefore, if an organic material layer is different, it is very difficult to infer the characteristics even if the core of an emission-auxiliary layer is similar.

According to the present invention, energy levels and $T_1$ values between organic material layers, inherent material properties (mobility, interfacial properties, etc.), and the like can be optimized by forming a hole transport layer and/or an emission-auxiliary layer which comprise the compound represented by the Formula 1, and thus it is possible to simultaneously improve the life span and efficiency of the organic electronic element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R(Red), G(Green), B(Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

An embodiment of the present invention provides an organic electric element in which a first electrode, an organic material layer and a second electrode are stacked in sequence, wherein the organic material layer comprises a hole transport layer, an emission-auxiliary layer, and a light emitting layer, at least one of the hole transport layer and the emission-auxiliary layer comprises the compound represented by the following formula 1, and the light emitting layer comprises the compound represented by the following formula 2.

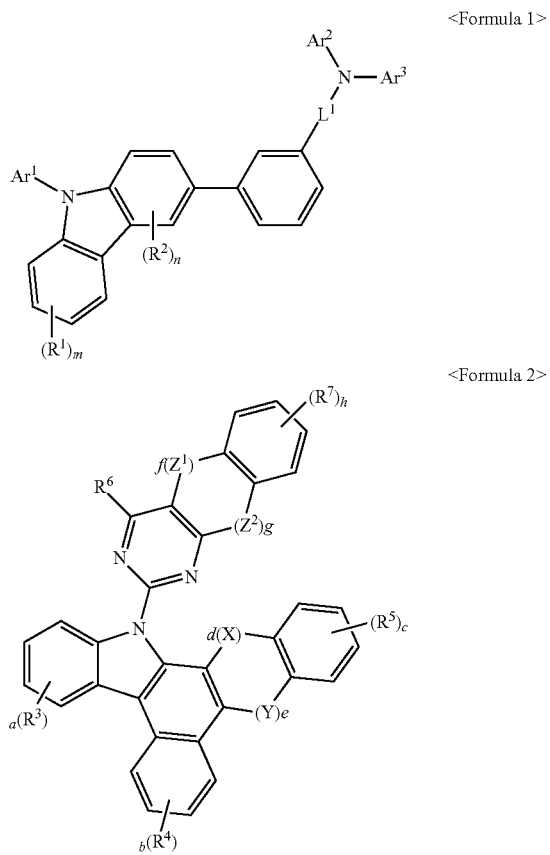

<Formula 1>

<Formula 2>

In formulas 1 and 2 above, each of symbols may be defined as follows.

$Ar^1$ to $Ar^3$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group.

$Ar^2$ and $Ar^3$ are optionally linked to each other to form a ring. Here, the formed ring may be a monocyclic or polycyclic alicyclic or aliphatic ring, specifically, may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring.

When $Ar^1$ is an aryl group, $Ar^1$ may be preferably a $C_6$-$C_{30}$ aryl group, more preferably a $C_6$-$C_{18}$ aryl group, for example, may be phenyl, biphenyl, terphenyl, naphthyl, etc.; when $Ar^1$ is a heterocyclic group, $Ar^1$ may be preferably a $C_2$-$C_{30}$ heterocyclic group, more preferably a $C_2$-$C_{12}$ heterocyclic group, for example, may be pyridyl, isoquinoline, dibenzothiophene, dibenzofurane, etc.; when $Ar^1$ is a fluorenyl group, for example, $Ar^1$ may be 9,9-dimethyl-9H-fluorenyl group, 9,9-diphenyl-9H-fluorenyl group, 9,9-spiro-bifluorenyl group, etc.; when $Ar^1$ is an alkyl group, $Ar^1$ may be preferably a $C_1$-$C_{20}$ alkyl group, more preferably a $C_1$-$C_{10}$ alkyl group, for example, may be an ethyl group; when $Ar^1$ is an alkenyl group, $Ar^1$ may be preferably a $C_2$-$C_{20}$ alkenyl group, more preferably a $C_1$-$C_{10}$ alkenyl group, for example, may be an prophenyl group.

When $Ar^2$ and $Ar^3$ are an aryl group, $Ar^2$ and $Ar^3$ may be preferably a $C_6$-$C_{30}$ aryl group, more preferably a $C_6$-$C_{18}$ aryl group, for example, may be phenyl, naphthyl, biphenyl, terphenyl, phenanthryl, etc.; when $Ar^2$ and $Ar^3$ are a heterocyclic group, $Ar^2$ and $Ar^3$ may be preferably a $C_2$-$C_{30}$ heterocyclic group, more preferably a $C_2$-$C_{12}$ heterocyclic group, for example, may be a thiophene, benzothiophene, dibenzothiophene, dibenzofurane, indole, pyridine, quinoline, isoquinoline, benzoquinoline, etc.; when $Ar^2$ and $Ar^3$ are a fluorenyl group, $Ar^2$ and $Ar^3$ may be, for example, 9,9-dimethyl-9H-fluorene, 9,9-diphenyl-9H-fluorenyl, 9,9'-spirobifluorene, 7,7-diphenyl-7H-benzofluorene and the like.

$L^1$ may be selected from the group consisting of a $C_6$-$C_{60}$ arylene group, a fluorenylene group, a divalent $C_2$-$C_{60}$ heterocyclic group containing at least one heteroatom selected from the group consisting of O, N, S, Si, and P, a divalent fused ring formed by a $C_3$-$C_{60}$ aliphatic ring and a $C_6$-$C_{60}$ aromatic ring, and a divalent $C_2$-$C_{60}$ aliphatic hydrocarbon group.

When $L^1$ is an arylene group, $L^1$ may be preferably a $C_6$-$C_{30}$ arylene group, more preferably a $C_6$-$C_{12}$ arylene group, for example, may be phenylene, biphenyl, naphthalene, etc.; when $L^1$ is a heterocyclic group, $L^1$ may be preferably a $C_2$-$C_{30}$ heterocyclic group, more preferably a $C_2$-$C_{12}$ heterocyclic group, for example, may be dibenzothiophene, dibenzofurane and the like; when $L^1$ is a fluorenyl group, $L^1$ may be, for example, 9,9-dimethyl-9H-fluorene, 9,9-diphenyl-9H-fluorenyl and the like.

$R^1$ and $R^2$ may be each independently selected from the group consisting of deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and -L'-N($R^a$)($R^b$).

When $R^1$ and $R^2$ are an aryl group, $R^1$ and $R^2$ may be preferably a $C_6$-$C_{30}$ aryl group, more preferably a $C_6$-$C_{12}$ aryl group, for example, may be phenyl, naphthyl, etc.

In addition, any two adjacent groups of $R^1$s or/and $R^2$s are optionally linked together to form at least one ring, and remaining groups not forming a ring are the same as defined above.

For example, when m and n are each an integer of 2, neighboring $R^1$s can be linked to each other to form a ring, and even though there are neighboring $R^2$s, $R^2$s may be each independently an aryl group or a heterocyclic ring. When neighboring $R^1$s, and/or $R^2$s are linked to each other to form a ring, the ring may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring.

m is an integer of 0 to 4, n is an integer of 0 to 3, and a plurality of $R^1$s, $R^2$s and a plurality of $R^3$s may be each the same or different from each other when m, n are each an integer of 2 or more.

$R^3$ to $R^5$, and $R^7$ may be each independently selected from the group consisting of deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and -L'-N($R^a$)($R^b$).

When $R^3$ to $R^5$, and $R^7$ are an aryl group, $R^3$ to $R^5$, and $R^7$ may be preferably a $C_6$-$C_{30}$ aryl group, more preferably a $C_6$-$C_{18}$ aryl group, for example, may be phenyl; when $R^3$ to $R^5$, and $R^7$ are a heterocyclic group, $R^3$ to $R^5$, and $R^7$ may be preferably a $C_2$-$C_{30}$ heterocyclic group, more preferably a $C_2$-$C_{12}$ heterocyclic group, for example, may be pyridine.

In addition, any two adjacent groups of $R^3$s to $R^5$s, and $R^7$s are optionally linked together to form at least one ring, and remaining groups not forming a ring are the same as defined above.

For example, when a and b are each an integer of 2, neighboring $R^3$s can be linked to each other to form a ring, and even though there are neighboring $R^4$s, $R^4$s may be each independently an aryl group or a heterocyclic ring. When neighboring $R^3$s, $R^4$s, $R^5$s, and/or $R^7$s are linked to each other to form a ring, the ring may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring. For example, the ring may be benzene and thus naphthalene or phenanthrene can be formed together with the benzene ring to which they are bonded.

a to c, and h are each independently an integer of 0 to 4, when a to c, and h are each an integer of 2 or more, a plurality of $R^3$s to $R^5$s, and $R^7$s may be each the same or different from each other.

$R^6$ may be selected from the group consisting of hydrogen, a $C_6$-$C_{60}$ aryl group, a fluorenyl group, and a $C_2$-$C_{60}$ heterocyclic group containing at least one heteroatom selected from the group consisting of O, N, S, Si, and P. When $R^6$ is an aryl group, $R^6$ may be preferably a $C_6$-$C_{30}$ aryl group, more preferably a $C_6$-$C_{18}$ aryl group, for example, may be phenyl, naphthyl, biphenyl, terphenyl, phenanthryl, etc.; when $R^6$ is a heterocyclic group, $R^6$ may be preferably a $C_2$-$C_{30}$ heterocyclic group, more preferably a $C_2$-$C_{16}$ heterocyclic group, for example, may be pyridine, carbazole, dibenzothiophene, dibenzofuran, thianthrene, etc.; when $R^6$ is a fluorenyl group, for example, $R^6$ may be 9,9-dimethyl-9H-fluorenyl and the like.

X and Y may be each independently selected from the group consisting of a single bond, S, O, N(R') and C(R')(R''). R' and R'' may be each independently selected from the group consisting of hydrogen, a $C_6$-$C_{60}$ aryl group, a fluorenyl group, a $C_2$-$C_{60}$ heterocyclic group containing at least one heteroatom selected from the group consisting of O, N, S, Si, and P, and a $C_1$-$C_{50}$ alkyl group.

d and e are each independently an integer of 0 or 1, and it is preferable that d+e is an integer of 1 or 2.

For example, when h and i are each an integer of 2, neighboring $R^8$s can be linked to each other to form a ring, and even though there are neighboring $R^9$s, $R^9$s may be each independently an aryl group or a heterocyclic ring. When neighboring $R^8$s, $R^9$s, and/or $R^{10}$s are linked to each other to form a ring, the ring may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring, for example, the ring may be a benzene and thus naphthalene or phenanthrene can be formed together with the benzene ring to which they are bonded.

In addition, R' and R'' can be optionally linked to each other to form a ring, and thus spiro compound can be formed. Here, the formed ring may be a monocyclic or polycyclic alicyclic or aliphatic ring, specifically, the ring may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring.

$Z^1$ and $Z^2$ may be each independently a single bond, O or S. f and g are each independently an integer of 0 or 1, and it is preferable that f+g is an integer of 1 or 2.

In -L'-N($R^a$)($R^b$) of $Ar^1$ to $Ar^3$, $R^1$ to $R^5$, and $R^7$, L' may be selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and $R^a$ and $R^b$ may be each independently selected from the group consisting of a $C_6$-$C_{60}$ aryl group, a fluorenyl group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

When $Ar^1$-$Ar^3$, $R^1$-$R^7$, R', R'', $L^1$, L', $R^a$ and $R^b$ are each the aryl group, heterocyclic group, fluorenyl group, alkyl group, alkenyl group, fused ring group, alkoxyl group, aryloxly group, arylene group, fluorenylene group, or aliphatic hydrocarbon group, they may be each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

Illustratively, Formula 1 above can be represented by any one of Formulas 3-1 to 3-3 below.

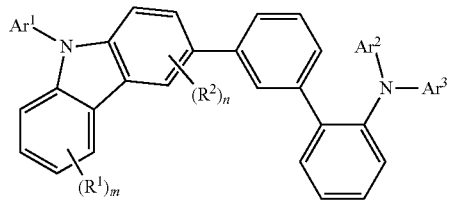

<Formula 3-1>

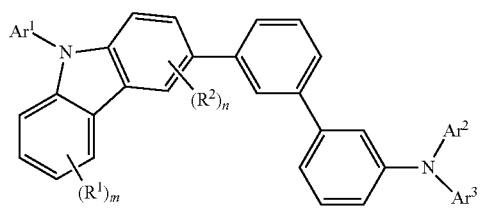
<Formula 3-2>
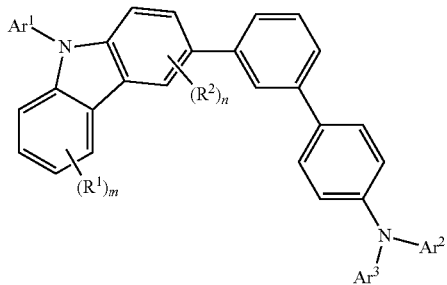
<Formula 3-3>
In Formulas 3-1 to 3-3, the symbols of Ar¹ to Ar³, $R^1$, $R^2$, m, n and the like are the same as defined in claim 1.
Specifically, the compound represented by Formula 1 may be any one of the following compounds.
A1
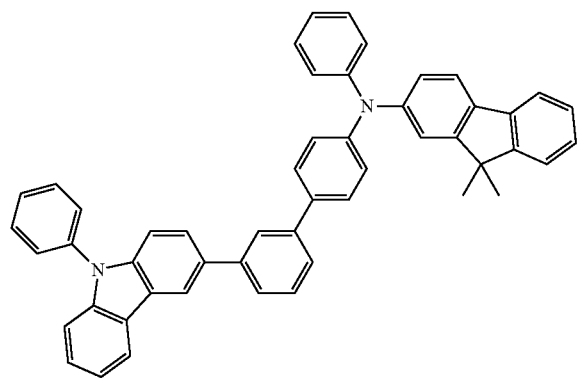
A2
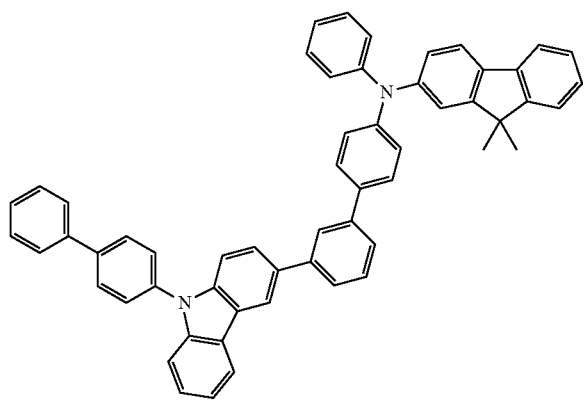
A6
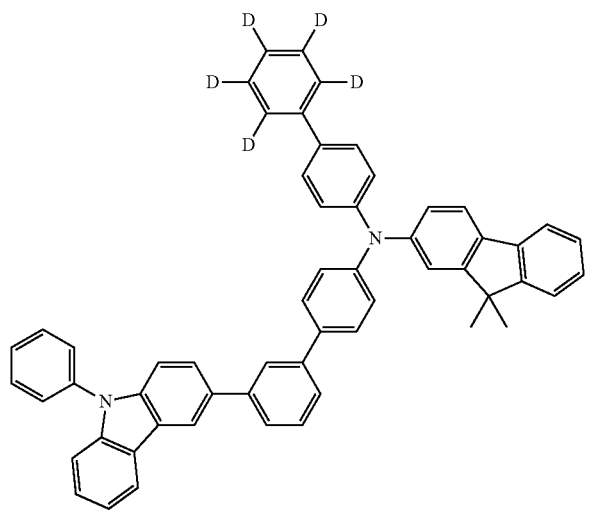
A7
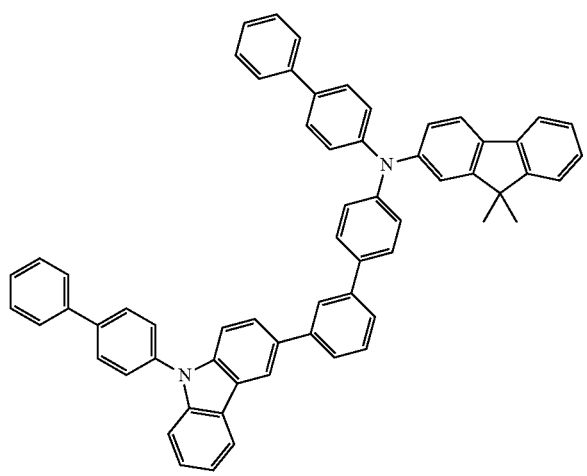

-continued
A11
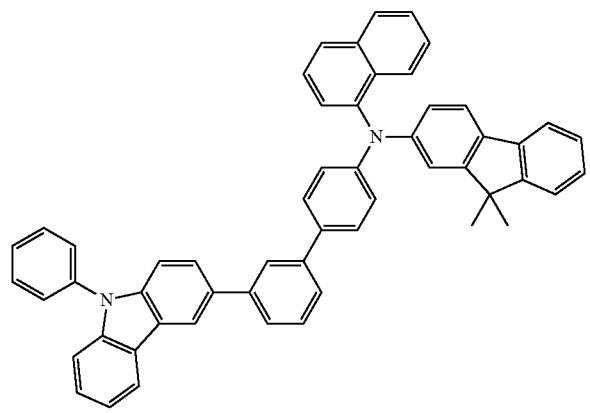
A12
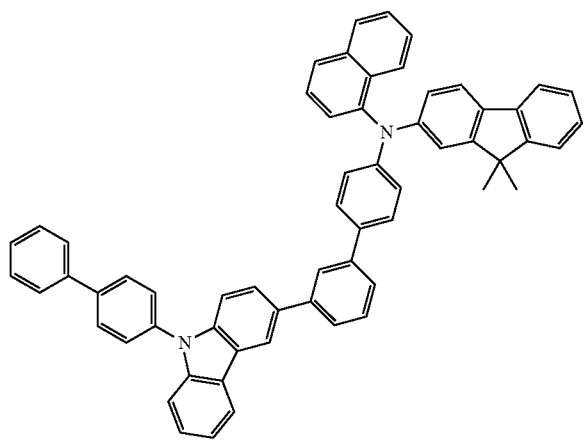
A16
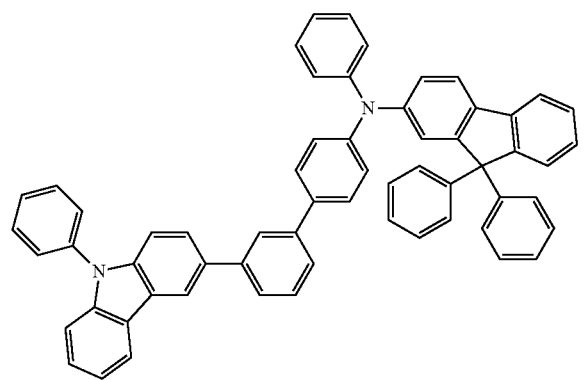
A17
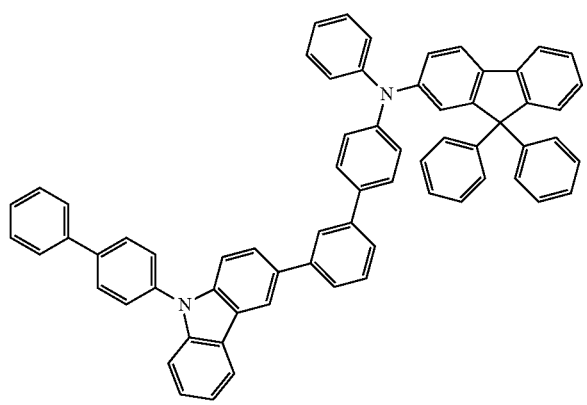
A19
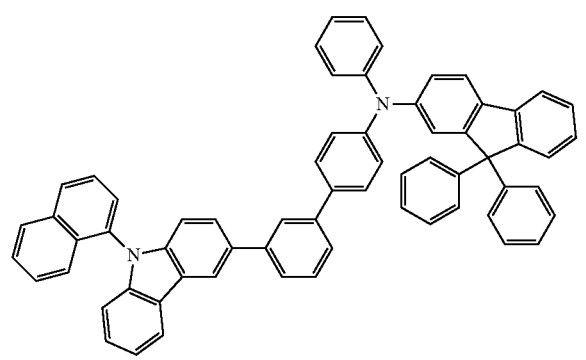
A21
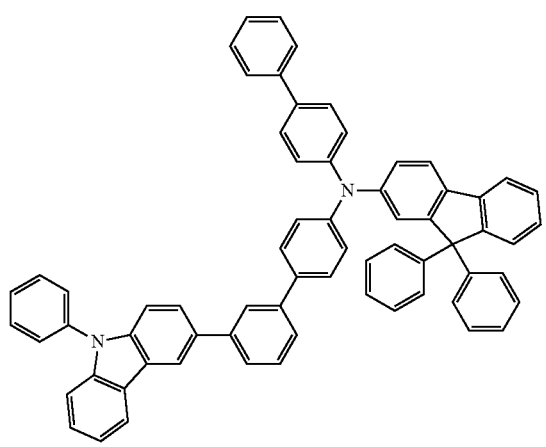

-continued
A22
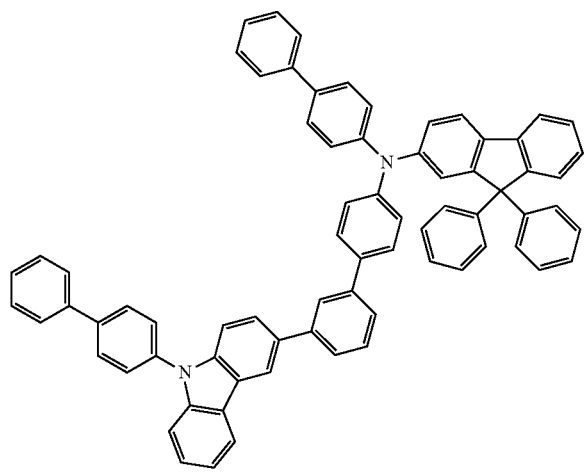
A23
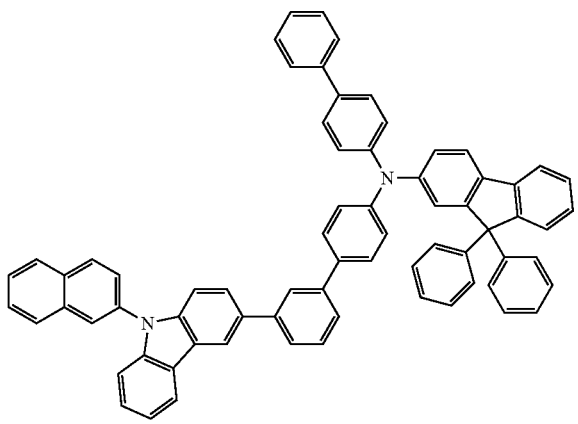
A24
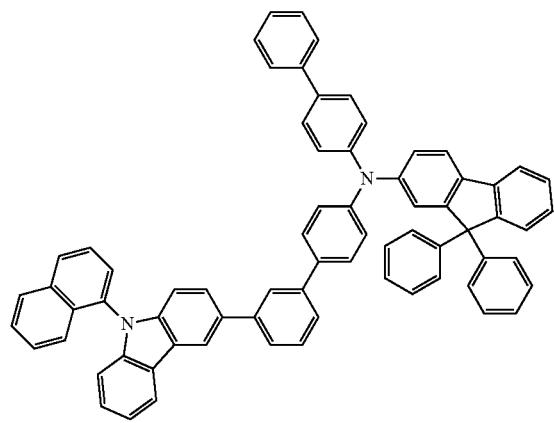
A25
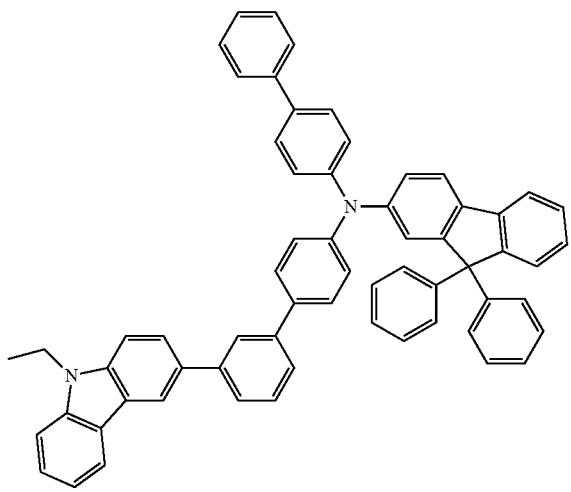
A26
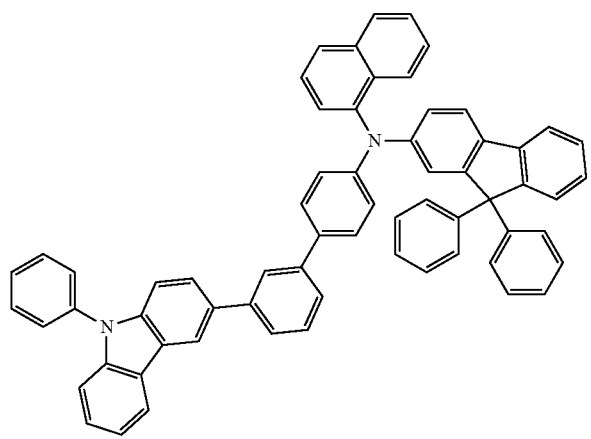
A27
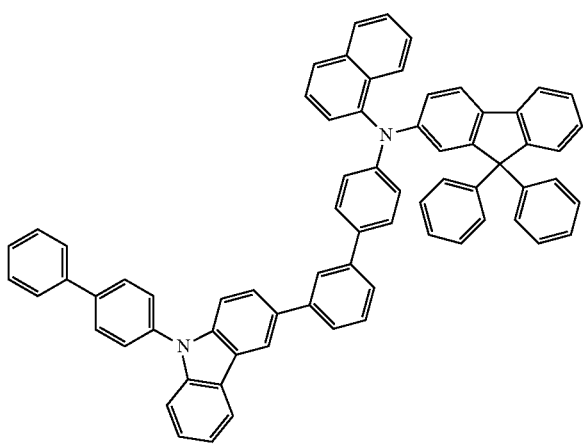

A31
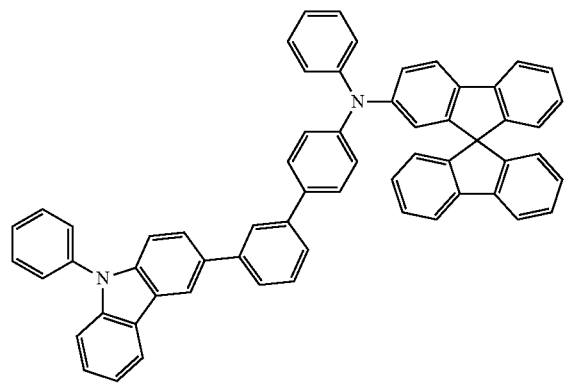
A36
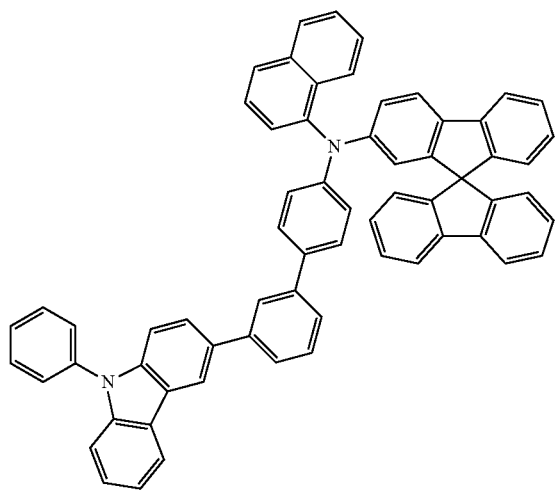
A47
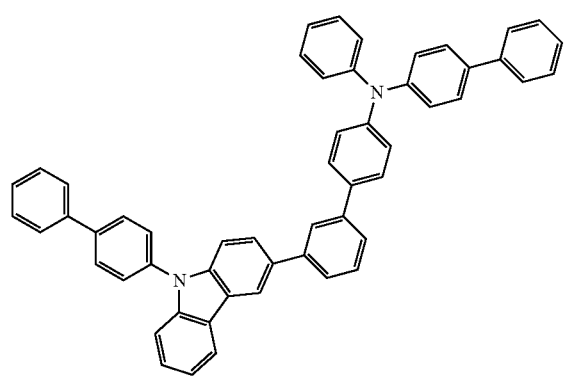
A51
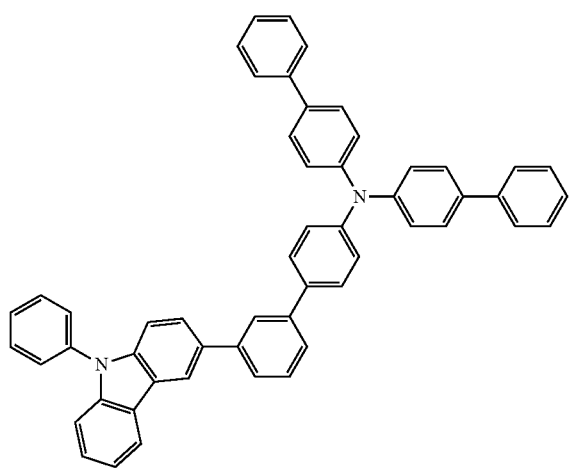
A56
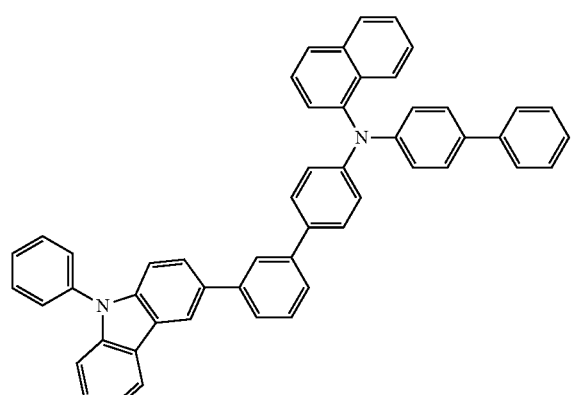
A62
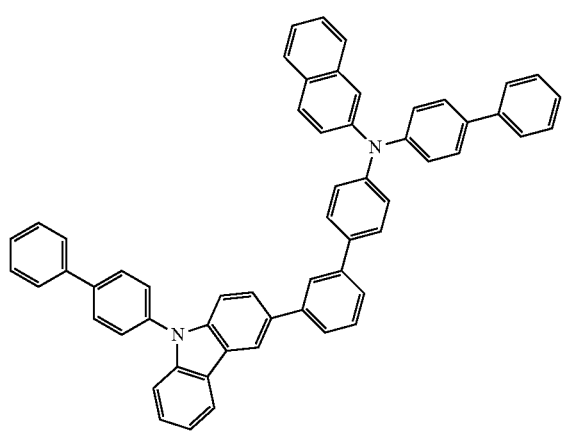

-continued
A66
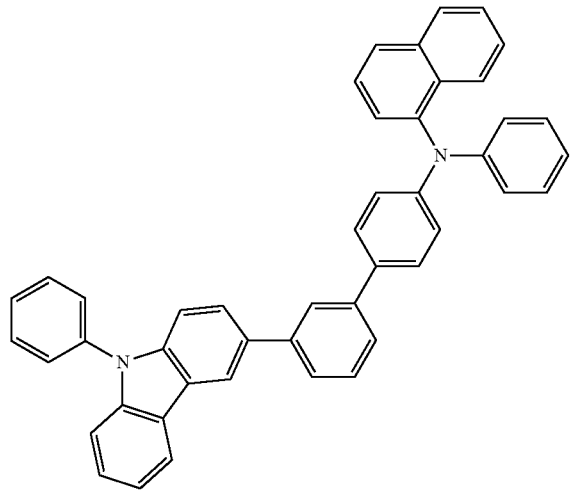
A72
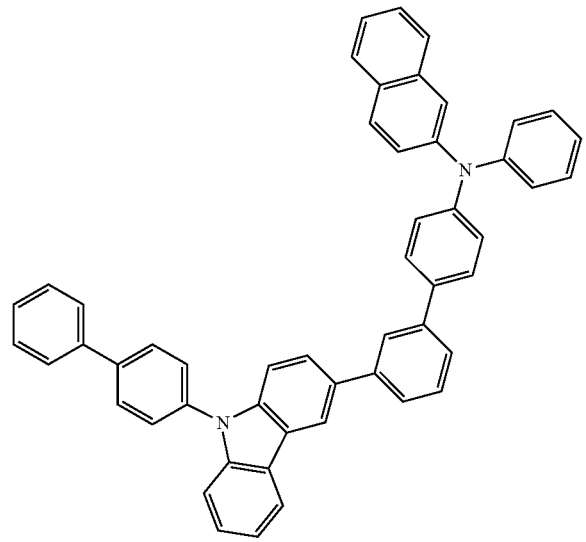
A87
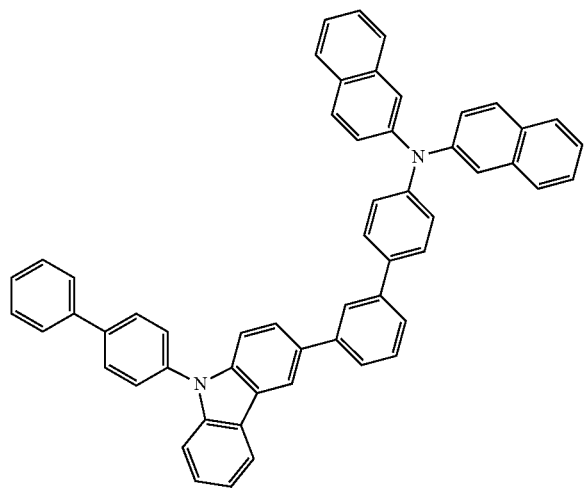
A97
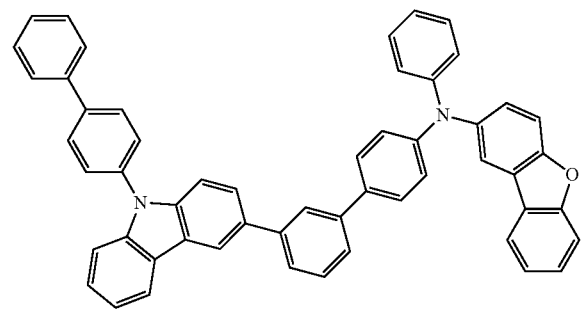
A101
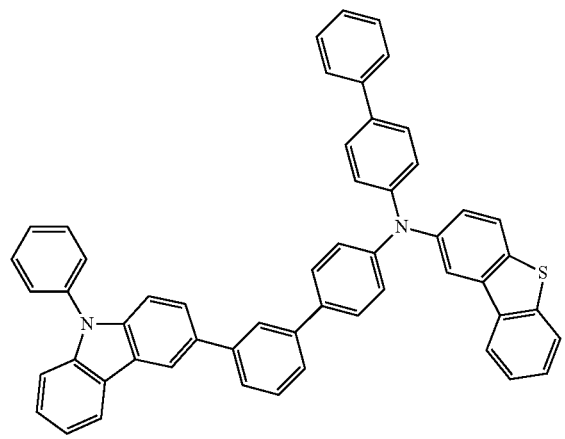
A121
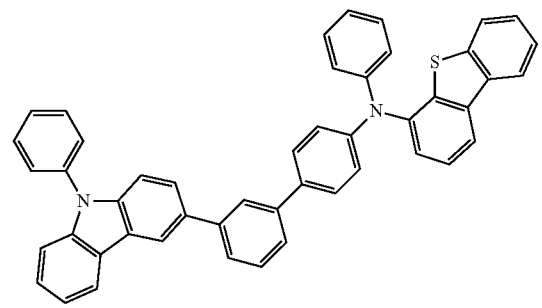

-continued
A123
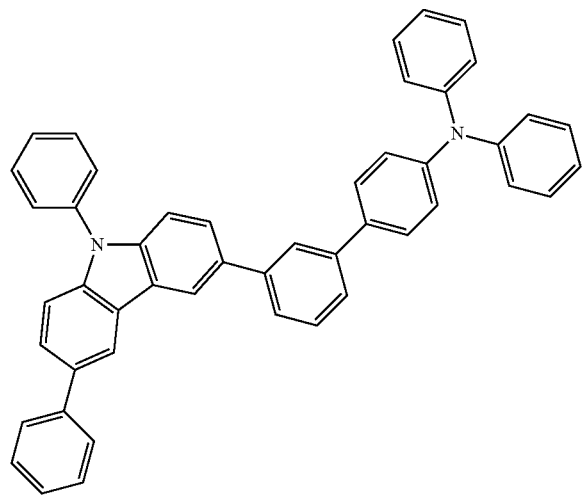
A124
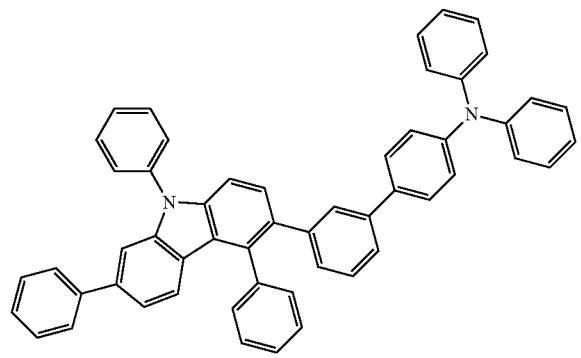
A125
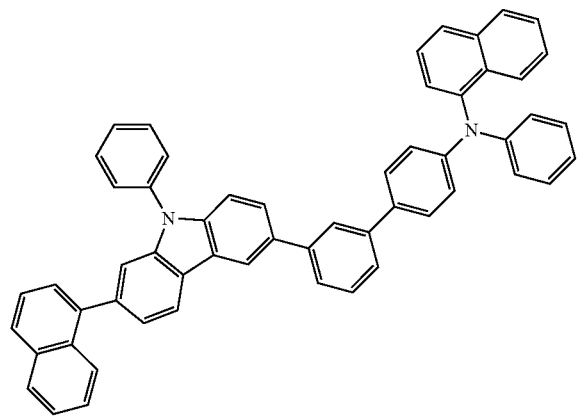
A127
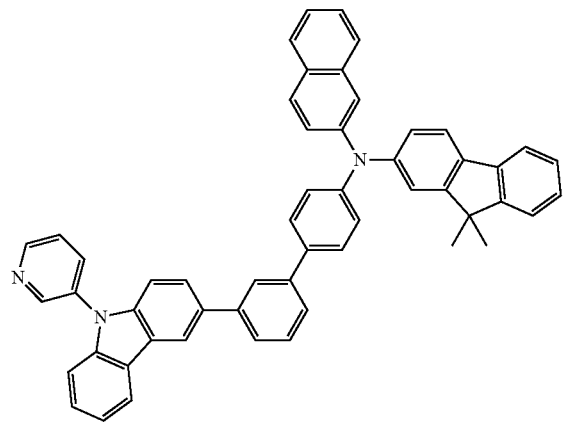
A128
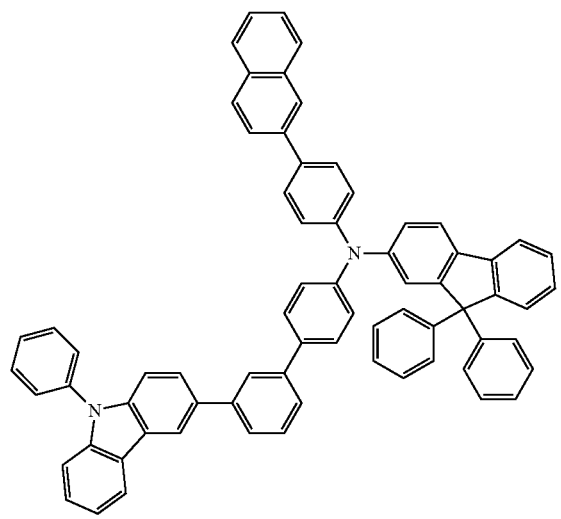
A129
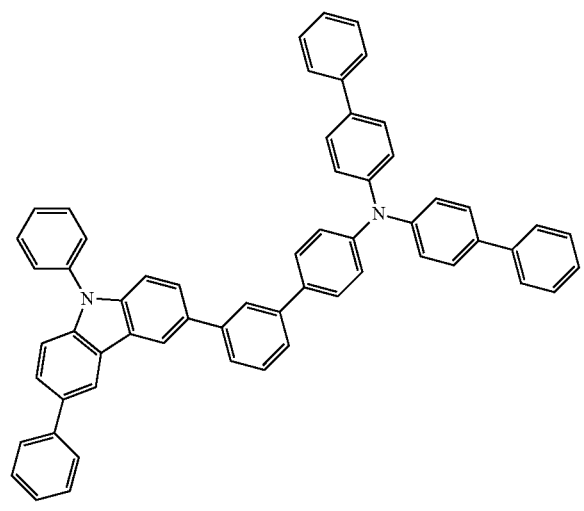

-continued
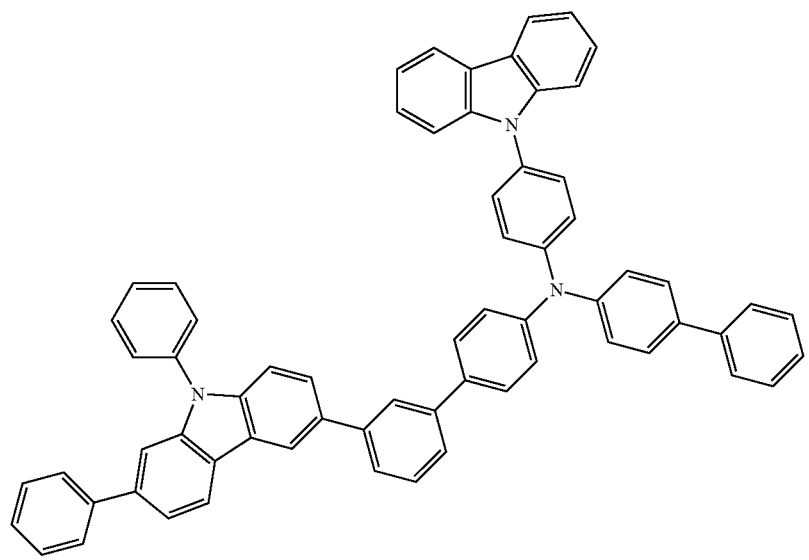
A130
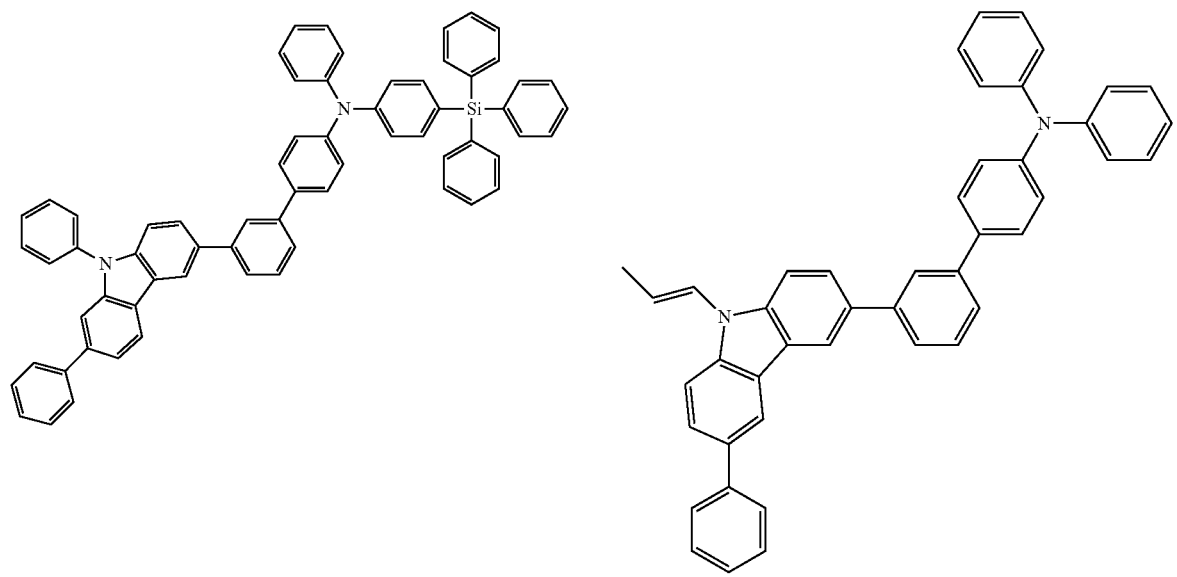
A131
A134

-continued
A135
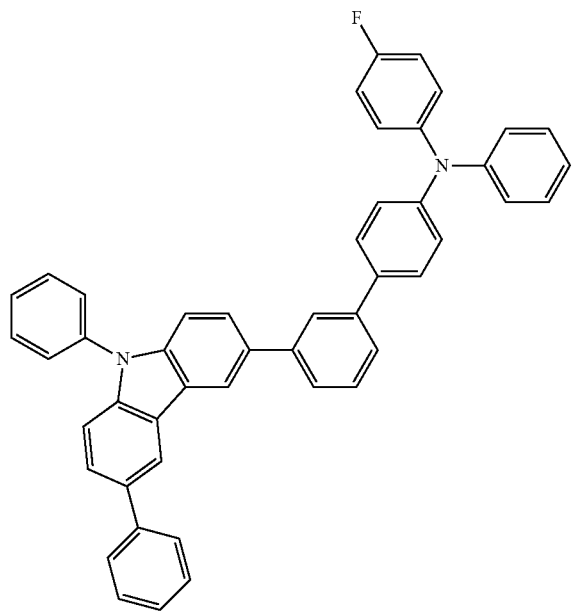
A142
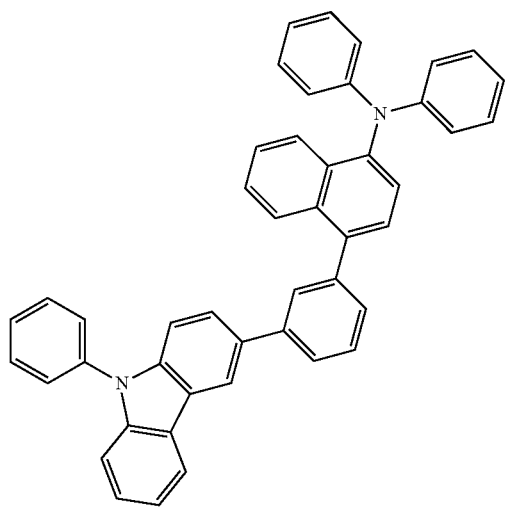
A146
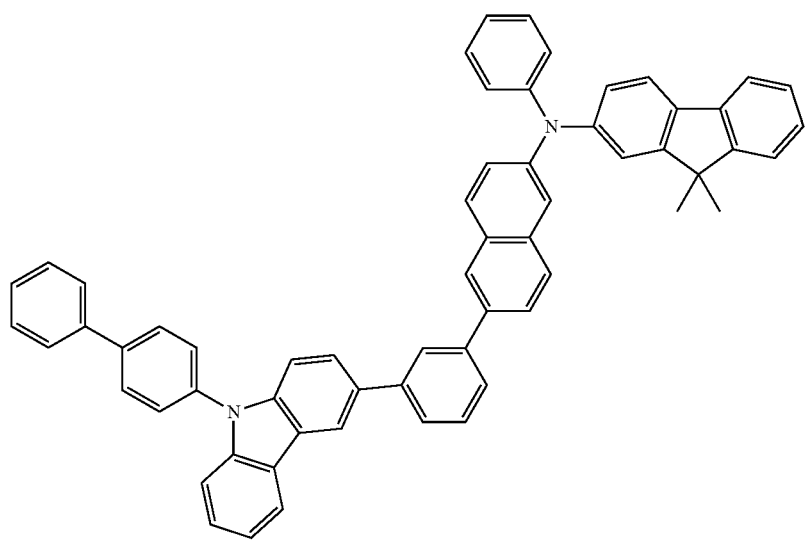
A161
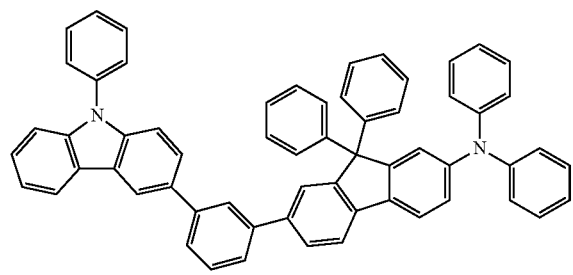
A162
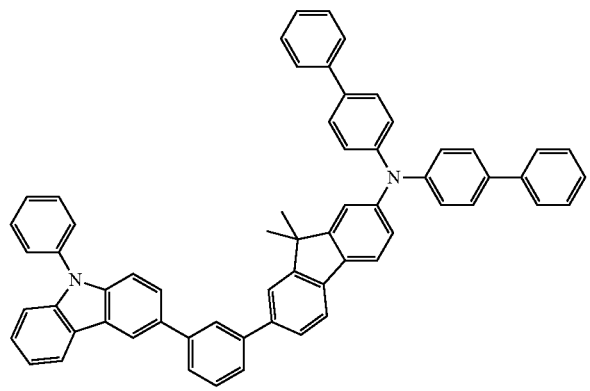

-continued
A165
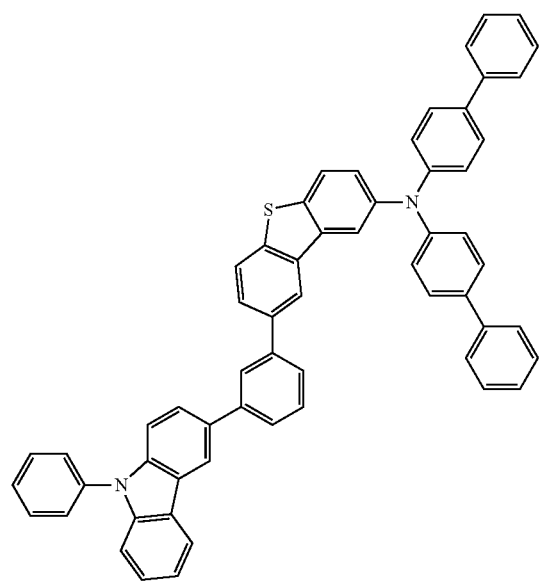
A168
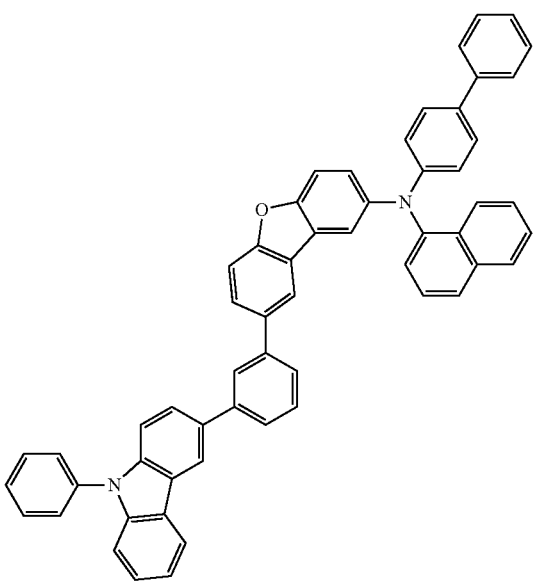
A169
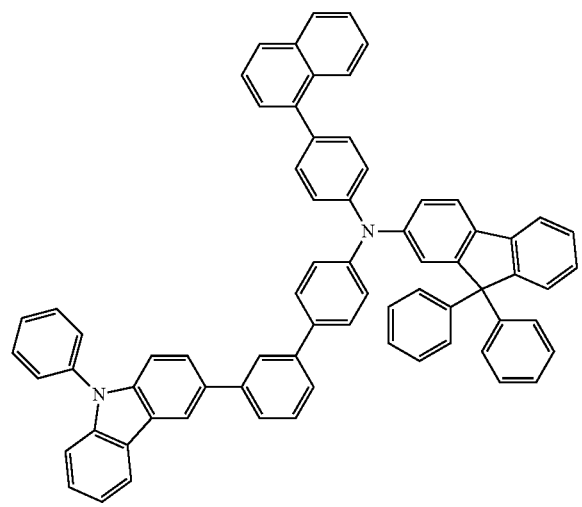
A170
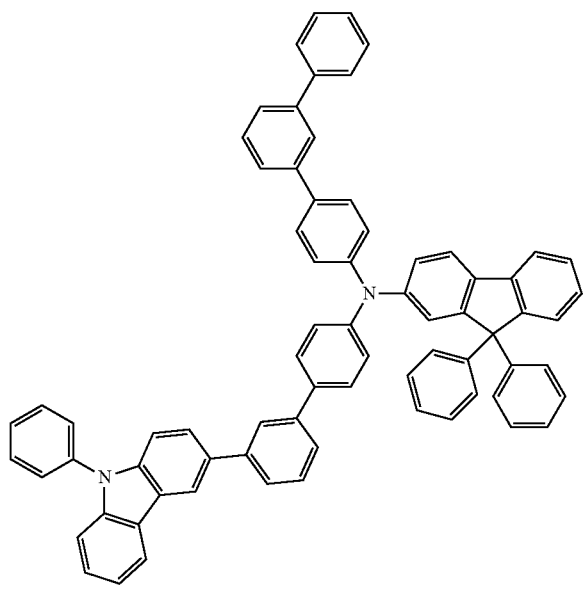
A171
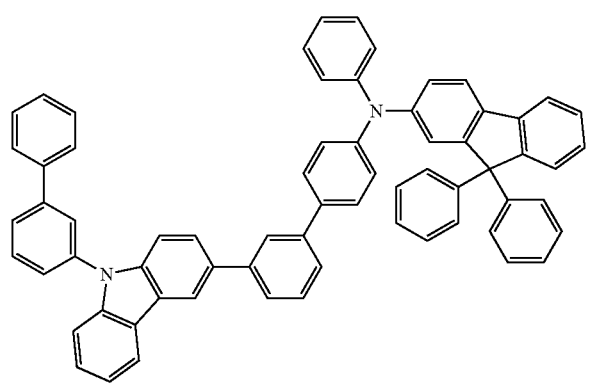
A172
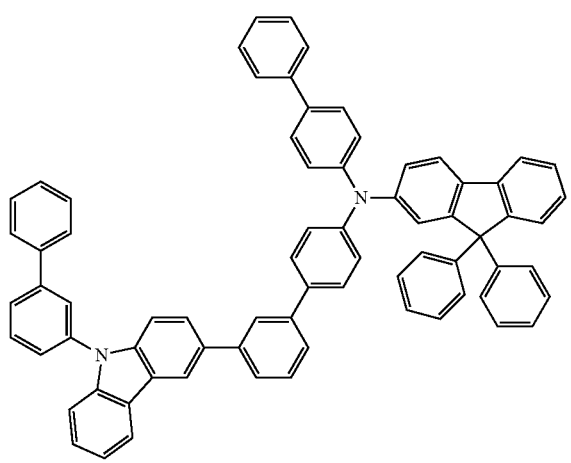

-continued
A173
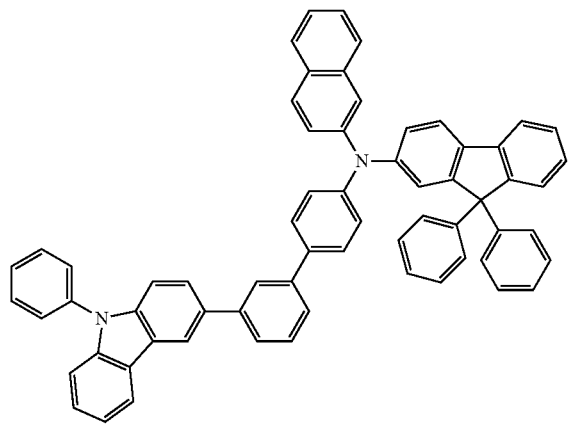
A174
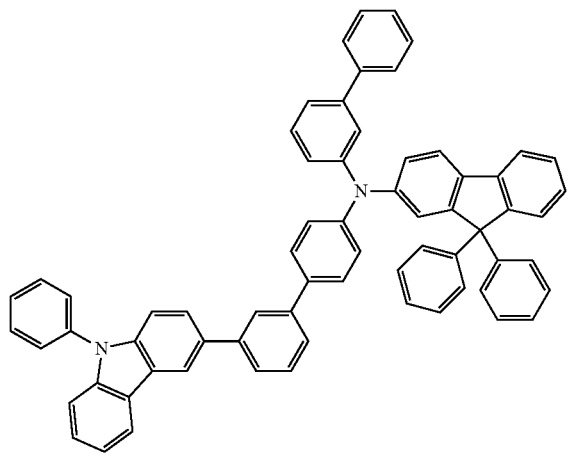
A175
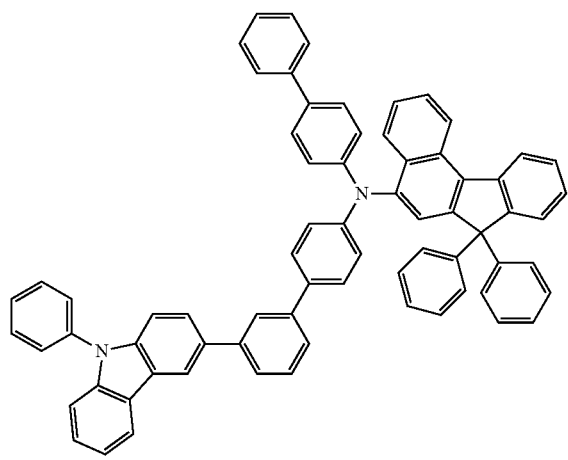
A176
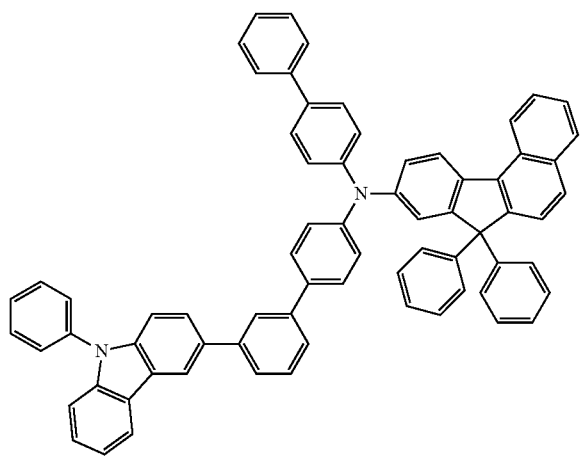
A177
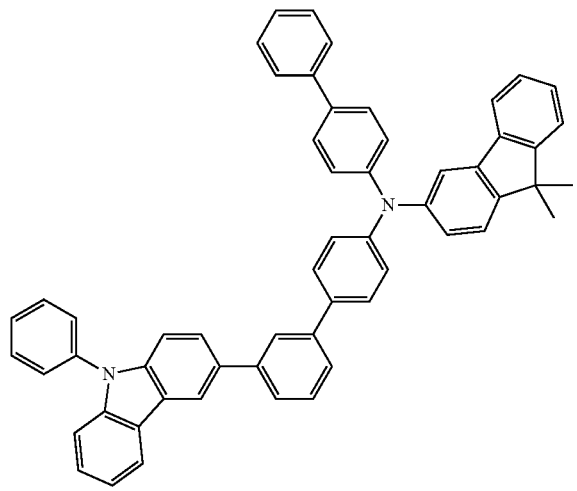
A178
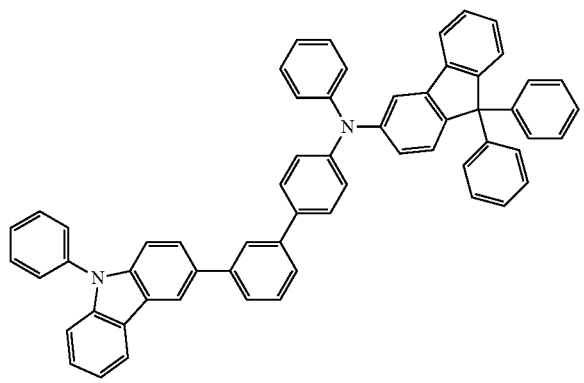

-continued
A179
A180
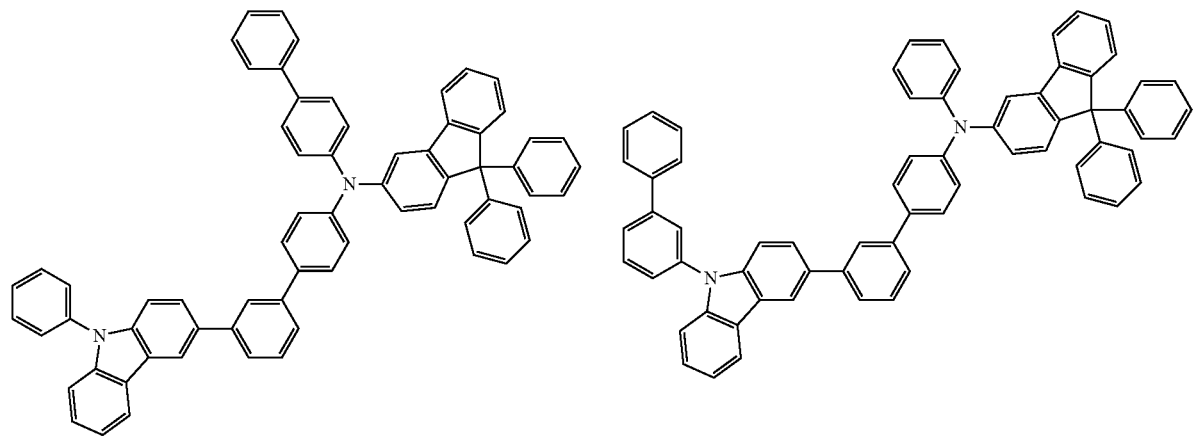
A181
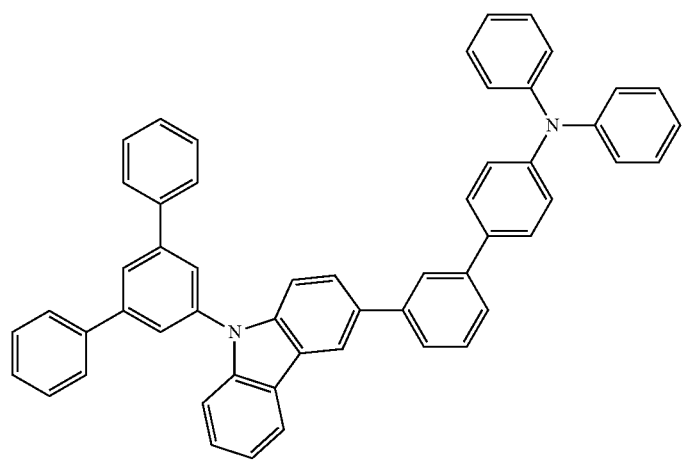
A182
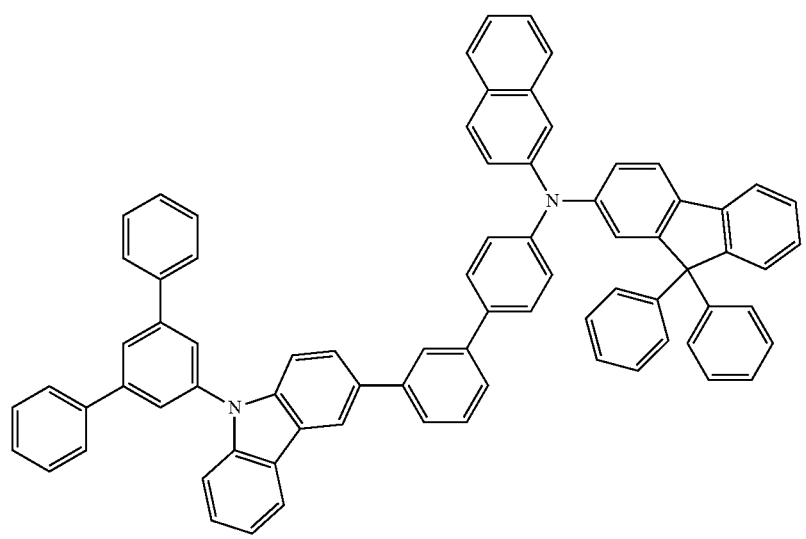

-continued
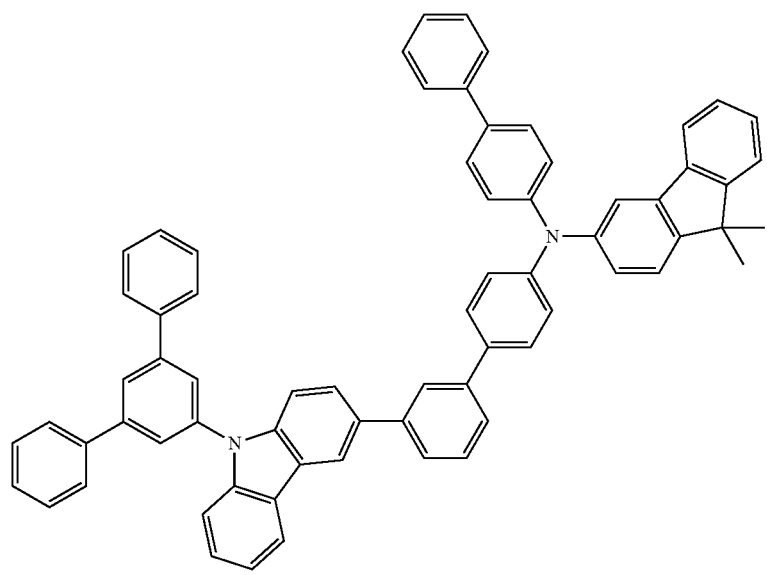
A183
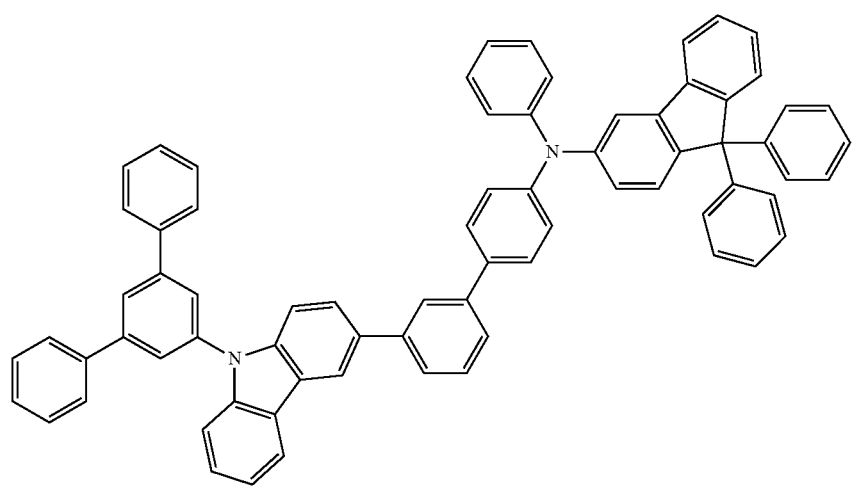
A184
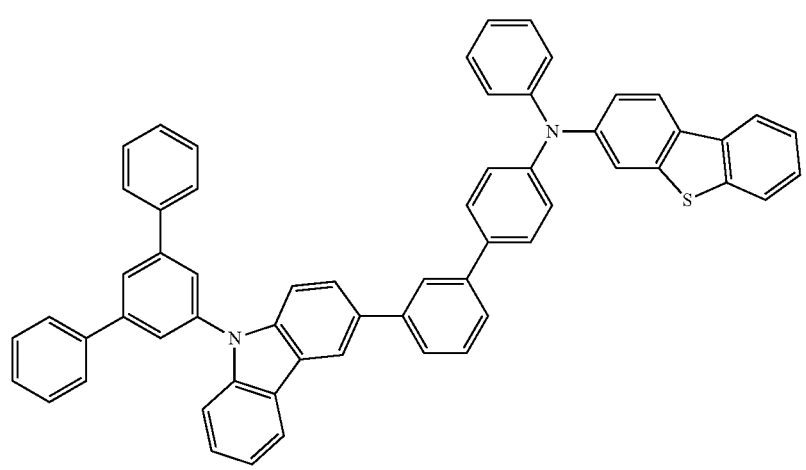
A185

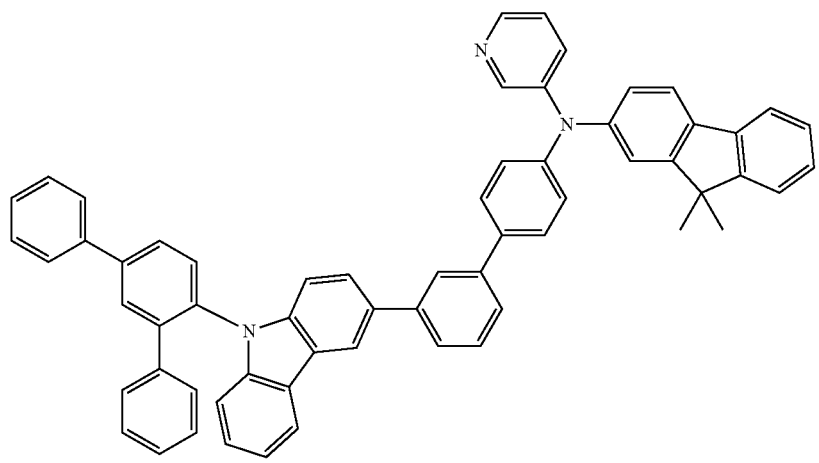
A186
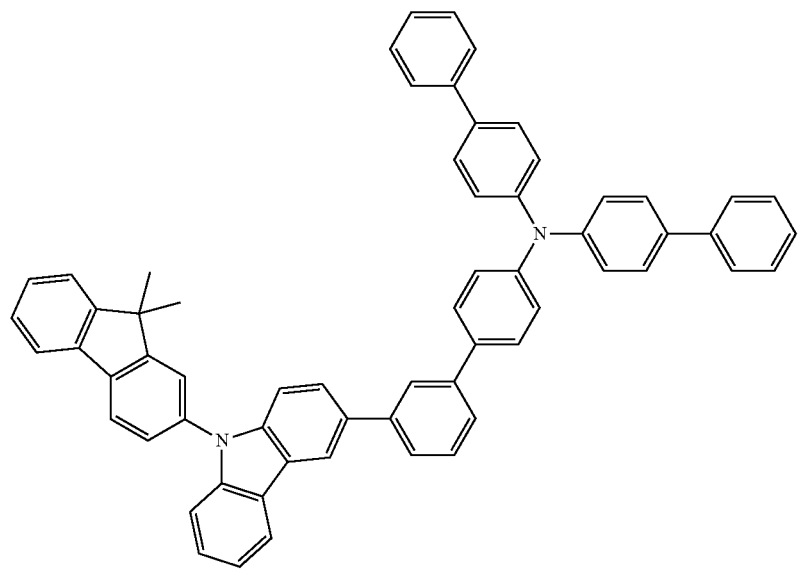
A187
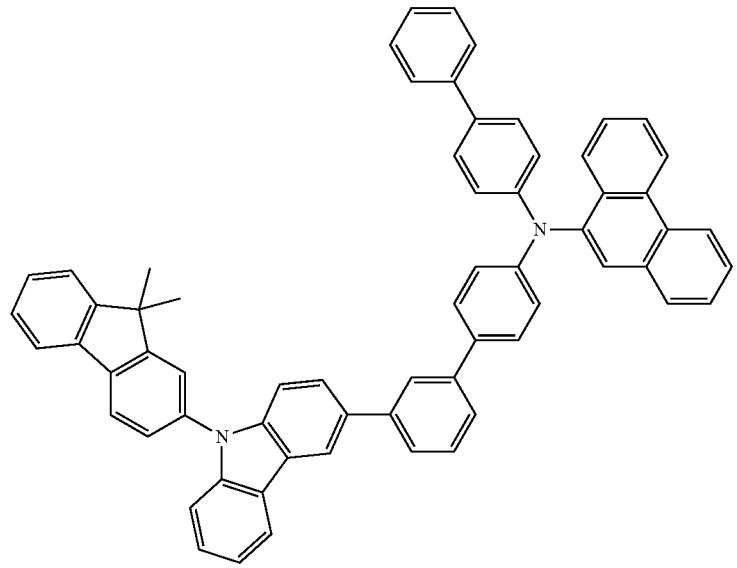
A188

-continued
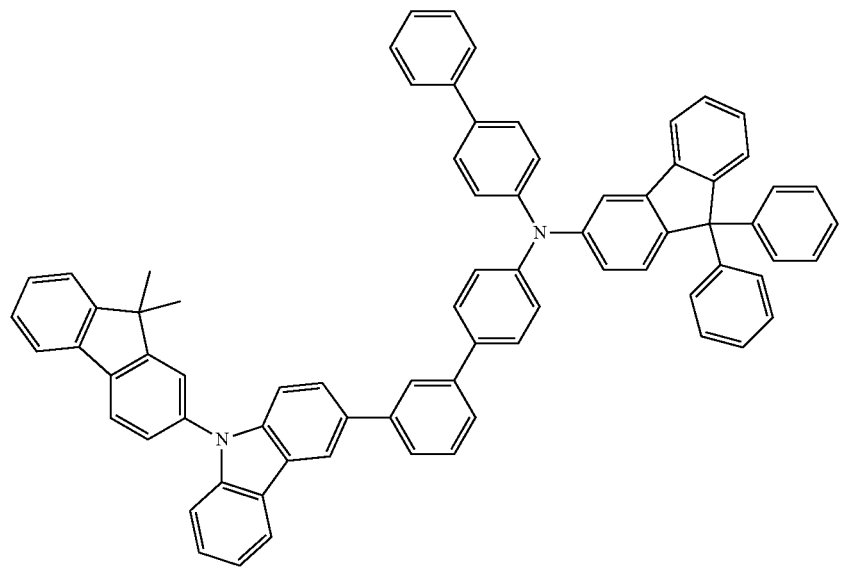
A189
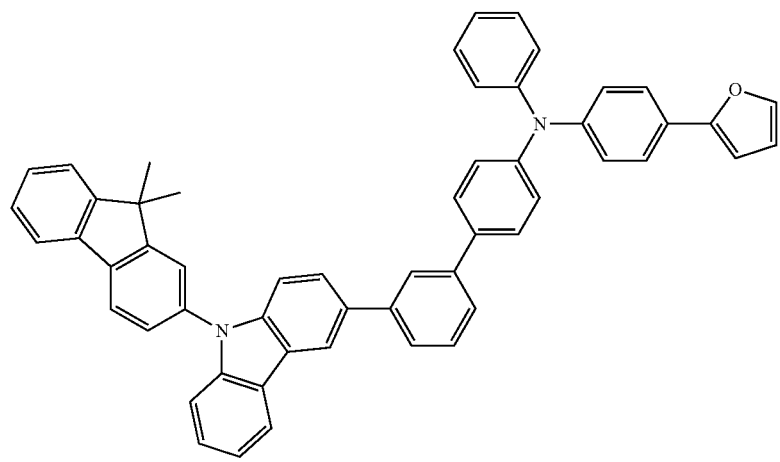
A190
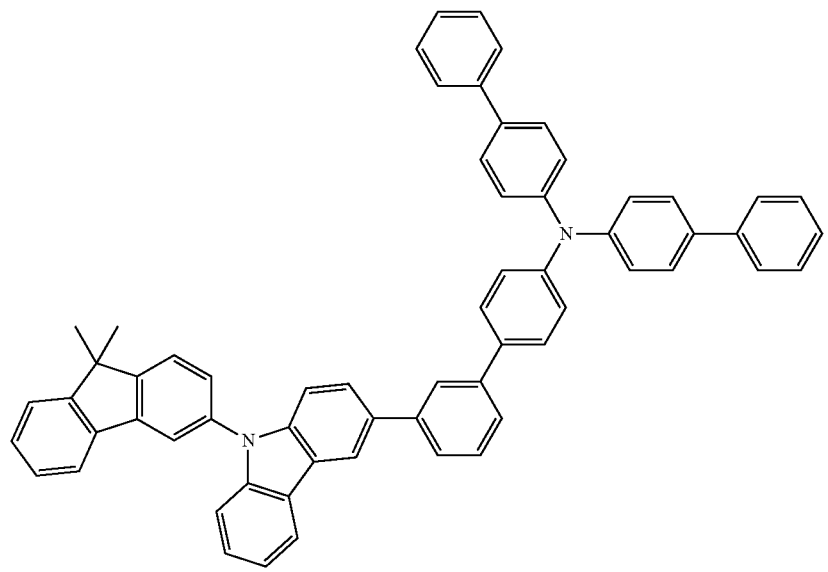
A191

-continued
A192
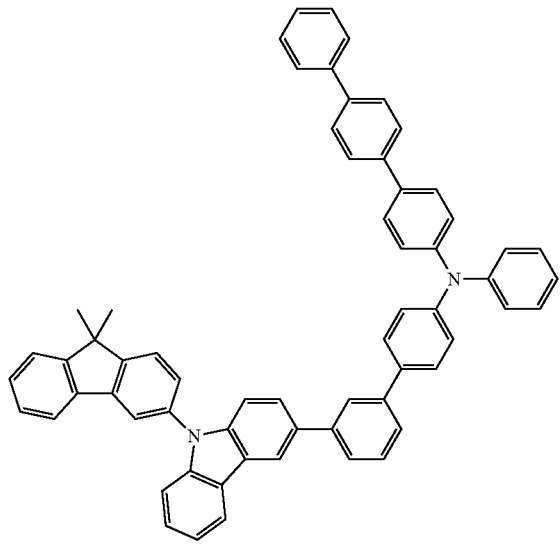
A193
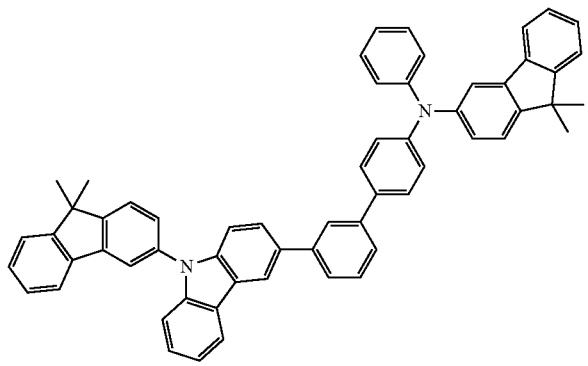
A194
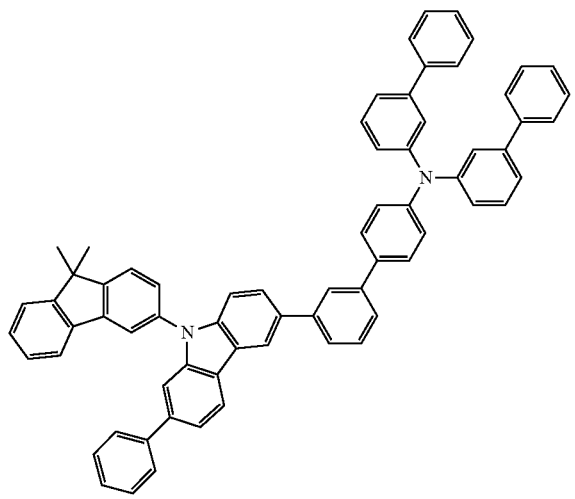
A195
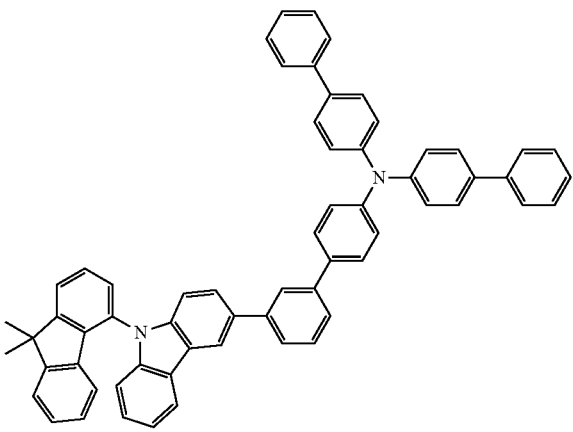
A196
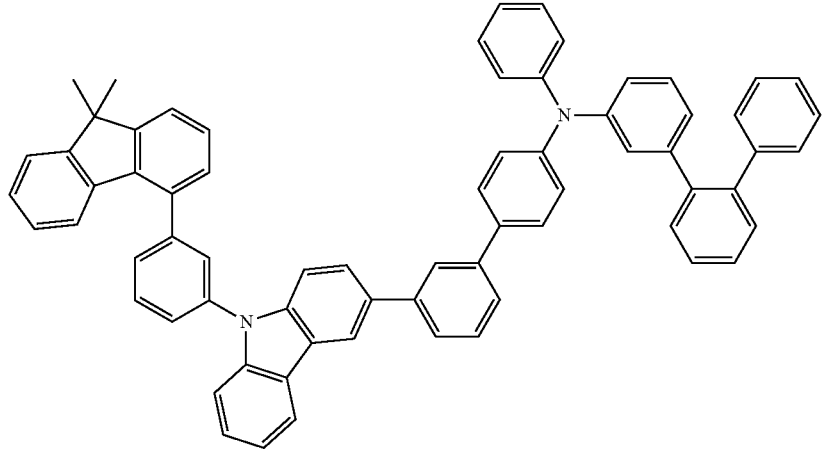

-continued
A197
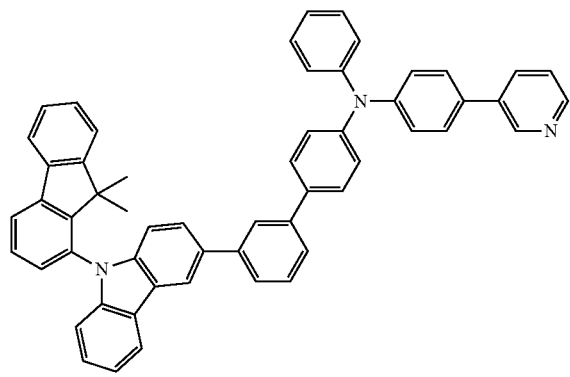
A198
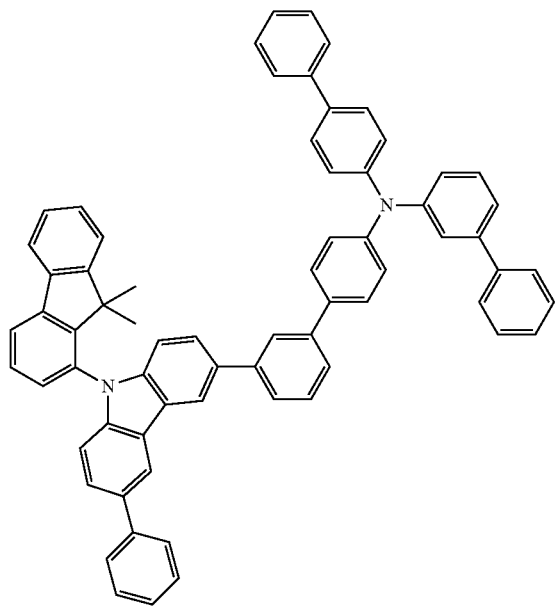
A199
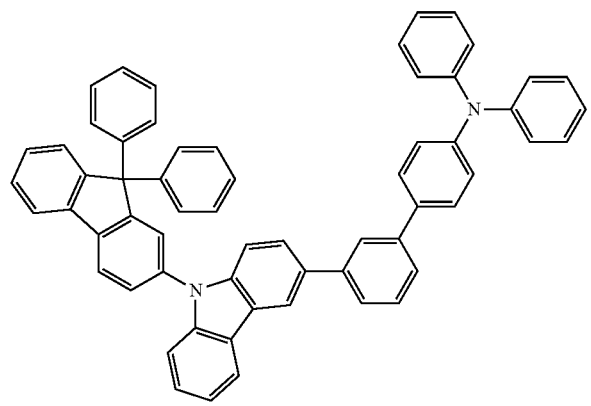
A200
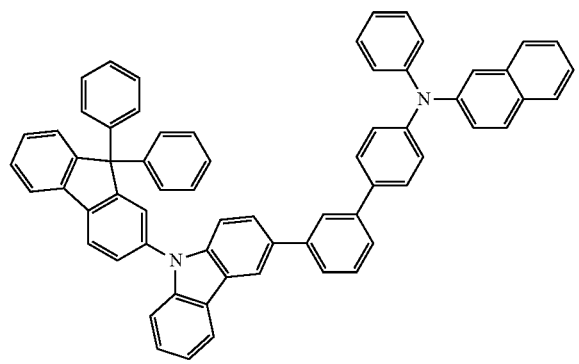
A201
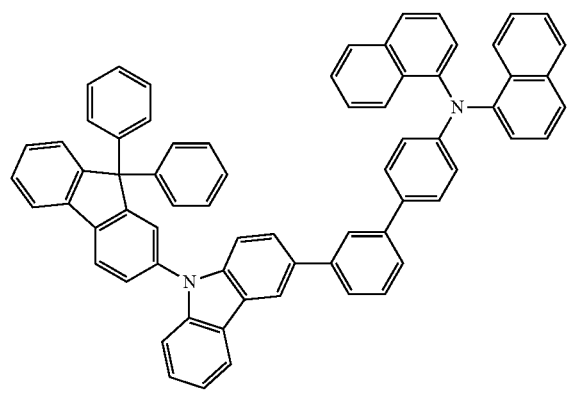
A202
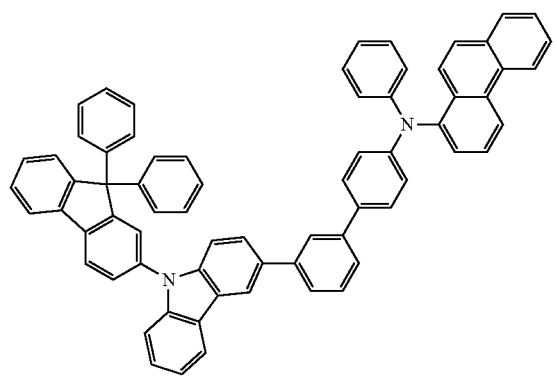

-continued
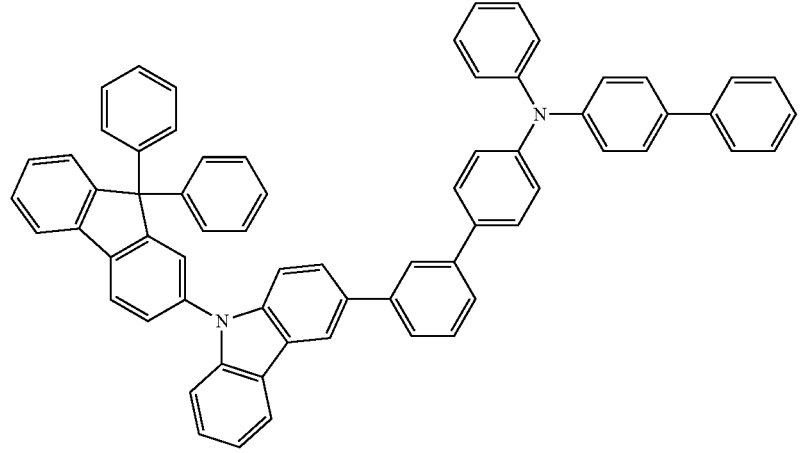
A203
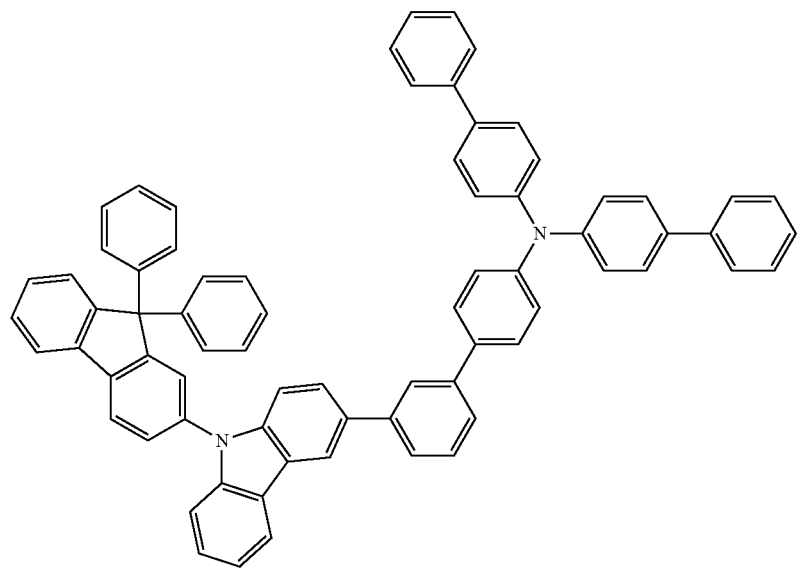
A204
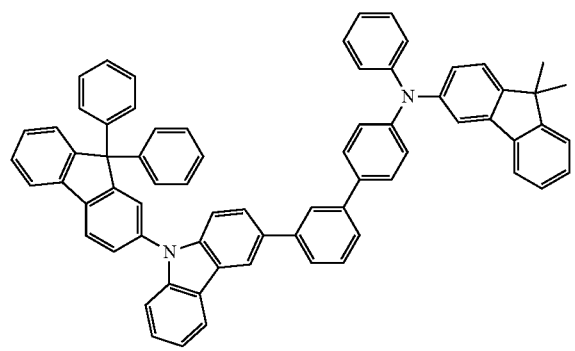
A205
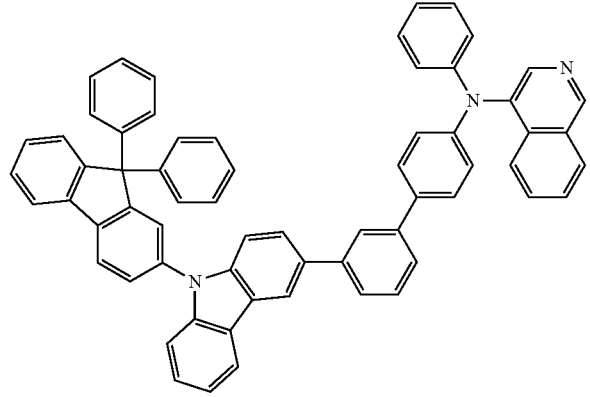
A206

-continued
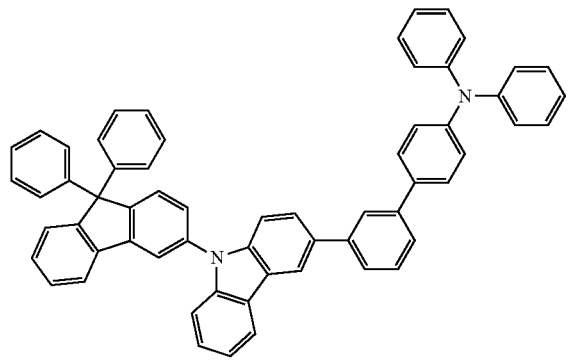
A207
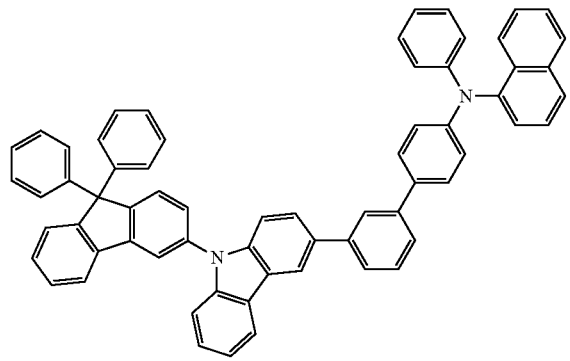
A208
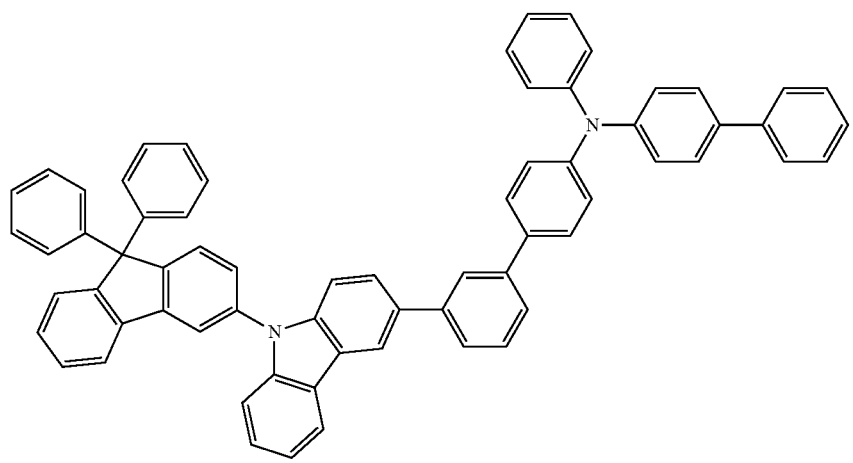
A209
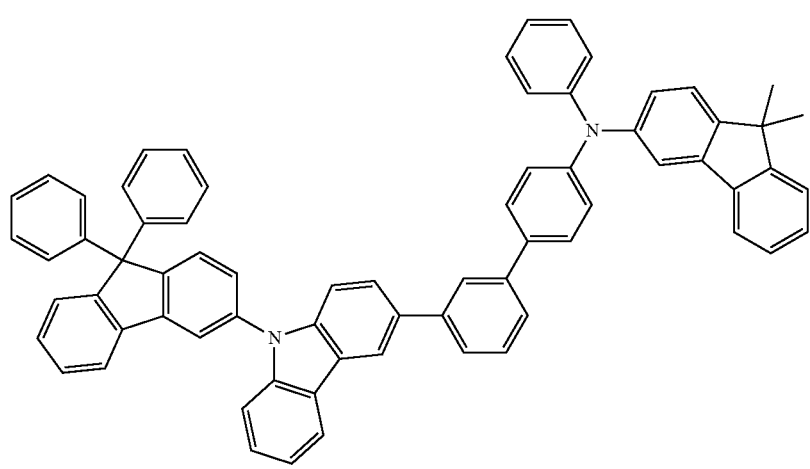
A210

-continued
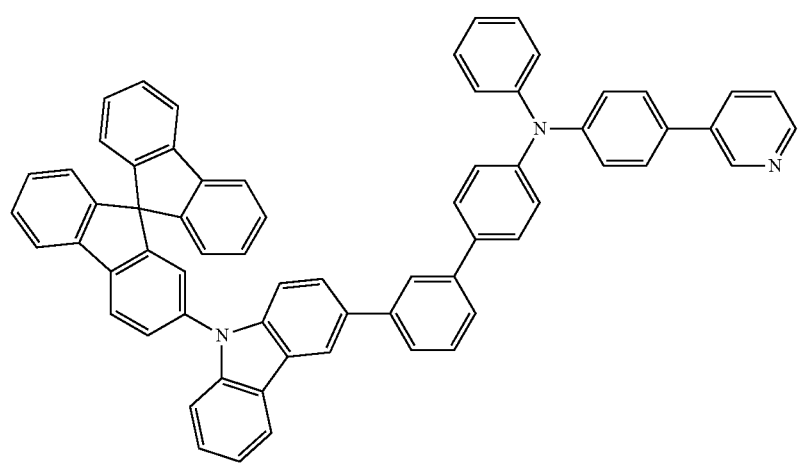
A211
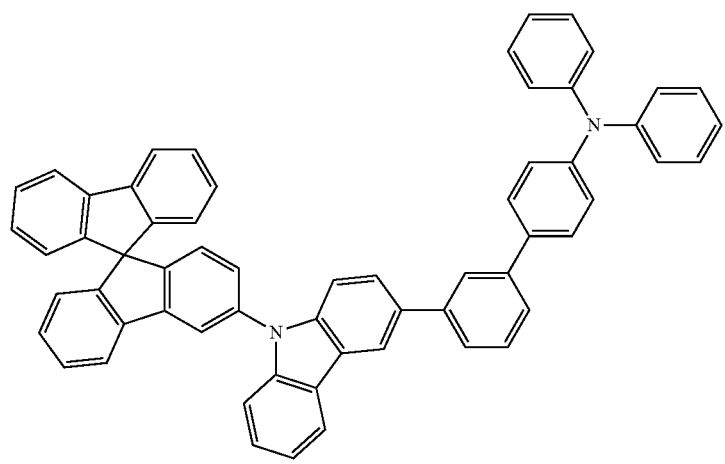
A212
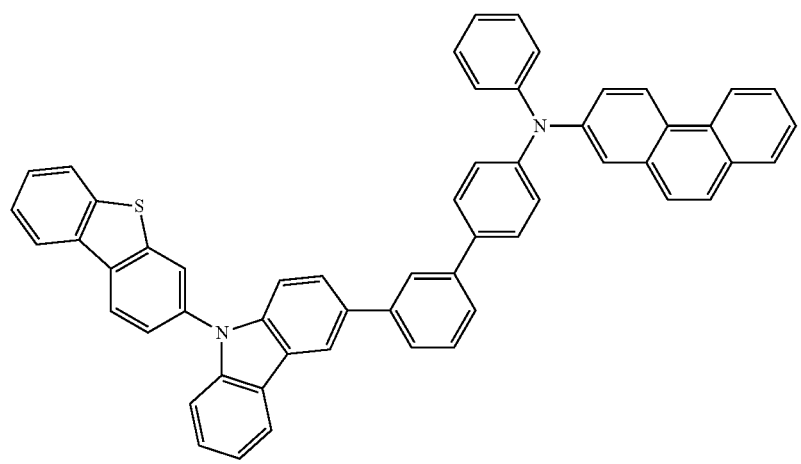
A213

-continued
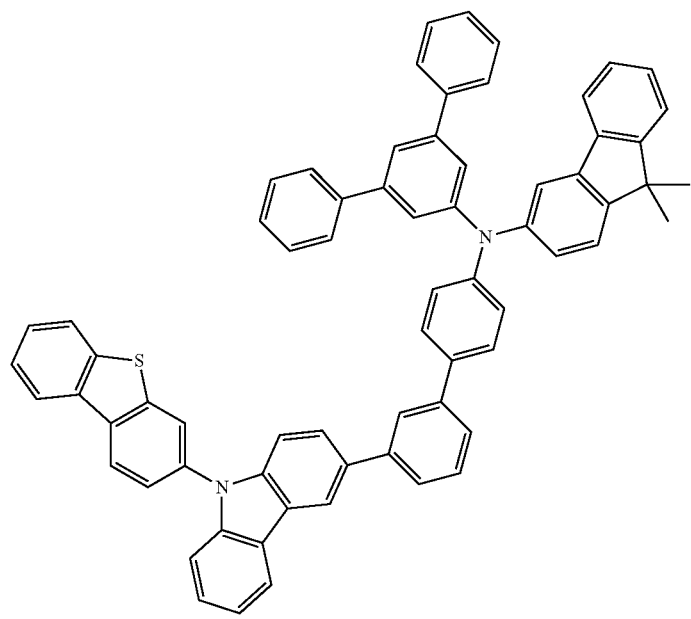
A214
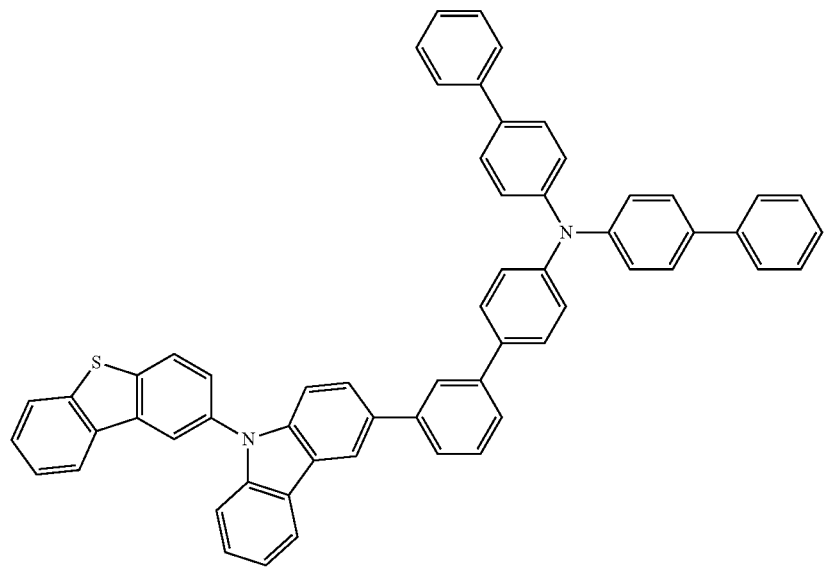
A215
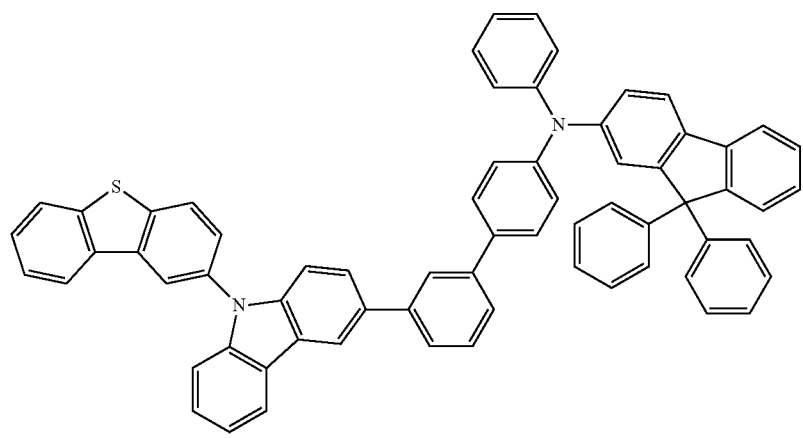
A216

-continued
A217
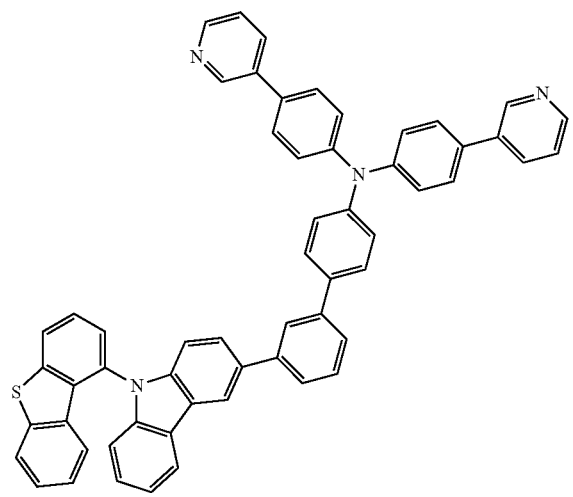
A218
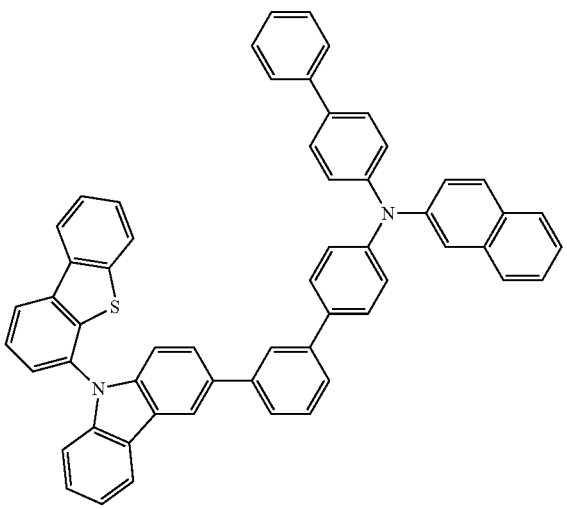
A219
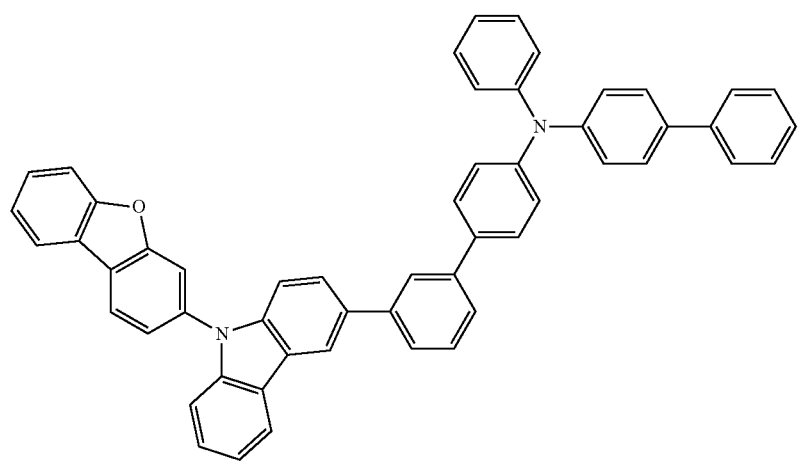
A220
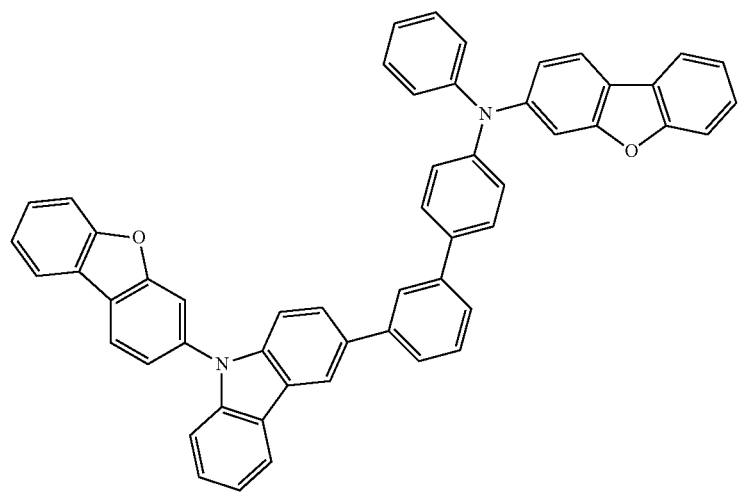

A221
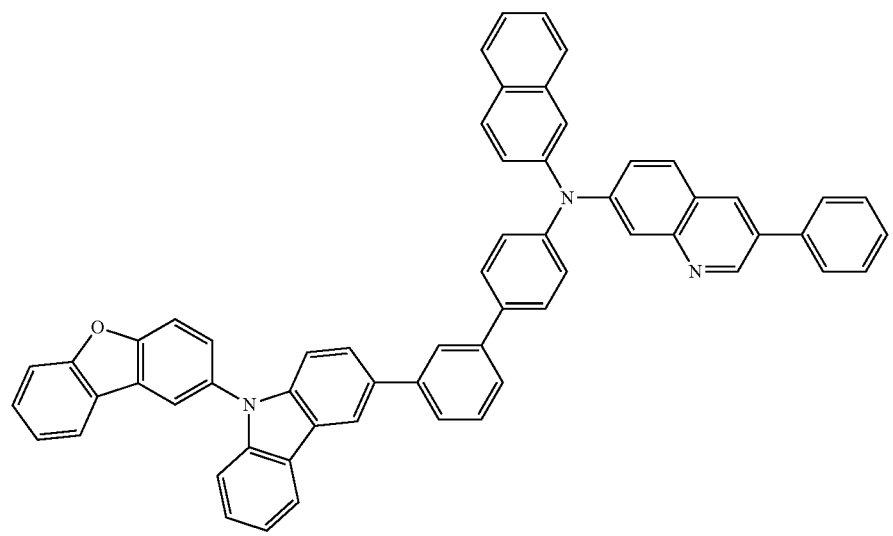
A222
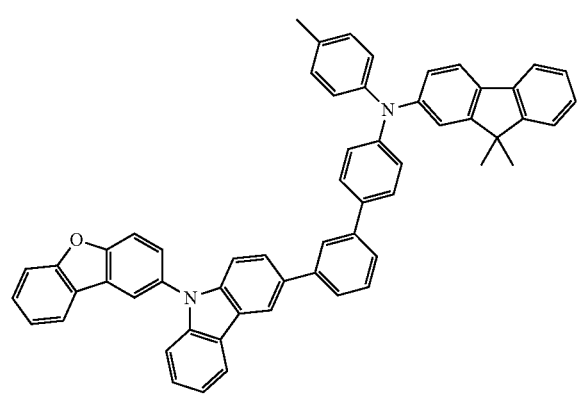
A223
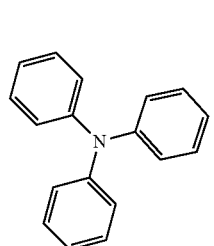
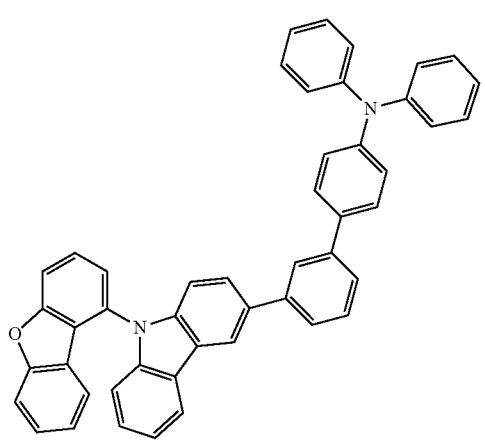
A224
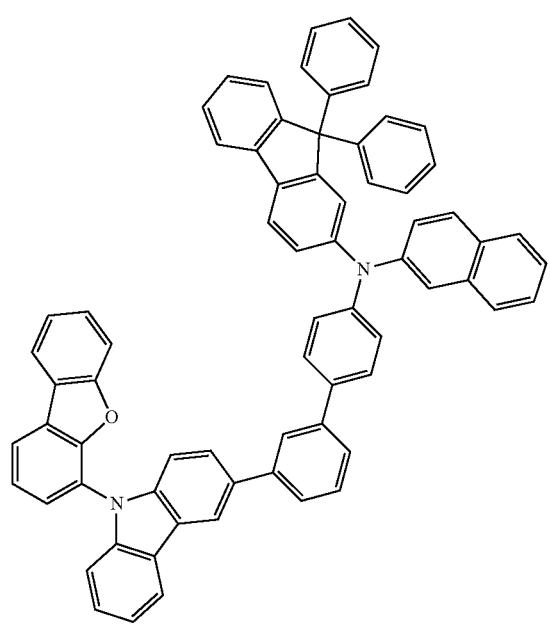
A225
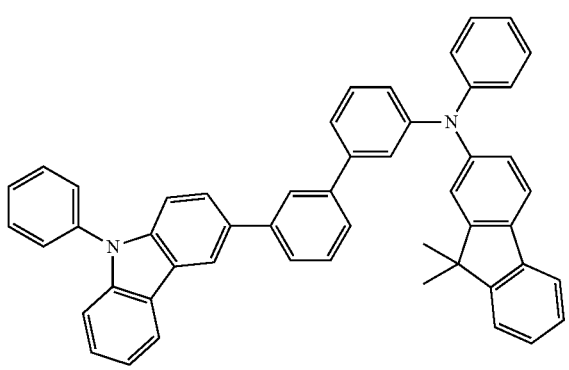

-continued
A226
A227
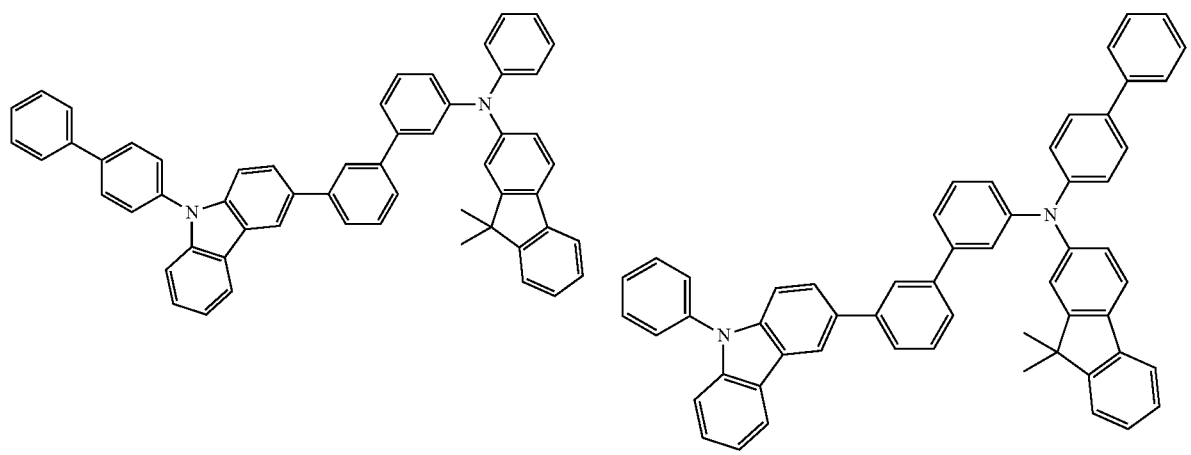
A228
A229
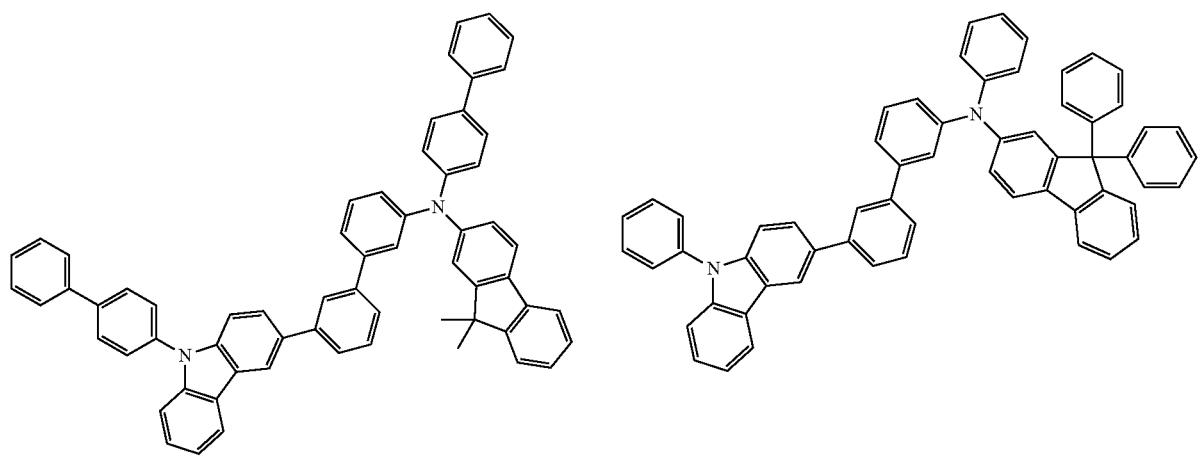
A230
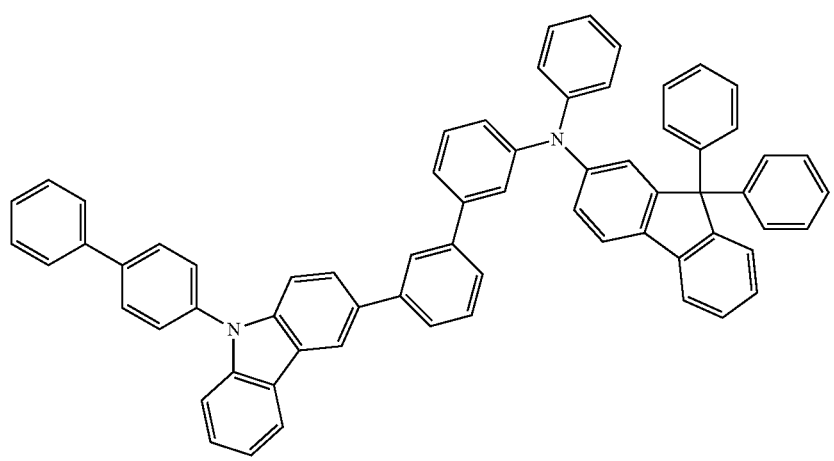

A231
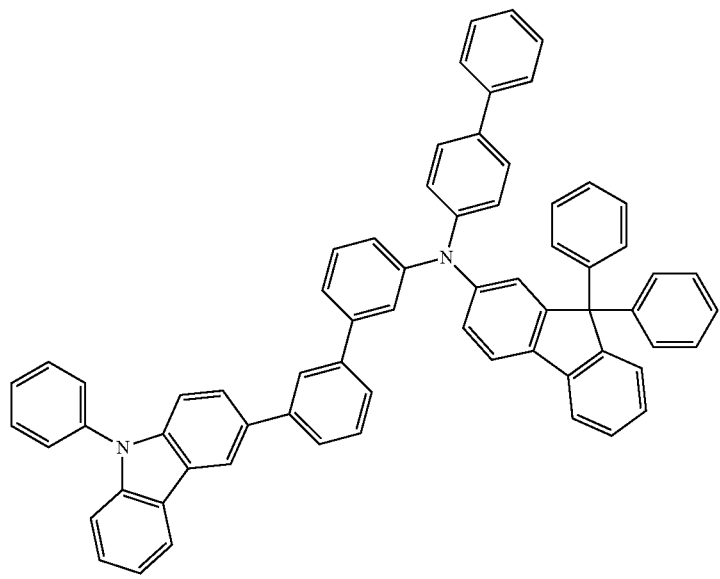
A232
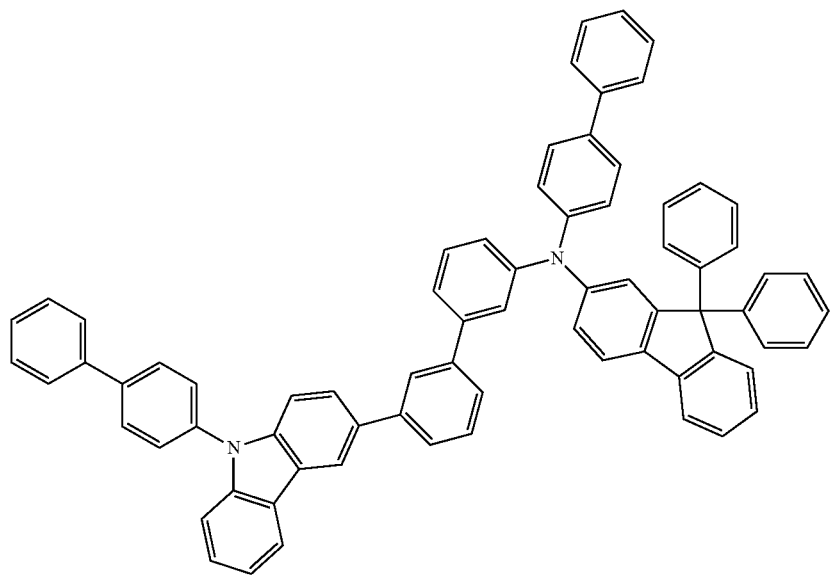
A233      A234
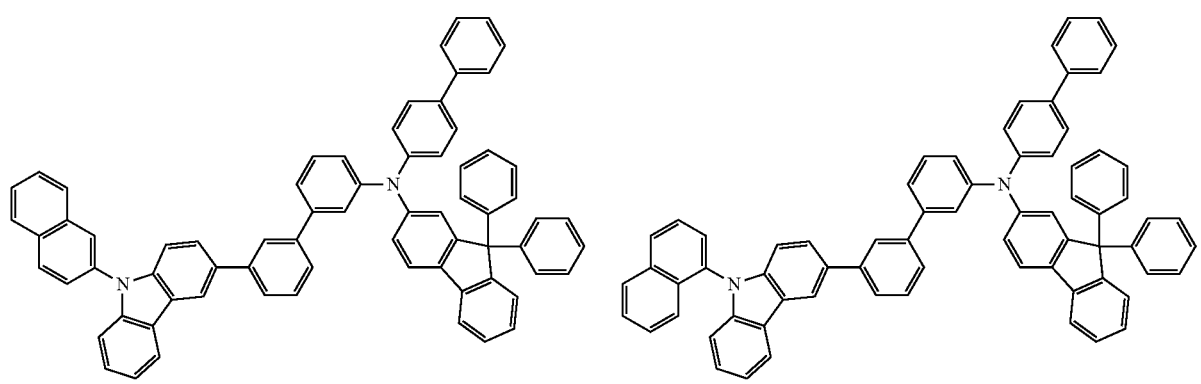

-continued
A235
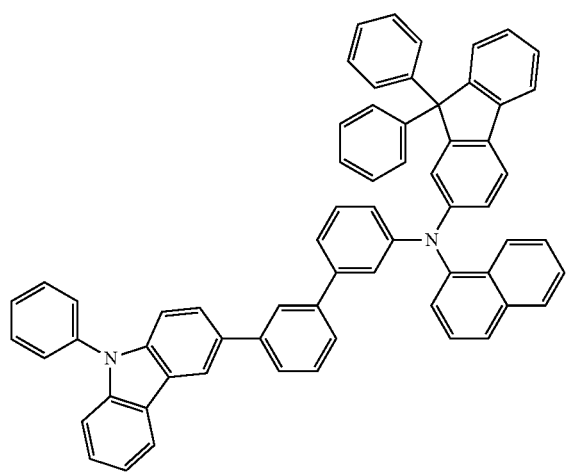
A236
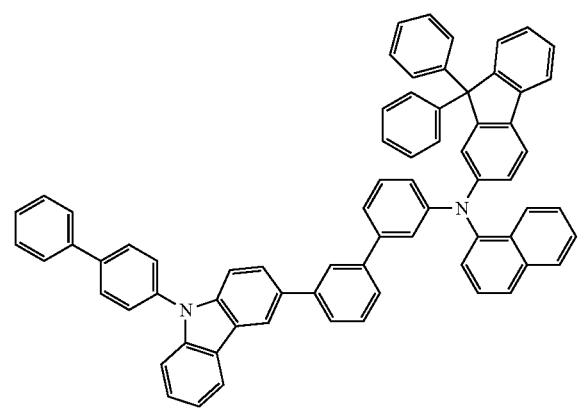
A237
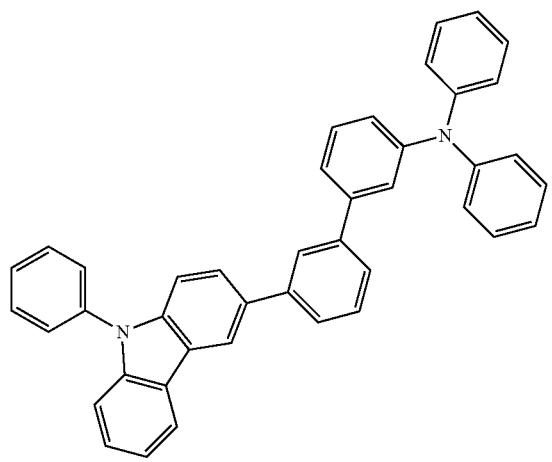
A238
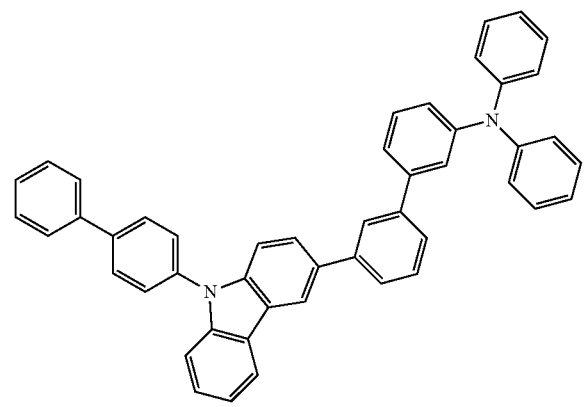
A239
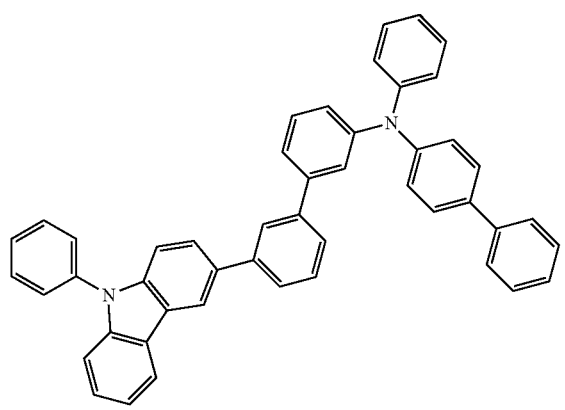
A240
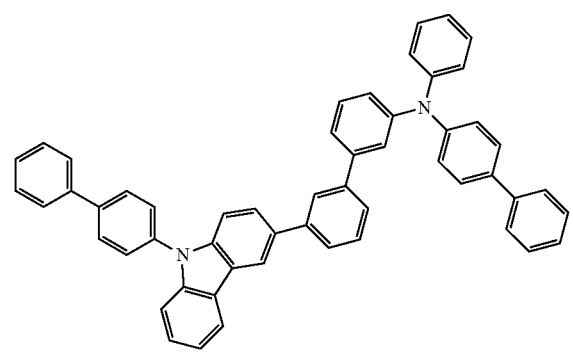

-continued
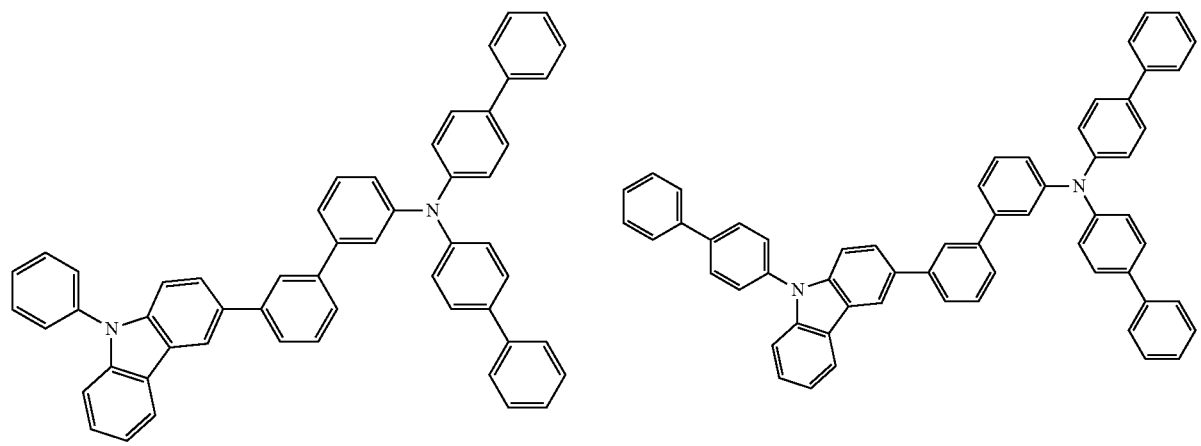
A241 A242
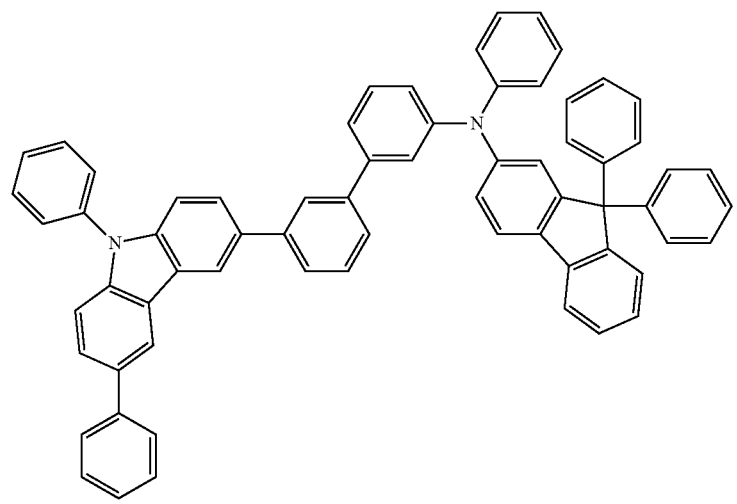
A243
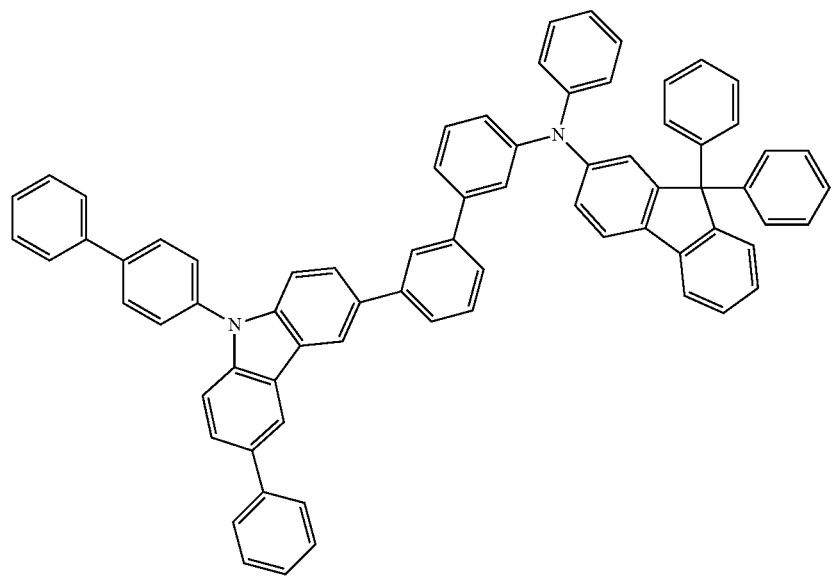
A244

A245
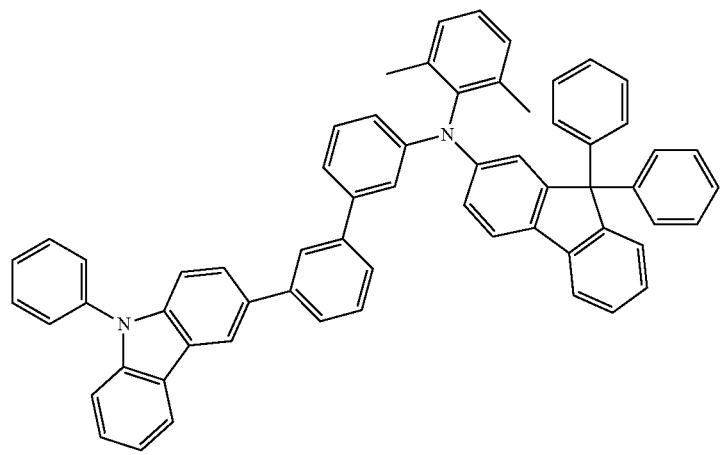
A246
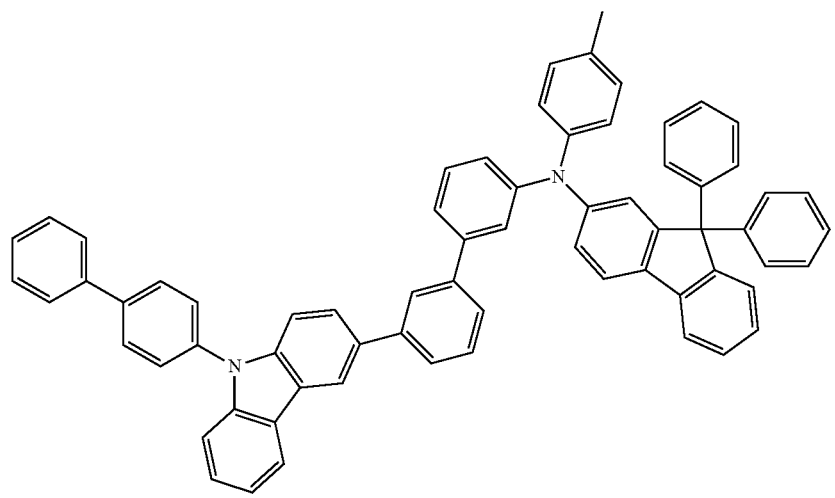
A247
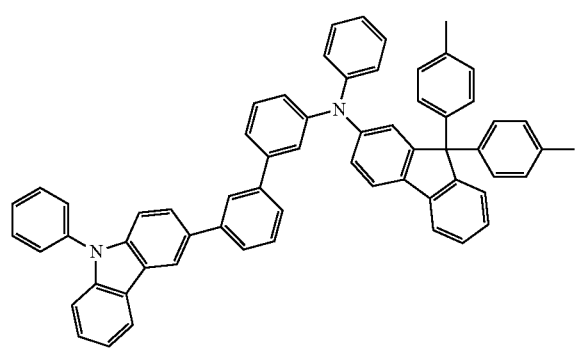
A248
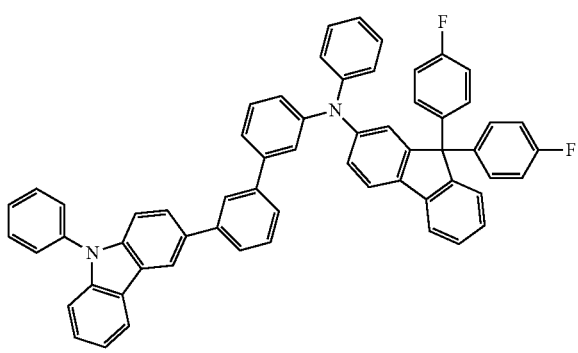

-continued
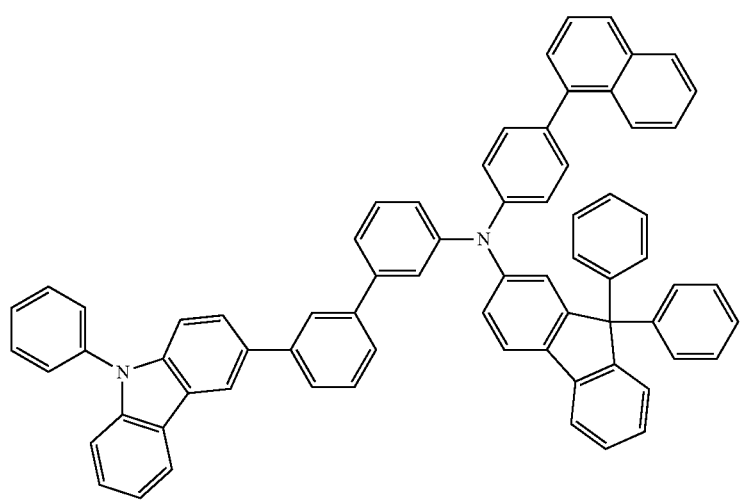
A249
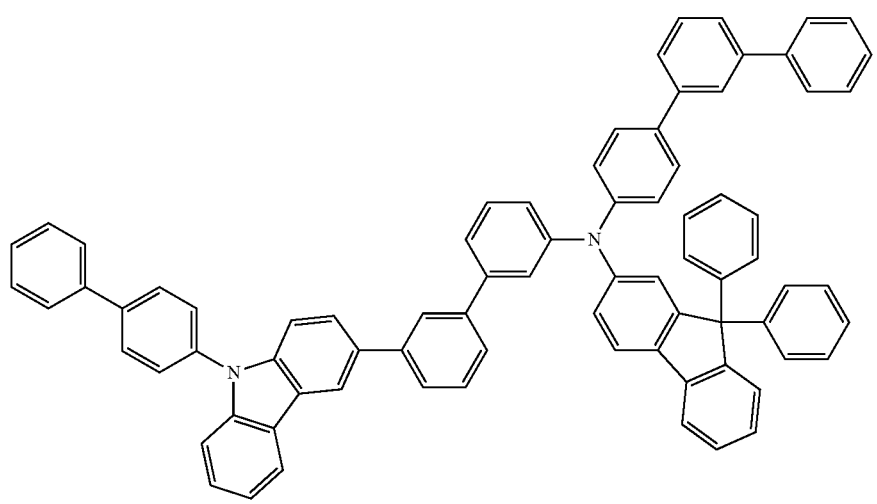
A250
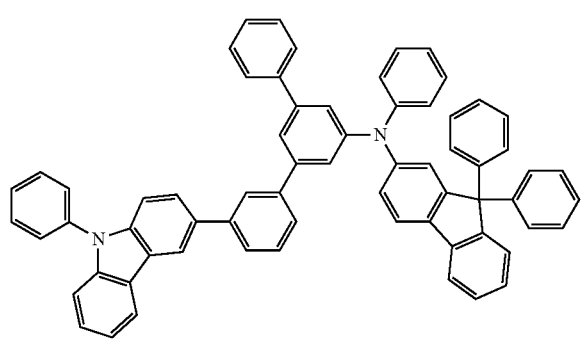
A251
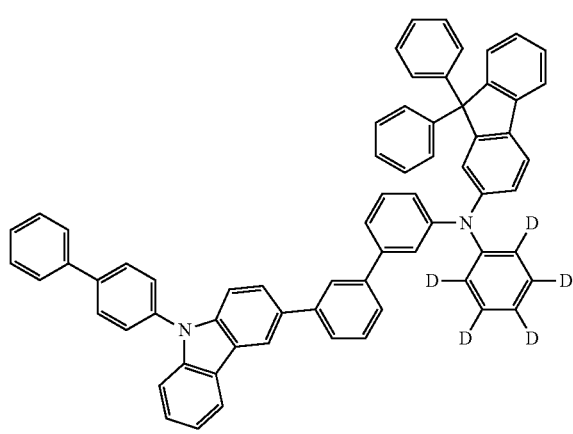
A252

-continued
A253
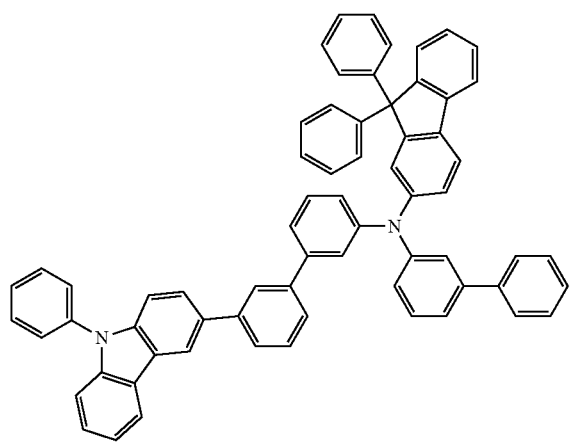
A254
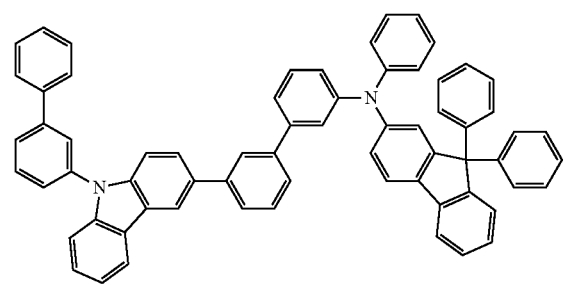
A255
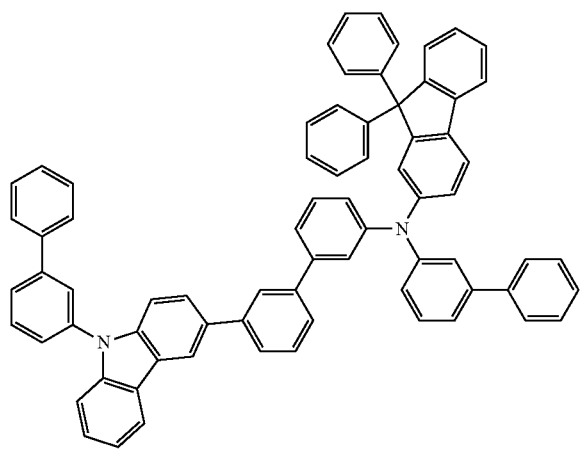
A256
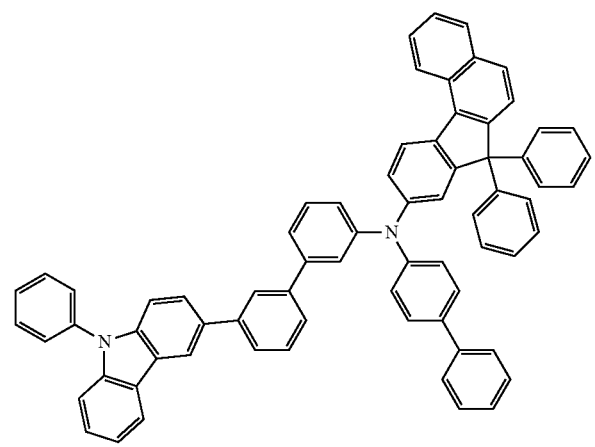
A257
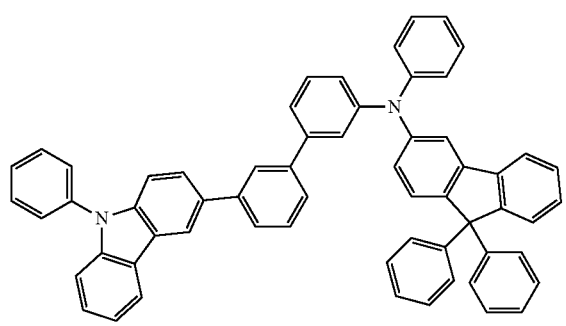
A258
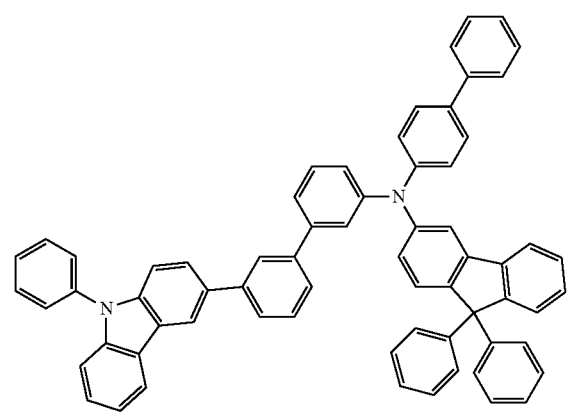

-continued
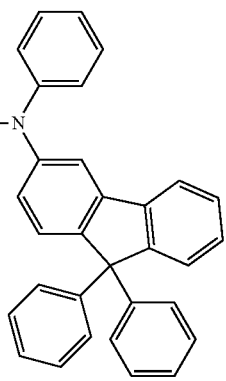
A259
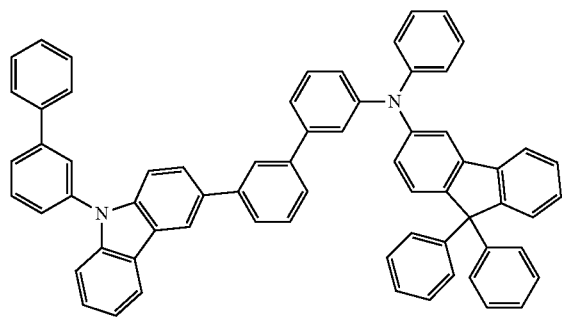
A260
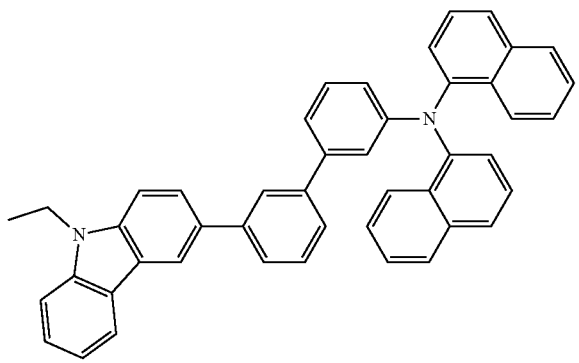
A261
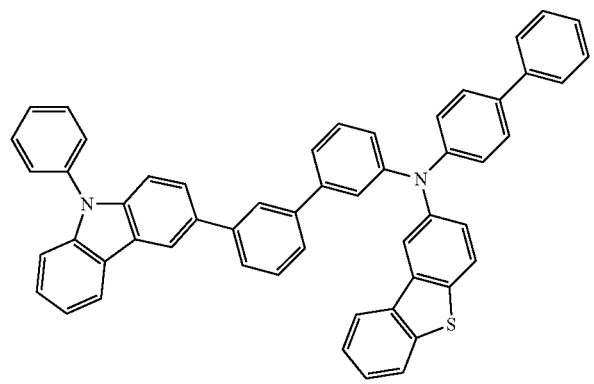
A262
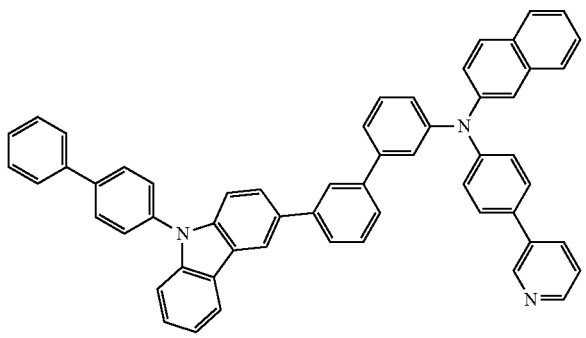
A263
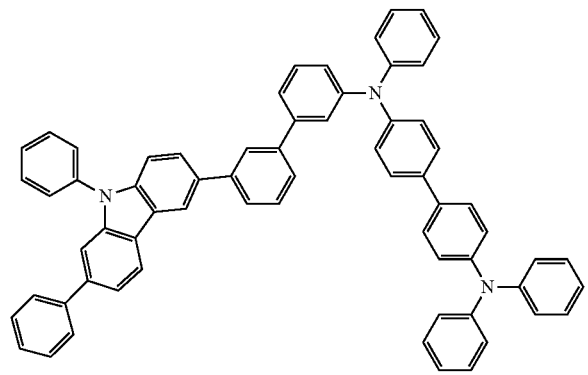
A264
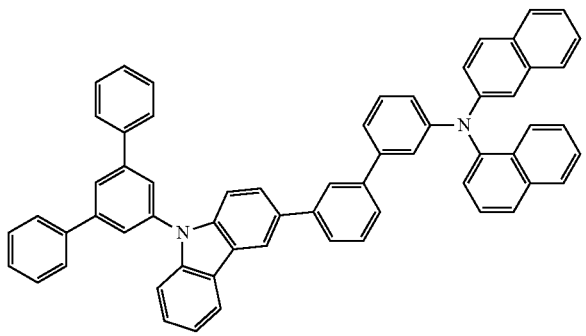
A265

-continued
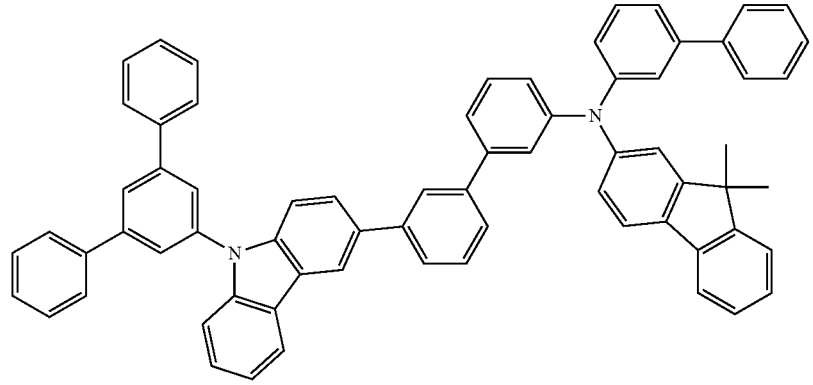
A266
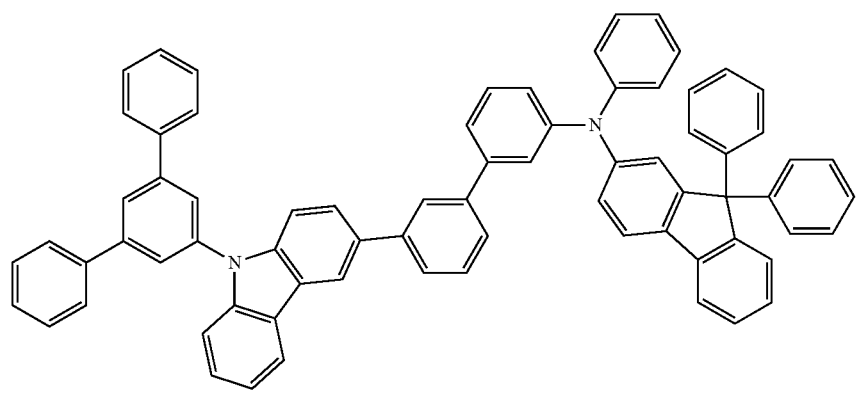
A267
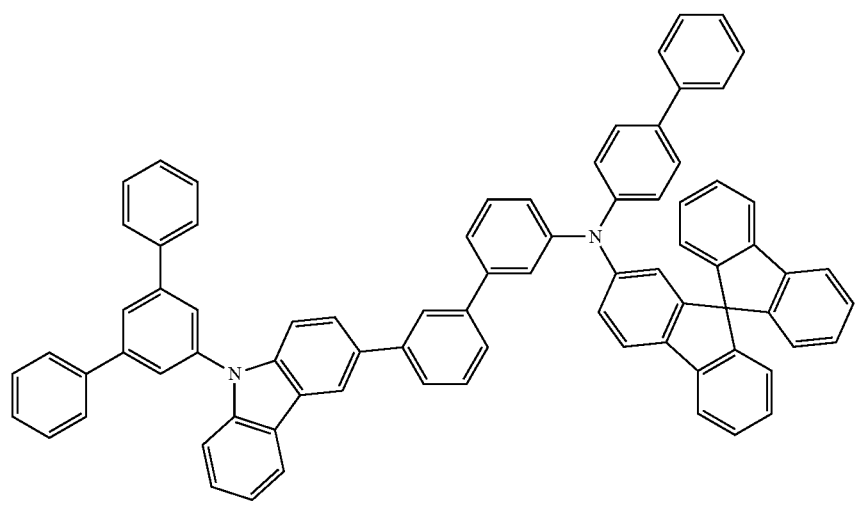
A268

-continued
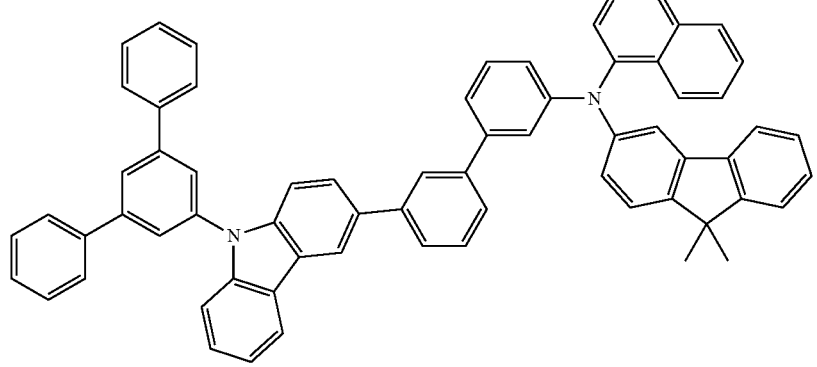
A269
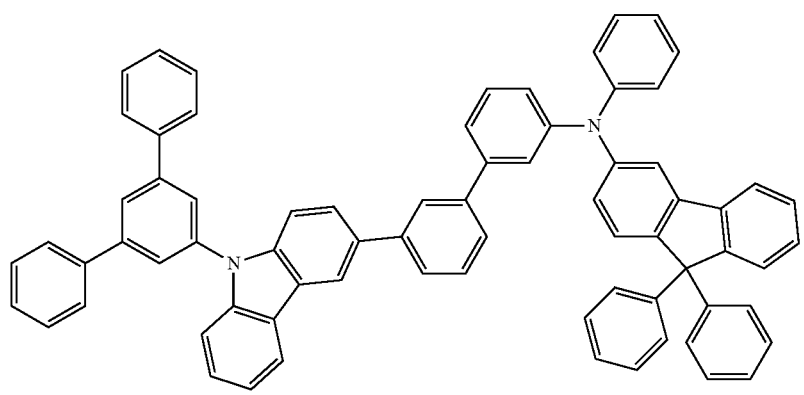
A270
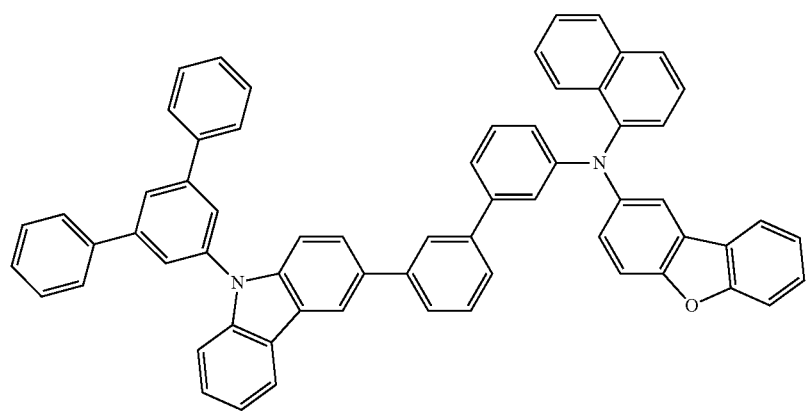
A271
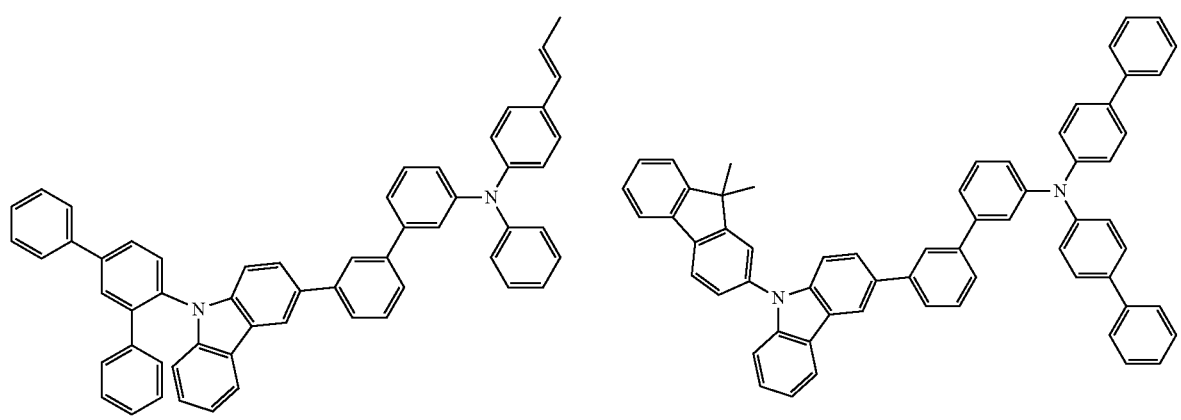
A272 A273

-continued
A274
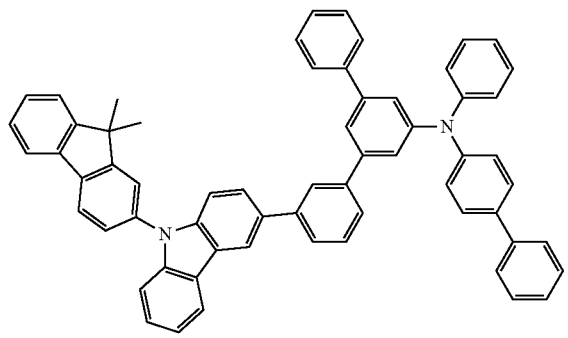
A275
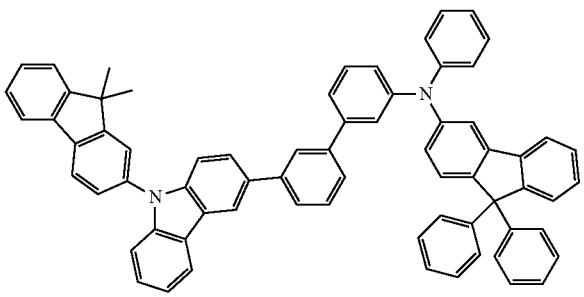
A276
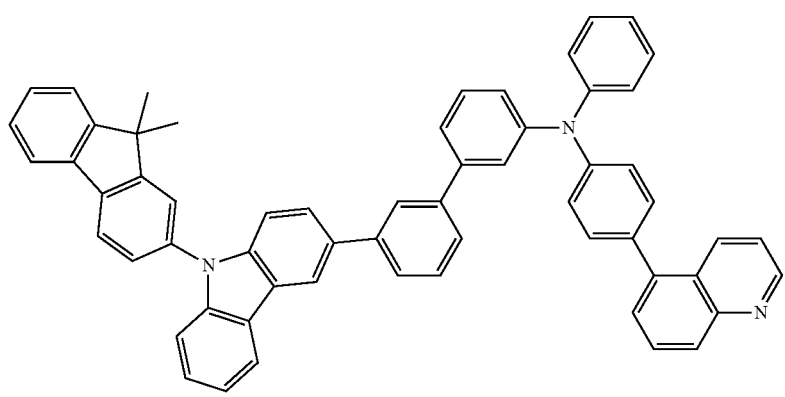
A277
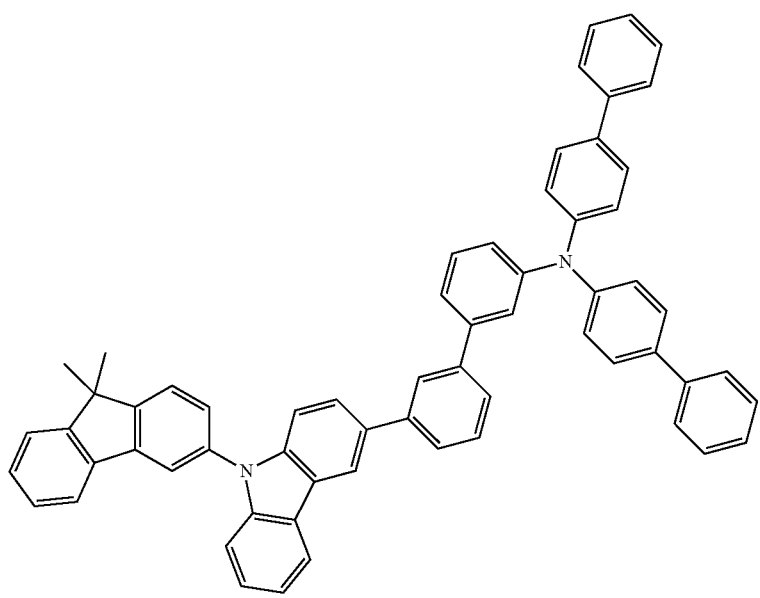

-continued
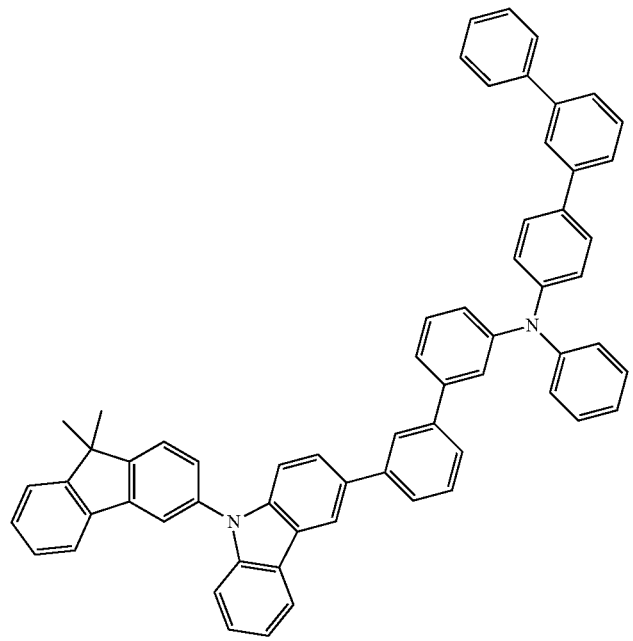
A278
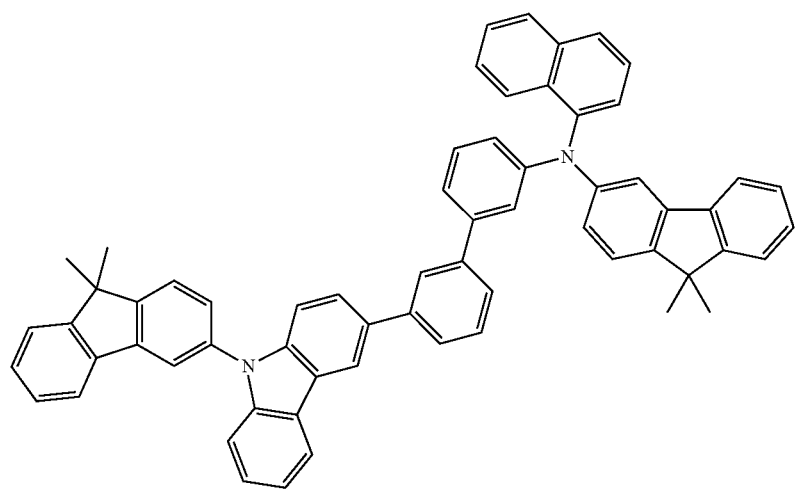
A279
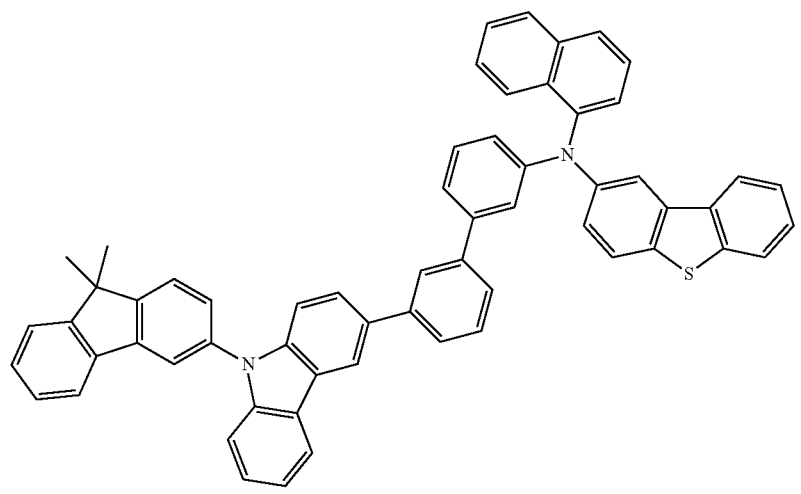
A280

-continued
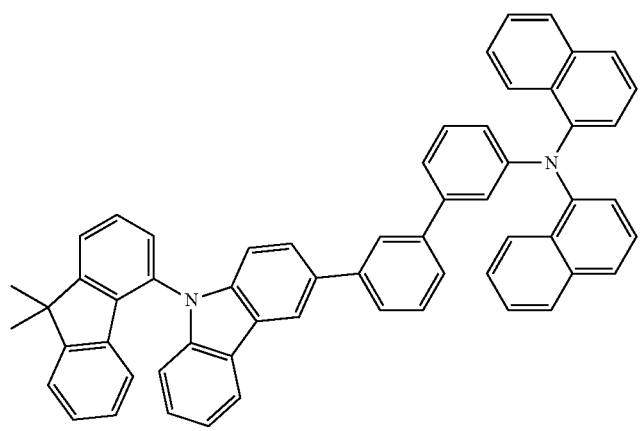
A281
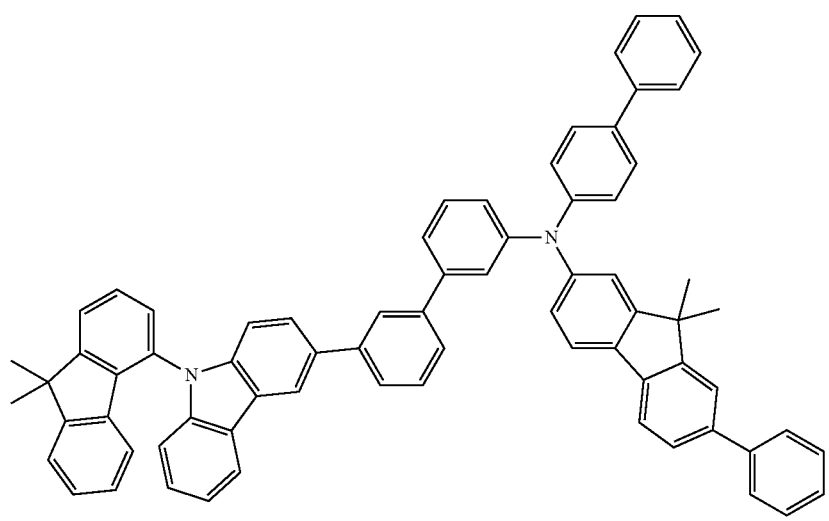
A282
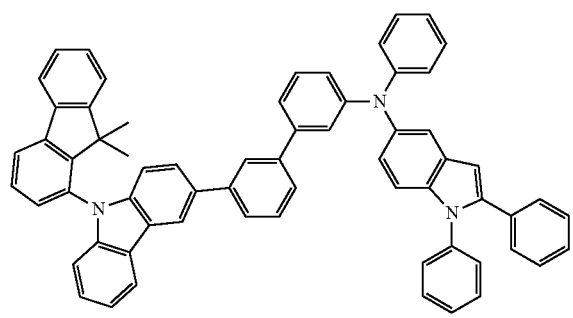
A283
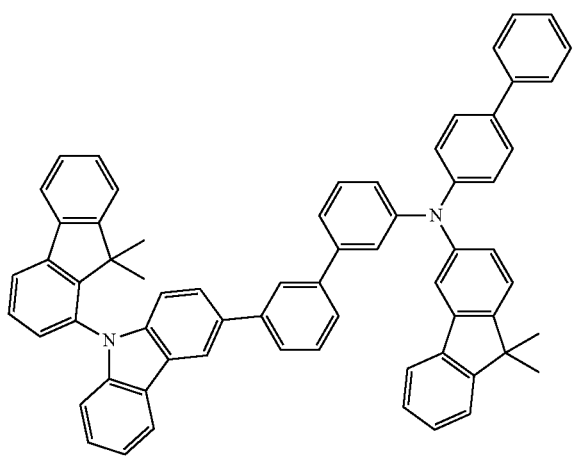
A284

-continued
A285
A286
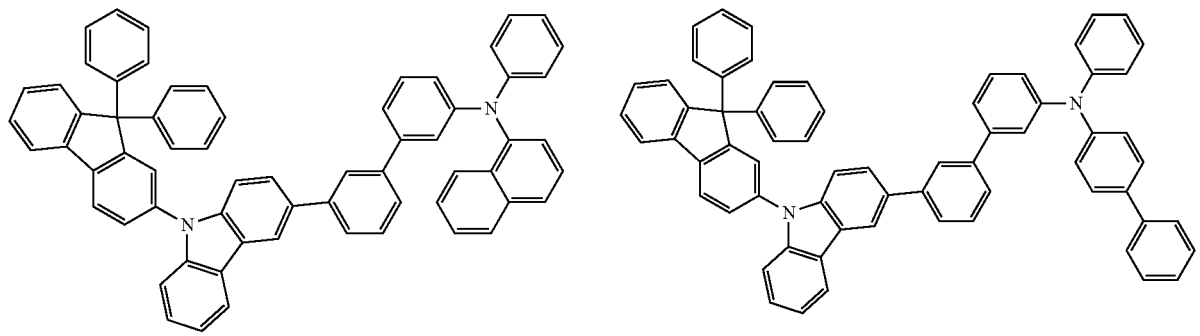
A287
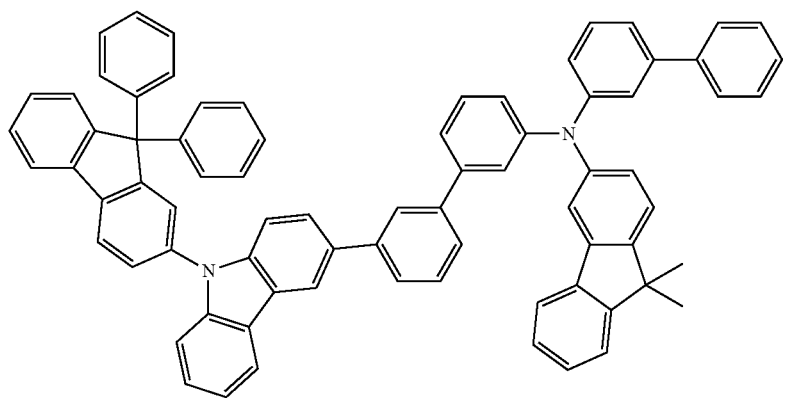
A288
A289
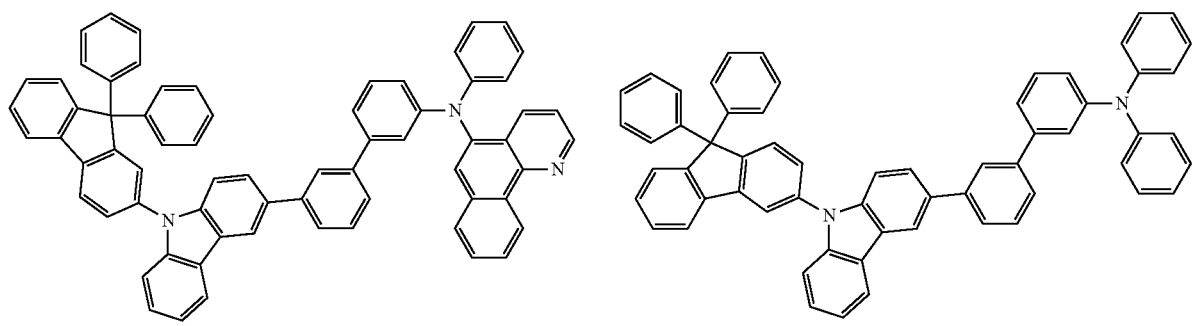
A290
A291
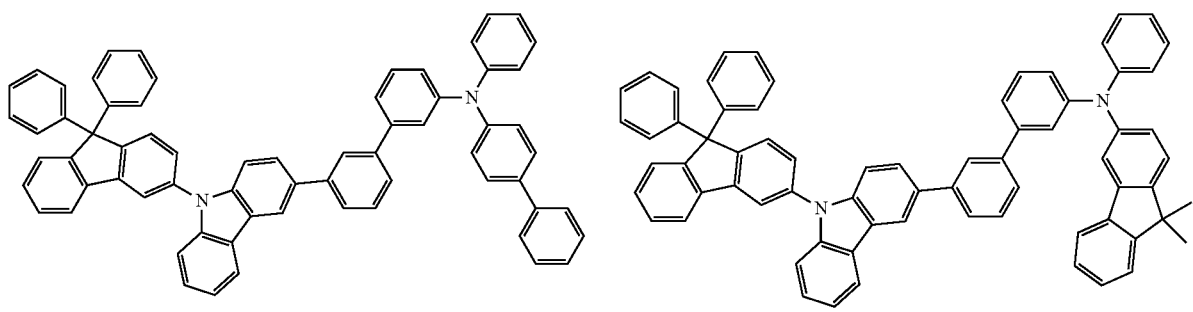

A292
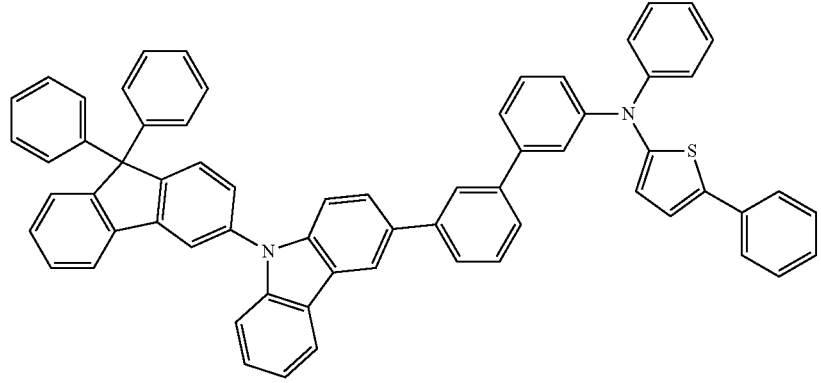
A293
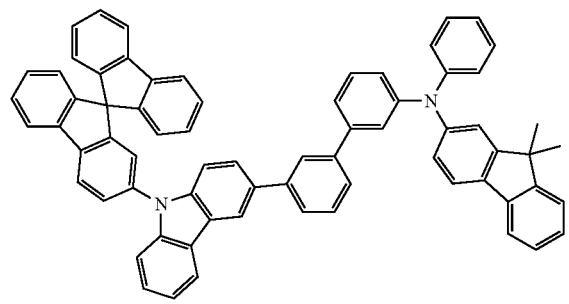
A294
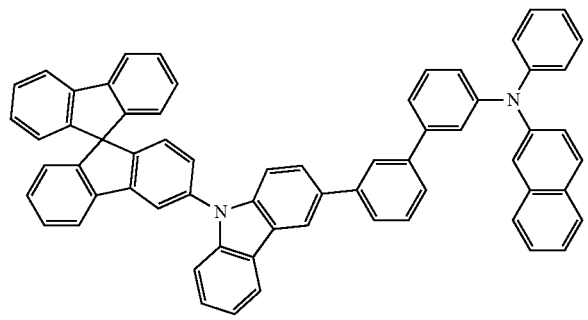
A295
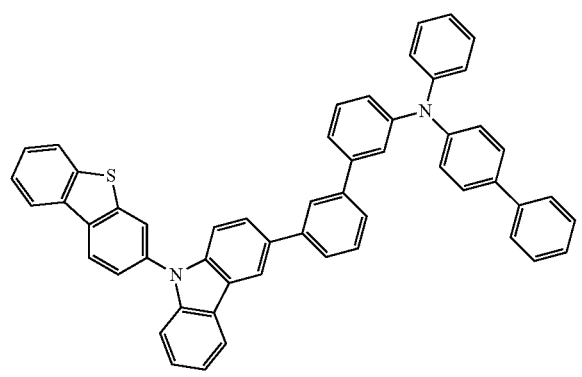
A296
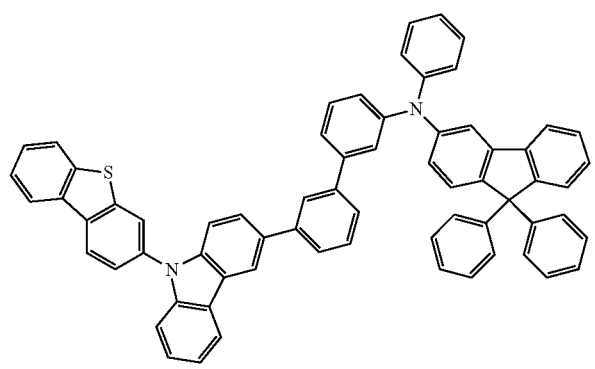
A297
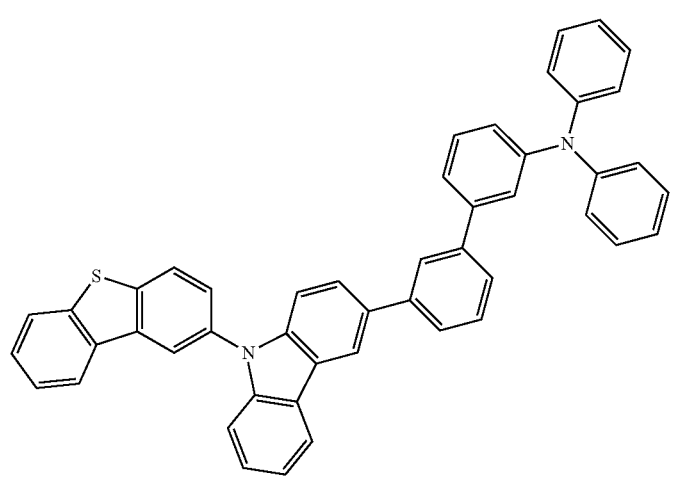

-continued
A298
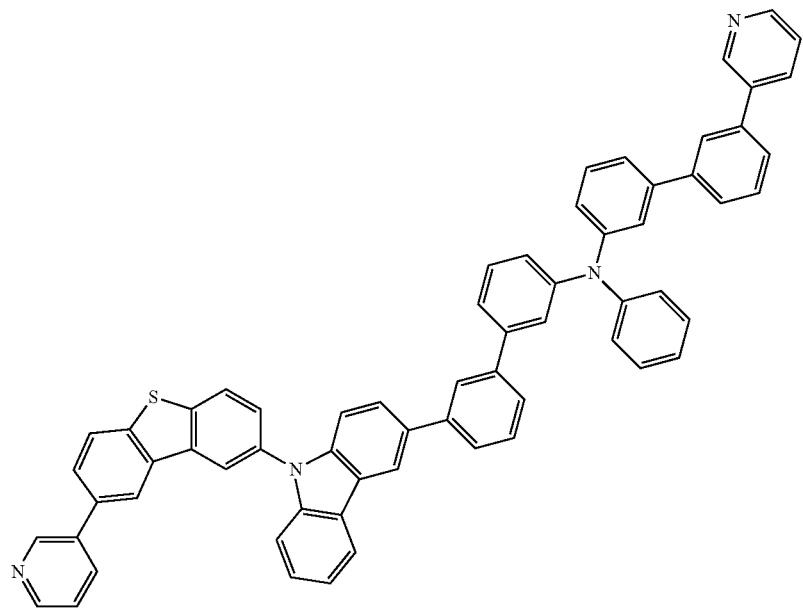
A299 A300
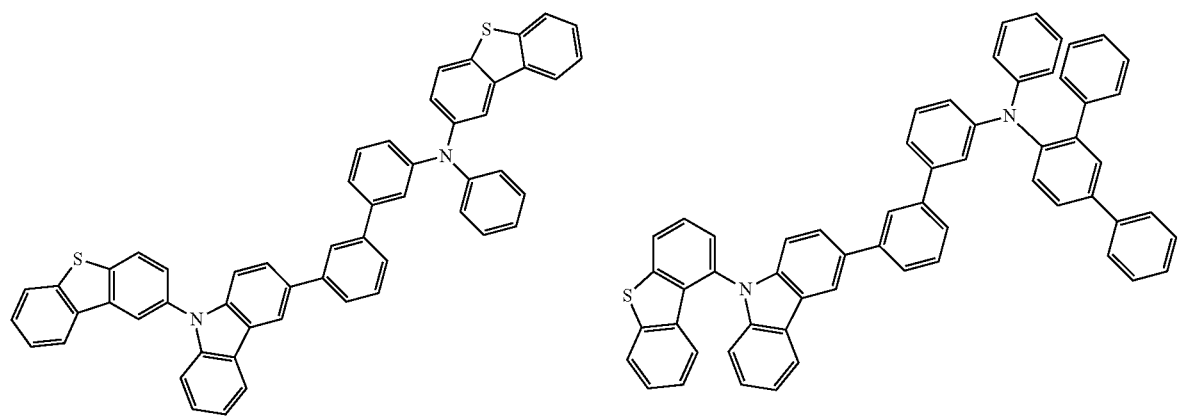
A301 A302
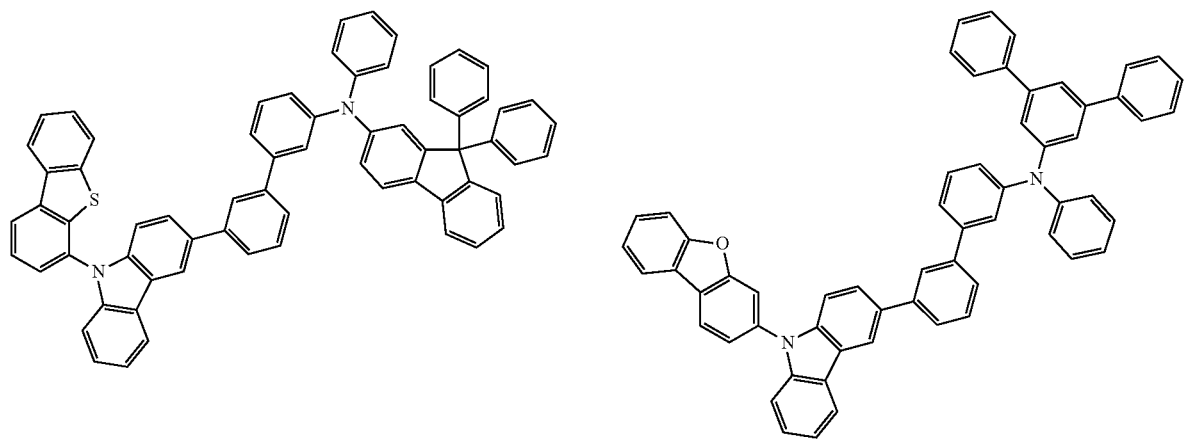

-continued
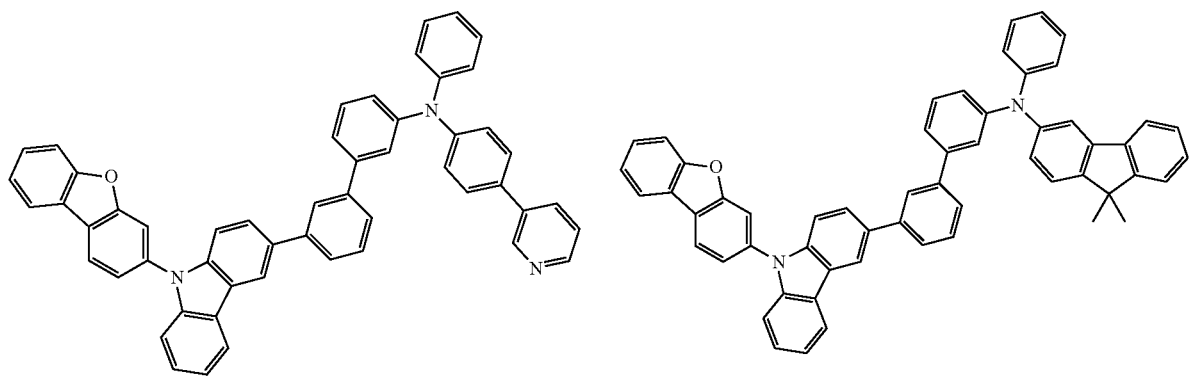
A303
A304
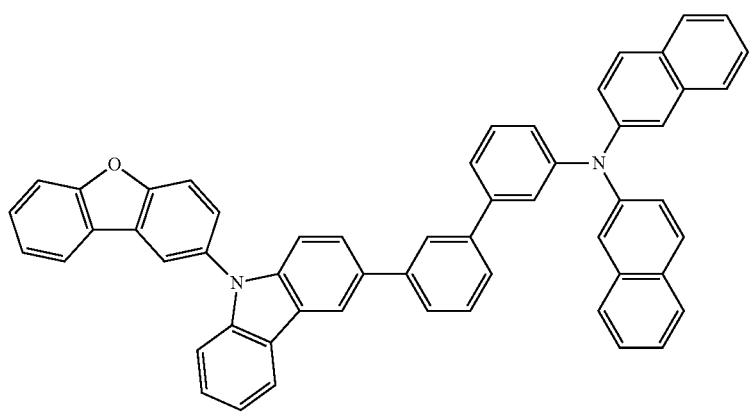
A305
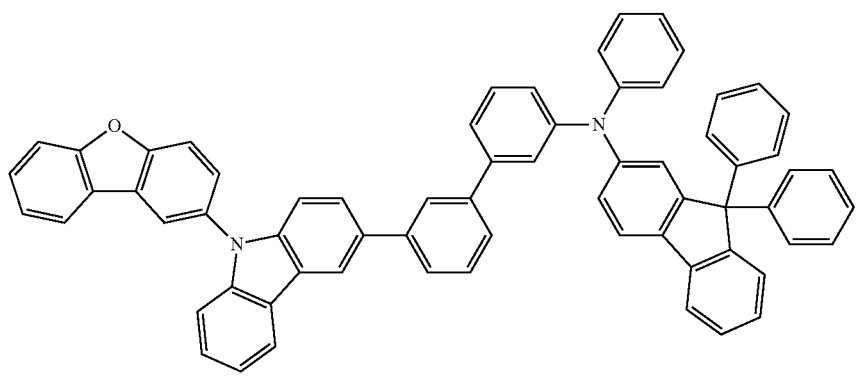
A306

-continued
A307
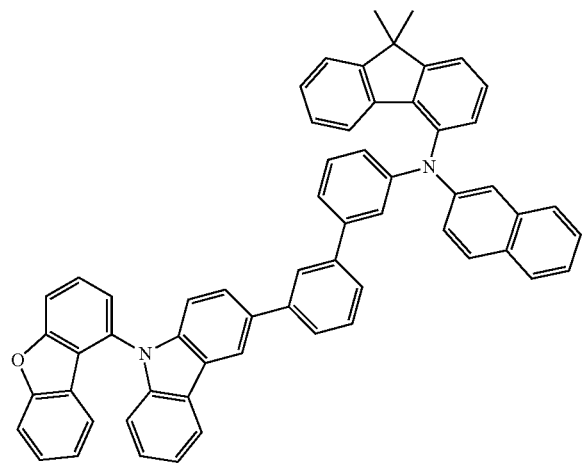
A308
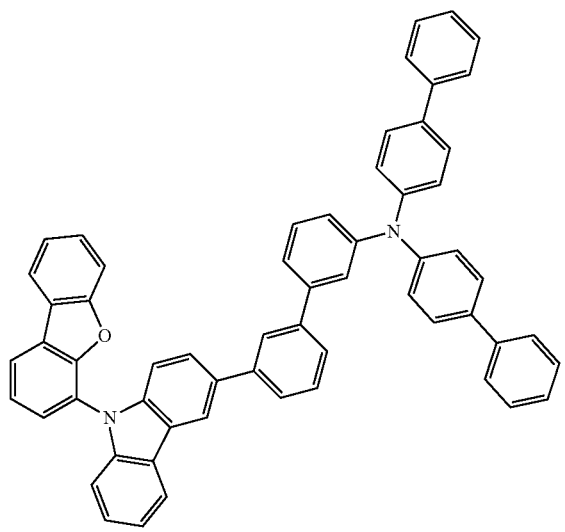
A309
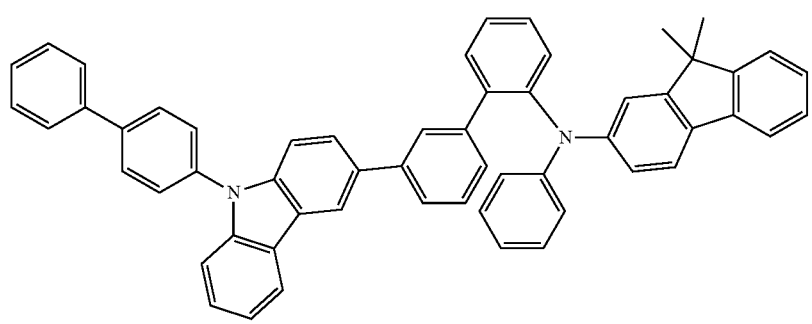
A310
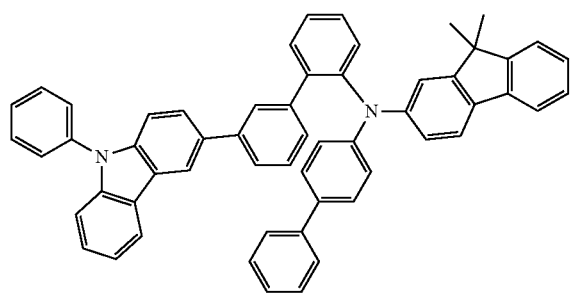
A311
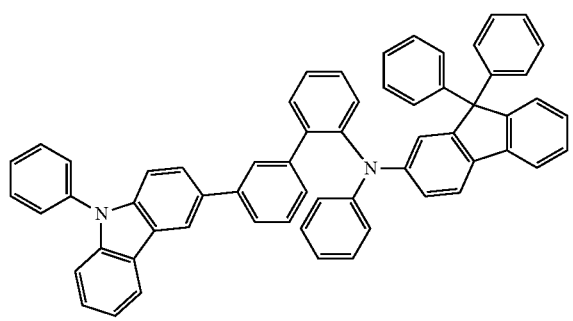
A312
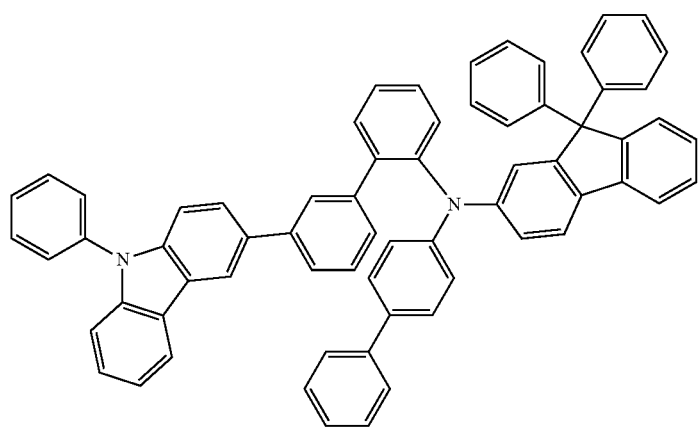

-continued
A313
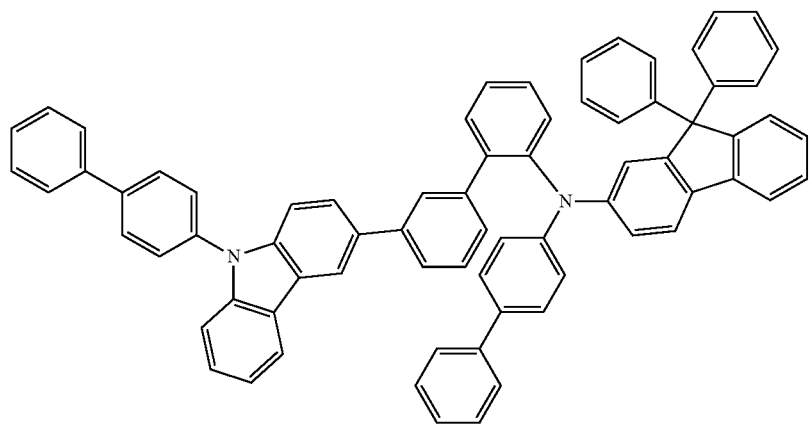
A314
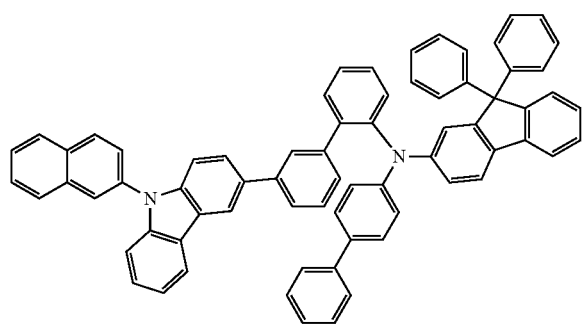
A315
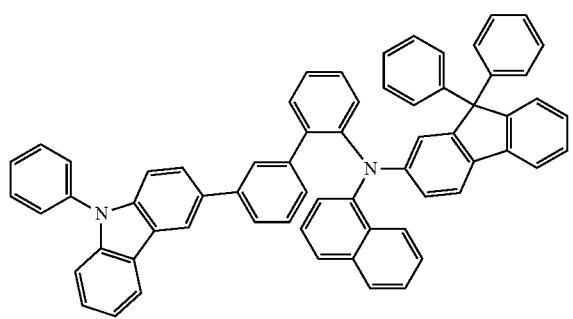
A316
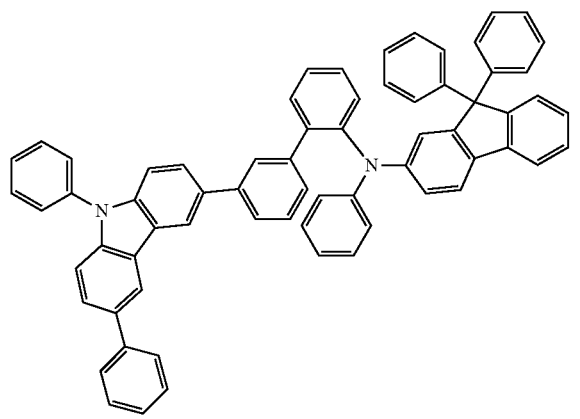
A317
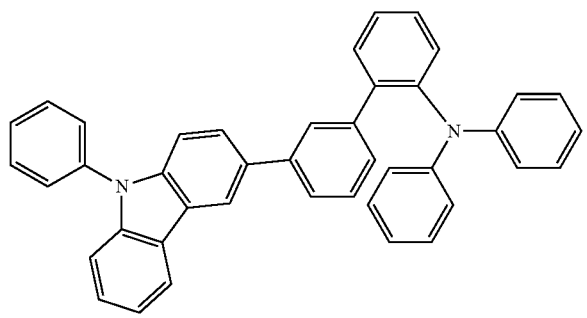
A318
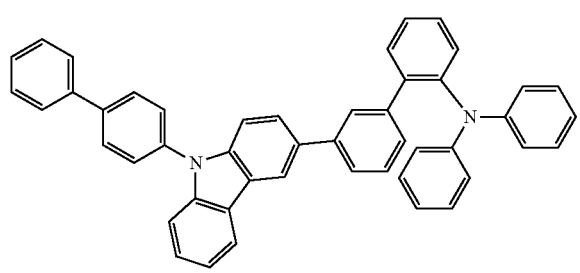
A319
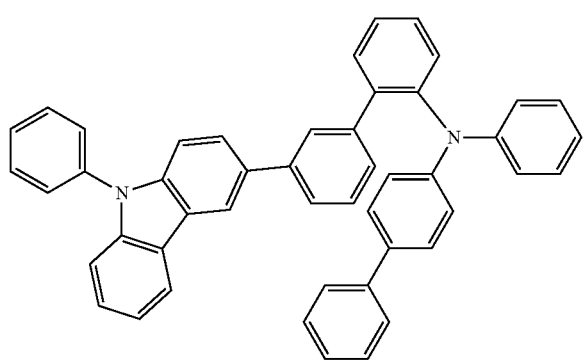

-continued
A320
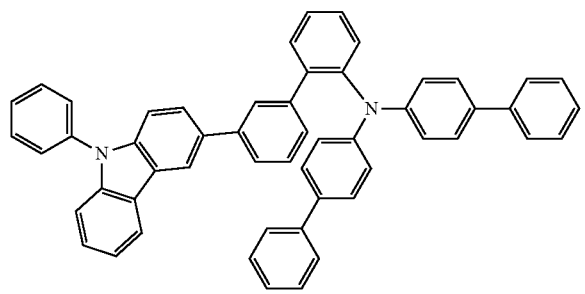
A321
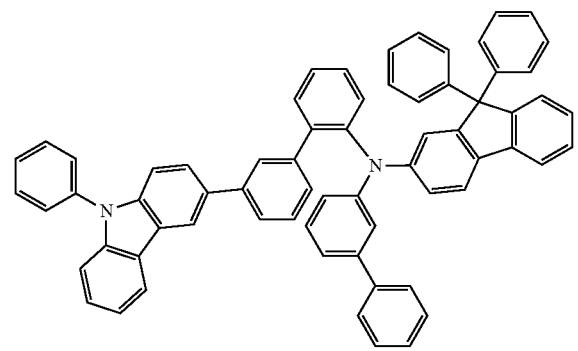
A322
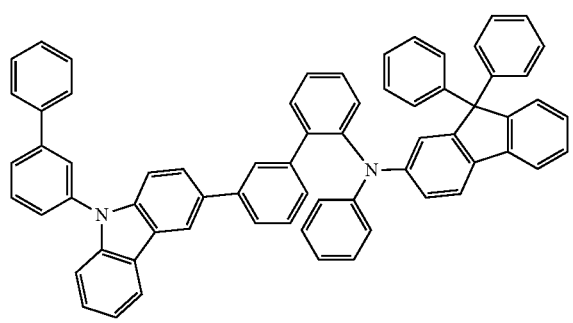
A323
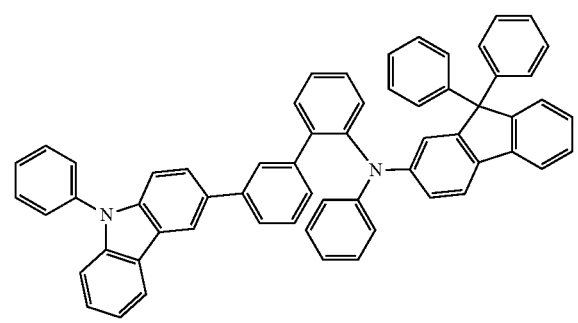
A324
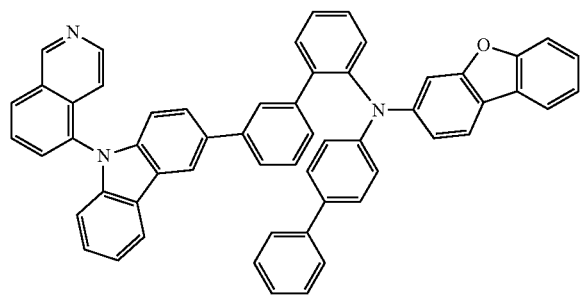
A325
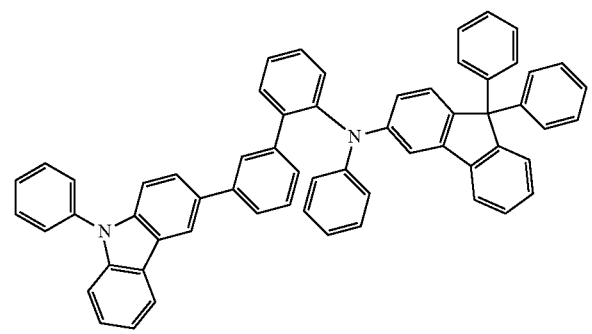
A326
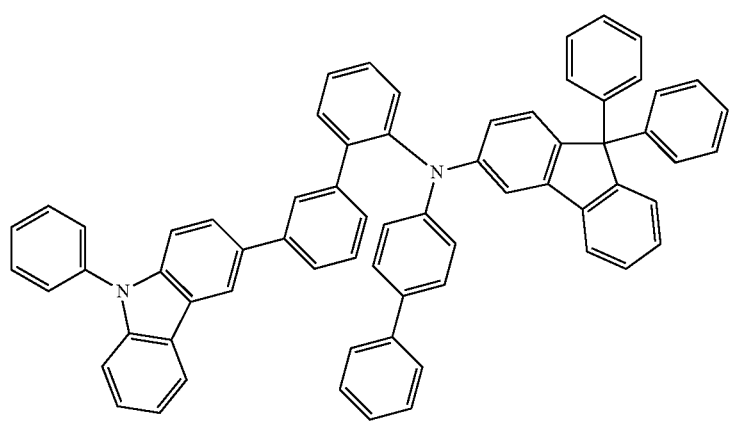

A327
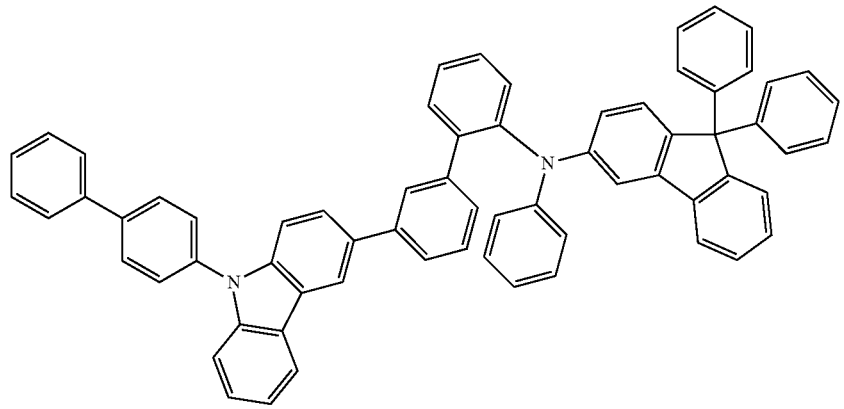
A328 A329
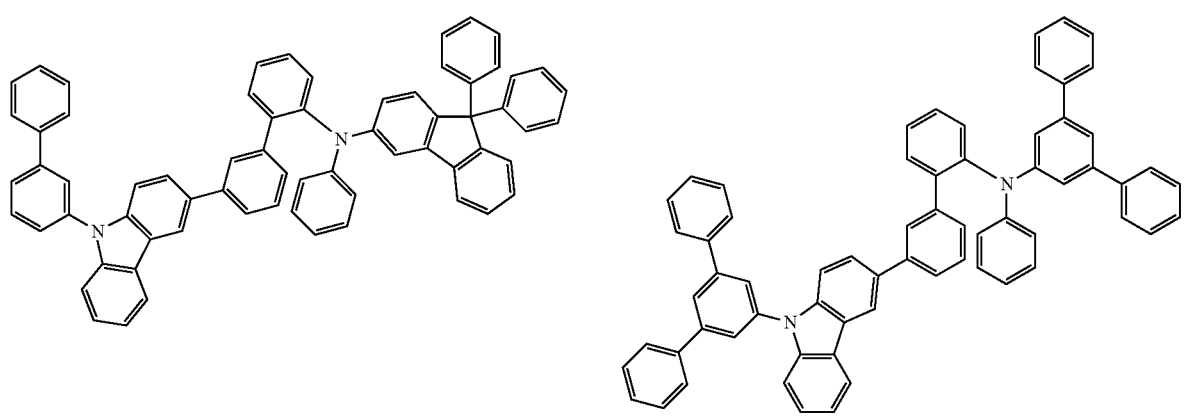
A330 A331
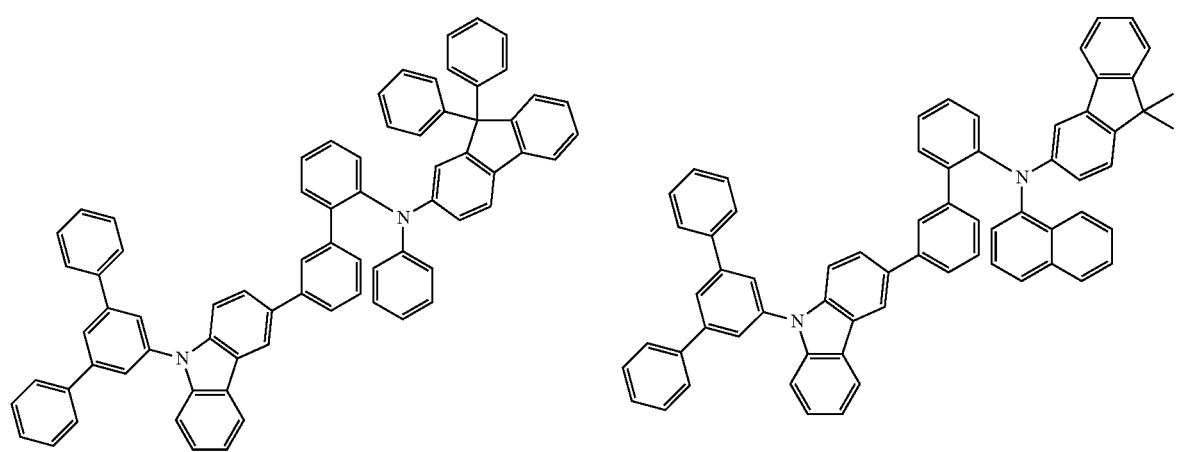

-continued
A332
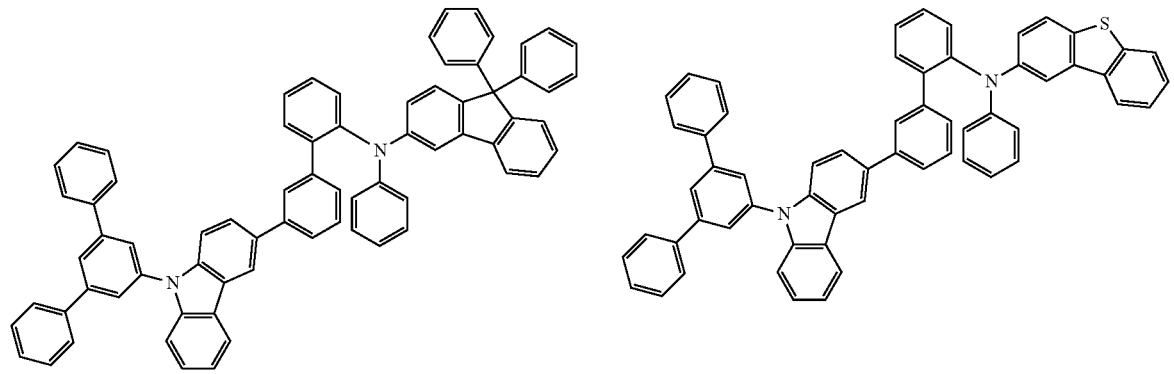
A333
A334
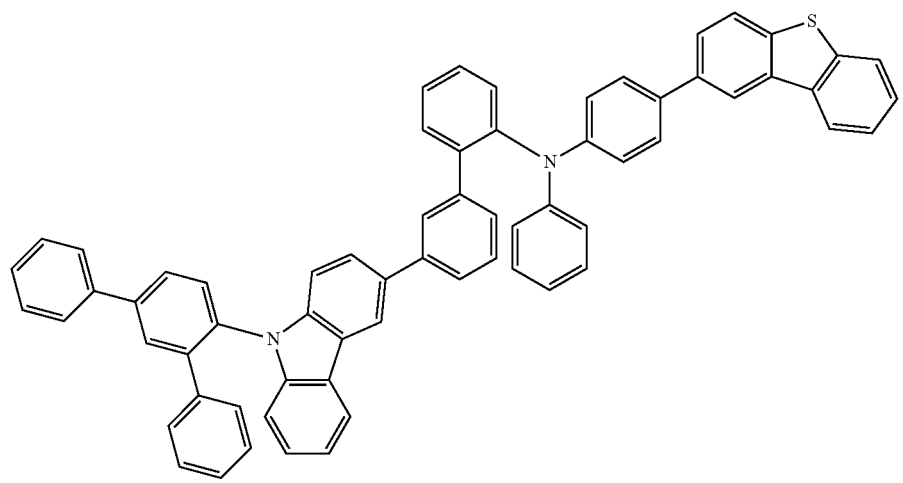
A335
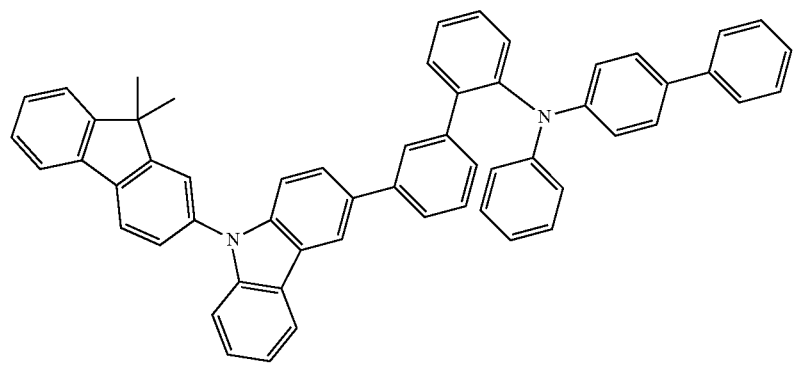
A336
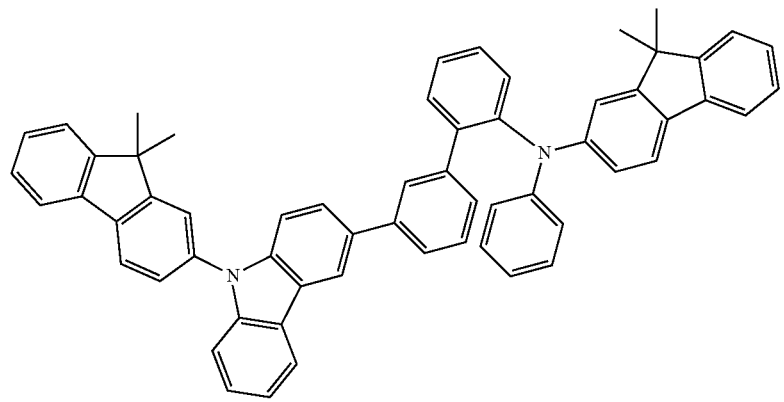

-continued
A337
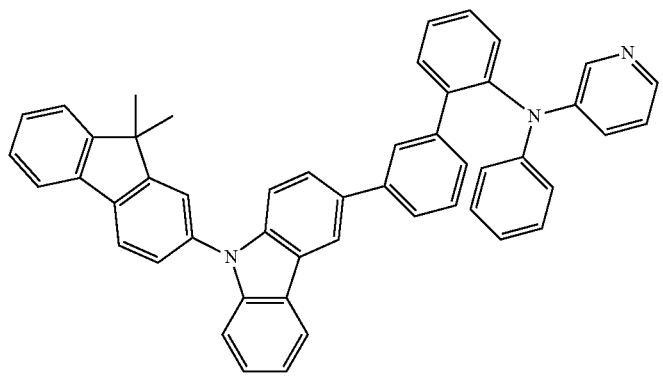
A338
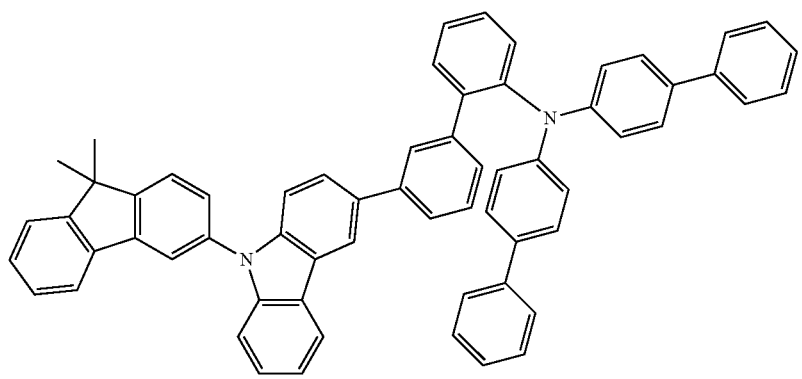
A339
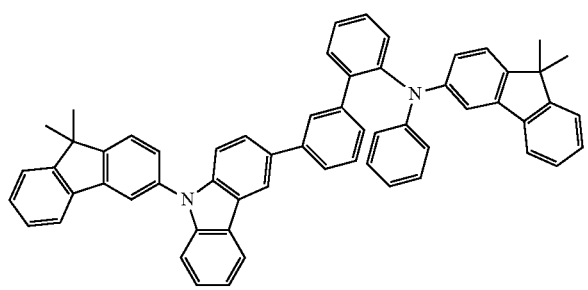
A340
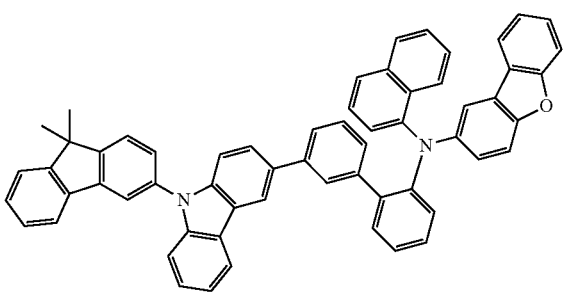
A341
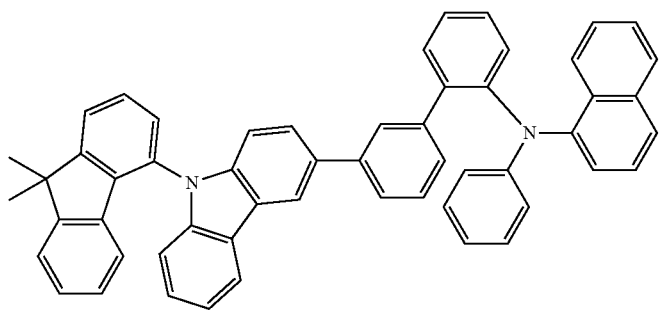

-continued
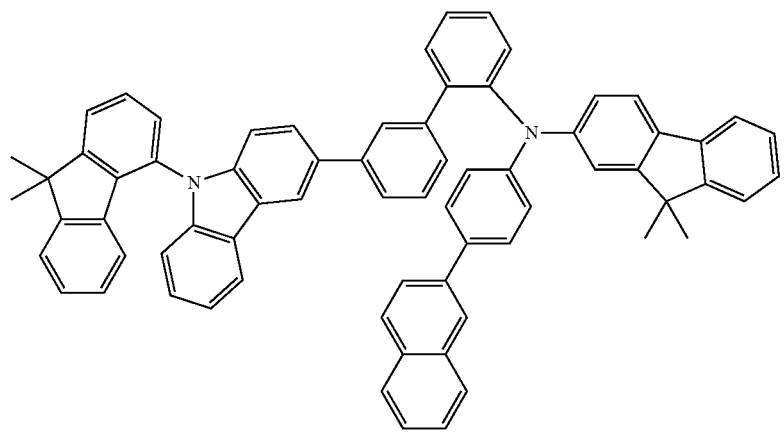
A342
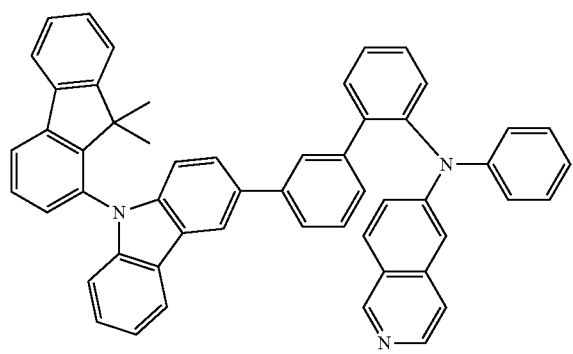
A343
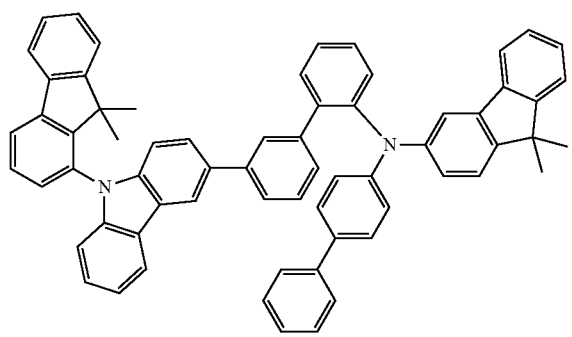
A344
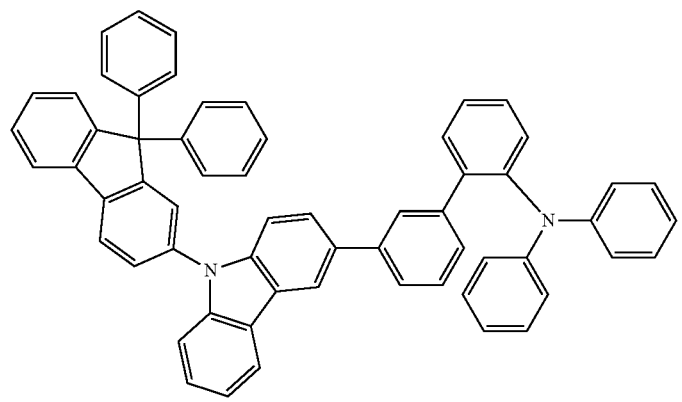
A345
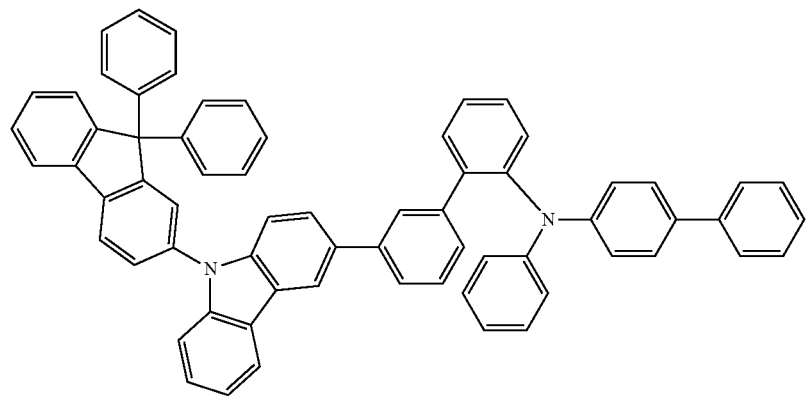
A346

-continued
A347
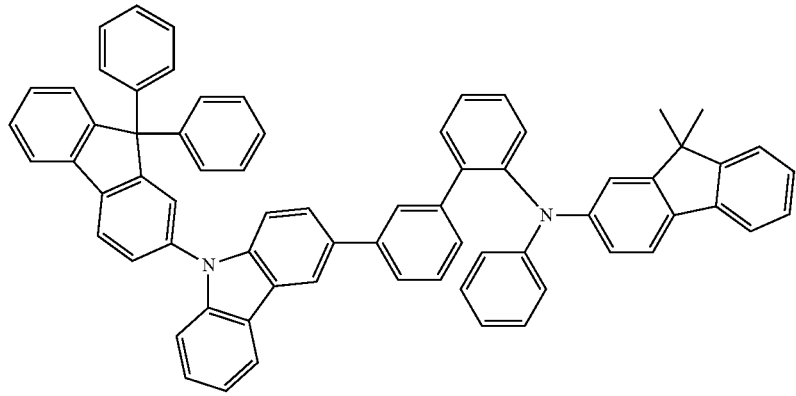
A348
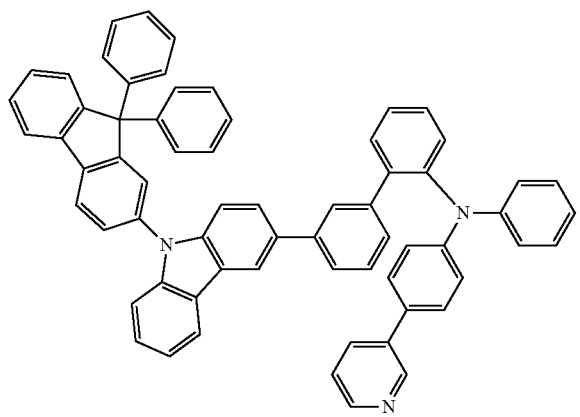
A349
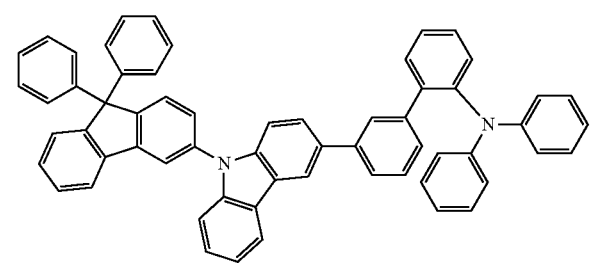
A350
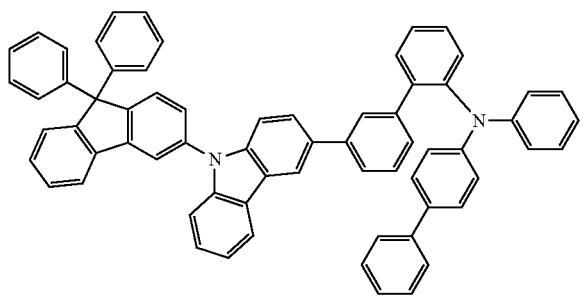
A351
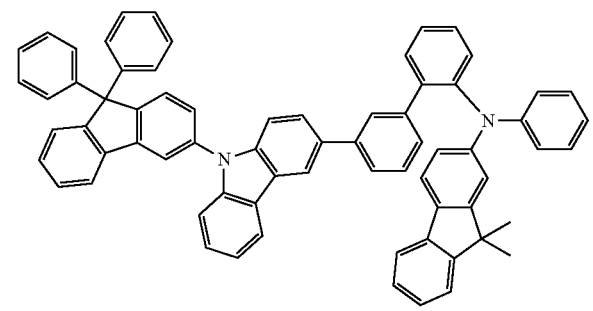
A352
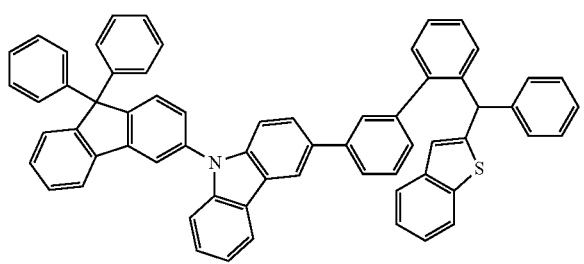
A353
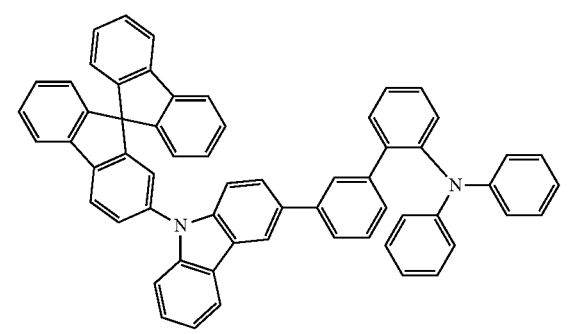

-continued
A354
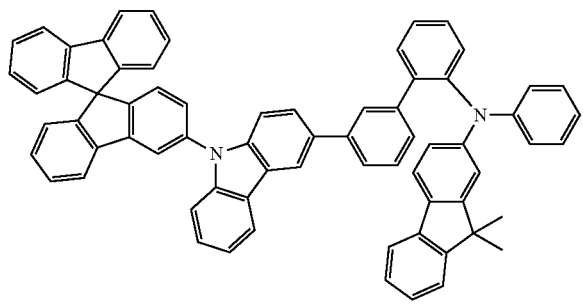
A355
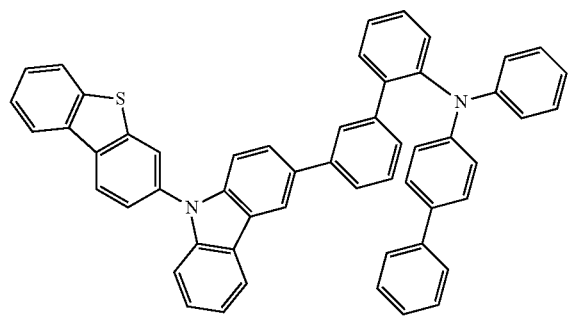
A356
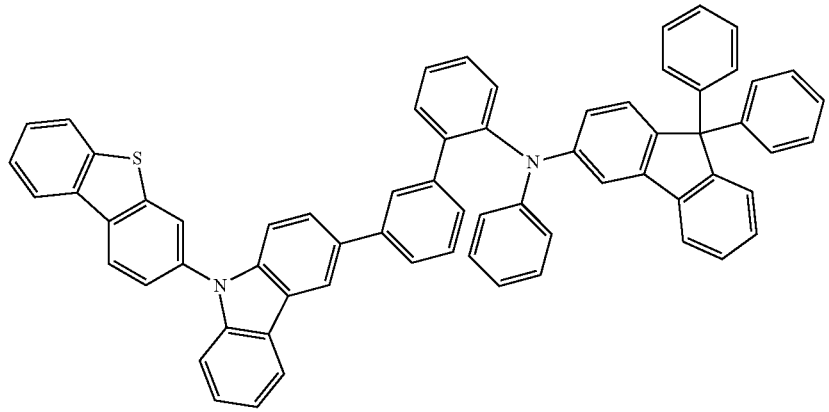
A357
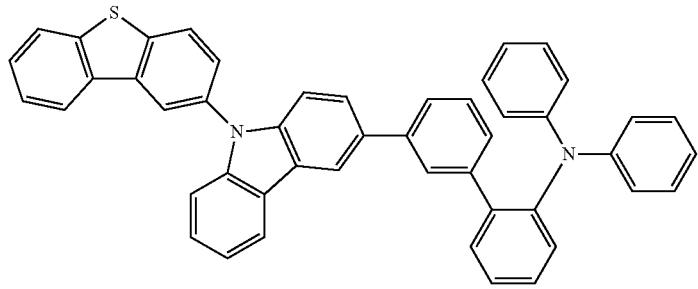
A358
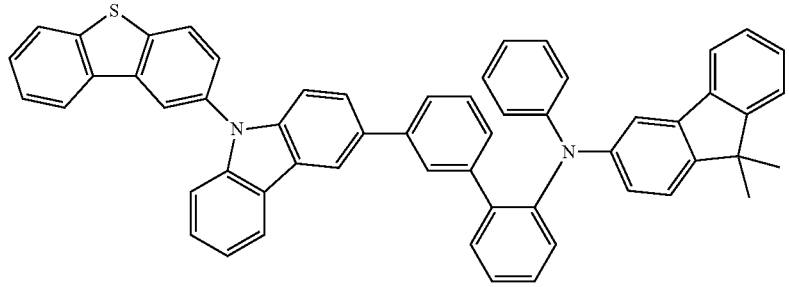
A359
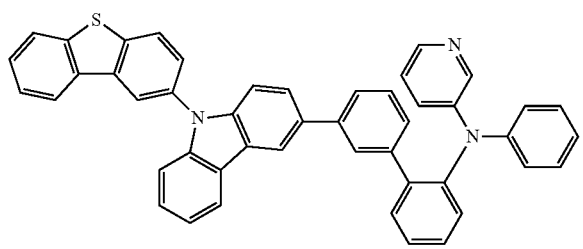
A360
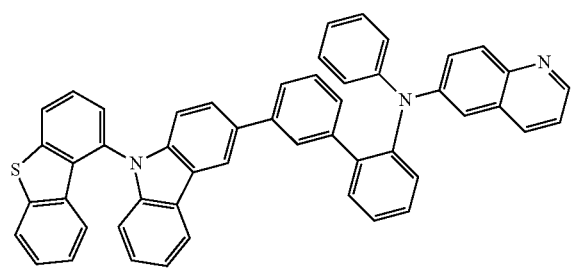

-continued
A361
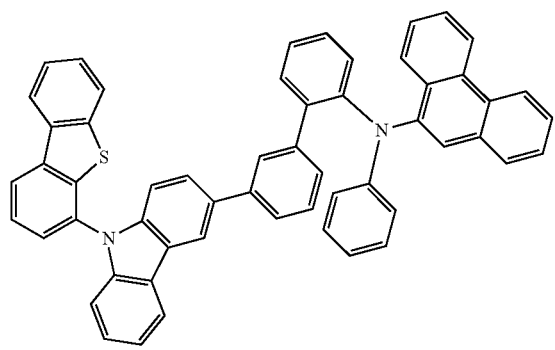
A362
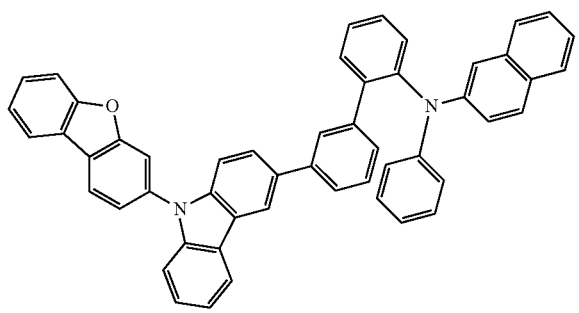
A363
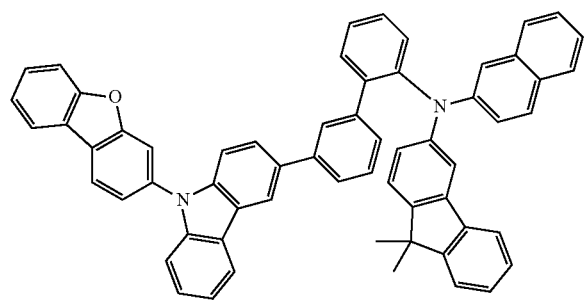
A364
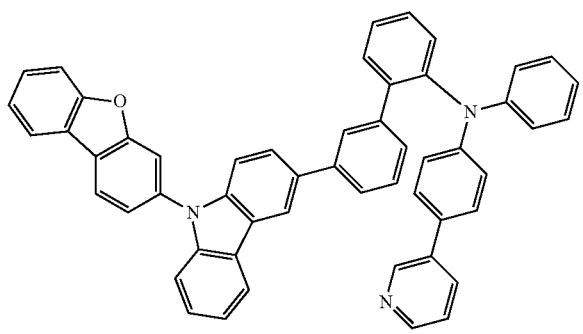
A365
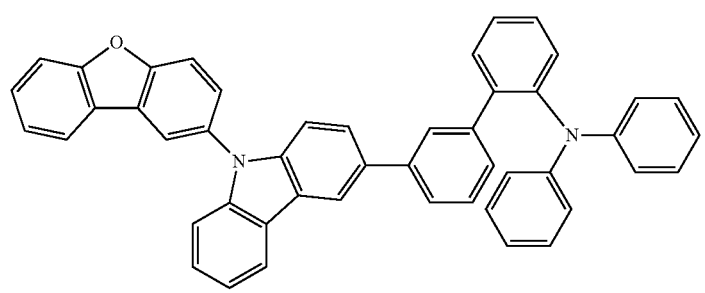
A366
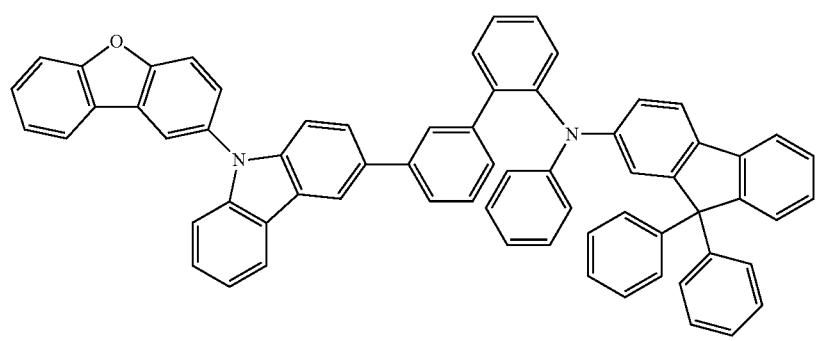

-continued
A367
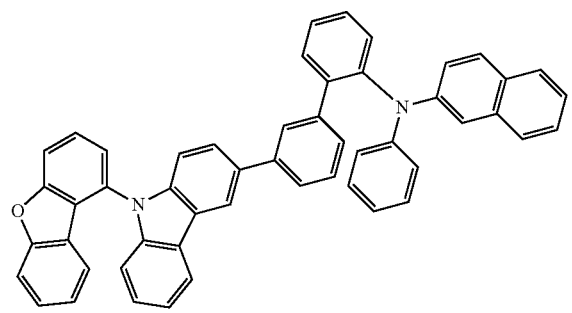
A368
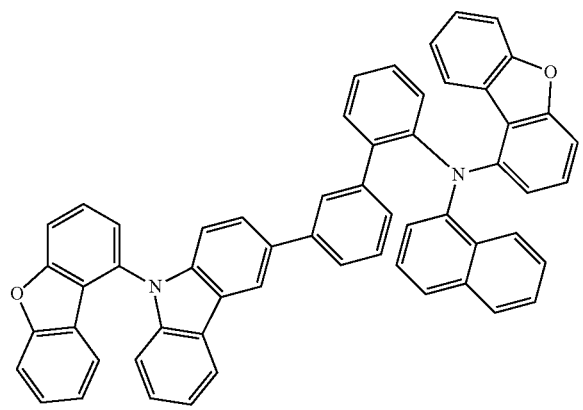
A369
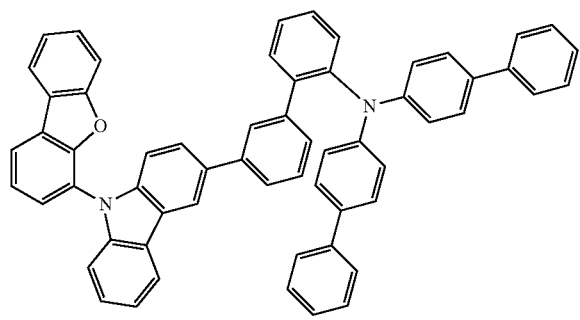
A370
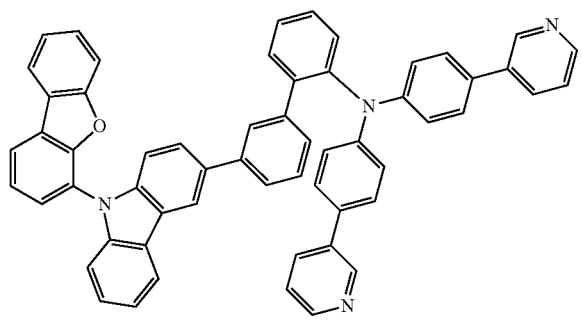
A371
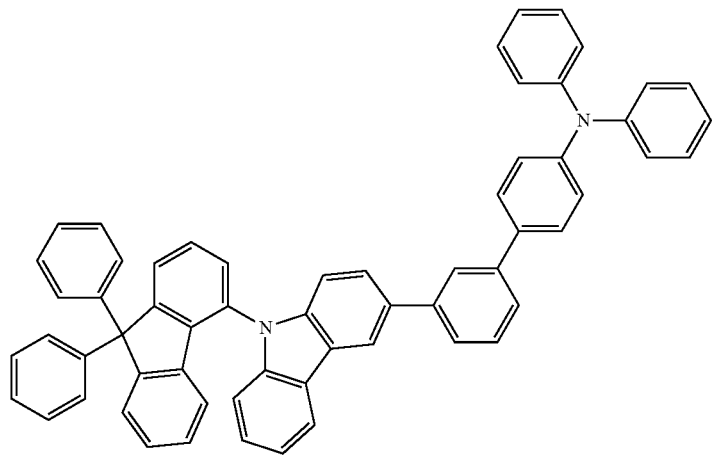

-continued
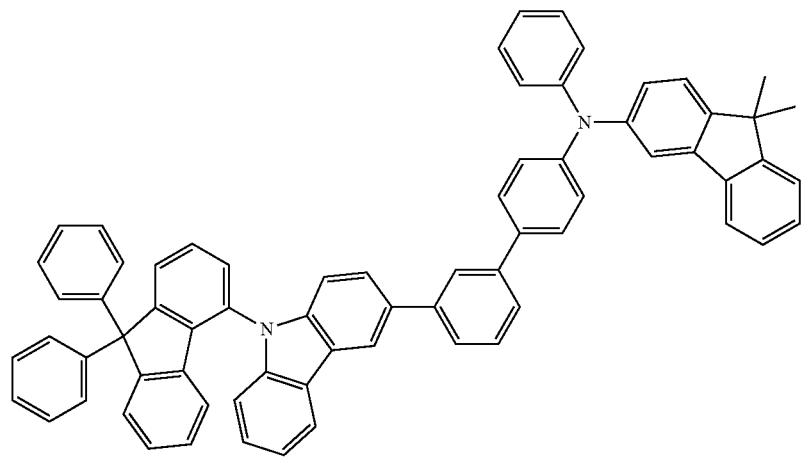
A372
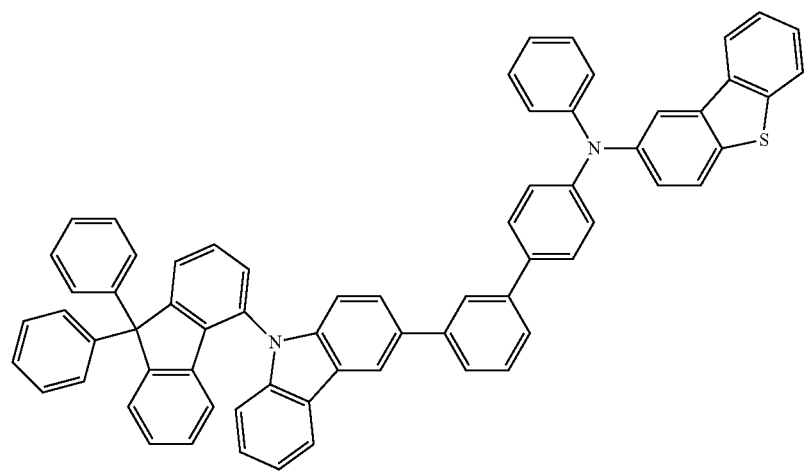
A373
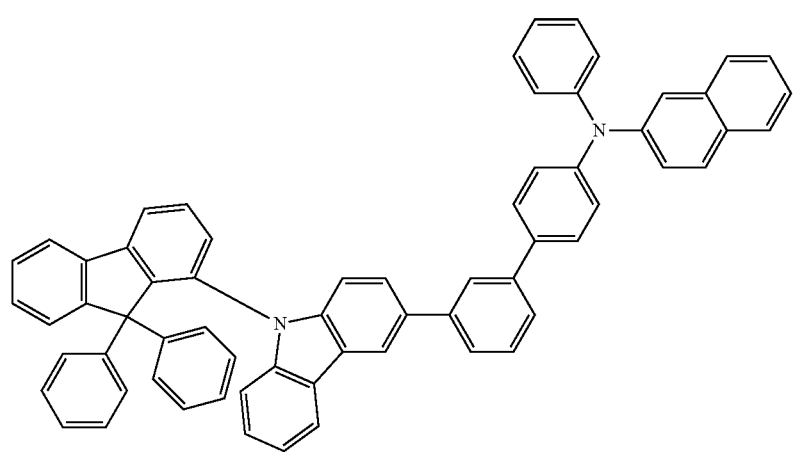
A374

A375
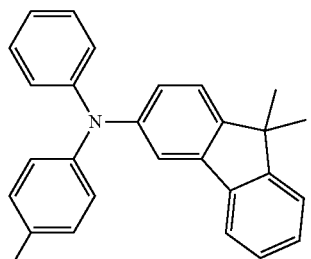
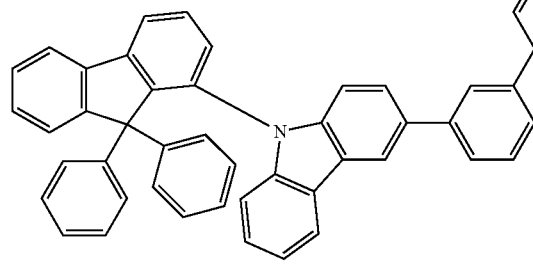
A376
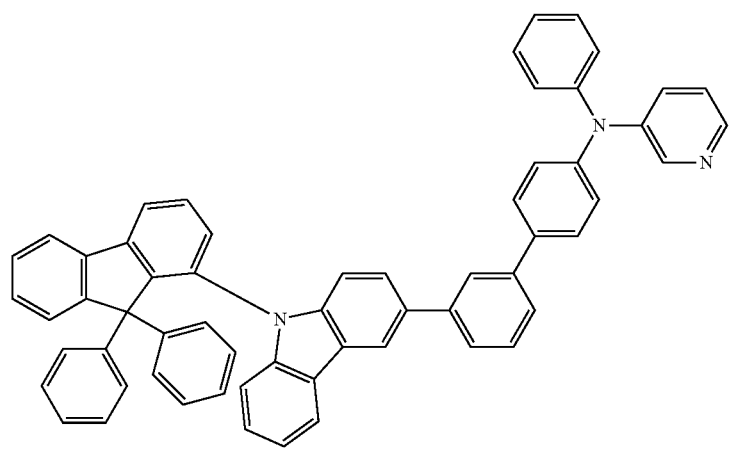
A377
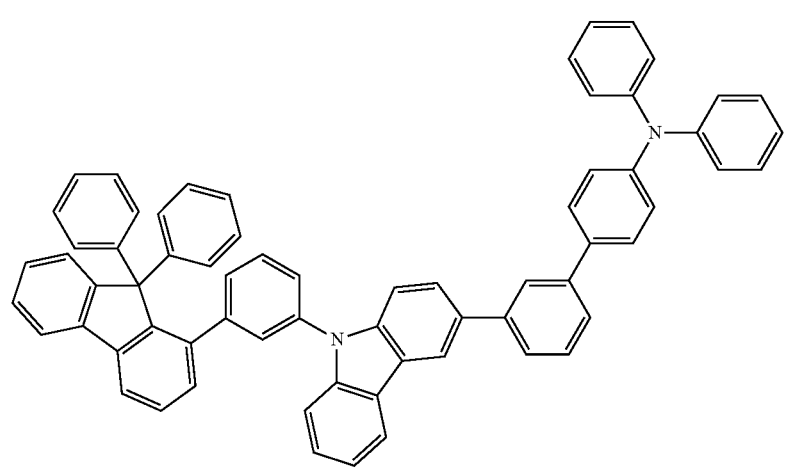

-continued
A378
A379
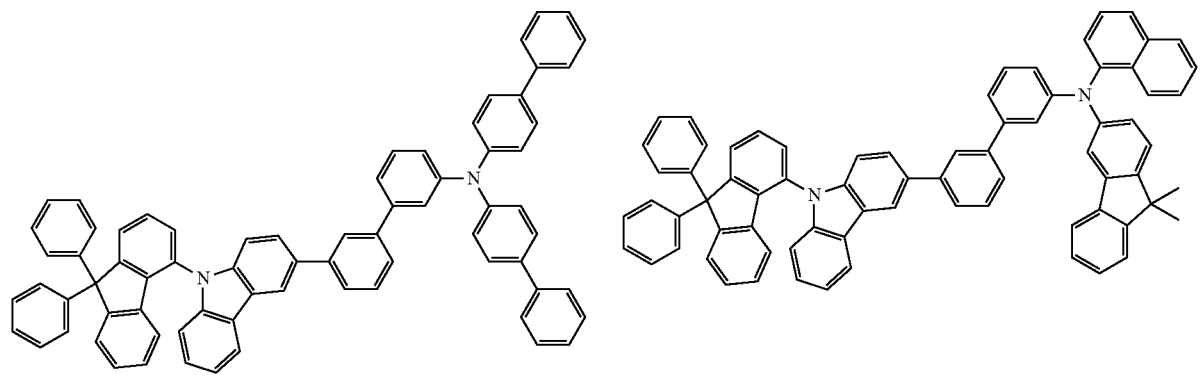
A380
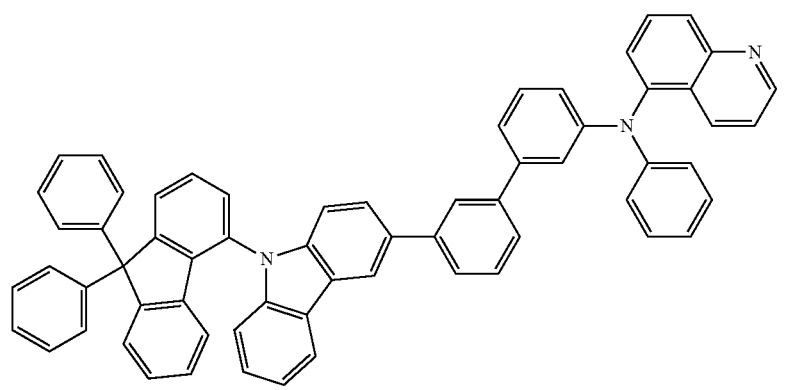
A381
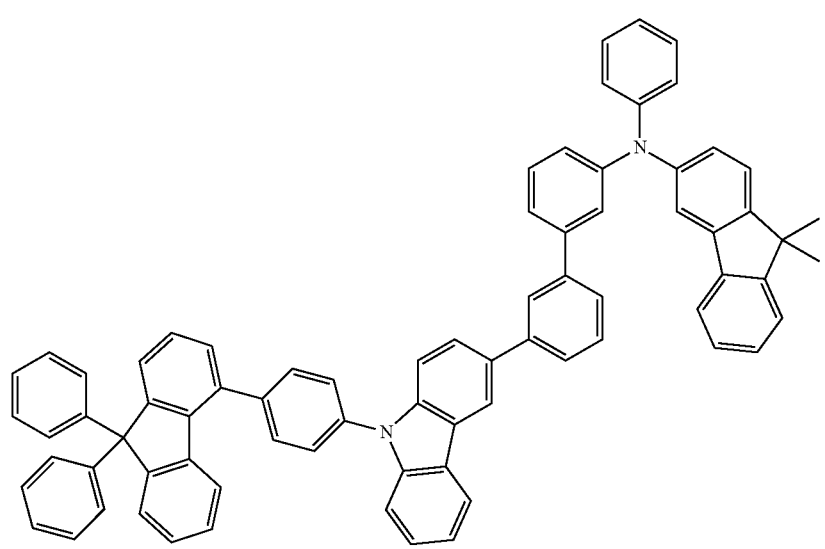

-continued
A382
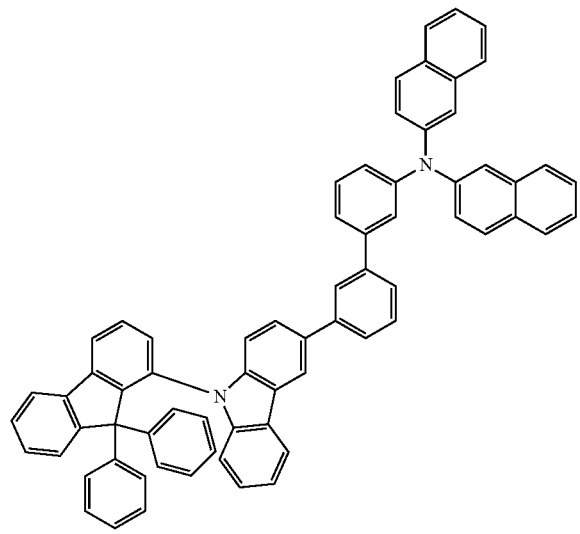
A383
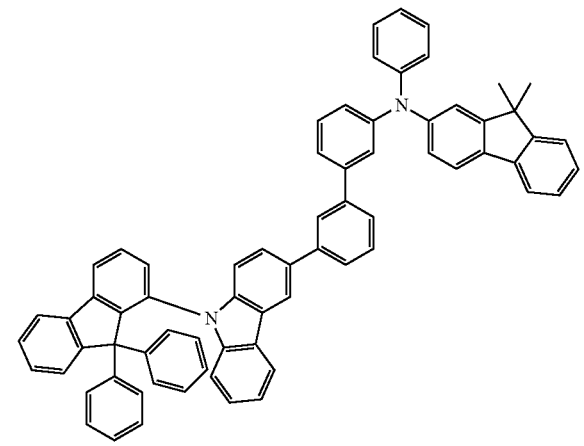
A384
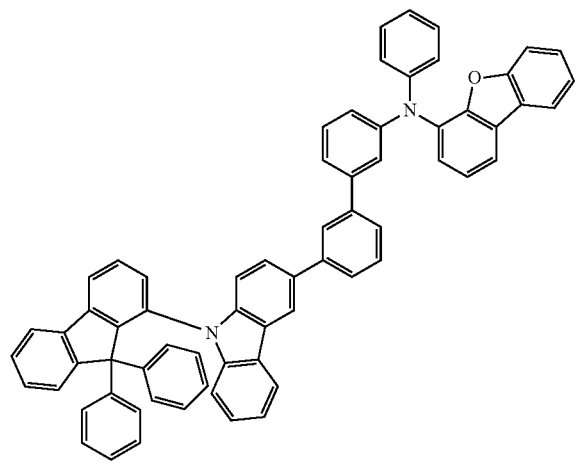
A385
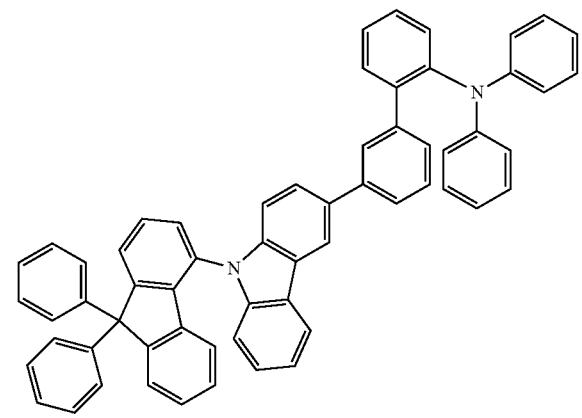
A386
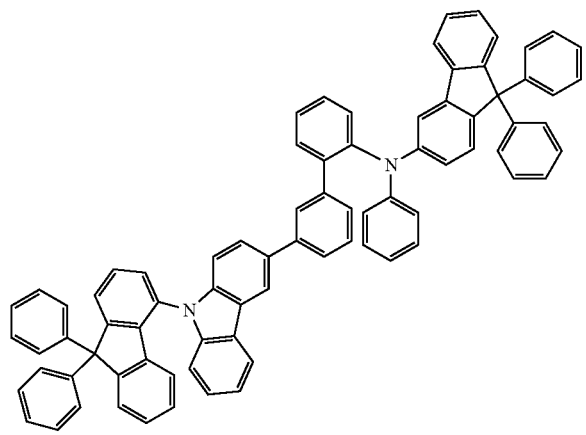
A387
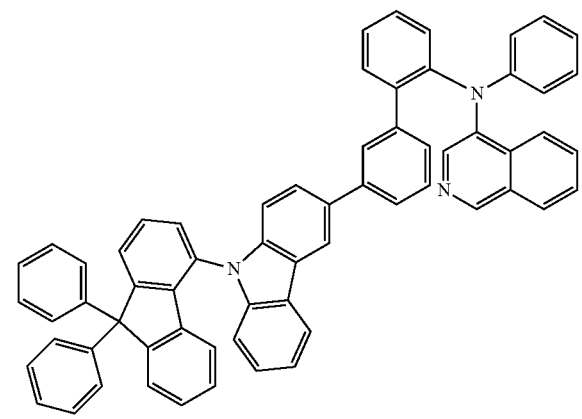

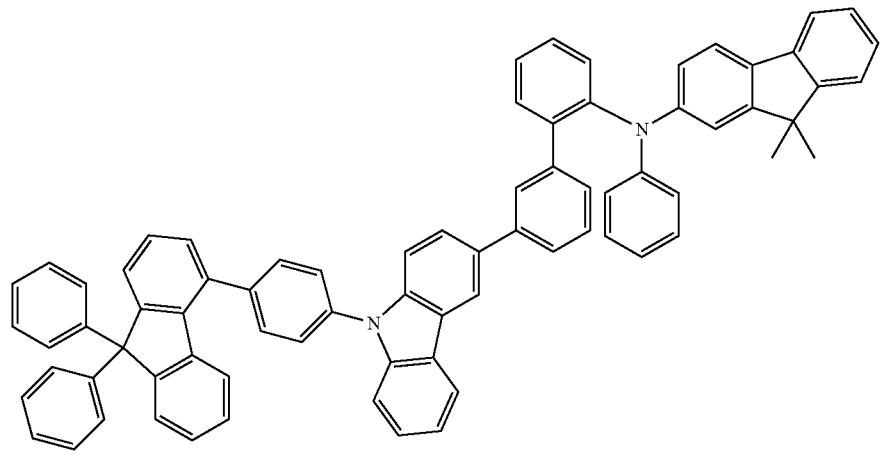
A388
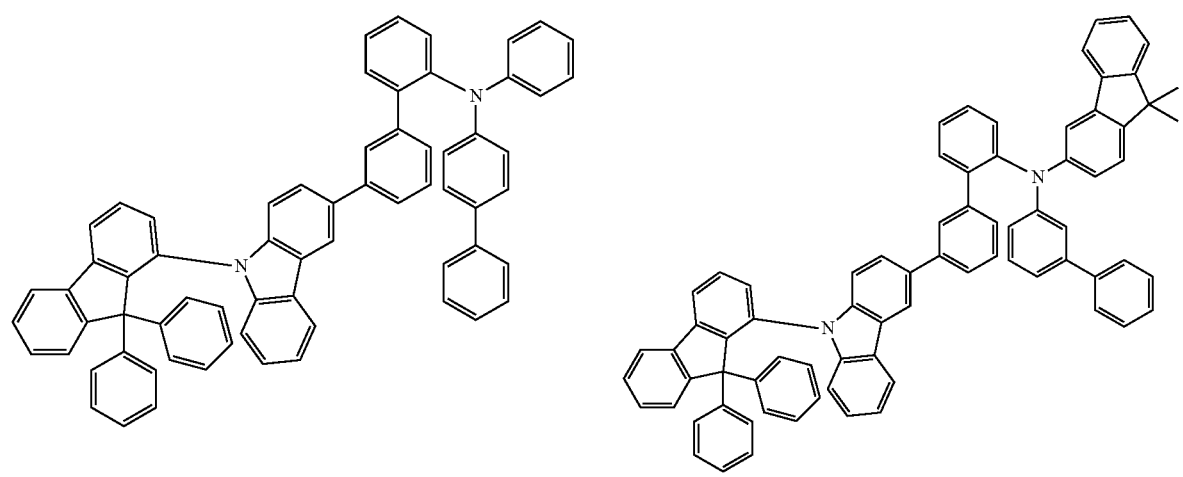
A389  A390
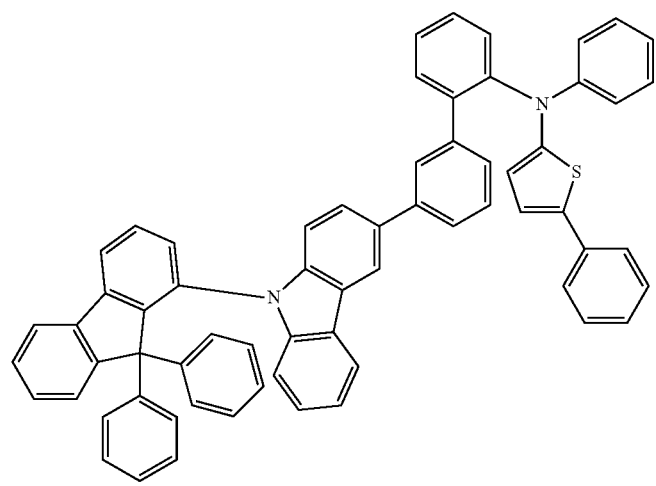
A391

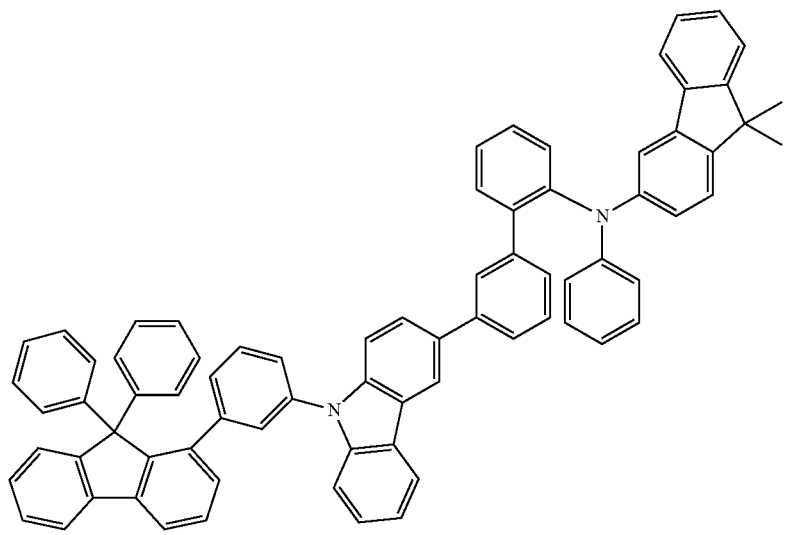
A392
In addition, illustratively, the compound represented by Formula 2 may be the compound represented by any one of the following formulas 4 to 7.
<Formula 4>
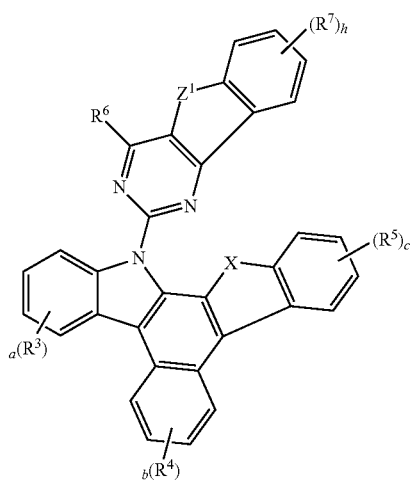
<Formula 5>
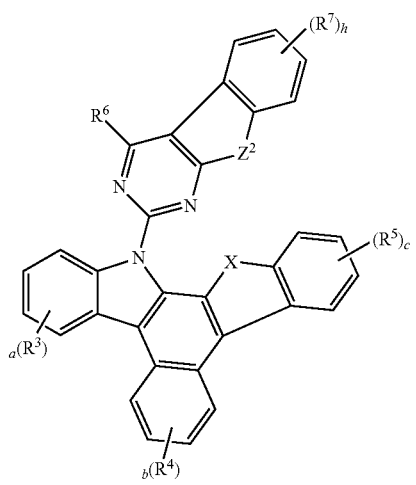
<Formula 6>
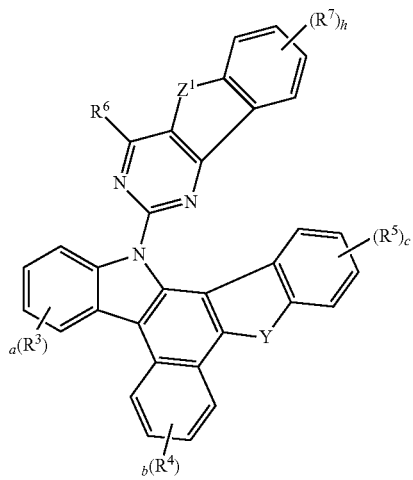
<Formula 7>
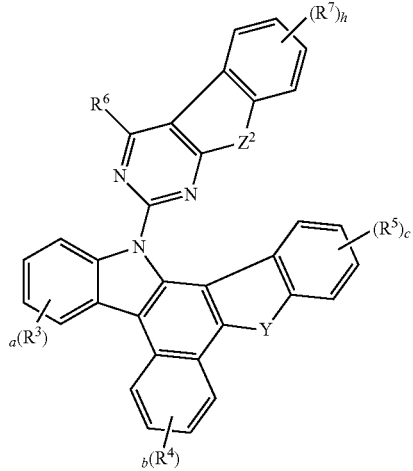
In Formulas 4 to 7, the symbols of $R^3$ to $R^7$, X, Y, $Z^1$, $Z^2$, a, b, c and h and the like are the same as defined in Formula 2 above.

Specifically, the compound represented by Formula 2 may be any one of the following compounds.
1-1-1-O-(1)
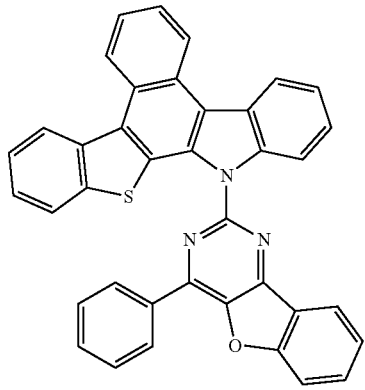
1-1-1-O-(2)
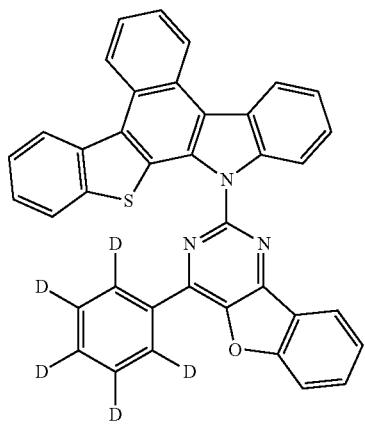
1-1-1-O-(3)
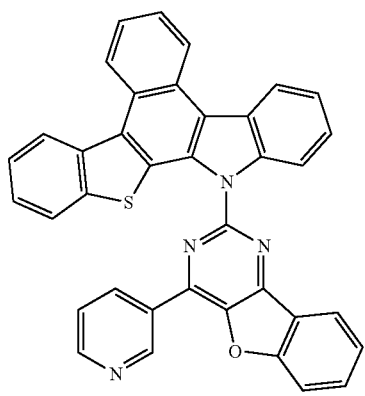
1-1-1-O-(4)
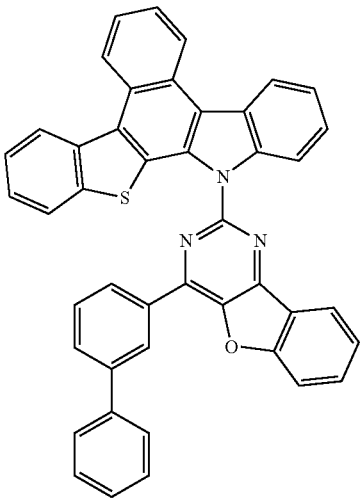
1-1-1-O-(5)
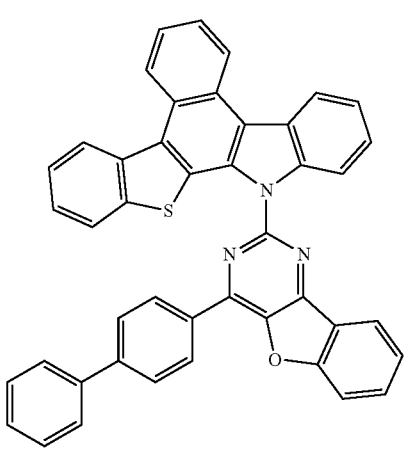
1-1-1-O-(6)
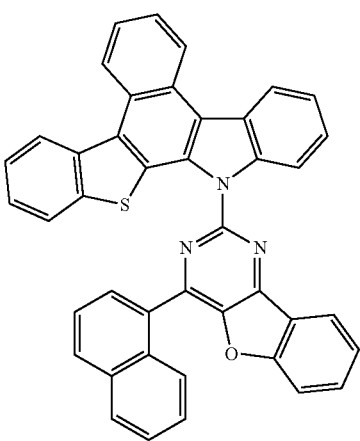

1-1-1-O-(7)
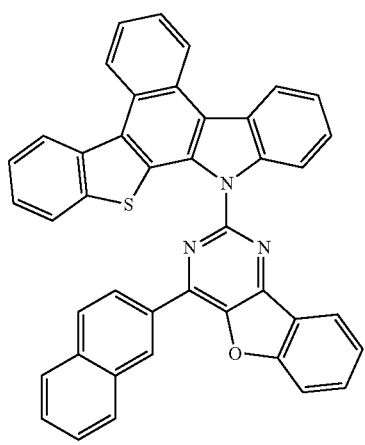
1-1-1-O-(8)
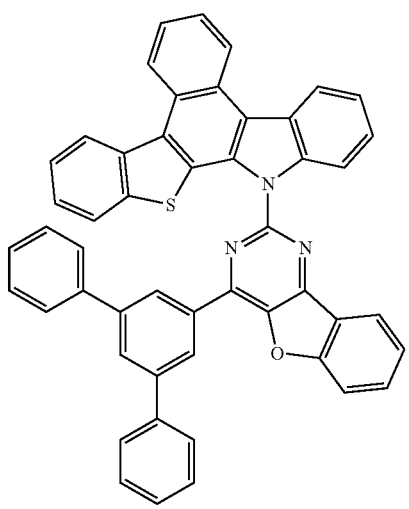
1-1-1-O-(9)
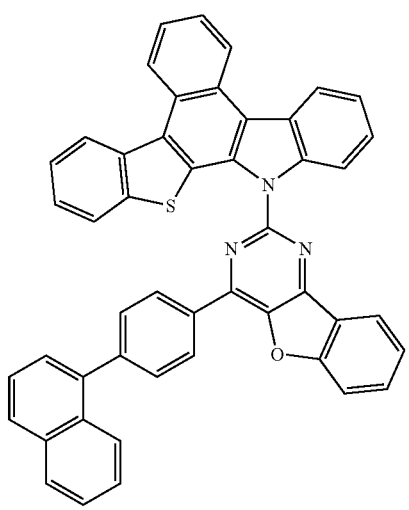
1-1-1-O-(10)
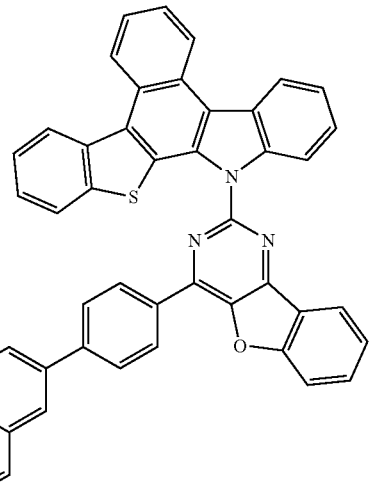
1-1-1-O-(11)
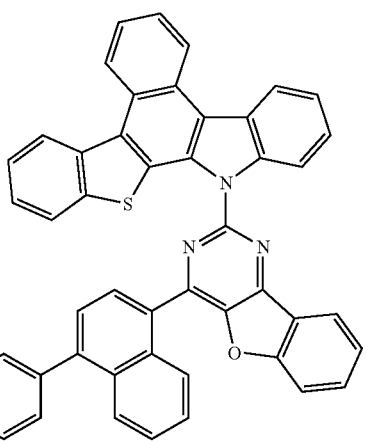
1-1-1-O-(12)
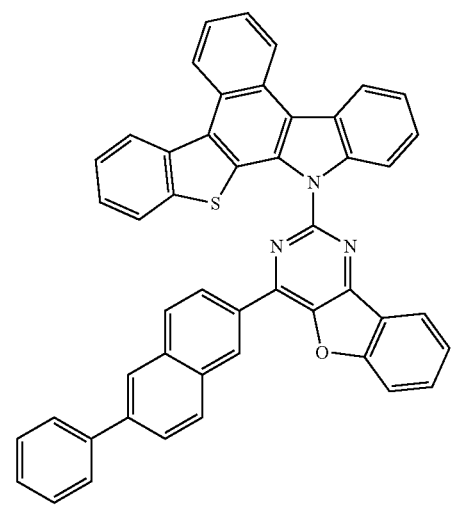

1-1-1-O-(13)
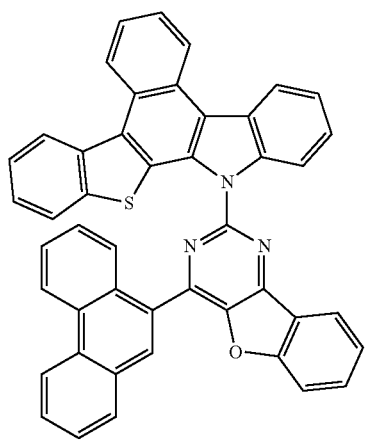
1-1-1-O-(14)
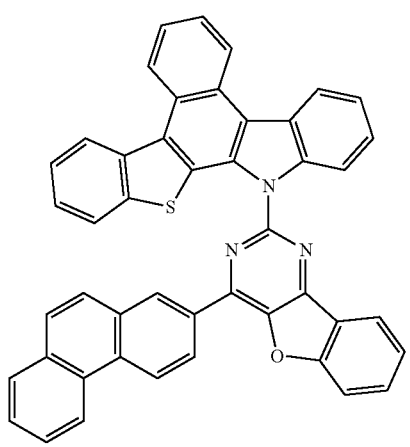
1-1-1-O-(15)
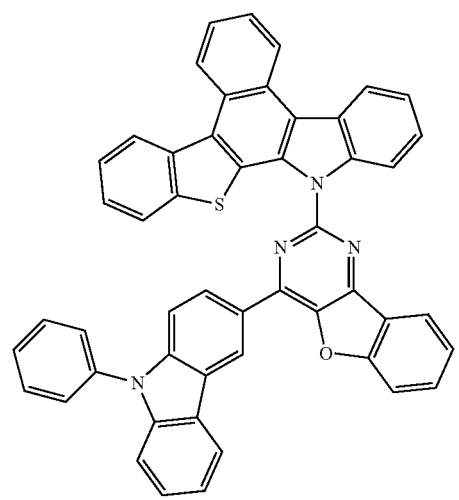
1-1-1-O-(16)
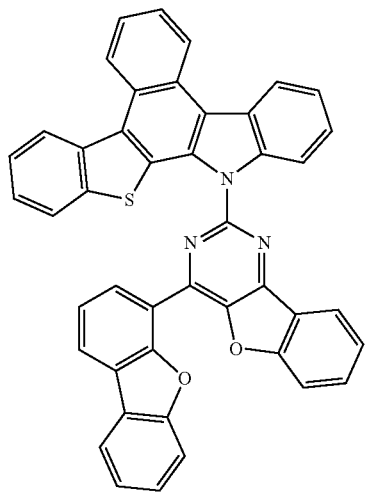
1-1-1-O-(17)
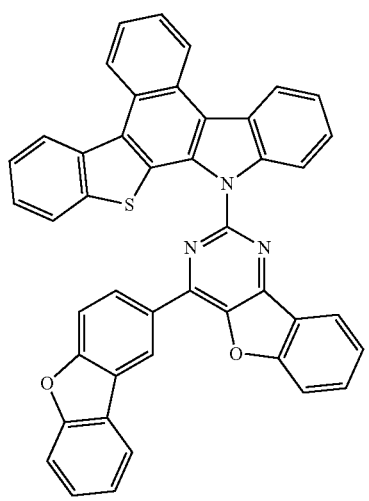
1-1-1-O-(18)
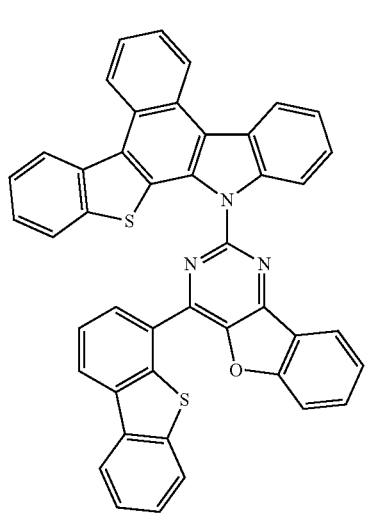

1-1-1-O-(19)
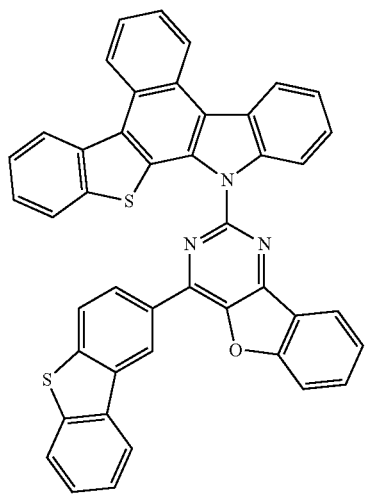
1-1-1-O-(20)
1-1-1-S-(1)
1-1-1-S-(2)
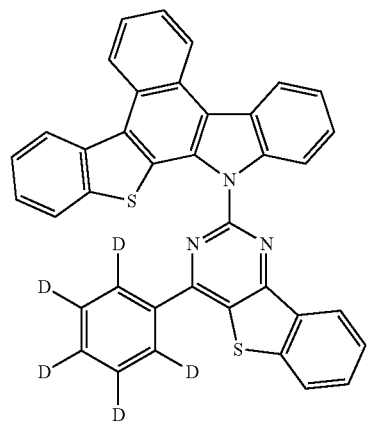
1-1-1-S-(3)
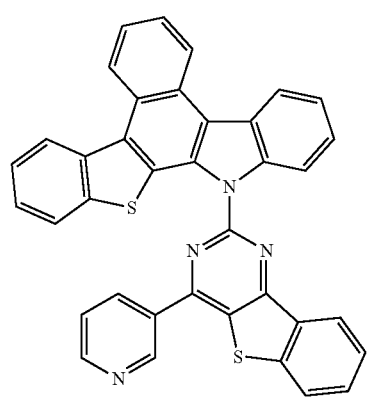
1-1-1-S-(4)
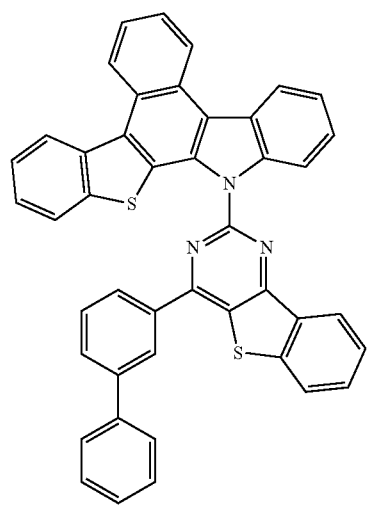

1-1-1-S-(5)
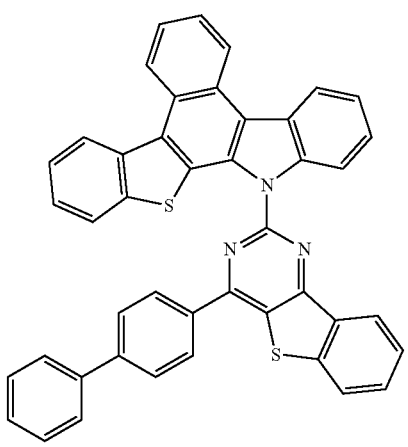
1-1-1-S-(6)
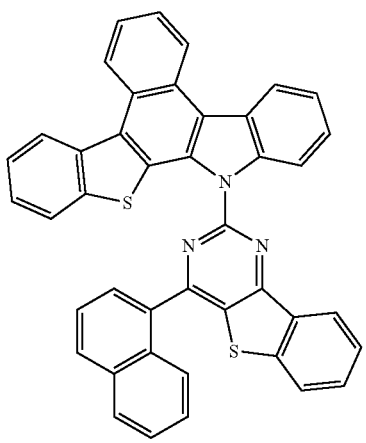
1-1-1-S-(7)
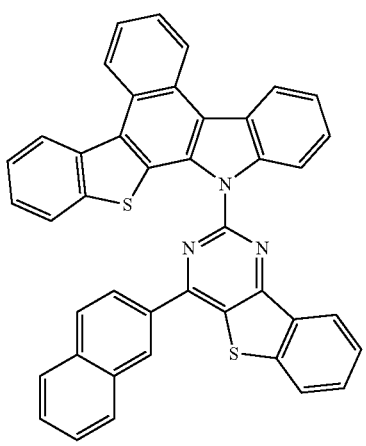
1-1-1-S-(8)
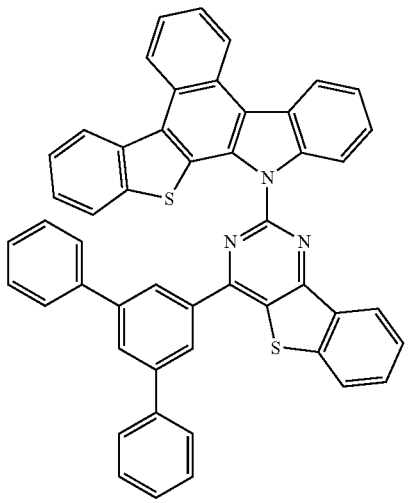
1-1-1-S-(9)
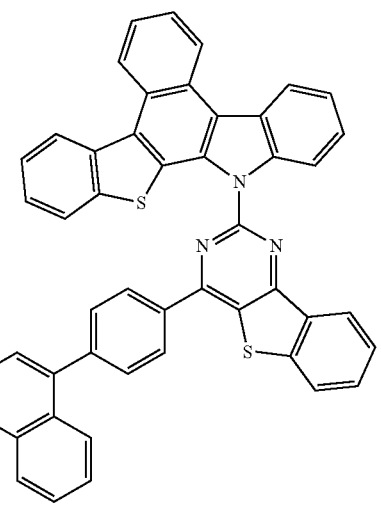
1-1-1-S-(10)
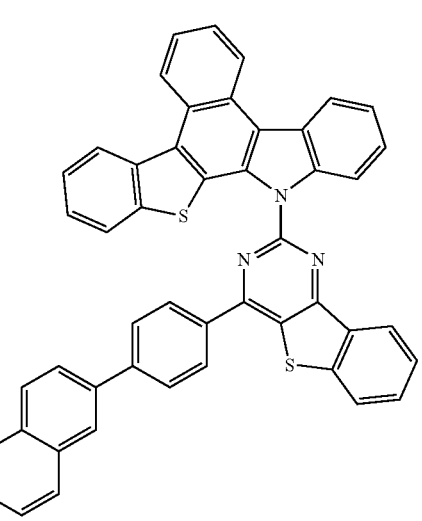

1-1-1-S-(11)
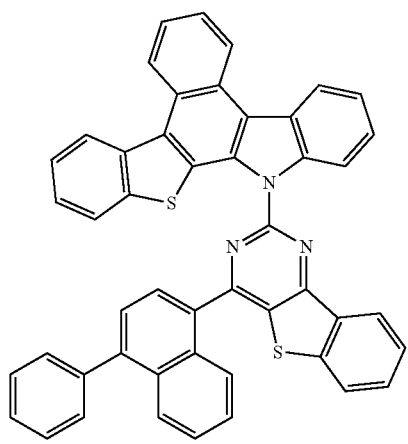
1-1-1-S-(12)
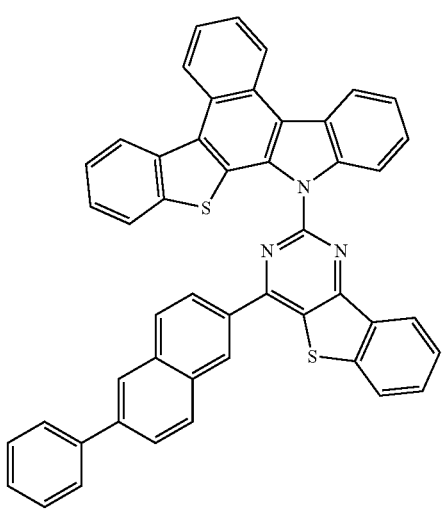
1-1-1-S-(13)
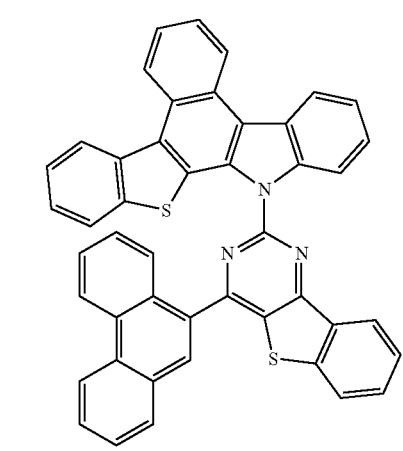
1-1-1-S-(14)
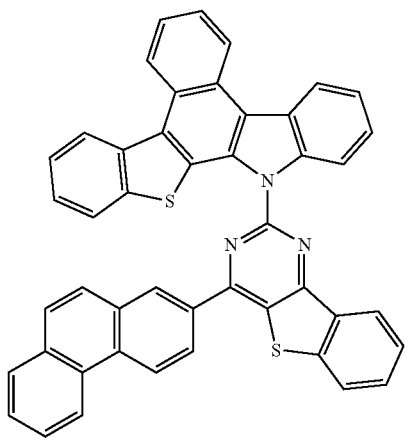
1-1-1-S-(15)
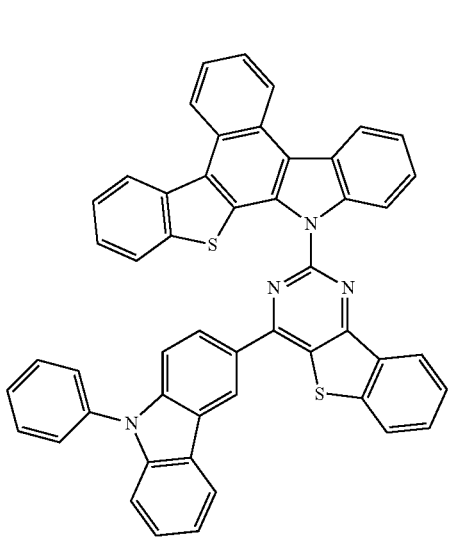
1-1-1-S-(16)
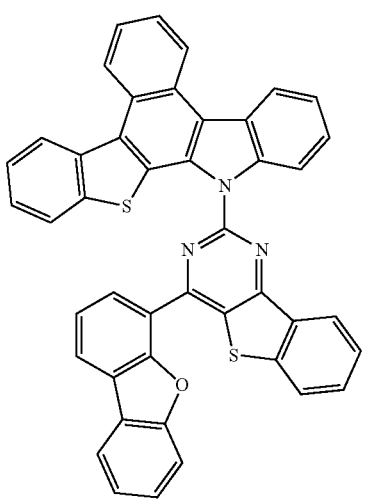

-continued
1-1-1-S-(17)
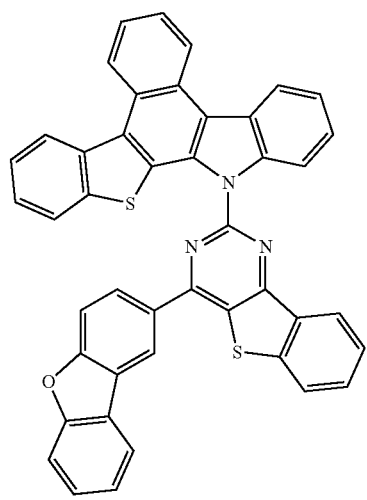
1-1-1-S-(18)
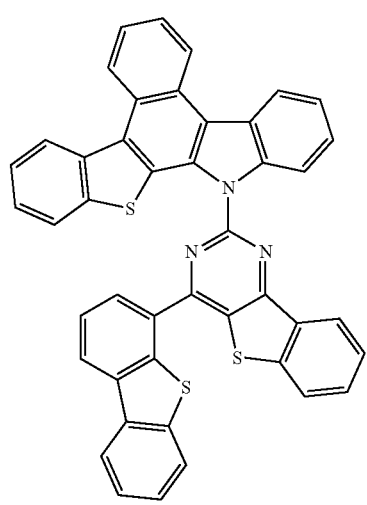
1-1-1-S-(19)
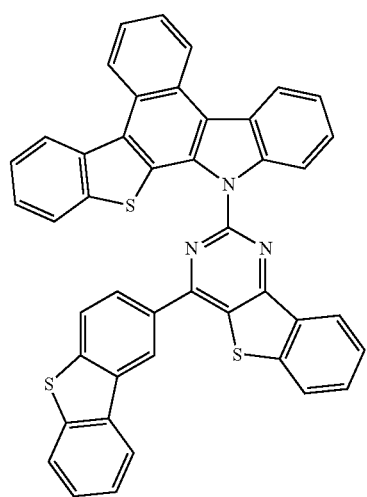
1-1-1-S-(20)
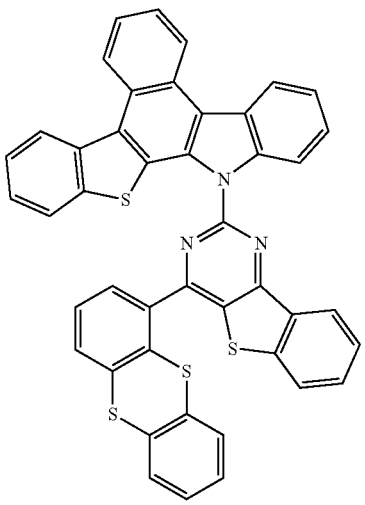
1-1-1-O-(21)
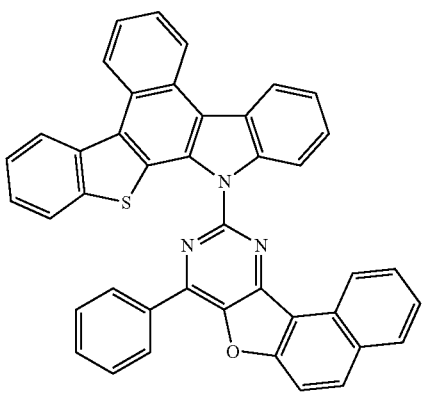
1-1-1-O-(22)
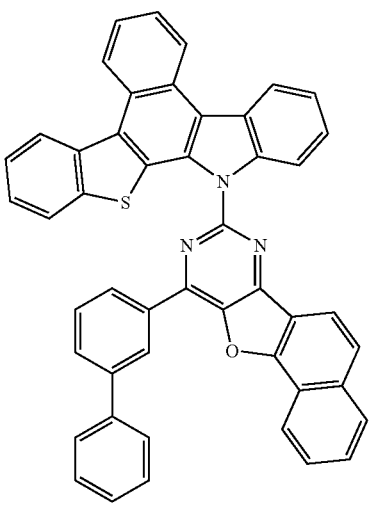

1-1-1-S-(21)
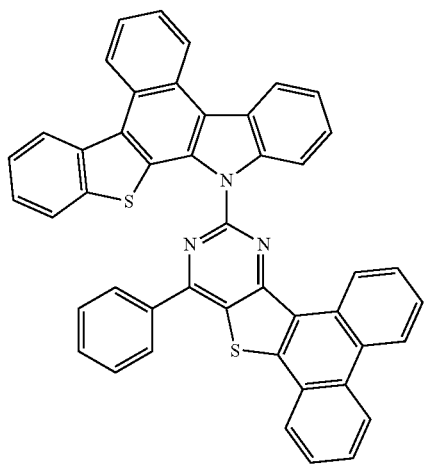
1-1-2-O-(1)
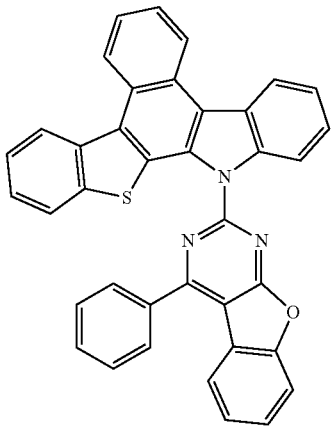
1-1-1-S-(22)
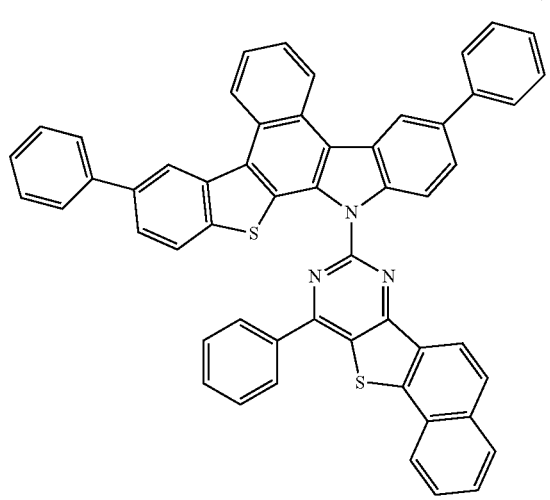
1-1-2-O-(2)
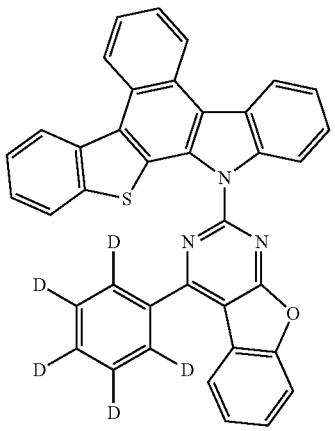
1-1-1-S-(23)
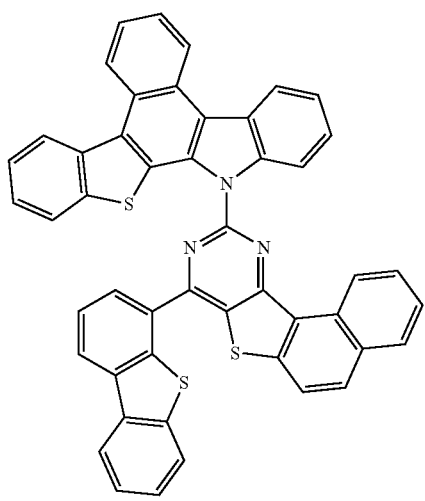
1-1-2-O-(3)
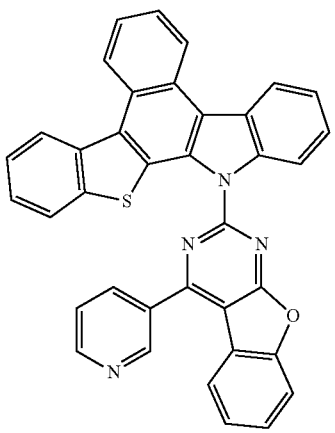

141
-continued
1-1-2-O-(4)
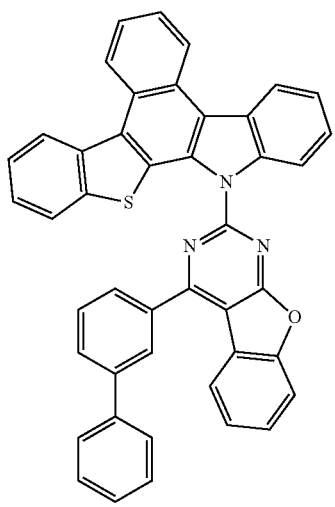
1-1-2-O-(5)
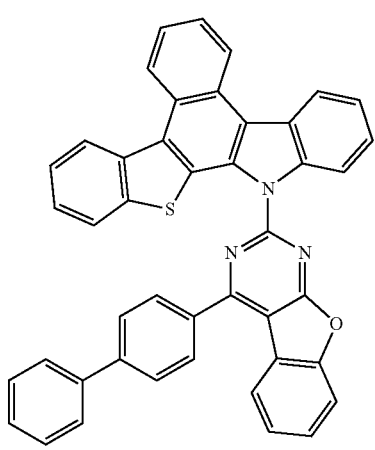
1-1-2-O-(6)
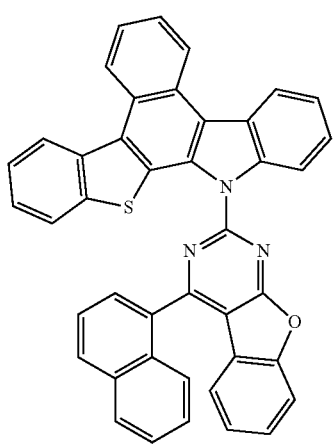
142
-continued
1-1-2-O-(7)
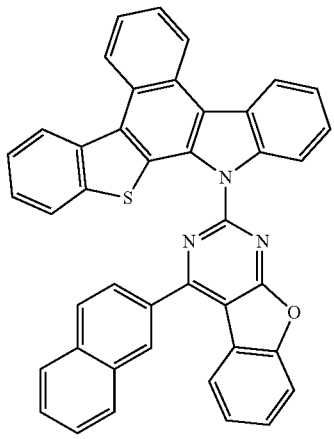
1-1-2-O-(8)
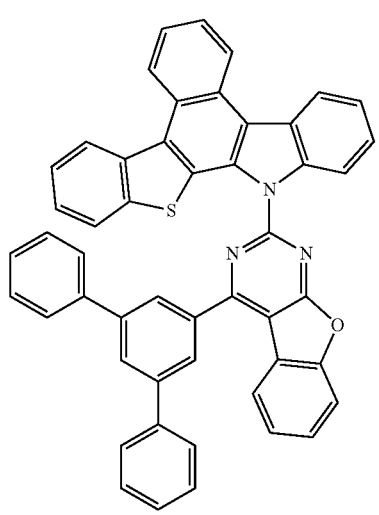
1-1-2-O-(9)
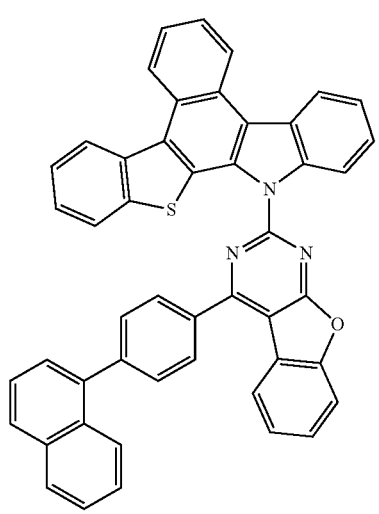

1-1-2-O-(10)
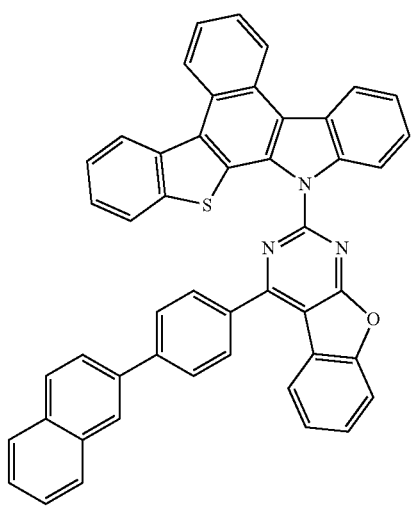
1-1-2-O-(11)
1-1-2-O-(12)
1-1-2-O-(13)
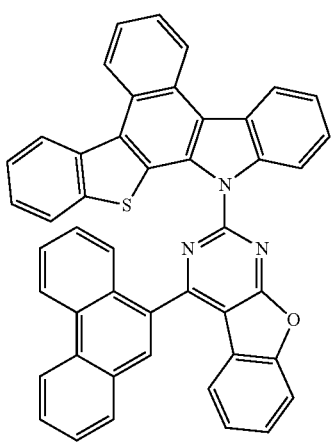
1-1-2-O-(14)
1-1-2-O-(15)

1-1-2-O-(16)
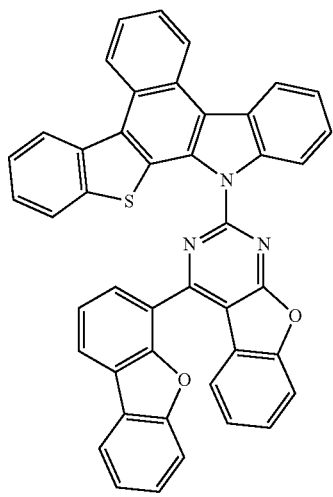
1-1-2-O-(17)
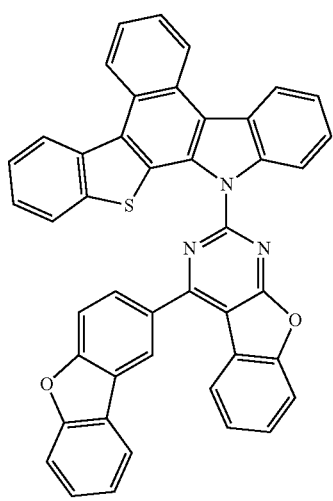
1-1-2-O-(18)
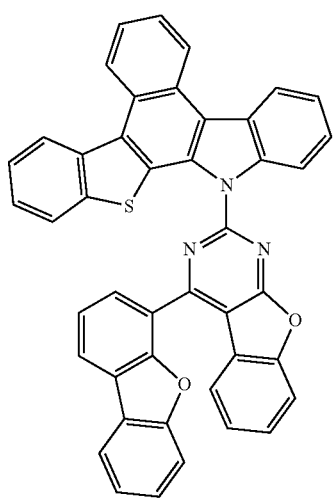
1-1-2-O-(19)
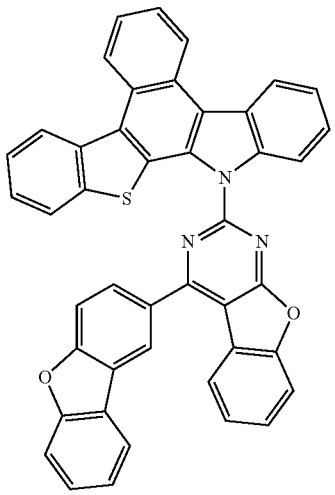
1-1-2-O-(20)
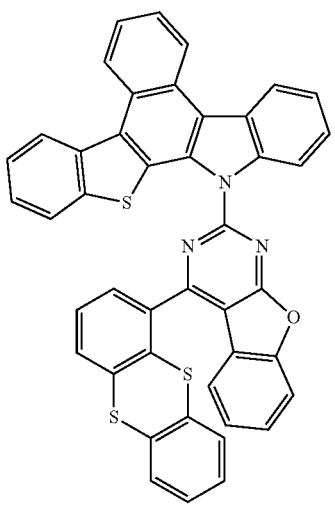
1-1-2-S-(1)
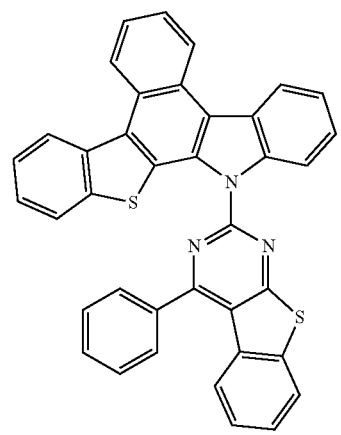

1-1-2-S-(2)
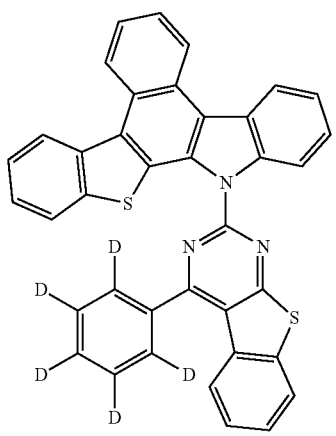
1-1-2-S-(3)
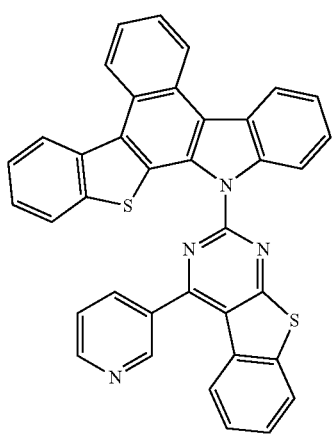
1-1-2-S-(4)
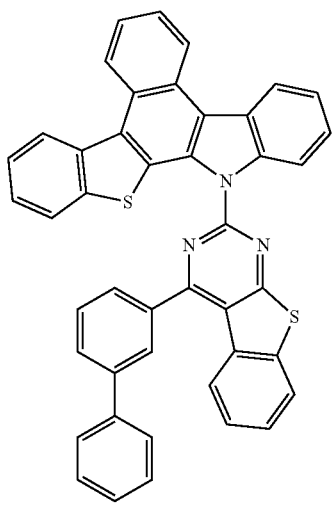
1-1-2-S-(5)
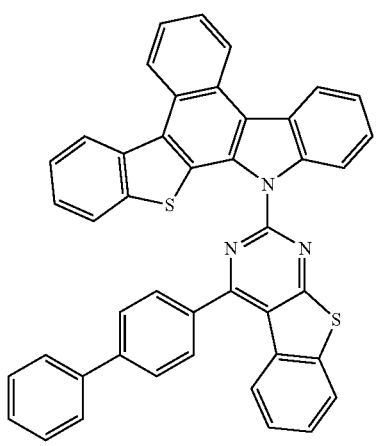
1-1-2-S-(6)
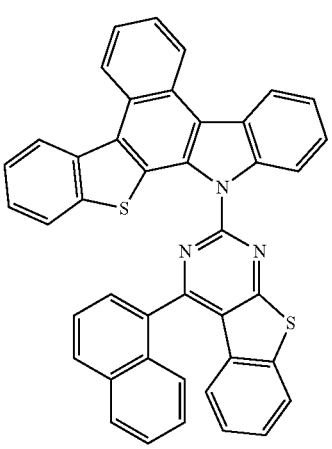
1-1-2-S-(7)
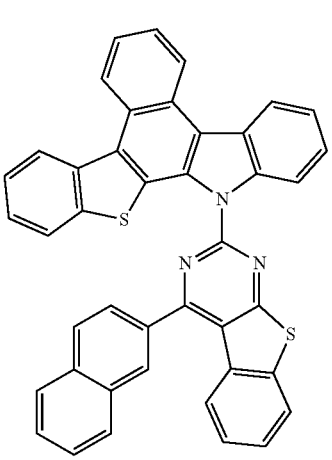

-continued
1-1-2-S-(8)
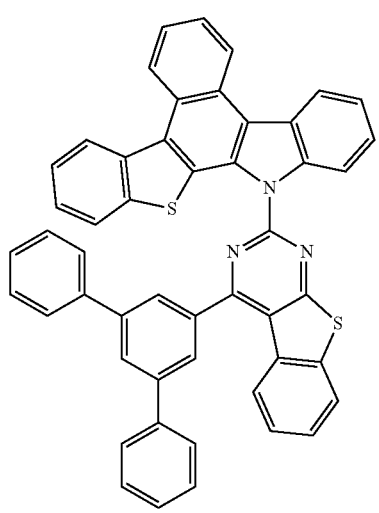
1-1-2-S-(9)
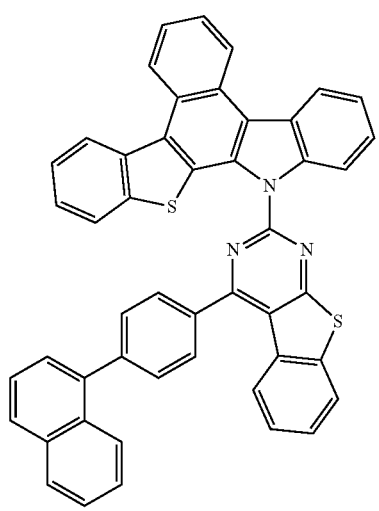
1-1-2-S-(10)
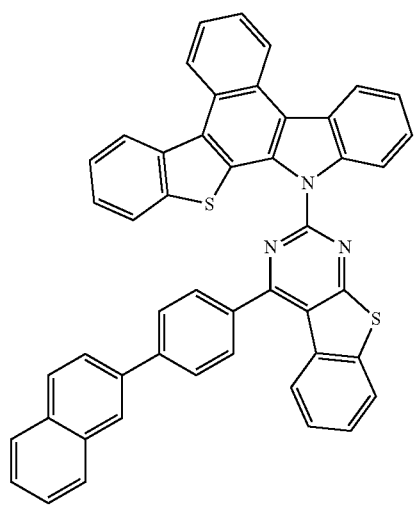
-continued
1-1-2-S-(11)
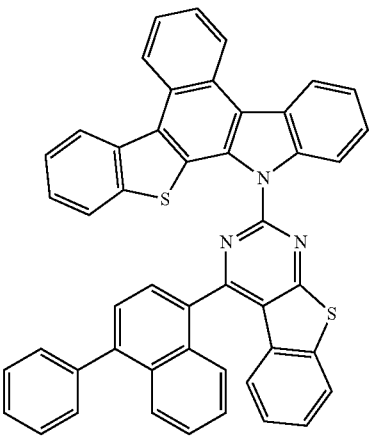
1-1-2-S-(12)
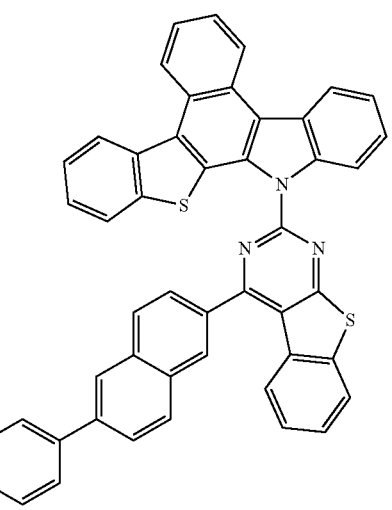
1-1-2-S-(13)
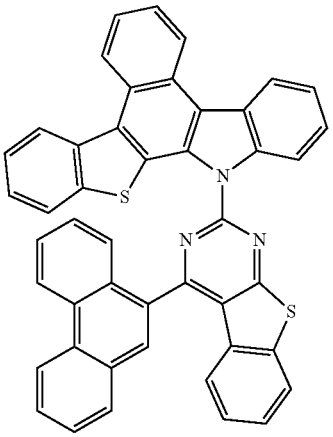

-continued
1-1-2-S-(14)
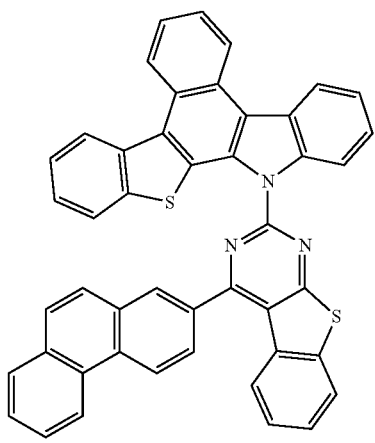
1-1-2-S-(15)
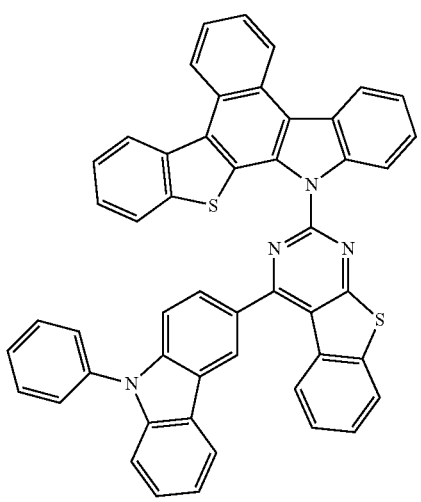
1-1-2-S-(16)
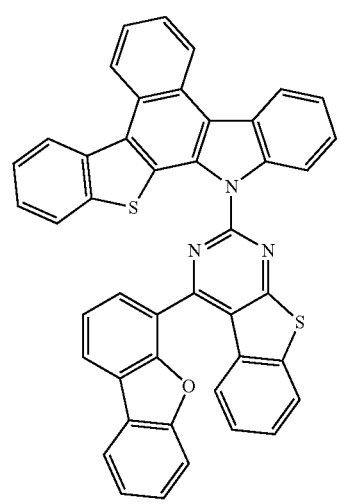
1-1-2-S-(17)
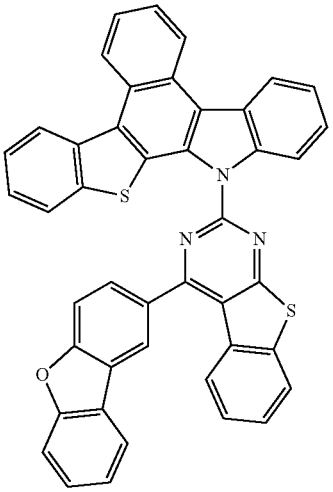
1-1-2-S-(18)
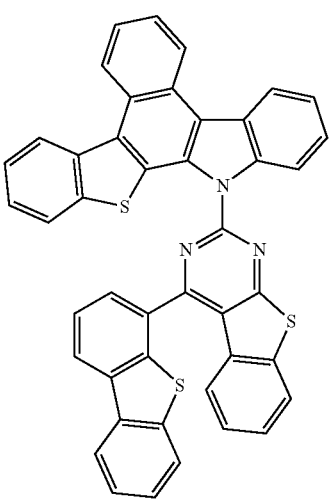
1-1-2-S-(19)
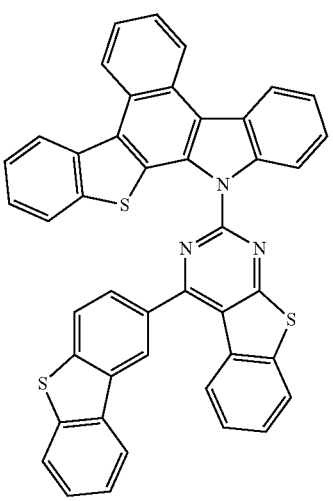

1-1-2-S-(20)
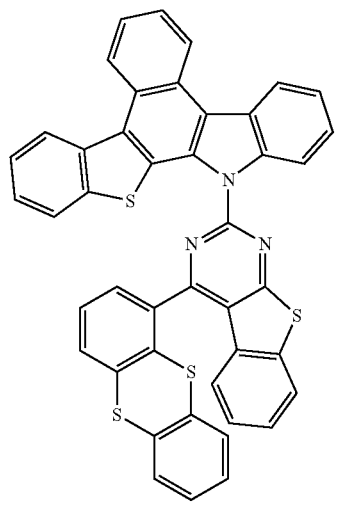
1-1-2-O-(21)
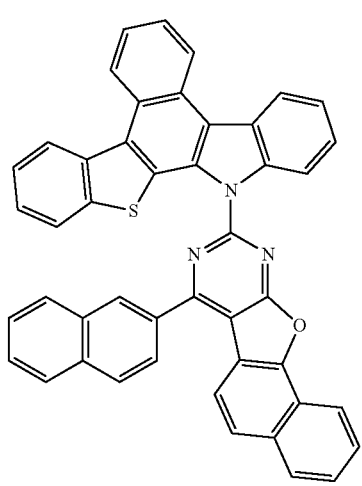
1-1-2-O-(22)
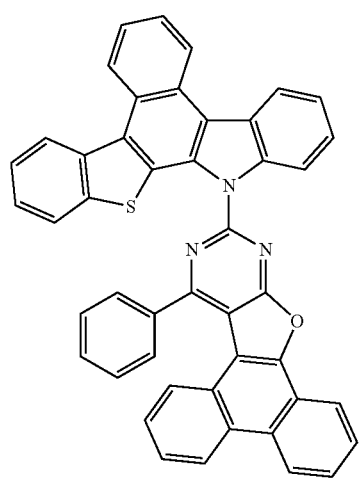
1-1-2-S-(21)
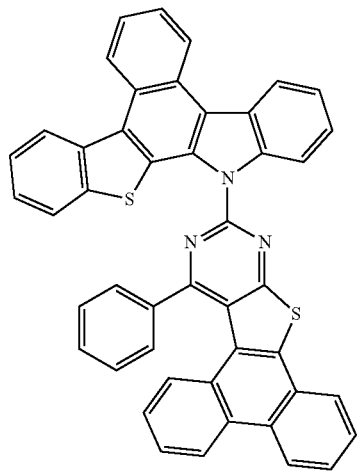
1-1-2-S-(22)
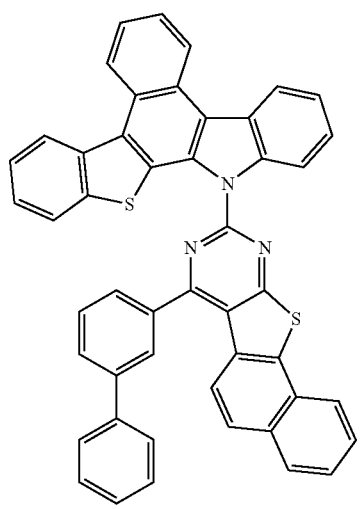
1-1-2-S-(23)
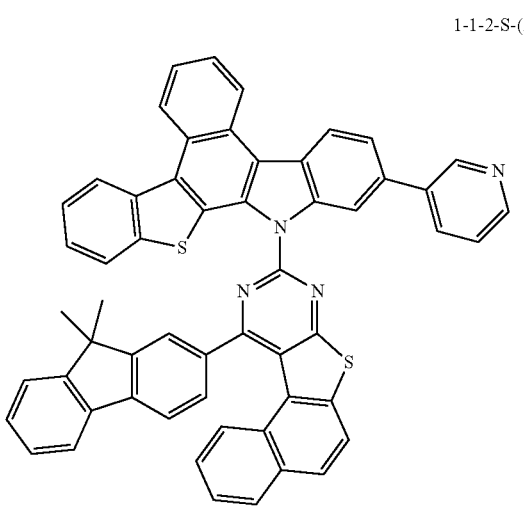

1-3-1-O-(1)
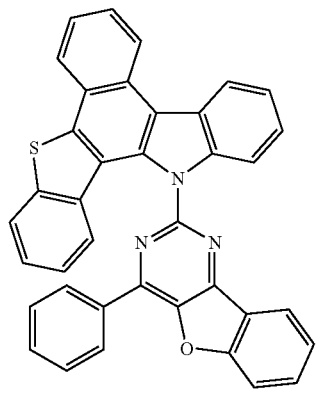
1-3-1-O-(2)
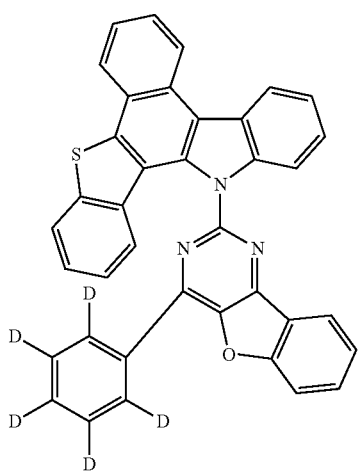
1-3-1-O-(3)
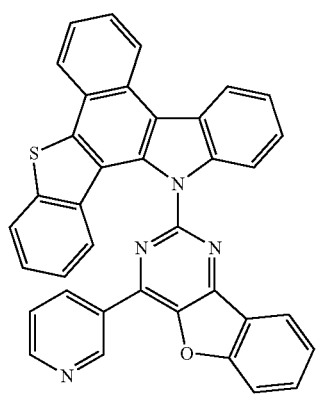
1-3-1-O-(4)
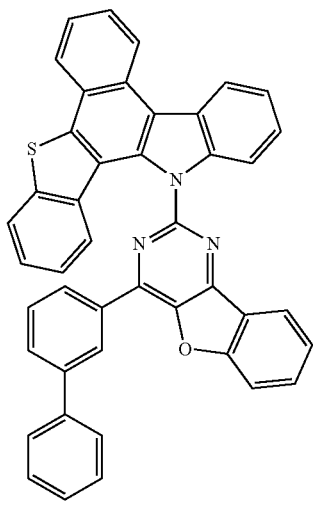
1-3-1-O-(5)
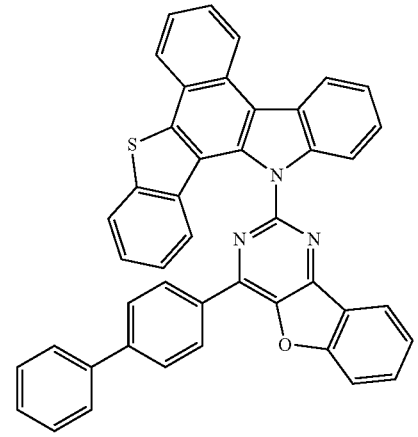
1-3-1-O-(6)
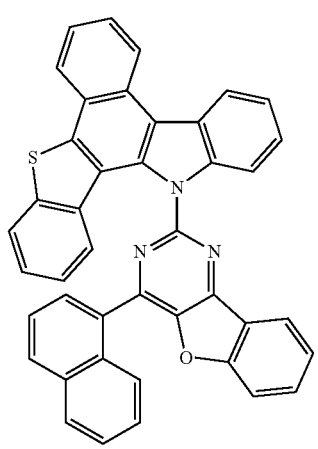

1-3-1-O-(7)
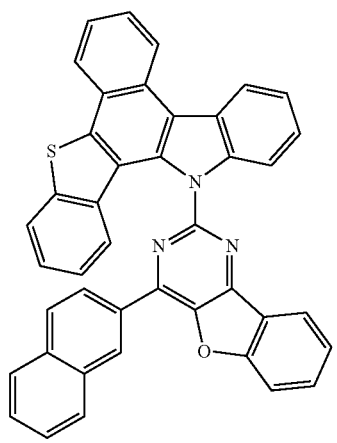
1-3-1-O-(8)
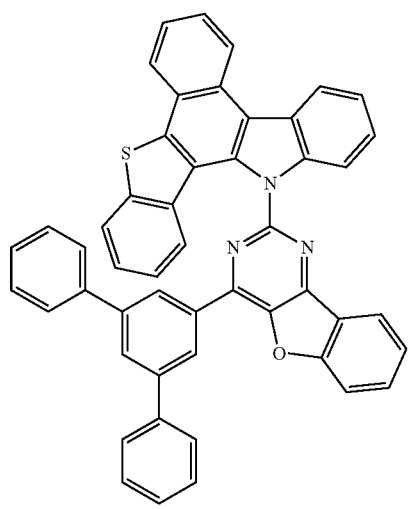
1-3-1-O-(9)
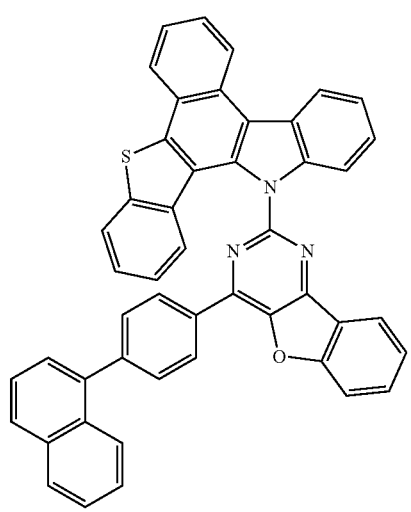
1-3-1-O-(10)
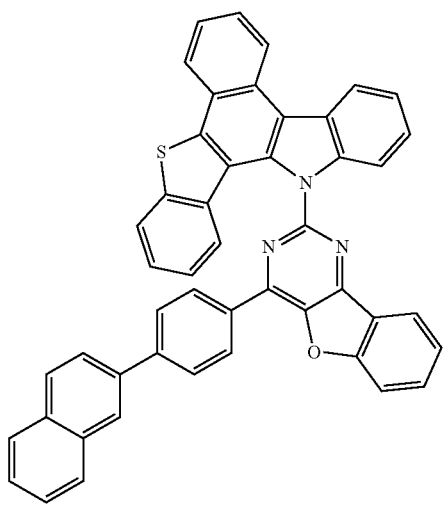
1-3-1-O-(11)
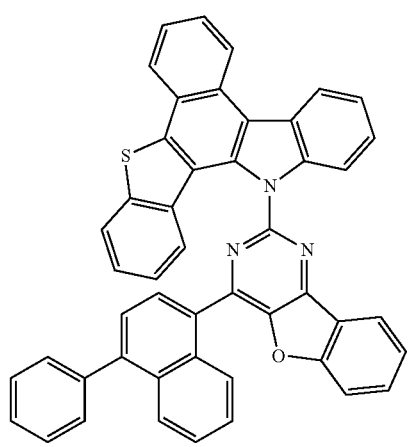
1-3-1-O-(12)
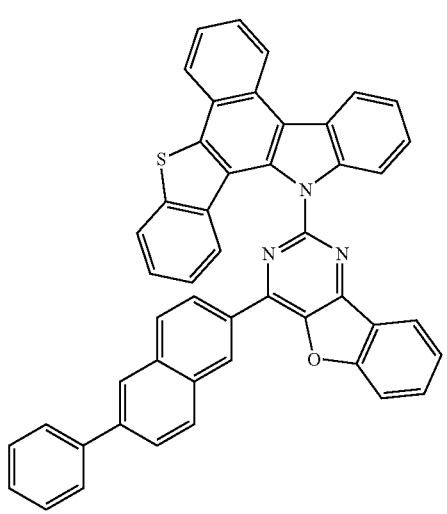

1-3-1-O-(13)
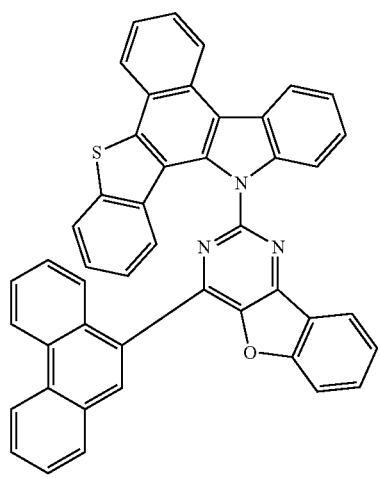
1-3-1-O-(14)
1-3-1-O-(15)
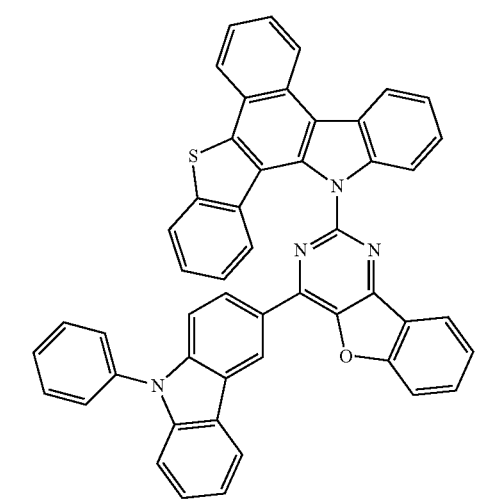
1-3-1-O-(16)
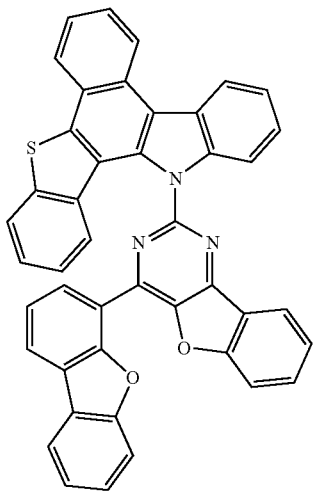
1-3-1-O-(17)
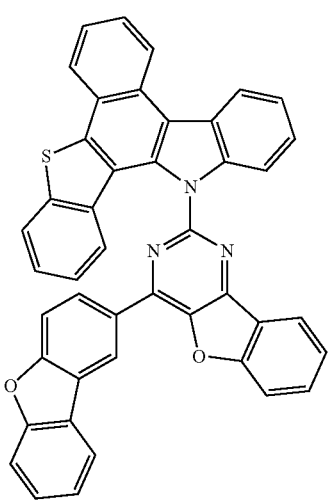
1-3-1-O-(18)
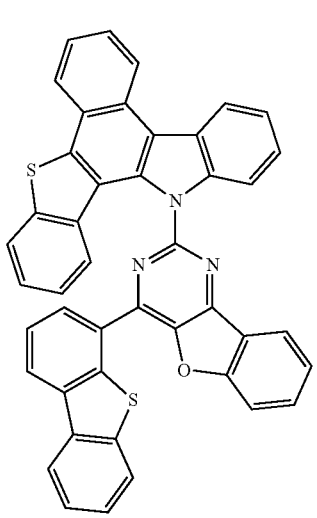

1-3-1-O-(19)
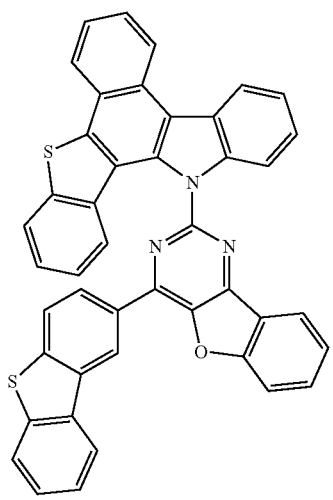
1-3-1-O-(20)
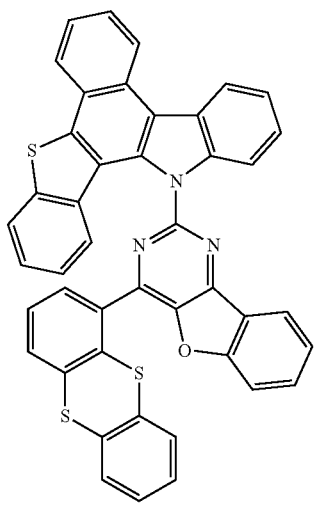
1-3-1-S-(1)
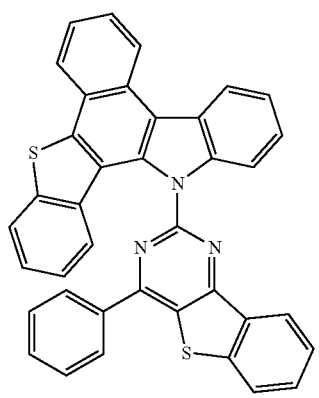
1-3-1-S-(2)
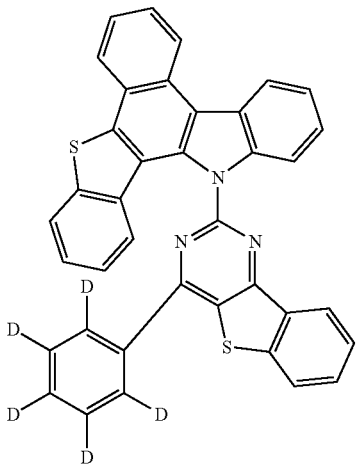
1-3-1-S-(3)
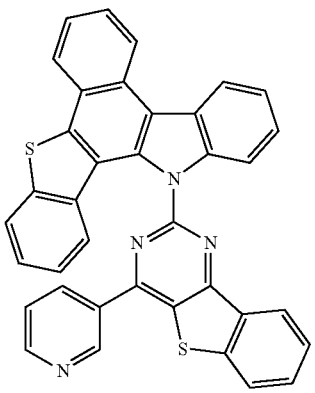
1-3-1-S-(4)
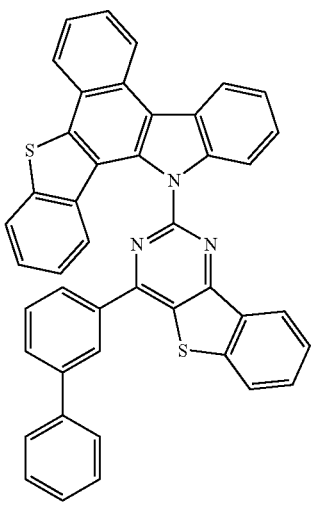

1-3-1-S-(5)
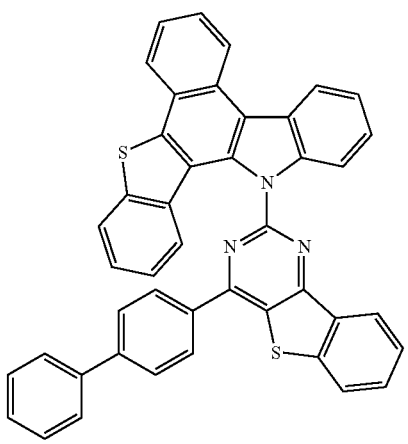
1-3-1-S-(6)
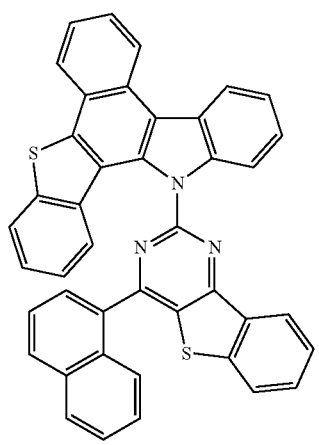
1-3-1-S-(7)
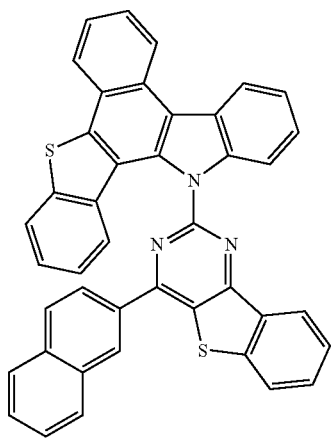
1-3-1-S-(8)
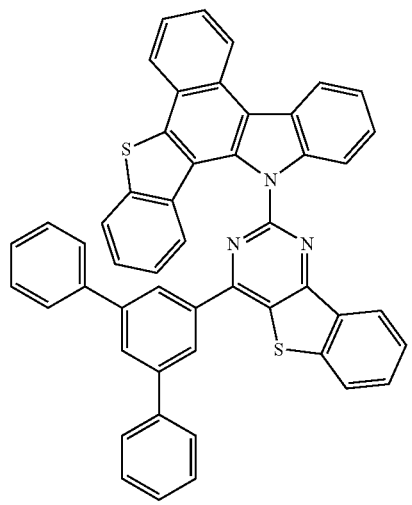
1-3-1-S-(9)
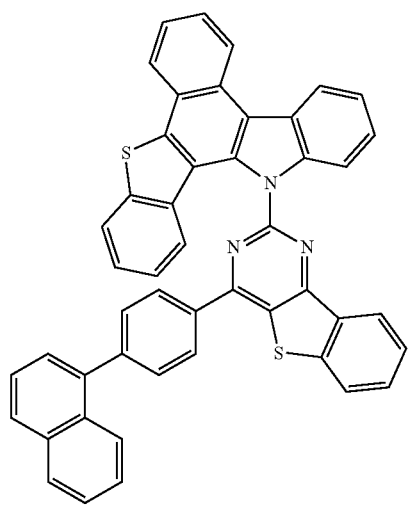
1-3-1-S-(10)
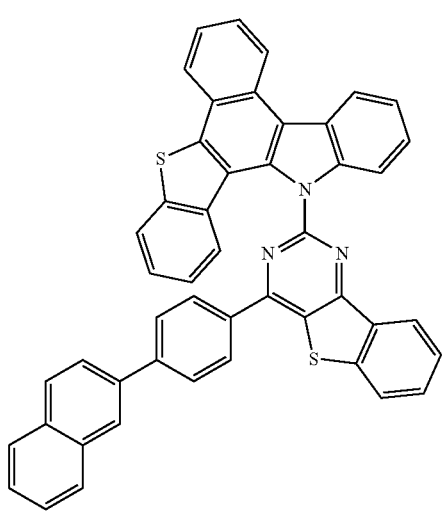

1-3-1-S-(11)
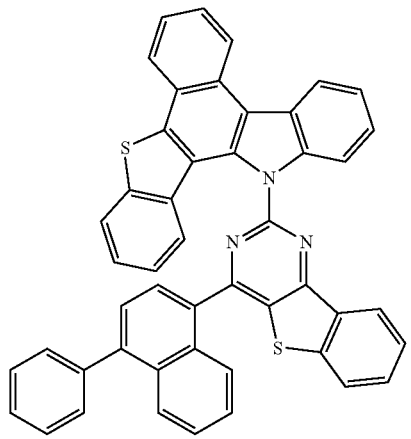
1-3-1-S-(12)
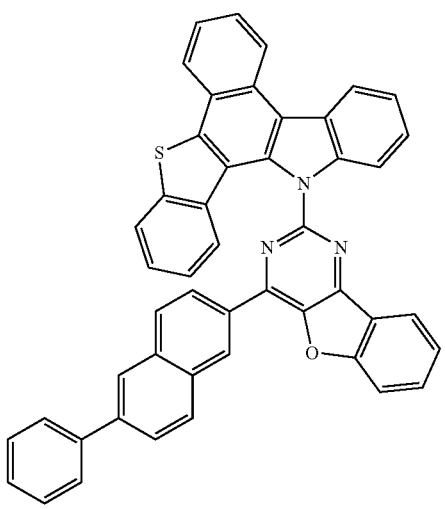
1-3-1-S-(13)
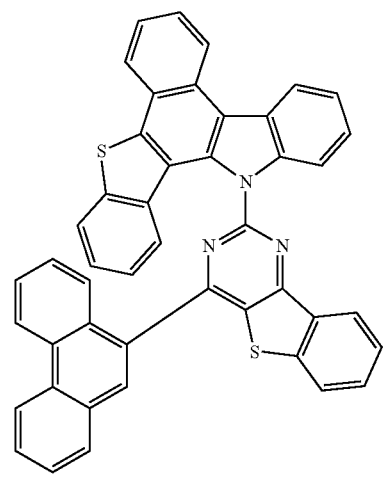
1-3-1-S-(14)
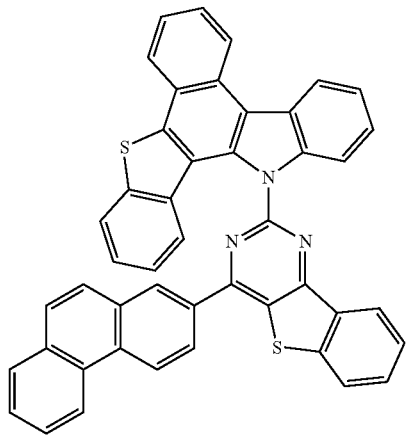
1-3-1-S-(15)
1-3-1-S-(16)
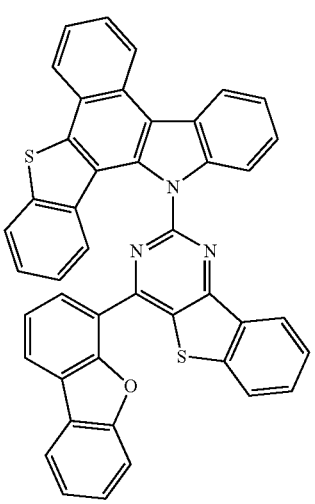

1-3-1-S-(17)
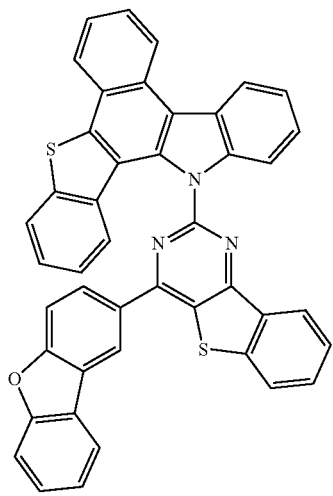
1-3-1-S-(18)
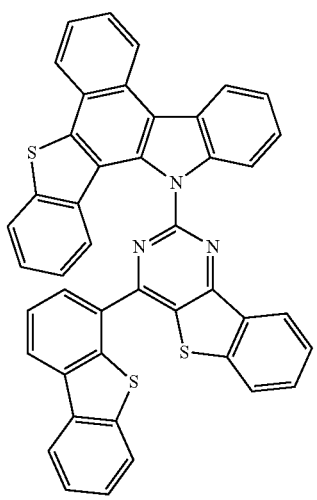
1-3-1-S-(19)
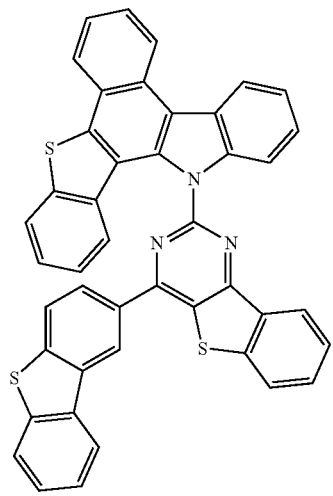
1-3-1-S-(20)
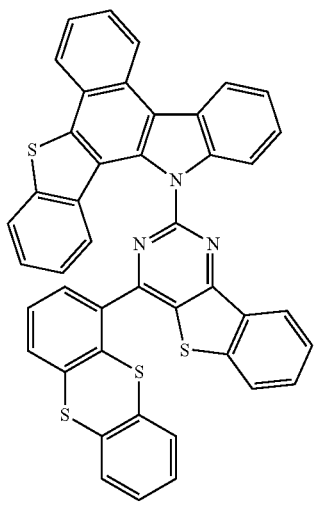
1-3-1-O-(21)
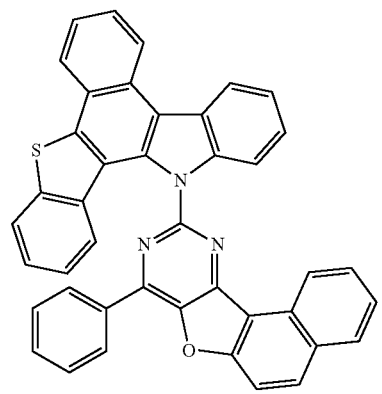
1-3-1-O-(22)
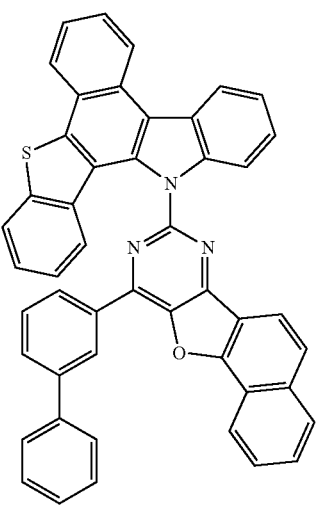

-continued
1-3-1-S-(21)
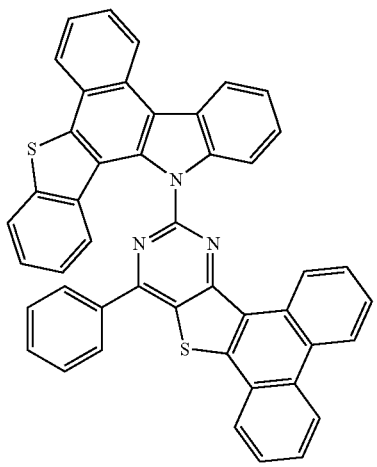
1-3-1-S-(22)
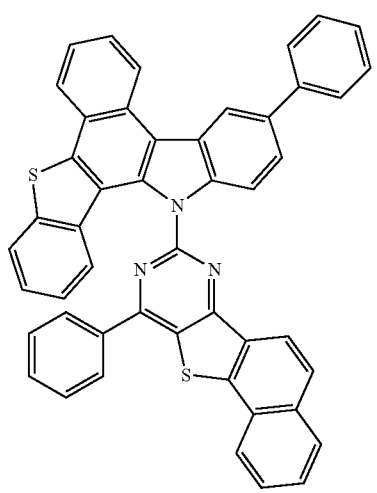
1-3-1-S-(23)
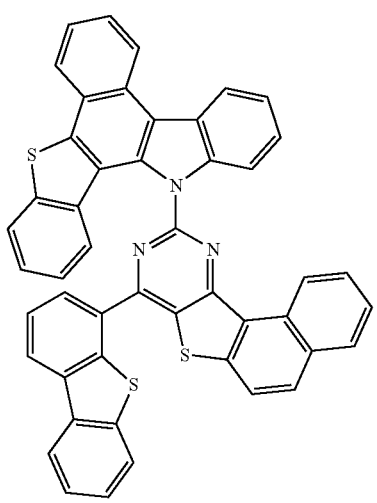
-continued
1-3-2-O-(1)
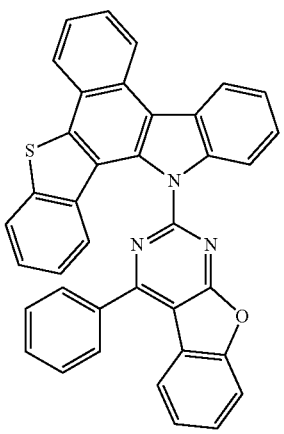
1-3-2-O-(2)
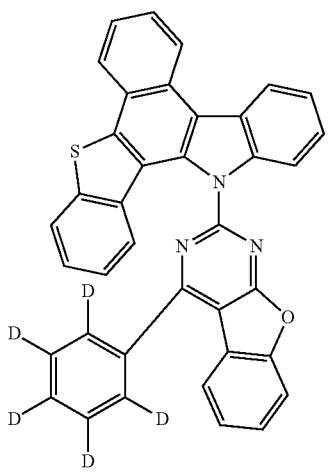
1-3-2-O-(3)
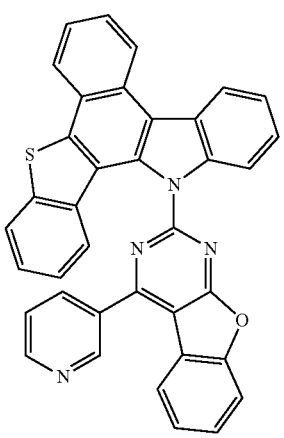

171
-continued
1-3-2-O-(4)
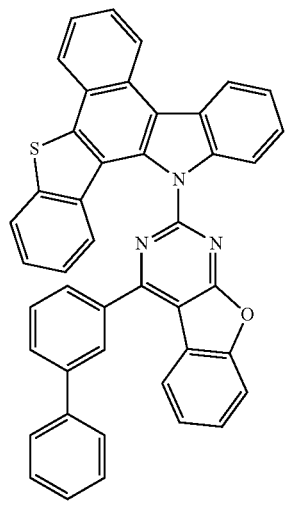
1-3-2-O-(5)
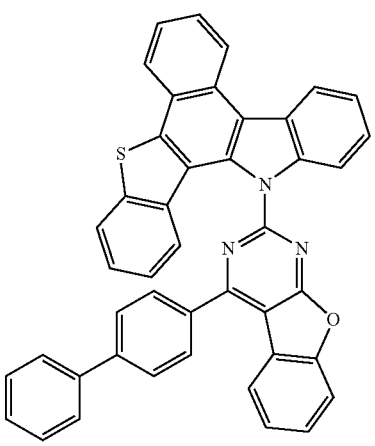
1-3-2-O-(6)
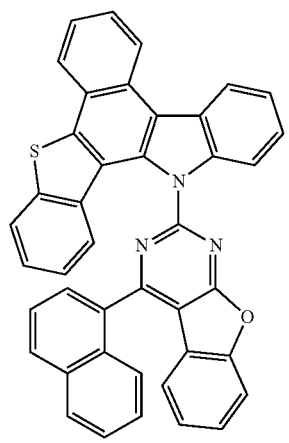
172
-continued
1-3-2-O-(7)
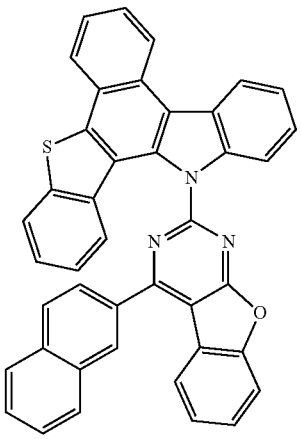
1-3-2-O-(8)
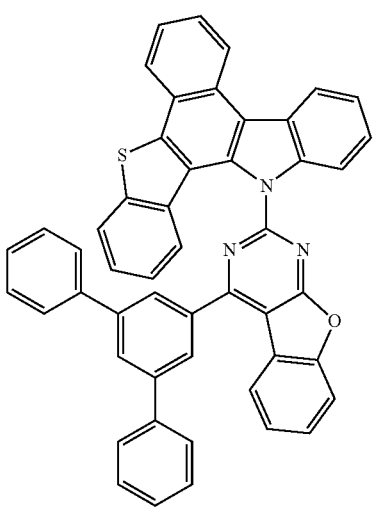
1-3-2-O-(9)
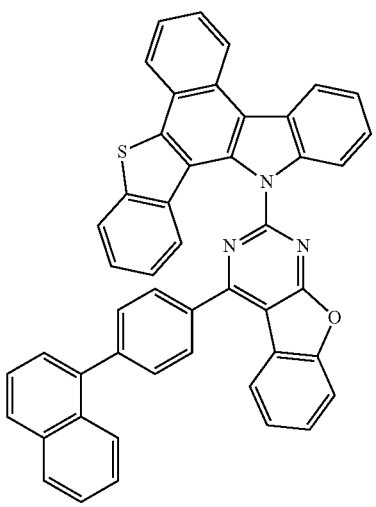

173
-continued
1-3-2-O-(10)
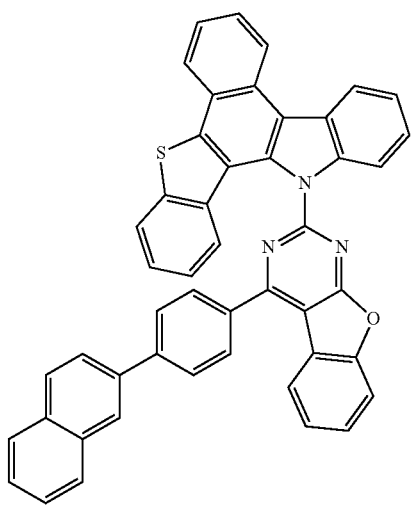
1-3-2-O-(11)
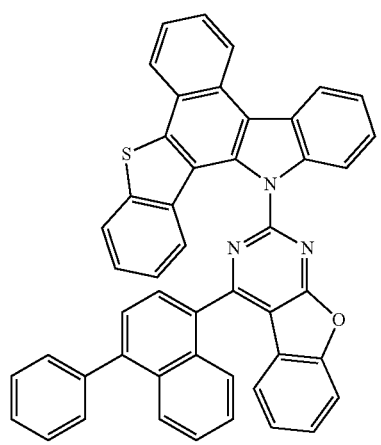
1-3-2-O-(12)
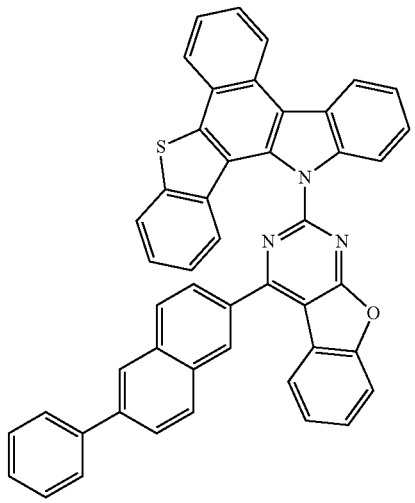
174
-continued
1-3-2-O-(13)
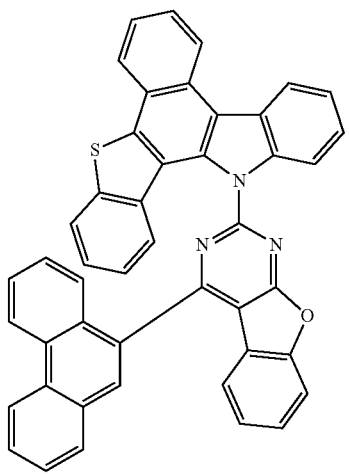
1-3-2-O-(14)
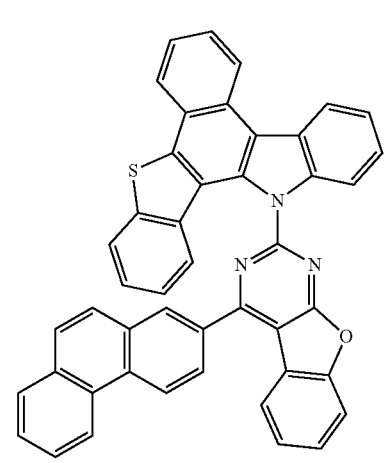
1-3-2-O-(15)
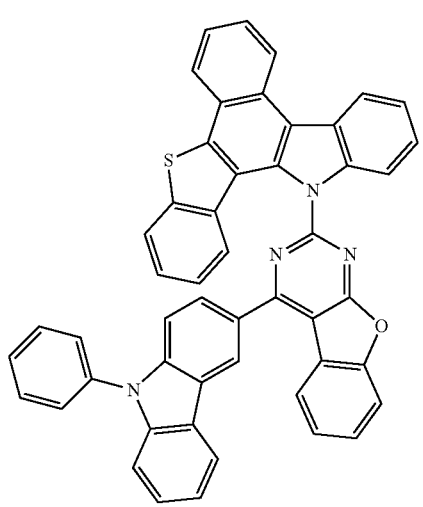

-continued
1-3-2-O-(16)
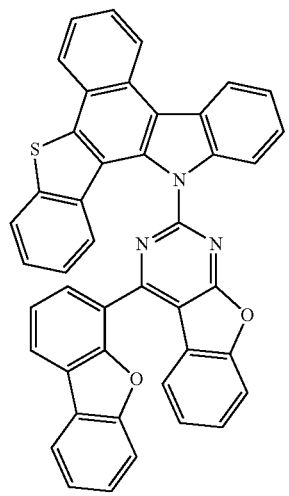
1-3-2-O-(17)
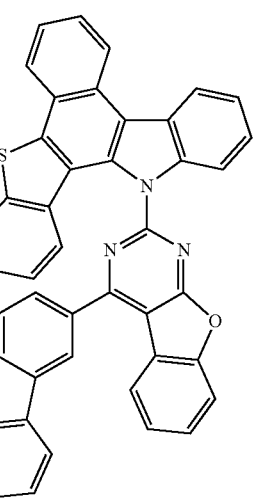
1-3-2-O-(18)
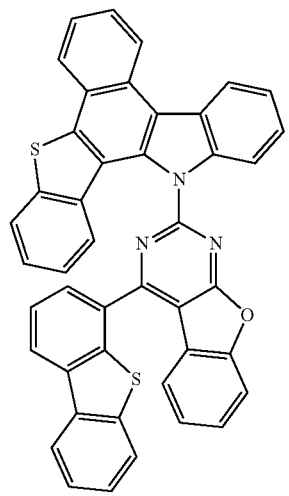
-continued
1-3-2-O-(19)
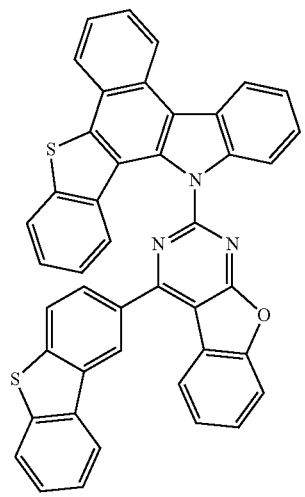
1-3-2-S-(20)
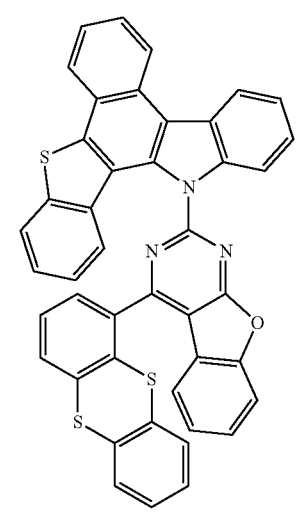
1-3-2-S-(1)
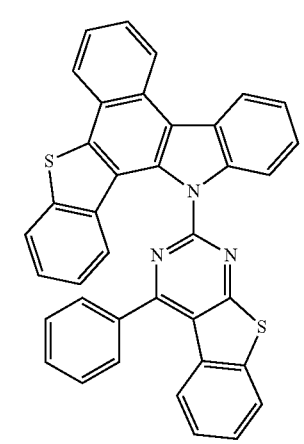

1-3-2-S-(2)
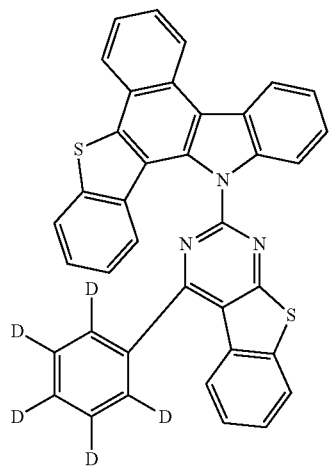
1-3-2-S-(3)
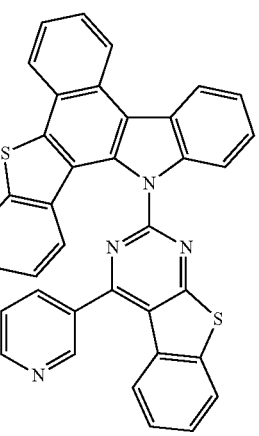
1-3-2-S-(4)
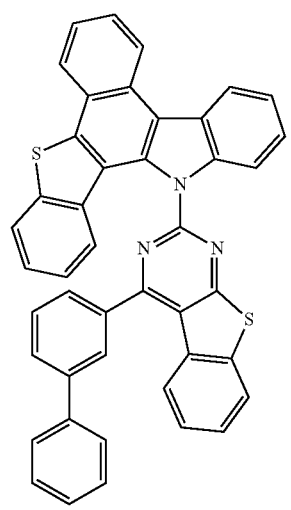
1-3-2-S-(5)
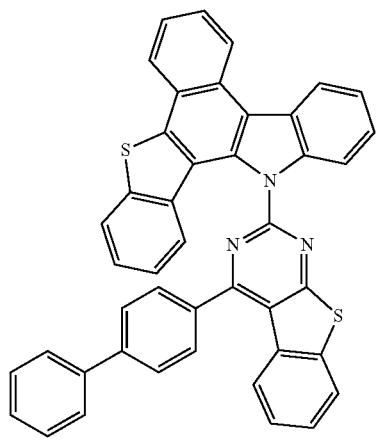
1-3-2-S-(6)
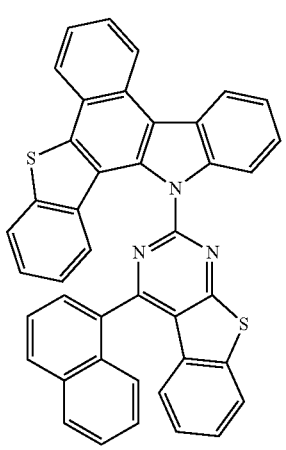
1-3-2-S-(7)
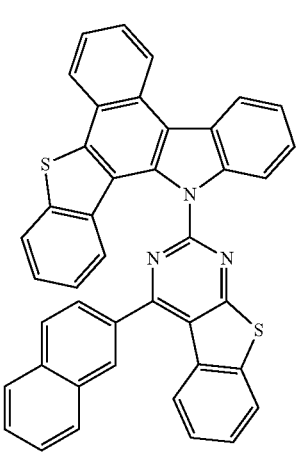

1-3-2-S-(8)
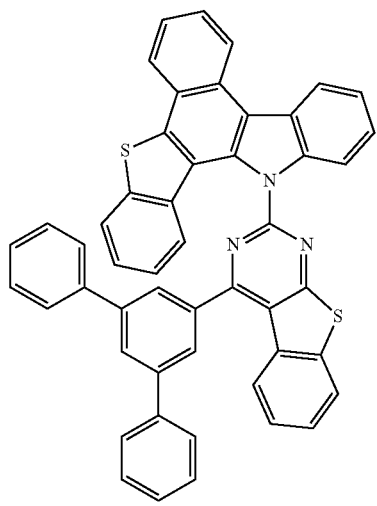
1-3-2-S-(11)
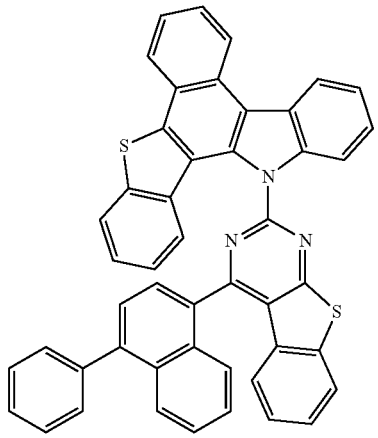
1-3-2-S-(9)
1-3-2-S-(12)
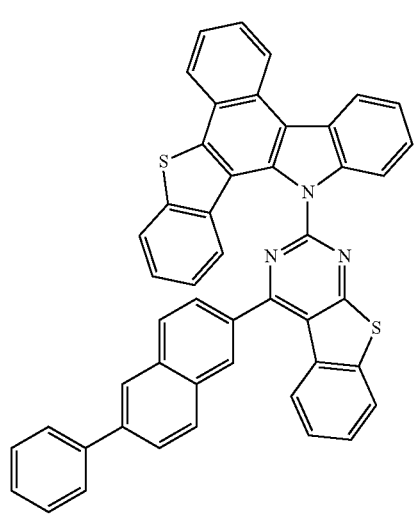
1-3-2-S-(10)
1-3-2-S-(13)
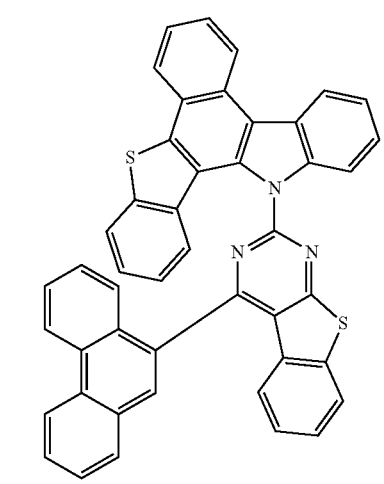

1-3-2-S-(14)
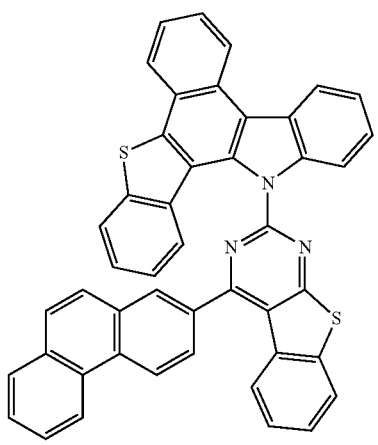
1-3-2-S-(15)
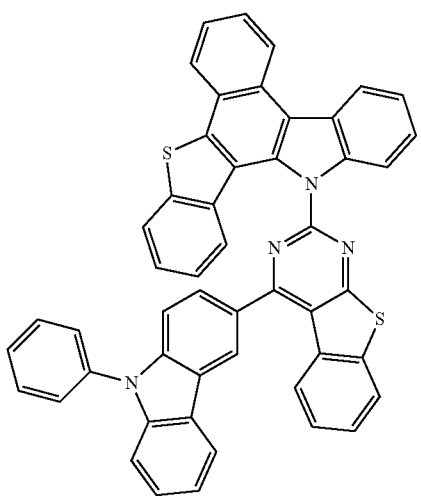
1-3-2-S-(16)
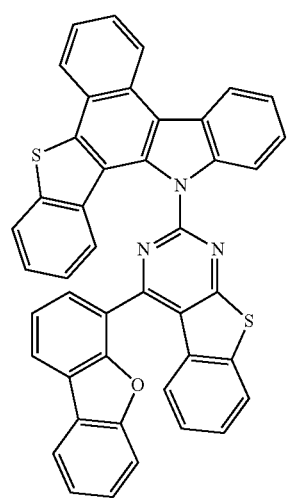
1-3-2-S-(17)
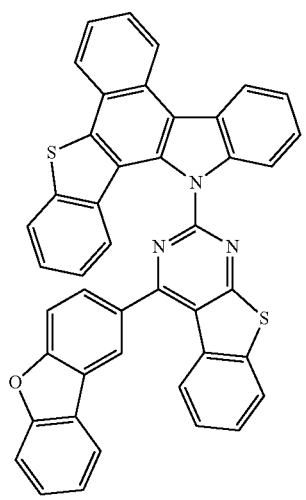
1-3-2-S-(18)
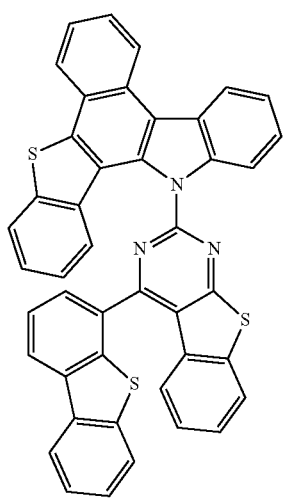
1-3-2-S-(19)
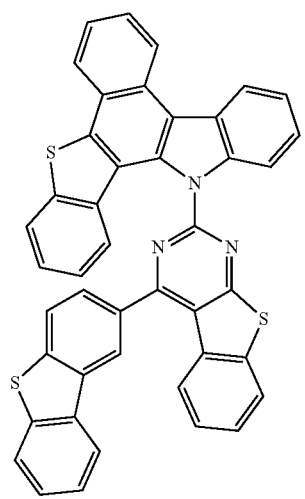

1-3-2-O-(20)
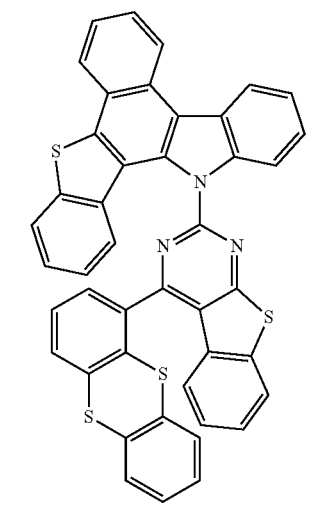
1-3-2-O-(21)
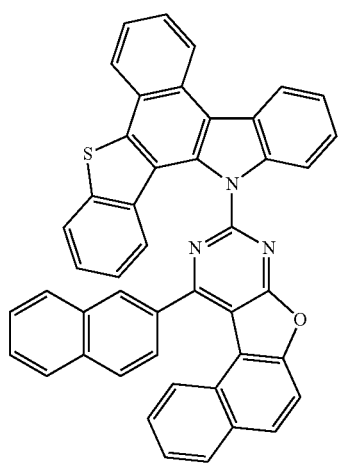
1-3-2-O-(22)
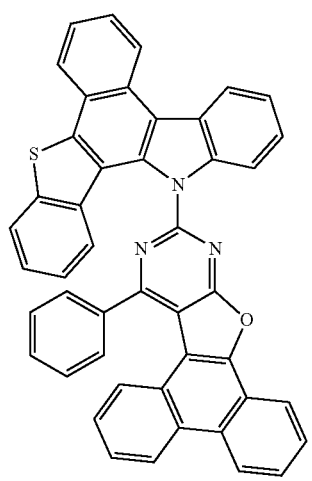
1-3-2-S-(21)
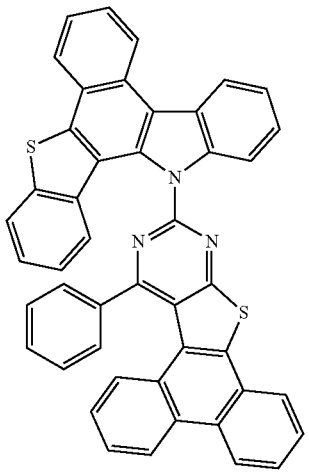
1-3-2-S-(22)
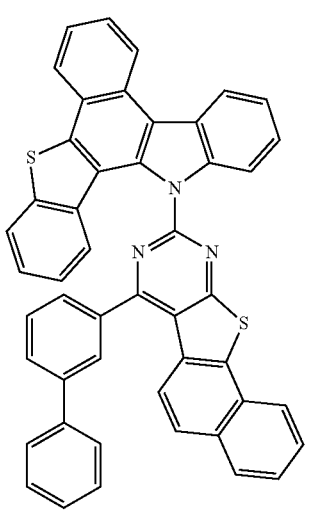
1-3-2-S-(23)
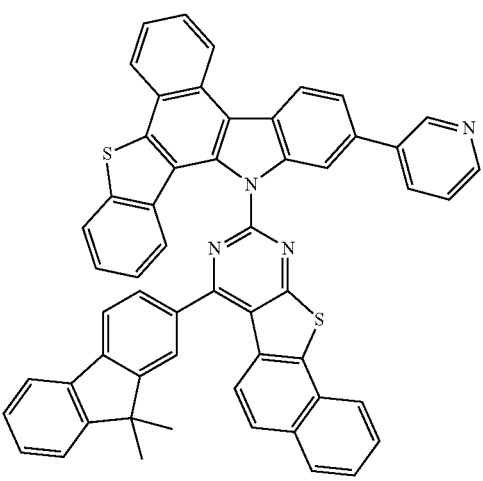
In another aspect of the present invention, the present invention provides an organic electric element, wherein an emission-auxiliary layer of an organic material layer comprises the compound represented by formula 1 above, a hole transport layer of the organic material layer comprises the compound represented by the following formula 8, and a light emitting layer of the organic material layer comprises the compound represented by formula 2 above.

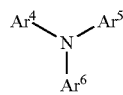
<Formula 8>

In formula 8 above, each of symbols may be defined as follows.

$Ar^4$ and $Ar^5$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group and -L'-N($R^a$)($R^b$).

When $Ar^4$ and $Ar^5$ are an aryl group, $Ar^4$ and $Ar^5$ may be preferably a $C_6$-$C_{30}$ aryl group, more preferably a $C_6$-$C_{12}$ aryl group, for example, may be phenyl, naphthyl, biphenyl, etc.; when $Ar^4$ and $Ar^5$ are a heterocyclic group, $Ar^4$ and $Ar^5$ may be preferably a $C_2$-$C_{30}$ heterocyclic group, more preferably a $C_2$-$C_{12}$ heterocyclic group, for example, may be dibenzothiophene, dibenzofuran, etc.; when $Ar^4$ and $Ar^5$ are a fluorenyl group, for example, $Ar^4$ and $Ar^5$ may be 9,9-dimethyl-9H-fluorene, 9,9-diphenyl-9H-fluorenyl, 9,9'-spirobifluorene and the like, and when $Ar^4$ and $Ar^5$ are -L'-N($R^a$)($R^b$), $Ar^4$ and $Ar^5$ may be, for example, a diphenylamine group.

$Ar^6$ is any one of the following 8-1, 8-2 and 8-3.

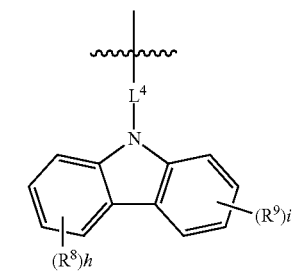
<Formula 8-1>

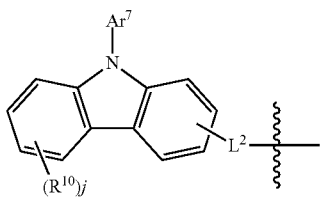
<Formula 8-2>

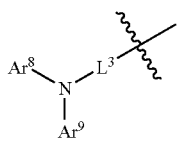
<Formula 8-3>

In formulas 8-1, 8-2 and 8-3 above, each of symbols may be defined as follows.

$Ar^7$, $Ar^8$ and $Ar^9$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group and -L'-N($R^a$)($R^b$).

When $Ar^7$, $Ar^8$ and $Ar^9$ are an aryl group, $Ar^7$, $Ar^8$ and $Ar^9$ may be preferably a $C_6$-$C_{30}$ aryl group, more preferably a $C_6$-$C_{12}$ aryl group, for example, phenyl, naphthyl, biphenyl, etc.; when $Ar^7$, $Ar^8$ and $Ar^9$ are a heterocyclic group, $Ar^7$, $Ar^8$ and $Ar^9$ may be preferably a $C_2$-$C_{30}$ heterocyclic group, more preferably a $C_2$-$C_{12}$ heterocyclic group, for example, may be dibenzothiophene, dibenzofuran, etc.; when $Ar^7$, $Ar^8$ and $Ar^9$ are a fluorenyl group, for example, $Ar^7$, $Ar^8$ and $Ar^9$ may be 9,9-dimethyl-9H-fluorene, 9,9-diphenyl-9H-fluorenyl, 9,9'-spirobifluorene and the like.

$R^8$ to $R^{10}$ are each independently selected from the group consisting of deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and -L'-N($R^a$)($R^b$).

In addition, Any two adjacent groups of $R^8$ to $R^{10}$ can be optionally linked together to form at least one ring, and remaining groups not forming a ring are the same as defined above.

For example, when h and i are each an integer of 2, neighboring $R^8$s can be linked to each other to form a ring, and even though there are neighboring $R^9$s, $R^9$s may be each independently an aryl group or a heterocyclic ring. When neighboring $R^8$s, $R^9$s, and/or $R^{10}$s are linked to each other to form a ring, the ring may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring, for example, the ring may be a benzene and thus naphthalene or phenanthrene can be formed together with the benzene ring to which they are bonded.

When $R^8$ to $R^{10}$ are an aryl group, $R^8$ to $R^{10}$ may be preferably a $C_6$-$C_{30}$ aryl group, more preferably a $C_6$-$C_{12}$ aryl group, for example, phenyl, etc.; when $R^8$ to $R^{10}$ are a heterocyclic group, $R^8$ to $R^{10}$ may be preferably a $C_2$-$C_{30}$ heterocyclic group, more preferably a $C_2$-$C_{12}$ heterocyclic group, for example, carbazole and the like.

h, i and j are each independently an integer of 0 to 4, when h, i and j are each an integer of 2 or more, a plurality of $R^8$s to $R^{10}$s may be each the same or different from each other, $L^2$ may be each independently selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

When $L^2$ is an arylene group, $L^2$ may be preferably a $C_6$-$C_{30}$ arylene group, more preferably a $C_6$-$C_{12}$ arylene group, for example, may be phenyl, biphenyl and the like.

$L^2$ to $L^4$ may be each independently selected from the group consisting of a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, When $L^3$ and $L^4$ are an arylene group, $L^3$ and $L^4$ may be preferably a $C_6$-$C_{30}$ arylene group, more preferably a $C_6$-$C_{12}$ arylene group, for example, may be biphenyl and the like, when L³ and L⁴ are a fluorenyl group, L³ and L⁴ may be, for example, 9,9-dimethyl-9H-fluorene, 9,9-diphenyl-9H-fluorenyl and the like.

In -L'-N(Rᵃ)(Rᵇ) of Ar⁴, Ar⁵, Ar⁷ to Ar⁹, R⁸ to R¹⁰, L' is selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and Rᵃ and Rᵇ are each independently selected from the group consisting of a $C_6$-$C_{60}$ aryl group, a fluorenyl group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and the aryl group, heterocyclic group, fluorenyl group, alkyl group, alkenyl group, fused ring group, alkoxyl group, aryloxly group, arylene group, fluorenylene group, aliphatic hydrocarbon group of Ar⁴-Ar⁵, Ar⁷-Ar⁹, R⁸-R¹⁰, R', R'', L², L³, L', Rᵃ and Rᵇ may be each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

Specifically, the compound represented by Formula 8 may be any one of the following compounds.

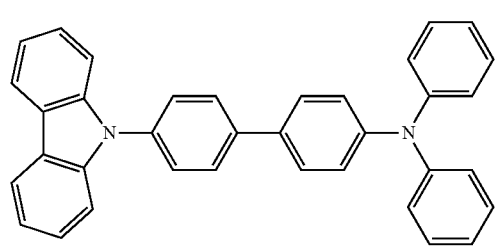

8-1

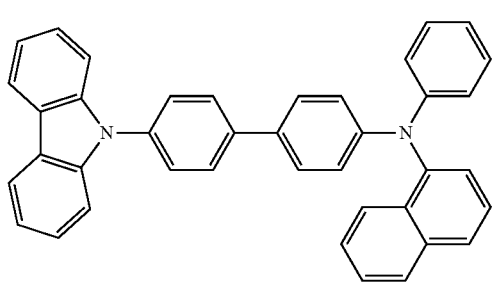

8-2

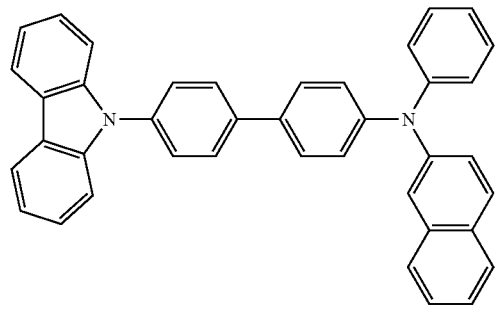

8-3

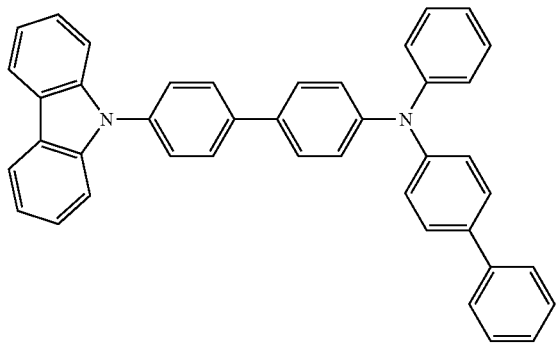

8-4

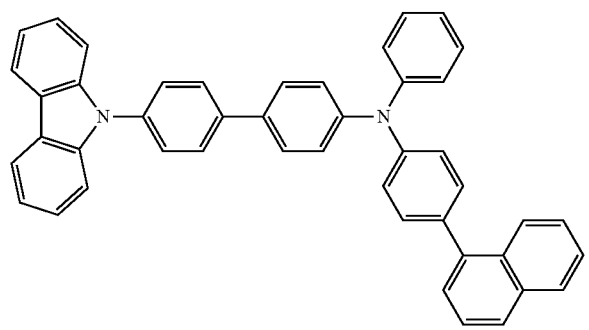

8-5

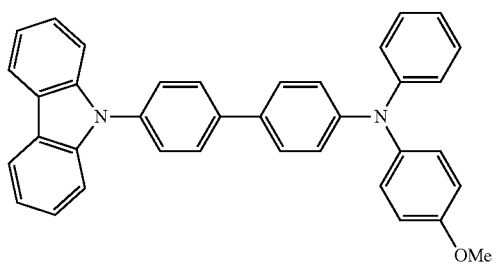

8-6

-continued
8-7
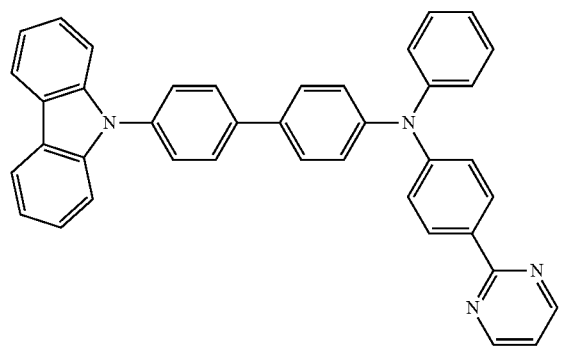
8-8
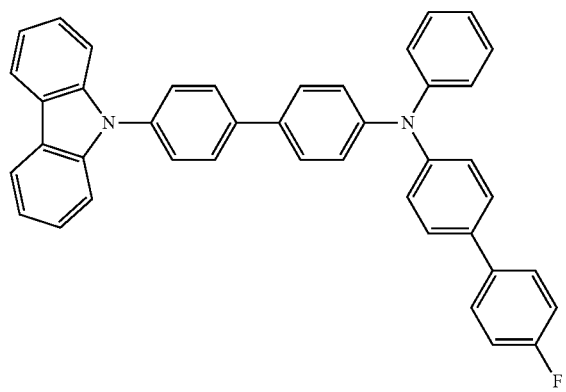
8-9
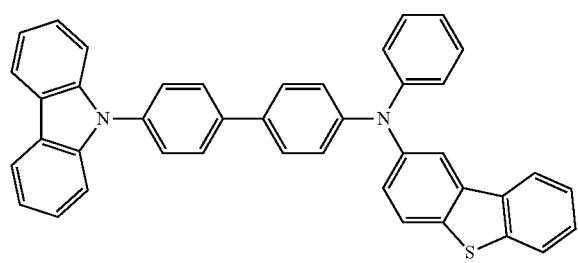
8-10
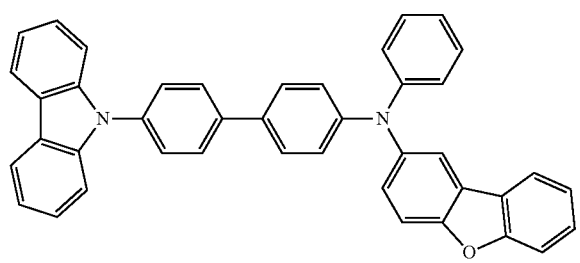
8-11
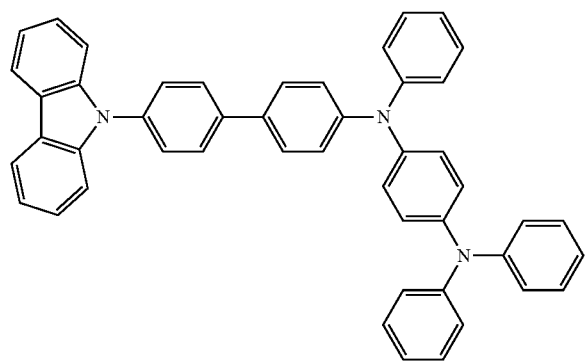
8-12
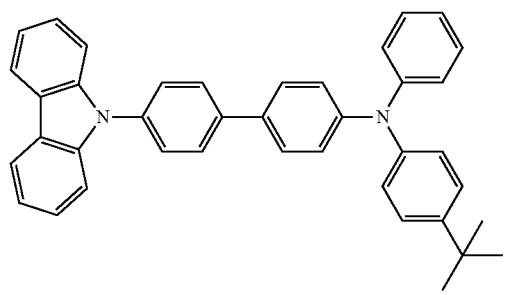
8-13
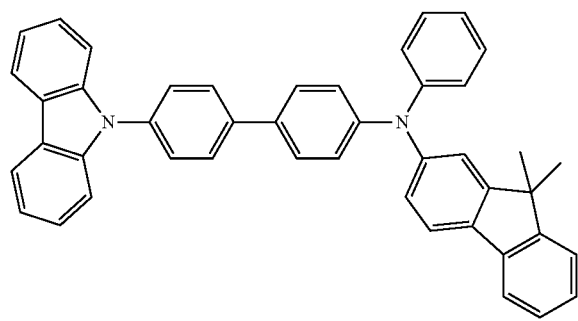
8-14
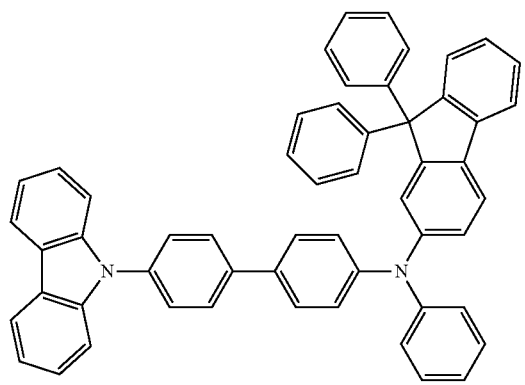

-continued
8-15
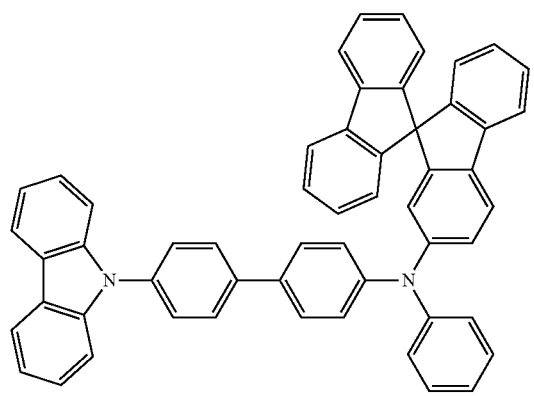
8-16
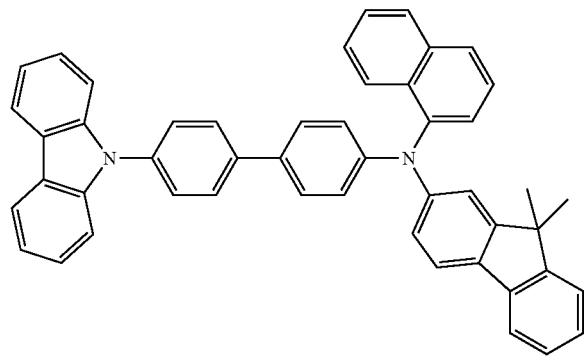
8-17
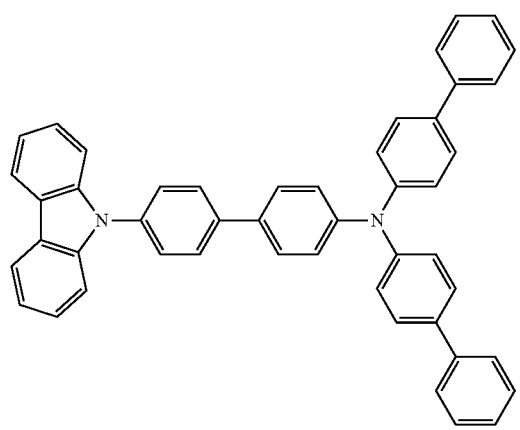
8-18
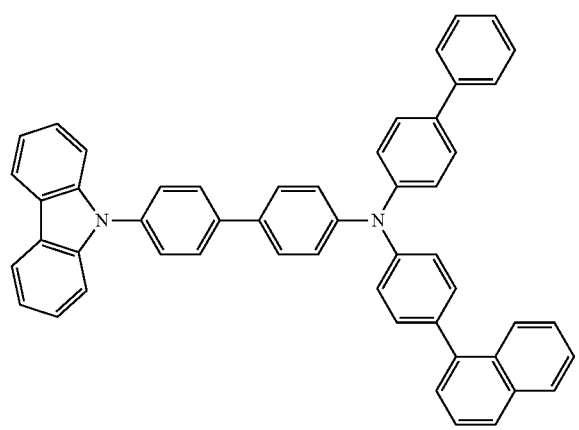
8-19
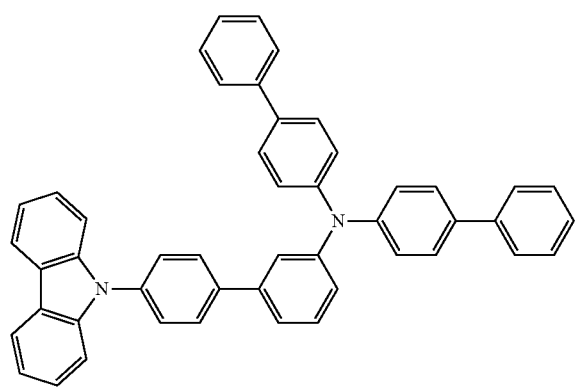
8-20
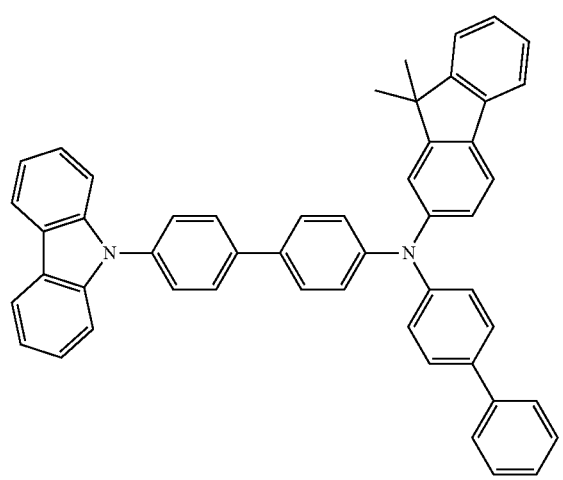

-continued
8-21
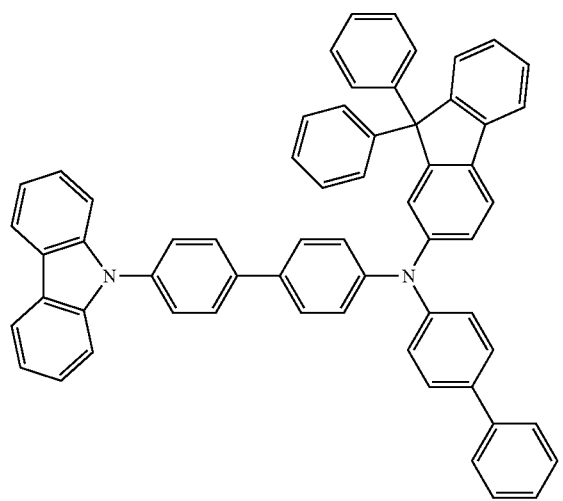
8-22
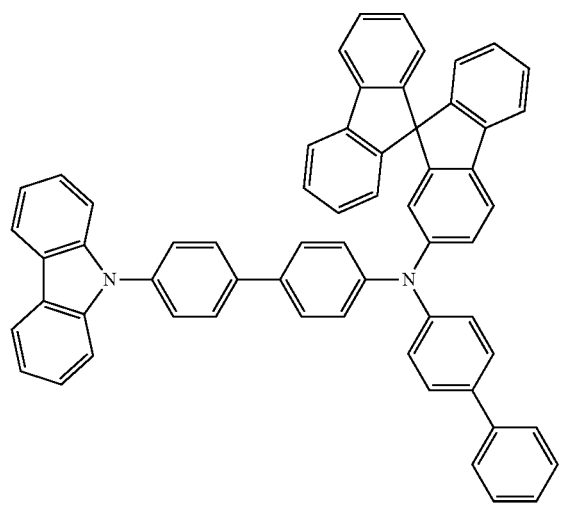
8-23
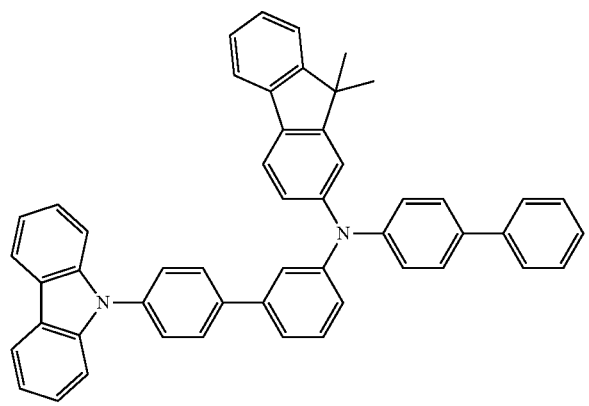
8-24
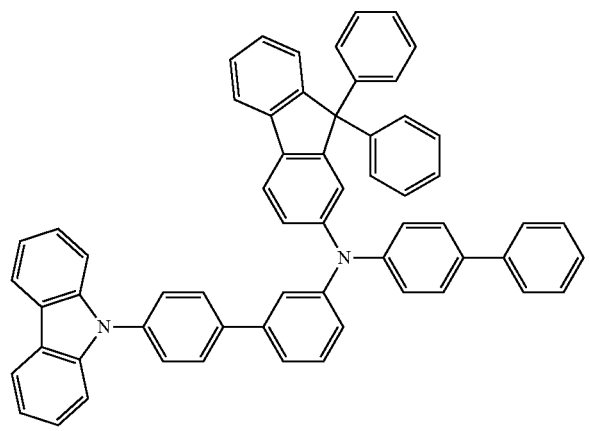
8-25
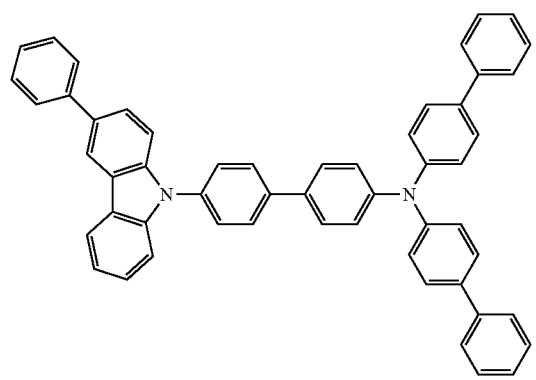
8-26
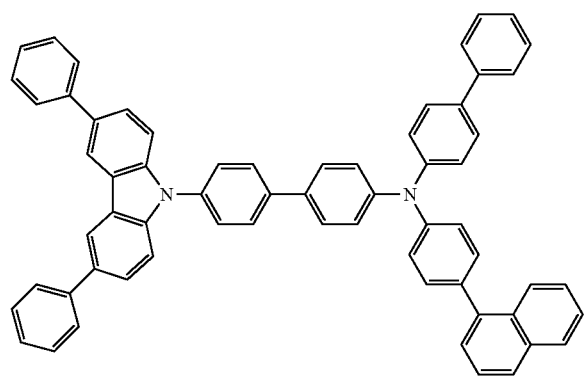

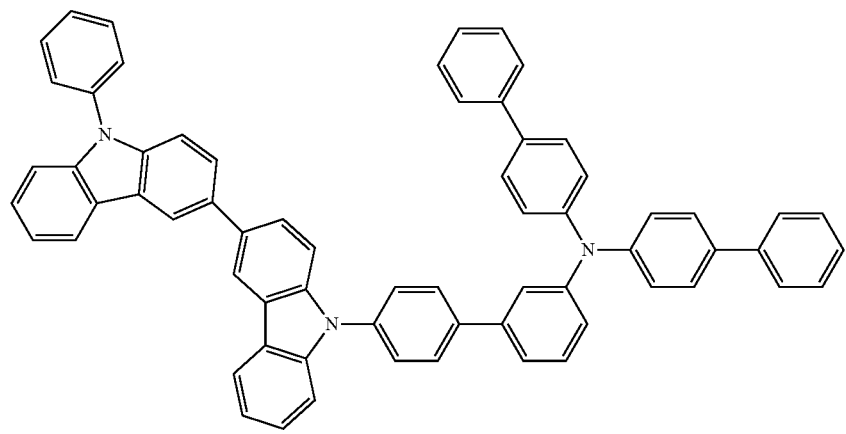
8-27
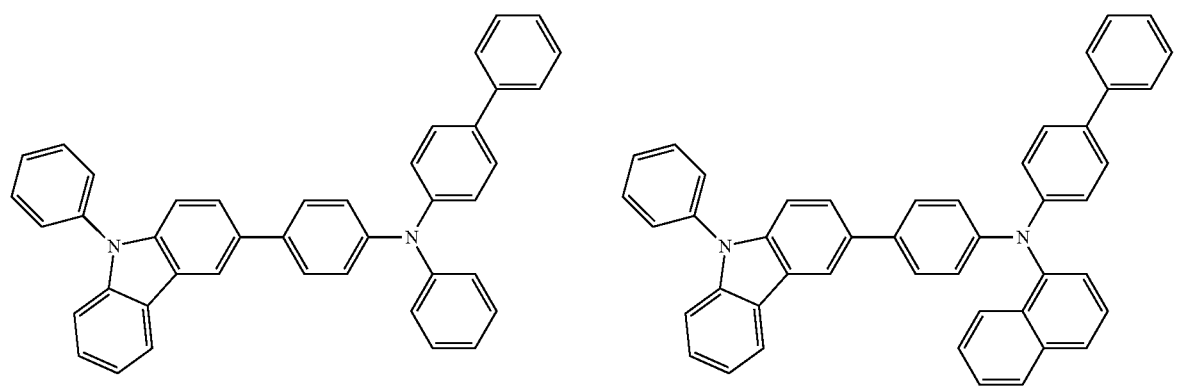
8-28
8-29
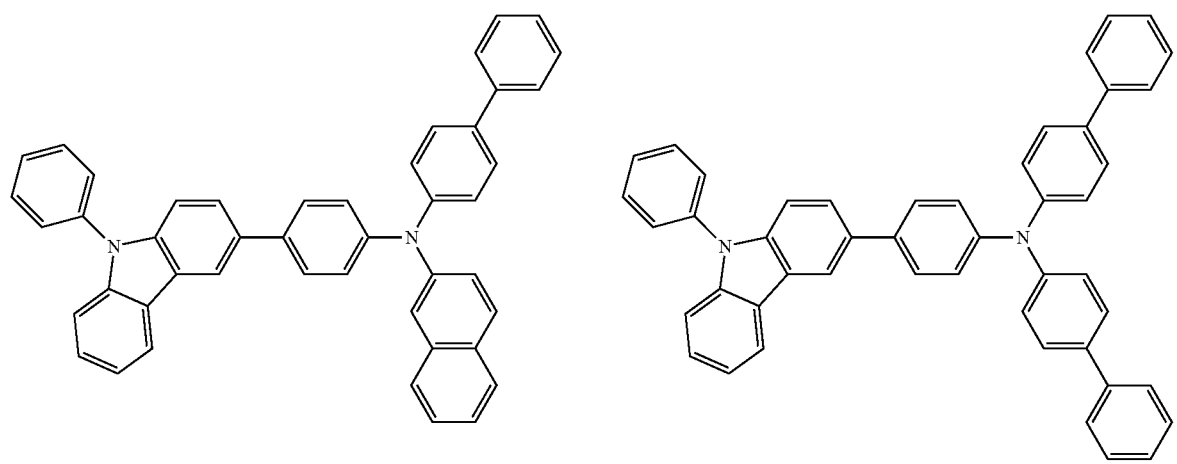
8-30
8-31

-continued
8-32
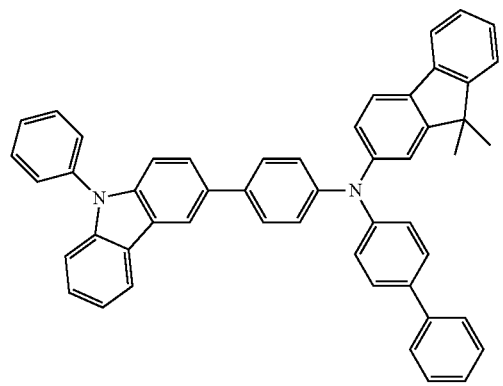
8-33
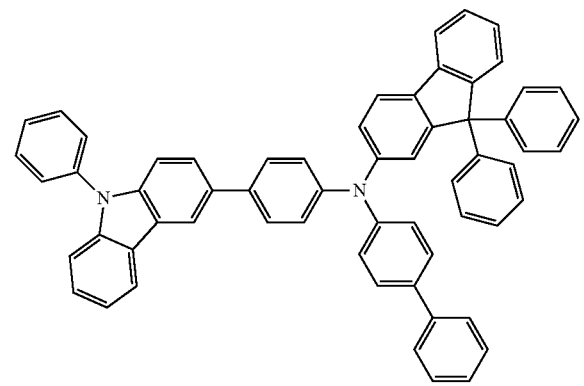
8-34
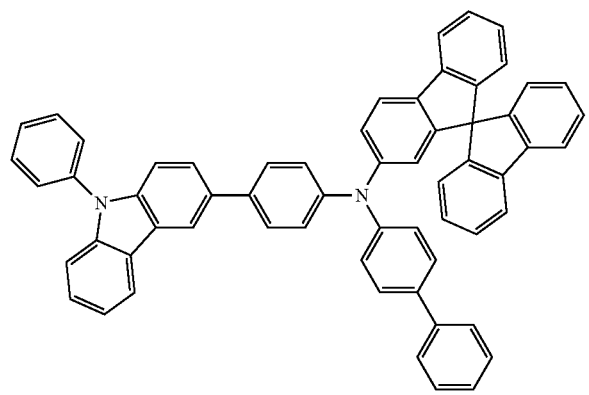
8-35
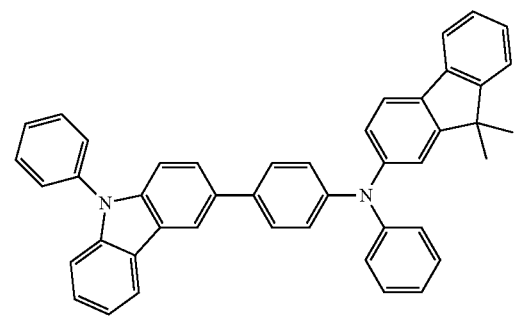
8-36
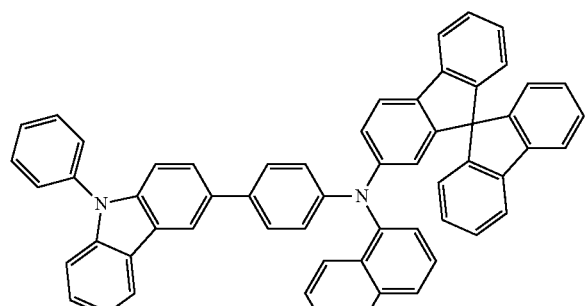
8-37
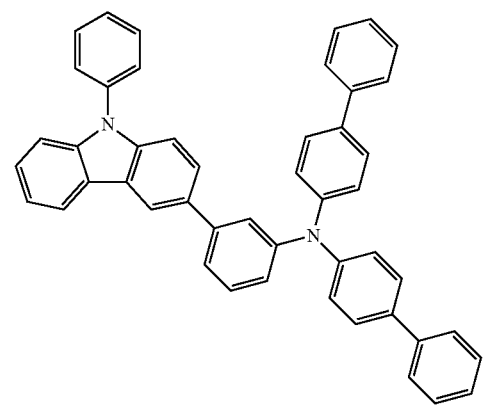

-continued
8-38
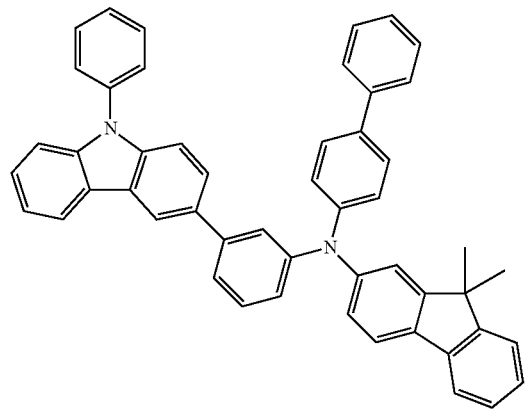
8-39
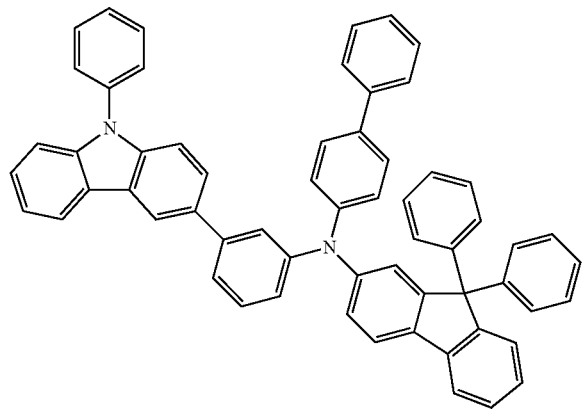
8-40
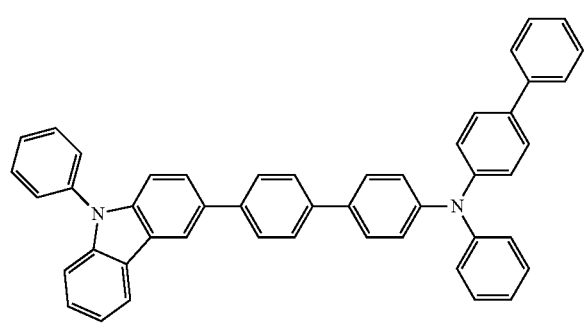
8-41
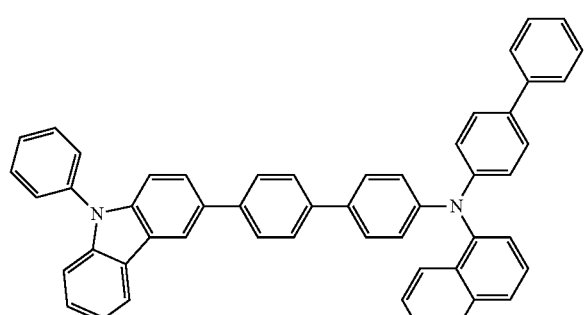
8-42
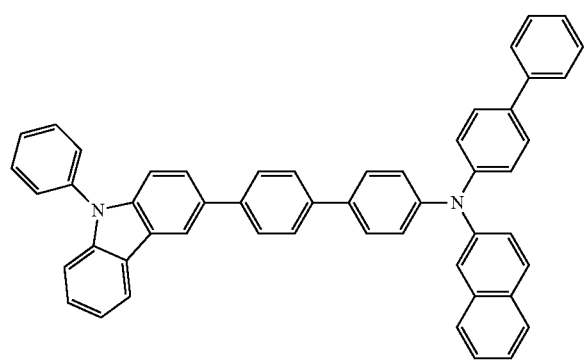
8-43
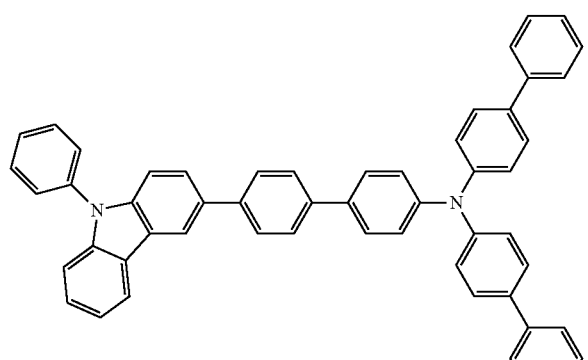
8-44
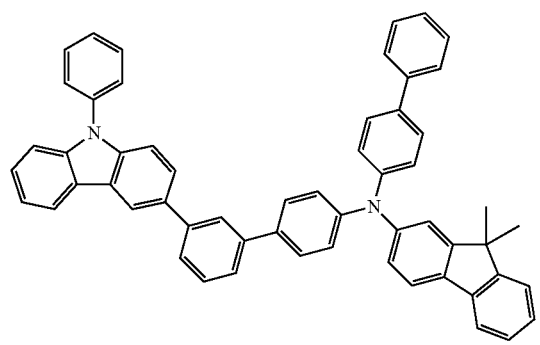
8-45
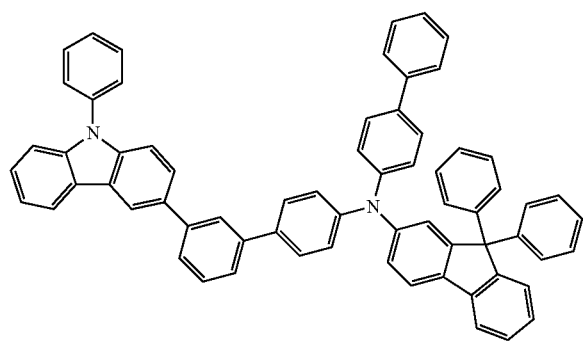

-continued
8-46
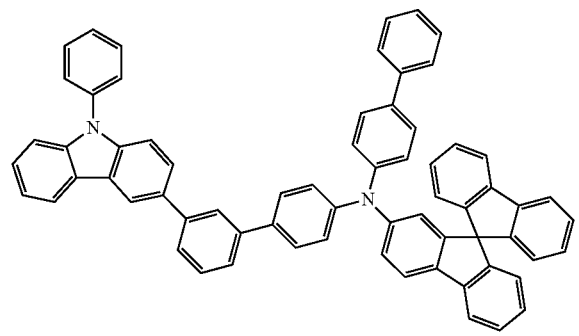
8-47
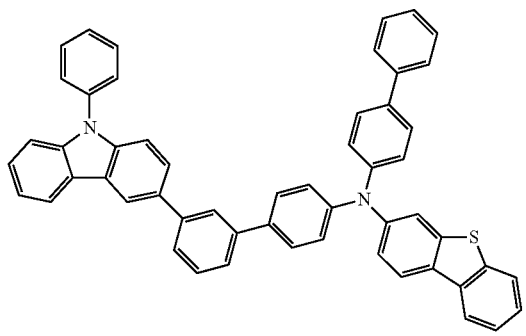
8-48
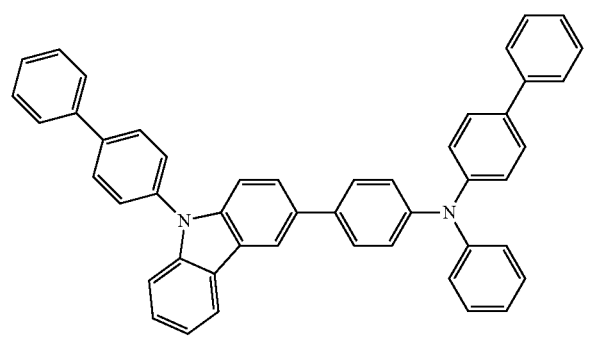
8-49
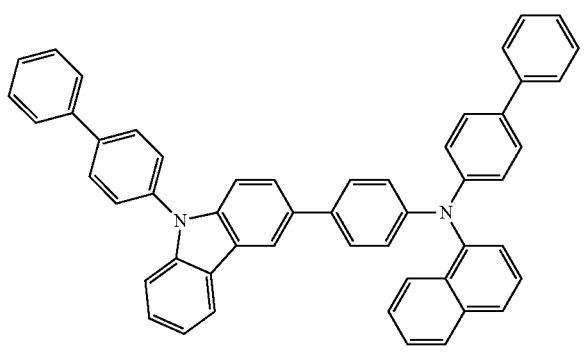
8-50
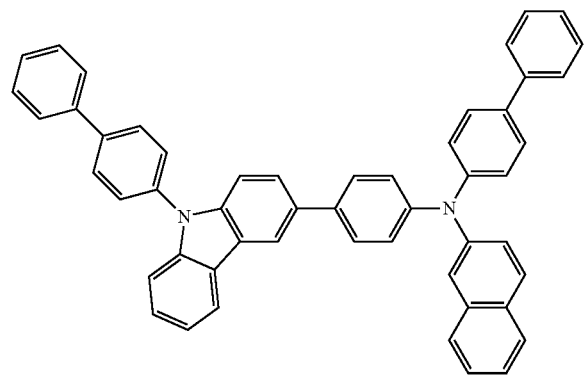
8-51
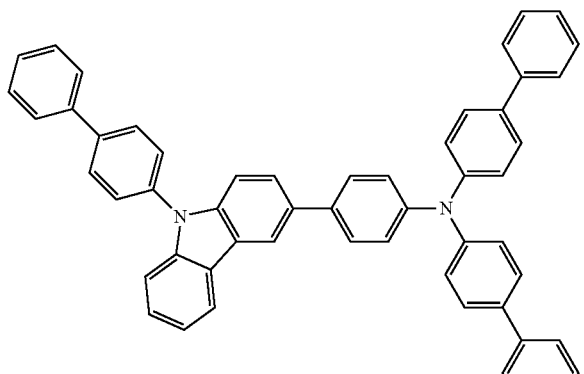
8-52
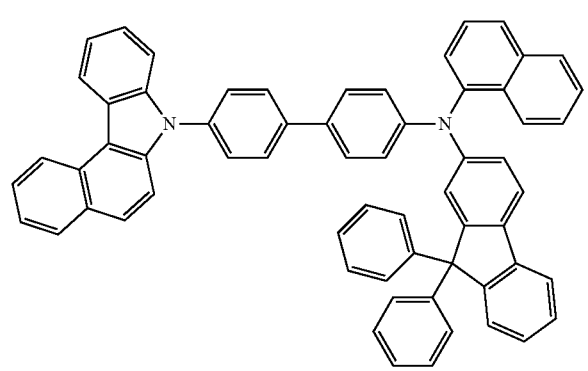
8-53
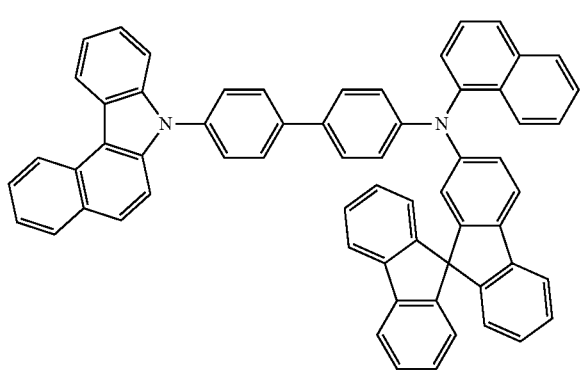

-continued
8-54
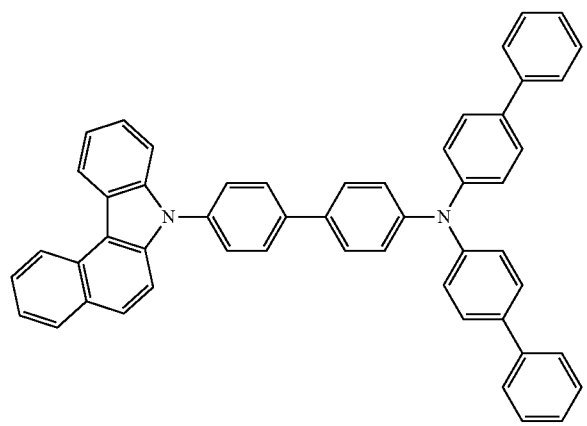
8-55
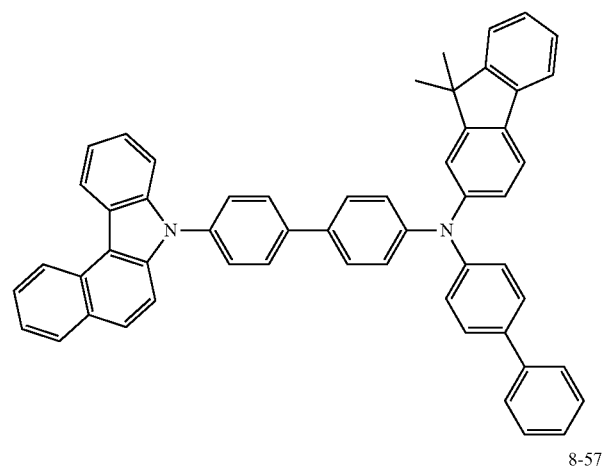
8-56
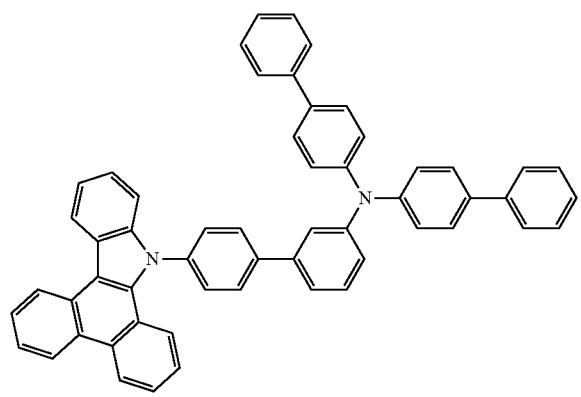
8-57
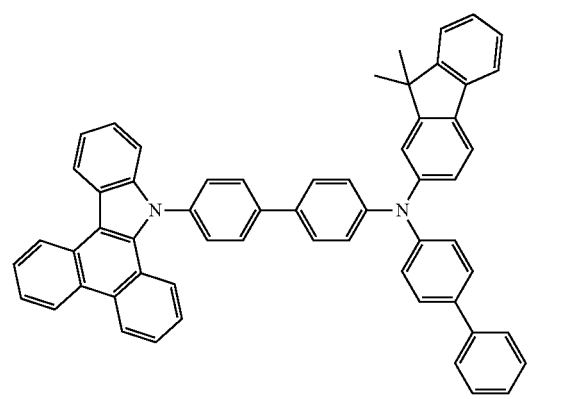
8-58
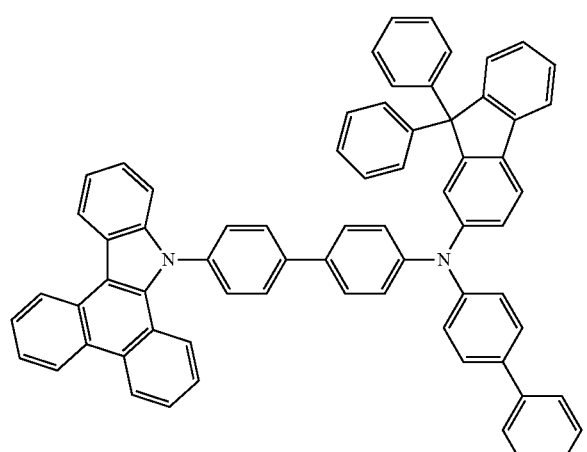
8-59
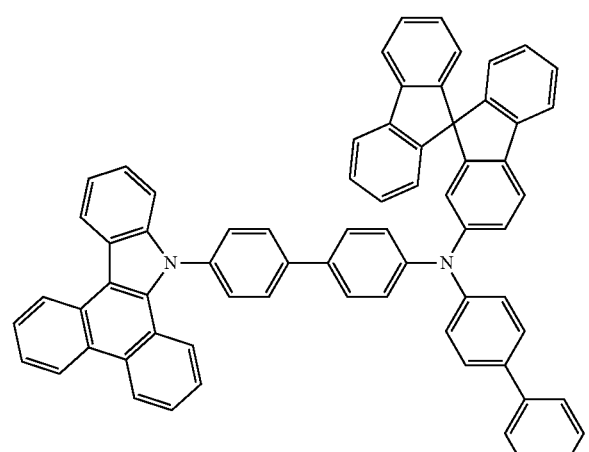
8-60
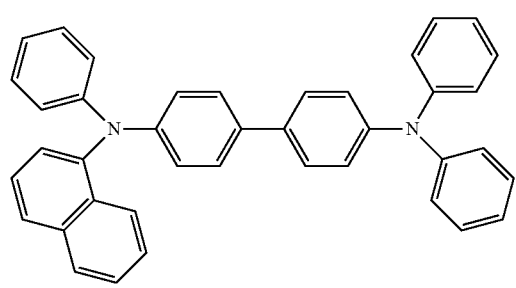
8-61

-continued
8-62
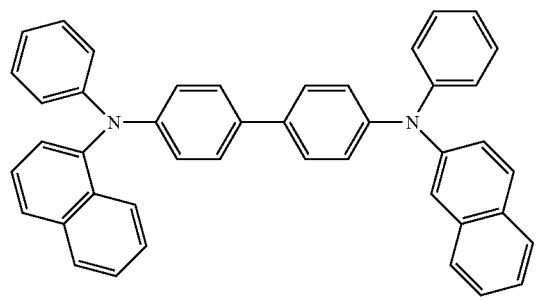
8-63
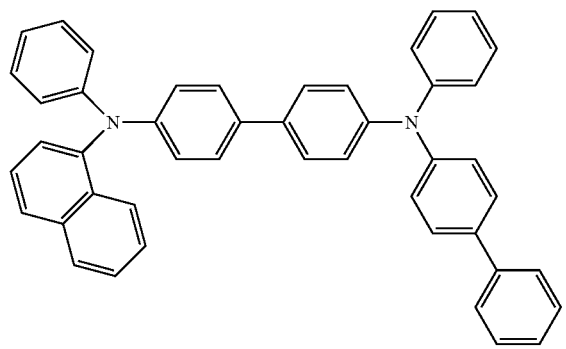
8-64
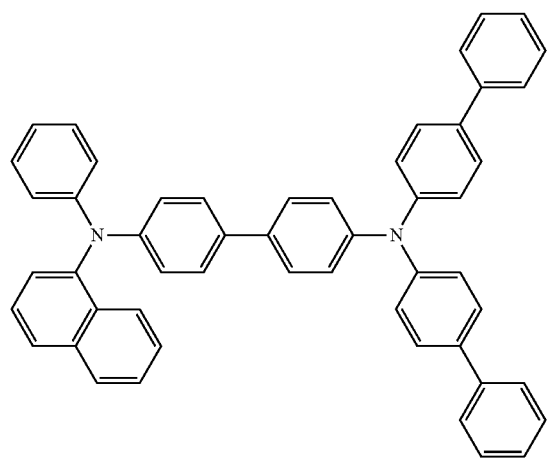
8-65
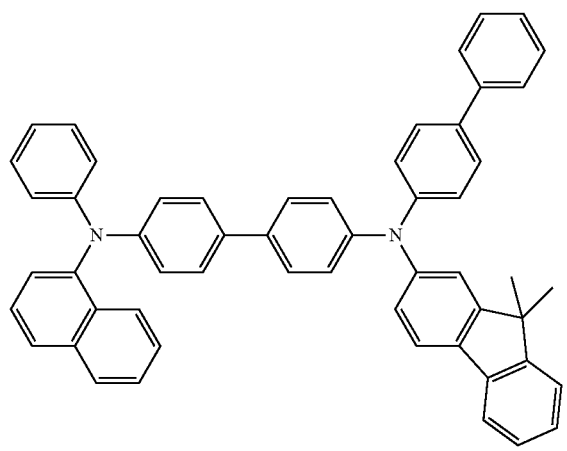
8-66
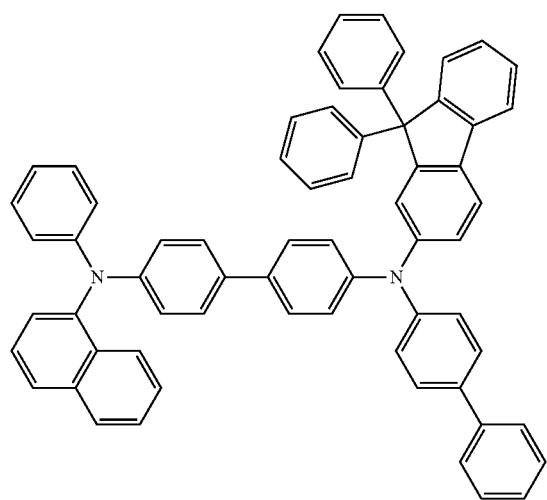
8-67
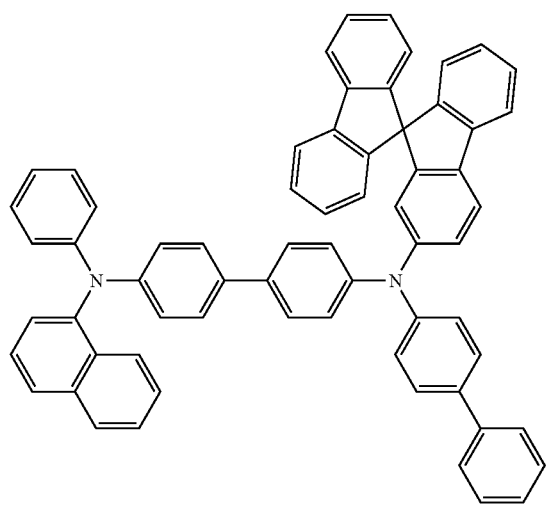

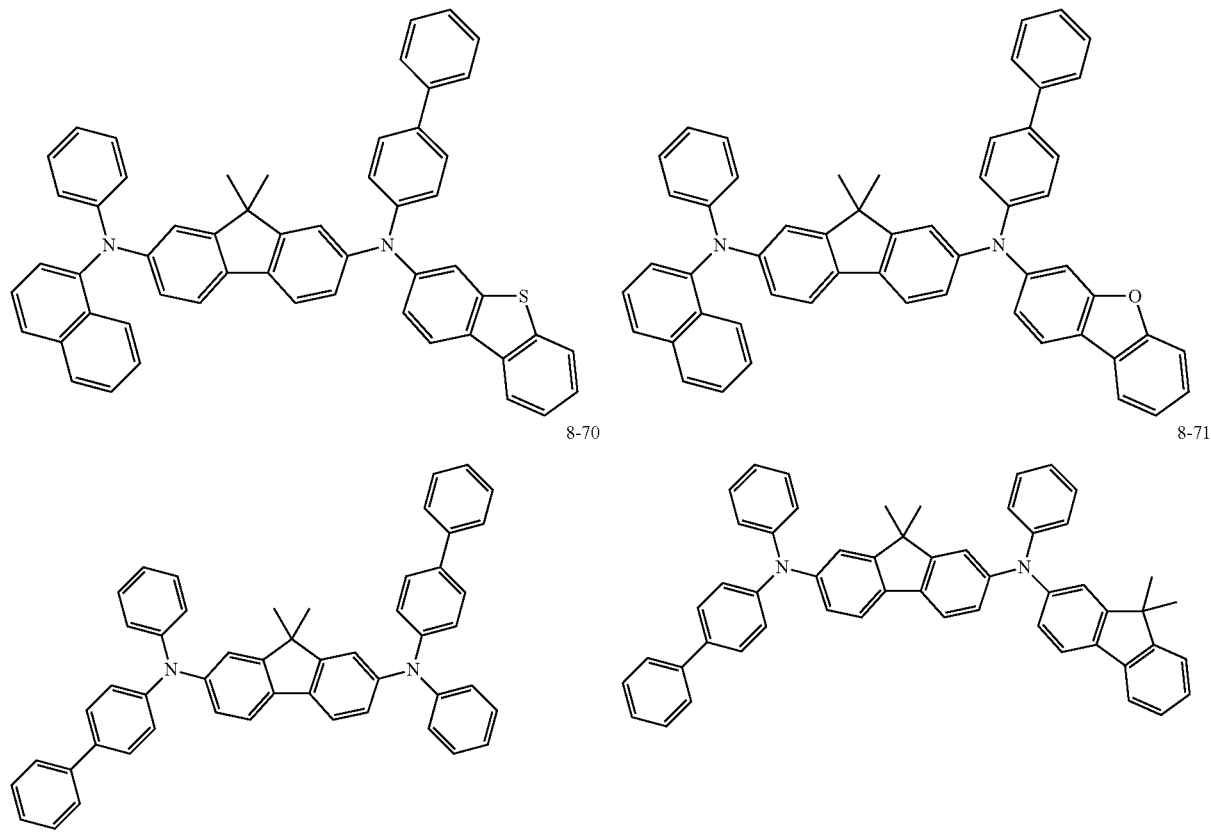

In another aspect of the present invention, the compound comprised in the hole transport layer and/or the emission-auxiliary layer may be a single compound or a mixture of two or more kinds represented by Formulas above. That is, the hole transport layer may comprise a single compound or a mixture of two or more kinds represented by Formula 1 or 8, the emission-auxiliary layer may comprise a single compound or a mixture of two or more kinds represented by Formula 1, and a light emitting layer may comprise a single compound or a mixture of two or more kinds represented by Formula 2.

In another aspect of the present invention, the present invention provides an organic electric element further including at least a layer to improve luminous efficiency which is formed on at least one of the sides the first and second electrodes, which is opposite to the organic material layer.

Hereinafter, Synthesis method of the compound represented by Formula 1 according to one embodiment of the present invention and preparation method of an organic electric element will be described in detail by way of examples. However, the present invention is not limited to the following examples.

SYNTHESIS EXAMPLE

Synthesis Example 1

Final products represented by Formula 1 according to the present invention are synthesized by reacting Sub 1 and Sub 2 as shown in Reaction Scheme 1, but are not limited thereto.

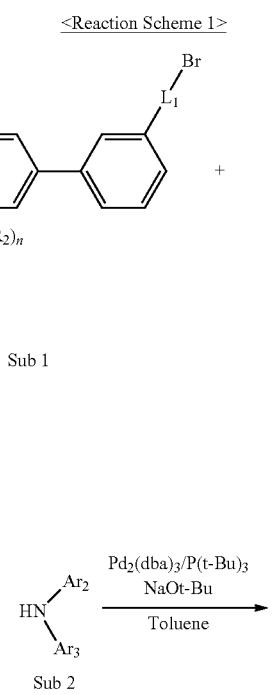

-continued

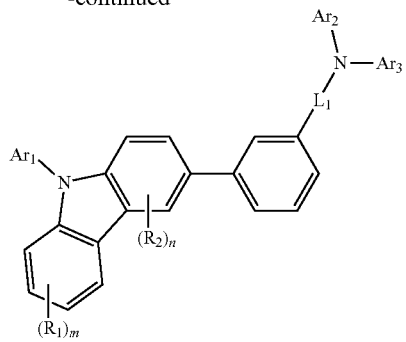

Final Products

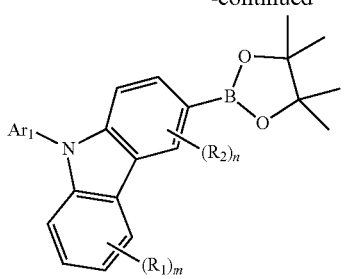 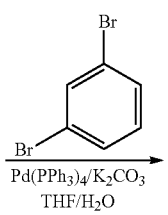

Sub 1-IV (Ar$_1$ to Ar$_3$, L$_1$, R$_1$, R$_2$, m and n are the same as definition in formula 1 above.)

I. Synthesis of Sub 1

Sub 1 of the Reaction Scheme 1 can be synthesized according to, but not limited to, the reaction route of the following Reaction Scheme 2.

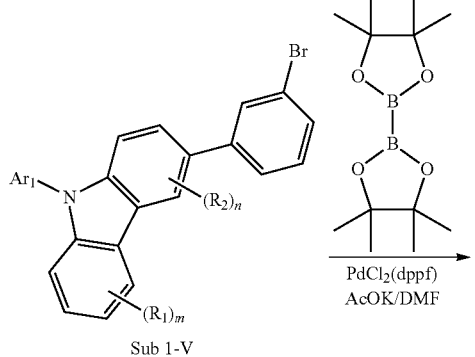 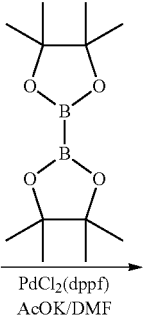

Sub 1-V

<Reaction Scheme 2>

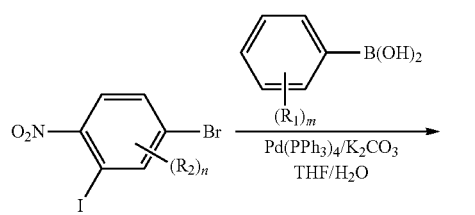

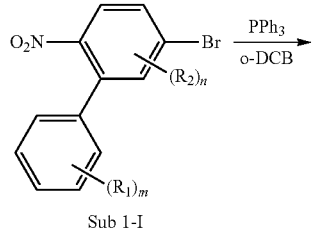

Sub 1-I

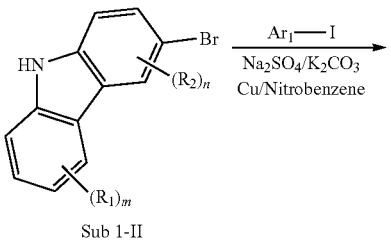

Sub 1-II

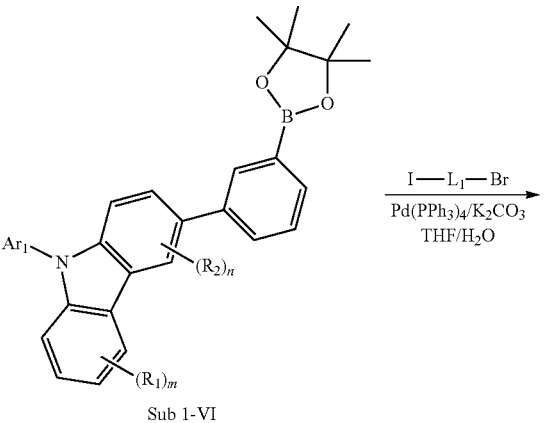

Sub 1-VI

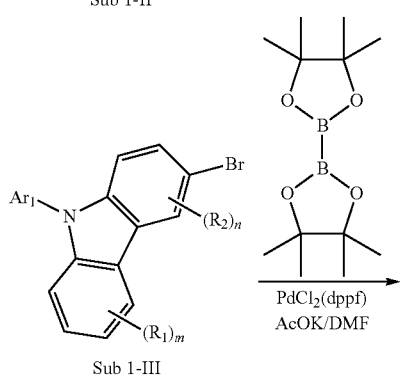

Sub 1-III

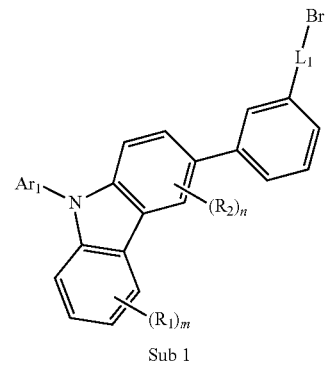

Sub 1

Synthesis Examples of compounds comprised in Sub 1 are as follows.

(1) Synthesis Example of Sub 1-A1

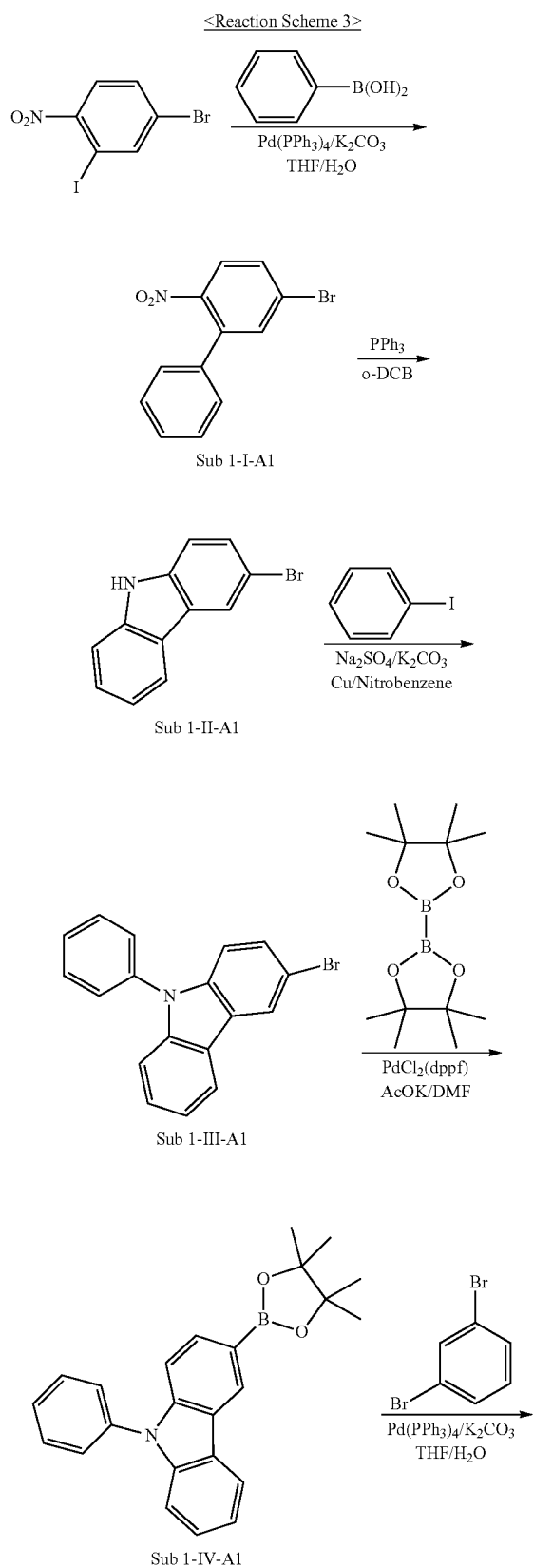

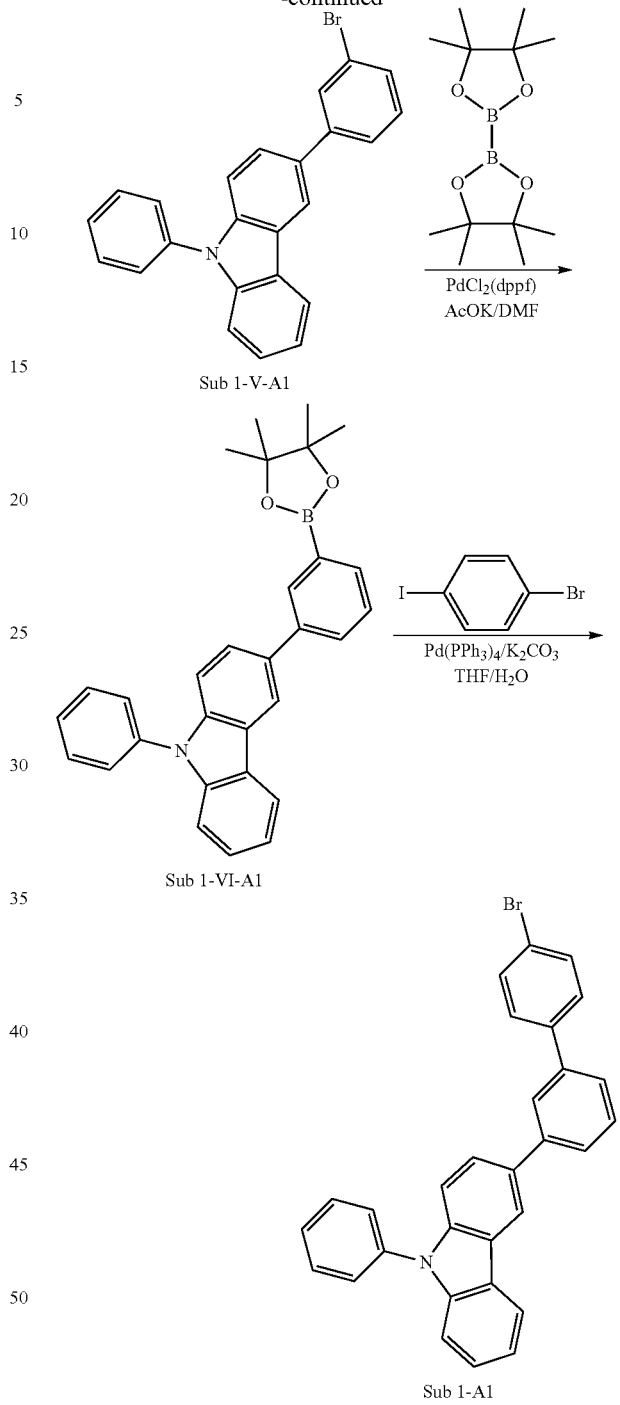

Synthesis of Intermediate Sub 1-I-A1

The starting material phenylboronic acid (412.96 g, 3386.9 mmol) was dissolved in THF in a round bottom flask, and then 4-bromo-2-iodo-1-nitrobenzene (1665.83 g, 5080.3 mmol), Pd(PPh$_3$)$_4$ (195.69 g, 169.3 mmol), K$_2$CO$_3$ (1404.29 g, 10160.6 mmol) and water were added and stirred at 80° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 659.32 g (yield: 70%) of the product.

Synthesis of Intermediate Sub 1-II-A1

Sub 1-I-A1 (659.32 g, 2370.8 mmol) obtained in the above synthesis was dissolved in o-dichlorobenzene in a round bottom flask, and then, triphenylphosphine (1554.59 g, 5927 mmol) was added and stirred at 200° C. When the reaction was completed, o-dichlorobenzene was removed and then the reaction product was extracted with CH$_2$Cl$_2$ and water. Then, the organic layer was dried with MgSO$_4$ and concentrated, and the concentrate was passed through silica gel column and recrystallized to obtain 431.76 g (yield: 74%) of the product.

Synthesis of Intermediate Sub 1-III-A1

Sub 1-II-A1 (50.69 g, 206 mmol) obtained in the above synthesis was dissolved in nitrobenzene in a round bottom flask, and then, iodobenzene (63.03 g, 309 mmol), Na$_2$SO$_4$ (29.26 g, 206 mmol), K$_2$CO$_3$ (28.47 g, 206 mmol), Cu (3.93 g, 61.8 mmol) were added and stirred at 200° C. When the reaction was completed, nitrobenzene was removed and then the reaction product was extracted with CH$_2$Cl$_2$ and water. Then, the organic layer was dried with MgSO$_4$ and concentrated, and the concentrate was passed through silica gel column and recrystallized to obtain 48.45 g (yield 73%) of the product.

Synthesis of Intermediate Sub 1-IV-A1

Sub 1-III-A1 (48.45 g, 150.4 mmol) obtained in the above synthesis was dissolved in DMF in a round bottom flask, and then, Bis(pinacolato)diboron (42 g, 165.4 mmol), Pd(dppf)Cl$_2$ (3.68 g, 4.5 mmol), KOAc (44.27 g, 451.1 mmol) were added and stirred at 90° C. When the reaction was completed, DMF was removed and then the reaction product was extracted with CH$_2$Cl$_2$ and water. Then, the organic layer was dried with MgSO$_4$ and concentrated, and the concentrate was passed through silica gel column and recrystallized to obtain 46.64 g (yield: 84%) of the product.

Synthesis of Intermediate Sub 1-V-A1

Sub 1-IV-A1 (46.64 g, 126.3 mmol) obtained in the above synthesis was dissolved in THF in a round bottom flask, and then, 1,3-dibromobenzene (44.69 g, 189.5 mmol), Pd(PPh$_3$)$_4$ (7.3 g, 6.3 mmol), K$_2$CO$_3$ (52.37 g, 378.9 mmol), water were added and stirred at 80° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 36.22 g (yield: 72%) of the product.

Synthesis of Intermediate Sub 1-VI-A1

Sub 1-V-A1 (36.22 g, 90.9 mmol) obtained in the above synthesis was dissolved in DMF in a round bottom flask, and then, Bis(pinacolato)diboron (25.4 g, 100 mmol), Pd(dppf)Cl$_2$ (2.23 g, 2.7 mmol), KOAc (26.77 g, 272.8 mmol) were added and stirred at 90° C. When the reaction was completed, DMF was removed and then the reaction product was extracted with CH$_2$Cl$_2$ and water. Then, the organic layer was dried with MgSO$_4$ and concentrated, and the concentrate was passed through silica gel column and recrystallized to obtain 33.21 g (yield: 82%) of the product.

Synthesis Example of Sub 1-A1

Sub 1-VI-A1 (10.52 g, 23.6 mmol) obtained in the above synthesis was dissolved in THF in a round bottom flask, and then, 1-bromo-4-iodobenzene (10.02 g, 35.4 mmol), Pd(PPh$_3$)$_4$ (1.36 g, 1.2 mmol), K$_2$CO$_3$ (9.79 g, 70.9 mmol), water were added and stirred at 80° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 9.08 g (yield: 81%) of the product.

(2) Synthesis Example of Sub 1-A2

<Reaction Scheme 4>

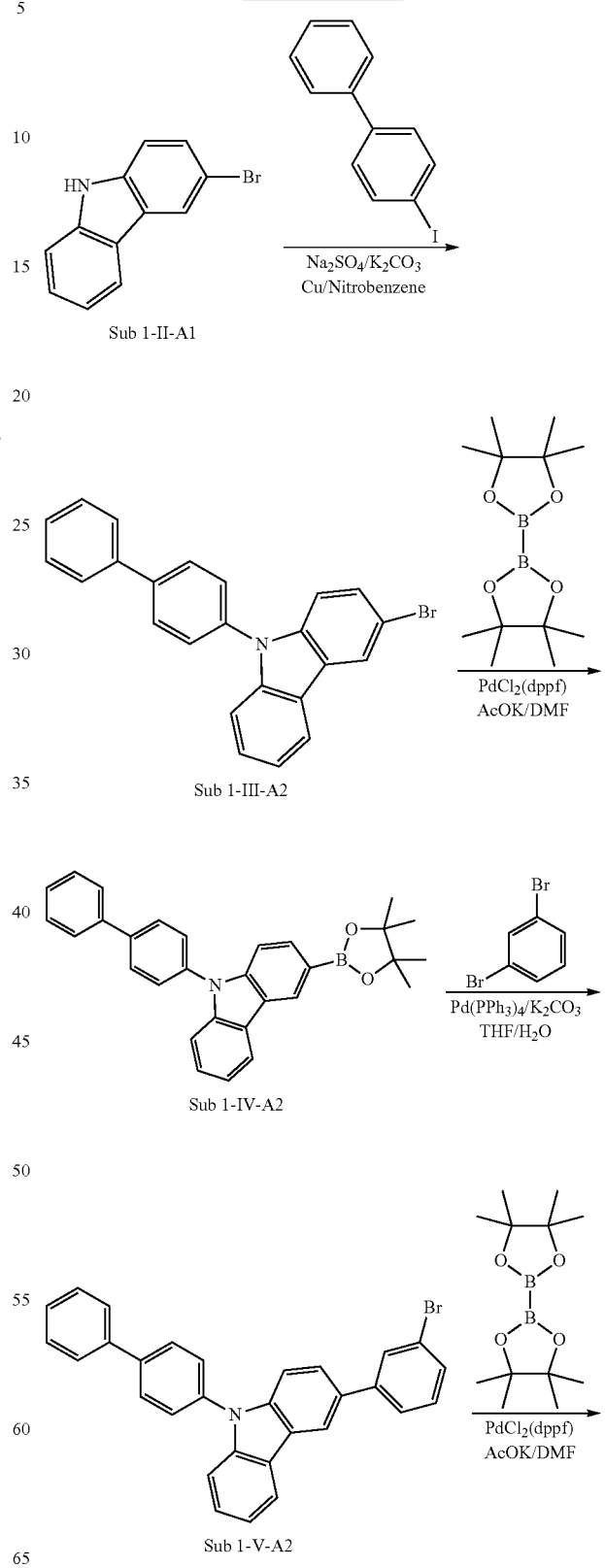

-continued

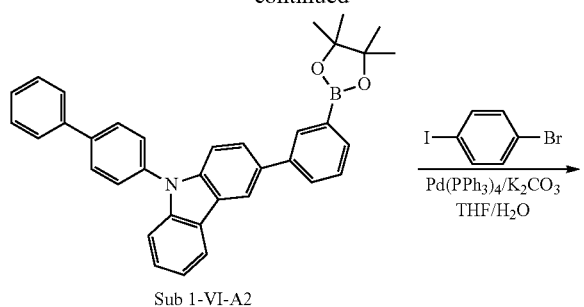

Sub 1-VI-A2

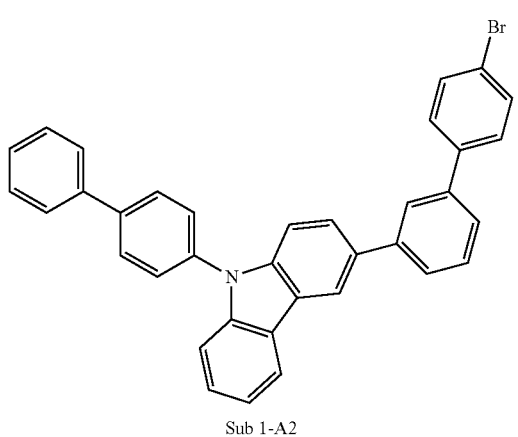 [SMILES: Brc1ccc(-c2cccc(-c3ccc4c(c3)c3ccccc3n4-c3ccc(-c4ccccc4)cc3)c2)cc1]

Sub 1-A2

Synthesis of Intermediate Sub 1-III-A2

4-iodo-1,1'-biphenyl (40.87 g, 145.9 mmol), $Na_2SO_4$ (13.82 g, 97.3 mmol), $K_2CO_3$ (13.44 g, 97.3 mmol), Cu (1.85 g, 29.2 mmol), nitrobenzene were added to Sub 1-II-A1 (23.94 g, 97.3 mmol) obtained in the above synthesis, and then 27.51 g (yield: 71%) of the product was obtained by using the same manner as described above for the synthesis example of Sub 1-III-A1.

Synthesis of Intermediate Sub 1-IV-A2

Bis(pinacolato)diboron (19.29 g, 76 mmol), $Pd(dppf)Cl_2$ (1.69 g, 2.1 mmol), KOAc (20.34 g, 207.2 mmol), DMF were added to Sub 1-III-A2 (27.51 g, 69.1 mmol) obtained in the above synthesis, and then 26.76 g (yield: 87%) of the product was obtained by using the same manner as described above for the synthesis example of Sub 1-IV-A1.

Synthesis of Intermediate Sub 1-V-A2

1,3-dibromobenzene (21.26 g, 90.1 mmol), $Pd(PPh_3)_4$ (3.47 g, 3 mmol), $K_2CO_3$ (24.91 g, 180.3 mmol), THF, water were added to Sub 1-IV-A2 (26.76 g, 60.1 mmol) obtained in the above synthesis, and then 22.23 g (yield: 78%) of the product was obtained by using the same manner as described above for the synthesis example of Sub 1-V-A1.

Synthesis of Intermediate Sub 1-VI-A2

Bis(pinacolato)diboron (13.09 g, 51.5 mmol), $Pd(dppf)Cl_2$ (1.15 g, 1.4 mmol), KOAc (13.8 g, 140.6 mmol), DMF were added to Sub 1-V-A2 (22.23 g, 46.9 mmol) obtained in the above synthesis, and then 20.53 g (yield: 84%) of the product was obtained by using the same manner as described above for the synthesis example of Sub 1-VI-A1.

Synthesis Example of Sub 1-A2

1-bromo-4-iodobenzene (7.07 g, 25 mmol), $Pd(PPh_3)_4$ (0.96 g, 0.8 mmol), $K_2CO_3$ (6.91 g, 50 mmol), THF, water were added to Sub 1-VI-A2 (8.69 g, 16.7 mmol) obtained in the above synthesis, and then 7.61 g (yield: 83%) of the product was obtained by using the same manner as described above for the synthesis example of Sub 1-A1.

(3) Synthesis Example of Sub 1-A21

<Reaction Scheme 5>

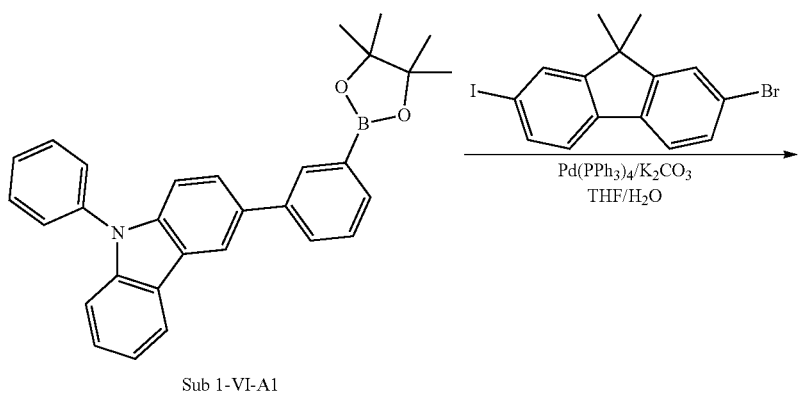

Sub 1-VI-A1

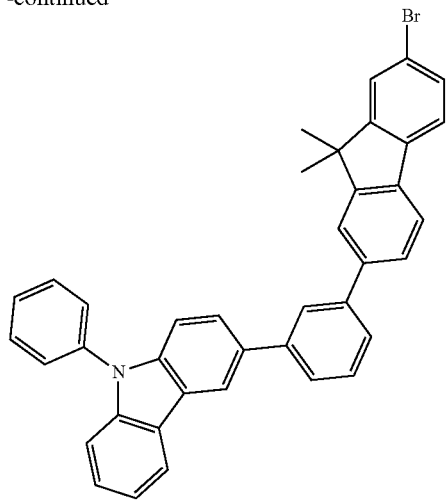
Sub 1-A21
2-bromo-7-iodo-9,9-dimethyl-9H-fluorene (16.61 g, 41.6 mmol), Pd(PPh$_3$)$_4$ (1.6 g, 1.4 mmol), K$_2$CO$_3$ (11.51 g, 83.3 mmol), THF, water were added to Sub 1-VI-A1 (12.36 g, 27.8 mmol) obtained in the above synthesis, and then 12.95 g (yield: 79%) of the product was obtained by using the same manner as described above for the synthesis example of Sub 1-A1.
(4) Synthesis Example of Sub 1-A26
<Reaction Scheme 6>
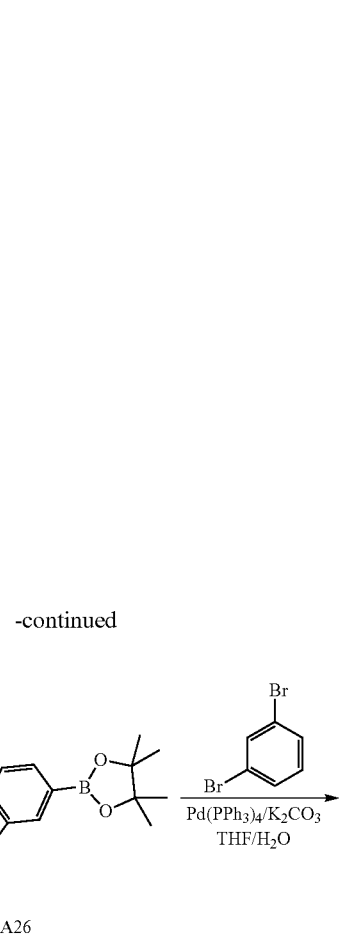
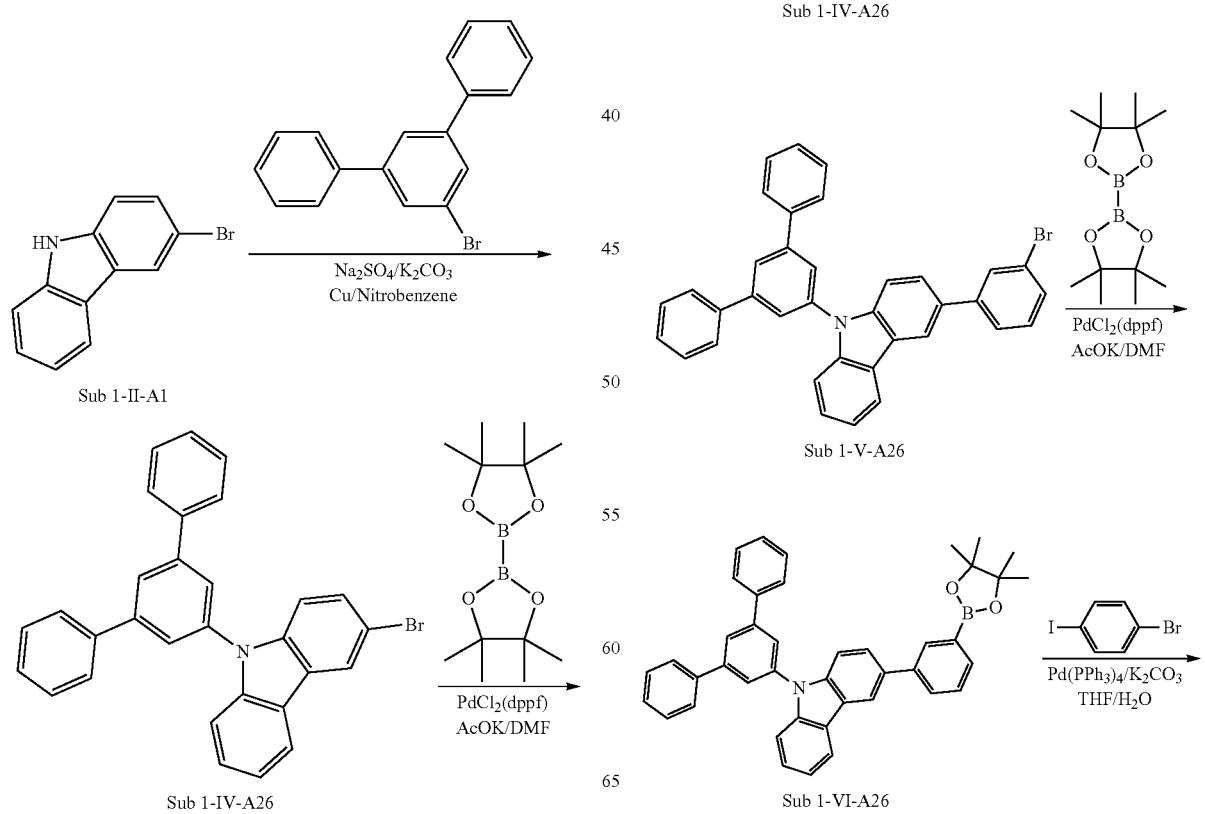

(5) Synthesis Example of Sub 1-A29

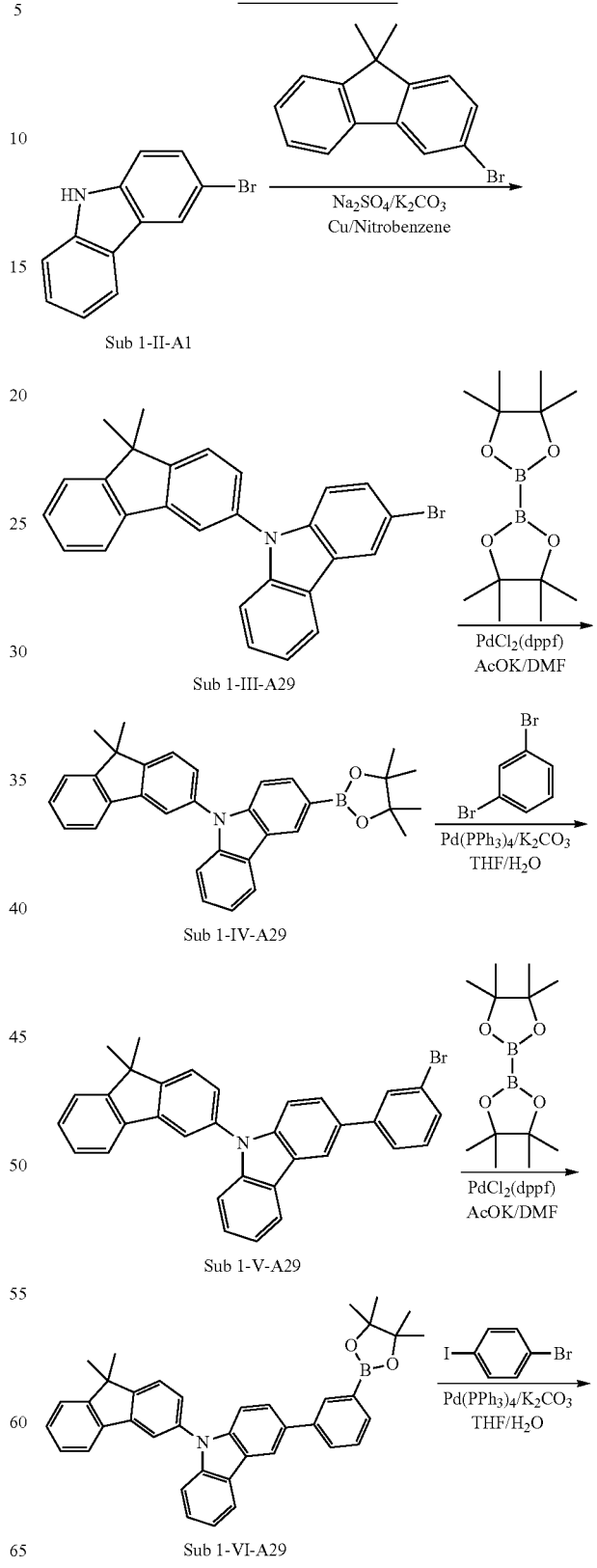

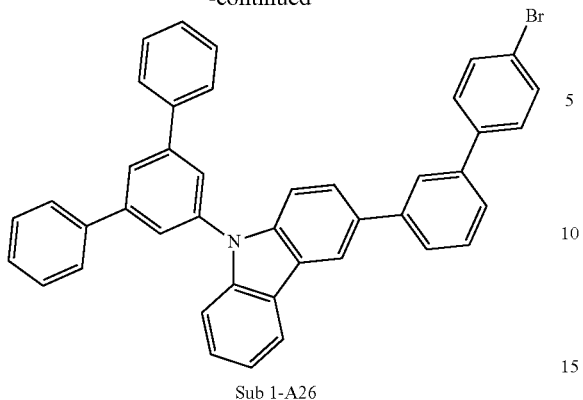

Sub 1-A26

Synthesis of Intermediate Sub 1-III-A26

5'-bromo-1,1':3',1''-terphenyl (90.54 g, 292.8 mmol), $Na_2SO_4$ (27.73 g, 195.2 mmol), $K_2CO_3$ (26.98 g, 195.2 mmol), Cu (3.72 g, 58.6 mmol), nitrobenzene were added to Sub 1-II-A1 (48.04 g, 195.2 mmol) obtained in the above synthesis, and then 62.97 g (yield: 68%) of the product was obtained by using the same manner as described above for the synthesis example of Sub 1-III-A1.

Synthesis of Intermediate Sub 1-IV-A26

Bis(pinacolato)diboron (37.08 g, 146 mmol), Pd(dppf)Cl$_2$ (3.25 g, 4 mmol), KOAc (39.08 g, 398.2 mmol), DMF were added to Sub 1-III-A26 (62.97 g, 132.7 mmol) obtained in the above synthesis, and then 56.07 g (yield: 81%) of the product was obtained by using the same manner as described above for the synthesis example of Sub 1-IV-A1.

Synthesis of Intermediate Sub 1-V-A26

1,3-dibromobenzene (38.05 g, 161.3 mmol), Pd(PPh$_3$)$_4$ (6.21 g, 5.4 mmol), $K_2CO_3$ (44.58 g, 322.6 mmol), THF, water were added to Sub 1-IV-A26 (56.07 g, 107.5 mmol) obtained in the above synthesis, and then 41.43 g (yield: 70%) of the product was obtained by using the same manner as described above for the synthesis example of Sub 1-V-A1.

Synthesis of Intermediate Sub 1-VI-A26

Bis(pinacolato)diboron (21.02 g, 82.8 mmol), Pd(dppf)Cl$_2$ (1.84 g, 2.3 mmol), KOAc (22.16 g, 225.8 mmol), DMF were added to Sub 1-V-A26 (41.43 g, 75.3 mmol) obtained in the above synthesis, and then 35.08 g (yield: 78%) of the product was obtained by using the same manner as described above for the synthesis example of Sub 1-VI-A1.

Synthesis Example of Sub 1-A26

1-bromo-4-iodobenzene (7.59 g, 26.8 mmol), Pd(PPh$_3$)$_4$ (1.03 g, 0.9 mmol), $K_2CO_3$ (7.42 g, 53.7 mmol), THF, water were added to Sub 1-VI-A26 (10.69 g, 17.9 mmol) obtained in the above synthesis, and then 8.52 g (yield: 76%) of the product was obtained by using the same manner as described above for the synthesis example of Sub 1-A1.

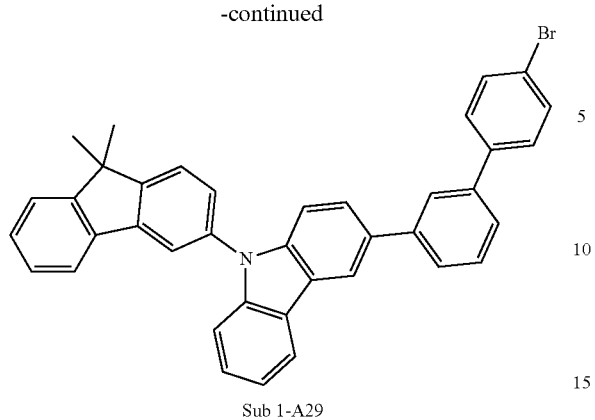

Sub 1-A29

Synthesis of Intermediate Sub 1-III-A29

3-bromo-9,9-dimethyl-9H-fluorene (68.41 g, 250.4 mmol), $Na_2SO_4$ (23.72 g, 167 mmol), $K_2CO_3$ (23.08 g, 167 mmol), Cu (3.18 g, 50.1 mmol), nitrobenzene were added to Sub 1-II-A1 (41.09 g, 167 mmol) obtained in the above synthesis, and then 51.23 g (yield: 70%) of the product was obtained by using the same manner as described above for the synthesis example of Sub 1-III-A1.

Synthesis of Intermediate Sub 1-IV-A29

Bis(pinacolato)diboron (32.65 g, 128.6 mmol), Pd(dppf)$Cl_2$ (2.86 g, 3.5 mmol), KOAc (34.41 g, 350.6 mmol), DMF were added to Sub 1-III-A29 (51.23 g, 116.9 mmol) obtained in the above synthesis, and then 48.22 g (yield: 85%) of the product was obtained by using the same manner as described above for the synthesis example of Sub 1-IV-A1.

Synthesis of Intermediate Sub 1-V-A29

1,3-dibromobenzene (35.15 g, 149 mmol), Pd(PPh$_3$)$_4$ (5.74 g, 5 mmol), $K_2CO_3$ (41.19 g, 298 mmol), THF, water were added to Sub 1-IV-A29 (48.22 g, 99.3 mmol) obtained in the above synthesis, and then 38.84 g (yield: 76%) of the product was obtained by using the same manner as described above for the synthesis example of Sub 1-V-A1.

Synthesis of Intermediate Sub 1-VI-A29

Bis(pinacolato)diboron (21.09 g, 83 mmol), Pd(dppf)$Cl_2$ (1.85 g, 2.3 mmol), KOAc (22.23 g, 226.5 mmol), DMF were added to Sub 1-V-A29 (38.84 g, 75.5 mmol) obtained in the above synthesis, and then 33.91 g (yield: 80%) of the product was obtained by using the same manner as described above for the synthesis example of Sub 1-VI-A1.

Synthesis Example of Sub 1-A29

1-bromo-4-iodobenzene (7.26 g, 25.7 mmol), Pd(PPh$_3$)$_4$ (0.99 g, 0.9 mmol), $K_2CO_3$ (7.1 g, 51.3 mmol), THF, water were added to Sub 1-VI-A29 (9.61 g, 17.1 mmol) obtained in the above synthesis, and then 8.09 g (yield: 80%) of the product was obtained by using the same manner as described above for the synthesis example of Sub 1-A1.

(6) Synthesis Example of Sub 1-A35

<Reaction Scheme 8>

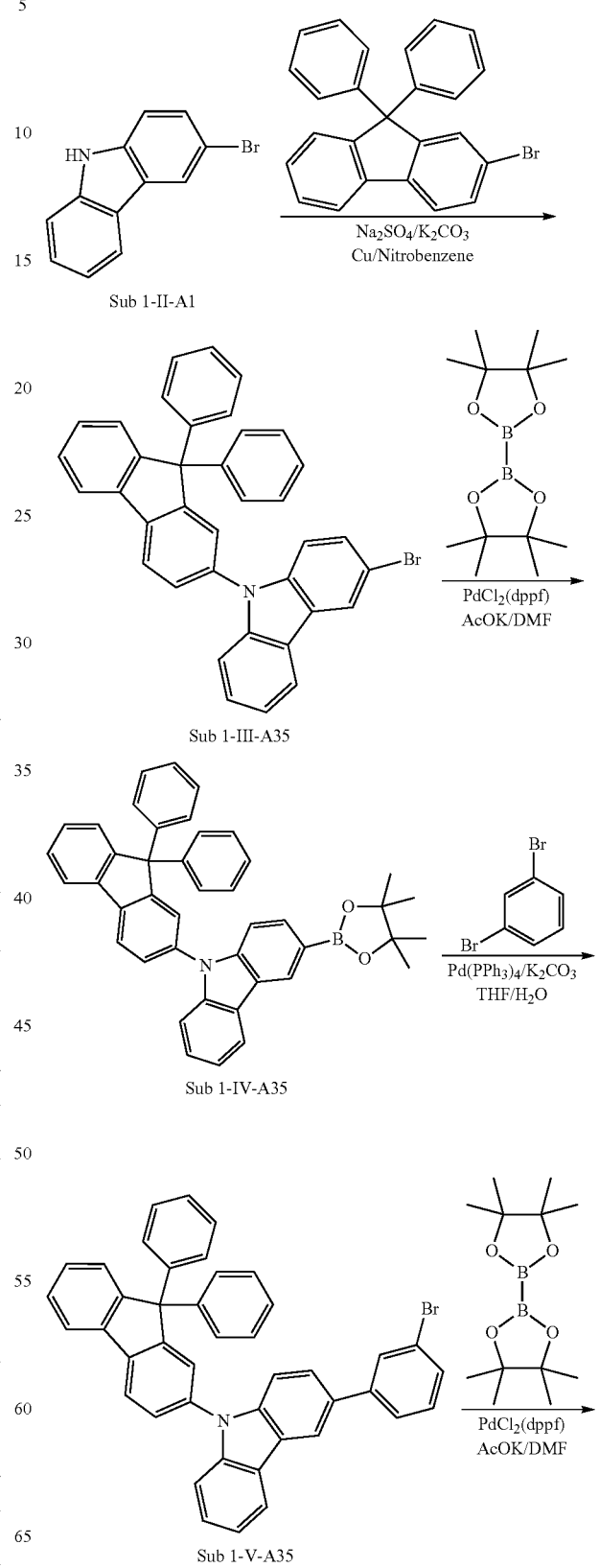

-continued

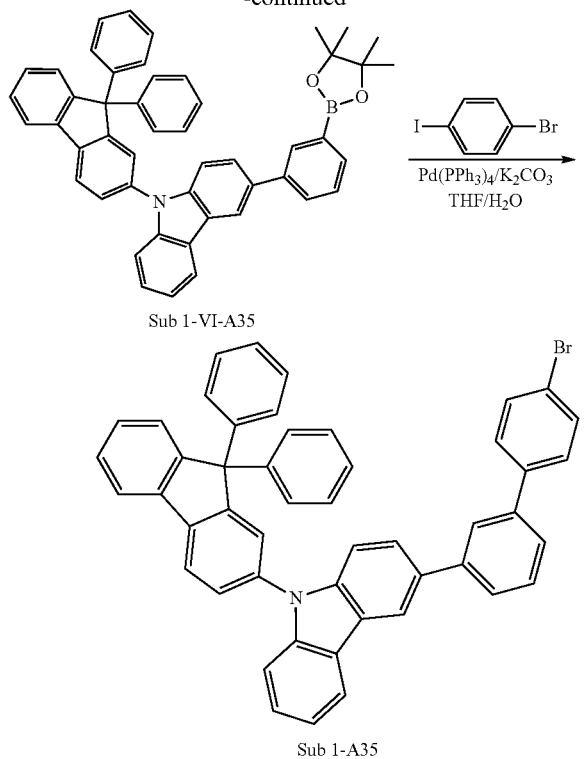

Synthesis of Intermediate Sub 1-III-A35
2-bromo-9,9-diphenyl-9H-fluorene (154.31 g, 388.4 mmol), $Na_2SO_4$ (36.78 g, 258.9 mmol), $K_2CO_3$ (35.79 g, 258.9 mmol), Cu (4.94 g, 77.7 mmol), nitrobenzene were added to Sub 1-II-A1 (63.72 g, 258.9 mmol) obtained in the above synthesis, and then 88.84 g (yield: 61%) of the product was obtained by using the same manner as described above for the synthesis example of Sub 1-III-A1.

Synthesis of Intermediate Sub 1-IV-A35
Bis(pinacolato)diboron (44.12 g, 173.7 mmol), Pd(dppf)$Cl_2$ (3.87 g, 4.7 mmol), KOAc (46.5 g, 473.8 mmol), DMF were added to Sub 1-III-A35 (88.84 g, 157.9 mmol) obtained in the above synthesis, and then 74.13 g (yield: 77%) of the product was obtained by using the same manner as described above for the synthesis example of Sub 1-IV-A1.

Synthesis of Intermediate Sub 1-V-A35
1,3-dibromobenzene (43.03 g, 182.4 mmol), Pd(PPh$_3$)$_4$ (7.03 g, 6.1 mmol), $K_2CO_3$ (50.42 g, 364.8 mmol), THF, water were added to Sub 1-IV-A35 (74.13 g, 121.6 mmol) obtained in the above synthesis, and then 54.36 g (yield: 70%) of the product was obtained by using the same manner as described above for the synthesis example of Sub 1-V-A1.

Synthesis of Intermediate Sub 1-VI-A35
Bis(pinacolato)diboron (23.78 g, 93.6 mmol), Pd(dppf)$Cl_2$ (2.09 g, 2.6 mmol), KOAc (25.06 g, 255.4 mmol), DMF were added to Sub 1-V-A35 (54.36 g, 85.1 mmol) obtained in the above synthesis, and then 43.19 g (yield: 74%) of the product was obtained by using the same manner as described above for the synthesis example of Sub 1-VI-A1.

Synthesis Example of Sub 1-A35
1-bromo-4-iodobenzene (7.61 g, 26.9 mmol), Pd(PPh$_3$)$_4$ (1.04 g, 0.9 mmol), $K_2CO_3$ (7.43 g, 53.8 mmol), THF, water were added to Sub 1-VI-A35 (12.29 g, 17.9 mmol) obtained in the above synthesis, and then 9.61 g (yield: 75%) of the product was obtained by using the same manner as described above for the synthesis example of Sub 1-A1.

(7) Synthesis Example of Sub 1-A36

<Reaction Scheme 9>

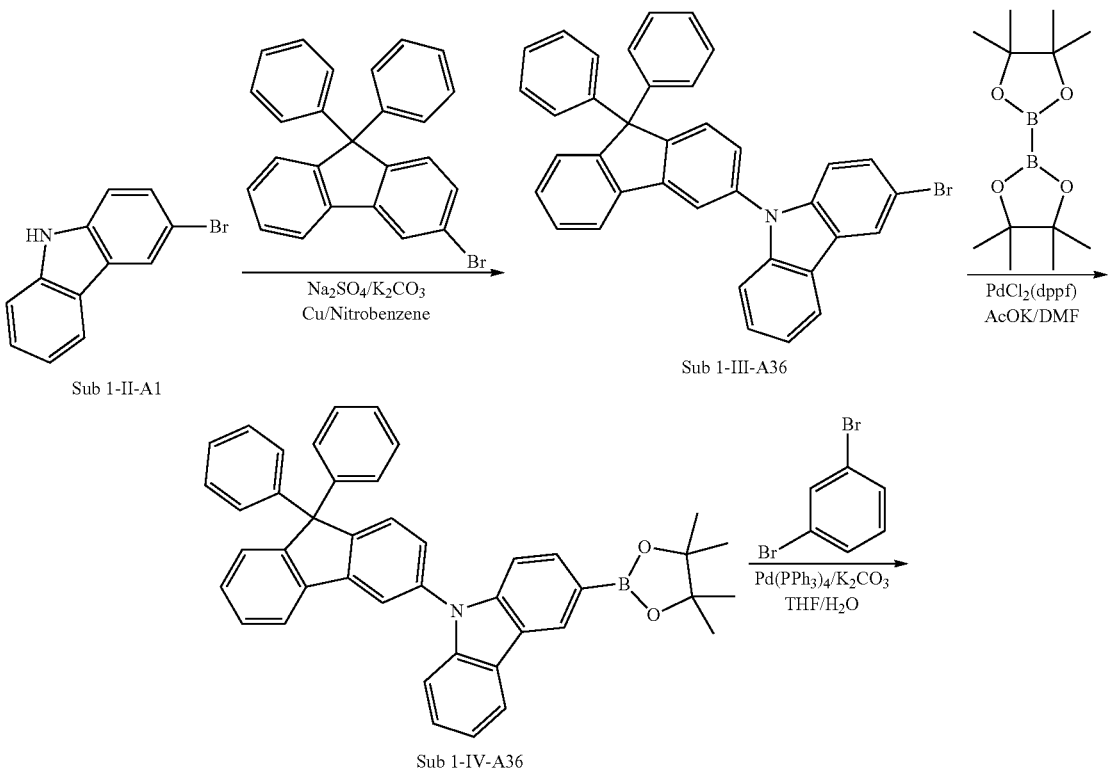

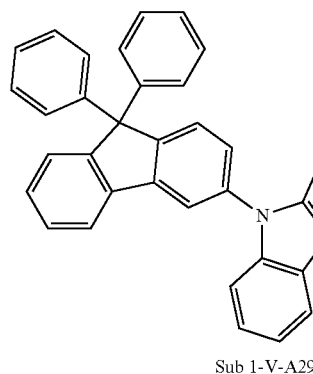

Sub 1-V-A29

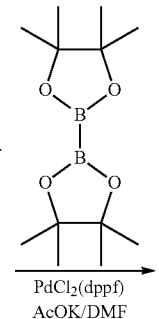

PdCl₂(dppf)
AcOK/DMF

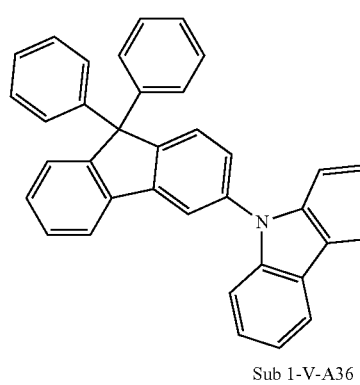

Sub 1-V-A36

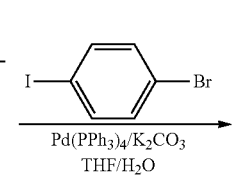

Pd(PPh₃)₄/K₂CO₃
THF/H₂O

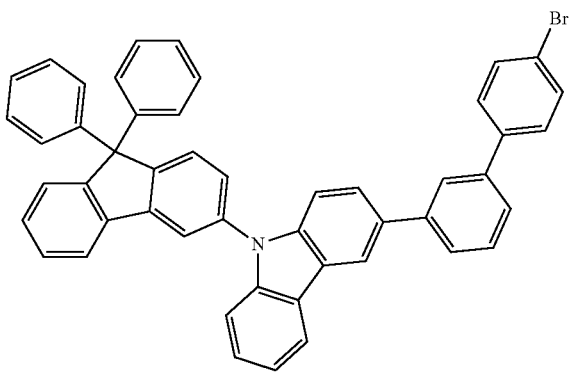

Sub 1-A36

Synthesis of Intermediate Sub 1-III-A36

3-bromo-9,9-diphenyl-9H-fluorene (143.48 g, 361.1 mmol), Na₂SO₄ (34.2 g, 240.8 mmol), K₂CO₃ (33.27 g, 240.8 mmol), Cu (4.59 g, 72.2 mmol), nitrobenzene were added to Sub 1-II-A1 (59.25 g, 240.8 mmol) obtained in the above synthesis, and then 85.32 g (yield: 63%) of the product was obtained by using the same manner as described above for the synthesis example of Sub 1-III-A1.

Synthesis of Intermediate Sub 1-IV-A36

Bis(pinacolato)diboron (42.37 g, 166.8 mmol), Pd(dppf)Cl₂ (3.72 g, 4.6 mmol), KOAc (44.66 g, 455 mmol), DMF were added to Sub 1-III-A36 (85.32 g, 151.7 mmol) obtained in the above synthesis, and then 73.04 g (yield: 79%) of the product was obtained by using the same manner as described above for the synthesis example of Sub 1-IV-A1.

Synthesis of Intermediate Sub 1-V-A36

1,3-dibromobenzene (42.4 g, 179.7 mmol), Pd(PPh₃)₄ (6.92 g, 6 mmol), K₂CO₃ (49.68 g, 359.5 mmol), THF, water were added to Sub 1-IV-A36 (73.04 g, 119.8 mmol) obtained in the above synthesis, and then 55.86 g (yield: 73%) of the product was obtained by using the same manner as described above for the synthesis example of Sub 1-V-A1.

Synthesis of Intermediate Sub 1-VI-A36

Bis(pinacolato)diboron (24.43 g, 96.2 mmol), Pd(dppf)Cl₂ (2.14 g, 2.6 mmol), KOAc (25.75 g, 262.4 mmol), DMF were added to Sub 1-V-A36 (55.86 g, 87.5 mmol) obtained in the above synthesis, and then 42.58 g (yield: 71%) of the product was obtained by using the same manner as described above for the synthesis example of Sub 1-VI-A1.

Synthesis Example of Sub 1-A36

1-bromo-4-iodobenzene (7.33 g, 25.9 mmol), Pd(PPh₃)₄ (1 g, 0.9 mmol), K₂CO₃ (7.17 g, 51.8 mmol), THF, water were added to Sub 1-VI-A36 (11.85 g, 17.3 mmol) obtained in the above synthesis, and then 9.39 g (yield: 76%) of the product was obtained by using the same manner as described above for the synthesis example of Sub 1-A1.

(8) Synthesis Example of Sub 1-A43
<Reaction Scheme 10>
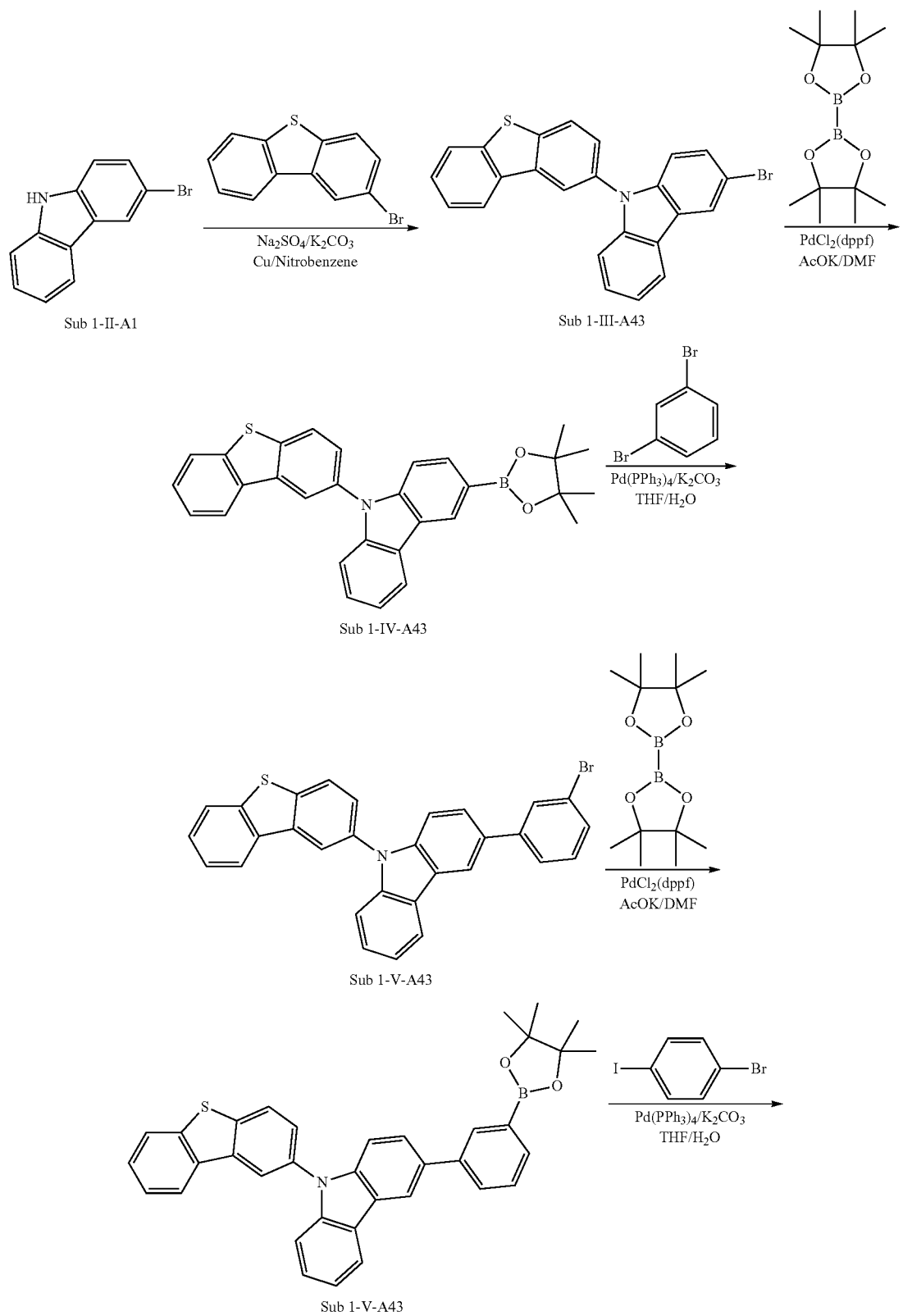

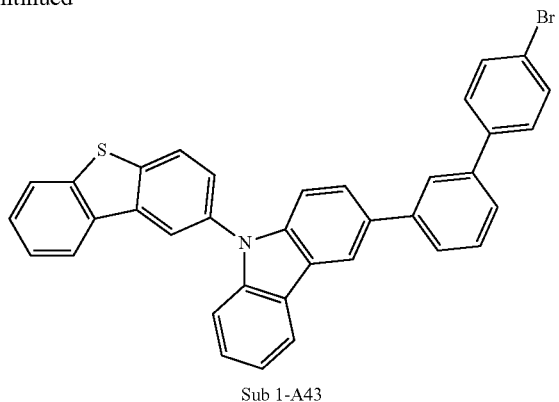

Sub 1-A43

Synthesis of Intermediate Sub 1-III-A43

2-bromodibenzo[b,d]thiophene (83.61 g, 317.7 mmol), $Na_2SO_4$ (30.09 g, 211.8 mmol), $K_2CO_3$ (29.28 g, 211.8 mmol), Cu (4.04 g, 63.5 mmol), nitrobenzene were added to Sub 1-II-A1 (52.13 g, 211.8 mmol) obtained in the above synthesis, and then 62.61 g (yield: 69%) of the product was obtained by using the same manner as described above for the synthesis example of Sub 1-III-A1.

Synthesis of Intermediate Sub 1-IV-A43

Bis(pinacolato)diboron (40.83 g, 160.8 mmol), Pd(dppf)$Cl_2$ (3.58 g, 4.4 mmol), KOAc (43.04 g, 438.5 mmol), DMF were added to Sub 1-III-A43 (62.61 g, 146.2 mmol) obtained in the above synthesis, and then 58.37 g (yield: 84%) of the product was obtained by using the same manner as described above for the synthesis example of Sub 1-IV-A1.

Synthesis of Intermediate Sub 1-V-A43

1,3-dibromobenzene (43.45 g, 184.2 mmol), Pd(PPh$_3$)$_4$ (7.09 g, 6.1 mmol), $K_2CO_3$ (50.91 g, 368.3 mmol), THF, water were added to Sub 1-IV-A43 (58.37 g, 122.8 mmol) obtained in the above synthesis, and then 46.45 g (yield: 75%) of the product was obtained by using the same manner as described above for the synthesis example of Sub 1-V-A1.

Synthesis of Intermediate Sub 1-VI-A43

Bis(pinacolato)diboron (25.72 g, 101.3 mmol), Pd(dppf)$Cl_2$ (2.26 g, 2.8 mmol), KOAc (27.11 g, 276.2 mmol), DMF were added to Sub 1-V-A43 (46.45 g, 92.1 mmol) obtained in the above synthesis, and then 40.63 g (yield: 80%) of the product was obtained by using the same manner as described above for the synthesis example of Sub 1-VI-A1.

Synthesis Example of Sub 1-A43

1-bromo-4-iodobenzene (7.53 g, 26.6 mmol), Pd(PPh$_3$)$_4$ (1.02 g, 0.9 mmol), $K_2CO_3$ (7.35 g, 53.2 mmol), THF, water were added to Sub 1-VI-A43 (9.78 g, 17.7 mmol) obtained in the above synthesis, and then 8.13 g (yield: 79%) of the product was obtained by using the same manner as described above for the synthesis example of Sub 1-A1.

(9) Synthesis Example of Sub 1-A46

<Reaction Scheme 11>

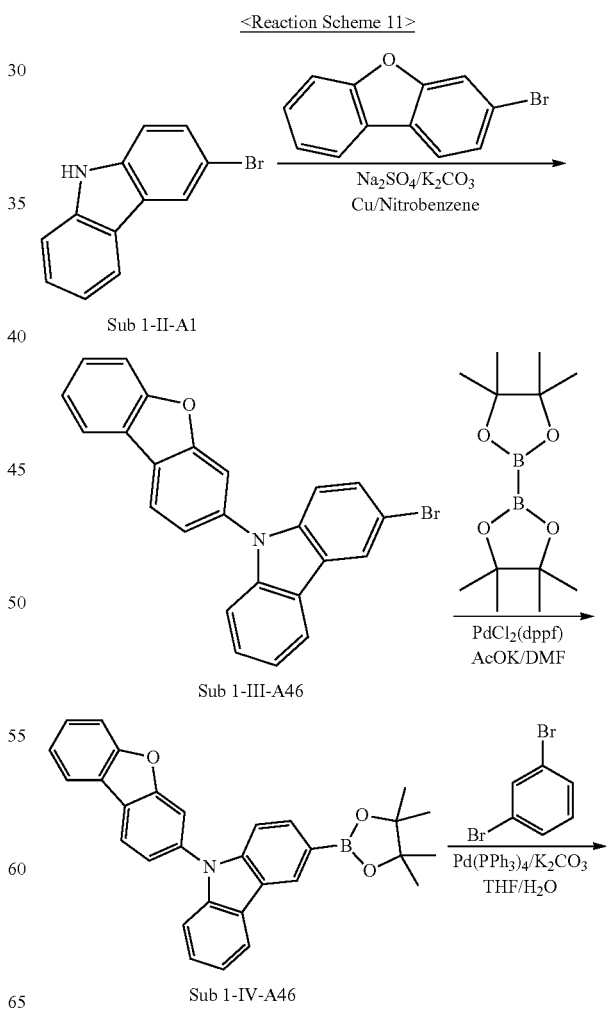

-continued

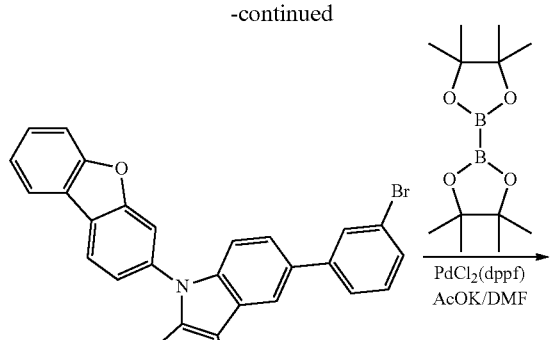

Sub 1-V-A46

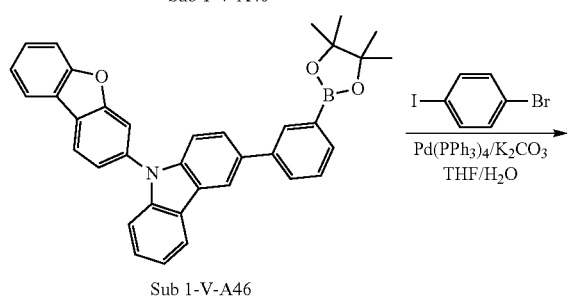

Sub 1-V-A46

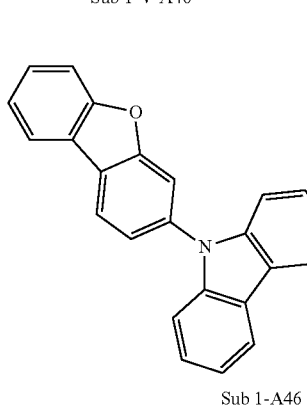

Sub 1-A46

Synthesis of Intermediate Sub 1-III-A46

3-bromodibenzo[b,d]furan (87.23 g, 353 mmol), Na₂SO₄ (33.43 g, 235.4 mmol), K₂CO₃ (32.53 g, 235.4 mmol), Cu (4.49 g, 70.6 mmol), nitrobenzene were added to Sub 1-II-A1 (57.92 g, 235.4 mmol) obtained in the above synthesis, and then 63.07 g (yield: 65%) of the product was obtained by using the same manner as described above for the synthesis example of Sub 1-III-A1.

Synthesis of Intermediate Sub 1-IV-A46

Bis(pinacolato)diboron (42.73 g, 168.3 mmol), Pd(dppf)Cl₂ (3.75 g, 4.6 mmol), KOAc (45.04 g, 458.9 mmol), DMF were added to Sub 1-III-A46 (63.07 g, 153 mmol) obtained in the above synthesis, and then 55.51 g (yield: 79%) of the product was obtained by using the same manner as described above for the synthesis example of Sub 1-IV-A1.

Synthesis of Intermediate Sub 1-V-A46

1,3-dibromobenzene (42.76 g, 181.3 mmol), Pd(PPh₃)₄ (6.98 g, 6 mmol), K₂CO₃ (50.11 g, 362.5 mmol), THF, water were added to Sub 1-IV-A46 (55.51 g, 120.8 mmol) obtained in the above synthesis, and then 44.26 g (yield: 75%) of the product was obtained by using the same manner as described above for the synthesis example of Sub 1-V-A1.

Synthesis of Intermediate Sub 1-VI-A46

Bis(pinacolato)diboron (25.32 g, 99.7 mmol), Pd(dppf)Cl₂ (2.22 g, 2.7 mmol), KOAc (26.68 g, 271.9 mmol), DMF were added to Sub 1-V-A46 (44.26 g, 90.6 mmol) obtained in the above synthesis, and then 37.36 g (yield: 77%) of the product was obtained by using the same manner as described above for the synthesis example of Sub 1-VI-A1.

Synthesis Example of Sub 1-A46

1-bromo-4-iodobenzene (8.44 g, 29.8 mmol), Pd(PPh₃)₄ (1.15 g, 1 mmol), K₂CO₃ (8.25 g, 59.7 mmol), THF, water were added to Sub 1-VI-A46 (10.65 g, 19.9 mmol) obtained in the above synthesis, and then 8.98 g (yield: 80%) of the product was obtained by using the same manner as described above for the synthesis example of Sub 1-A1.

(10) Synthesis Example of Sub 1-A51

<Reaction Scheme 12>

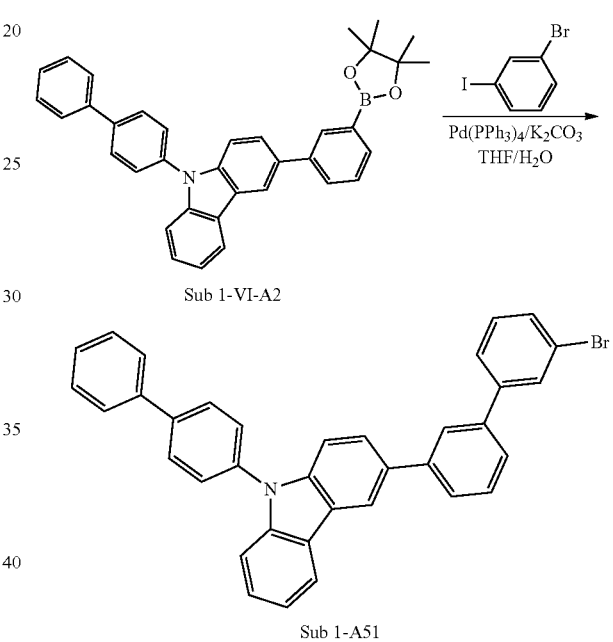

Sub 1-VI-A2

Sub 1-A51

1-bromo-3-iodobenzene (8.27 g, 29.2 mmol), Pd(PPh₃)₄ (1.13 g, 1 mmol), K₂CO₃ (8.08 g, 58.5 mmol), THF, water were added to Sub 1-VI-A2 (10.16 g, 19.5 mmol) obtained in the above synthesis, and then 7.94 g (yield: 74%) of the product was obtained by using the same manner as described above for the synthesis example of Sub 1-A1.

(11) Synthesis Example of Sub 1-A59

<Reaction Scheme 13>

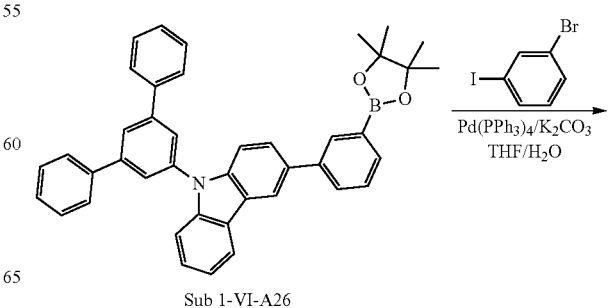

Sub 1-VI-A26

-continued

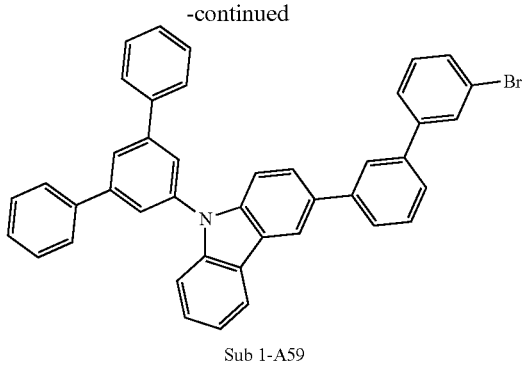

Sub 1-A59

1-bromo-3-iodobenzene (7.68 g, 27.1 mmol), Pd(PPh₃)₄ (1.05 g, 0.9 mmol), K₂CO₃ (7.5 g, 54.3 mmol), THF, water were added to Sub 1-VI-A26 (10.81 g, 18.1 mmol) obtained in the above synthesis, and then 8.05 g (yield: 71%) of the product was obtained by using the same manner as described above for the synthesis example of Sub 1-A1.

(12) Synthesis Example of Sub 1-A64

<Reaction Scheme 14>

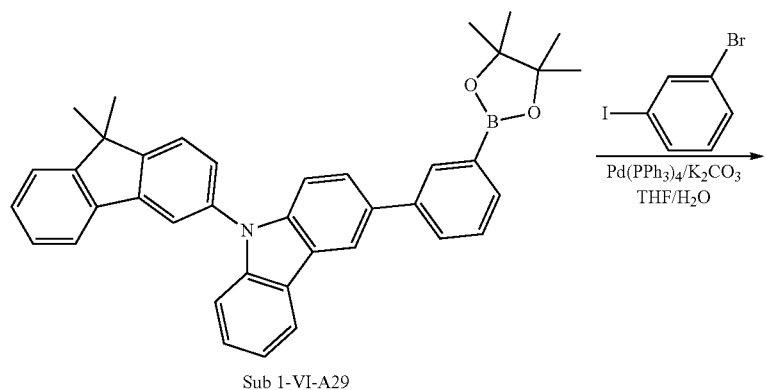

Sub 1-VI-A29

1-bromo-3-iodobenzene (7.78 g, 27.5 mmol), Pd(PPh₃)₄ (1.06 g, 0.9 mmol), K₂CO₃ (7.6 g, 55 mmol), THF, water were added to Sub 1-VI-A29 (10.29 g, 18.3 mmol) obtained in the above synthesis, and then 8.33 g (yield: 77%) of the product was obtained by using the same manner as described above for the synthesis example of Sub 1-A1.

(13) Synthesis Example of Sub 1-A67

<Reaction Scheme 15>

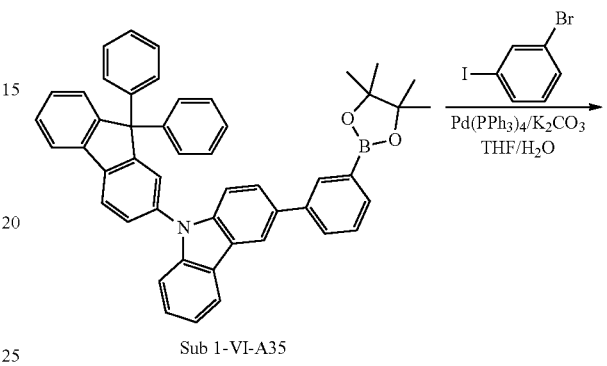

Sub 1-VI-A35

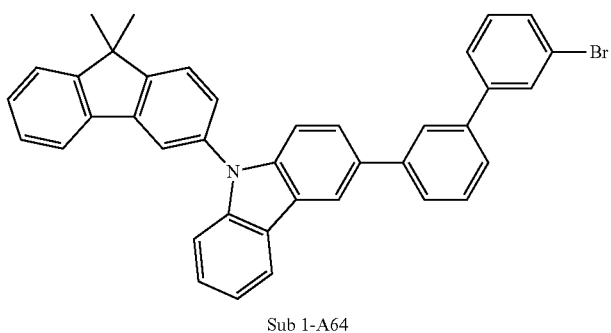

Sub 1-A64

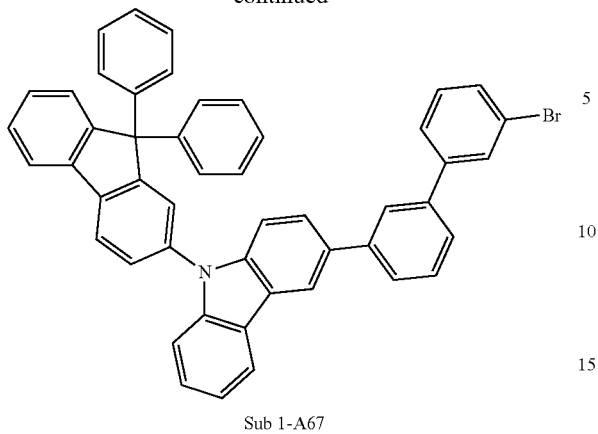

Sub 1-A67

1-bromo-3-iodobenzene (8.43 g, 29.8 mmol), Pd(PPh$_3$)$_4$ (1.15 g, 1 mmol), K$_2$CO$_3$ (8.24 g, 59.6 mmol), THF, water were added to Sub 1-VI-A35 (13.62 g, 19.9 mmol) obtained in the above synthesis, and then 9.94 g (yield: 70%) of the product was obtained by using the same manner as described above for the synthesis example of Sub 1-A1.

(14) Synthesis Example of Sub 1-A68

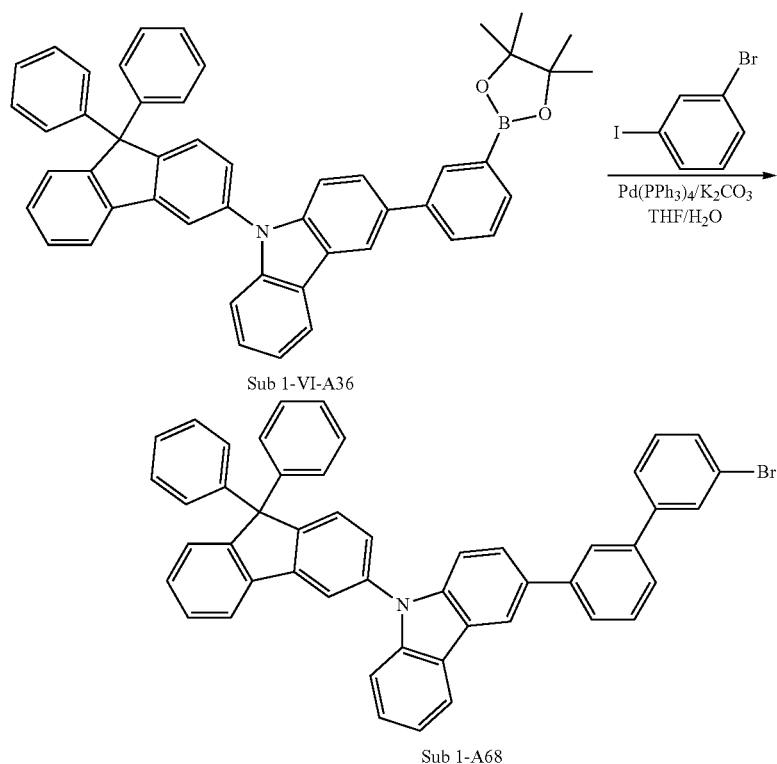

1-bromo-3-iodobenzene (7.97 g, 28.2 mmol), Pd(PPh$_3$)$_4$ (1.08 g, 0.9 mmol), K$_2$CO$_3$ (7.78 g, 56.3 mmol), THF, water were added to Sub 1-VI-A36 (12.87 g, 18.8 mmol) obtained in the above synthesis, and then 9.66 g (yield: 72%) of the product was obtained by using the same manner as described above for the synthesis example of Sub 1-A1.

(15) Synthesis Example of Sub 1-A75
<Reaction Scheme 17>
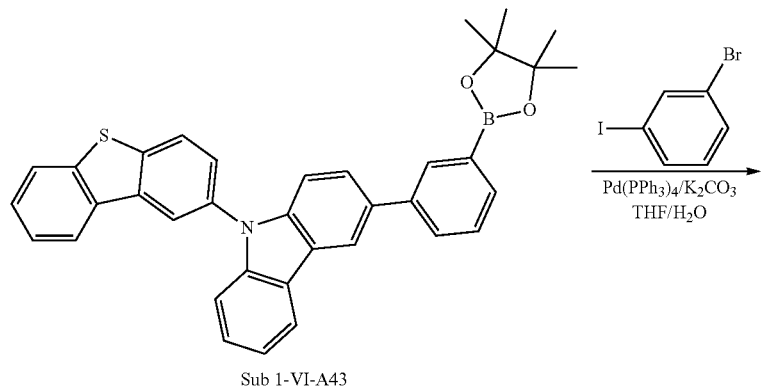
Sub 1-VI-A43
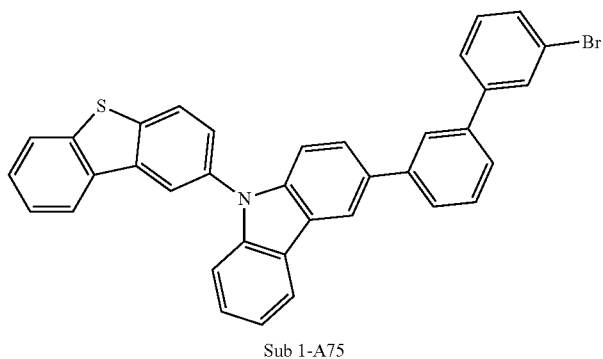
Sub 1-A75
1-bromo-3-iodobenzene (9.46 g, 33.4 mmol), Pd(PPh$_3$)$_4$ (1.29 g, 1.1 mmol), K$_2$CO$_3$ (9.24 g, 66.9 mmol), THF, water were added to Sub 1-VI-A43 (12.29 g, 22.3 mmol) obtained in the above synthesis, and then 10.09 g (yield: 78%) of the product was obtained by using the same manner as described above for the synthesis example of Sub 1-A1.
(16) Synthesis Example of Sub 1-A79
<Reaction Scheme 18>
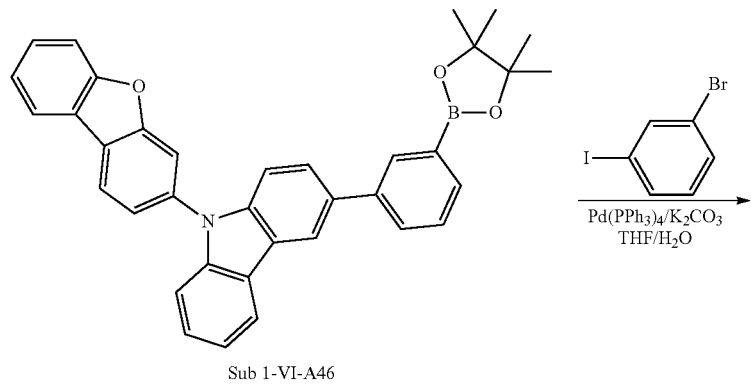
Sub 1-VI-A46

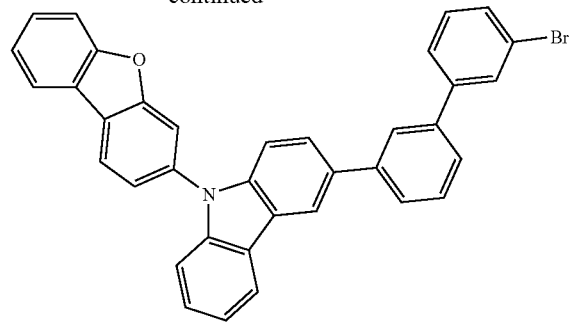

Sub 1-A79

1-bromo-3-iodobenzene (9.45 g, 33.4 mmol), Pd(PPh$_3$)$_4$ (1.29 g, 1.1 mmol), K$_2$CO$_3$ (9.24 g, 66.8 mmol), THF, water were added to Sub 1-VI-A46 (11.93 g, 22.3 mmol) obtained in the above synthesis, and then 9.43 g (yield: 75%) of the product was obtained by using the same manner as described above for the synthesis example of Sub 1-A1.

(17) Synthesis Example of Sub 1-A83

<Reaction Scheme 19>

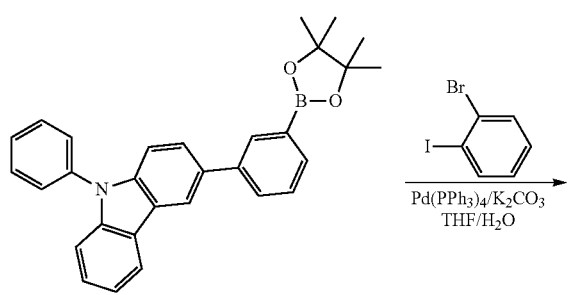

Sub 1-VI-A1

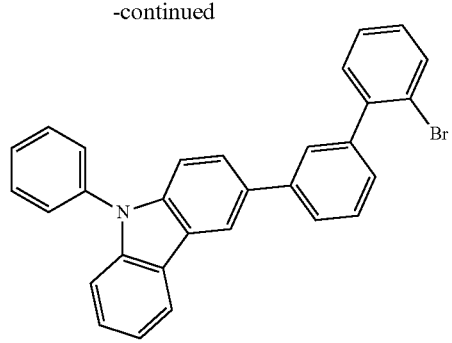

Sub 1-A83

1-bromo-2-iodobenzene (8.94 g, 31.6 mmol), Pd(PPh$_3$)$_4$ (1.22 g, 1.1 mmol), K$_2$CO$_3$ (8.73 g, 63.2 mmol), THF, water were added to Sub 1-VI-A1 (9.38 g, 21.1 mmol) obtained in the above synthesis, and then 6.99 g (yield: 70%) of the product was obtained by using the same manner as described above for the synthesis example of Sub 1-A1.

(18) Synthesis Example of Sub 1-A89

<Reaction Scheme 20>

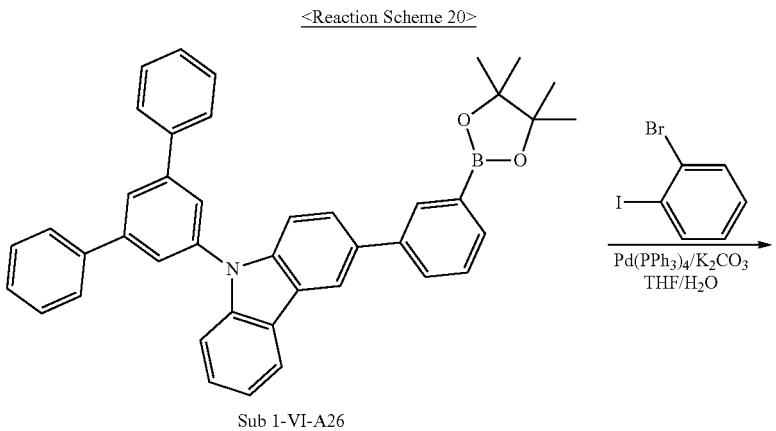

Sub 1-VI-A26

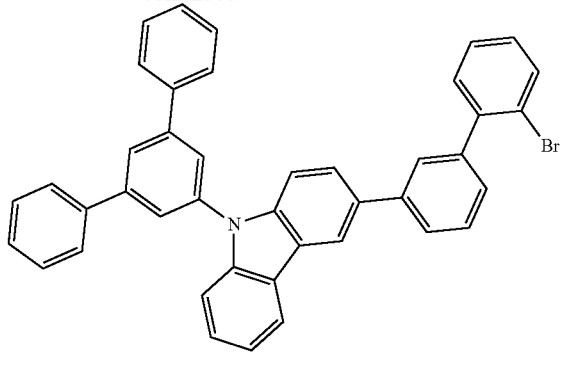

Sub 1-A89

1-bromo-2-iodobenzene (8.22 g, 29 mmol), Pd(PPh$_3$)$_4$ (1.12 g, 1 mmol), K$_2$CO$_3$ (8.03 g, 58.1 mmol), THF, water were added to Sub 1-VI-A26 (11.57 g, 19.4 mmol) obtained in the above synthesis, and then 7.76 g (yield: 64%) of the product was obtained by using the same manner as described above for the synthesis example of Sub 1-A1.

(19) Synthesis Example of Sub 1-A92

<Reaction Scheme 21>

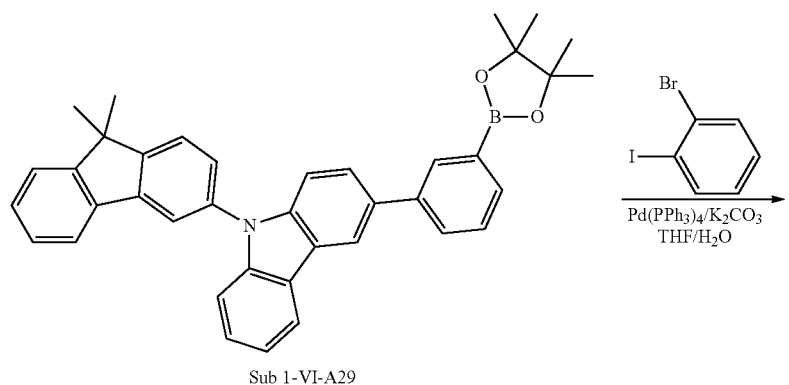

Sub 1-VI-A29

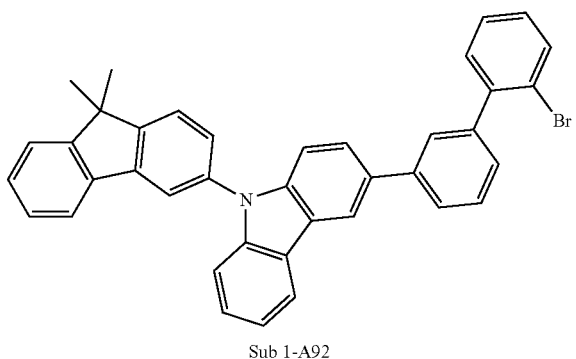

Sub 1-A92

1-bromo-2-iodobenzene (9.13 g, 32.3 mmol), Pd(PPh$_3$)$_4$ (1.24 g, 1.1 mmol), K$_2$CO$_3$ (8.92 g, 64.5 mmol), THF, water were added to Sub 1-VI-A29 (12.08 g, 21.5 mmol) obtained in the above synthesis, and then 8.64 g (yield: 68%) of the product was obtained by using the same manner as described above for the synthesis example of Sub 1-A1.

(20) Synthesis Example of Sub 1-A95

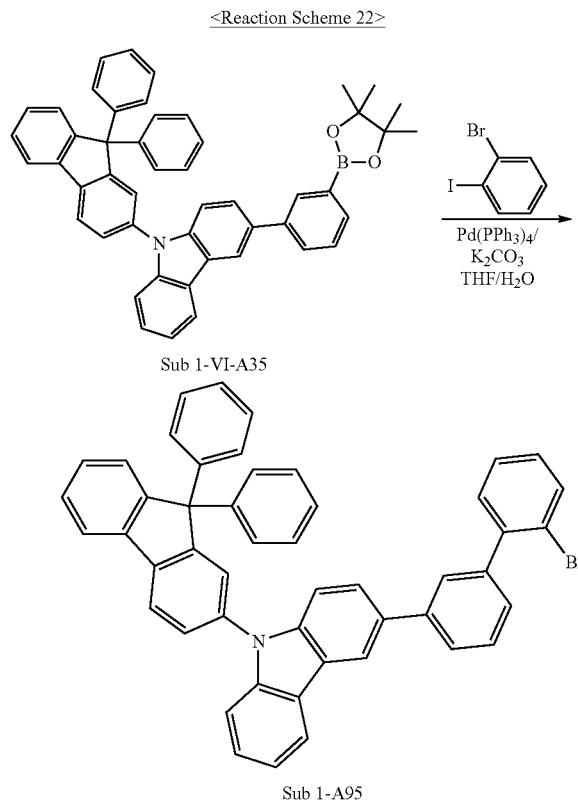

Sub 1-A95

1-bromo-2-iodobenzene (10.25 g, 36.2 mmol), Pd(PPh$_3$)$_4$ (1.4 g, 1.2 mmol), K$_2$CO$_3$ (10.01 g, 72.5 mmol), THF, water were added to Sub 1-VI-A35 (16.56 g, 24.2 mmol) obtained in the above synthesis, and then 10.18 g (yield: 59%) of the product was obtained by using the same manner as described above for the synthesis example of Sub 1-A1.

(21) Synthesis Example of Sub 1-A96

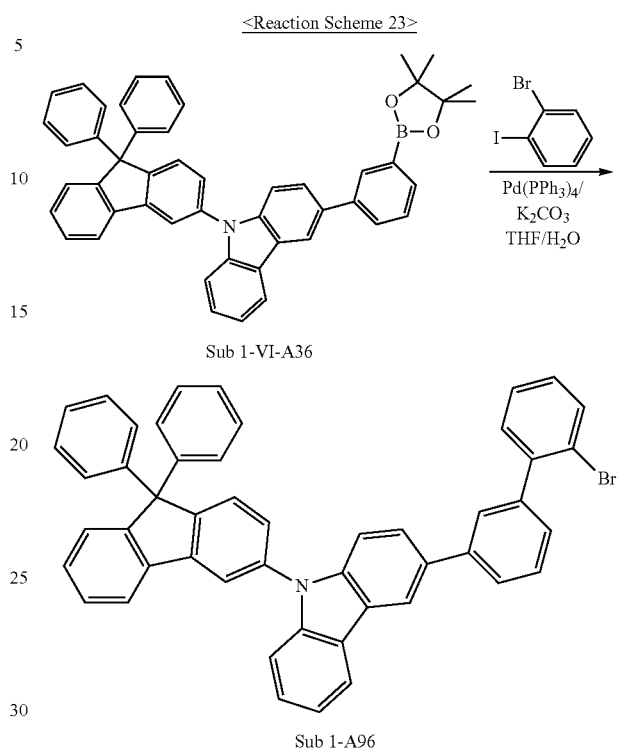

Sub 1-A96

1-bromo-2-iodobenzene (9.71 g, 34.3 mmol), Pd(PPh$_3$)$_4$ (1.32 g, 1.1 mmol), K$_2$CO$_3$ (9.49 g, 68.6 mmol), THF, water were added to Sub 1-VI-A36 (15.69 g, 22.9 mmol) obtained in the above synthesis, and then 9.81 g (yield: 60%) of the product was obtained by using the same manner as described above for the synthesis example of Sub 1-A1.

(22) Synthesis Example of Sub 1-A101

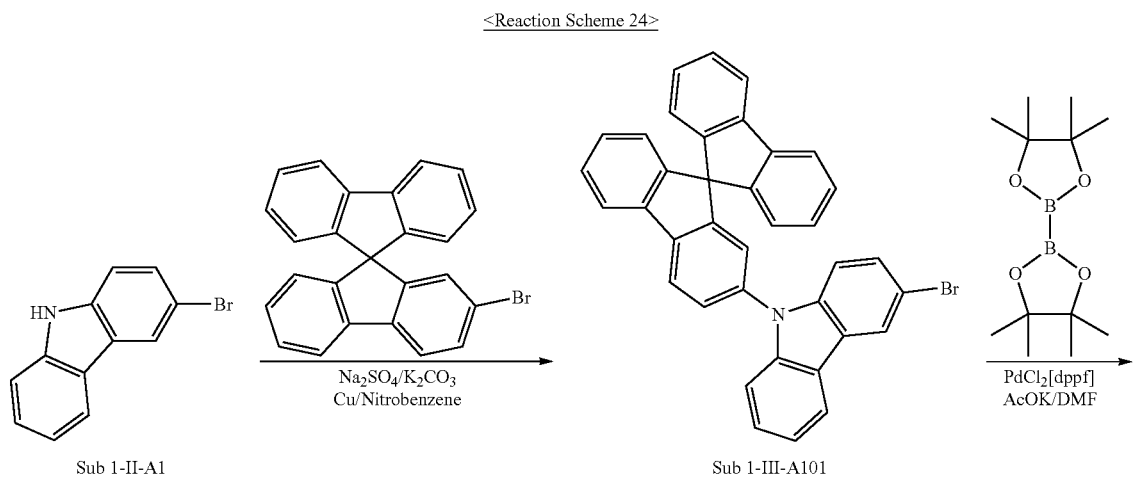

-continued
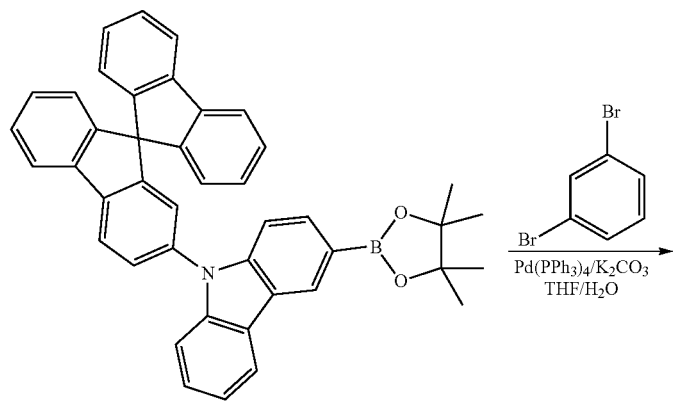
Sub 1-IV-A101
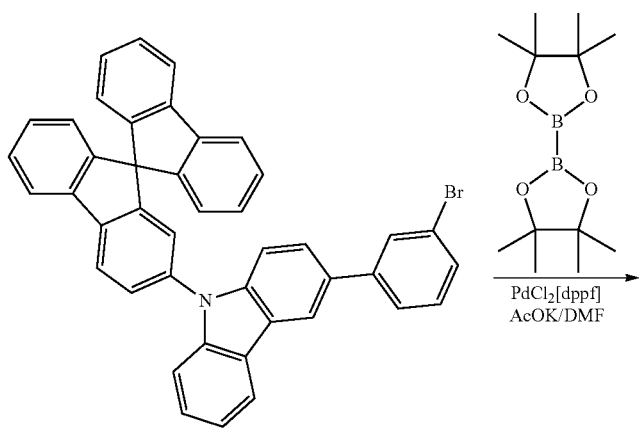
Sub 1-V-A101
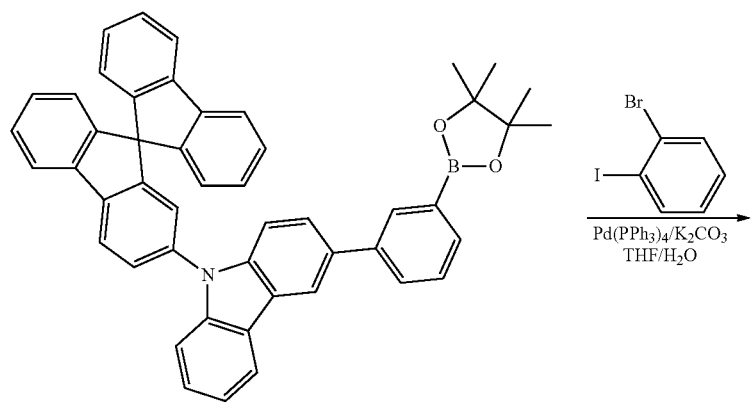
Sub 1-VI-A101

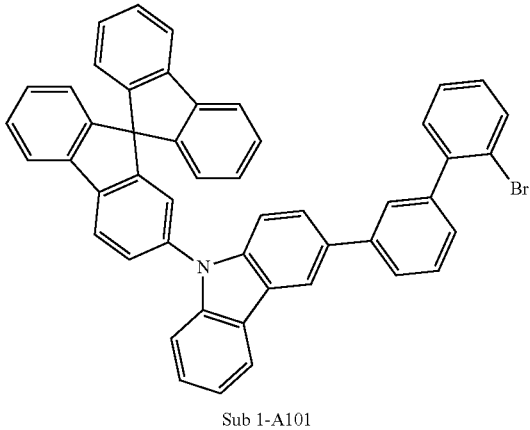 [SMILES: Brc1ccccc1-c1cccc(-c2ccc3c(c2)c2ccccc2n3-c2ccc3c(c2)C2(c4ccccc4-c4ccccc42)c2ccccc2-3)c1]

Sub 1-A101

Synthesis of Intermediate Sub 1-III-A101

2-bromo-9,9'-spirobi[fluorene] (79.53 g, 201.2 mmol), $Na_2SO_4$ (19.05 g, 134.1 mmol), $K_2CO_3$ (18.54 g, 134.1 mmol), Cu (2.56 g, 40.2 mmol), nitrobenzene were added to Sub 1-II-A1 (33.01 g, 134.1 mmol) obtained in the above synthesis, and then 39.84 g (yield: 53%) of the product was obtained by using the same manner as described above for the synthesis example of Sub 1-III-A1.

Synthesis of Intermediate Sub 1-IV-A101

Bis(pinacolato)diboron (19.86 g, 78.2 mmol), Pd(dppf)Cl$_2$ (1.74 g, 2.1 mmol), KOAc (20.93 g, 213.2 mmol), DMF were added to Sub 1-III-A101 (39.84 g, 71.1 mmol) obtained in the above synthesis, and then 32.82 g (yield: 76%) of the product was obtained by using the same manner as described above for the synthesis example of Sub 1-IV-A1.

Synthesis of Intermediate Sub 1-V-A101

1,3-dibromobenzene (19.12 g, 81 mmol), Pd(PPh$_3$)$_4$ (3.12 g, 2.7 mmol), $K_2CO_3$ (22.4 g, 162.1 mmol), THF, water were added to Sub 1-IV-A101 (32.82 g, 54 mmol) obtained in the above synthesis, and then 24.42 g (yield: 71%) of the product was obtained by using the same manner as described above for the synthesis example of Sub 1-V-A1.

Synthesis of Intermediate Sub 1-VI-A101

Bis(pinacolato)diboron (10.72 g, 42.2 mmol), Pd(dppf)Cl$_2$ (0.94 g, 1.2 mmol), KOAc (11.29 g, 115.1 mmol), DMF were added to Sub 1-V-A101 (24.42 g, 38.4 mmol) obtained in the above synthesis, and then 18.88 g (yield: 72%) of the product was obtained by using the same manner as described above for the synthesis example of Sub 1-VI-A1.

Synthesis Example of Sub 1-A101

1-bromo-2-iodobenzene (11.01 g, 38.9 mmol), Pd(PPh$_3$)$_4$ (1.5 g, 1.3 mmol), $K_2CO_3$ (10.76 g, 77.8 mmol), THF, water were added to Sub 1-VI-A101 (17.74 g, 25.9 mmol) obtained in the above synthesis, and then 10.36 g (yield: 56%) of the product was obtained by using the same manner as described above for the synthesis example of Sub 1-A1.

(23) Synthesis Example of Sub 1-A104

<Reaction Scheme 25>

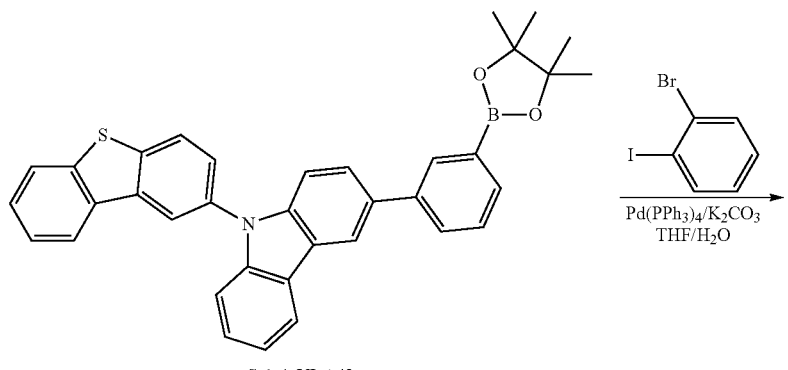

Sub 1-VI-A43

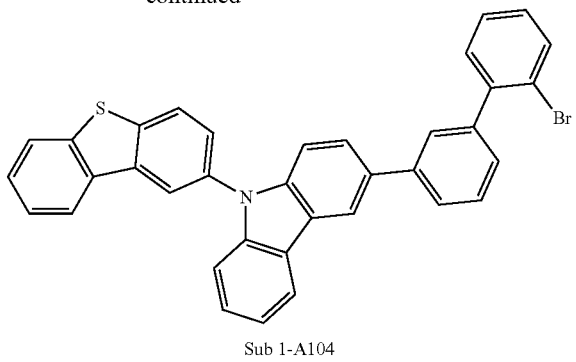

Sub 1-A104

1-bromo-2-iodobenzene (12.41 g, 43.9 mmol), Pd(PPh$_3$)$_4$ (1.69 g, 1.5 mmol), K$_2$CO$_3$ (12.13 g, 87.7 mmol), THF, water were added to Sub 1-VI-A43 (16.13 g, 29.2 mmol) obtained in the above synthesis, and then 10.7 g (yield: 63%) of the product was obtained by using the same manner as described above for the synthesis example of Sub 1-A1.

(24) Synthesis Example of Sub 1-A107

<Reaction Scheme 26>

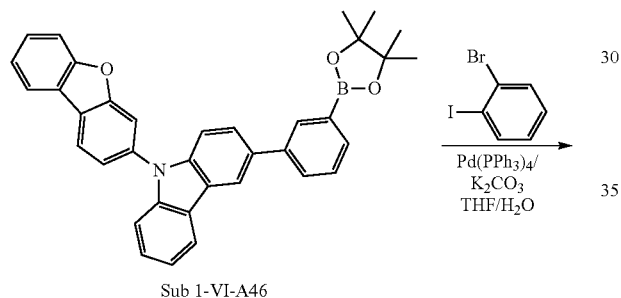

Sub 1-VI-A46

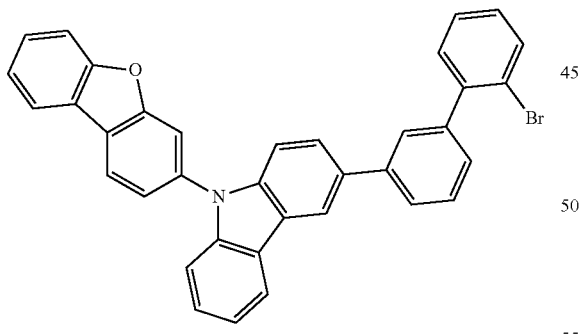

Sub 1-A107

1-bromo-2-iodobenzene (10.26 g, 36.3 mmol), Pd(PPh$_3$)$_4$ (1.4 g, 1.2 mmol), K$_2$CO$_3$ (10.02 g, 72.5 mmol), THF, water were added to Sub 1-VI-A46 (12.94 g, 24.2 mmol) obtained in the above synthesis, and then 8.87 g (yield: 65%) of the product was obtained by using the same manner as described above for the synthesis example of Sub 1-A1.

The compound belonging to Sub 1 may be, but not limited to, the following compounds, and Table 1 shows FD-MS (Field Desorption-Mass Spectrometry) values of compounds belonging to Sub 1.

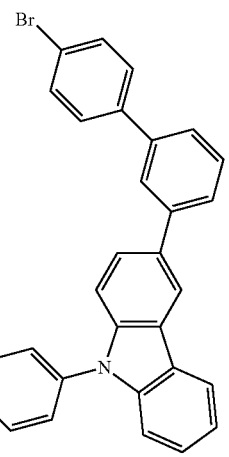

Sub 1-A1

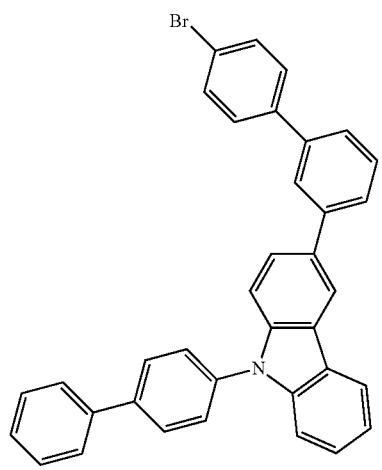

Sub 1-A2

-continued
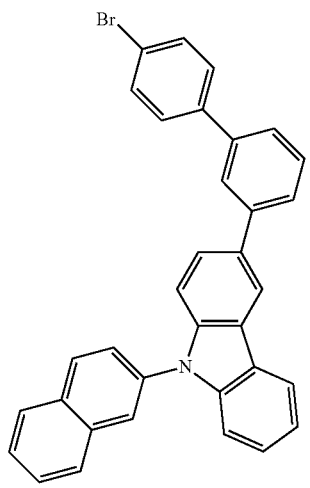
Sub 1-A3
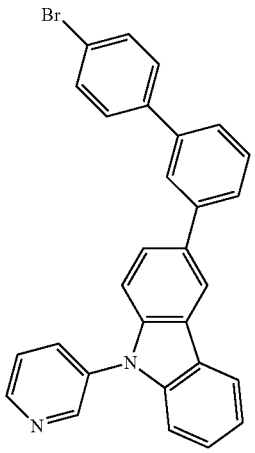
Sub 1-A6
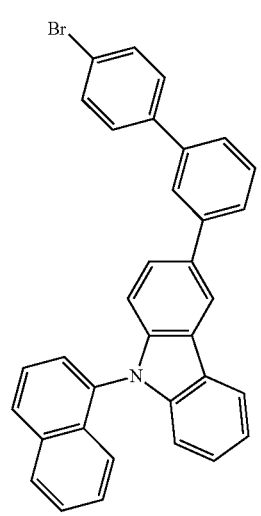
Sub 1-A4
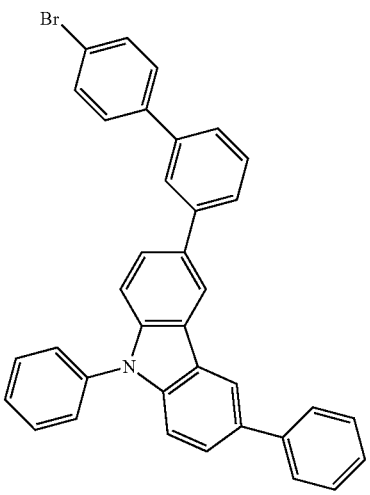
Sub 1-A7
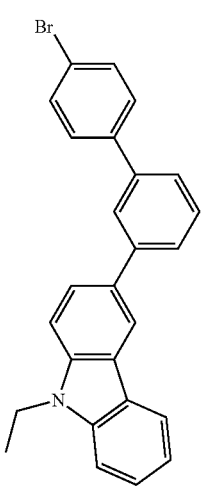
Sub 1-A5
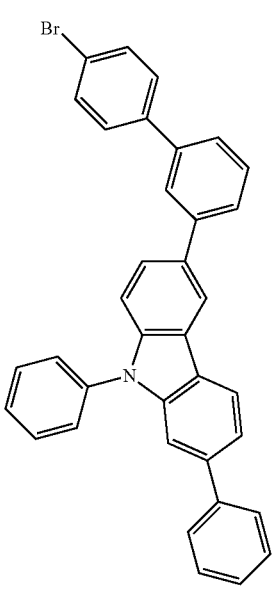
Sub 1-A8

Sub 1-A10
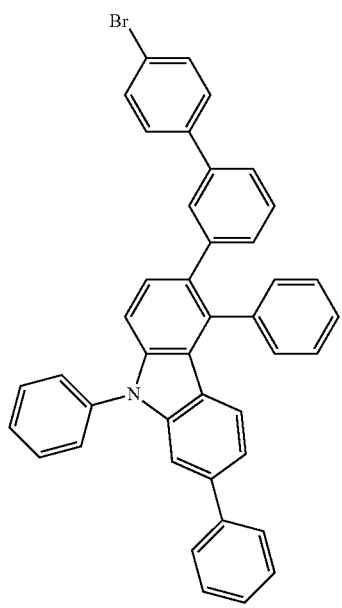
Sub 1-A11
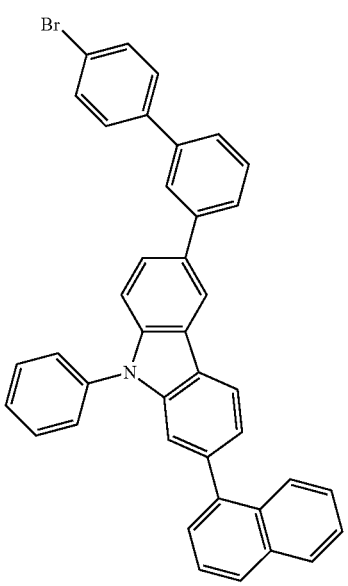
Sub 1-A13
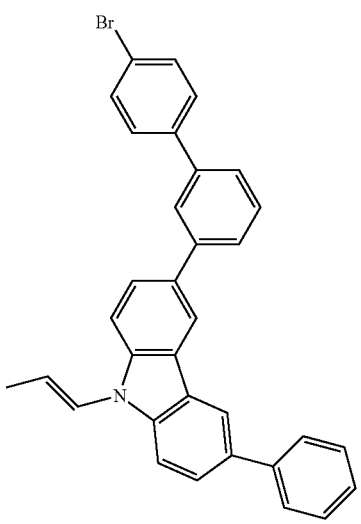
Sub 1-A14
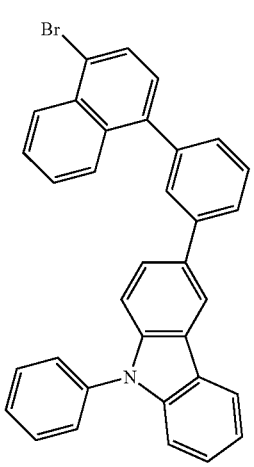
Sub 1-A18
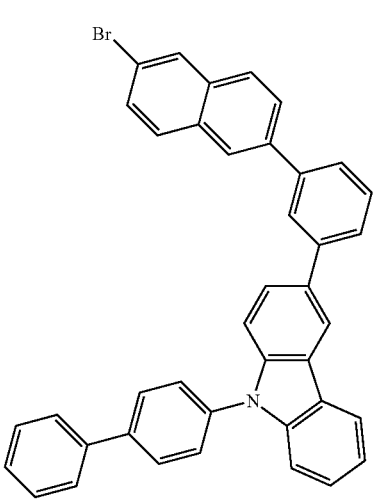

Sub 1-A21
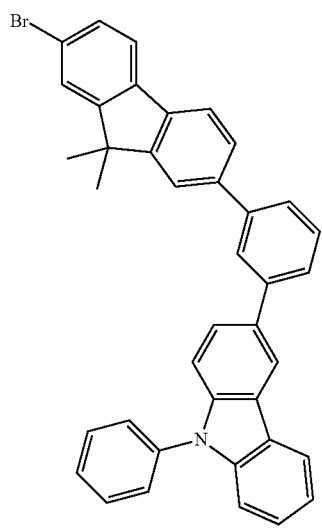
Sub 1-A22
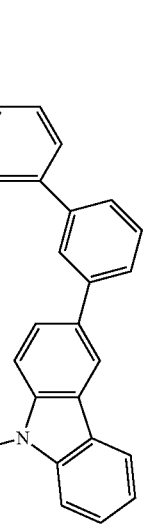
Sub 1-A23
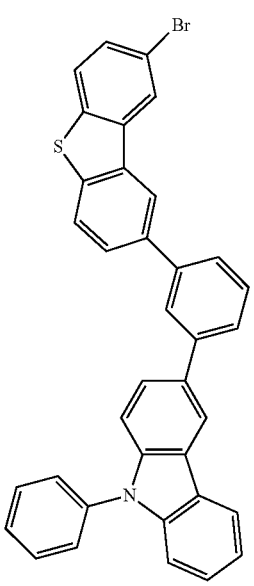
Sub 1-A24
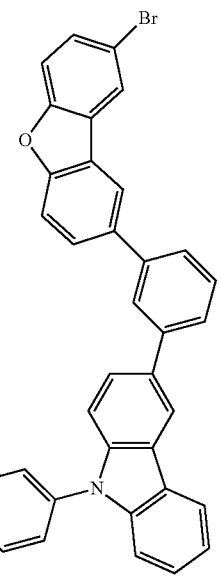
Sub 1-A25
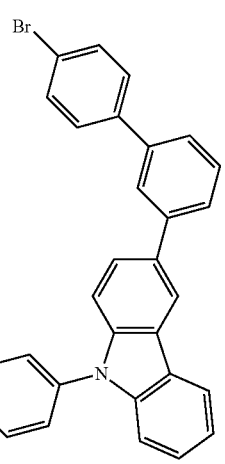
Sub 1-A26
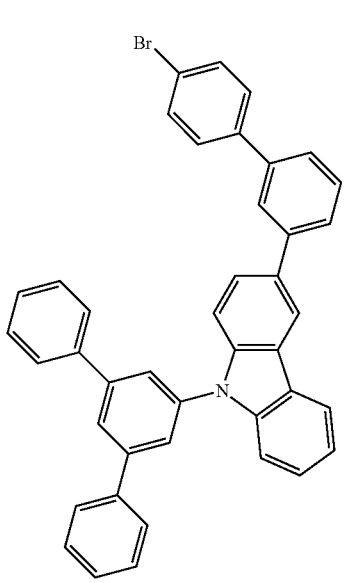

Sub 1-A27
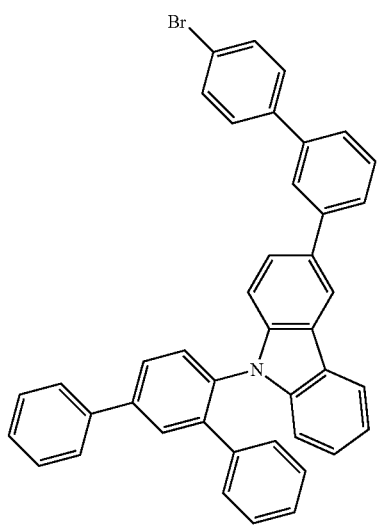
Sub 1-A30
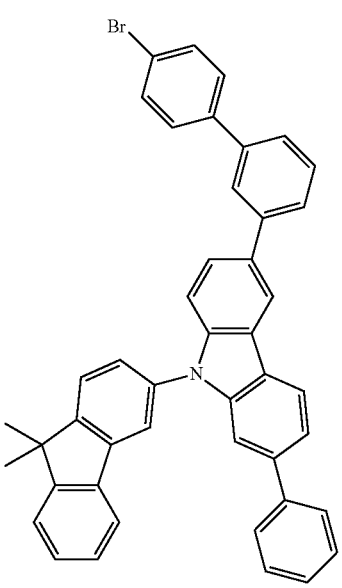
Sub 1-A28
Sub 1-A29
Sub 1-A31
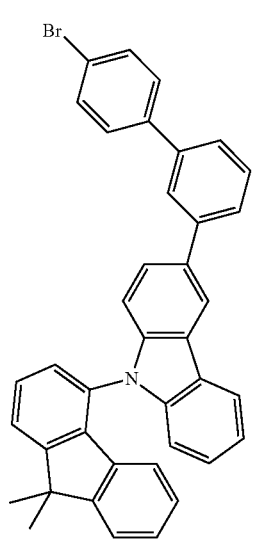

Sub 1-A32
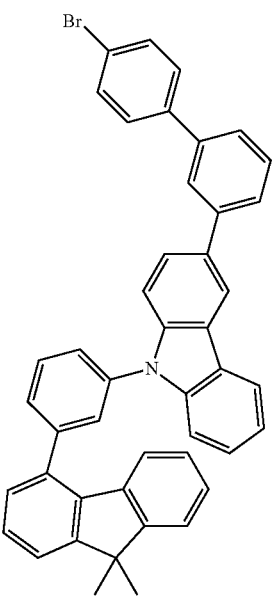
Sub 1-A35
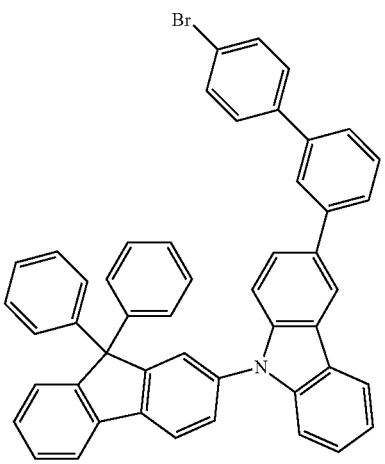
Sub 1-A33
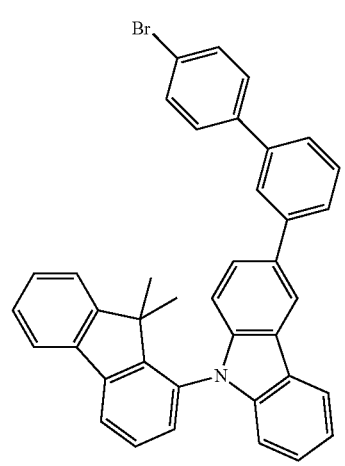
Sub 1-A36
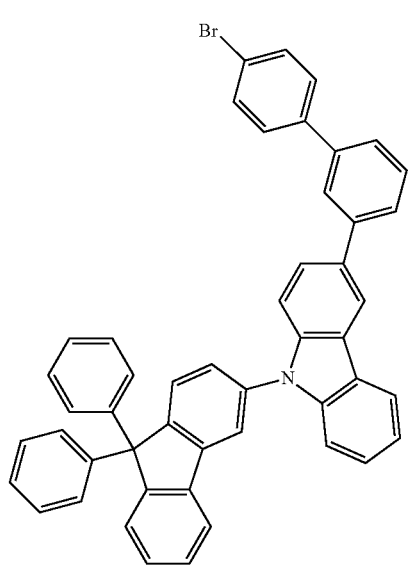
Sub 1-A34
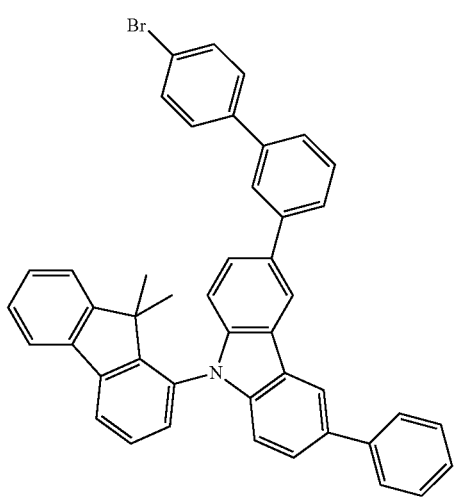
Sub 1-A37
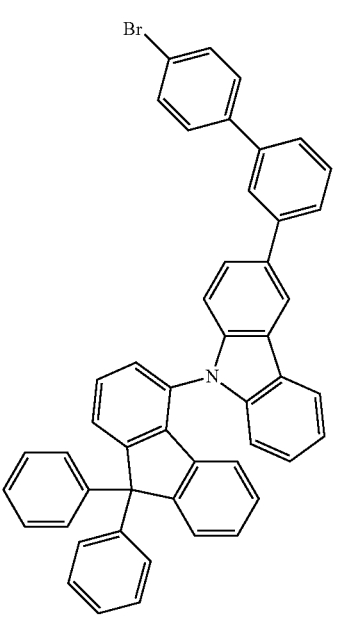

Sub1-A38
Sub 1-A39
Sub 1-A40
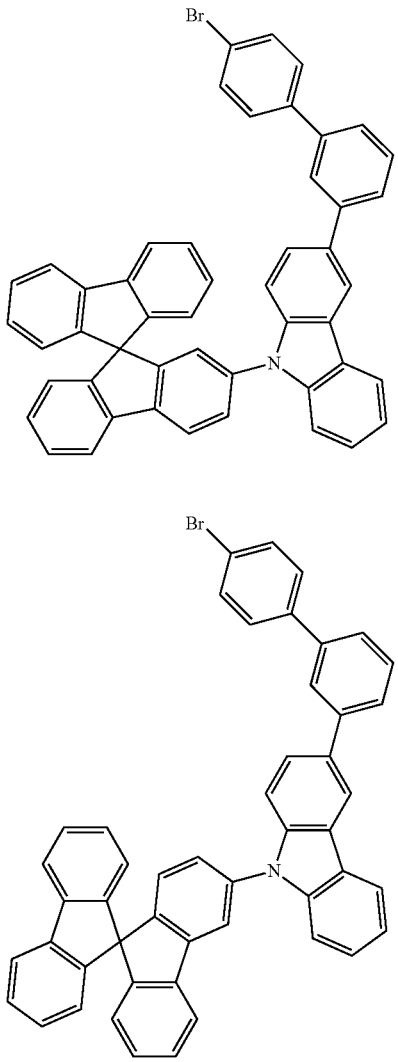
Sub 1-A41
Sub 1-A42
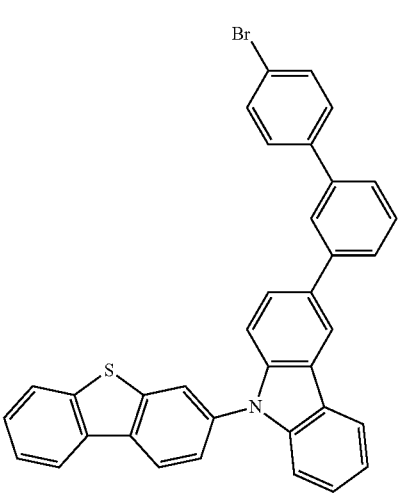

Sub 1-A43
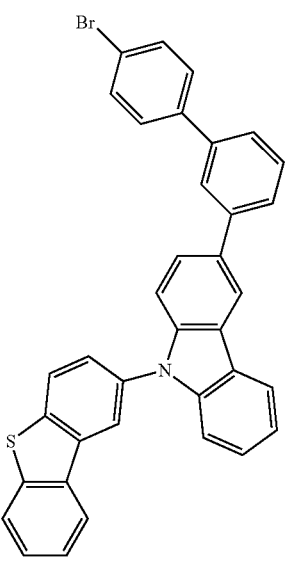
Sub 1-A44
Sub 1-A45
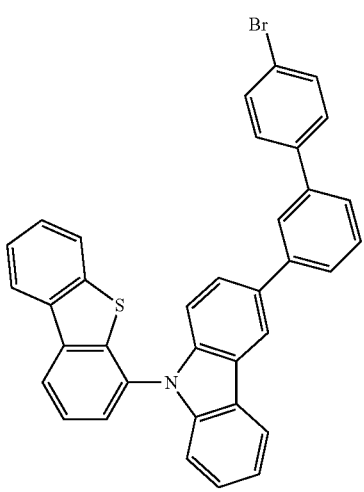
Sub 1-A46
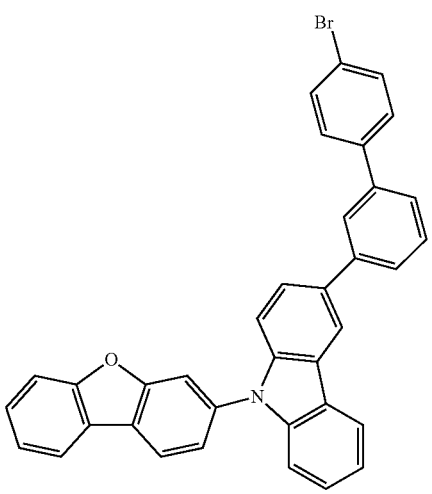
Sub 1-A47
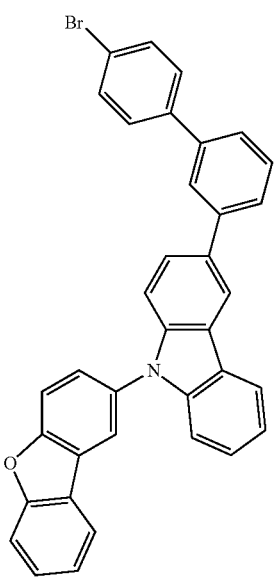
Sub 1-A48
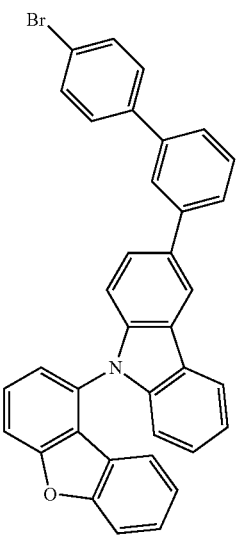

Sub 1-A49
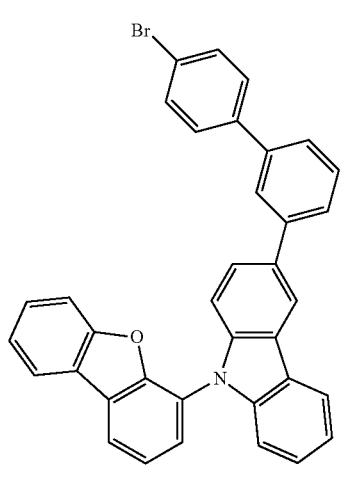
Sub 1-A52
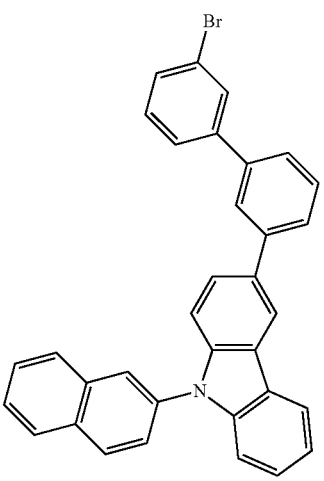
Sub 1-A50
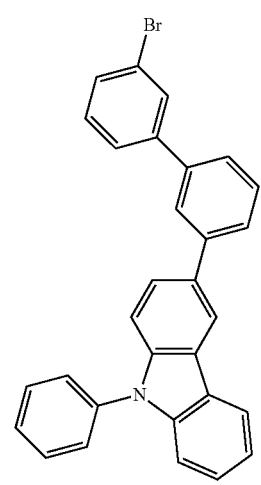
Sub 1-A53
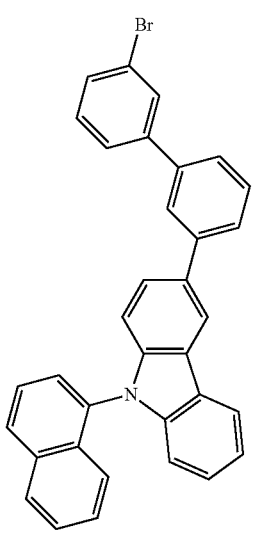
Sub 1-A51
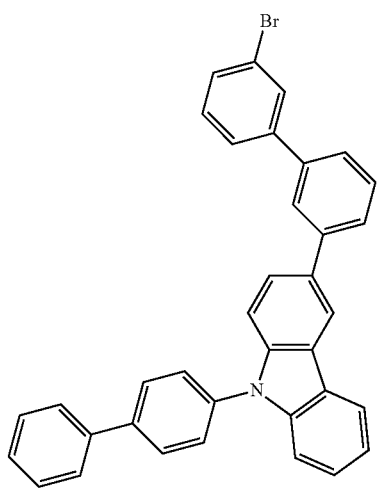
Sub 1-A54
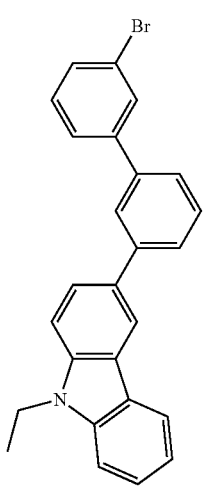

Sub 1-A-55
Sub 1-A56
Sub 1-A57
Sub 1-A58
Sub 1-A59
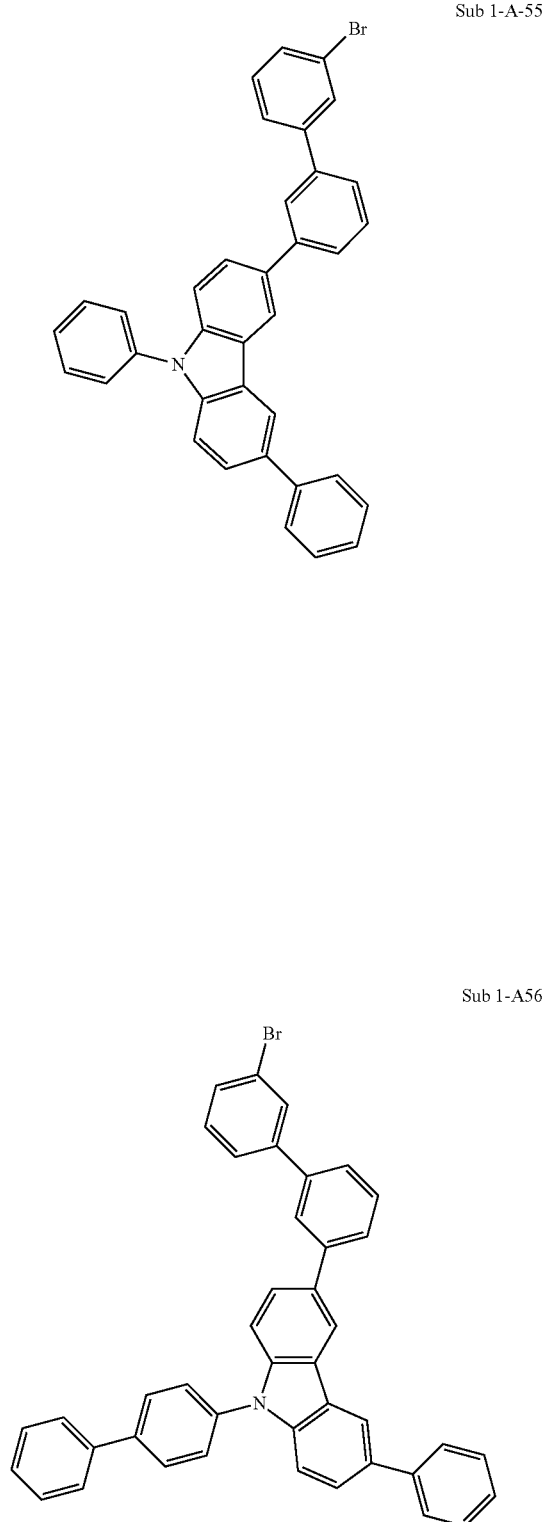
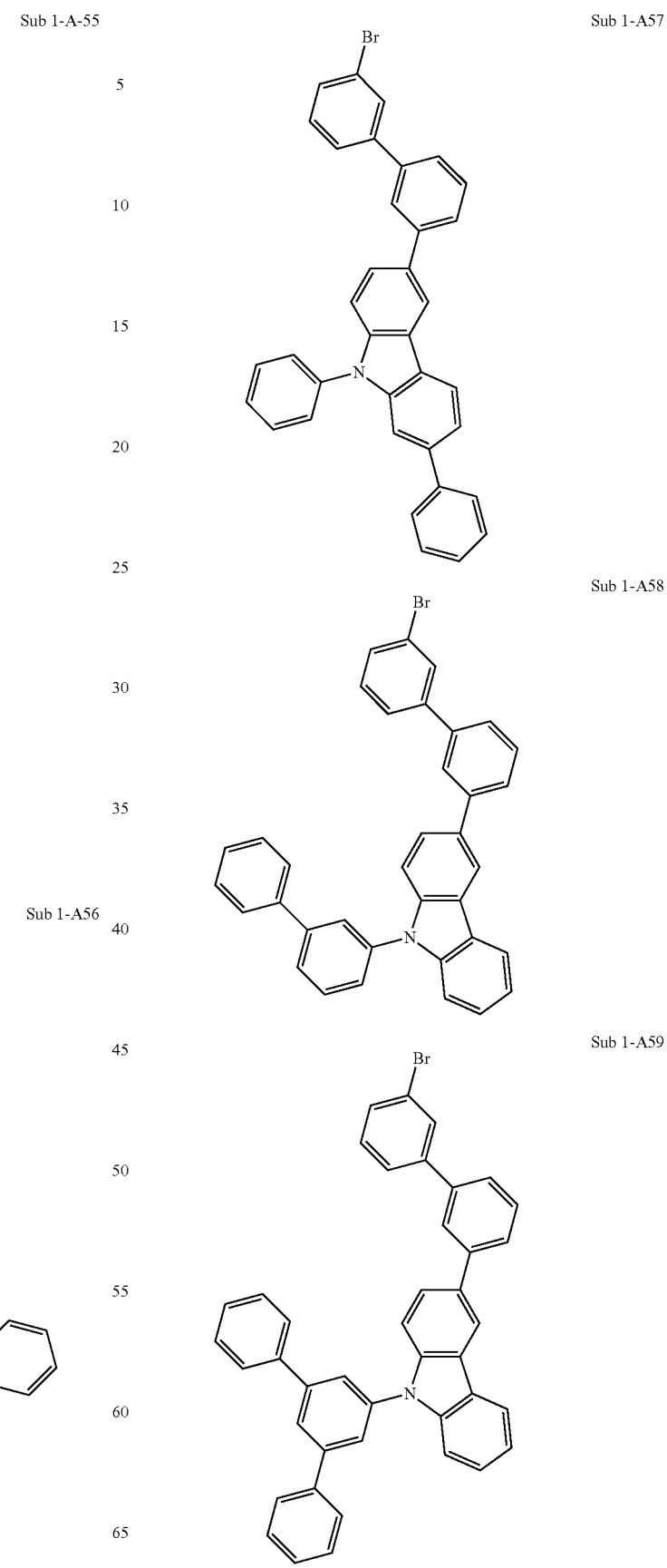

Sub 1-A60
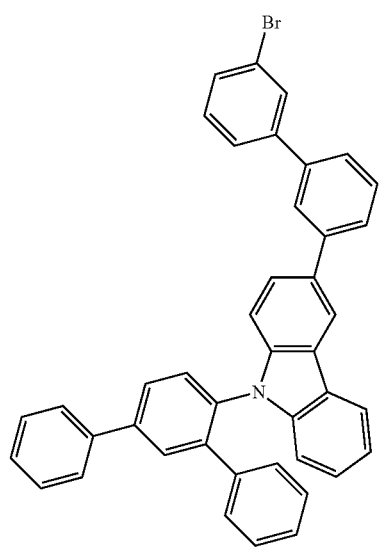
Sub 1-A61
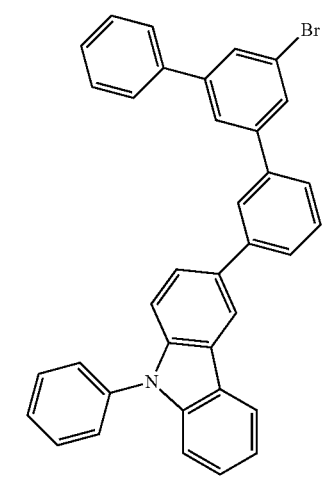
Sub 1-A62
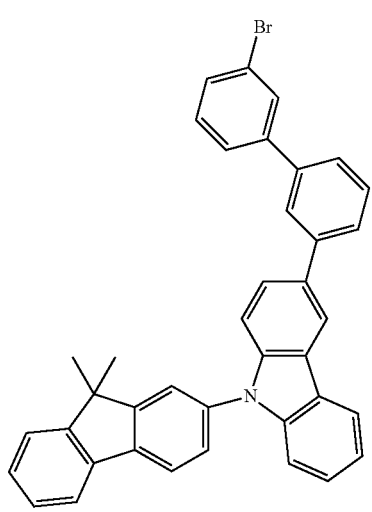
Sub 1-A63
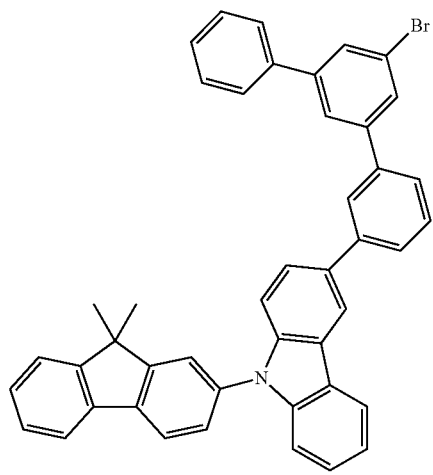
Sub 1-A64
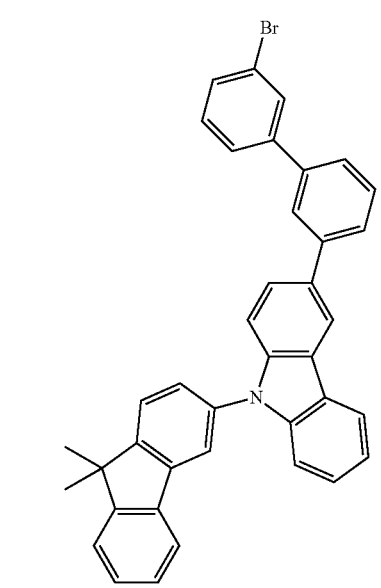
Sub 1-A65
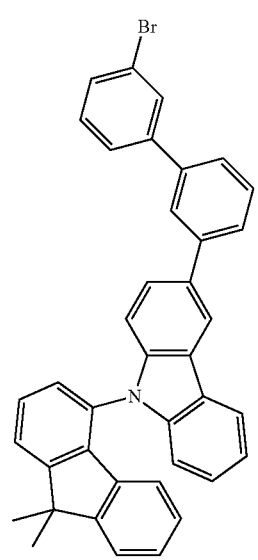

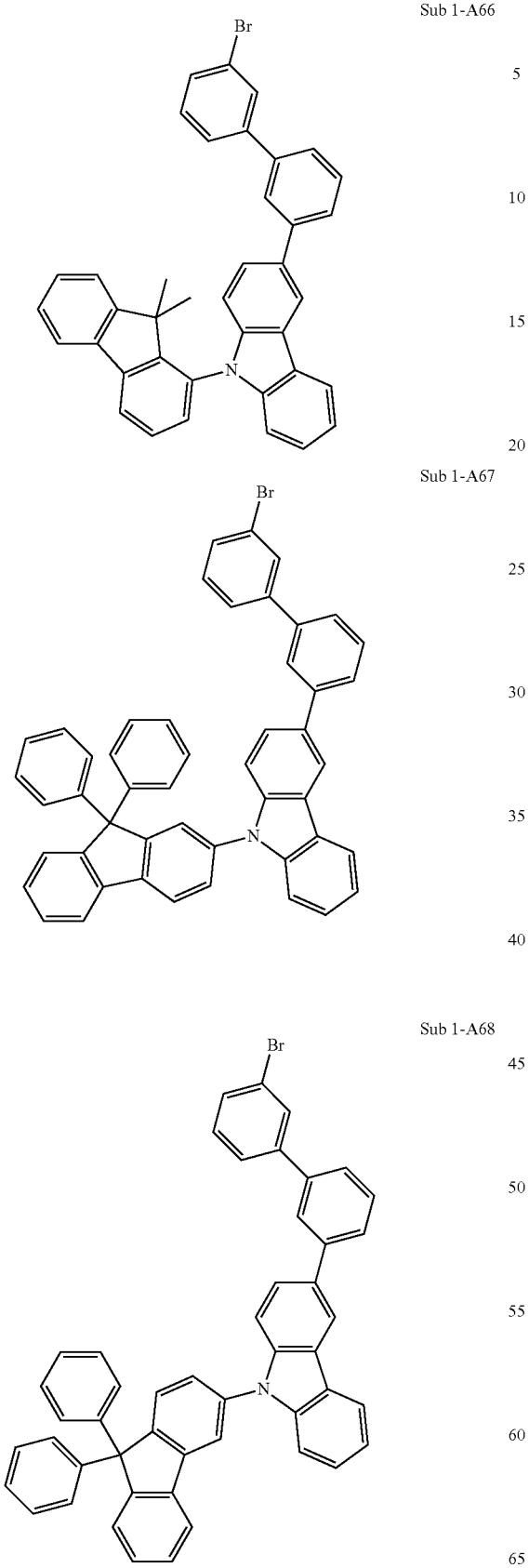
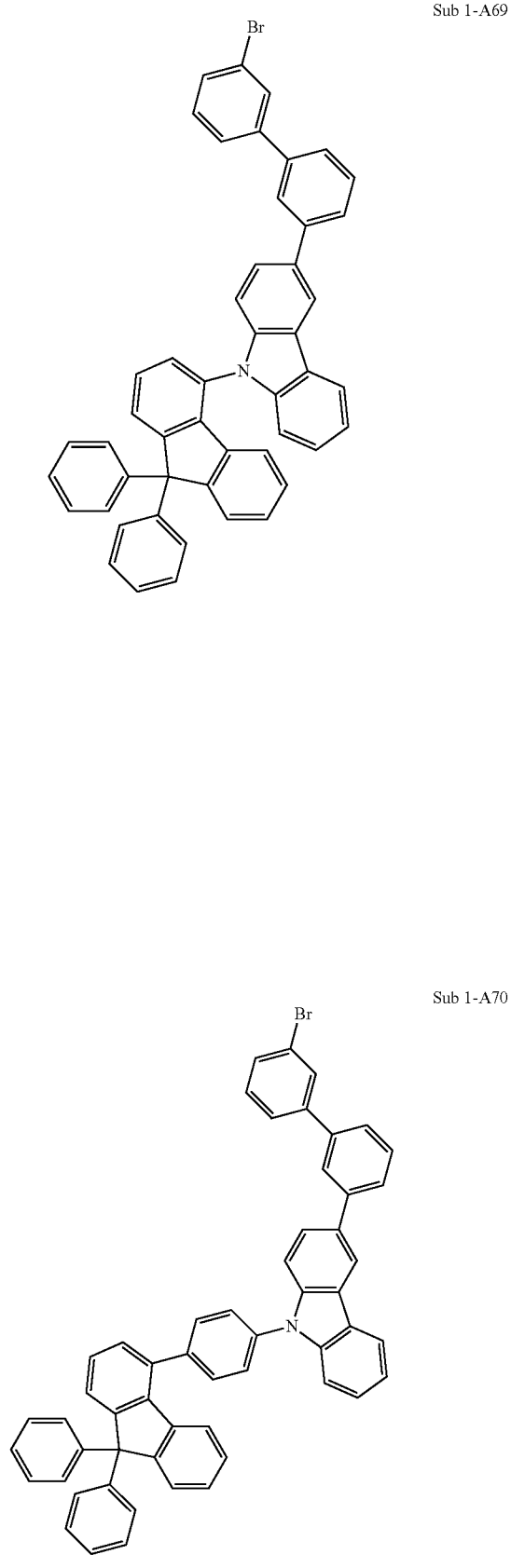

Sub 1-A71
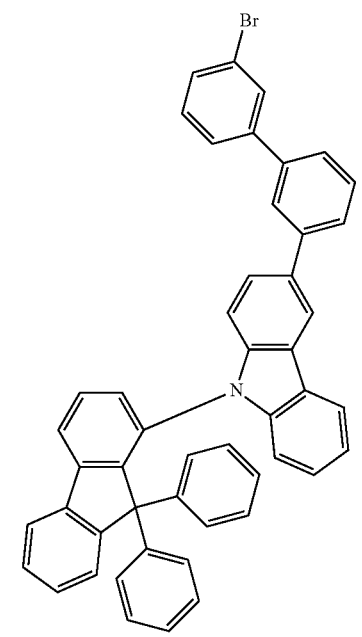
Sub 1-A72
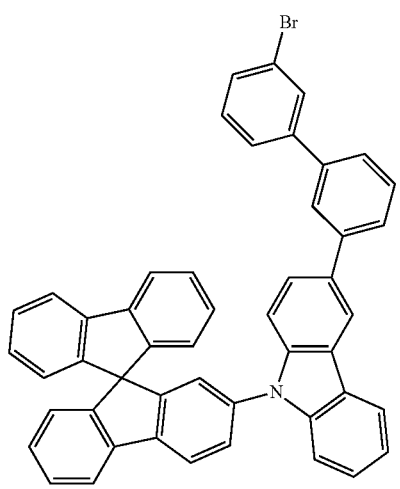
Sub 1-A73
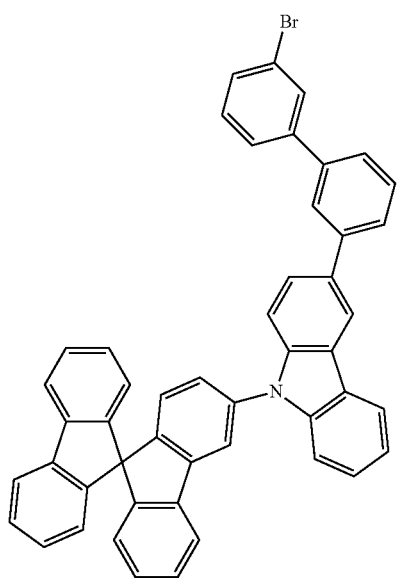
Sub 1-A74
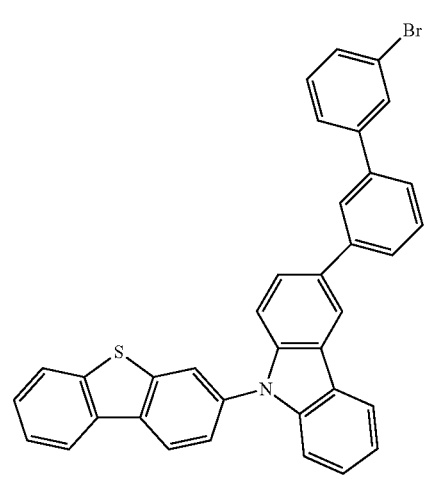
Sub 1-A75
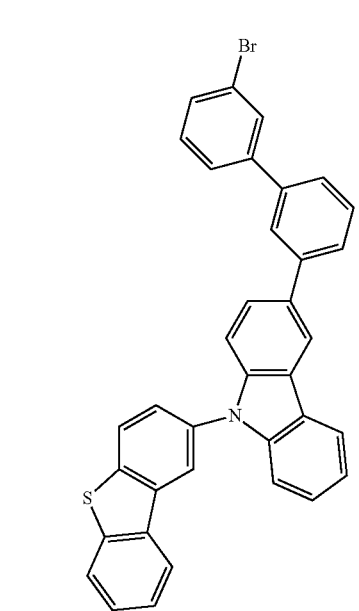

Sub 1-A76
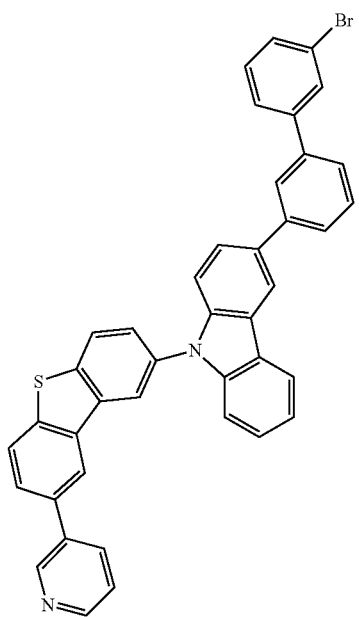
Sub 1-A77
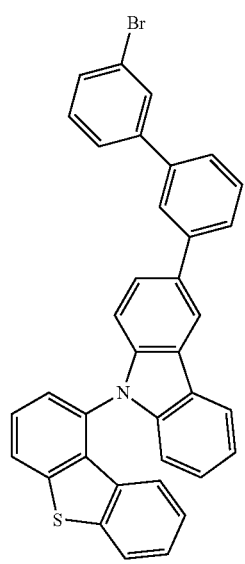
Sub 1-A78
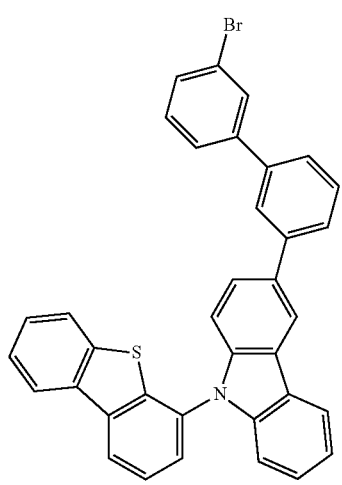
Sub 1-A79
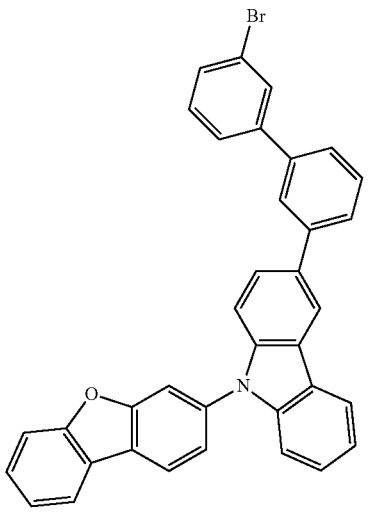
Sub 1-A80
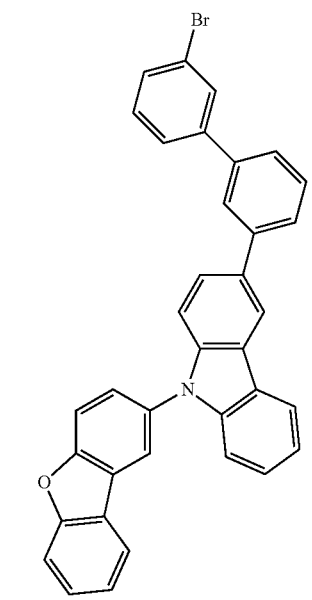
Sub 1-A81
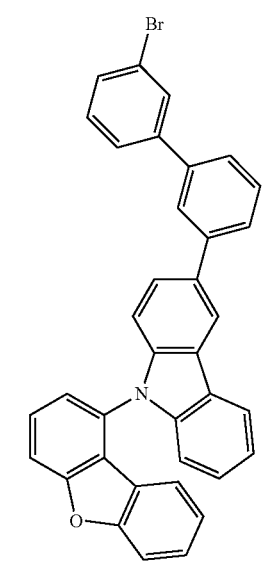

Sub 1-A82
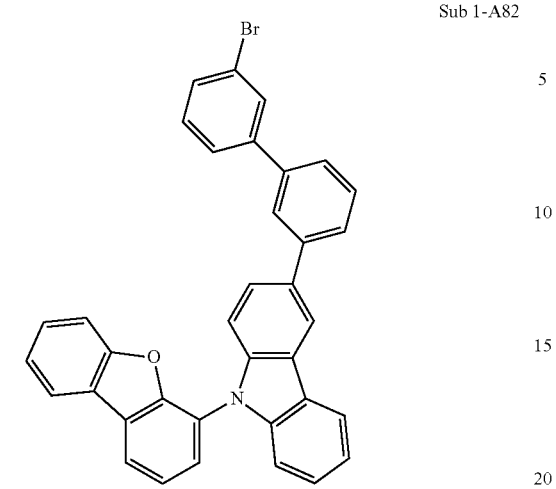
Sub 1-A85
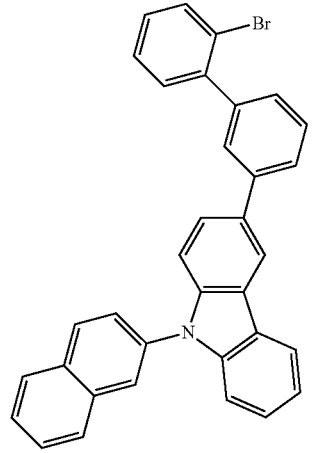
Sub 1-A83
Sub 1-A86
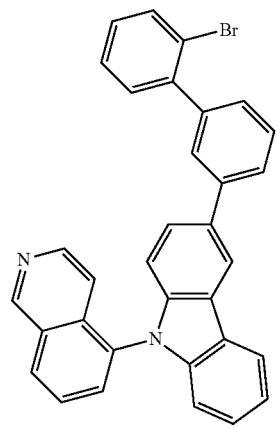
Sub 1-A84
Sub 1-A87
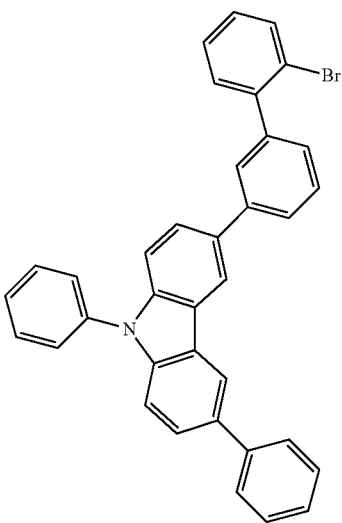

Sub 1-A88
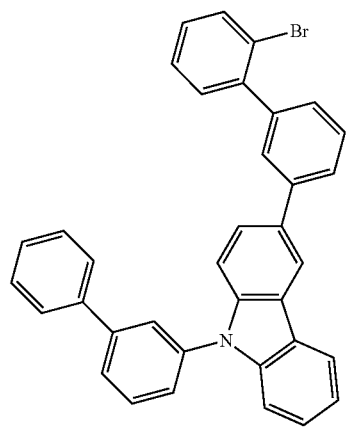
Sub 1-A89
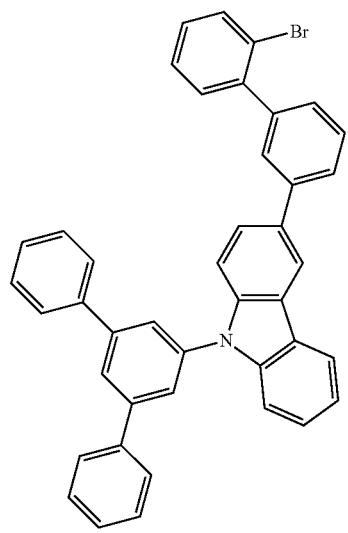
Sub 1-A90
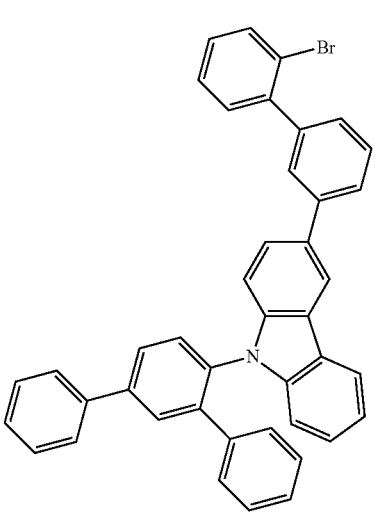
Sub 1-A91
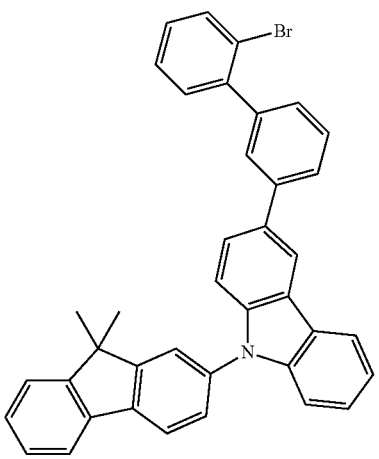
Sub 1-A92
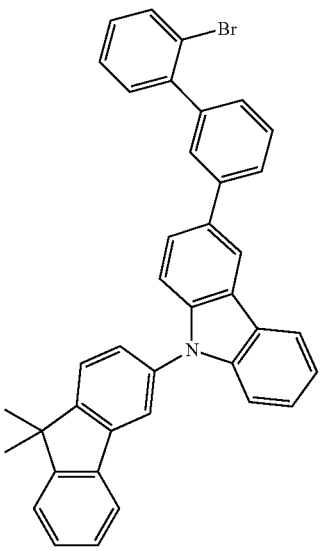
Sub 1-A93
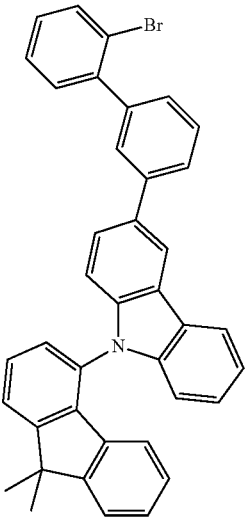

Sub 1-A94
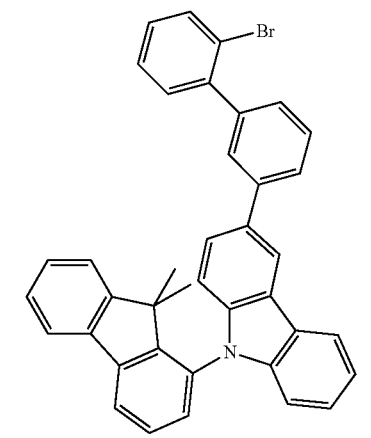
Sub 1-A95
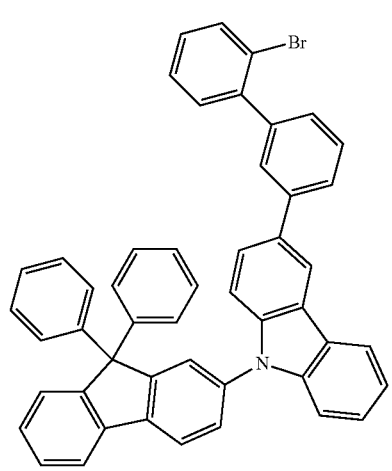
Sub 1-A96
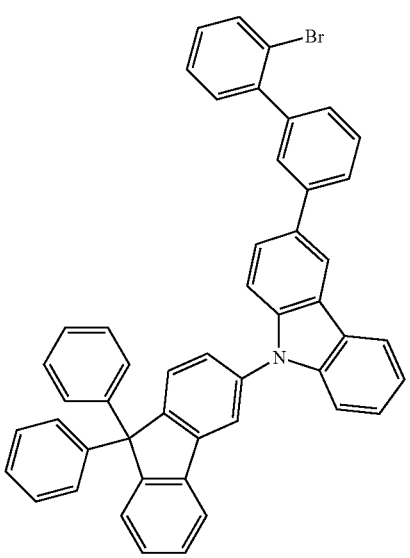
Sub 1-A97
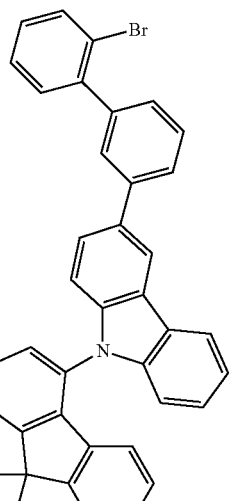
Sub 1-A98
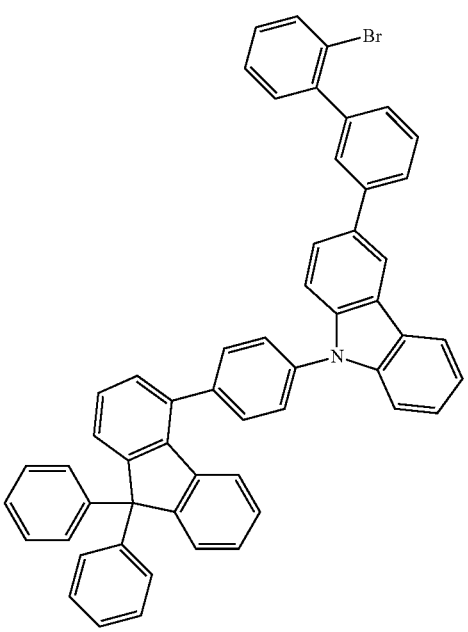

-continued
Sub 1-A99
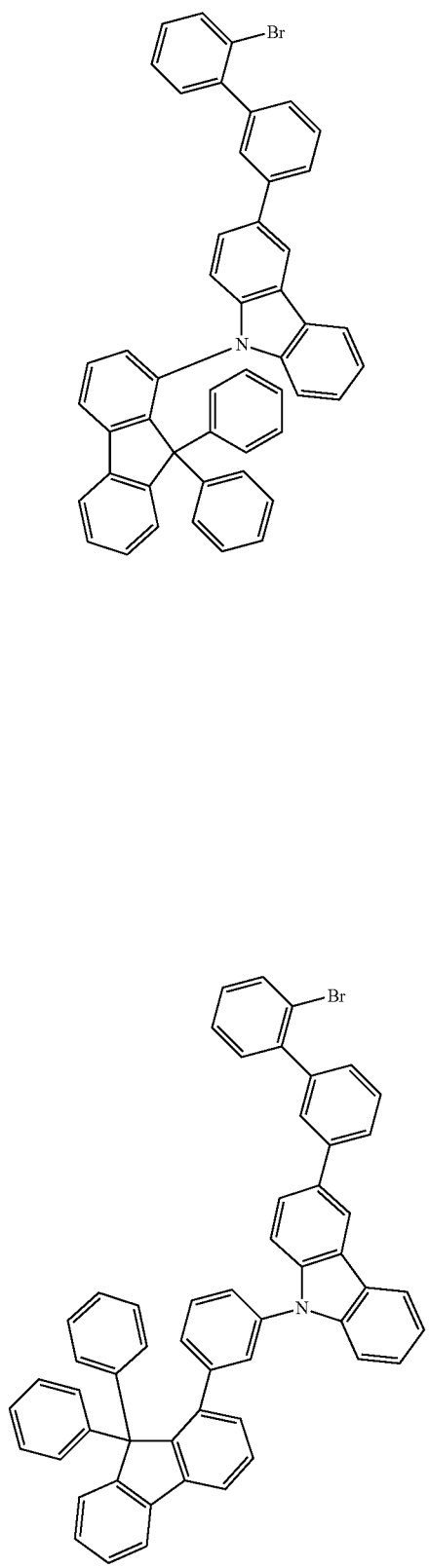
Sub 1-A100
Sub 1-A101
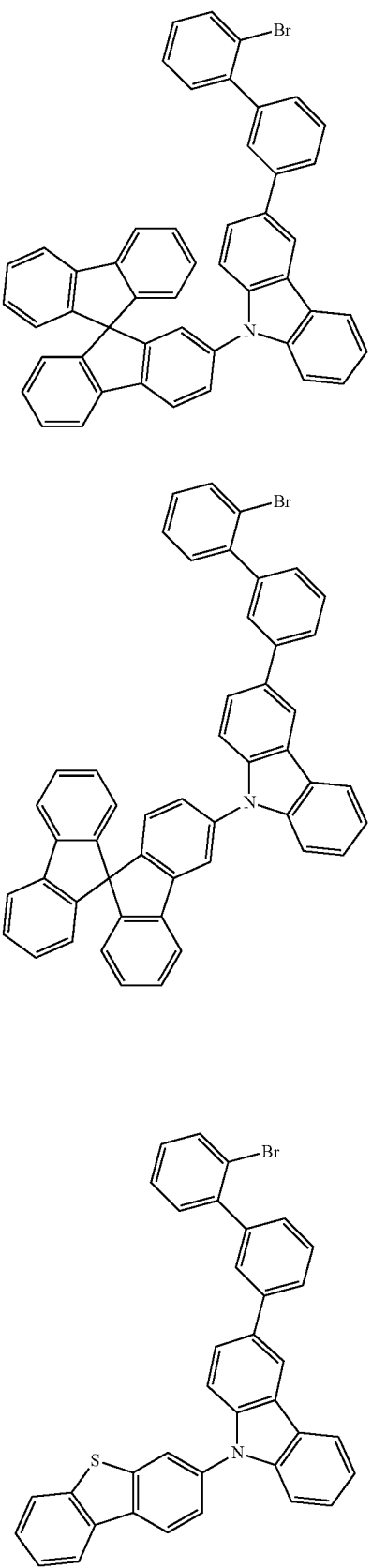
Sub 1-A102
Sub 1-A103

Sub 1-A104
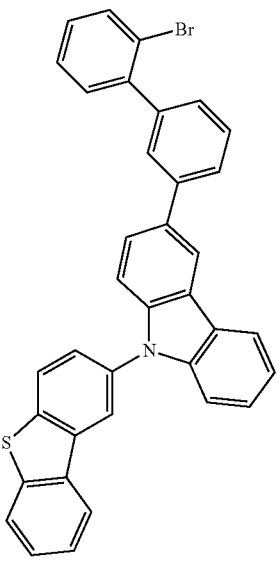
Sub 1-A105
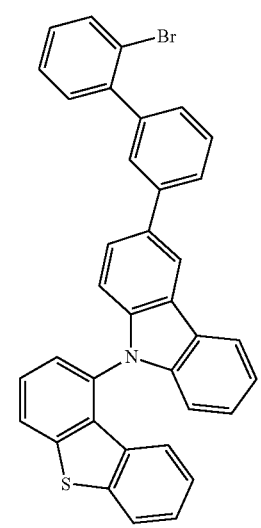
Sub 1-A106
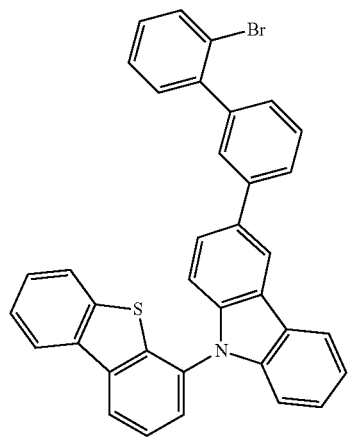
Sub 1-A107
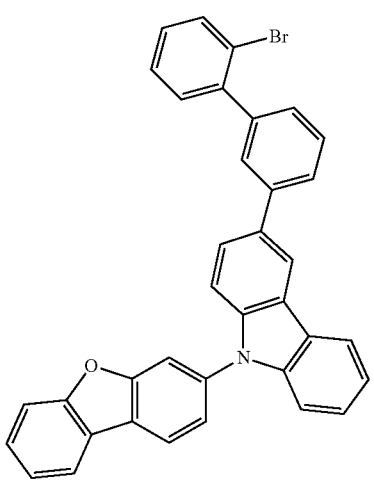
Sub 1-A108
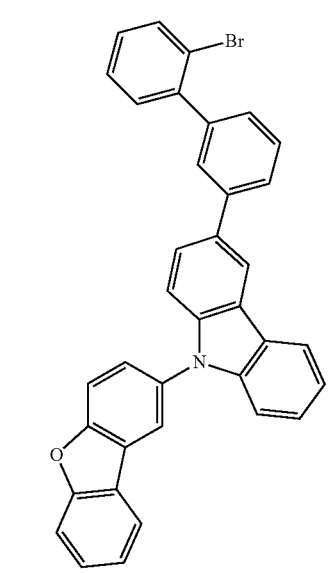
Sub 1-A109
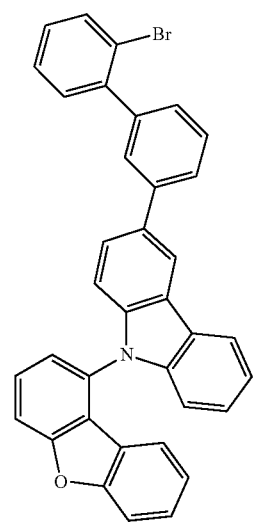

Sub 1-A110

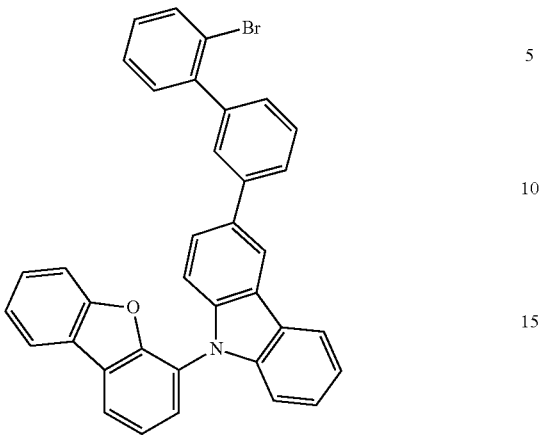

TABLE 1

| compound | FD-MS | compound | FD-MS |
| --- | --- | --- | --- |
| Sub1-A1 | m/z = 473.08($C_{30}H_{20}BrN$ = 474.39) | Sub1-A2 | m/z = 549.11($C_{36}H_{24}BrN$ = 550.49) |
| Sub1-A3 | m/z = 523.09($C_{34}H_{22}BrN$ = 524.45) | Sub1-A4 | m/z = 523.09($C_{34}H_{22}BrN$ = 524.45) |
| Sub1-A5 | m/z = 425.08($C_{26}H_{20}BrN$ = 426.35) | Sub1-A6 | m/z = 474.07($C_{29}H_{19}BrN_2$ = 475.38) |
| Sub1-A7 | m/z = 549.11($C_{36}H_{24}BrN$ = 550.49) | Sub1-A8 | m/z = 549.11($C_{36}H_{24}BrN$ = 550.49) |
| Sub1-A9 | m/z = 487.09($C_{31}H_{22}BrN$ = 488.42) | Sub1-A10 | m/z = 625.14($C_{42}H_{28}BrN$ = 626.58) |
| Sub1-A11 | m/z = 599.12($C_{40}H_{26}BrN$ = 600.55) | Sub1-A12 | m/z = 487.09($C_{31}H_{22}BrN$ = 488.42) |
| Sub1-A13 | m/z = 513.11($C_{33}H_{24}BrN$ = 514.45) | Sub1-A14 | m/z = 523.09($C_{34}H_{22}BrN$ = 524.45) |
| Sub1-A15 | m/z = 475.09($C_{30}H_{22}BrN$ = 476.41) | Sub1-A16 | m/z = 599.12($C_{40}H_{26}BrN$ = 600.55) |
| Sub1-A17 | m/z = 523.09($C_{34}H_{22}BrN$ = 524.45) | Sub1-A18 | m/z = 599.12($C_{40}H_{26}BrN$ = 600.55) |
| Sub1-A19 | m/z = 599.12($C_{40}H_{26}BrN$ = 600.55) | Sub1-A20 | m/z = 599.12($C_{40}H_{26}BrN$ = 600.55) |
| Sub1-A21 | m/z = 589.14($C_{39}H_{28}BrN$ = 590.55) | Sub1-A22 | m/z = 713.17($C_{49}H_{32}BrN$ = 714.69) |
| Sub1-A23 | m/z = 579.07($C_{36}H_{22}BrNS$ = 580.54) | Sub1-A24 | m/z = 563.09($C_{36}H_{22}BrNO$ = 564.47) |
| Sub1-A25 | m/z = 549.11($C_{36}H_{24}BrN$ = 550.49) | Sub1-A26 | m/z = 625.14($C_{42}H_{28}BrN$ = 626.58) |
| Sub1-A27 | m/z = 625.14($C_{42}H_{28}BrN$ = 626.58) | Sub1-A28 | m/z = 589.14($C_{39}H_{28}BrN$ = 590.55) |
| Sub1-A29 | m/z = 589.14($C_{39}H_{28}BrN$ = 590.55) | Sub1-A30 | m/z = 665.17($C_{45}H_{32}BrN$ = 666.65) |
| Sub1-A31 | m/z = 589.14($C_{39}H_{28}BrN$ = 590.55) | Sub1-A32 | m/z = 665.17($C_{45}H_{32}BrN$ = 666.65) |
| Sub1-A33 | m/z = 589.14($C_{39}H_{28}BrN$ = 590.55) | Sub1-A34 | m/z = 665.17($C_{45}H_{32}BrN$ = 666.65) |
| Sub1-A35 | m/z = 713.17($C_{49}H_{32}BrN$ = 714.69) | Sub1-A36 | m/z = 713.17($C_{49}H_{32}BrN$ = 714.69) |
| Sub1-A37 | m/z = 713.17($C_{49}H_{32}BrN$ = 714.69) | Sub1-A38 | m/z = 713.17($C_{49}H_{32}BrN$ = 714.69) |
| Sub1-A39 | m/z = 789.20($C_{55}H_{36}BrN$ = 790.79) | Sub1-A40 | m/z = 711.16($C_{49}H_{30}BrN$ = 712.67) |
| Sub1-A41 | m/z = 711.16($C_{49}H_{30}BrN$ = 712.67) | Sub1-A42 | m/z = 579.07($C_{36}H_{22}BrNS$ = 580.54) |
| Sub1-A43 | m/z = 579.07($C_{36}H_{22}BrNS$ = 580.54) | Sub1-A44 | m/z = 579.07($C_{36}H_{22}BrNS$ = 580.54) |
| Sub1-A45 | m/z = 579.07($C_{36}H_{22}BrNS$ = 580.54) | Sub1-A46 | m/z = 563.09($C_{36}H_{22}BrNO$ = 564.47) |
| Sub1-A47 | m/z = 563.09($C_{36}H_{22}BrNO$ = 564.47) | Sub1-A48 | m/z = 563.09($C_{36}H_{22}BrNO$ = 564.47) |
| Sub1-A49 | m/z = 563.09($C_{36}H_{22}BrNO$ = 564.47) | Sub1-A50 | m/z = 473.08($C_{30}H_{20}BrN$ = 474.39) |
| Sub1-A51 | m/z = 549.11($C_{36}H_{24}BrN$ = 550.49) | Sub1-A52 | m/z = 523.09($C_{34}H_{22}BrN$ = 524.45) |
| Sub1-A53 | m/z = 523.09($C_{34}H_{22}BrN$ = 524.45) | Sub1-A54 | m/z = 425.08($C_{26}H_{20}BrN$ = 426.35) |
| Sub1-A55 | m/z = 549.11($C_{36}H_{24}BrN$ = 550.49) | Sub1-A56 | m/z = 625.14($C_{42}H_{28}BrN$ = 626.58) |
| Sub1-A57 | m/z = 549.11($C_{36}H_{24}BrN$ = 550.49) | Sub1-A58 | m/z = 549.11($C_{36}H_{24}BrN$ = 550.49) |
| Sub1-A59 | m/z = 625.14($C_{42}H_{28}BrN$ = 626.58) | Sub1-A60 | m/z = 625.14($C_{42}H_{28}BrN$ = 626.58) |
| Sub1-A61 | m/z = 549.11($C_{36}H_{24}BrN$ = 550.49) | Sub1-A62 | m/z = 589.14($C_{39}H_{28}BrN$ = 590.55) |
| Sub1-A63 | m/z = 665.17($C_{45}H_{32}BrN$ = 666.65) | Sub1-A64 | m/z = 589.14($C_{39}H_{28}BrN$ = 590.55) |
| Sub1-A65 | m/z = 589.14($C_{39}H_{28}BrN$ = 590.55) | Sub1-A66 | m/z = 589.14($C_{39}H_{28}BrN$ = 590.55) |
| Sub1-A67 | m/z = 713.17($C_{49}H_{32}BrN$ = 714.69) | Sub1-A68 | m/z = 713.17($C_{49}H_{32}BrN$ = 714.69) |
| Sub1-A69 | m/z = 713.17($C_{49}H_{32}BrN$ = 714.69) | Sub1-A70 | m/z = 789.20($C_{55}H_{36}BrN$ = 790.79) |
| Sub1-A71 | m/z = 713.17($C_{49}H_{32}BrN$ = 714.69) | Sub1-A72 | m/z = 711.16($C_{49}H_{30}BrN$ = 712.67) |
| Sub1-A73 | m/z = 711.16($C_{49}H_{30}BrN$ = 712.67) | Sub1-A74 | m/z = 579.07($C_{36}H_{22}BrNS$ = 580.54) |
| Sub1-A75 | m/z = 579.07($C_{36}H_{22}BrNS$ = 580.54) | Sub1-A76 | m/z = 656.09($C_{41}H_{25}BrN_2S$ = 657.62) |
| Sub1-A77 | m/z = 579.07($C_{36}H_{22}BrNS$ = 580.54) | Sub1-A78 | m/z = 579.07($C_{36}H_{22}BrNS$ = 580.54) |
| Sub1-A79 | m/z = 563.09($C_{36}H_{22}BrNO$ = 564.47) | Sub1-A80 | m/z = 563.09($C_{36}H_{22}BrNO$ = 564.47) |
| Sub1-A81 | m/z = 563.09($C_{36}H_{22}BrNO$ = 564.47) | Sub1-A82 | m/z = 563.09($C_{36}H_{22}BrNO$ = 564.47) |
| Sub1-A83 | m/z = 473.08($C_{30}H_{20}BrN$ = 474.39) | Sub1-A84 | m/z = 549.11($C_{36}H_{24}BrN$ = 550.49) |
| Sub1-A85 | m/z = 523.09($C_{34}H_{22}BrN$ = 524.45) | Sub1-A86 | m/z = 524.09($C_{33}H_{21}BrN_2$ = 525.44) |
| Sub1-A87 | m/z = 549.11($C_{36}H_{24}BrN$ = 550.49) | Sub1-A88 | m/z = 549.11($C_{36}H_{24}BrN$ = 550.49) |
| Sub1-A89 | m/z = 625.14($C_{42}H_{28}BrN$ = 626.58) | Sub1-A90 | m/z = 625.14($C_{42}H_{28}BrN$ = 626.58) |
| Sub1-A91 | m/z = 589.14($C_{39}H_{28}BrN$ = 590.55) | Sub1-A92 | m/z = 589.14($C_{39}H_{28}BrN$ = 590.55) |
| Sub1-A93 | m/z = 589.14($C_{39}H_{28}BrN$ = 590.55) | Sub1-A94 | m/z = 589.14($C_{39}H_{28}BrN$ = 590.55) |
| Sub1-A95 | m/z = 713.17($C_{49}H_{32}BrN$ = 714.69) | Sub1-A96 | m/z = 713.17($C_{49}H_{32}BrN$ = 714.69) |
| Sub1-A97 | m/z = 713.17($C_{49}H_{32}BrN$ = 714.69) | Sub1-A98 | m/z = 789.20($C_{55}H_{36}BrN$ = 790.79) |
| Sub1-A99 | m/z = 713.17($C_{49}H_{32}BrN$ = 714.69) | Sub1-A100 | m/z = 789.20($C_{55}H_{36}BrN$ = 790.79) |
| Sub1-A101 | m/z = 711.16($C_{49}H_{30}BrN$ = 712.67) | Sub1-A102 | m/z = 711.16($C_{49}H_{30}BrN$ = 712.67) |

TABLE 1-continued

| compound | FD-MS | compound | FD-MS |
|---|---|---|---|
| Sub1-A103 | m/z = 579.07($C_{36}H_{22}BrNS$ = 580.54) | Sub1-A104 | m/z = 579.07($C_{36}H_{22}BrNS$ = 580.54) |
| Sub1-A105 | m/z = 579.07($C_{36}H_{22}BrNS$ = 580.54) | Sub1-A106 | m/z = 579.07($C_{36}H_{22}BrNS$ = 580.54) |
| Sub1-A107 | m/z = 563.09($C_{36}H_{22}BrNO$ = 564.47) | Sub1-A108 | m/z = 563.09($C_{36}H_{22}BrNO$ = 564.47) |
| Sub1-A109 | m/z = 563.09($C_{36}H_{22}BrNO$ = 564.47) | Sub1-A110 | m/z = 563.09($C_{36}H_{22}BrNO$ = 564.47) |

II. Synthesis of Sub 2

Sub 2 of the Reaction Scheme 1 can be synthesized according to, but not limited to, the reaction route of the following Reaction Scheme 27.

<Reaction Scheme 27>

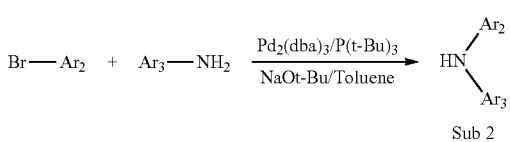

Synthesis Examples of compounds comprised in Sub 2 are as follows.

(1) Synthesis Example of Sub 2-6

<Reaction Scheme 28>

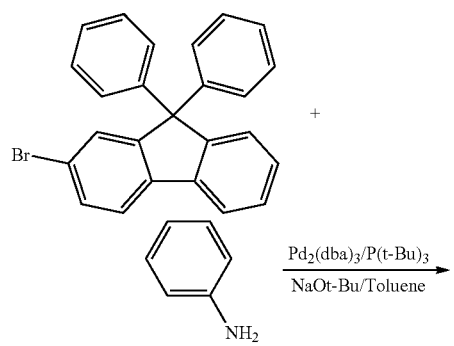

Sub 2-6

The starting material 2-bromo-9,9-diphenyl-9H-fluorene (41.72 g, 105 mmol) was dissolved in toluene in a round bottom flask, and then aniline (19.56 g, 210 mmol), $Pd_2(dba)_3$ (2.88 g, 3.2 mmol), 50% P(t-Bu)$_3$ (4.1 ml, 8.4 mmol), NaOt-Bu (30.28 g, 315 mmol) were added and stirred at 40° C. When the reaction was completed, the reaction product was extracted with $CH_2Cl_2$ and water, and then, the organic layer was dried with $MgSO_4$ and concentrated. Then, the concentrate was passed through silica gel column and recrystallized to obtain 32.25 g (yield: 75%) of the product.

(2) Synthesis Example of Sub 2-7

<Reaction Scheme 29>

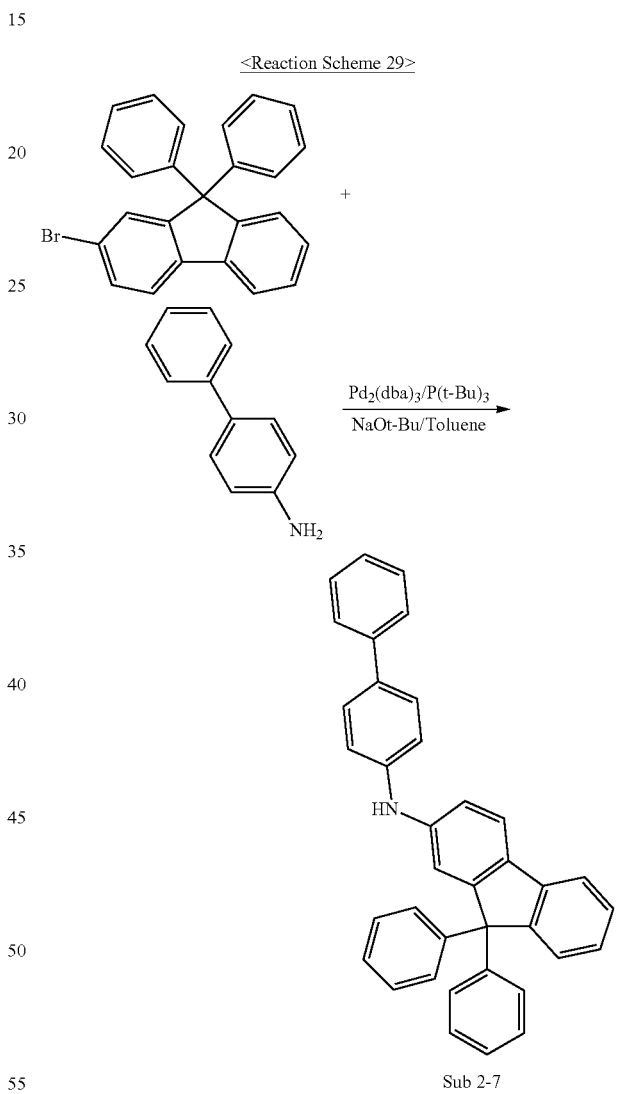

Sub 2-7

[1,1'-biphenyl]-4-amine (13.31 g, 78.7 mmol), $Pd_2(dba)_3$ (1.08 g, 1.2 mmol), 50% P(t-Bu)$_3$ (1.5 ml, 3.1 mmol), NaOt-Bu (11.34 g, 118 mmol), toluene were added to the starting material 2-bromo-9,9-diphenyl-9H-fluorene (15.63 g, 39.3 mmol), and then 14.52 g (yield: 76%) of the product was obtained by using the same manner as described above for the synthesis example of Sub 2-6.

(3) Synthesis Example of Sub 2-13

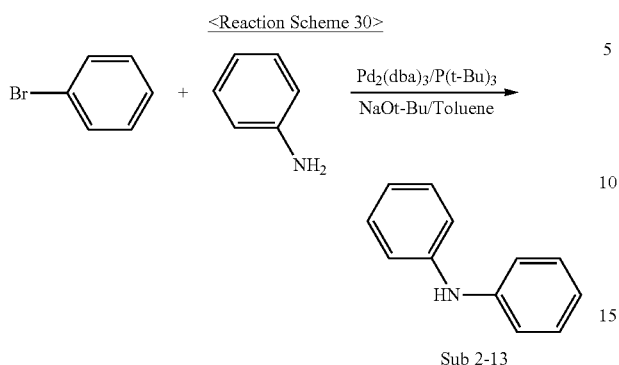

Sub 2-13

Aniline (14.02 g, 150.6 mmol), Pd$_2$(dba)$_3$ (2.07 g, 2.3 mmol), 50% P(t-Bu)$_3$ (2.9 ml, 6 mmol), NaOt-Bu (21.71 g, 225.8 mmol), toluene were added to the starting material bromobenzene (11.82 g, 75.3 mmol), and then 10.19 g (yield: 80%) of the product was obtained by using the same manner as described above for the synthesis example of Sub 2-6.

(4) Synthesis Example of Sub 2-16

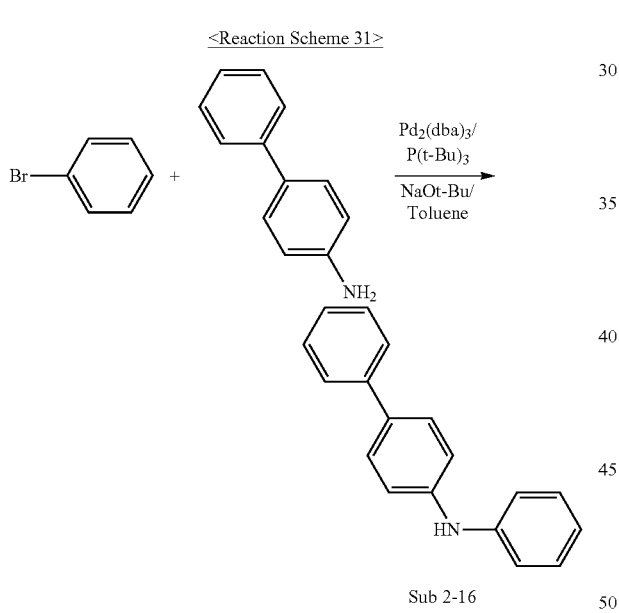

Sub 2-16

[1,1'-biphenyl]-4-amine (32.18 g, 190.2 mmol), Pd$_2$(dba)$_3$ (2.61 g, 2.9 mmol), 50% P(t-Bu)$_3$ (3.7 ml, 7.6 mmol), NaOt-Bu (27.42 g, 285.3 mmol), toluene were added to the starting material bromobenzene (14.93 g, 95.1 mmol), and then 19.36 g (yield: 83%) of the product was obtained by using the same manner as described above for the synthesis example of Sub 2-6.

(5) Synthesis Example of Sub 2-17

<Reaction Scheme 32>

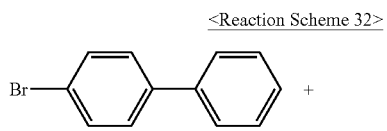

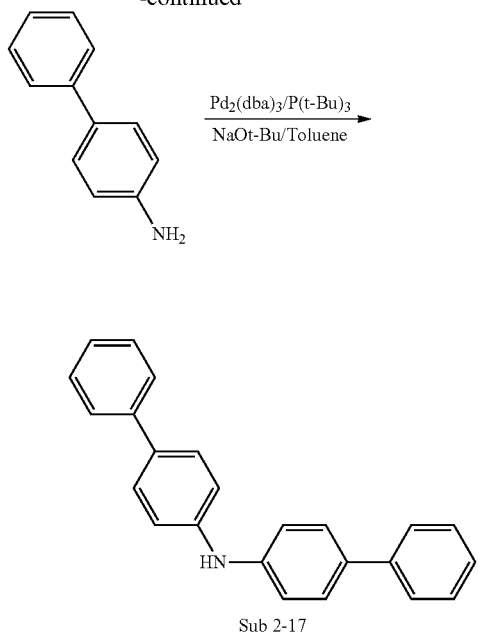

Sub 2-17

[1,1'-biphenyl]-4-amine (37.15 g, 219.6 mmol), Pd$_2$(dba)$_3$ (3.02 g, 3.3 mmol), 50% P(t-Bu)$_3$ (4.3 ml, 8.8 mmol), NaOt-Bu (31.65 g, 329.3 mmol), toluene were added to the starting material 4-bromo-1,1'-biphenyl (25.59 g, 109.8 mmol), and then 27.87 g (yield: 79%) of the product was obtained by using the same manner as described above for the synthesis example of Sub 2-6.

(6) Synthesis Example of Sub 2-20

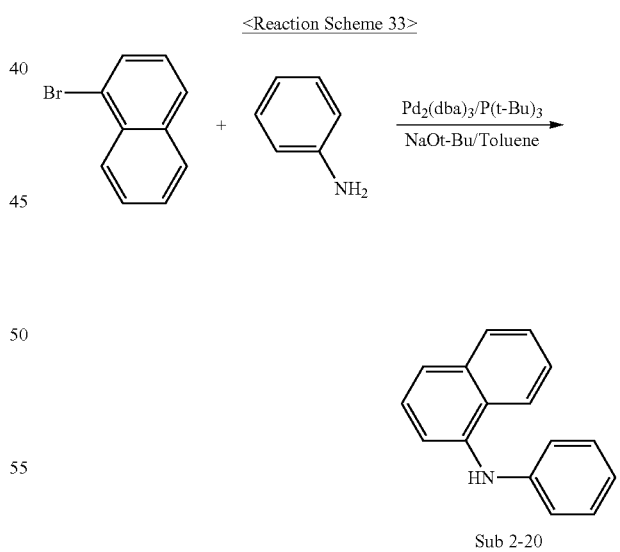

Sub 2-20

Aniline (11.56 g, 124.1 mmol), Pd$_2$(dba)$_3$ (1.7 g, 1.9 mmol), 50% P(t-Bu)$_3$ (2.4 ml, 5 mmol), NaOt-Bu (17.89 g, 186.2 mmol), toluene were added to the starting material 1-bromonaphthalene (12.85 g, 62.1 mmol), and then 10.07 g (yield: 74%) of the product was obtained by using the same manner as described above for the synthesis example of Sub 2-6.

(7) Synthesis Example of Sub 2-40

<Reaction Scheme 34>

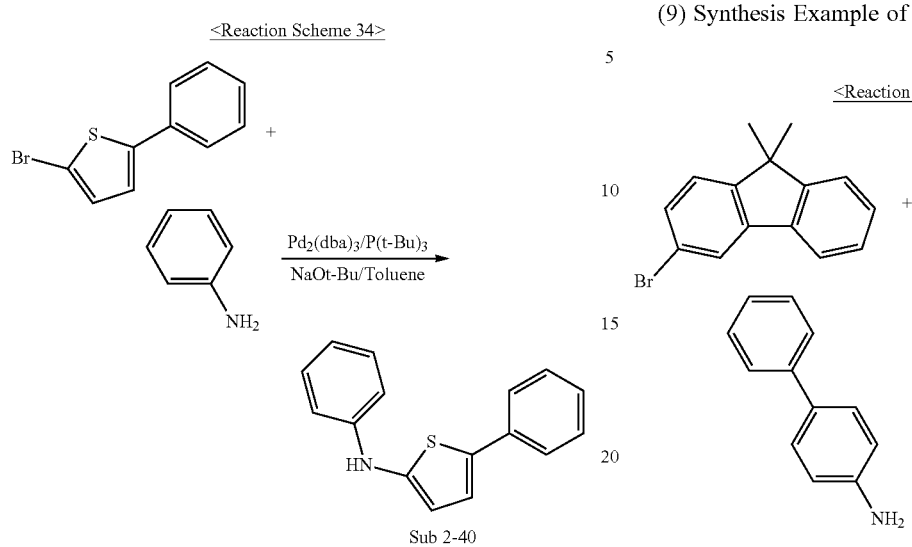

Sub 2-40

Aniline (11.43 g, 122.7 mmol), Pd₂(dba)₃ (1.69 g, 1.8 mmol), 50% P(t-Bu)₃ (2.4 ml, 4.9 mmol), NaOt-Bu (17.69 g, 184 mmol), toluene were added to the starting material 2-bromo-5-phenylthiophene (14.67 g, 61.3 mmol), and then 14.52 g (yield: 76%) of the product was obtained by using the same manner as described above for the synthesis example of Sub 2-6.

(8) Synthesis Example of Sub 2-70

<Reaction Scheme 35>

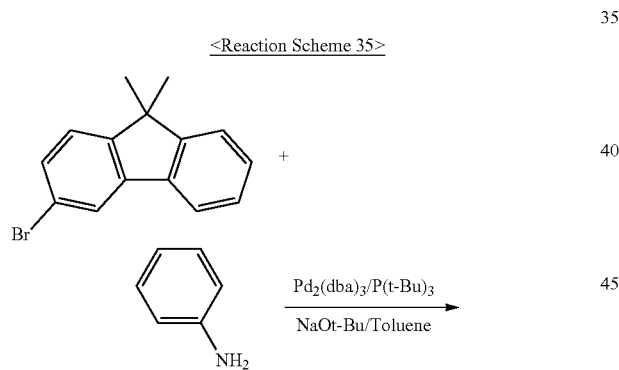

Sub 2-70

Aniline (10.73 g, 115.2 mmol), Pd₂(dba)₃ (1.58 g, 1.7 mmol), 50% P(t-Bu)₃ (2.2 ml, 4.6 mmol), NaOt-Bu (16.61 g, 172.9 mmol), toluene were added to the starting material 3-bromo-9,9-dimethyl-9H-fluorene (15.74 g, 57.6 mmol), and then 13.81 g (yield: 84%) of the product was obtained by using the same manner as described above for the synthesis example of Sub 2-6.

(9) Synthesis Example of Sub 2-71

<Reaction Scheme 36>

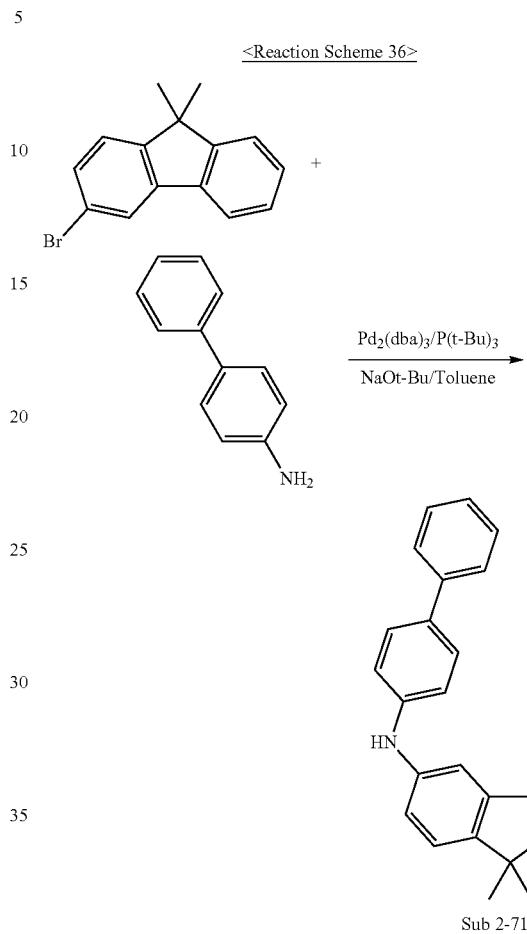

Sub 2-71

[1,1'-biphenyl]-4-amine (11.73 g, 69.3 mmol), Pd₂(dba)₃ (0.95 g, 1 mmol), 50% P(t-Bu)₃ (1.4 ml, 2.8 mmol), NaOt-Bu (10 g, 104 mmol), toluene were added to the starting material 3-bromo-9,9-dimethyl-9H-fluorene (9.47 g, 34.7 mmol), and then 10.28 g (yield: 82%) of the product was obtained by using the same manner as described above for the synthesis example of Sub 2-6.

(10) Synthesis Example of Sub 2-74

<Reaction Scheme 37>

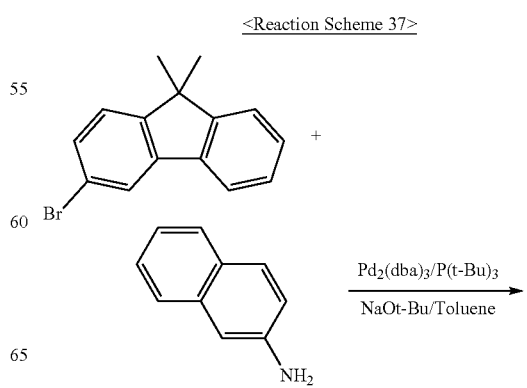

-continued

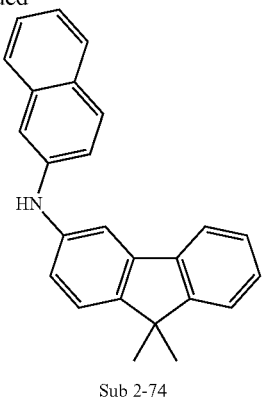

Sub 2-74

Naphthalen-2-amine (12.24 g, 85.5 mmol), Pd$_2$(dba)$_3$ (1.17 g, 1.3 mmol), 50% P(t-Bu)$_3$ (1.7 ml, 3.4 mmol), NaOt-Bu (12.33 g, 128.3 mmol), toluene were added to the starting material 3-bromo-9,9-dimethyl-9H-fluorene (11.68 g, 42.8 mmol), and then 11.04 g (yield: 77%) of the product was obtained by using the same manner as described above for the synthesis example of Sub 2-6.

(11) Synthesis Example of Sub 2-76

<Reaction Scheme 38>

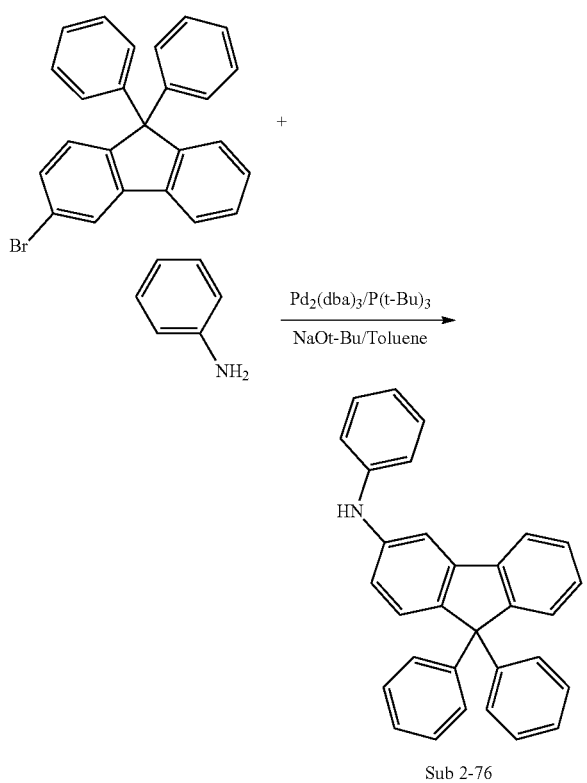

Sub 2-76

Aniline (6.86 g, 73.2 mmol), Pd$_2$(dba)$_3$ (1.01 g, 1.1 mmol), 50% P(t-Bu)$_3$ (1.4 ml, 2.9 mmol), NaOt-Bu (10.55 g, 109.8 mmol), toluene were added to the starting material 3-bromo-9,9-diphenyl-9H-fluorene (14.54 g, 36.6 mmol), and then 11.24 g (yield: 75%) of the product was obtained by using the same manner as described above for the synthesis example of Sub 2-6.

(12) Synthesis Example of Sub 2-81

<Reaction Scheme 39>

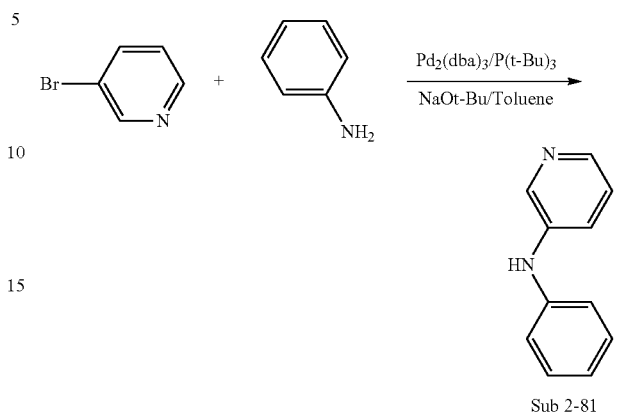

Sub 2-81

Aniline (16.28 g, 174.8 mmol), Pd$_2$(dba)$_3$ (2.4 g, 2.6 mmol), 50% P(t-Bu)$_3$ (3.4 ml, 7 mmol), NaOt-Bu (25.2 g, 262.2 mmol), toluene were added to the starting material 3-bromopyridine (13.81 g, 87.4 mmol), and then 9.97 g (yield: 67%) of the product was obtained by using the same manner as described above for the synthesis example of Sub 2-6.

(13) Synthesis Example of Sub 2-82

<Reaction Scheme 40>

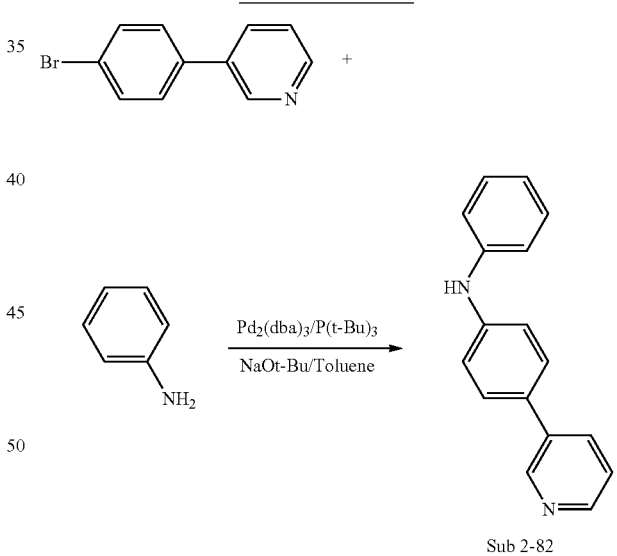

Sub 2-82

Aniline (18.02 g, 193.5 mmol), Pd$_2$(dba)$_3$ (2.66 g, 2.9 mmol), 50% P(t-Bu)$_3$ (3.8 ml, 7.7 mmol), NaOt-Bu (27.9 g, 290.3 mmol), toluene were added to the starting material 3-(4-bromophenyl)pyridine (22.65 g, 96.8 mmol), and then 16.44 g (yield: 69%) of the product was obtained by using the same manner as described above for the synthesis example of Sub 2-6.

The compound belonging to Sub 2 may be, but not limited to, the following compounds, and Table 1 shows FD-MS (Field Desorption-Mass Spectrometry) values of the following compounds.

-continued
| | |
|---|---|
| Sub 2-1 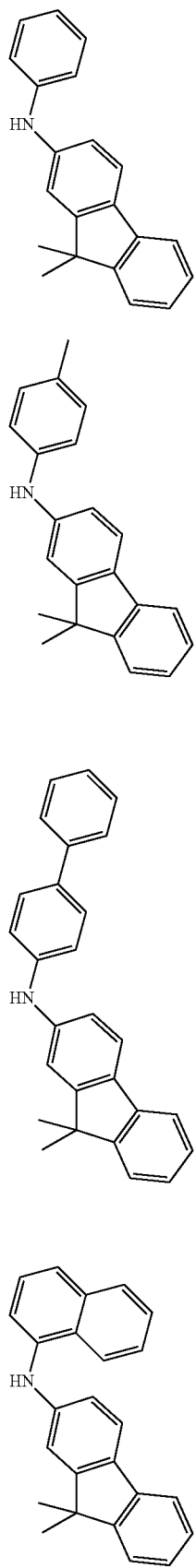 | Sub 2-5 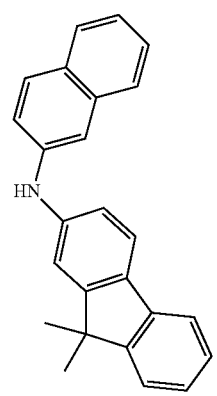 |
| Sub 2-2 | |
| Sub 2-3 | Sub 2-6 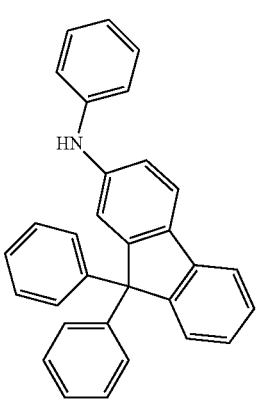 |
| Sub 2-4 | Sub 2-7 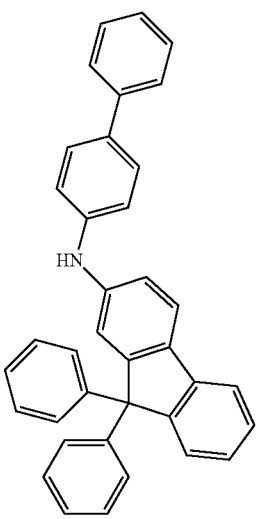 |

Sub 2-8
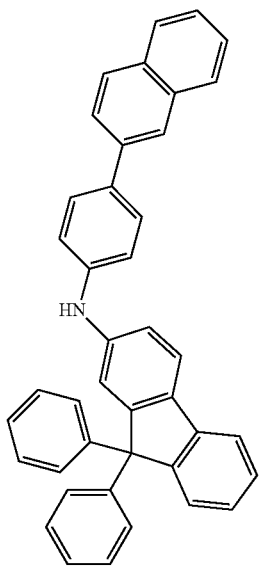
Sub 2-9
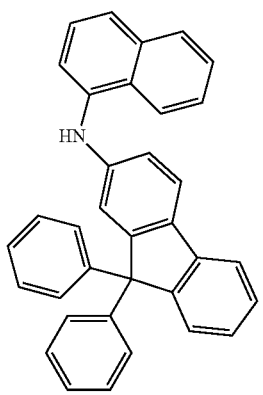
Sub 2-10
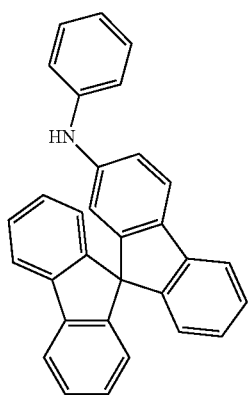
Sub 2-11
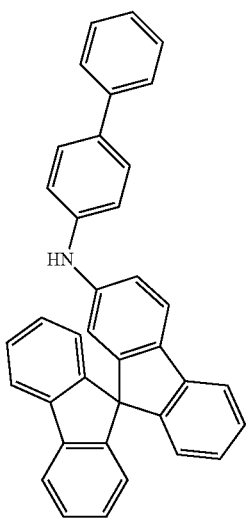
Sub 2-12
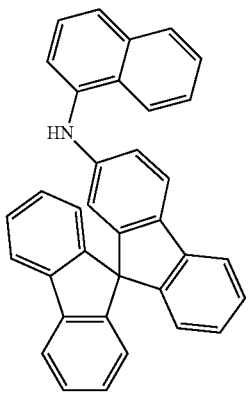
Sub 2-13
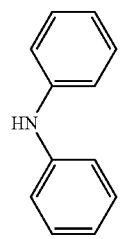
Sub 2-14
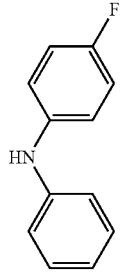

-continued
Sub 2-15
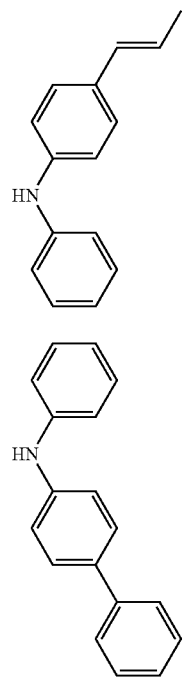
Sub 2-16
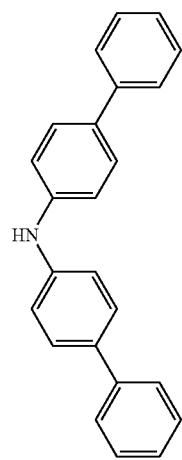
Sub 2-17
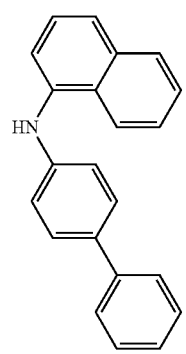
Sub 2-18
-continued
Sub 2-19
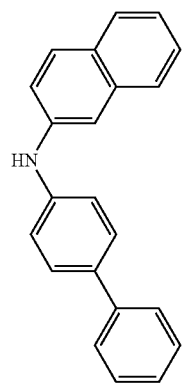
Sub 2-20
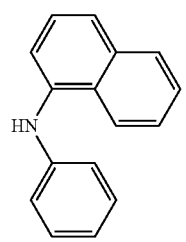
Sub 2-21
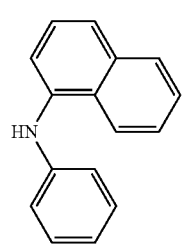
Sub 2-22
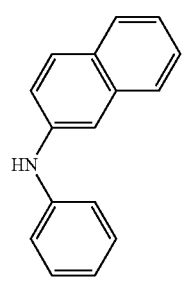
Sub 2-23
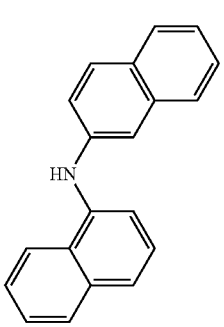

-continued
Sub 2-24
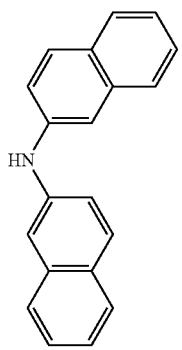
Sub 2-25
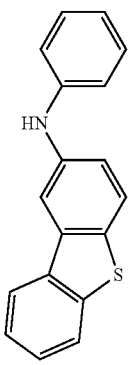
Sub 2-26
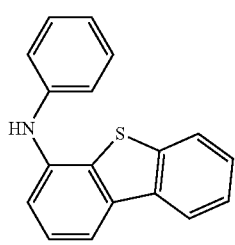
Sub 2-27
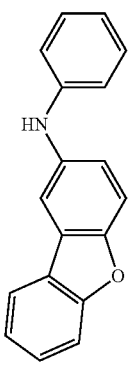
-continued
Sub 2-28
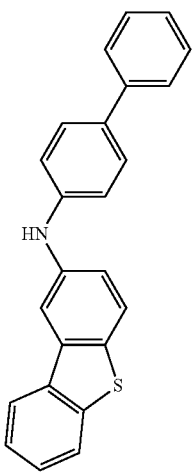
Sub 2-30
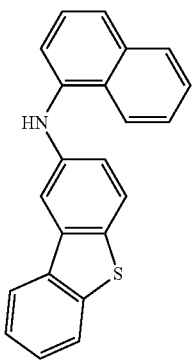
Sub 2-31
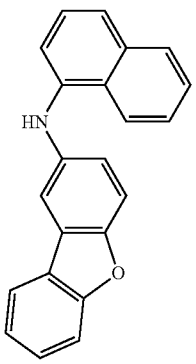

SuB 2-32
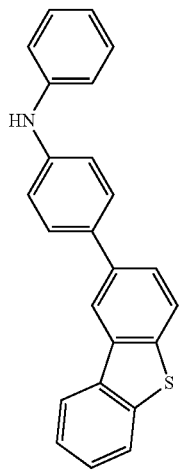
Sub 2-33
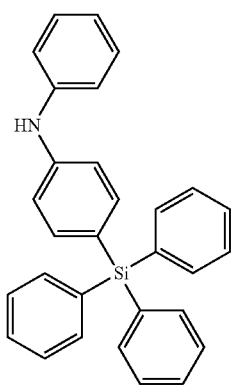
Sub 2-34
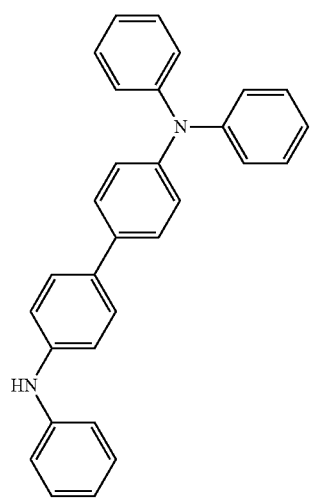
Sub 2-35
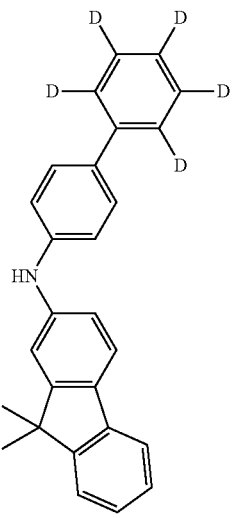
Sub 2-37
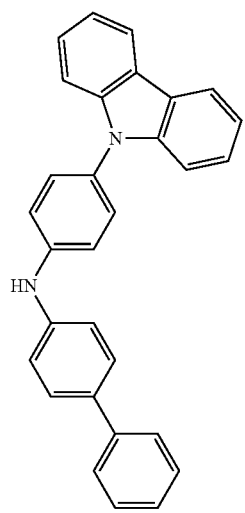
Sub 2-38
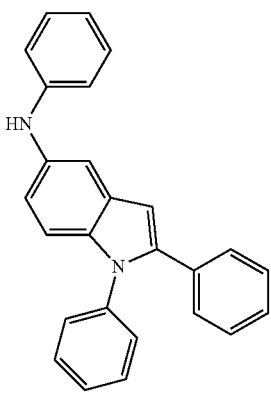

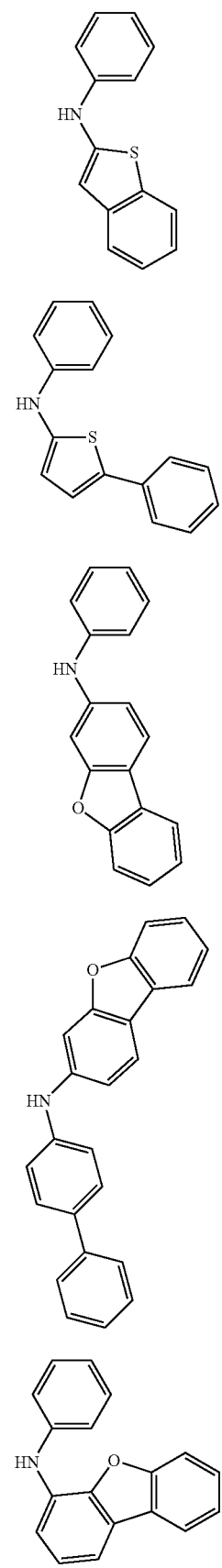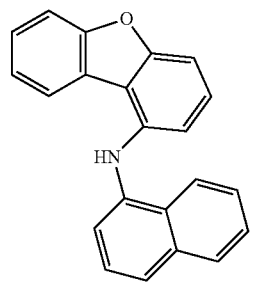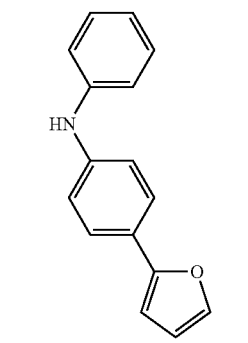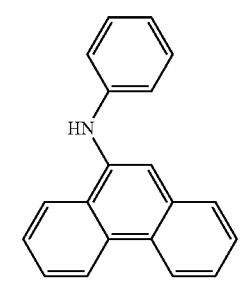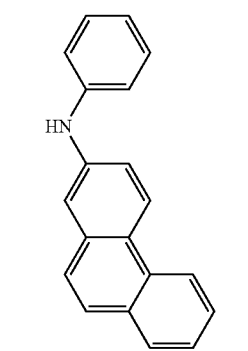
Sub 2-39
Sub 2-40
Sub 2-41
Sub 2-42
Sub 2-43
Sub 2-44
Sub 2-45
Sub 2-46
Sub 2-47

Sub 2-48
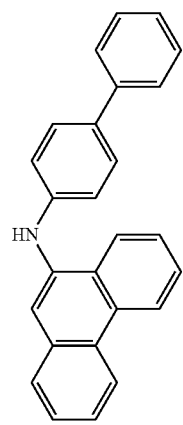
Sub 2-49
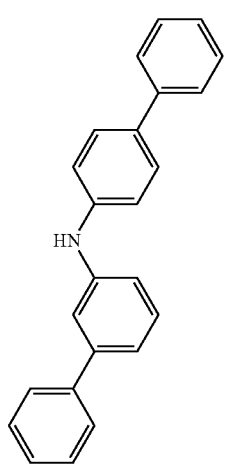
Sub 2-50
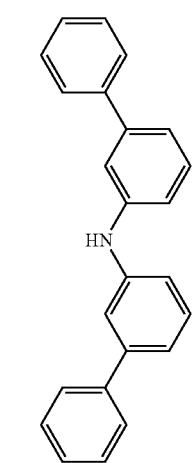
Sub 2-51
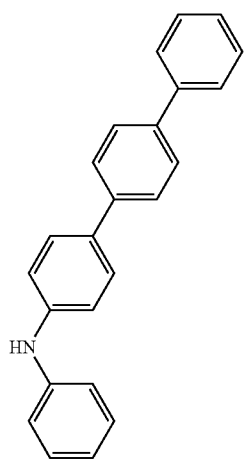
Sub 2-52
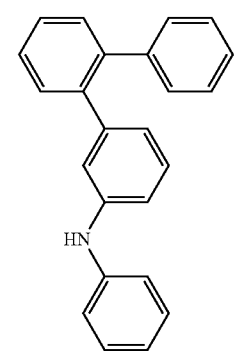
Sub 2-53
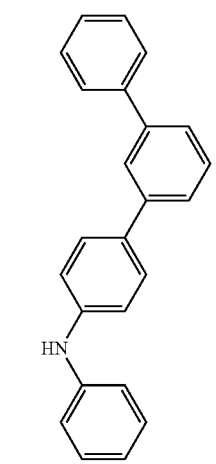
Sub 2-54
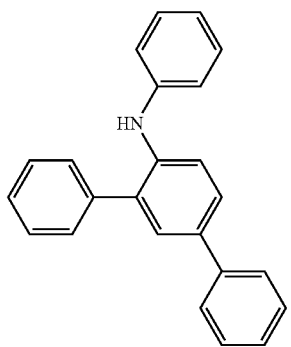

311
-continued
Sub 2-55
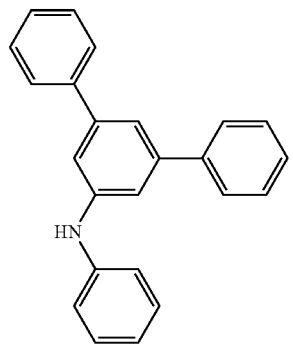
Sub 2-56
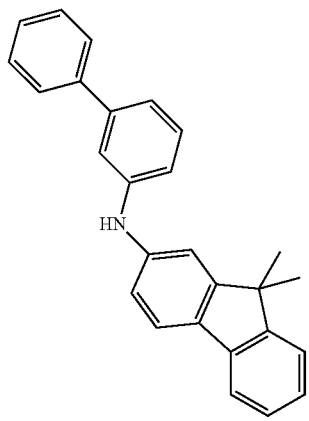
Sub 2-57
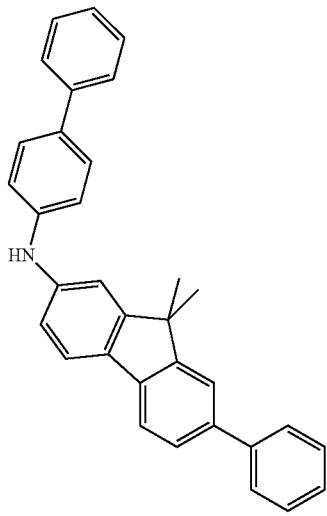
312
-continued
Sub 2-58
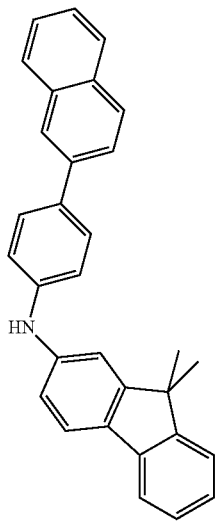
Sub 2-59
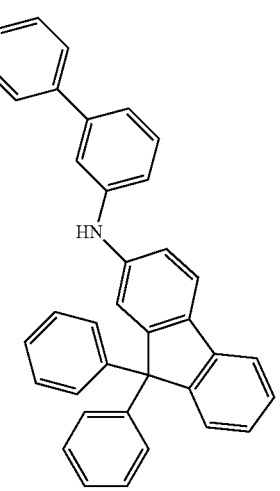
Sub 2-60
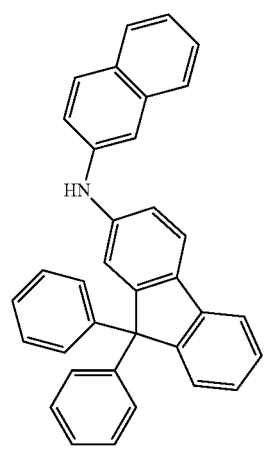

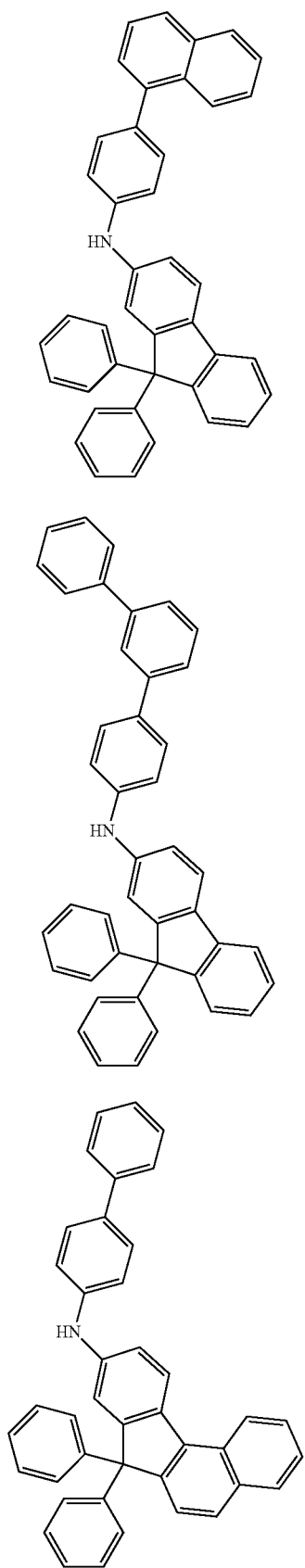
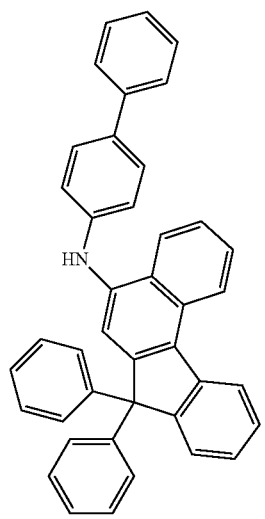
Sub 2-61
Sub 2-62
Sub 2-63
Sub 2-64
Sub 2-65
Sub 2-66

Sub 2-67
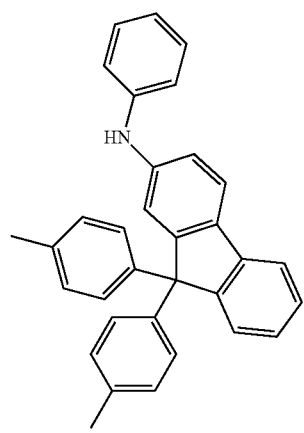
Sub 2-68
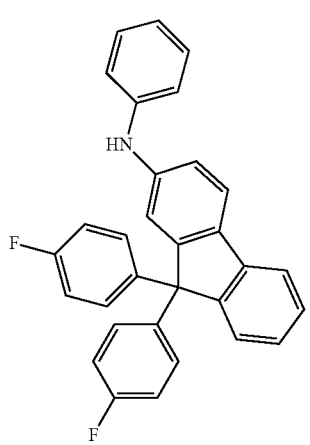
Sub 2-69
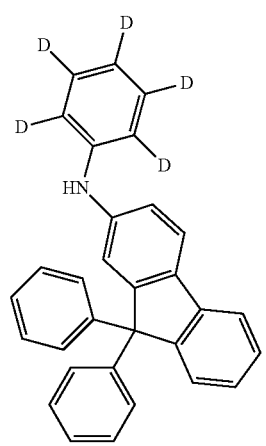
Sub 2-70
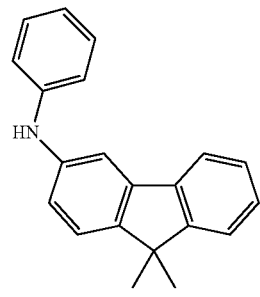
Sub 2-71
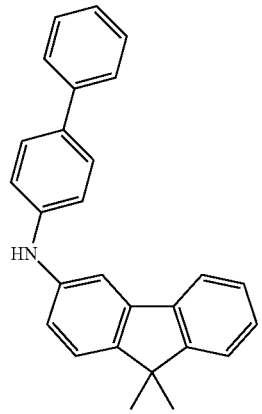
Sub 2-72
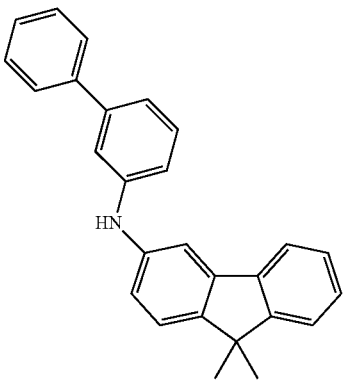
Sub 2-73
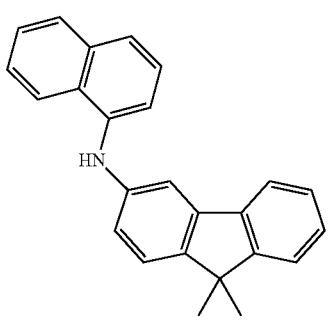
Sub 2-74
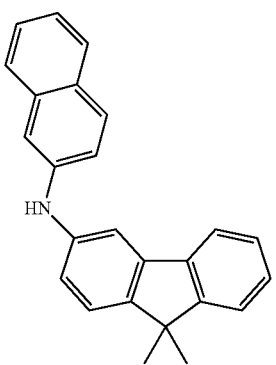

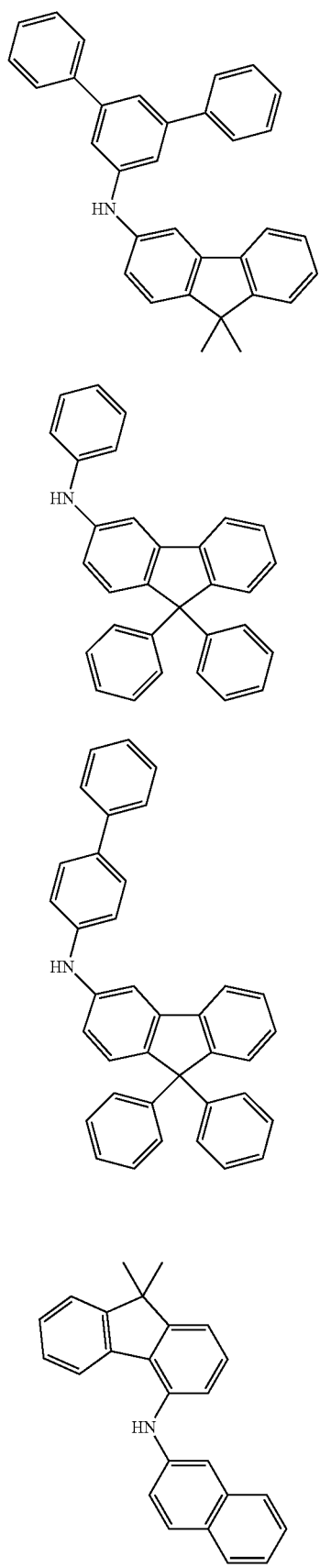
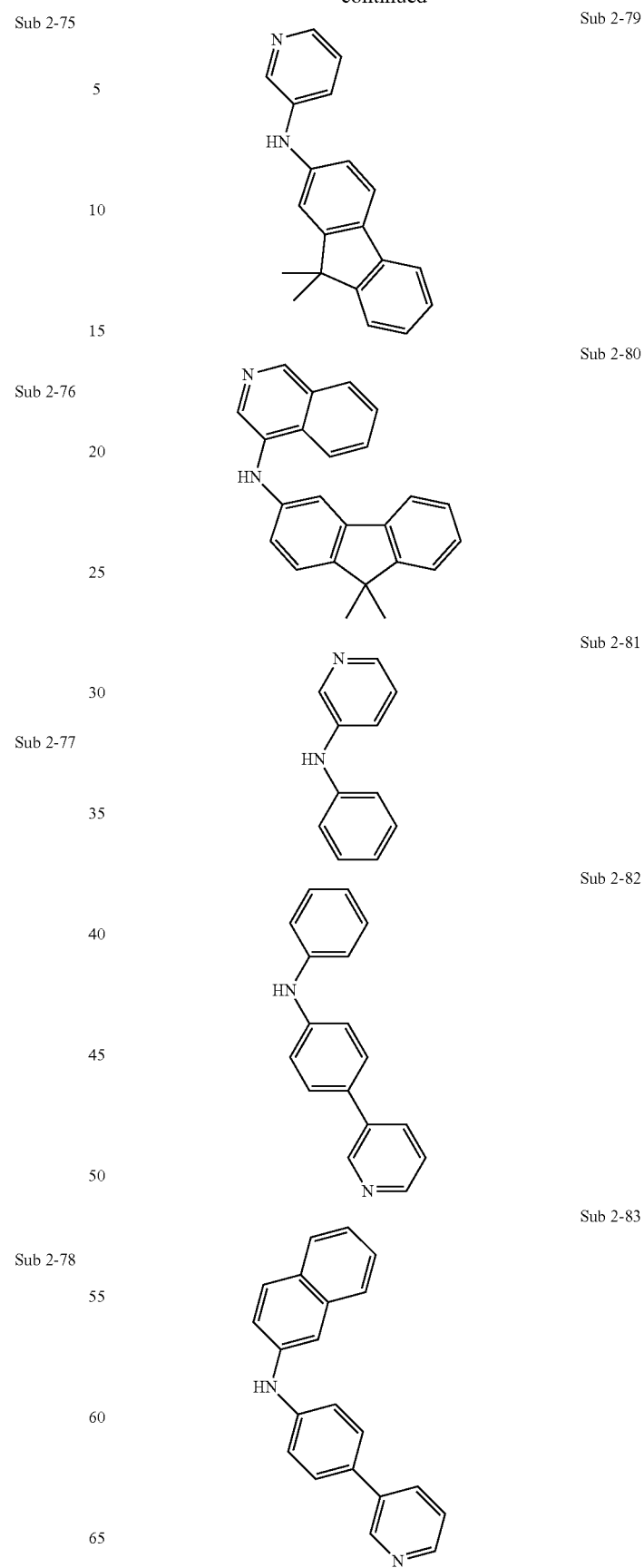

319
-continued
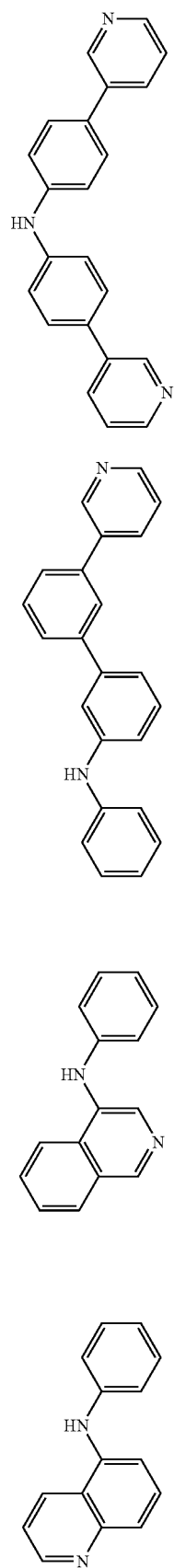
Sub 2-84
Sub 2-85
Sub 2-86
Sub 2-87
320
-continued
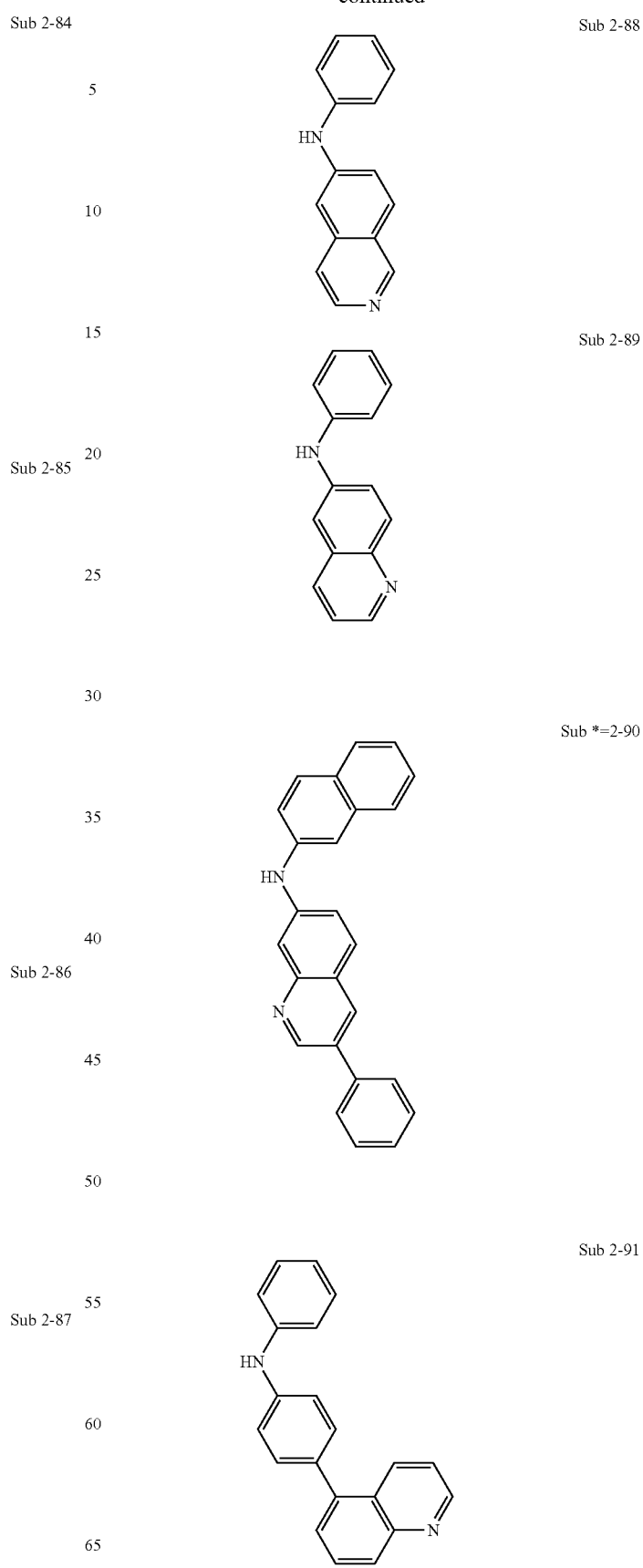
Sub 2-88
Sub 2-89
Sub *=2-90
Sub 2-91

Sub 2-92

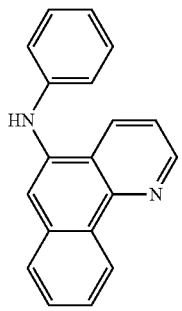

TABLE 2

| compound | FD-MS | compound | FD-MS |
|---|---|---|---|
| Sub 2-1 | m/z = 285.15($C_{21}H_{19}N$ = 285.38) | Sub 2-2 | m/z = 299.17($C_{22}H_{21}N$ = 299.41) |
| Sub 2-3 | m/z = 361.18($C_{27}H_{23}N$ = 361.48) | Sub 2-4 | m/z = 335.17($C_{25}H_{21}N$ = 335.44) |
| Sub 2-5 | m/z = 335.17($C_{25}H_{21}N$ = 335.44) | Sub 2-6 | m/z = 409.18($C_{31}H_{23}N$ = 409.52) |
| Sub 2-7 | m/z = 485.21($C_{37}H_{27}N$ = 485.62) | Sub 2-8 | m/z = 535.23($C_{41}H_{29}N$ = 535.68) |
| Sub 2-9 | m/z = 459.20($C_{35}H_{25}N$ = 459.58) | Sub 2-10 | m/z = 407.17($C_{31}H_{21}N$ = 407.51) |
| Sub 2-11 | m/z = 483.20($C_{37}H_{25}N$ = 483.60) | Sub 2-12 | m/z = 457.18($C_{35}H_{23}N$ = 457.56) |
| Sub 2-13 | m/z = 169.09($C_{12}H_{11}N$ = 169.22) | Sub 2-14 | m/z = 187.08($C_{12}H_{10}FN$ = 187.21) |
| Sub 2-15 | m/z = 209.12($C_{15}H_{15}N$ = 209.29) | Sub 2-16 | m/z = 245.12($C_{18}H_{15}N$ = 245.32) |
| Sub 2-17 | m/z = 321.15($C_{24}H_{19}N$ = 321.41) | Sub 2-18 | m/z = 295.14($C_{22}H_{17}N$ = 295.38) |
| Sub 2-19 | m/z = 295.14($C_{22}H_{17}N$ = 295.38) | Sub 2-20 | m/z = 219.10($C_{16}H_{13}N$ = 219.28) |
| Sub 2-21 | m/z = 219.10($C_{16}H_{13}N$ = 219.28) | Sub 2-22 | m/z = 269.12($C_{20}H_{15}N$ = 269.34) |
| Sub 2-23 | m/z = 269.12($C_{20}H_{13}N$ = 269.34) | Sub 2-24 | m/z = 269.12($C_{20}H_{15}N$ = 269.34) |
| Sub 2-25 | m/z = 275.08($C_{18}H_{13}NS$ = 275.37) | Sub 2-26 | m/z = 275.08($C_{18}H_{13}NS$ = 275.37) |
| Sub 2-27 | m/z = 259.10($C_{18}H_{13}NO$ = 259.30) | Sub 2-28 | m/z = 351.11($C_{24}H_{17}NS$ = 351.46) |
| Sub 2-30 | m/z = 325.09($C_{22}H_{15}NS$ = 325.43) | Sub 2-31 | m/z = 309.12($C_{22}H_{15}NO$ = 309.36) |
| Sub 2-32 | m/z = 351.11($C_{24}H_{17}NS$ = 351.46) | Sub 2-33 | m/z = 427.18($C_{30}H_{25}NSi$ = 427.61) |
| Sub 2-34 | m/z = 412.19($C_{30}H_{24}N_2$ = 412.52) | Sub 2-35 | m/z = 366.21($C_{27}H_{18}D_5N$ = 366.51) |
| Sub 2-37 | m/z = 410.18($C_{30}H_{22}N_2$ = 410.51) | Sub 2-38 | m/z = 360.16($C_{26}H_{20}N_2$ = 360.45) |
| Sub 2-39 | m/z = 225.06($C_{14}H_{11}NS$ = 225.31) | Sub 2-40 | m/z = 251.08($C_{16}H_{13}NS$ = 251.35) |
| Sub 2-41 | m/z = 259.10($C_{18}H_{13}NO$ = 259.30) | Sub 2-42 | m/z = 335.13($C_{24}H_{17}NO$ = 335.40) |
| Sub 2-43 | m/z = 259.10($C_{18}H_{13}NO$ = 259.30) | Sub 2-44 | m/z = 309.12($C_{22}H_{15}NO$ = 309.36) |
| Sub 2-45 | m/z = 235.10($C_{16}H_{13}NO$ = 235.28) | Sub 2-46 | m/z = 269.12($C_{20}H_{15}N$ = 269.34) |
| Sub 2-47 | m/z = 269.12($C_{20}H_{15}N$ = 269.34) | Sub 2-48 | m/z = 345.15($C_{26}H_{19}N$ = 345.44) |
| Sub 2-49 | m/z = 321.15($C_{24}H_{19}N$ = 321.41) | Sub 2-50 | m/z = 321.15($C_{24}H_{19}N$ = 321.41) |
| Sub 2-51 | m/z = 321.15($C_{24}H_{19}N$ = 321.41) | Sub 2-52 | m/z = 321.15($C_{24}H_{19}N$ = 321.41) |
| Sub 2-53 | m/z = 321.15($C_{24}H_{19}N$ = 321.41) | Sub 2-54 | m/z = 321.15($C_{24}H_{19}N$ = 321.41) |
| Sub 2-55 | m/z = 321.15($C_{24}H_{19}N$ = 321.41) | Sub 2-56 | m/z = 361.18($C_{27}H_{23}N$ = 361.48) |
| Sub 2-57 | m/z = 437.21($C_{33}H_{27}N$ = 437.57) | Sub 2-58 | m/z = 411.20($C_{31}H_{25}N$ = 411.54) |
| Sub 2-59 | m/z = 485.21($C_{37}H_{27}N$ = 485.62) | Sub 2-60 | m/z = 459.20($C_{35}H_{25}N$ = 459.58) |
| Sub 2-61 | m/z = 535.23($C_{41}H_{29}N$ = 535.68) | Sub 2-62 | m/z = 561.25($C_{43}H_{31}N$ = 561.71) |
| Sub 2-63 | m/z = 535.23($C_{41}H_{29}N$ = 535.68) | Sub 2-64 | m/z = 535.23($C_{41}H_{29}N$ = 535.68) |
| Sub 2-65 | m/z = 437.21($C_{33}H_{27}N$ = 437.57) | Sub 2-66 | m/z = 423.20($C_{32}H_{25}N$ = 423.55) |
| Sub 2-67 | m/z = 437.21($C_{33}H_{27}N$ = 437.57) | Sub 2-68 | m/z = 445.16($C_{31}H_{21}F_2N$ = 445.50) |
| Sub 2-69 | m/z = 414.21($C_{31}H_{18}D_5N$ = 414.55) | Sub 2-70 | m/z = 285.15($C_{21}H_{19}N$ = 285.38) |
| Sub 2-71 | m/z = 361.18($C_{27}H_{23}N$ = 361.48) | Sub 2-72 | m/z = 361.18($C_{27}H_{23}N$ = 361.48) |
| Sub 2-73 | m/z = 335.17($C_{25}H_{21}N$ = 335.44) | Sub 2-74 | m/z = 335.17($C_{25}H_{21}N$ = 335.44) |
| Sub 2-75 | m/z = 437.21($C_{33}H_{27}N$ = 437.57) | Sub 2-76 | m/z = 409.18($C_{31}H_{23}N$ = 409.52) |
| Sub 2-77 | m/z = 485.21($C_{37}H_{27}N$ = 485.62) | Sub 2-78 | m/z = 335.17($C_{25}H_{21}N$ = 335.44) |
| Sub 2-79 | m/z = 286.15($C_{20}H_{18}N_2$ = 286.37) | Sub 2-80 | m/z = 336.16($C_{24}H_{20}N_2$ = 336.43) |
| Sub 2-81 | m/z = 170.08($C_{11}H_{10}N_2$ = 170.21) | Sub 2-82 | m/z = 246.12($C_{17}H_{14}N_2$ = 246.31) |
| Sub 2-83 | m/z = 296.13($C_{21}H_{16}N_2$ = 296.37) | Sub 2-84 | m/z = 323.14($C_{22}H_{17}N_3$ = 323.39) |
| Sub 2-85 | m/z = 322.15($C_{23}H_{18}N_2$ = 322.40) | Sub 2-86 | m/z = 220.10($C_{15}H_{12}N_2$ = 220.27) |
| Sub 2-87 | m/z = 220.10($C_{15}H_{12}N_2$ = 220.27) | Sub 2-88 | m/z = 220.10($C_{15}H_{12}N_2$ = 220.27) |
| Sub 2-89 | m/z = 220.10($C_{15}H_{12}N_2$ = 220.27) | Sub 2-90 | m/z = 346.15($C_{25}H_{18}N_2$ = 346.42) |
| Sub 2-91 | m/z = 296.13($C_{21}H_{16}N_2$ = 296.37) | Sub 2-92 | m/z = 270.12($C_{19}H_{14}N_2$ = 270.33) |

III. Synthesis of Final Products

Sub 2 (1 eq.) was dissolved in toluene in a round bottom flask, and Sub 1 (1.2 eq.), $Pd_2(dba)_3$ (0.03 eq.), $P(t-Bu)_3$ (0.08 eq.) and NaOt-Bu (3 eq.) were added, then, stirring at 100° C. was followed. When the reaction was completed, the reaction product was extracted with $CH_2Cl_2$ and water, and then the organic layer was dried with $MgSO_4$ and concentrated. Then, the concentrate was passed through silica gel column and recrystallized to obtain final product.

(1) Synthesis Example of Product A17

<Reaction Scheme 41>

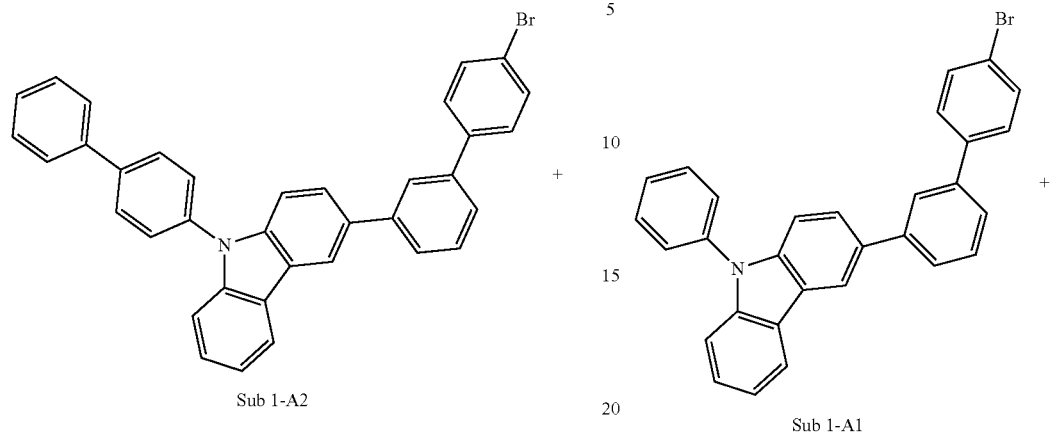

(2) Synthesis Example of Product A21

<Reaction Scheme 42>

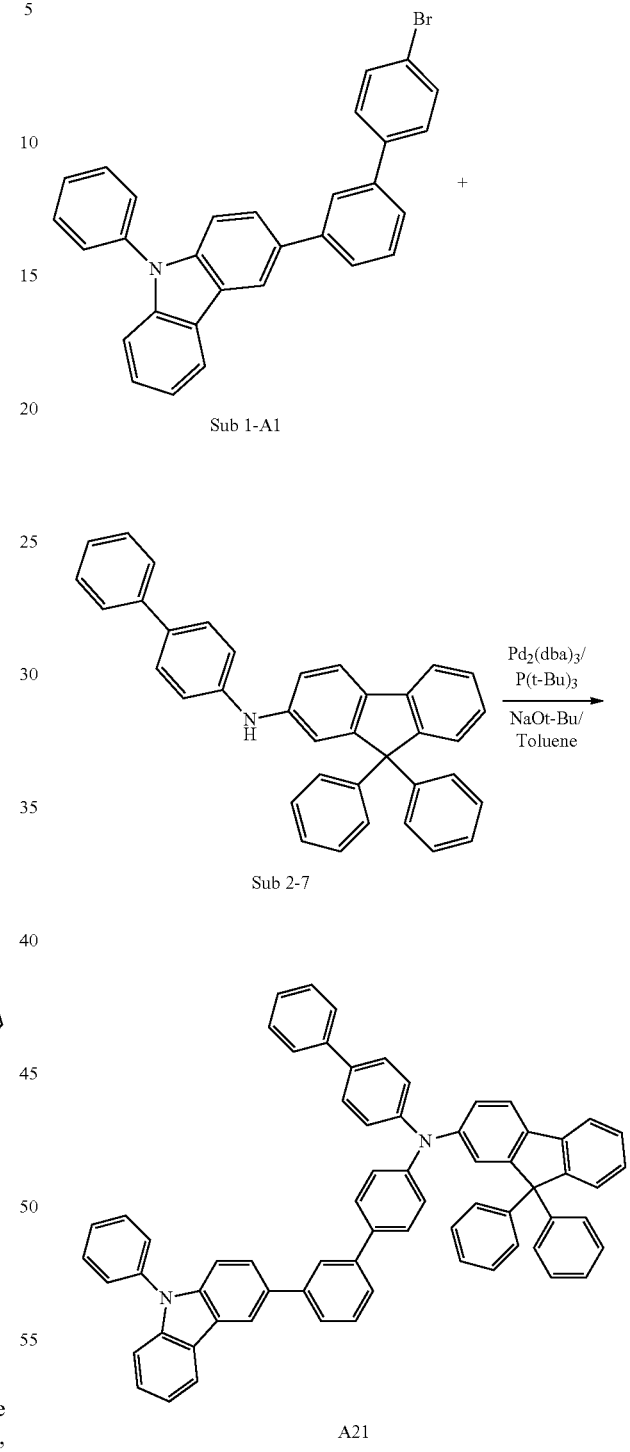

Sub 2-6 (4.46 g, 10.9 mmol) obtained in the above synthesis was dissolved in toluene in a round bottom flask, and Sub 1-A2 (7.19 g, 13.1 mmol), Pd$_2$(dba)$_3$ (0.3 g, 0.3 mmol), 50% P(t-Bu)$_3$ (0.4 ml, 0.9 mmol), NaOt-Bu (3.14 g, 32.7 mmol) were added, then, stirring at 100° C. was followed. When the reaction was completed, the reaction product was extracted with CH$_2$Cl$_2$ and water, and then the organic layer was dried with MgSO$_4$ and concentrated. Then, the concentrate was passed through silica gel column and recrystallized to obtain 6.8 g (yield: 71%) of product.

Sub 1-A1 (8.89 g, 18.7 mmol), Pd$_2$(dba)$_3$ (0.43 g, 0.5 mmol), 50% P(t-Bu)$_3$ (0.6 ml, 1.2 mmol), NaOt-Bu (4.5 g, 46.8 mmol), toluene were added to Sub 2-7 (7.58 g, 15.6 mmol) obtained in the above synthesis, and then 10.02 g (yield: 73%) of the product was obtained by using the same manner as described above for the synthesis example of Product A17.

(3) Synthesis Example of Product A162

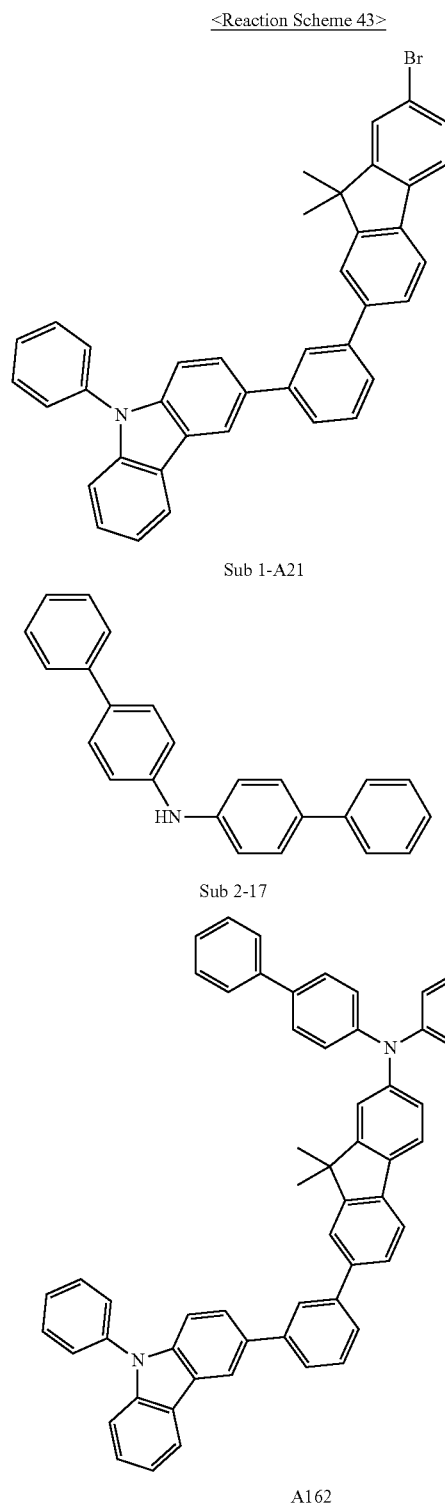

<Reaction Scheme 43>

Sub 1-A21

Sub 2-17

A162

NaOt-Bu (5.1 g, 53 mmol), toluene were added to Sub 2-17 (5.68 g, 17.7 mmol) obtained in the above synthesis, and then 10.28 g (yield: 70%) of the product was obtained by using the same manner as described above for the synthesis example of Product A17.

(4) Synthesis Example of Product A183

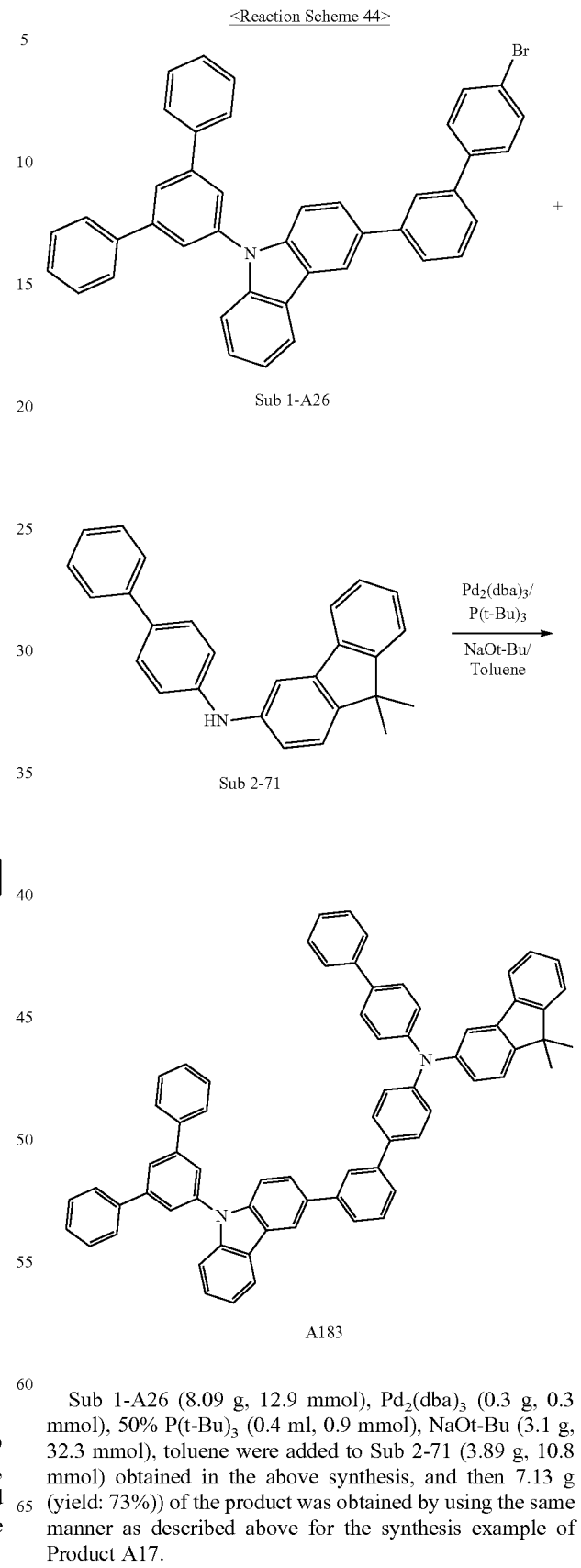

<Reaction Scheme 44>

Sub 1-A26

Sub 2-71

A183

Sub 1-A26 (8.09 g, 12.9 mmol), Pd$_2$(dba)$_3$ (0.3 g, 0.3 mmol), 50% P(t-Bu)$_3$ (0.4 ml, 0.9 mmol), NaOt-Bu (3.1 g, 32.3 mmol), toluene were added to Sub 2-71 (3.89 g, 10.8 mmol) obtained in the above synthesis, and then 7.13 g (yield: 73%)) of the product was obtained by using the same manner as described above for the synthesis example of Product A17.

(5) Synthesis Example of Product A191

<Reaction Scheme 45>

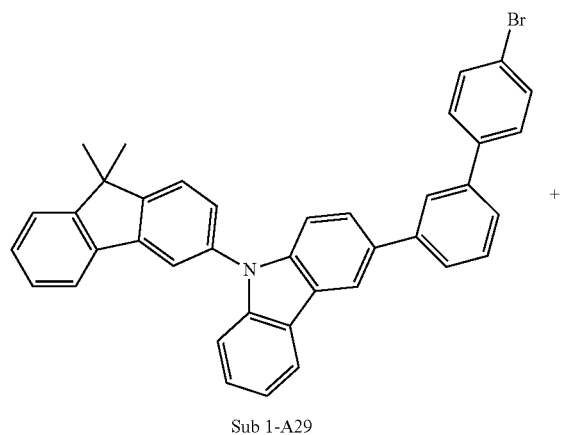

Sub 1-A29

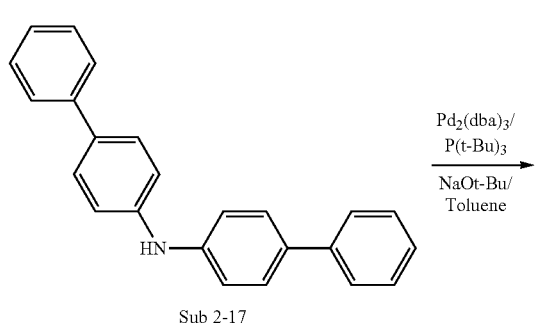

Sub 2-17

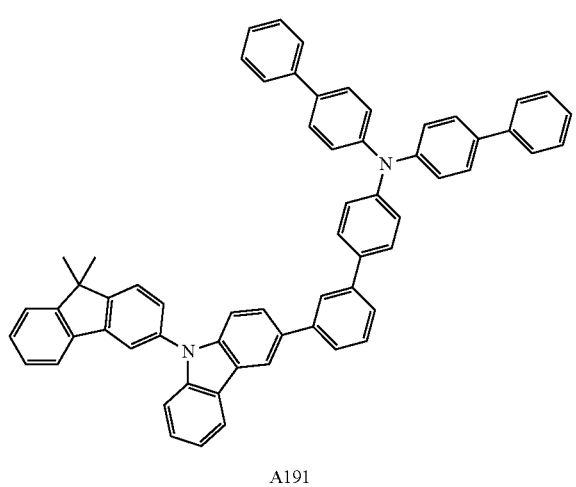

A191

Sub 1-A29 (7.89 g, 13.4 mmol), Pd$_2$(dba)$_3$ (0.31 g, 0.3 mmol), 50% P(t-Bu)$_3$ (0.4 ml, 0.9 mmol), NaOt-Bu (3.21 g, 33.4 mmol), toluene were added to Sub 2-17 (3.58 g, 11.1 mmol) obtained in the above synthesis, and then 7.04 g (yield: 76%) of the product was obtained by using the same manner as described above for the synthesis example of Product A17.

(6) Synthesis Example of Product A203

<Reaction Scheme 46>

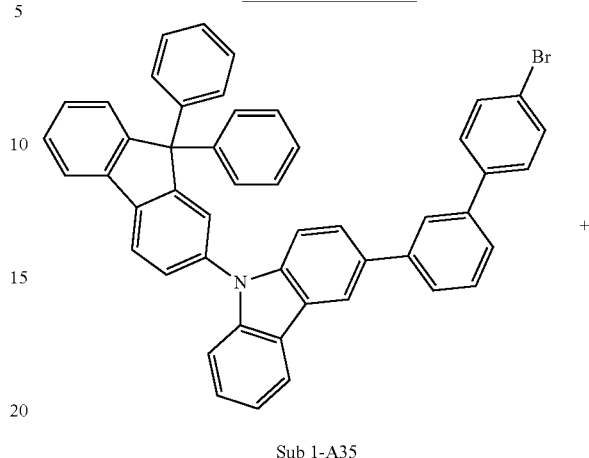

Sub 1-A35

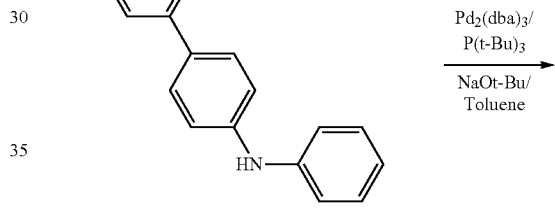

Sub 2-16

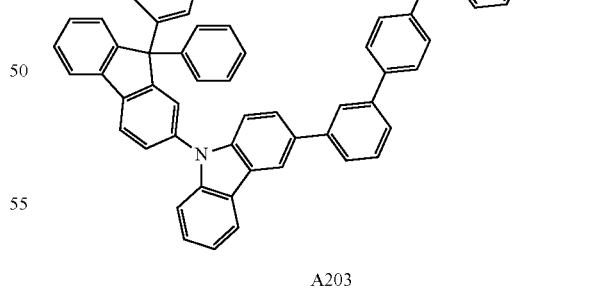

A203

Sub 1-A35 (9.33 g, 13.1 mmol), Pd$_2$(dba)$_3$ (0.3 g, 0.3 mmol), 50% P(t-Bu)$_3$ (0.4 ml, 0.9 mmol), NaOt-Bu (3.14 g, 32.7 mmol), toluene were added to Sub 2-16 (2.67 g, 10.9 mmol) obtained in the above synthesis, and then 6.79 g (yield: 71%) of the product was obtained by using the same manner as described above for the synthesis example of Product A17.

(7) Synthesis Example of Product A210
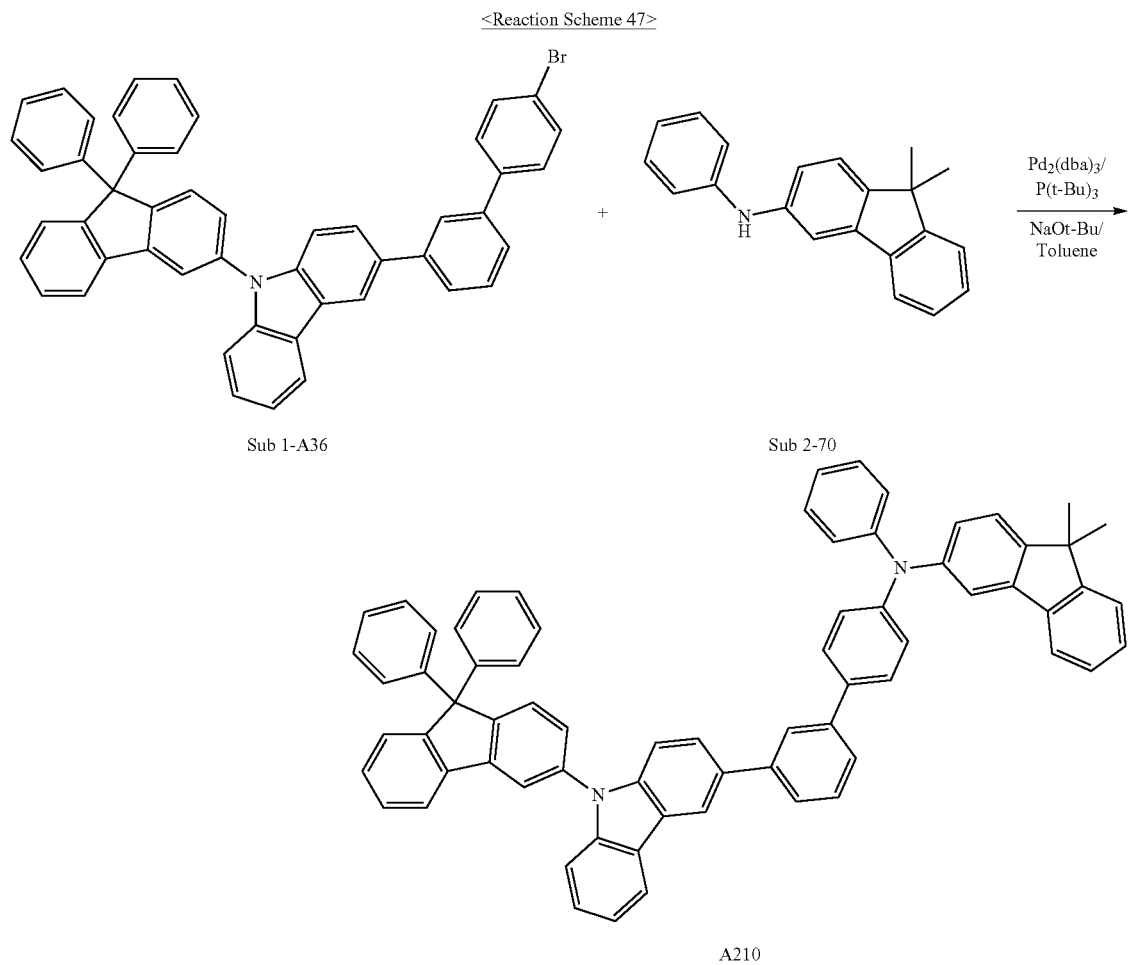
Sub 1-A36 (9.14 g, 12.8 mmol), Pd$_2$(dba)$_3$ (0.29 g, 0.3 mmol), 50% P(t-Bu)$_3$ (0.4 ml, 0.9 mmol), NaOt-Bu (3.07 g, 32 mmol), toluene were added to Sub 2-70 (3.04 g, 10.7 mmol) obtained in the above synthesis, and then 7.25 g (yield: 74%) of the product was obtained by using the same manner as described above for the synthesis example of Product A17.
(8) Synthesis Example of Product A216
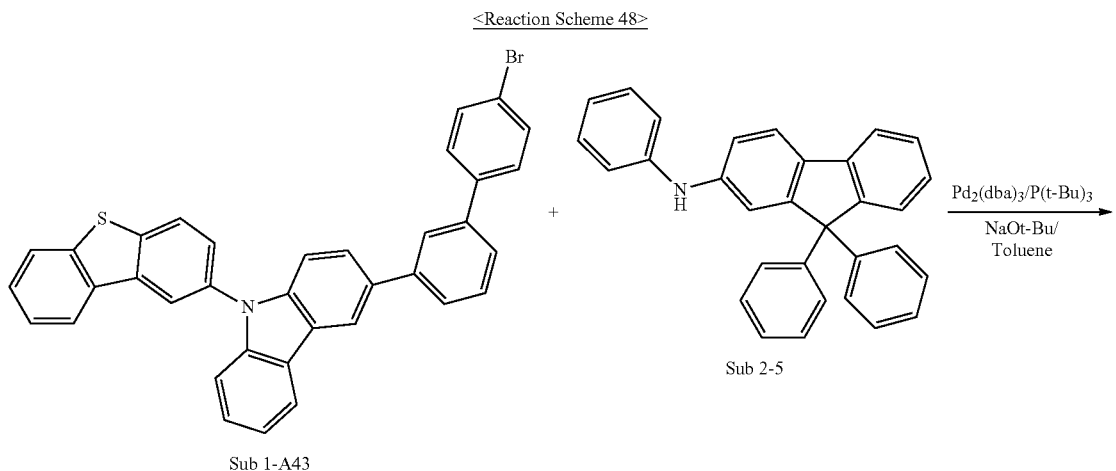

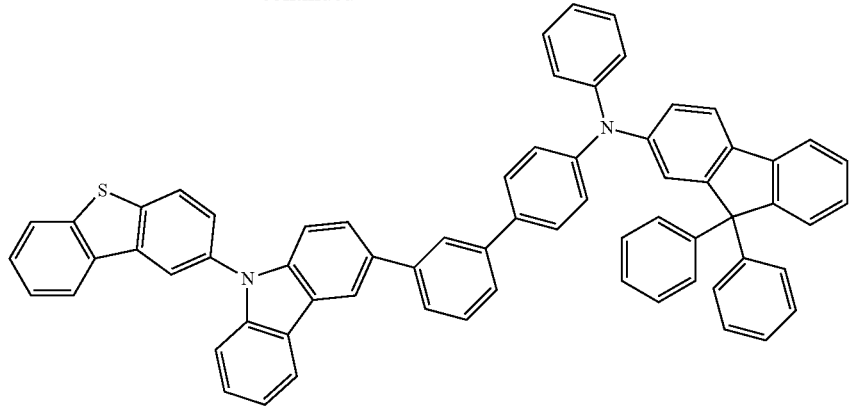

A216

Sub 1-A43 (7.57 g, 13 mmol), Pd₂(dba)₃ (0.3 g, 0.3 mmol), 50% P(t-Bu)₃ (0.4 ml, 0.9 mmol), NaOt-Bu (3.13 g, 32.6 mmol), toluene were added to Sub 2-6 (4.45 g, 10.9 mmol) obtained in the above synthesis, and then 6.82 g (yield: 69%) of the product was obtained by using the same manner as described above for the synthesis example of Product A17.

(9) Synthesis Example of Product A219

<Reaction Scheme 49>

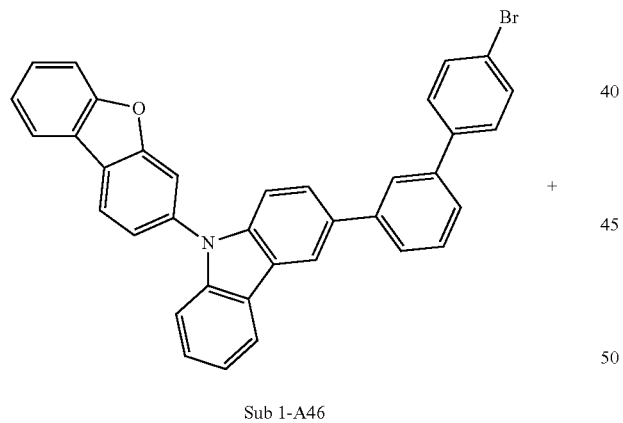

A219

Sub 1-A46 (8.75 g, 15.5 mmol), Pd₂(dba)₃ (0.35 g, 0.4 mmol), 50% P(t-Bu)₃ (0.5 ml, 1 mmol), NaOt-Bu (3.73 g, 38.8 mmol), toluene were added to Sub 2-16 (3.17 g, 12.9 mmol) obtained in the above synthesis, and then 6.97 g (yield: 74%) of the product was obtained by using the same manner as described above for the synthesis example of Product A17.

(10) Synthesis Example of Product A230
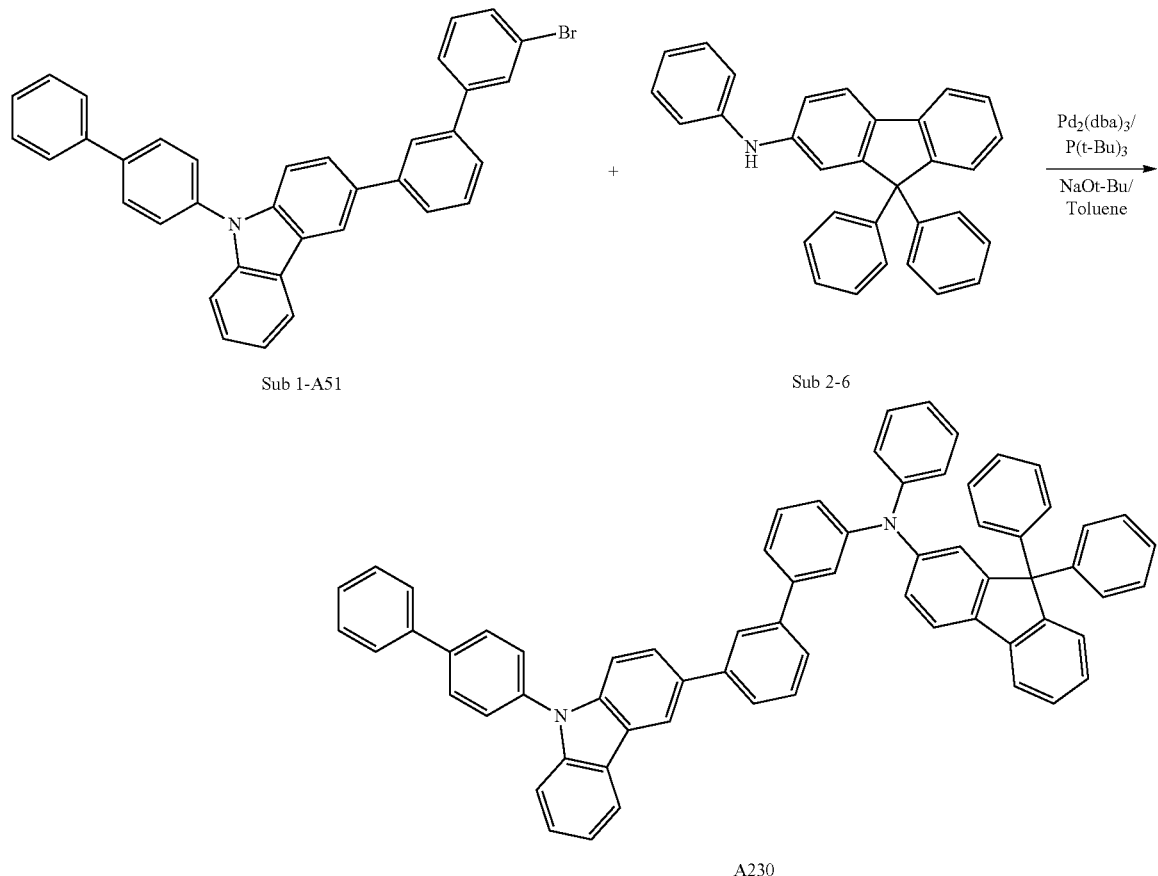
Sub 1-A51 (7.47 g, 13.6 mmol), Pd$_2$(dba)$_3$ (0.31 g, 0.3 mmol), 50% P(t-Bu)$_3$ (0.4 ml, 0.9 mmol), NaOt-Bu (3.26 g, 33.9 mmol), toluene were added to Sub 2-6 (4.63 g, 11.3 mmol) obtained in the above synthesis, and then 7.16 g (yield: 72%) of the product was obtained by using the same manner as described above for the synthesis example of Product A17.
(11) Synthesis Example of Product A270
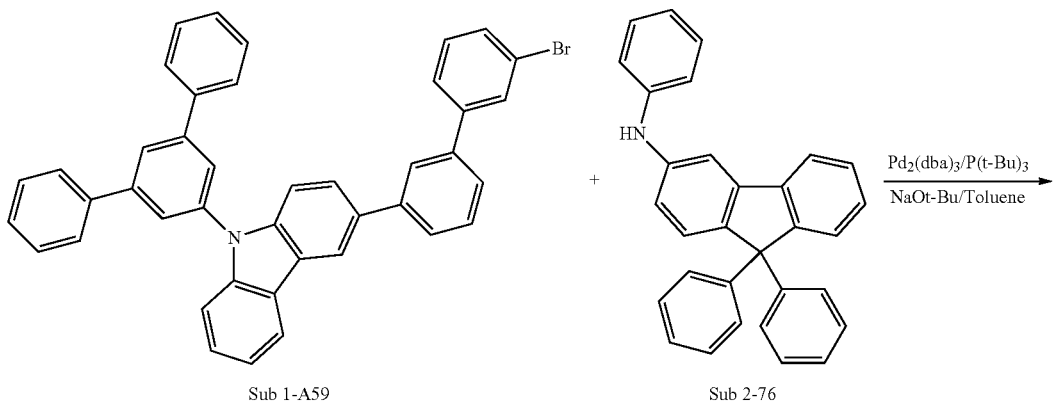

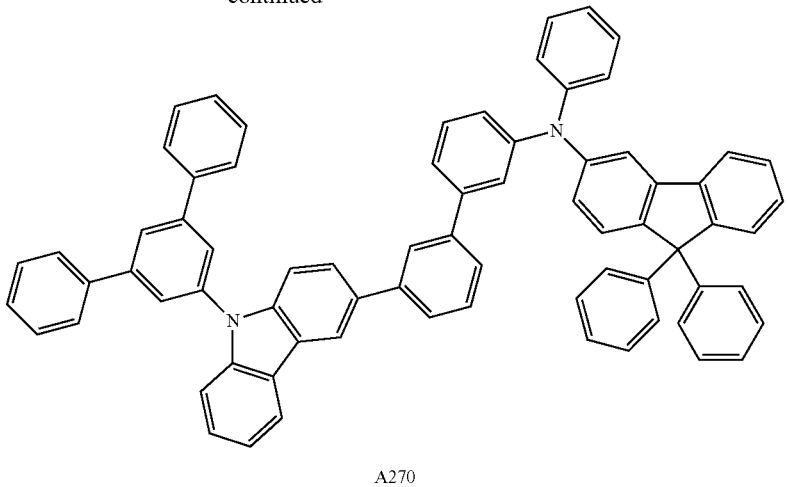

A270

Sub 1-A59 (7.84 g, 12.5 mmol), Pd₂(dba)₃ (0.29 g, 0.3 mmol), 50% P(t-Bu)₃ (0.4 ml, 0.8 mmol), NaOt-Bu (3.01 g, 31.3 mmol), toluene were added to Sub 2-76 (4.27 g, 10.4 mmol) obtained in the above synthesis, and then 6.47 g (yield: 65%) of the product was obtained by using the same manner as described above for the synthesis example of Product A17.

(12) Synthesis Example of Product A277

<Reaction Scheme 52>

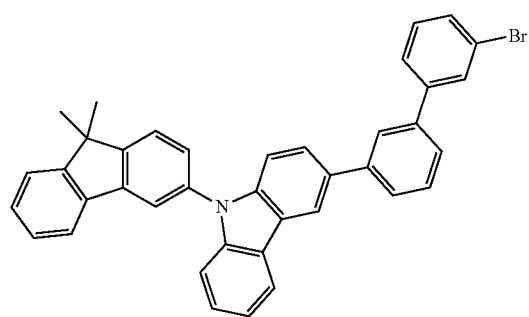

Sub 1-A64

+

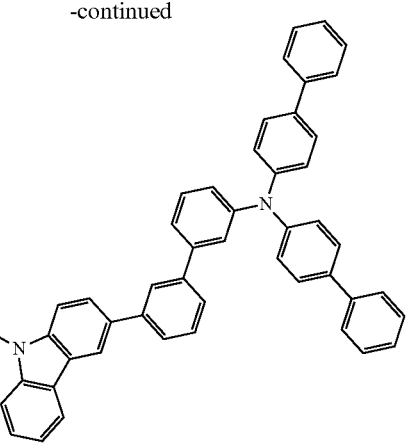

A277

Sub 1-A64 (8.18 g, 13.9 mmol), Pd₂(dba)₃ (0.32 g, 0.3 mmol), 50% P(t-Bu)₃ (0.5 ml, 0.9 mmol), NaOt-Bu (3.33 g, 34.6 mmol), toluene were added to Sub 2-17 (3.71 g, 11.5 mmol) obtained in the above synthesis, and then 7.39 g (yield: 77%) of the product was obtained by using the same manner as described above for the synthesis example of Product A17.

(13) Synthesis Example of Product A285

<Reaction Scheme 53>

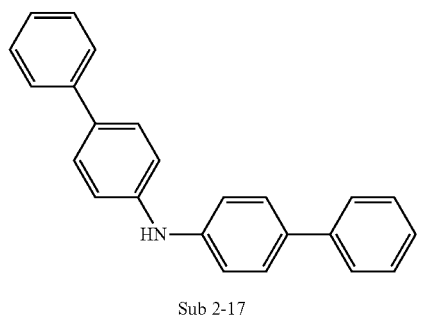

Sub 2-17

Pd₂(dba)₃/
P(t-Bu)₃
―――――→
NaOt-Bu/
Toluene

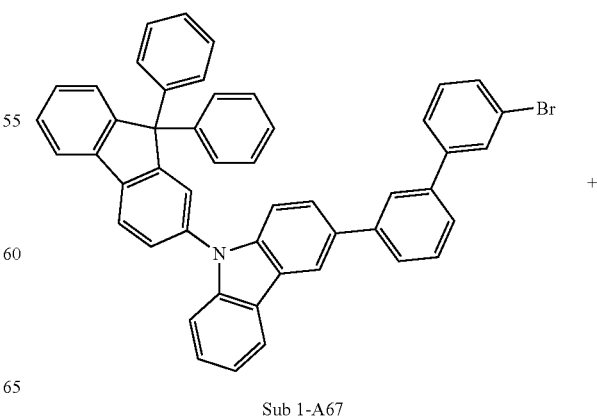

Sub 1-A67

+

337
-continued
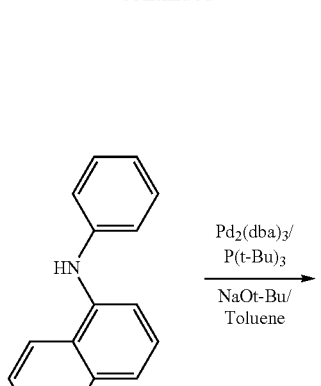
Sub 2-20
338
-continued
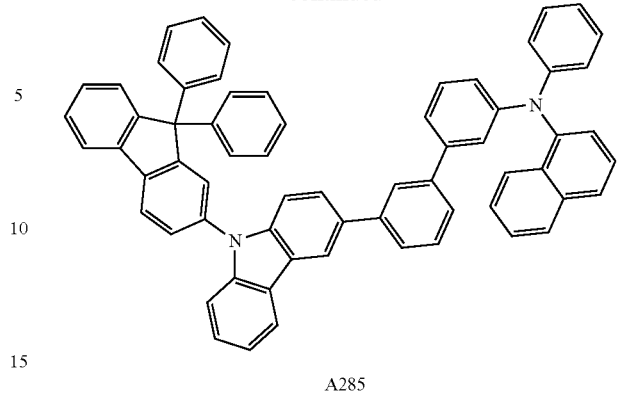
A285
Sub 1-A67 (9.62 g, 13.5 mmol), Pd$_2$(dba)$_3$ (0.31 g, 0.3 mmol), 50% P(t-Bu)$_3$ (0.4 ml, 0.9 mmol), NaOt-Bu (3.23 g, 33.7 mmol), toluene were added to Sub 2-20 (2.46 g, 11.2 mmol) obtained in the above synthesis, and then 6.99 g (yield: 73%) of the product was obtained by using the same manner as described above for the synthesis example of Product A17.
(14) Synthesis Example of Product A292
<Reaction Scheme 54>
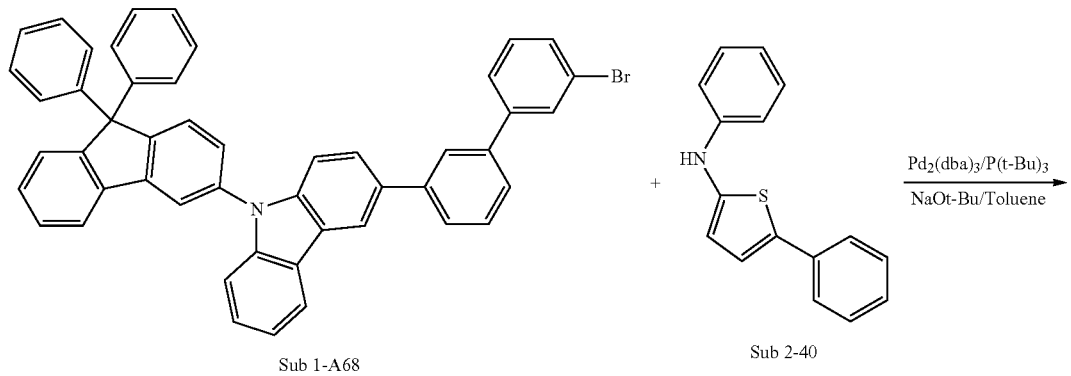
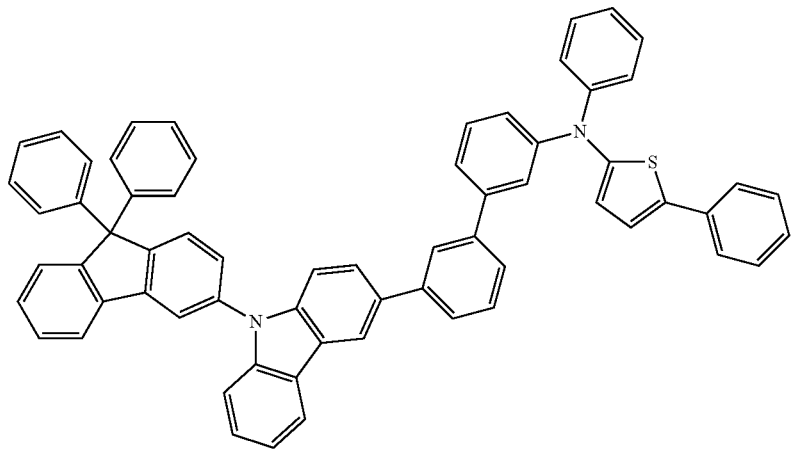
A292

Sub 1-A68 (9.28 g, 13 mmol), Pd$_2$(dba)$_3$ (0.3 g, 0.3 mmol), 50% P(t-Bu)$_3$ (0.4 ml, 0.9 mmol), NaOt-Bu (3.12 g, 32.5 mmol), toluene were added to Sub 2-40 (2.72 g, 10.8 mmol) obtained in the above synthesis, and then 6.42 g (yield: 67%) of the product was obtained by using the same manner as described above for the synthesis example of Product A17.

(15) Synthesis Example of Product A297

<Reaction Scheme 55>

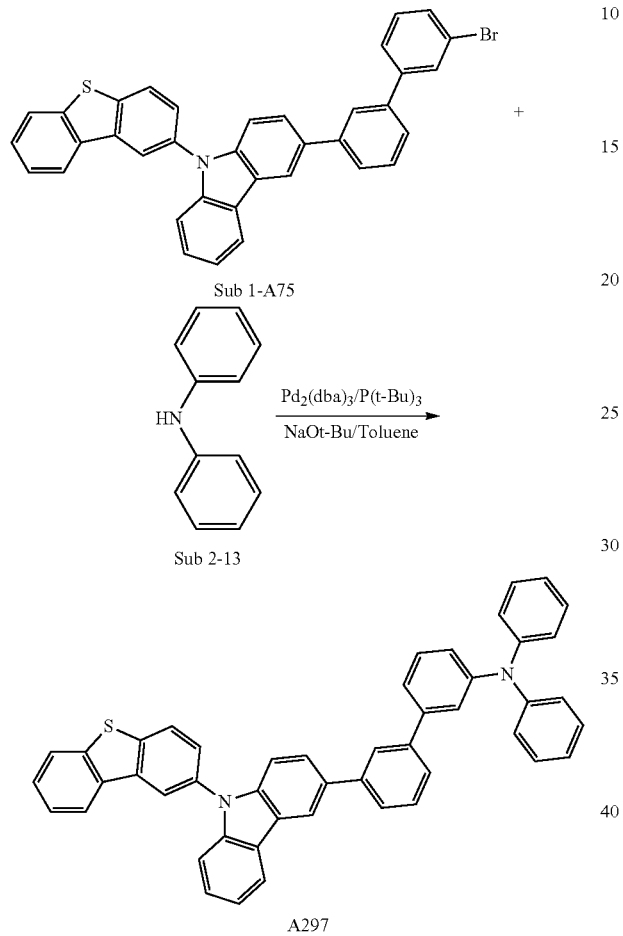

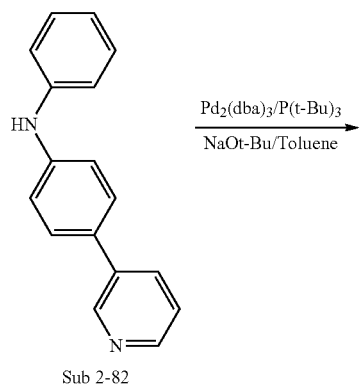

Sub 1-A75 (9.84 g, 16.9 mmol), Pd$_2$(dba)$_3$ (0.39 g, 0.4 mmol), 50% P(t-Bu)$_3$ (0.6 ml, 1.1 mmol), NaOt-Bu (4.07 g, 42.4 mmol), toluene were added to Sub 2-13 (2.39 g, 14.1 mmol) obtained in the above synthesis, and then 6.61 g (yield: 70%) of the product was obtained by using the same manner as described above for the synthesis example of Product A17.

(16) Synthesis Example of Product A303

<Reaction Scheme 56>

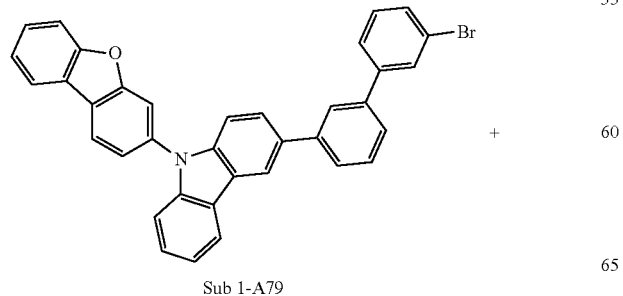

Sub 1-A79 (9.24 g, 16.4 mmol), Pd$_2$(dba)$_3$ (0.37 g, 0.4 mmol), 50% P(t-Bu)$_3$ (0.5 ml, 1.1 mmol), NaOt-Bu (3.93 g, 40.9 mmol), toluene were added to Sub 2-82 (3.36 g, 13.6 mmol) obtained in the above synthesis, and then 6.07 g (yield: 61%) of the product was obtained by using the same manner as described above for the synthesis example of Product A17.

(17) Synthesis Example of Product A311

<Reaction Scheme 57>

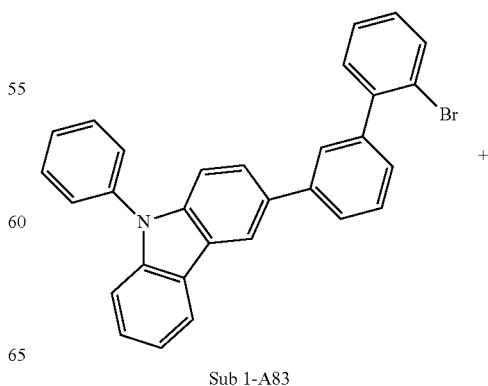

-continued

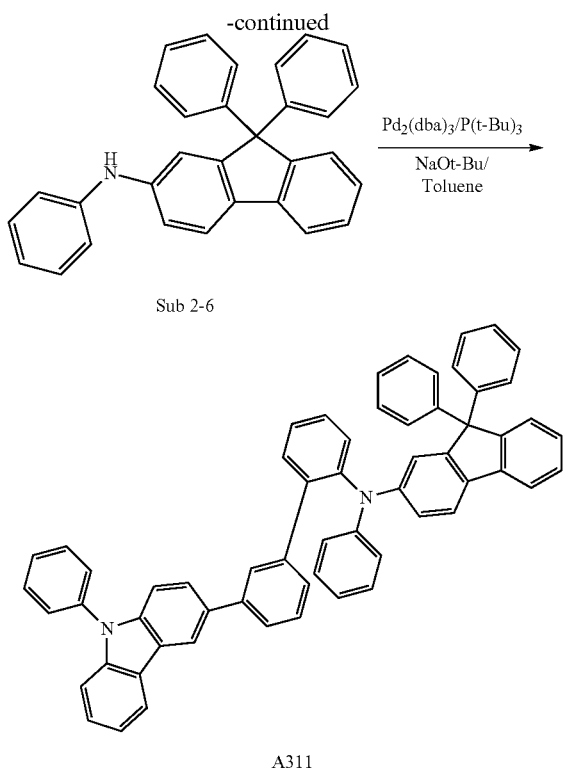

Sub 2-6

A311

Sub 1-A83 (6.8 g, 14.3 mmol), Pd₂(dba)₃ (0.33 g, 0.4 mmol), 50% P(t-Bu)₃ (0.5 ml, 1 mmol), NaOt-Bu (3.44 g, 35.8 mmol), toluene were added to Sub 2-6 (4.89 g, 11.9 mmol) obtained in the above synthesis, and then 6.42 g (yield: 67%) of the product was obtained by using the same manner as described above for the synthesis example of Product A17.

(18) Synthesis Example of Product A330

<Reaction Scheme 58>

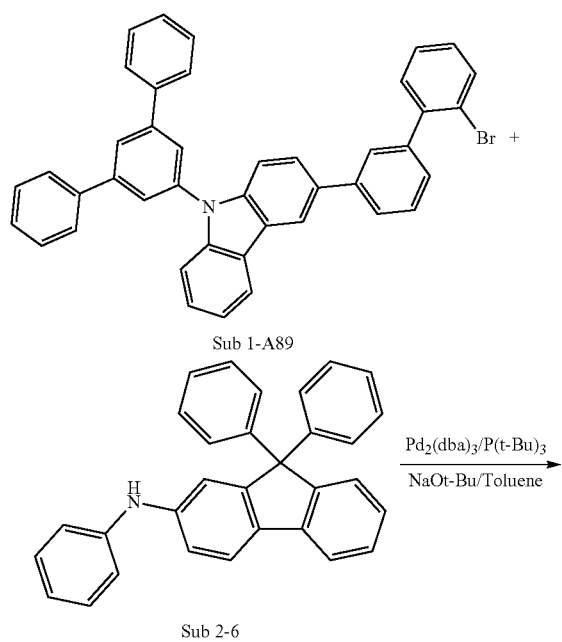

Sub 1-A89

Sub 2-6

-continued

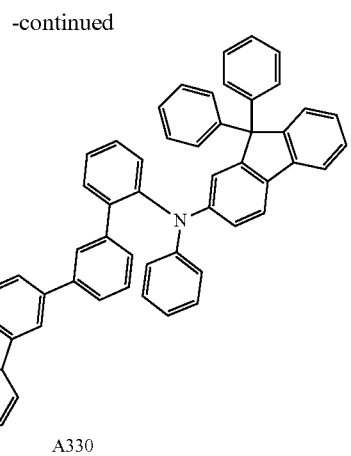

A330

Sub 1-A89 (7.56 g, 12.1 mmol), Pd₂(dba)₃ (0.28 g, 0.3 mmol), 50% P(t-Bu)₃ (0.4 ml, 0.8 mmol), NaOt-Bu (2.9 g, 30.2 mmol), toluene were added to Sub 2-6 (4.12 g, 10.1 mmol) obtained in the above synthesis, and then 6.15 g (yield: 64%) of the product was obtained by using the same manner as described above for the synthesis example of Product A17.

(19) Synthesis Example of Product A339

<Reaction Scheme 59>

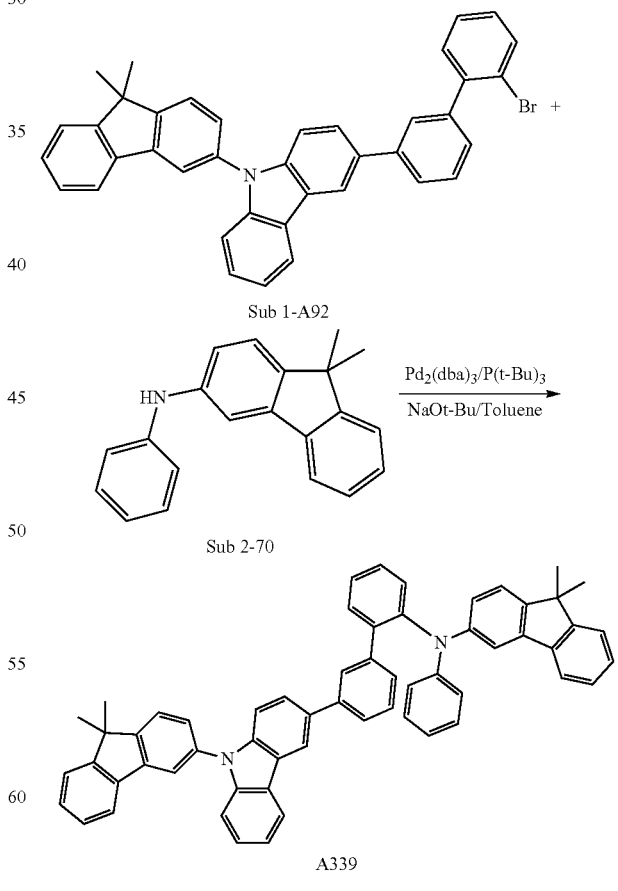

Sub 1-A92

Sub 2-70

A339

Sub 1-A92 (8.49 g, 14.4 mmol), Pd₂(dba)₃ (0.33 g, 0.4 mmol), 50% P(t-Bu)₃ (0.5 ml, 1 mmol), NaOt-Bu (3.46 g, 36 mmol), toluene were added to Sub 2-70 (3.42 g, 12 mmol)

obtained in the above synthesis, and then 6.57 g (yield: 69%) of the product was obtained by using the same manner as described above for the synthesis example of Product A17.

(20) Synthesis Example of Product A348

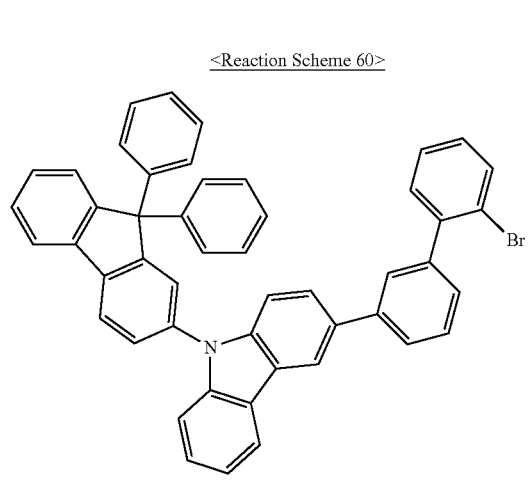

Sub 1-A95

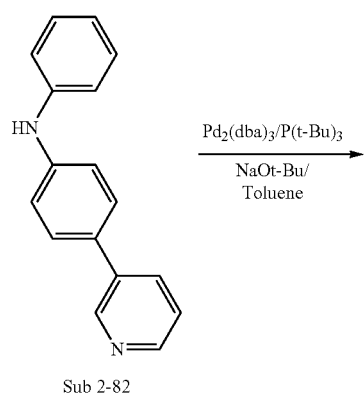

Sub 2-82

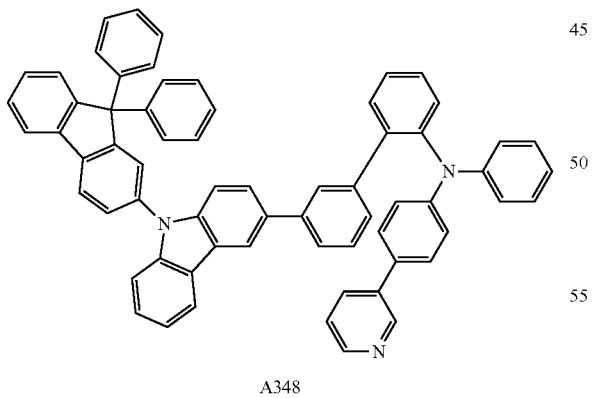

A348

Sub 1-A95 (9.85 g, 13.8 mmol), Pd$_2$(dba)$_3$ (0.32 g, 0.3 mmol), 50% P(t-Bu)$_3$ (0.4 ml, 0.9 mmol), NaOt-Bu (3.31 g, 34.5 mmol), toluene were added to Sub 2-82 (2.83 g, 11.5 mmol) obtained in the above synthesis, and then 5.76 g (yield: 57%) of the product was obtained by using the same manner as described above for the synthesis example of Product A17.

(21) Synthesis Example of Product A350

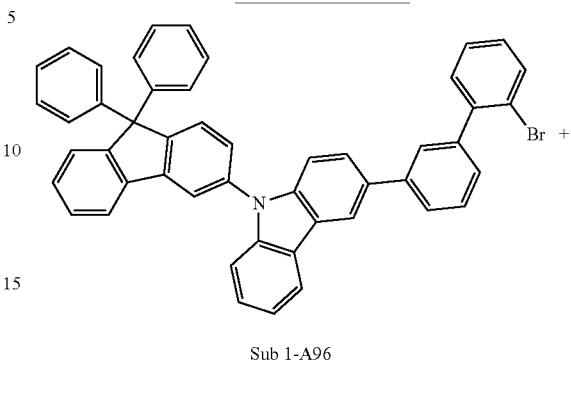

Sub 1-A96

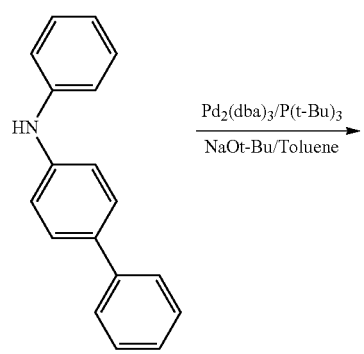

Sub 2-16

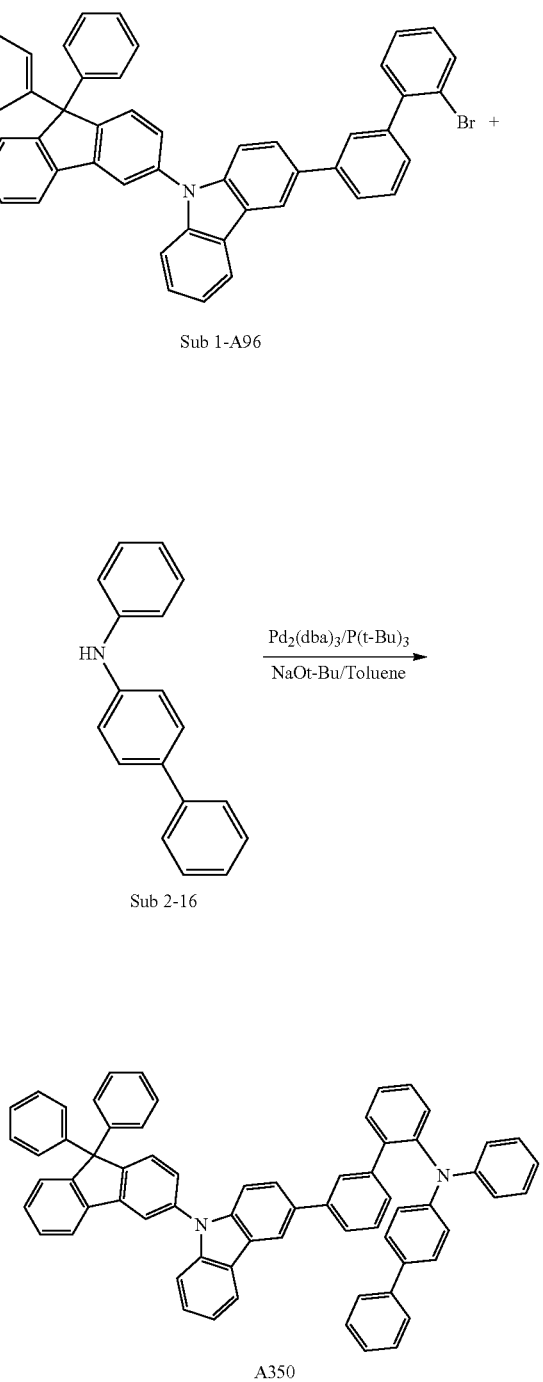

A350

Sub 1-A96 (9.58 g, 13.4 mmol), Pd$_2$(dba)$_3$ (0.31 g, 0.3 mmol), 50% P(t-Bu)$_3$ (0.4 ml, 0.9 mmol), NaOt-Bu (3.22 g, 33.5 mmol), toluene were added to Sub 2-16 (2.74 g, 11.2 mmol) obtained in the above synthesis, and then 6.38 g (yield: 65%) of the product was obtained by using the same manner as described above for the synthesis example of Product A17.

(22) Synthesis Example of Product A353

<Reaction Scheme 62>

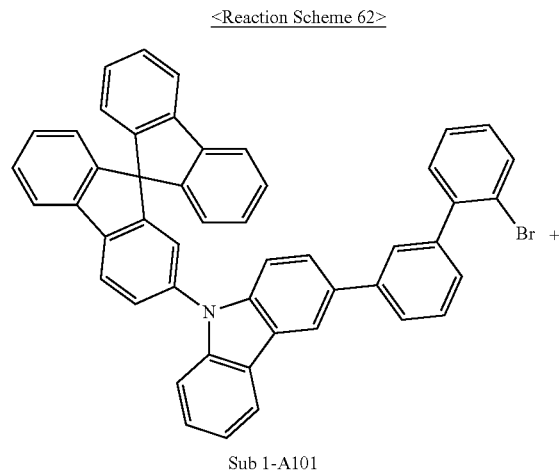

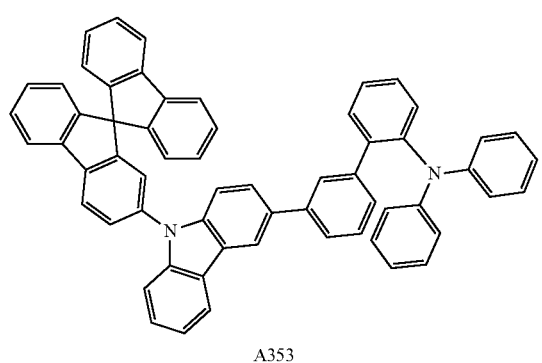

Sub 1-A101 (9.85 g, 13.8 mmol), Pd$_2$(dba)$_3$ (0.32 g, 0.3 mmol), 50% P(t-Bu)$_3$ (0.4 ml, 0.9 mmol), NaOt-Bu (3.32 g, 34.6 mmol), toluene were added to Sub 2-13 (1.95 g, 11.5 mmol) obtained in the above synthesis, and then 6.37 g (yield: 69%) of the product was obtained by using the same manner as described above for the synthesis example of Product A17.

(23) Synthesis Example of Product A359

<Reaction Scheme 63>

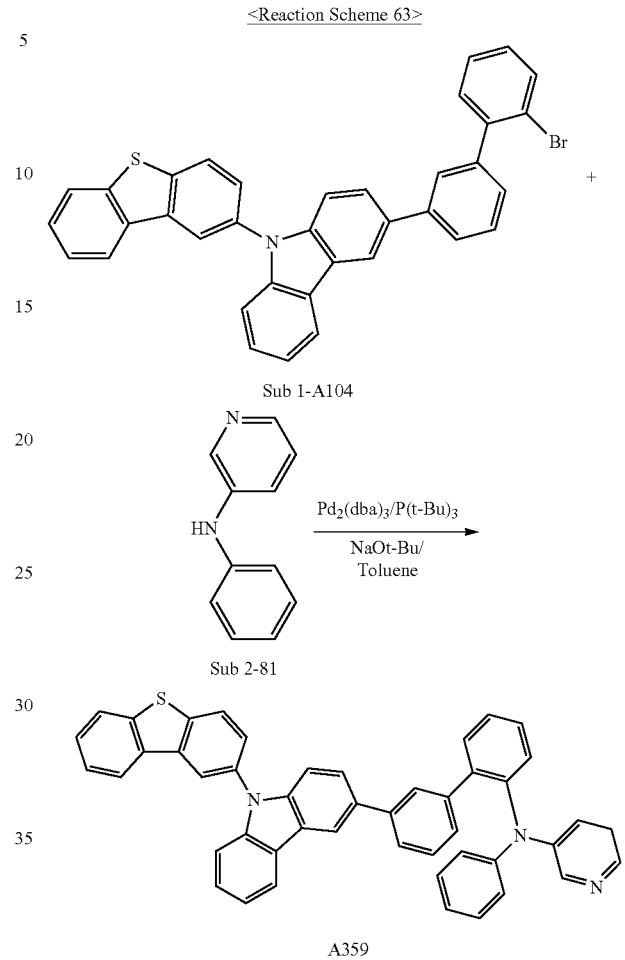

Sub 1-A104 (10.19 g, 17.6 mmol), Pd$_2$(dba)$_3$ (0.4 g, 0.4 mmol), 50% P(t-Bu)$_3$ (0.6 ml, 1.2 mmol), NaOt-Bu (4.22 g, 43.9 mmol), toluene were added to Sub 2-81 (2.49 g, 14.6 mmol) obtained in the above synthesis, and then 6.17 g (yield: 63%) of the product was obtained by using the same manner as described above for the synthesis example of Product A17.

(24) Synthesis Example of Product A363

<Reaction Scheme 64>

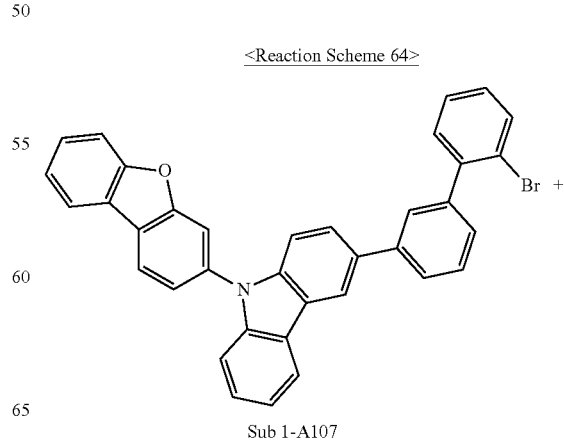

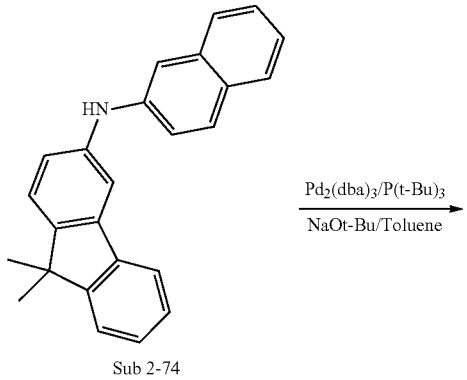

Sub 2-74

Pd₂(dba)₃/P(t-Bu)₃
NaOt-Bu/Toluene
→

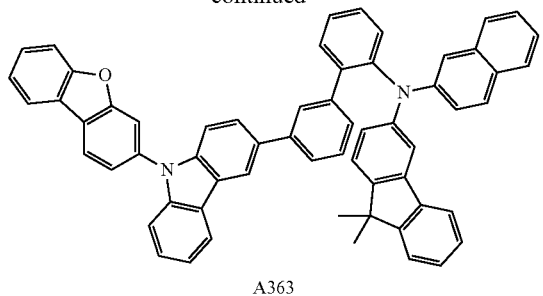

A363

Sub 1-A107 (8.44 g, 15 mmol), Pd₂(dba)₃ (0.34 g, 0.4 mmol), 50% P(t-Bu)₃ (0.5 ml, 1 mmol), NaOt-Bu (3.59 g, 37.4 mmol), toluene were added to Sub 2-74 (4.18 g, 12.5 mmol) obtained in the above synthesis, and then 6.74 g (yield: 66%) of the product was obtained by using the same manner as described above for the synthesis example of Product A17.

On the other hand, the FD-MS values of compounds A1~A392 of the present invention prepared according to the above synthesis examples are shown in Table 3 below.

TABLE 3

| compound | FD-MS | compound | FD-MS |
|---|---|---|---|
| A1 | m/z = 678.30($C_{51}H_{38}N_2$ = 678.86) | A2 | m/z = 754.33($C_{57}H_{42}N_2$ = 754.96) |
| A6 | m/z = 759.37($C_{57}H_{37}D_5N_2$ = 759.99) | A7 | m/z = 830.37($C_{63}H_{46}N_2$ = 831.05) |
| A11 | m/z = 728.32($C_{55}H_{40}N_2$ = 728.92) | A12 | m/z = 804.35($C_{61}H_{44}N_2$ = 805.02) |
| A16 | m/z = 802.33($C_{61}H_{42}N_2$ = 803.00) | A17 | m/z = 878.37($C_{67}H_{46}N_2$ = 879.10) |
| A19 | m/z = 852.35($C_{65}H_{44}N_2$ = 853.06) | A21 | m/z = 878.37($C_{67}H_{46}N_2$ = 879.10) |
| A22 | m/z = 954.40($C_{73}H_{50}N_2$ = 955.19) | A23 | m/z = 928.38($C_{71}H_{48}N_2$ = 929.15) |
| A24 | m/z = 928.38($C_{71}H_{48}N_2$ = 929.15) | A25 | m/z = 830.37($C_{63}H_{46}N_2$ = 831.05) |
| A26 | m/z = 852.35($C_{65}H_{44}N_2$ = 853.06) | A27 | m/z = 928.38($C_{71}H_{48}N_2$ = 929.15) |
| A31 | m/z = 800.32($C_{61}H_{40}N_2$ = 800.98) | A36 | m/z = 850.33($C_{65}H_{42}N_2$ = 851.04) |
| A47 | m/z = 714.30($C_{54}H_{38}N_2$ = 714.89) | A51 | m/z = 714.30($C_{54}H_{38}N_2$ = 714.89) |
| A56 | m/z = 688.29($C_{52}H_{36}N_2$ = 688.86) | A62 | m/z = 764.32($C_{58}H_{40}N_2$ = 764.95) |
| A66 | m/z = 612.26($C_{46}H_{32}N_2$ = 612.76) | A72 | m/z = 688.29($C_{52}H_{36}N_2$ = 688.86) |
| A87 | m/z = 738.30($C_{56}H_{38}N_2$ = 738.91) | A97 | m/z = 728.28($C_{54}H_{36}N_2O$ = 728.88) |
| A101 | m/z = 744.26($C_{54}H_{36}N_2S$ = 744.94) | A121 | m/z = 668.23($C_{48}H_{32}N_2S$ = 668.85) |
| A123 | m/z = 638.27($C_{48}H_{34}N_2$ = 638.80) | A124 | m/z = 714.30($C_{54}H_{38}N_2$ = 714.89) |
| A125 | m/z = 738.30($C_{56}H_{38}N_2$ = 738.91) | A127 | m/z = 729.31($C_{54}H_{39}N_3$ = 729.91) |
| A128 | m/z = 928.38($C_{71}H_{48}N_2$ = 929.15) | A129 | m/z = 790.33($C_{60}H_{42}N_2$ = 790.99) |
| A130 | m/z = 879.36($C_{66}H_{45}N_3$ = 880.08) | A131 | m/z = 896.36($C_{66}H_{48}N_2Si$ = 897.19) |
| A134 | m/z = 602.27($C_{45}H_{34}N_2$ = 602.76) | A135 | m/z = 656.26($C_{48}H_{33}FN_2$ = 656.79) |
| A142 | m/z = 612.26($C_{46}H_{32}N_2$ = 612.76) | A146 | m/z = 804.35($C_{61}H_{44}N_2$ = 805.02) |
| A161 | m/z = 802.33($C_{61}H_{42}N_2$ = 803.00) | A162 | m/z = 830.37($C_{63}H_{46}N_2$ = 831.05) |
| A165 | m/z = 820.29($C_{60}H_{40}N_2S$ = 821.04) | A168 | m/z = 778.30($C_{58}H_{38}N_2O$ = 778.94) |
| A169 | m/z = 928.38($C_{71}H_{48}N_2$ = 929.15) | A170 | m/z = 954.40($C_{73}H_{50}N_2$ = 955.19) |
| A171 | m/z = 878.37($C_{67}H_{46}N_2$ = 879.10) | A172 | m/z = 954.40($C_{73}H_{50}N_2$ = 955.19) |
| A173 | m/z = 852.35($C_{65}H_{44}N_2$ = 853.06) | A174 | m/z = 878.37($C_{67}H_{46}N_2$ = 879.10) |
| A175 | m/z = 928.38($C_{71}H_{48}N_2$ = 929.15) | A176 | m/z = 928.38($C_{71}H_{48}N_2$ = 929.15) |
| A177 | m/z = 754.33($C_{57}H_{42}N_2$ = 754.96) | A178 | m/z = 802.33($C_{61}H_{42}N_2$ = 803.00) |
| A179 | m/z = 878.37($C_{67}H_{46}N_2$ = 879.10) | A180 | m/z = 878.37($C_{67}H_{46}N_2$ = 879.10) |
| A181 | m/z = 714.30($C_{54}H_{38}N_2$ = 714.89) | A182 | m/z = 1004.41($C_{77}H_{52}N_2$ = 1005.25) |
| A183 | m/z = 906.40($C_{69}H_{50}N_2$ = 907.15) | A184 | m/z = 954.40($C_{73}H_{50}N_2$ = 955.19) |
| A185 | m/z = 820.29($C_{60}H_{40}N_2S$ = 821.04) | A186 | m/z = 831.36($C_{62}H_{45}N_3$ = 832.04) |
| A187 | m/z = 830.37($C_{63}H_{46}N_2$ = 831.05) | A188 | m/z = 854.37($C_{65}H_{46}N_2$ = 855.07) |
| A189 | m/z = 994.43($C_{76}H_{54}N_2$ = 995.26) | A190 | m/z = 744.31($C_{55}H_{40}N_2O$ = 744.92) |
| A191 | m/z = 830.37($C_{63}H_{46}N_2$ = 831.05) | A192 | m/z = 830.37($C_{63}H_{46}N_2$ = 831.05) |
| A193 | m/z = 794.37($C_{60}H_{46}N_2$ = 795.02) | A194 | m/z = 906.40($C_{69}H_{50}N_2$ = 907.15) |
| A195 | m/z = 830.37($C_{63}H_{46}N_2$ = 831.05) | A196 | m/z = 906.40($C_{69}H_{50}N_2$ = 907.15) |
| A197 | m/z = 755.33($C_{56}H_{41}N_3$ = 755.94) | A198 | m/z = 906.40($C_{69}H_{50}N_2$ = 907.15) |
| A199 | m/z = 802.33($C_{61}H_{42}N_2$ = 803.00) | A200 | m/z = 852.35($C_{65}H_{44}N_2$ = 853.06) |
| A201 | m/z = 902.37($C_{69}H_{46}N_2$ = 903.12) | A202 | m/z = 902.37($C_{69}H_{46}N_2$ = 903.12) |
| A203 | m/z = 878.37($C_{67}H_{46}N_2$ = 879.10) | A204 | m/z = 954.40($C_{73}H_{50}N_2$ = 955.19) |
| A205 | m/z = 918.40($C_{70}H_{50}N_2$ = 919.16) | A206 | m/z = 853.35($C_{64}H_{43}N_3$ = 854.05) |
| A207 | m/z = 802.33($C_{61}H_{42}N_2$ = 803.00) | A208 | m/z = 852.35($C_{65}H_{44}N_2$ = 853.06) |

TABLE 3-continued

| compound | FD-MS | compound | FD-MS |
|---|---|---|---|
| A209 | m/z = 878.37($C_{67}H_{46}N_2$ = 879.10) | A210 | m/z = 918.40($C_{70}H_{50}N_2$ = 919.16) |
| A211 | m/z = 877.35($C_{66}H_{43}N_3$ = 878.07) | A212 | m/z = 800.32($C_{61}H_{40}N_2$ = 800.98) |
| A213 | m/z = 768.26($C_{56}H_{36}N_2S$ = 768.96) | A214 | m/z = 936.35($C_{69}H_{48}N_2S$ = 937.20) |
| A215 | m/z = 820.29($C_{60}H_{40}N_2S$ = 821.04) | A216 | m/z = 908.32($C_{67}H_{44}N_2S$ = 909.14) |
| A217 | m/z = 822.28($C_{58}H_{38}N_4S$ = 823.01) | A218 | m/z = 794.28($C_{58}H_{38}N_2S$ = 795.00) |
| A219 | m/z = 728.28($C_{54}H_{36}N_2O$ = 728.88) | A220 | m/z = 742.26($C_{54}H_{34}N_2O_2$ = 742.86) |
| A221 | m/z = 829.31($C_{61}H_{39}N_3O$ = 829.98) | A222 | m/z = 782.33($C_{58}H_{42}N_2O$ = 782.97) |
| A223 | m/z = 652.25($C_{48}H_{32}N_2O$ = 652.78) | A224 | m/z = 942.36($C_{71}H_{46}N_2O$ = 943.14) |
| A225 | m/z = 678.30($C_{51}H_{38}N_2$ = 678.86) | A226 | m/z = 754.33($C_{57}H_{42}N_2$ = 754.96) |
| A227 | m/z = 754.33($C_{57}H_{42}N_2$ = 754.96) | A228 | m/z = 830.37($C_{63}H_{46}N_2$ = 831.05) |
| A229 | m/z = 802.33($C_{61}H_{42}N_2$ = 803.00) | A230 | m/z = 878.37($C_{67}H_{46}N_2$ = 879.10) |
| A231 | m/z = 878.37($C_{67}H_{46}N_2$ = 879.10) | A232 | m/z = 954.40($C_{73}H_{50}N_2$ = 955.19) |
| A233 | m/z = 928.38($C_{71}H_{48}N_2$ = 929.15) | A234 | m/z = 928.38($C_{71}H_{48}N_2$ = 929.15) |
| A235 | m/z = 852.35($C_{65}H_{44}N_2$ = 853.06) | A236 | m/z = 928.38($C_{71}H_{48}N_2$ = 929.15) |
| A237 | m/z = 562.24($C_{42}H_{30}N_2$ = 562.70) | A238 | m/z = 638.27($C_{48}H_{34}N_2$ = 638.80) |
| A239 | m/z = 638.27($C_{48}H_{34}N_2$ = 638.80) | A240 | m/z = 714.30($C_{54}H_{38}N_2$ = 714.89) |
| A241 | m/z = 714.30($C_{54}H_{38}N_2$ = 714.89) | A242 | m/z = 790.33($C_{60}H_{42}N_2$ = 790.99) |
| A243 | m/z = 878.37($C_{67}H_{46}N_2$ = 879.10) | A244 | m/z = 954.40($C_{73}H_{50}N_2$ = 955.19) |
| A245 | m/z = 830.37($C_{63}H_{46}N_2$ = 831.05) | A246 | m/z = 892.38($C_{68}H_{48}N_2$ = 893.12) |
| A247 | m/z = 830.37($C_{63}H_{46}N_2$ = 831.05) | A248 | m/z = 838.32($C_{61}H_{40}F_2N_2$ = 838.98) |
| A249 | m/z = 928.38($C_{71}H_{48}N_2$ = 929.15) | A250 | m/z = 1030.43($C_{79}H_{54}N_2$ = 1031.29) |
| A251 | m/z = 878.37($C_{67}H_{46}N_2$ = 879.10) | A252 | m/z = 883.40($C_{67}H_{41}D_5N_2$ = 884.13) |
| A253 | m/z = 878.37($C_{67}H_{46}N_2$ = 879.10) | A254 | m/z = 878.37($C_{67}H_{46}N_2$ = 879.10) |
| A255 | m/z = 954.40($C_{73}H_{50}N_2$ = 955.19) | A256 | m/z = 928.38($C_{71}H_{48}N_2$ = 929.15) |
| A257 | m/z = 802.33($C_{61}H_{42}N_2$ = 803.00) | A258 | m/z = 878.37($C_{67}H_{46}N_2$ = 879.10) |
| A259 | m/z = 878.37($C_{67}H_{46}N_2$ = 879.10) | A260 | m/z = 878.37($C_{67}H_{46}N_2$ = 879.10) |
| A261 | m/z = 614.27($C_{46}H_{34}N_2$ = 614.78) | A262 | m/z = 744.26($C_{54}H_{36}N_2S$ = 744.94) |
| A263 | m/z = 765.31($C_{57}H_{39}N_3$ = 765.94) | A264 | m/z = 881.38($C_{66}H_{47}N_3$ = 882.10) |
| A265 | m/z = 814.33($C_{62}H_{42}N_2$ = 815.01) | A266 | m/z = 906.40($C_{69}H_{50}N_2$ = 907.15) |
| A267 | m/z = 954.40($C_{73}H_{50}N_2$ = 955.19) | A268 | m/z = 1028.41($C_{79}H_{52}N_2$ = 1029.27) |
| A269 | m/z = 881.38($C_{66}H_{47}N_3$ = 882.10) | A270 | m/z = 954.40($C_{73}H_{50}N_2$ = 955.19) |
| A271 | m/z = 854.33($C_{64}H_{42}N_2O$ = 855.03) | A272 | m/z = 754.33($C_{57}H_{42}N_2$ = 754.96) |
| A273 | m/z = 830.37($C_{63}H_{46}N_2$ = 831.05) | A274 | m/z = 830.37($C_{63}H_{46}N_2$ = 831.05) |
| A275 | m/z = 918.40($C_{70}H_{50}N_2$ = 919.16) | A276 | m/z = 805.35($C_{60}H_{43}N_3$ = 806.00) |
| A277 | m/z = 830.37($C_{63}H_{46}N_2$ = 831.05) | A278 | m/z = 830.37($C_{63}H_{46}N_2$ = 831.05) |
| A279 | m/z = 844.38($C_{64}H_{48}N_2$ = 845.08) | A280 | m/z = 834.31($C_{61}H_{42}N_2S$ = 835.06) |
| A281 | m/z = 778.33($C_{59}H_{42}N_2$ = 778.98) | A282 | m/z = 946.43($C_{72}H_{54}N_2$ = 947.21) |
| A283 | m/z = 869.38($C_{65}H_{47}N_3$ = 870.09) | A284 | m/z = 870.40($C_{66}H_{50}N_2$ = 871.12) |
| A285 | m/z = 852.35($C_{65}H_{44}N_2$ = 853.06) | A286 | m/z = 878.37($C_{67}H_{46}N_2$ = 879.10) |
| A287 | m/z = 994.43($C_{76}H_{54}N_2$ = 995.26) | A288 | m/z = 903.36($C_{68}H_{45}N_3$ = 904.10) |
| A289 | m/z = 802.33($C_{61}H_{42}N_2$ = 803.00) | A290 | m/z = 878.37($C_{67}H_{46}N_2$ = 879.10) |
| A291 | m/z = 918.40($C_{70}H_{50}N_2$ = 919.16) | A292 | m/z = 884.32($C_{65}H_{44}N_2S$ = 885.12) |
| A293 | m/z = 916.38($C_{70}H_{48}N_2$ = 917.14) | A294 | m/z = 850.33($C_{65}H_{42}N_2$ = 851.04) |
| A295 | m/z = 744.26($C_{54}H_{36}N_2S$ = 744.94) | A296 | m/z = 908.32($C_{67}H_{44}N_2S$ = 909.14) |
| A297 | m/z = 668.23($C_{48}H_{32}N_2S$ = 668.85) | A298 | m/z = 898.31($C_{64}H_{42}N_4S$ = 899.11) |
| A299 | m/z = 774.22($C_{54}H_{34}N_2S_2$ = 774.99) | A300 | m/z = 820.29($C_{60}H_{40}N_2S$ = 821.04) |
| A301 | m/z = 908.32($C_{67}H_{44}N_2S$ = 909.14) | A302 | m/z = 804.31($C_{60}H_{40}N_2O$ = 804.97) |
| A303 | m/z = 729.28($C_{53}H_{35}N_3O$ = 729.86) | A304 | m/z = 768.31($C_{57}H_{40}N_2O$ = 768.94) |
| A305 | m/z = 752.28($C_{56}H_{36}N_2O$ = 752.90) | A306 | m/z = 892.35($C_{67}H_{44}N_2O$ = 893.08) |
| A307 | m/z = 818.33($C_{61}H_{42}N_2O$ = 819.00) | A308 | m/z = 804.31($C_{60}H_{40}N_2O$ = 804.97) |
| A309 | m/z = 754.33($C_{57}H_{42}N_2$ = 754.96) | A310 | m/z = 754.33($C_{57}H_{42}N_2$ = 754.96) |
| A311 | m/z = 802.33($C_{61}H_{42}N_2$ = 803.00) | A312 | m/z = 878.37($C_{67}H_{46}N_2$ = 879.10) |
| A313 | m/z = 954.40($C_{73}H_{50}N_2$ = 955.19) | A314 | m/z = 928.38($C_{71}H_{48}N_2$ = 929.15) |
| A315 | m/z = 852.35($C_{65}H_{44}N_2$ = 853.06) | A316 | m/z = 878.37($C_{67}H_{46}N_2$ = 879.10) |
| A317 | m/z = 562.24($C_{42}H_{30}N_2$ = 562.70) | A318 | m/z = 638.27($C_{48}H_{34}N_2$ = 638.80) |
| A319 | m/z = 638.27($C_{48}H_{34}N_2$ = 638.80) | A320 | m/z = 714.30($C_{54}H_{38}N_2$ = 714.89) |
| A321 | m/z = 878.37($C_{67}H_{46}N_2$ = 879.10) | A322 | m/z = 878.37($C_{67}H_{46}N_2$ = 879.10) |
| A323 | m/z = 800.32($C_{61}H_{40}N_2$ = 800.98) | A324 | m/z = 779.29($C_{57}H_{37}N_3O$ = 779.92) |
| A325 | m/z = 802.33($C_{61}H_{42}N_2$ = 803.00) | A326 | m/z = 878.37($C_{67}H_{46}N_2$ = 879.10) |
| A327 | m/z = 878.37($C_{67}H_{46}N_2$ = 879.10) | A328 | m/z = 878.37($C_{67}H_{46}N_2$ = 879.10) |
| A329 | m/z = 866.37($C_{66}H_{46}N_2$ = 867.08) | A330 | m/z = 954.40($C_{73}H_{50}N_2$ = 955.19) |
| A331 | m/z = 880.38($C_{67}H_{48}N_2$ = 881.11) | A332 | m/z = 954.40($C_{73}H_{50}N_2$ = 955.19) |
| A333 | m/z = 820.29($C_{60}H_{40}N_2S$ = 821.04) | A334 | m/z = 896.32($C_{66}H_{44}N_2S$ = 897.13) |
| A335 | m/z = 754.33($C_{57}H_{42}N_2$ = 754.96) | A336 | m/z = 794.37($C_{60}H_{46}N_2$ = 795.02) |
| A337 | m/z = 679.30($C_{50}H_{37}N_3$ = 679.85) | A338 | m/z = 830.37($C_{63}H_{46}N_2$ = 831.05) |
| A339 | m/z = 794.37($C_{60}H_{46}N_2$ = 795.02) | A340 | m/z = 818.33($C_{61}H_{42}N_2O$ = 819.00) |
| A341 | m/z = 728.32($C_{55}H_{40}N_2$ = 728.92) | A342 | m/z = 920.41($C_{70}H_{52}N_2$ = 921.18) |
| A343 | m/z = 729.31($C_{54}H_{39}N_3$ = 729.91) | A344 | m/z = 870.40($C_{66}H_{50}N_2$ = 871.12) |
| A345 | m/z = 802.33($C_{61}H_{42}N_2$ = 803.00) | A346 | m/z = 878.37($C_{67}H_{46}N_2$ = 879.10) |
| A347 | m/z = 918.40($C_{70}H_{50}N_2$ = 919.16) | A348 | m/z = 879.36($C_{66}H_{45}N_3$ = 880.08) |
| A349 | m/z = 802.33($C_{61}H_{42}N_2$ = 803.00) | A350 | m/z = 878.37($C_{67}H_{46}N_2$ = 879.10) |
| A351 | m/z = 918.40($C_{70}H_{50}N_2$ = 919.16) | A352 | m/z = 858.31($C_{63}H_{42}N_2S$ = 859.09) |
| A353 | m/z = 800.32($C_{61}H_{40}N_2$ = 800.98) | A354 | m/z = 916.38($C_{70}H_{48}N_2$ = 917.14) |
| A355 | m/z = 744.26($C_{54}H_{36}N_2S$ = 744.94) | A356 | m/z = 908.32($C_{67}H_{44}N_2S$ = 909.14) |
| A357 | m/z = 668.23($C_{48}H_{32}N_2S$ = 668.85) | A358 | m/z = 784.29($C_{57}H_{40}N_2S$ = 785.01) |
| A359 | m/z = 669.22($C_{47}H_{31}N_3S$ = 669.83) | A360 | m/z = 719.24($C_{51}H_{33}N_3S$ = 719.89) |
| A361 | m/z = 768.26($C_{56}H_{36}N_2S$ = 768.96) | A362 | m/z = 702.27($C_{52}H_{34}N_2O$ = 702.84) |
| A363 | m/z = 818.33($C_{61}H_{42}N_2O$ = 819.00) | A364 | m/z = 729.28($C_{53}H_{35}N_3O$ = 729.86) |

TABLE 3-continued

| compound | FD-MS | compound | FD-MS |
|---|---|---|---|
| A365 | m/z = 652.25($C_{48}H_{32}N_2O$ = 652.78) | A366 | m/z = 892.35($C_{67}H_{44}N_2O$ = 893.08) |
| A367 | m/z = 702.27($C_{52}H_{34}N_2O$ = 702.84) | A368 | m/z = 792.28($C_{58}H_{36}N_2O_2$ = 792.92) |
| A369 | m/z = 804.31($C_{60}H_{40}N_2O$ = 804.97) | A370 | m/z = 806.30($C_{58}H_{38}N_4O$ = 806.95) |
| A371 | m/z = 802.33($C_{61}H_{42}N_2$ = 803.00) | A372 | m/z = 918.40($C_{70}H_{50}N_2$ = 919.16) |
| A373 | m/z = 908.32($C_{67}H_{44}N_2S$ = 909.14) | A374 | m/z = 852.35($C_{65}H_{44}N_2$ = 853.06) |
| A375 | m/z = 918.40($C_{70}H_{50}N_2$ = 919.16) | A376 | m/z = 803.33($C_{60}H_{41}N_3$ = 803.99) |
| A377 | m/z = 878.37($C_{67}H_{46}N_2$ = 879.10) | A378 | m/z = 954.40($C_{73}H_{50}N_2$ = 955.19) |
| A379 | m/z = 968.41($C_{74}H_{52}N_2$ = 969.22) | A380 | m/z = 853.35($C_{64}H_{43}N_3$ = 854.05) |
| A381 | m/z = 994.43($C_{76}H_{54}N_2$ = 995.26) | A382 | m/z = 902.37($C_{69}H_{46}N_2$ = 903.12) |
| A383 | m/z = 918.40($C_{70}H_{50}N_2$ = 919.16) | A384 | m/z = 892.35($C_{67}H_{44}N_2O$ = 893.08) |
| A385 | m/z = 802.33($C_{61}H_{42}N_2$ = 803.00) | A386 | m/z = 1042.43($C_{80}H_{54}N_2$ = 1043.30) |
| A387 | m/z = 853.35($C_{64}H_{43}N_3$ = 854.05) | A388 | m/z = 994.43($C_{76}H_{54}N_2$ = 995.26) |
| A389 | m/z = 878.37($C_{67}H_{46}N_2$ = 879.10) | A390 | m/z = 994.43($C_{76}H_{54}N_2$ = 995.26) |
| A391 | m/z = 884.32($C_{65}H_{44}N_2S$ = 885.12) | A392 | m/z = 994.43($C_{76}H_{54}N_2$ = 995.26) |

Synthesis Example 2

The compound(final products) represented by Formula 2 according to the present invention are synthesized by reacting Sub 3 and Sub 4 as shown in Reaction Scheme 65, but are not limited thereto.

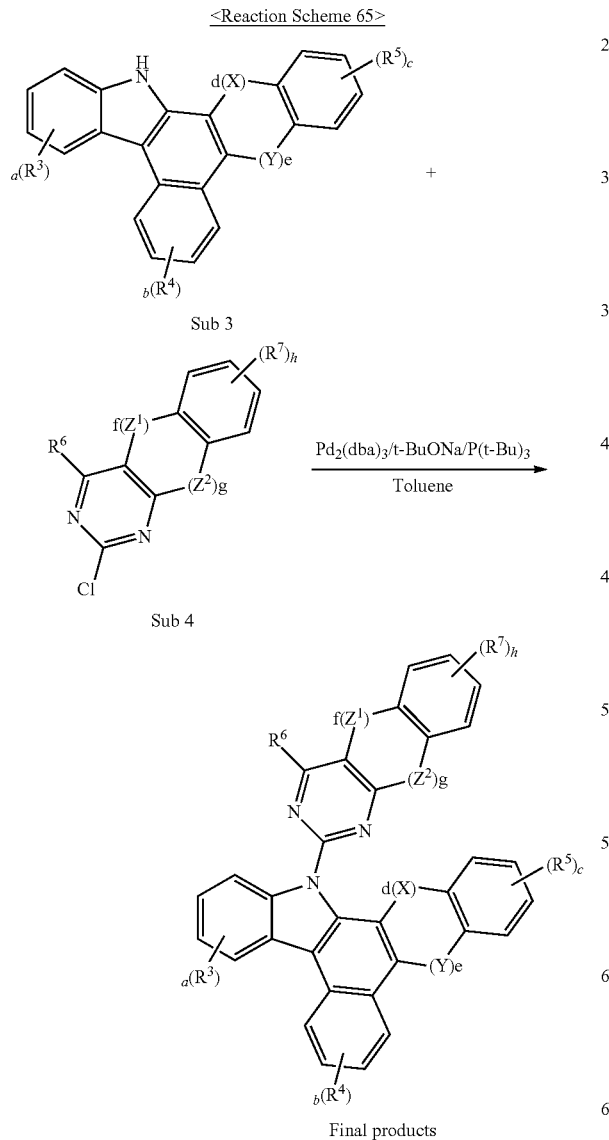

Sub 3 + Sub 4 → Final products

I. Synthesis of Sub 3

1. Synthesis Example of 3-1 Core

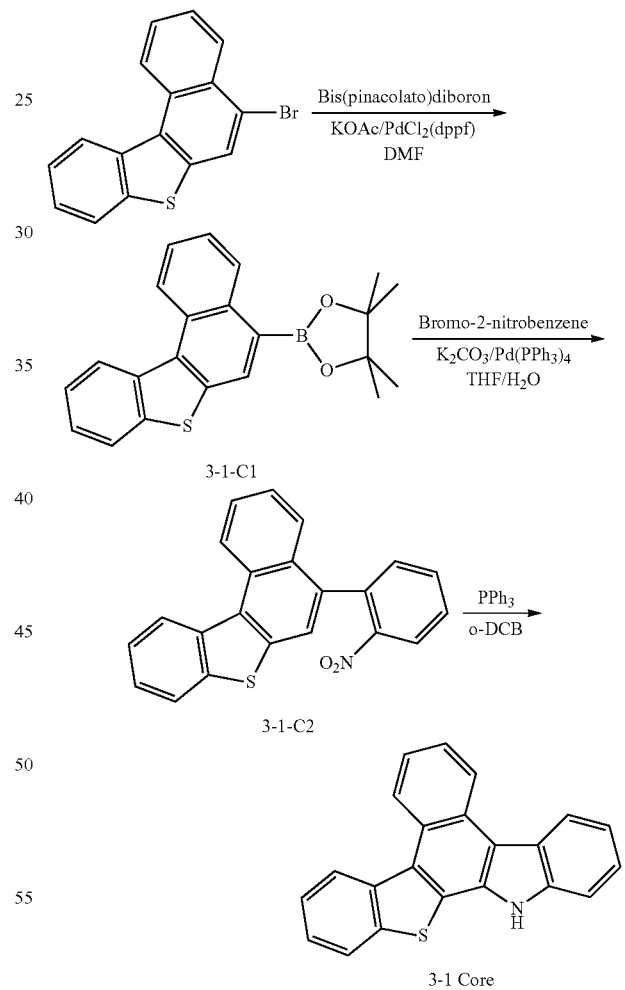

3-1 Core

Synthesis Example of 3-1-C1

5-bromobenzo[b]naphtha[1,2-d]thiophene (50 g, 0.16 mol), bis(pinacolato)diboron (48.65 g, 0.19 mol), KOAc (47 g, 0.48 mol), $PdCl_2$(dppf) (5.21 g, 4 mol %) were dissolved in DMF solvent in a round bottom flask, and then refluxing at 120° C. for 12 hours was followed. When the reaction was completed, the reaction product is cooled to room temperature, was extracted with CH$_2$Cl$_2$ and was washed with water. Then, the organic layer was dried with MgSO$_4$ and concentrated, and recrystallization of the concentrate was carried out using CH$_2$Cl$_2$ and a methanol solvent to obtain the desired 3-1-C1 (46 g, 80%).

Synthesis Example of 3-1-C2

3-1-C1 (40 g, 0.11 mol), bromo-2-nitrobenzene (26.91 g, 0.13 mol), K$_2$CO$_3$ (46.03 g, 0.33 mol), Pd(PPh$_3$)$_4$ (5.13 g, 4 mol %) were dissolved in anhydrous THF and a small amount of water, and then, refluxing was followed at 80° C. for 12 hours. When the reaction was completed, the reaction product is cooled to room temperature, was extracted with CH$_2$Cl$_2$ and was washed with water. Then, the organic layer was dried with MgSO$_4$ and concentrated, and recrystallization of the concentrate was carried out using CH$_2$Cl$_2$ and a methanol solvent to obtain the desired 3-1-C2 (27.62 g, 70%).

Synthesis Example of 3-1 Core 3-1-C2 (20 g, 0.05 mol) and triphenylphosphine (44.28 g, 0.17 mol) were dissolved in o-dichlorobenzene and refluxed for 24 hours. When the reaction was completed, the solvent was removed by vacuum distillation, and the concentrated product was passed through silica gel column and recrystallized to obtain 3-1 Core (13.65 g, 75%) of the product.

2. Synthesis Example of 3-2 Core

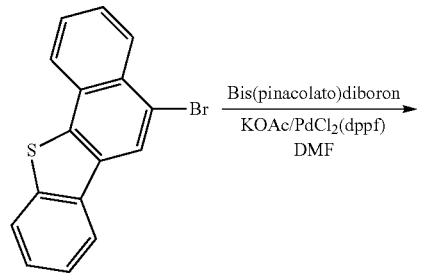

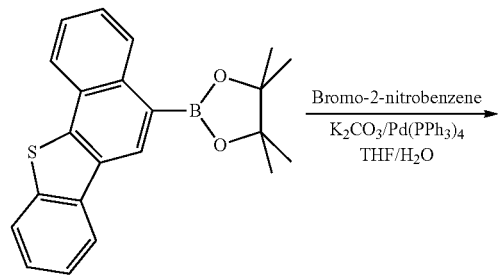

3-2-C1

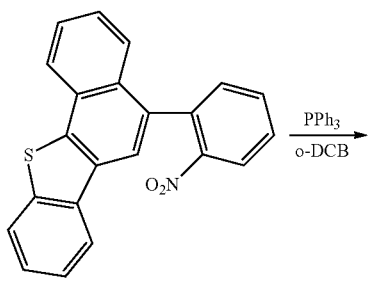

3-2-C2

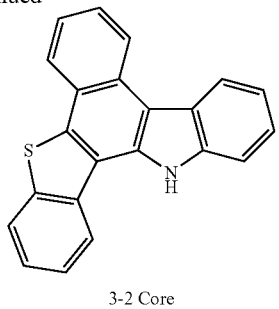

3-2 Core

Synthesis Example of 3-2-C1

5-bromobenzo[b]naphtha[2,1-d]thiophene (50 g, 0.16 mol), bis(pinacolato)diboron (48.65 g, 0.19 mol), KOAc (47 g, 0.48 mol), PdCl$_2$(dppf) (5.21 g, 4 mol %) were dissolved in DMF solvent in a round bottom flask, and then refluxing at 120° C. for 12 hours was followed. When the reaction was completed, the reaction product is cooled to room temperature, was extracted with CH$_2$Cl$_2$ and was washed with water. Then, the organic layer was dried with MgSO$_4$ and concentrated, and recrystallization of the concentrate was carried out using CH$_2$Cl$_2$ and a methanol solvent to obtain the desired -2-C1 (49.5 g, 86%).

Synthesis Example of 3-2-C2

3-2-C1 (40 g, 0.11 mol), bromo-2-nitrobenzene (26.91 g, 0.13 mol), K$_2$CO$_3$ (46.03 g, 0.33 mol), Pd(PPh$_3$)$_4$ (5.13 g, 4 mol %) were dissolved in anhydrous THF and a small amount of water, and then, refluxing was followed at 80° C. for 12 hours. When the reaction was completed, the reaction product is cooled to room temperature, was extracted with CH$_2$Cl$_2$ and was washed with water. Then, the organic layer was dried with MgSO$_4$ and concentrated, and the concentrate was separated using a silica gel column to obtain the desired 3-2-C2 (30 g, 76%).

Synthesis Example of 3-2 Core 3-1-C2 (20 g, 0.05 mol) and triphenylphosphine (44.28 g, 0.17 mol) were dissolved in o-dichlorobenzene and refluxed for 24 hours. When the reaction was completed, the solvent was removed by vacuum distillation, and the concentrated product was passed through silica gel column and recrystallized to obtain 3-2 Core (12.43 g, 68%) of the product.

II. Synthesis of Sub 4

1. Synthesis Example of Sub 4-1-O (1) Synthesis Example of Sub 4-1-O-(1)

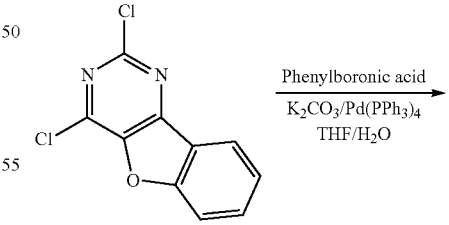

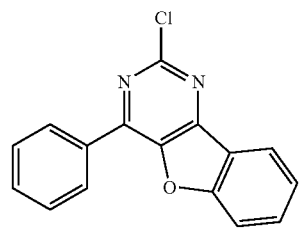

2,4-Dichlorobenzofuro[3,2-d]pyrimidine (10 g, 0.04 mol), phenylboronic acid (5.1 g, 0.04 mol), K$_2$CO$_3$ (17.34 g, 0.12 mol), Pd(PPh$_3$)$_4$ (1.93 g, 4 mol %) were dissolved in anhydrous THF and a small amount of water, and then, refluxing was followed at 80° C. for 12 hours. When the reaction was completed, the reaction product is cooled to room temperature, was extracted with CH$_2$Cl$_2$ and was washed with water. Then, the organic layer was dried with MgSO$_4$ and concentrated, and the concentrate was passed through silica gel column and recrystallized to obtain Sub 4-1-O-(1) (9.39 g, 80%) of the product.

(2) Synthesis Example of Sub 4-1-O-(2)

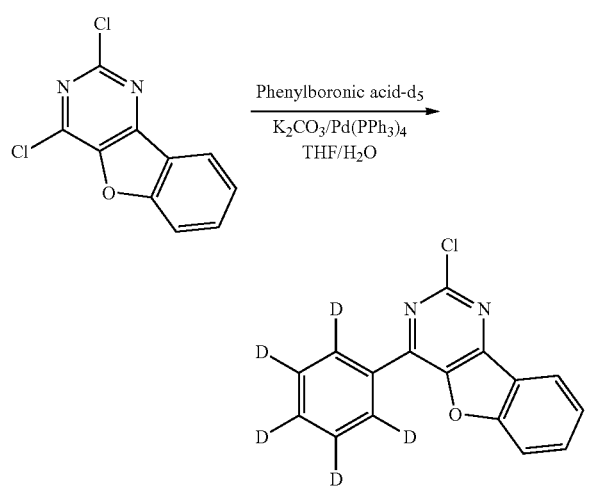

Sub 4-1-O-(2) (9.80 g, 82%) was obtained by using 2,4-Dichlorobenzofuro[3,2-]pyrimidine (10 g, 0.04 mol), phenylboronic acid-d$_5$ (5.31 g, 0.04 mol), K$_2$CO$_3$ (17.34 g, 0.12 mol), Pd(PPh$_3$)$_4$ (1.93 g, 4 mol %), anhydrous THF and water in the same manner as described above for the synthesis example of Sub 4-1-O-(1).

(3) Synthesis Example of Sub 4-1-O-(3)

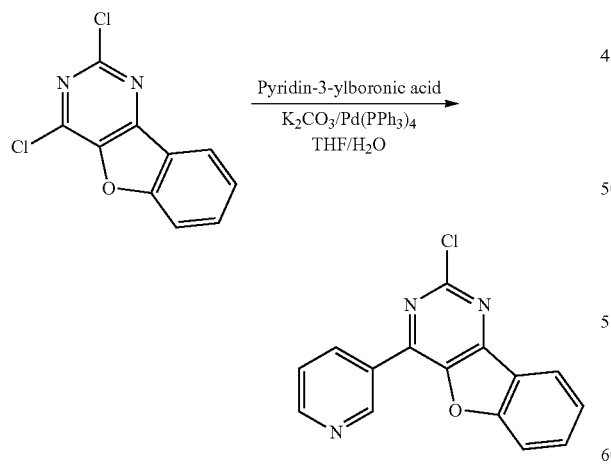

Sub 4-1-O-(3) (11.78 g, 73%) was obtained by using 2,4-Dichlorobenzofuro[3,2-d]pyrimidine (10 g, 0.04 mol), pyridine-3-ylboronic acid (5.14 g, 0.04 mol), K$_2$CO$_3$ (17.34 g, 0.12 mol), Pd(PPh$_3$)$_4$ (1.93 g, 4 mol %), anhydrous THF and water in the same manner as described above for the synthesis example of Sub 4-1-O-(1).

(4) Synthesis Example of Sub 4-1-O-(4)

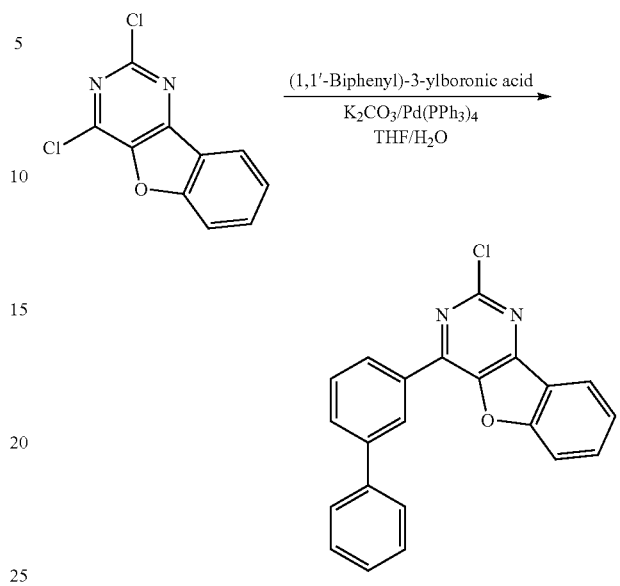

Sub 4-1-O-(4) (11.19 g, 75%) was obtained by using 2,4-Dichlorobenzofuro[3,2-d]pyrimidine (10 g, 0.04 mol), (1,1'-biphenyl)-3-ylboronic acid (8.28 g, 0.04 mol), K$_2$CO$_3$ (17.34 g, 0.12 mol), Pd(PPh$_3$)$_4$ (1.93 g, 4 mol %), anhydrous THF and water in the same manner as described above for the synthesis example of Sub 4-1-O-(1).

(5) Synthesis Example of Sub 4-1-O-(5)

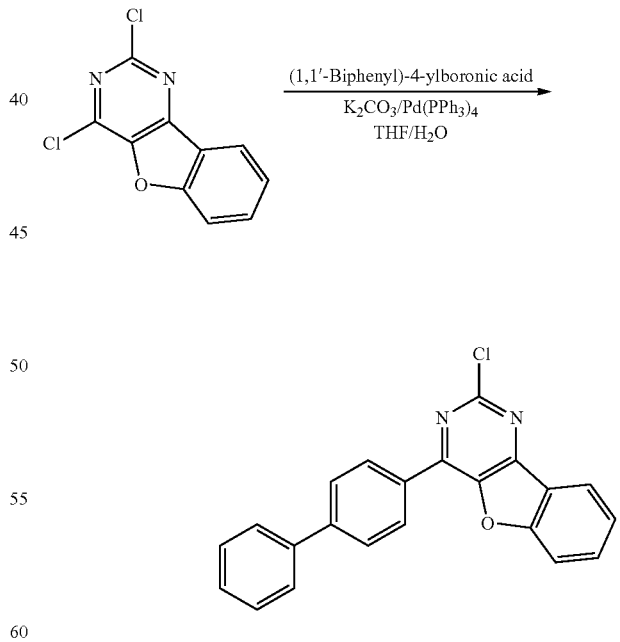

Sub 4-1-O-(5) (11.93 g, 80%) was obtained by using 2,4-Dichlorobenzofuro[3,2-d]pyrimidine (10 g, 0.04 mol), (1,1'-biphenyl)-4-ylboronic acid (8.28 g, 0.04 mol), K$_2$CO$_3$ (17.34 g, 0.12 mol), Pd(PPh$_3$)$_4$ (1.93 g, 4 mol %), anhydrous THF and water in the same manner as described above for the synthesis example of Sub 4-1-O-(1).

2. Synthesis Example of Sub 4-1-S (1) Synthesis Example of Sub 4-1-S-(6)

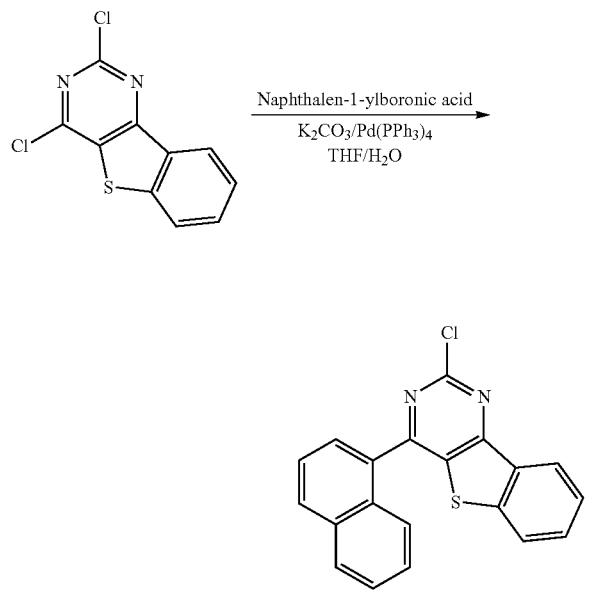

Sub 4-1-S-(6) (11.55 g, 85%) was obtained by using 2,4-Dichlorobenzo[4,5]thieno[3,2-d]pyrimidine (10 g, 0.04 mol), naphthalene-1-ylboronic acid (6.74 g, 0.04 mol), K$_2$CO$_3$ (16.25 g, 0.12 mol), Pd(PPh$_3$)$_4$ (1.81 g, 4 mol %), anhydrous THF and water in the same manner as described above for the synthesis example of Sub 4-1-O-(1).

(2) Synthesis Example of Sub 4-1-S-(7)

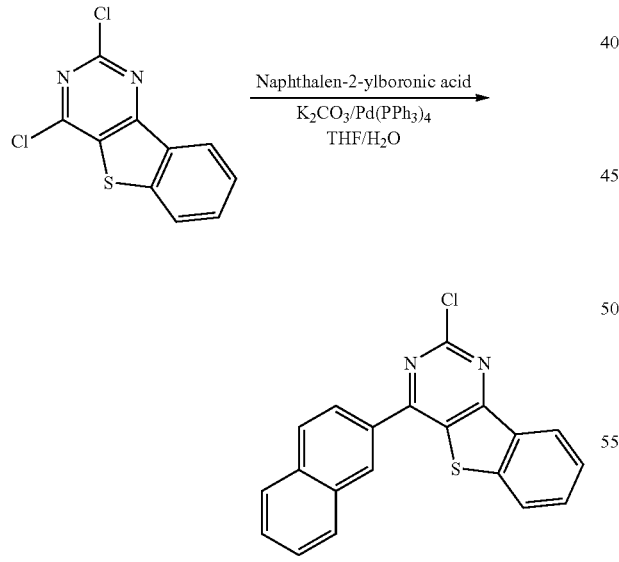

Sub 4-1-S-(7) (11.23 g, 83%) was obtained by using 2,4-Dichlorobenzo[4,5]thieno[3,2-d]pyrimidine (10 g, 0.04 mol), naphthalene-2-ylboronic acid (6.74 g, 0.04 mol), K$_2$CO$_3$ (16.25 g, 0.12 mol), Pd(PPh$_3$)$_4$ (1.81 g, 4 mol %), anhydrous THF and water in the same manner as described above for the synthesis example of Sub 4-1-O-(1).

(3) Synthesis Example of Sub 4-1-S-(8)

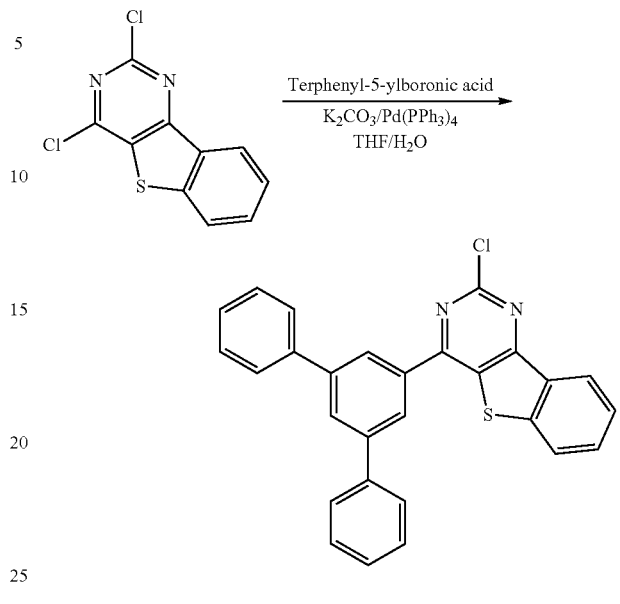

Sub 4-1-S-(8) (12.14 g, 69%) was obtained by using 2,4-Dichlorobenzo[4,5]thieno[3,2-d]pyrimidine (10 g, 0.04 mol), terphenyl-5-ylboronic acid (10.74 g, 0.04 mol), K$_2$CO$_3$ (16.25 g, 0.12 mol), Pd(PPh$_3$)$_4$ (1.81 g, 4 mol %), anhydrous THF and water in the same manner as described above for the synthesis example of Sub 4-1-O-(1).

(4) Synthesis Example of Sub 4-1-S-(9)

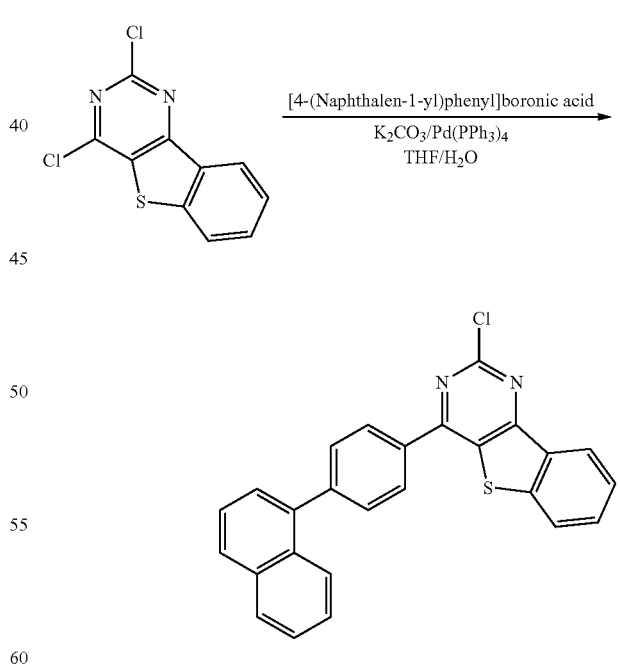

Sub 4-1-S-(9) (12.76 g, 77%) was obtained by using 2,4-Dichlorobenzo[4,5]thieno[3,2-d]pyrimidine (10 g, 0.04 mol), [4-(naphthalene-1-yl)phenyl]-boronic acid (9.72 g, 0.04 mol), K$_2$CO$_3$ (16.25 g, 0.12 mol), Pd(PPh$_3$)$_4$ (1.81 g, 4 mol %), anhydrous THF and water in the same manner as described above for the synthesis example of Sub 4-1-O-(1).

(5) Synthesis Example of Sub 4-1-S-(10)

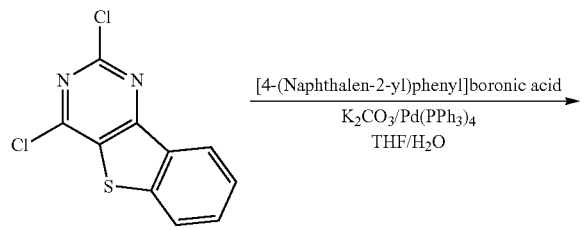

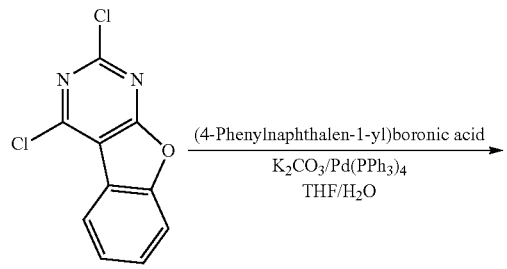

Sub 4-1-S-(10) (12.93 g, 78%) was obtained by using 2,4-Dichlorobenzo[4,5]thieno[3,2-d]pyrimidine (10 g, 0.04 mol), [4-(naphthalene-2-yl)phenyl]-boronic acid (9.72 g, 0.04 mol), K$_2$CO$_3$ (16.25 g, 0.12 mol), Pd(PPh$_3$)$_4$ (1.81 g, 4 mol %), anhydrous THF and water in the same manner as described above for the synthesis example of Sub 4-1-O-(1).

3. Synthesis Example of Sub 4-2-O (1) Synthesis Example of Sub 4-2-O-(11)

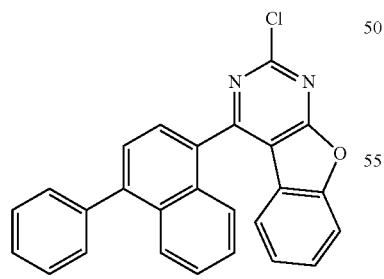

Sub 4-2-O-(11) (10.89 g, 64%) was obtained by using 2,4-Dichlorobenzofuro[2,3-d]pyrimidine (10 g, 0.04 mol), (4-phenylnaphthalen-1-yl)boronic acid (10.37 g, 0.04 mol), K$_2$CO$_3$ (17.34 g, 0.12 mol), Pd(PPh$_3$)$_4$ (1.93 g, 4 mol %), anhydrous THF and water in the same manner as described above for the synthesis example of Sub 4-1-O-(1).

(2) Synthesis Example of Sub 4-2-O-(12)

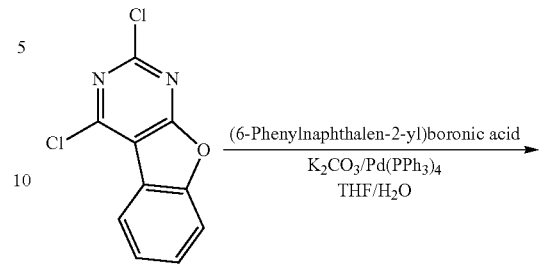

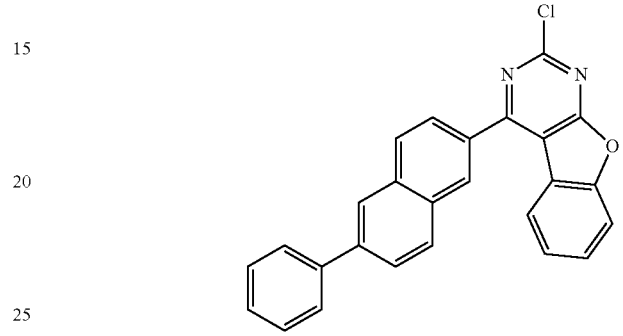

Sub 4-2-O-(12) (11.23 g, 66%) was obtained by using 2,4-Dichlorobenzofuro[2,3-d]pyrimidine (10 g, 0.04 mol), (6-phenylnaphthalen-2-yl)boronic acid (10.37 g, 0.04 mol), K$_2$CO$_3$ (17.34 g, 0.12 mol), Pd(PPh$_3$)$_4$ (1.93 g, 4 mol %), anhydrous THF and water in the same manner as described above for the synthesis example of Sub 4-1-O-(1).

(3) Synthesis Example of Sub 4-2-O-(13)

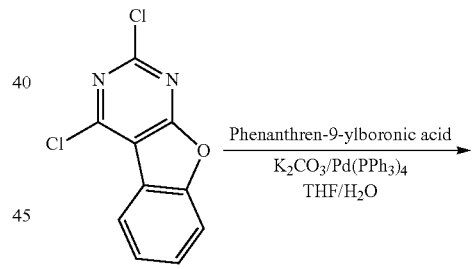

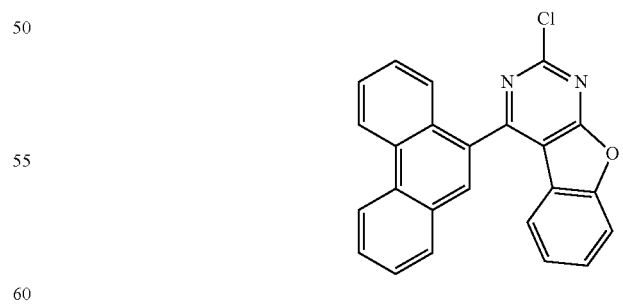

Sub 4-2-O-(13) (12.9 g, 81%) was obtained by using 2,4-Dichlorobenzofuro[2,3-d]pyrimidine (10 g, 0.04 mol), phenanthren-9-ylboronic acid (9.28 g, 0.04 mol), K$_2$CO$_3$ (17.34 g, 0.12 mol), Pd(PPh$_3$)$_4$ (1.93 g, 4 mol %), anhydrous THF and water in the same manner as described above for the synthesis example of Sub 4-1-O-(1).

(4) Synthesis Example of Sub 4-2-O-(14)

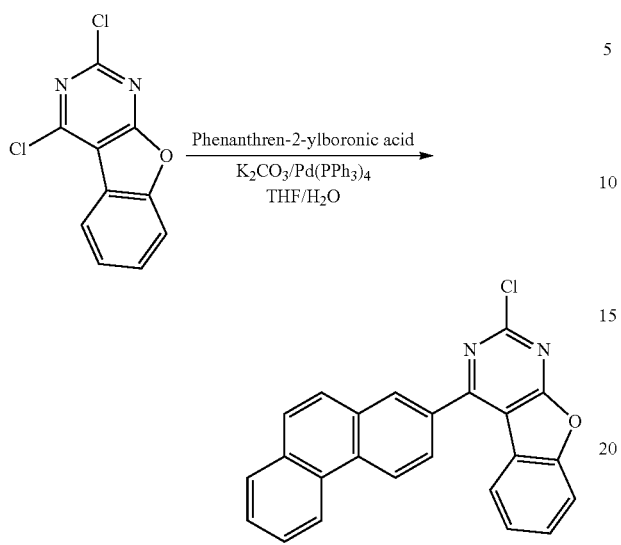

Sub 4-2-O-(14) (12.74 g, 80%) was obtained by using 2,4-Dichlorobenzofuro[2,3-d]pyrimidine (10 g, 0.04 mol), phenanthren-2-ylboronic acid (9.28 g, 0.04 mol), $K_2CO_3$ (17.34 g, 0.12 mol), $Pd(PPh_3)_4$ (1.93 g, 4 mol %), anhydrous THF and water in the same manner as described above for the synthesis example of Sub 4-1-O-(1).

(5) Synthesis Example of Sub 4-2-O-(15)

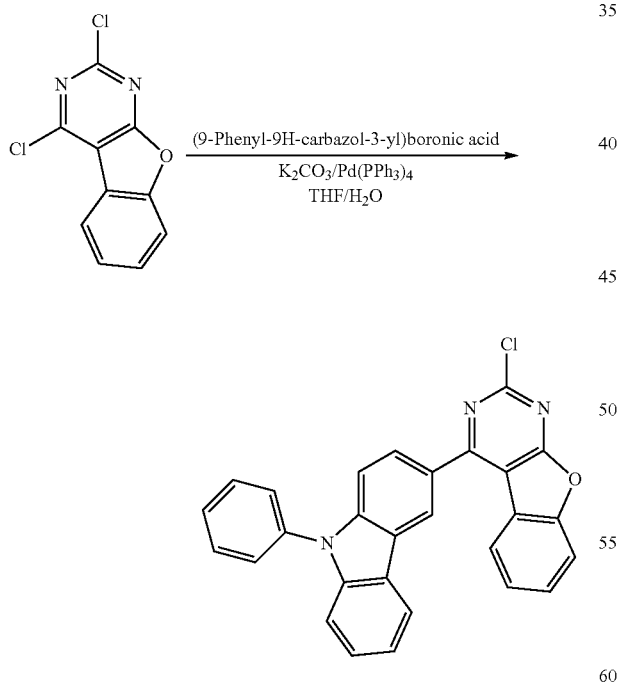

Sub 4-2-O-(15) (11.56 g, 62%) was obtained by using 2,4-Dichlorobenzofuro[2,3-d]pyrimidine (10 g, 0.04 mol), (9-phenyl-9H-carbazol-3-yl)boronic acid (12.01 g, 0.04 mol), $K_2CO_3$ (17.34 g, 0.12 mol), $Pd(PPh_3)_4$ (1.93 g, 4 mol %), anhydrous THF and water in the same manner as described above for the synthesis example of Sub 4-1-O-(1).

4. Synthesis Example of Sub 4-2-S

(1) Synthesis Example of Sub 4-2-S-(16)

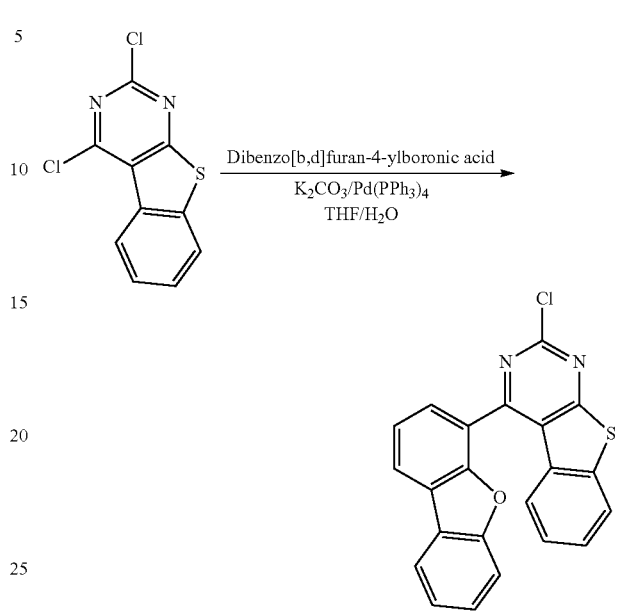

Sub 4-2-S-(16) (8.79 g, 58%) was obtained by using 2,4-Dichlorobenzo[4,5]thieno[2,3-d]pyrimidine (10 g, 0.04 mol), dibenzo[b,d]furan-4-ylboronic acid (8.31 g, 0.04 mol), $K_2CO_3$ (16.25 g, 0.12 mol), $Pd(PPh_3)_4$ (1.81 g, 4 mol %), anhydrous THF and water in the same manner as described above for the synthesis example of Sub 4-1-O-(1).

(2) Synthesis Example of Sub 4-2-S-(17)

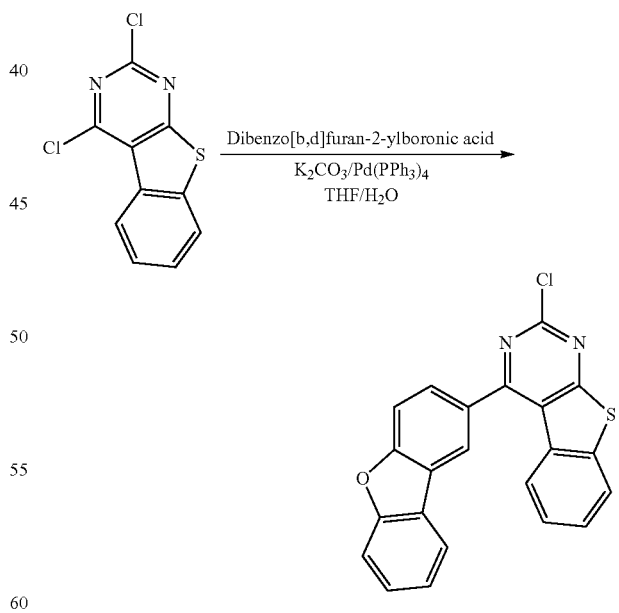

Sub 4-2-S-(17) (9.09 g, 60%) was obtained by using 2,4-Dichlorobenzo[4,5]thieno[2,3-d]pyrimidine (10 g, 0.04 mol), dibenzo[b,d]furan-2-ylboronic acid (8.31 g, 0.04 mol), $K_2CO_3$ (16.25 g, 0.12 mol), $Pd(PPh_3)_4$ (1.81 g, 4 mol %), anhydrous THF and water in the same manner as described above for the synthesis example of Sub 4-1-O-(1).

(3) Synthesis Example of Sub 4-2-S-(18)

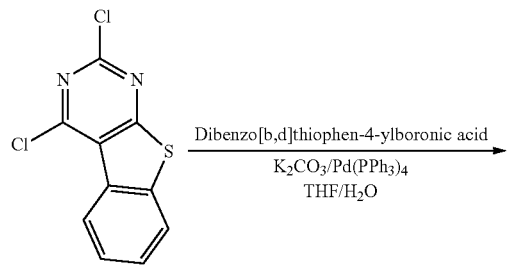

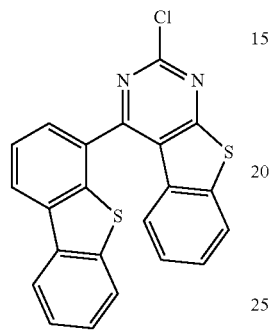

Sub 4-2-S-(18) (10.73 g, 68%) was obtained by using 2,4-Dichlorobenzo[4,5]thieno[2,3-d]pyrimidine (10 g, 0.04 mol), dibenzo[b,d]thiophen-4-ylboronic acid (8.93 g, 0.04 mol), K$_2$CO$_3$ (16.25 g, 0.12 mol), Pd(PPh$_3$)$_4$ (1.81 g, 4 mol %), anhydrous THF and water in the same manner as described above for the synthesis example of Sub 4-1-O-(1).

(4) Synthesis Example of Sub 4-2-S-(19)

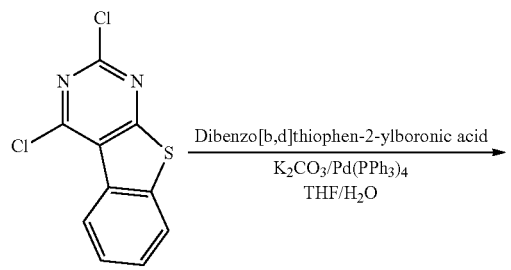

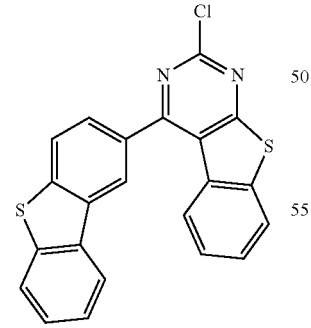

Sub 4-2-S-(19) (11.21 g, 71%) was obtained by using 2,4-Dichlorobenzo[4,5]thieno[2,3-d]pyrimidine (10 g, 0.04 mol), dibenzo[b,d]thiophen-2-ylboronic acid (8.93 g, 0.04 mol), K$_2$CO$_3$ (16.25 g, 0.12 mol), Pd(PPh$_3$)$_4$ (1.81 g, 4 mol %), anhydrous THF and water in the same manner as described above for the synthesis example of Sub 4-1-O-(1).

(5) Synthesis Example of Sub 4-2-S-(20)

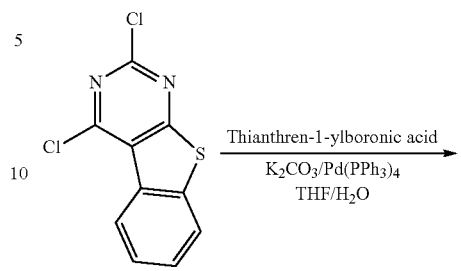

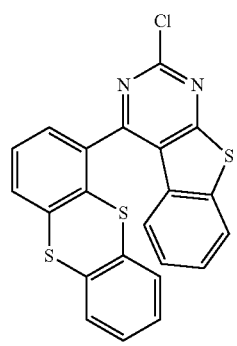

Sub 4-2-S-(20) (13.98 g, 82%) was obtained by using 2,4-Dichlorobenzo[4,5]thieno[2,3-d]pyrimidine (10 g, 0.04 mol), thianthren-1-ylboronic acid (10.19 g, 0.04 mol), K$_2$CO$_3$ (16.25 g, 0.12 mol), Pd(PPh$_3$)$_4$ (1.81 g, 4 mol %), anhydrous THF and water in the same manner as described above for the synthesis example of Sub 4-1-O-(1).

The compound belonging to Sub 4 may be, but not limited to, the following compounds, and Table 4 shows FD-MS (Field Desorption-Mass Spectrometry) values of the following compounds.

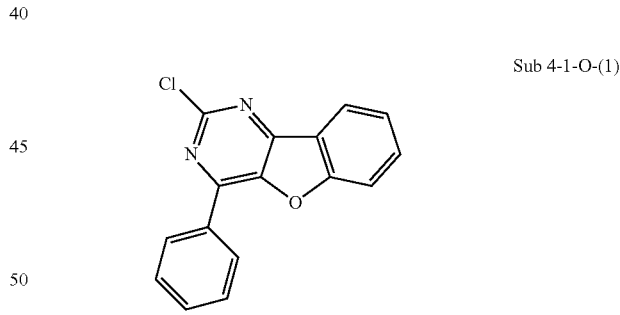

Sub 4-1-O-(1)

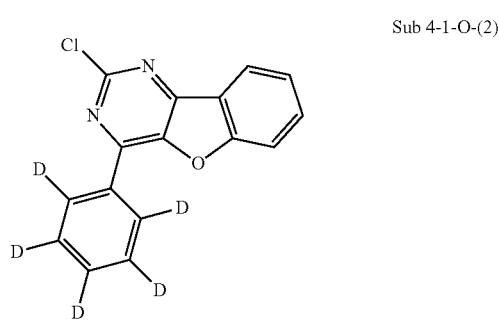

Sub 4-1-O-(2)

Sub 4-1-O-(3)
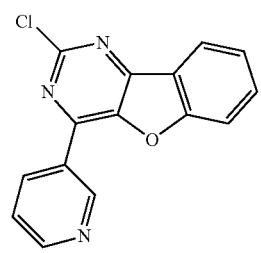
Sub 4-1-O-(4)
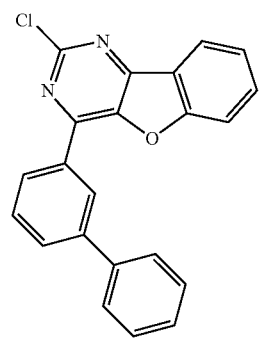
Sub 4-1-O-(5)
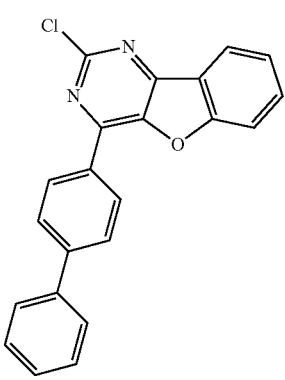
Sub 4-1-O-(6)
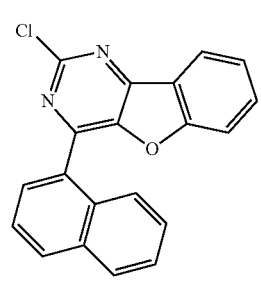
Sub 4-1-O-(7)
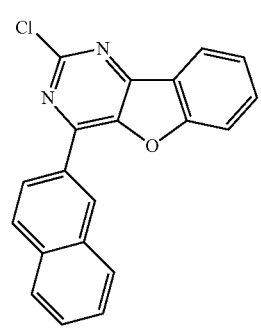
Sub 4-1-O-(8)
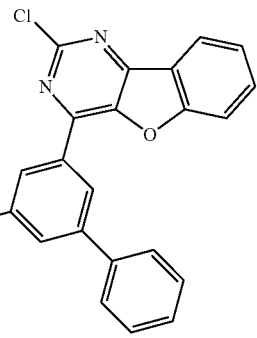
Sub 4-1-O-(9)
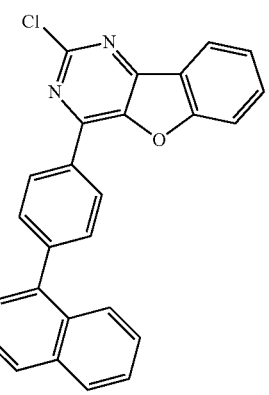
Sub 4-1-O-(10)
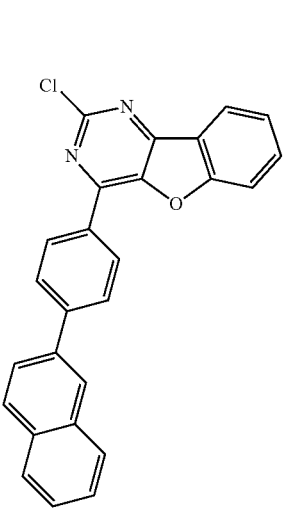
Sub 4-1-O-(11)
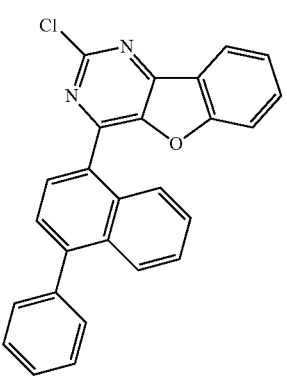

-continued
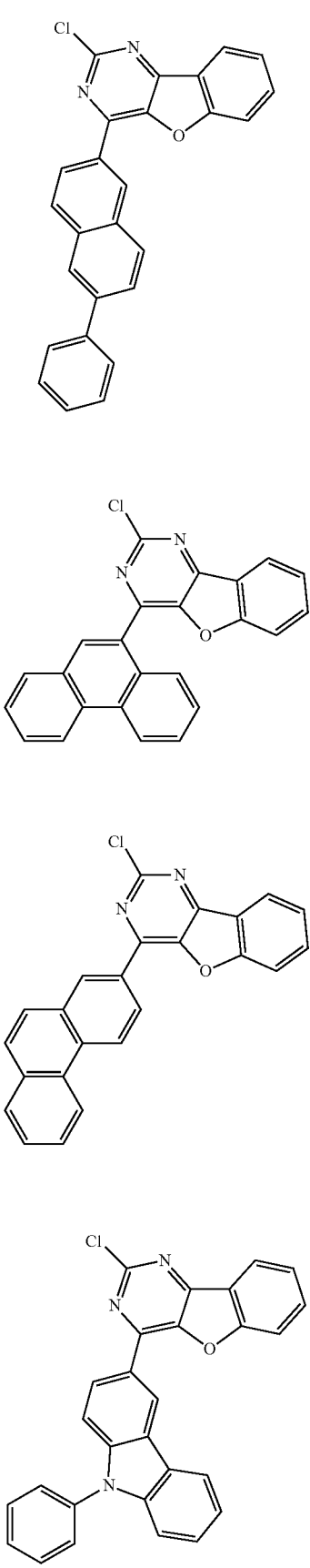
Sub 4-1-O-(12)
Sub 4-1-O-(13)
Sub 4-1-O-(14)
Sub 4-1-O-(15)
-continued
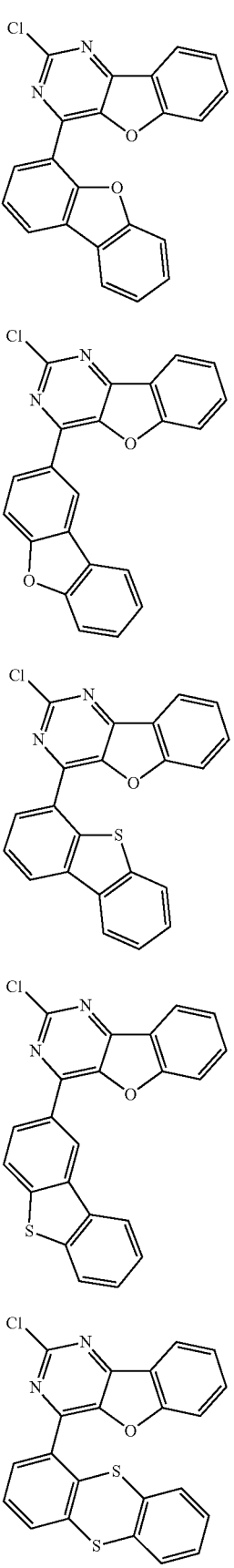
Sub 4-1-O-(16)
Sub 4-1-O-(17)
Sub 4-1-S-(18)
Sub 4-1-O-(19)
Sub 4-1-O-(20)

-continued
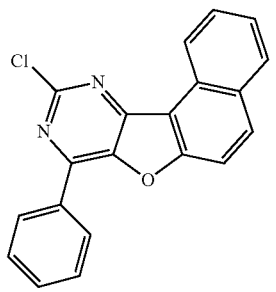
Sub 4-1-O-(21)
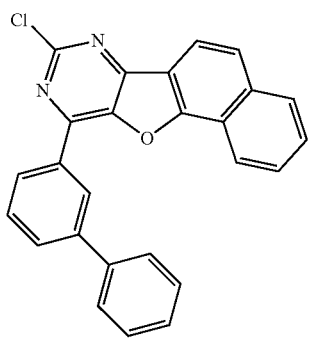
Sub 4-1-O-(22)
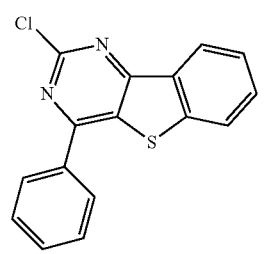
Sub 4-1-S-(1)
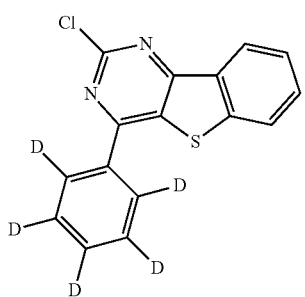
Sub 4-1-S-(2)
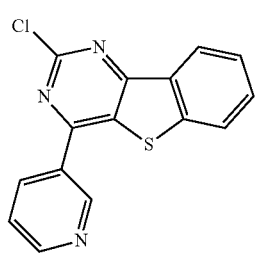
Sub 4-1-S-(3)
-continued
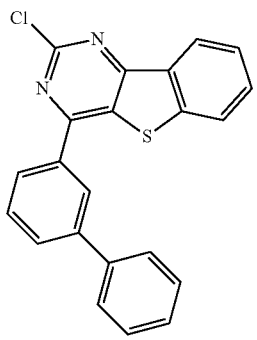
Sub 4-1-S-(4)
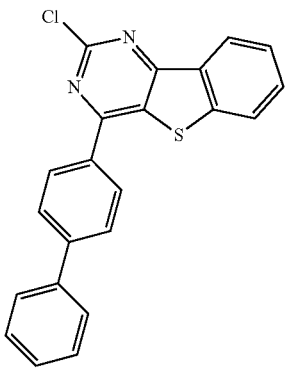
Sub 4-1-S-(5)
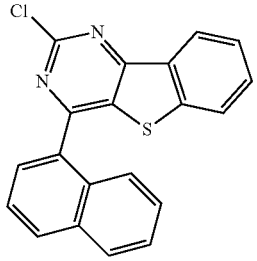
Sub 4-1-S-(6)
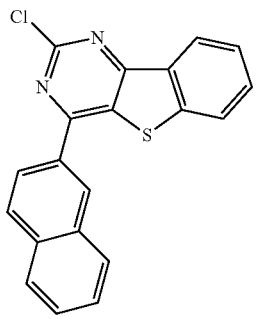
Sub 4-1-S-(7)
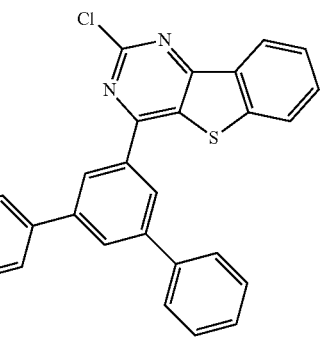
Sub 4-1-S-(8)

Sub 4-1-S-(9)
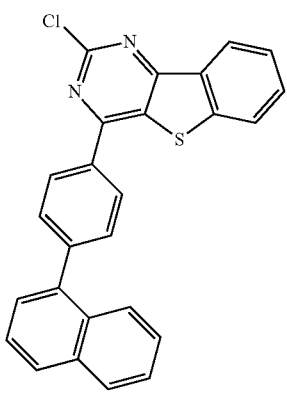
Sub 4-1-S-(10)
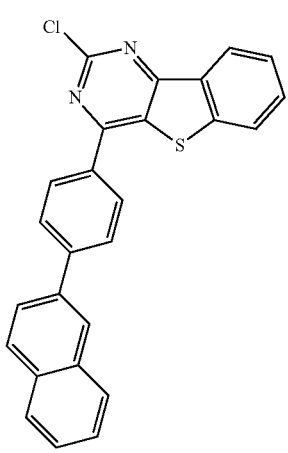
Sub 4-1-S-(11)
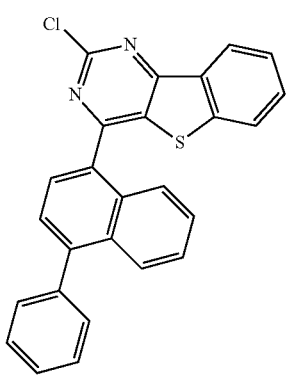
Sub 4-1-S-(12)
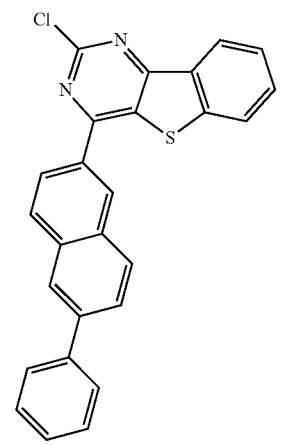
Sub 4-1-S-(13)
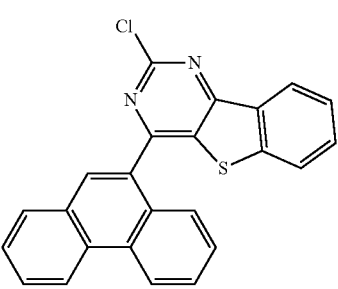
Sub 4-1-S-(14)
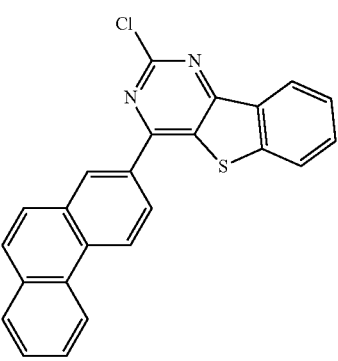
Sub 4-1-S-(15)
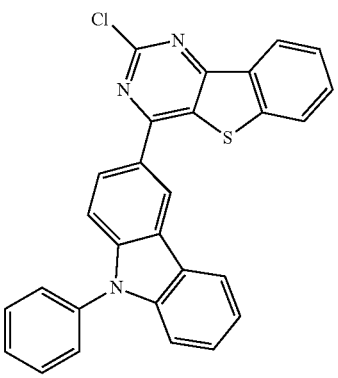
Sub 4-1-S-(16)
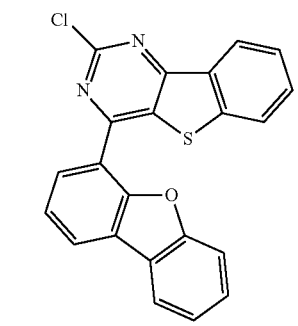

Sub 4-1-S-(17)
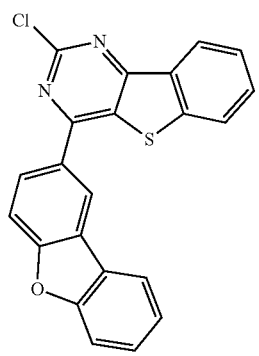
Sub 4-1-O-(18)
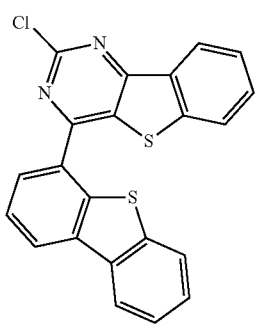
Sub 4-1-S-(19)
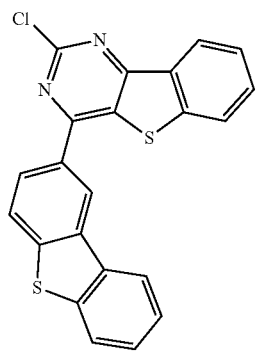
Sub 4-1-S-(20)
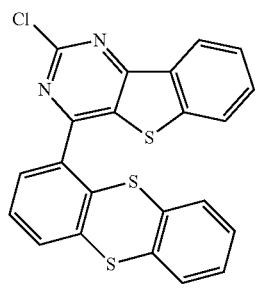
Sub 4-1-S-(21)
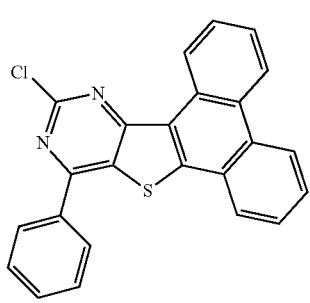
Sub 4-1-S-(22)
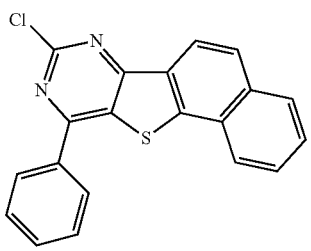
Sub 4-1-S-(23)
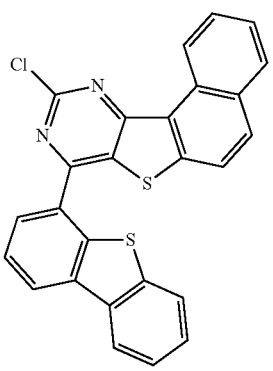
Sub 4-1-S-(24)
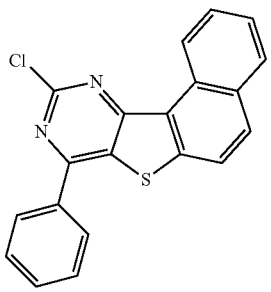
Sub 4-1-S-(25)
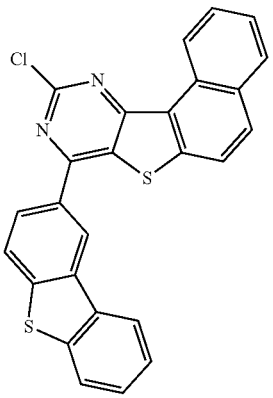
Sub 4-2-O-(1)
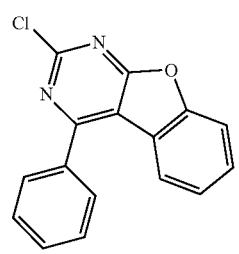

-continued
Sub 4-2-O-(2)
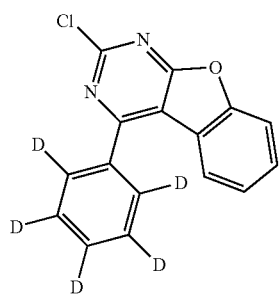
Sub 4-2-O-(3)
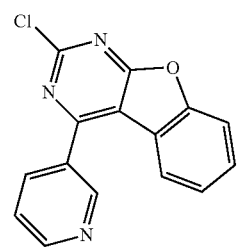
Sub 4-2-O-(4)
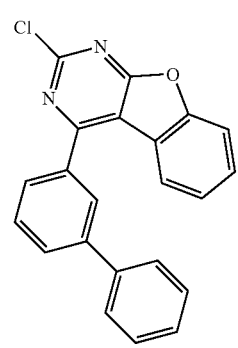
Sub 4-2-O-(5)
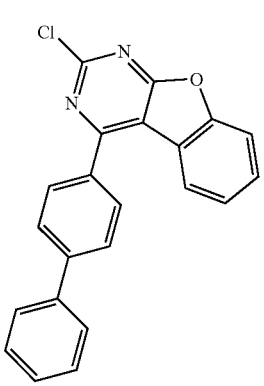
Sub 4-2-O-(6)
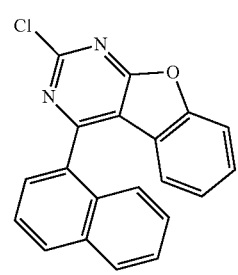
-continued
Sub 4-2-O-(7)
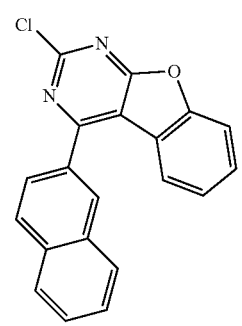
Sub 4-2-O-(8)
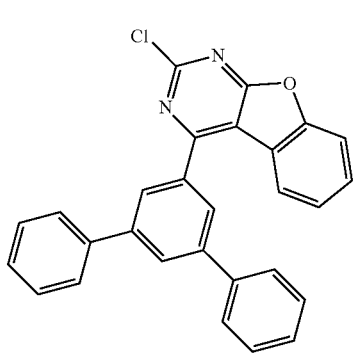
Sub 4-2-O-(9)
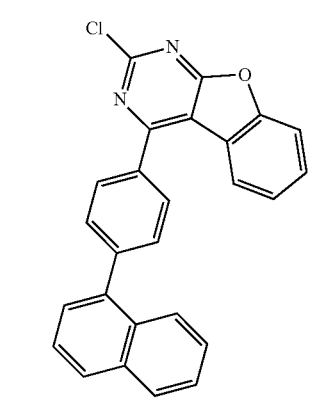
Sub 4-2-O-(10)
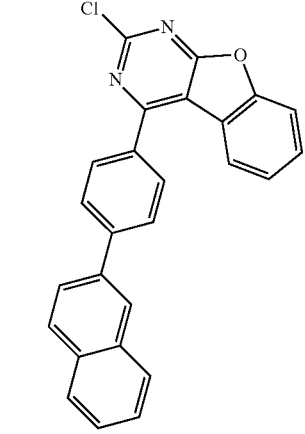

Sub 4-2-O-(11)
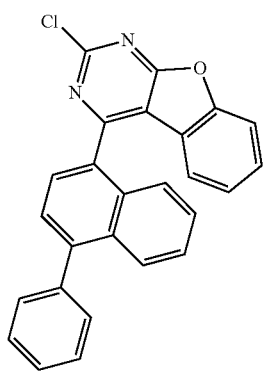
Sub 4-2-O-(12)
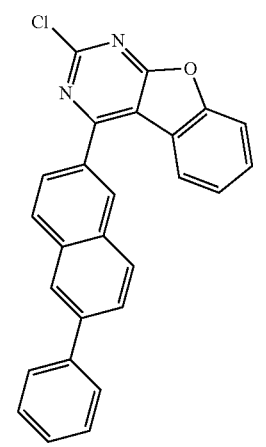
Sub 4-2-O-(13)
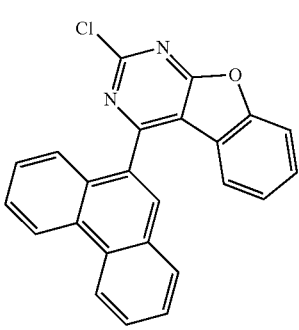
Sub 4-2-O-(14)

Sub 4-2-O-(15)
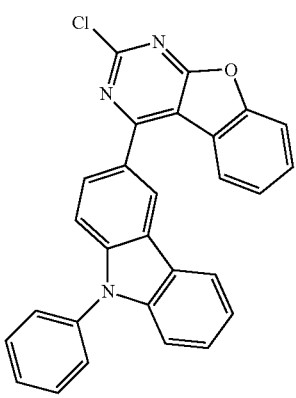
Sub 4-2-O-(16)
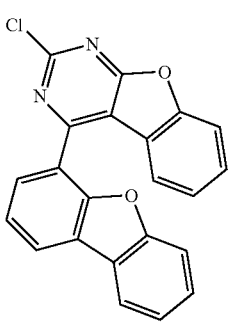
Sub 4-2-O-(17)
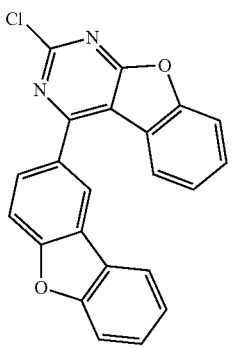
Sub 4-2-O-(18)

-continued
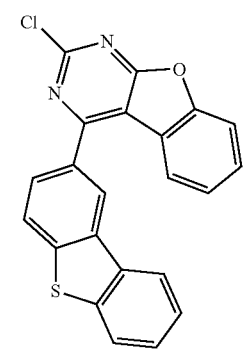 Sub 4-2-O-(19)
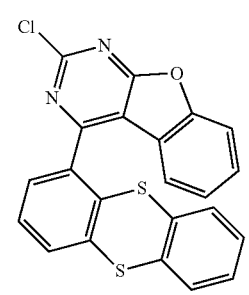 Sub 4-2-O-(20)
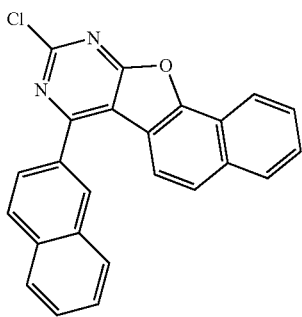 Sub 4-2-O-(21)
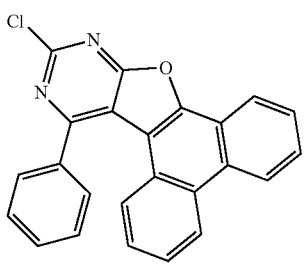 Sub 4-2-O-(22)
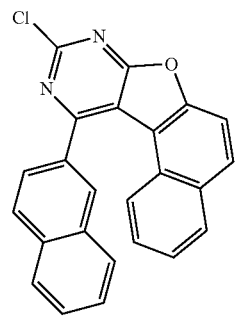 Sub 4-2-O-(23)
-continued
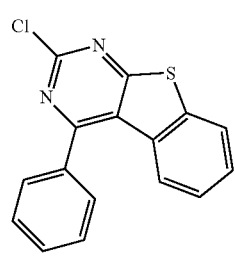 Sub 4-2-S-(1)
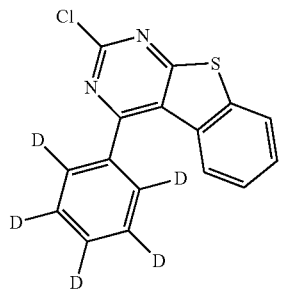 Sub 4-2-S-(2)
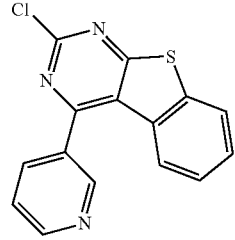 Sub 4-2-S-(3)
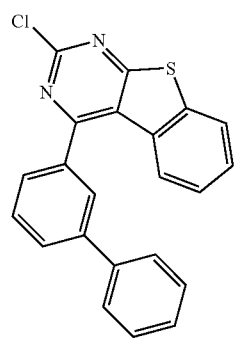 Sub 4-2-S-(4)
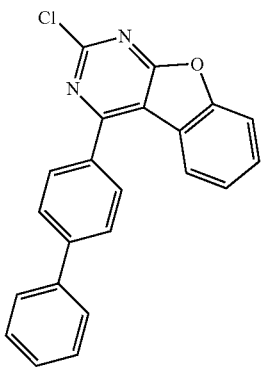 Sub 4-2-S-(5)

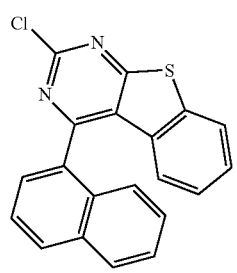 Sub 4-2-S-(6)
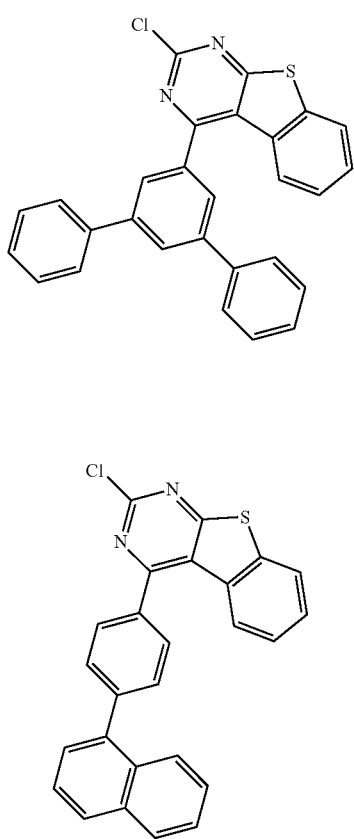
Sub 4-2-S-(7)
Sub 4-2-S-(8)
Sub 4-2-S-(9)
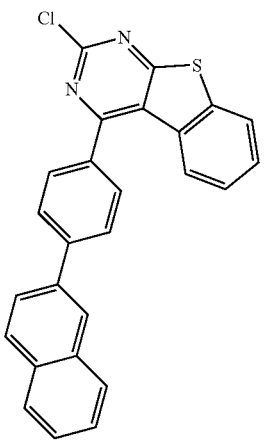 Sub 4-2-S-(10)
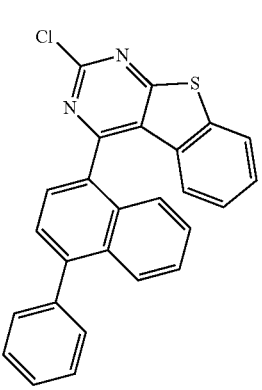 Sub 4-2-S-(11)
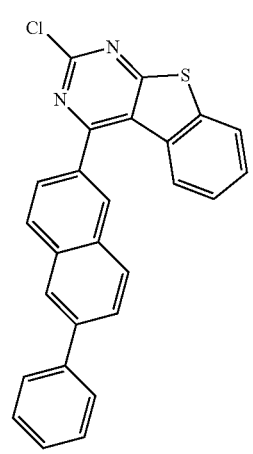 Sub 4-2-S-(12)
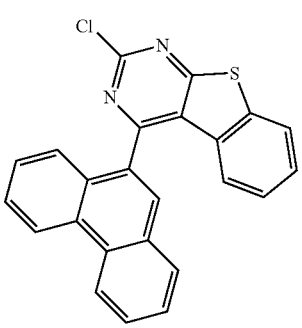 Sub 4-2-S-(13)

Sub 4-2-S-(14)

Sub 4-2-S-(15)

Sub 4-2-S-(16)

Sub 4-2-S-(17)

Sub 4-2-S-(18)

Sub 4-2-S-(19)

Sub 4-2-S-(20)

Sub 4-2-S-(21)

Sub 4-2-S-(22)

-continued

Sub 4-2-S-(23)

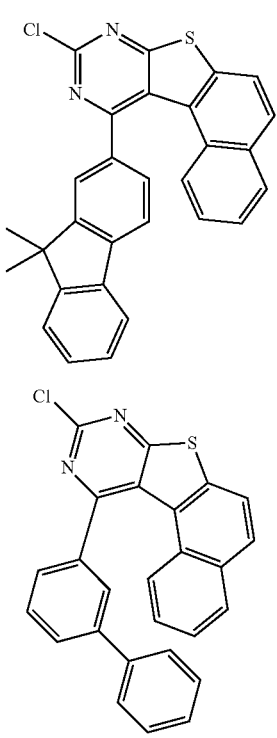

Sub 4-2-S-(24)

-continued

Sub 4-2-S-(25)

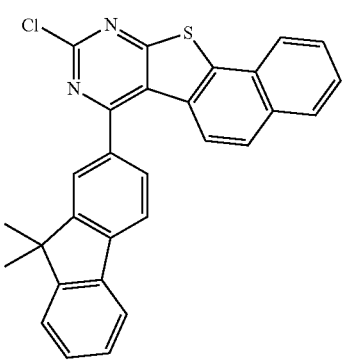

TABLE 4

| compound | FD-MS | compound | FD-MS |
|---|---|---|---|
| Sub 4-1-O-(1) | m/z = 280.04($C_{16}H_9ClN_2O$ = 280.71) | Sub 4-1-O-(2) | m/z = 285.07($C_{16}H_4D_5ClN_2O$ = 285.74) |
| Sub 4-1-O-(3) | m/z = 281.04($C_{15}H_8ClN_3O$ = 281.70) | Sub 4-1-O-(4) | m/z = 356.07($C_{22}H_{13}ClN_2O$ = 356.80) |
| Sub 4-1-O-(5) | m/z = 356.07($C_{22}H_{13}ClN_2O$ = 356.80) | Sub 4-1-O-(6) | m/z = 330.06($C_{20}H_{11}ClN_2O$ = 330.77) |
| Sub 4-1-O-(7) | m/z = 330.06($C_{20}H_{11}ClN_2O$ = 330.77) | Sub 4-1-O-(8) | m/z = 432.10($C_{28}H_{17}ClN_2O$ = 432.90) |
| Sub 4-1-O-(9) | m/z = 406.09($C_{26}H_{15}ClN_2O$ = 406.86) | Sub 4-1-O-(10) | m/z = 406.09($C_{26}H_{15}ClN_2O$ = 406.86) |
| Sub 4-1-O-(11) | m/z = 406.09($C_{26}H_{15}ClN_2O$ = 406.86) | Sub 4-1-O-(12) | m/z = 406.09($C_{26}H_{15}ClN_2O$ = 406.86) |
| Sub 4-1-O-(13) | m/z = 380.07($C_{24}H_{13}ClN_2O$ = 380.83) | Sub 4-1-O-(14) | m/z = 380.07($C_{24}H_{13}ClN_2O$ = 380.83) |
| Sub 4-1-O-(15) | m/z = 445.10($C_{28}H_{16}ClN_3O$ = 445.90) | Sub 4-1-O-(16) | m/z = 370.05($C_{22}H_{11}ClN_2O_2$ = 370.79) |
| Sub 4-1-O-(17) | m/z = 370.05($C_{22}H_{11}ClN_2O_2$ = 370.79) | Sub 4-1-O-(18) | m/z = 386.03($C_{22}H_{11}ClN_2OS$ = 386.85) |
| Sub 4-1-O-(19) | m/z = 386.03($C_{22}H_{11}ClN_2OS$ = 386.85) | Sub 4-1-O-(20) | m/z = 418.00($C_{22}H_{11}ClN_2OS_2$ = 418.92) |
| Sub 4-1-O-(21) | m/z = 330.06($C_{20}H_{11}ClN_2O$ = 330.77) | Sub 4-1-O-(22) | m/z = 406.09($C_{26}H_{15}ClN_2O$ = 406.86) |
| Sub 4-1-S-(1) | m/z = 296.02($C_{16}H_9ClN_2S$ = 296.77) | Sub 4-1-S-(2) | m/z = 301.05($C_{16}H_4D_5ClN_2S$ = 301.80) |
| Sub 4-1-S-(3) | m/z = 297.01($C_{15}H_8ClN_3S$ = 297.76) | Sub 4-1-S-(4) | m/z = 372.05($C_{22}H_{13}ClN_2S$ = 372.87) |
| Sub 4-1-S-(5) | m/z = 372.05($C_{22}H_{13}ClN_2S$ = 372.87) | Sub 4-1-S-(6) | m/z = 346.03($C_{20}H_{11}ClN_2S$ = 346.83) |
| Sub 4-1-S-(7) | m/z = 346.03($C_{20}H_{11}ClN_2S$ = 346.83) | Sub 4-1-S-(8) | m/z = 448.08($C_{28}H_{17}ClN_2S$ = 448.97) |
| Sub 4-1-S-(9) | m/z = 422.06($C_{26}H_{15}ClN_2S$ = 422.93) | Sub 4-1-S-(10) | m/z = 422.06($C_{26}H_{15}ClN_2S$ = 422.93) |
| Sub 4-1-S-(11) | m/z = 346.03($C_{20}H_{11}ClN_2S$ = 346.83) | Sub 4-1-S-(12) | m/z = 346.03($C_{20}H_{11}ClN_2S$ = 346.83) |
| Sub 4-1-S-(13) | m/z = 396.05($C_{24}H_{13}ClN_2S$ = 396.89) | Sub 4-1-S-(14) | m/z = 396.05($C_{24}H_{13}ClN_2S$ = 396.89) |
| Sub 4-1-S-(15) | m/z = 461.08($C_{28}H_{16}ClN_3S$ = 461.96) | Sub 4-1-S-(16) | m/z = 386.03($C_{22}H_{11}ClN_2OS$ = 386.85) |
| Sub 4-1-S-(17) | m/z = 386.03($C_{22}H_{11}ClN_2OS$ = 386.85) | Sub 4-1-S-(18) | m/z = 402.01($C_{22}H_{11}ClN_2S_2$ = 402.92) |
| Sub 4-1-S-(19) | m/z = 402.01($C_{22}H_{11}ClN_2S_2$ = 402.92) | Sub 4-1-S-(20) | m/z = 433.98($C_{22}H_{11}ClN_2S_3$ = 434.98) |
| Sub 4-1-S-(21) | m/z = 396.05($C_{24}H_{13}ClN_2S$ = 396.89) | Sub 4-1-S-(22) | m/z = 346.03($C_{20}H_{11}ClN_2S$ = 346.83) |
| Sub 4-1-S-(23) | m/z = 452.02($C_{26}H_{13}ClN_2S_2$ = 452.98) | Sub 4-1-S-(24) | m/z = 346.03($C_{20}H_{11}ClN_2S$ = 346.83) |
| Sub 4-1-S-(25) | m/z = 452.02($C_{26}H_{13}ClN_2S_2$ = 452.98) | | |
| Sub 4-2-O-(1) | m/z = 280.04($C_{16}H_9ClN_2O$ = 280.71) | Sub 4-2-O-(2) | m/z = 285.07($C_{16}H_4D_5ClN_2O$ = 285.74) |
| Sub 4-2-O-(3) | m/z = 281.04($C_{15}H_8ClN_3O$ = 281.70) | Sub 4-2-O-(4) | m/z = 356.07($C_{22}H_{13}ClN_2O$ = 356.80) |
| Sub 4-2-O-(5) | m/z = 356.07($C_{22}H_{13}ClN_2O$ = 356.80) | Sub 4-2-O-(6) | m/z = 330.06($C_{20}H_{11}ClN_2O$ = 330.77) |
| Sub 4-2-O-(7) | m/z = 330.06($C_{20}H_{11}ClN_2O$ = 330.77) | Sub 4-2-O-(8) | m/z = 432.10($C_{28}H_{17}ClN_2O$ = 432.90) |
| Sub 4-2-O-(9) | m/z = 406.09($C_{26}H_{15}ClN_2O$ = 406.86) | Sub 4-2-O-(10) | m/z = 406.09($C_{26}H_{15}ClN_2O$ = 406.86) |
| Sub 4-2-O-(11) | m/z = 406.09($C_{26}H_{15}ClN_2O$ = 406.86) | Sub 4-2-O-(12) | m/z = 406.09($C_{26}H_{15}ClN_2O$ = 406.86) |
| Sub 4-2-O-(13) | m/z = 380.07($C_{24}H_{13}ClN_2O$ = 380.83) | Sub 4-2-O-(14) | m/z = 380.07($C_{24}H_{13}ClN_2O$ = 380.83) |
| Sub 4-2-O-(15) | m/z = 445.10($C_{28}H_{16}ClN_3O$ = 445.90) | Sub 4-2-O-(16) | m/z = 370.05($C_{22}H_{11}ClN_2O_2$ = 370.79) |
| Sub 4-2-O-(17) | m/z = 370.05($C_{22}H_{11}ClN_2O_2$ = 370.79) | Sub 4-2-O-(18) | m/z = 386.03($C_{22}H_{11}ClN_2OS$ = 386.85) |
| Sub 4-2-O-(19) | m/z = 386.03($C_{22}H_{11}ClN_2OS$ = 386.85) | Sub 4-2-O-(20) | m/z = 418.00($C_{22}H_{11}ClN_2OS_2$ = 418.92) |
| Sub 4-2-O-(21) | m/z = 380.07($C_{24}H_{13}ClN_2O$ = 380.83) | Sub 4-2-O-(22) | m/z = 380.07($C_{24}H_{13}ClN_2O$ = 380.83) |
| Sub 4-2-O-(23) | m/z = 380.07($C_{24}H_{13}ClN_2O$ = 380.83) | | |
| Sub 4-2-S-(1) | m/z = 296.02($C_{16}H_9ClN_2S$ = 296.77) | Sub 4-2-S-(2) | m/z = 301.05($C_{16}H_4D_5ClN_2S$ = 301.80) |
| Sub 4-2-S-(3) | m/z = 297.01($C_{15}H_8ClN_3S$ = 297.76) | Sub 4-2-S-(4) | m/z = 372.05($C_{22}H_{13}ClN_2S$ = 372.87) |
| Sub 4-2-S-(5) | m/z = 372.05($C_{22}H_{13}ClN_2S$ = 372.87) | Sub 4-2-S-(6) | m/z = 346.03($C_{20}H_{11}ClN_2S$ = 346.83) |
| Sub 4-2-S-(7) | m/z = 346.03($C_{20}H_{11}ClN_2S$ = 346.83) | Sub 4-2-S-(8) | m/z = 448.08($C_{28}H_{17}ClN_2S$ = 448.97) |

TABLE 4-continued

| compound | FD-MS | compound | FD-MS |
|---|---|---|---|
| Sub 4-2-S-(9) | m/z = 422.06($C_{26}H_{15}ClN_2S$ = 422.93) | Sub 4-2-S-(10) | m/z = 422.06($C_{26}H_{15}ClN_2S$ = 422.93) |
| Sub 4-2-S-(11) | m/z = 346.03($C_{20}H_{11}ClN_2S$ = 346.83) | Sub 4-2-S-(12) | m/z = 346.03($C_{20}H_{11}ClN_2S$ = 346.83) |
| Sub 4-2-S-(13) | m/z = 396.05($C_{24}H_{13}ClN_2S$ = 396.89) | Sub 4-2-S-(14) | m/z = 396.05($C_{24}H_{13}ClN_2S$ = 396.89) |
| Sub 4-2-S-(15) | m/z = 461.08($C_{28}H_{16}ClN_3S$ = 461.96) | Sub 4-2-S-(16) | m/z = 386.03($C_{22}H_{11}ClN_2OS$ = 386.85) |
| Sub 4-2-S-(17) | m/z = 386.03($C_{22}H_{11}ClN_2OS$ = 386.85) | Sub 4-2-S-(18) | m/z = 402.01($C_{22}H_{11}ClN_2S_2$ = 402.92) |
| Sub 4-2-S-(19) | m/z = 402.01($C_{22}H_{11}ClN_2S_2$ = 402.92) | Sub 4-2-S-(20) | m/z = 433.98($C_{22}H_{11}ClN_2S_3$ = 434.98) |
| Sub 4-2-S-(21) | m/z = 396.05($C_{24}H_{13}ClN_2S$ = 396.89) | Sub 4-2-S-(22) | m/z = 422.06($C_{26}H_{15}ClN_2S$ = 422.93) |
| Sub 4-2-S-(23) | m/z = 462.10($C_{29}H_{19}ClN_2S$ = 462.99) | Sub 4-2-S-(24) | m/z = 422.06($C_{26}H_{15}ClN_2S$ = 422.93) |
| Sub 4-2-S-(25) | m/z = 462.10($C_{29}H_{19}ClN_2S$ = 462.99) | | |

III. Synthesis Example of Final Products

1. Synthesis Example of 1-1-1-O (1) Synthesis Example of 1-1-1-O-(1)

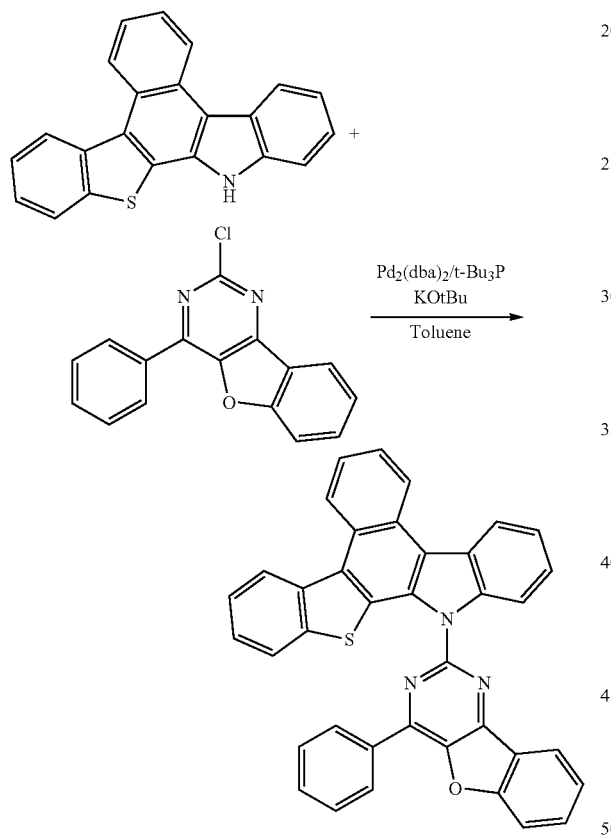

3-1 Core (5 g, 15.46 mmol), Sub 4-1-O-(1) (5.2 g, 18.55 mmol), Pd$_2$(dba)$_3$ (0.56 g, 4 mol %), t-Bu$_3$P (0.25 g, 8 mol %), KOtBu (5.2 g, 46.38 mmol) were dissolved in toluene solvent, and then, refluxing was followed at 100° C. for 12 hours. When the reaction was completed, the reaction product is cooled to room temperature, was extracted with CH$_2$Cl$_2$ and was washed with water. Then, the organic layer was dried with MgSO$_4$ and concentrated, and the concentrate was passed through silica gel column and recrystallized to obtain the desired compound 1-1-1-O-(1) (7.28 g, 83%).

(2) Synthesis Example of 1-1-1-O-(2)

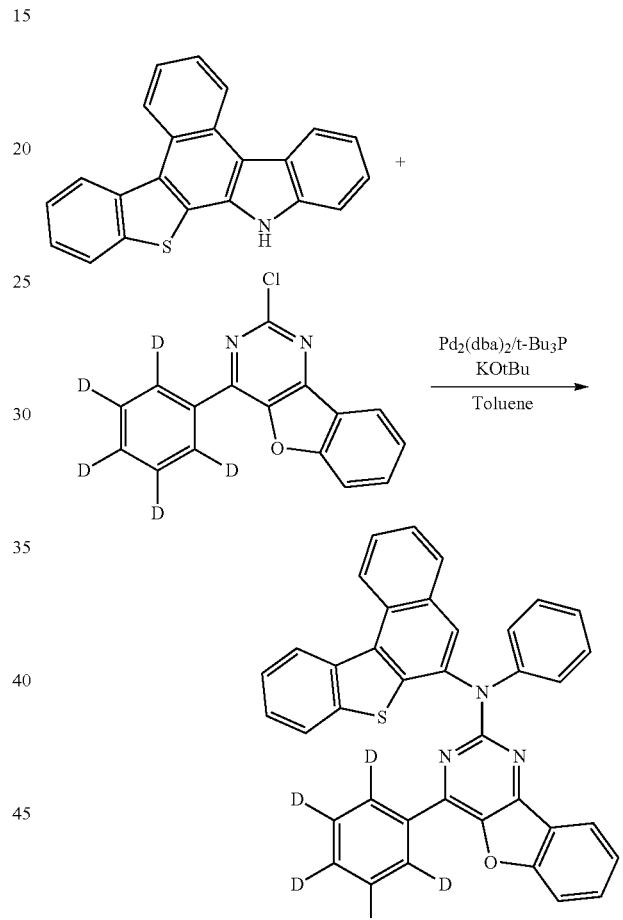

Compound 1-1-1-O-(2) (7.52 g, 85%) was obtained by using 3-1 Core (5 g, 15.46 mmol), Sub 4-1-O-(2) (5.3 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(3) Synthesis Example of 1-1-1-O-(3)

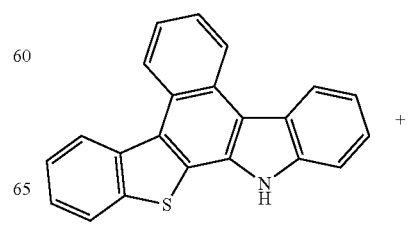

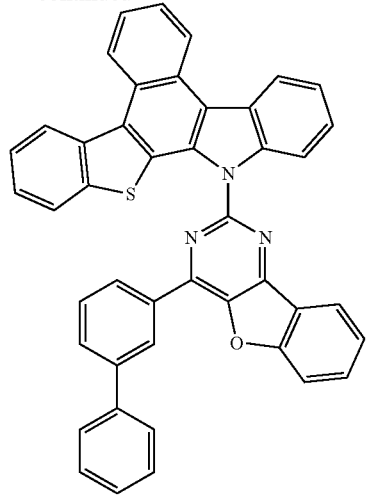

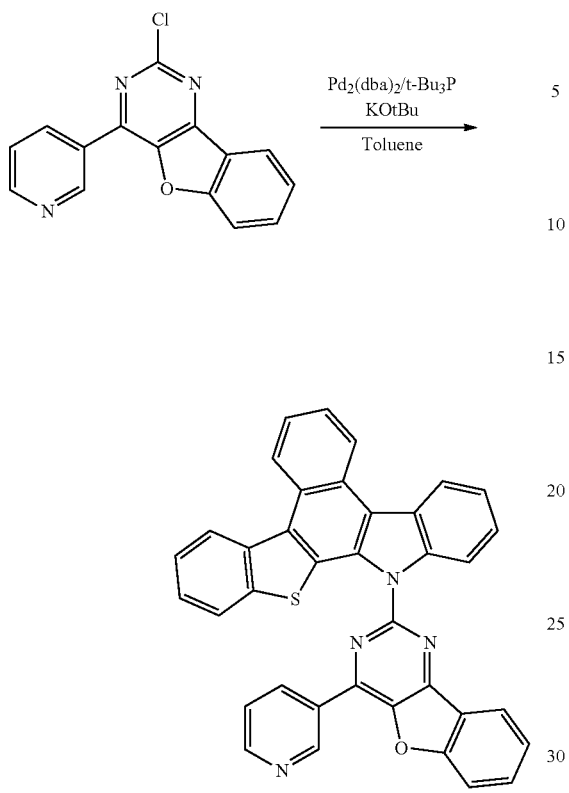

Compound 1-1-1-O-(3) (7.12 g, 81%) was obtained by using 3-1 Core (5 g, 15.46 mmol), Sub 4-1-O-(3) (4.35 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(4) Synthesis Example of 1-1-1-O-(4)

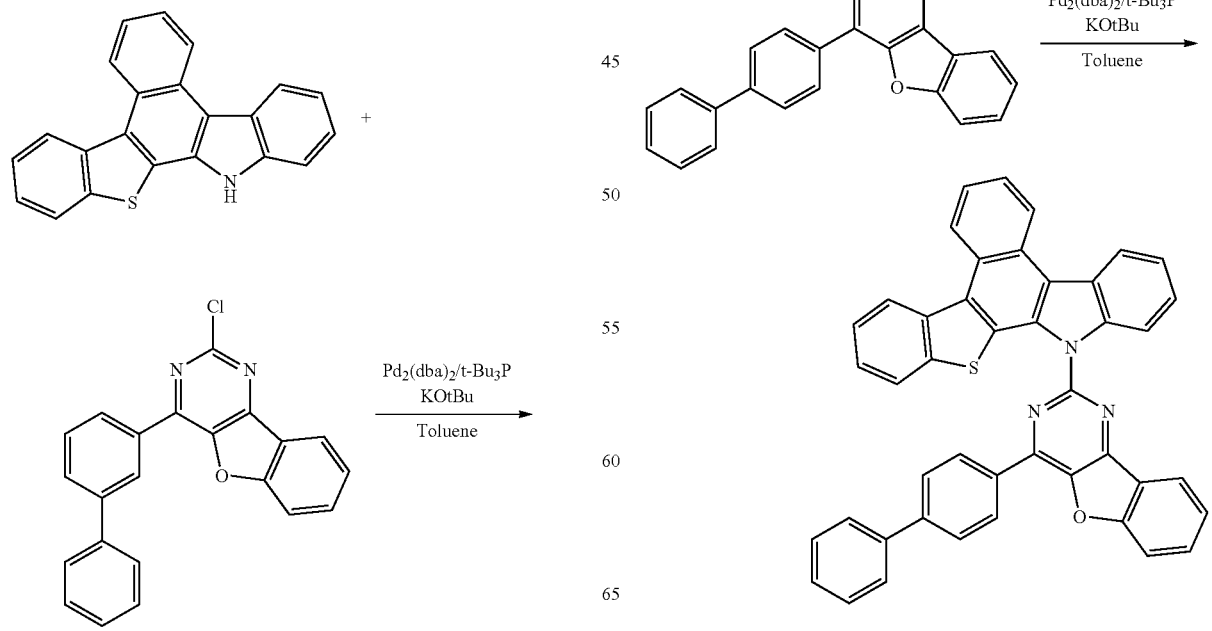

Compound 1-1-1-O-(4) (7.96 g, 80%) was obtained by using 3-1 Core (5 g, 15.46 mmol), Sub 4-1-O-(4) (6.61 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(5) Synthesis Example of 1-1-1-O-(5)

Compound 1-1-1-O-(5) (8.26 g, 83%) was obtained by using 3-1 Core (5 g, 15.46 mmol), Sub 4-1-O-(5) (6.61 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

2. Synthesis Example of 1-1-1-S (1) Synthesis Example of 1-1-1-S-(6)

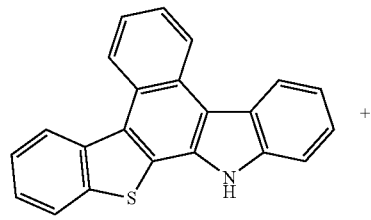

+

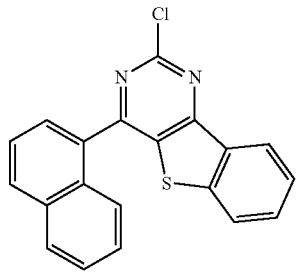

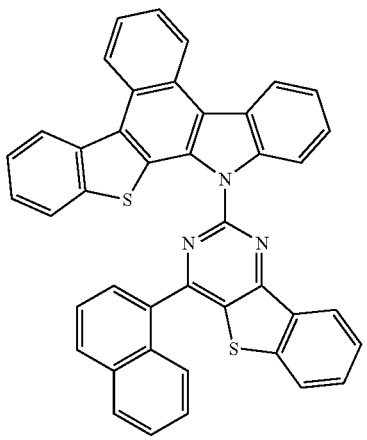

Compound 1-1-1-S-(6) (7.34 g, 75% was obtained by using 3-1 Core (5 g, 15.46 mmol), Sub 4-1-S-(6) (6.43 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(2) Synthesis Example of 1-1-1-S-(7)

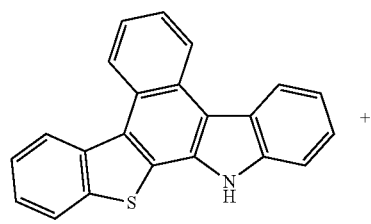

+

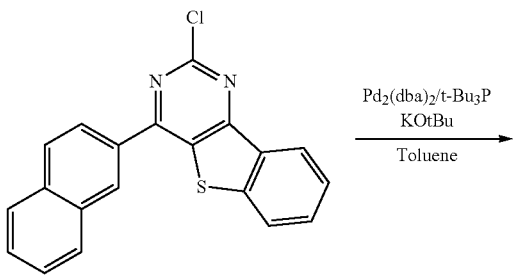

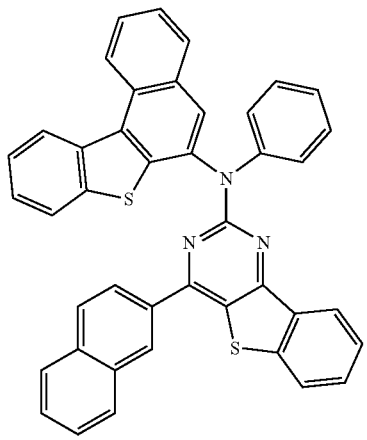

Compound 1-1-1-S-(7) (7.05 g, 72%) was obtained by using 3-1 Core (5 g, 15.46 mmol), Sub 4-1-S-(7) (6.43 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(3) Synthesis Example of 1-1-1-S-(8)

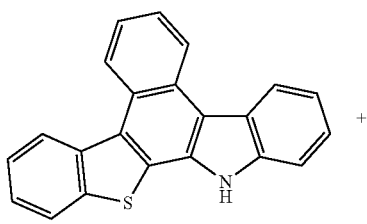

+

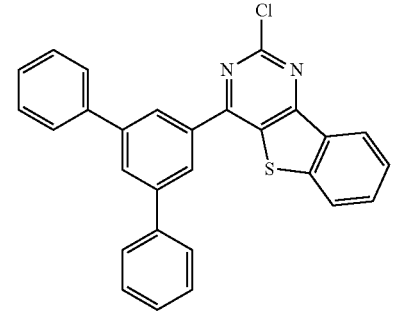

-continued

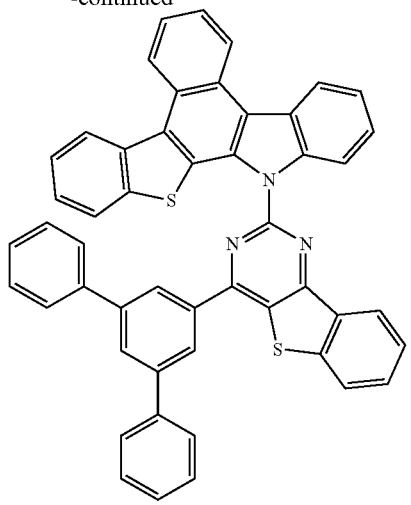

Compound 1-1-1-S-(8) (9.1 g, 80%) was obtained by using 3-1 Core (5 g, 15.46 mmol), Sub 4-1-S-(8) (8.32 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(4) Synthesis Example of 1-1-1-S-(9)

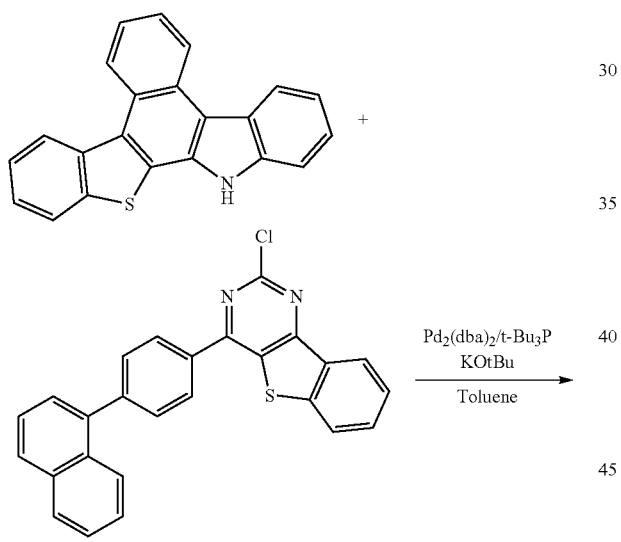

Compound 1-1-1-S-(9) (8.45 g, 77%) was obtained by using 3-1 Core (5 g, 15.46 mmol), Sub 4-1-S-(9) (7.84 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(5) Synthesis Example of 1-1-1-S-(10)

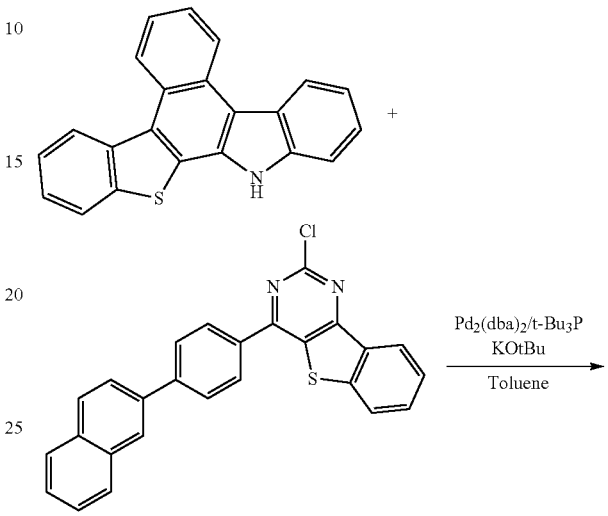

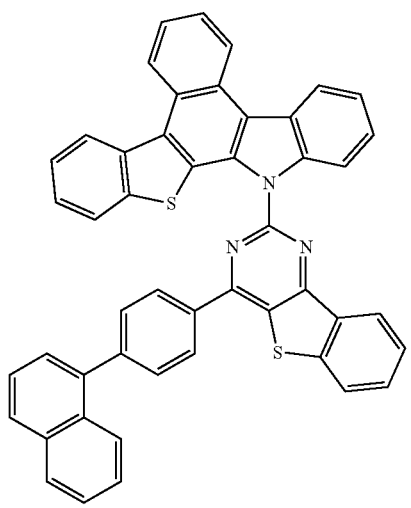

Compound 1-1-1-S-(10) (8.88 g, 81%) was obtained by using 3-1 Core (5 g, 15.46 mmol), Sub 4-1-S-(10) (7.84 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

3. Synthesis Example of 1-1-2-O (1) Synthesis Example of 1-1-2-O-(11)

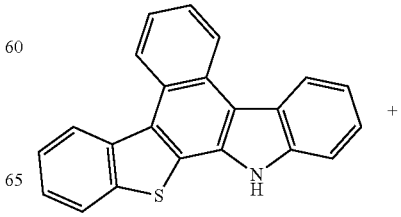

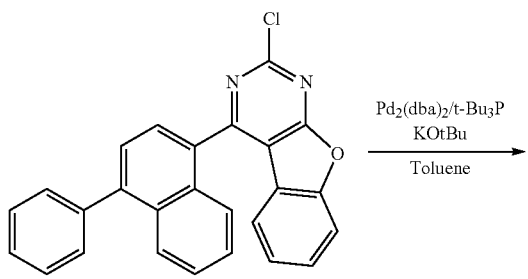

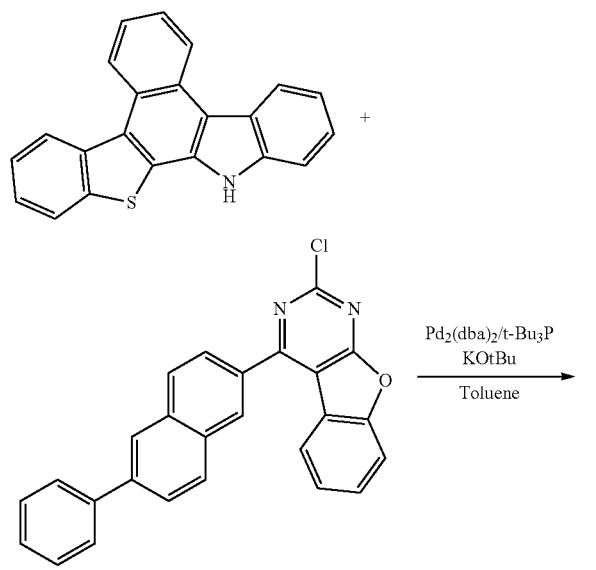

Compound 1-1-2-O-(11) (8.58 g, 80%) was obtained by using 3-1 Core (5 g, 15.46 mmol), Sub 4-2-O-(11) (7.54 g, 18.55 mmol), Pd₂(dba)₃ (0.56 g, 4 mol %), t-Bu₃P (0.25 g, 8 mol %), KOtBu (5.2 g, 46.38 mmol) and toluene in the same manner as described above for the synthesis example of the compound 1-1-1-O-(1).

(2) Synthesis Example of 1-1-2-O-(12)

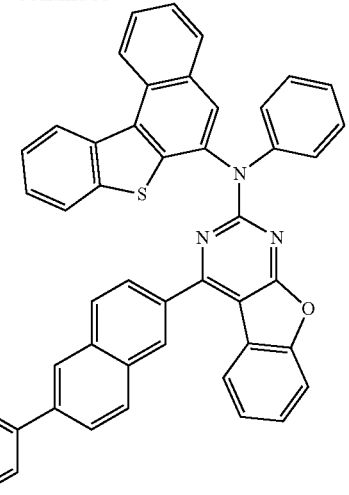

Compound 1-1-2-O-(12) (7.83 g, 73%) was obtained by using 3-1 Core (5 g, 15.46 mmol), Sub 4-2-O-(12) (7.54 g, 18.55 mmol), Pd₂(dba)₃ (0.56 g, 4 mol %), t-Bu₃P (0.25 g, 8 mol %), KOtBu (5.2 g, 46.38 mmol) and toluene in the same manner as described above for the synthesis example of the compound 1-1-1-O-(1).

(3) Synthesis Example of 1-1-2-O-(13)

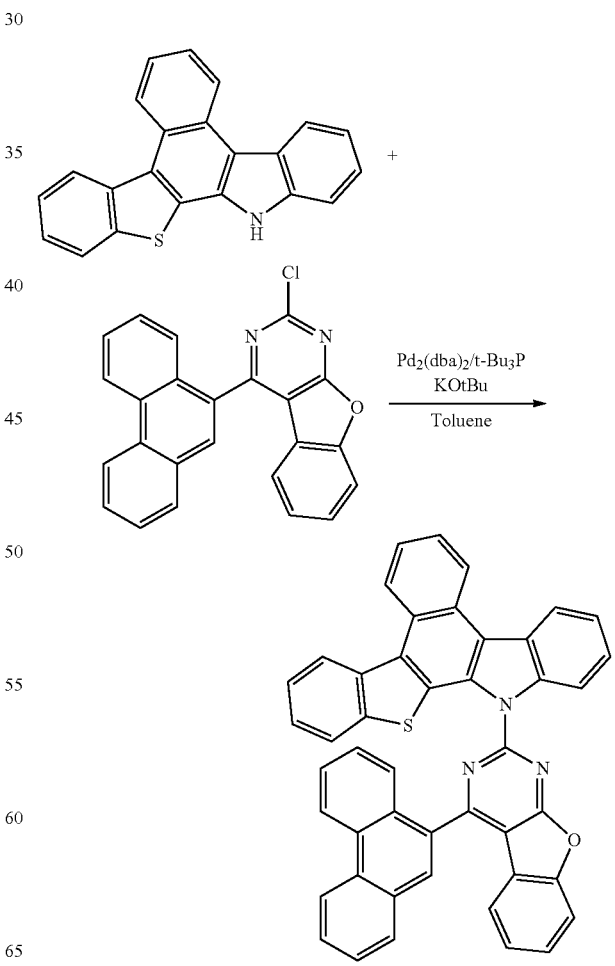

Compound 1-1-2-O-(13) (7.74 g, 75%) was obtained by using 3-1 Core (5 g, 15.46 mmol), Sub 4-2-O-(13) (7.06 g, 18.55 mmol), Pd$_2$(dba)$_3$(0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(4) Synthesis Example of 1-1-2-O-(14)

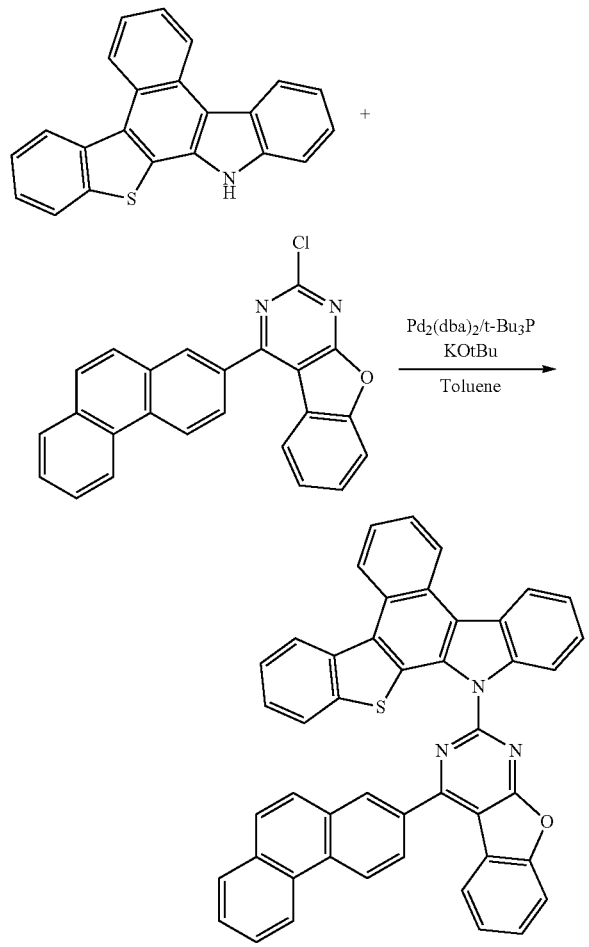

Compound 1-1-2-O-(14) (8.36 g, 81%) was obtained by using 3-1 Core (5 g, 15.46 mmol), Sub 4-2-O-(14) (7.06 g, 18.55 mmol), Pd$_2$(dba)$_3$(0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(5) Synthesis Example of 1-1-2-O-(15)

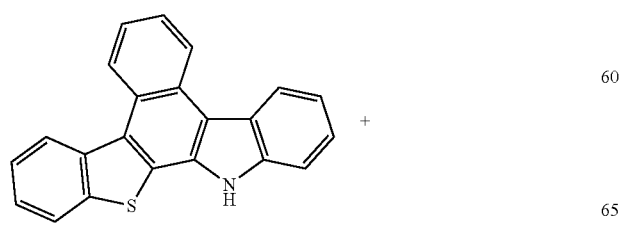

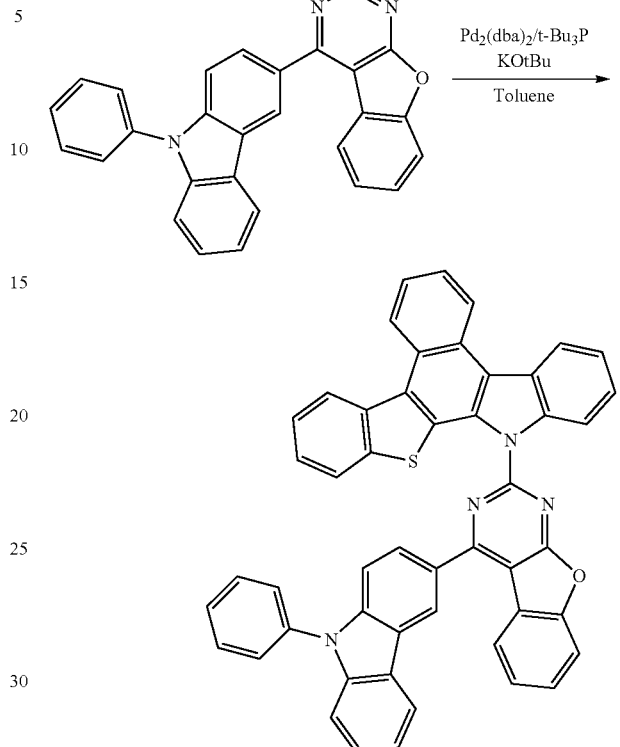

Compound 1-1-2-O-(15) (7.93 g, 70%) was obtained by using 3-1 Core (5 g, 15.46 mmol), Sub 4-2-O-(15) (8.27 g, 18.55 mmol), Pd$_2$(dba)$_3$(0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

4. Synthesis Example of 1-1-2-S (1) Synthesis Example of 1-1-2-S-(16)

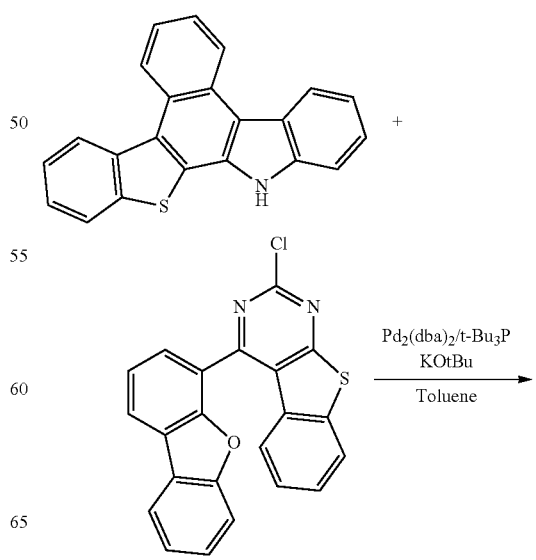

-continued

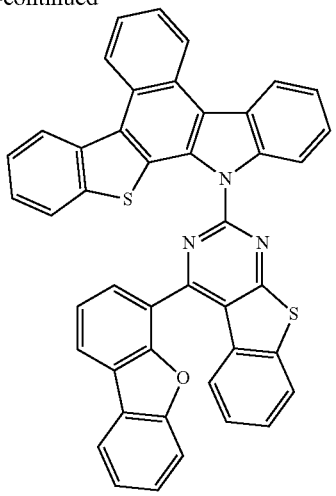

Compound 1-1-2-S-(16) (7.5 g, 72%) was obtained by using 3-1 Core (5 g, 15.46 mmol), Sub 4-2-S-(16) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(2) Synthesis Example of 1-1-2-S-(17)

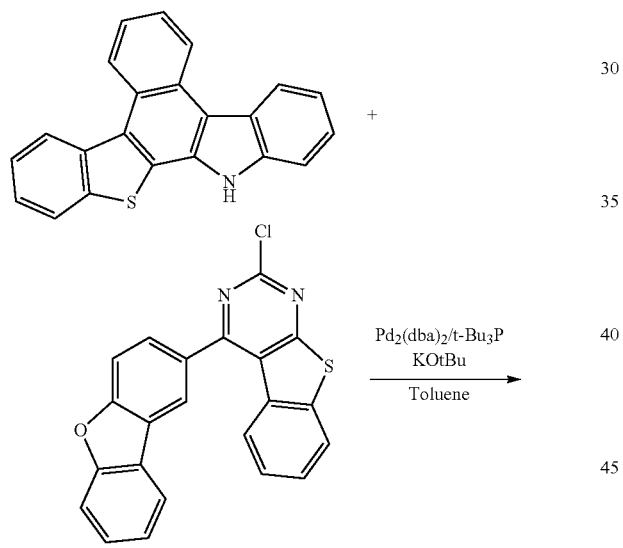

Compound 1-1-2-S-(17) (7.7 g, 74%) was obtained by using 3-1 Core (5 g, 15.46 mmol), Sub 4-2-S-(17) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(3) Synthesis Example of 1-1-2-S-(18)

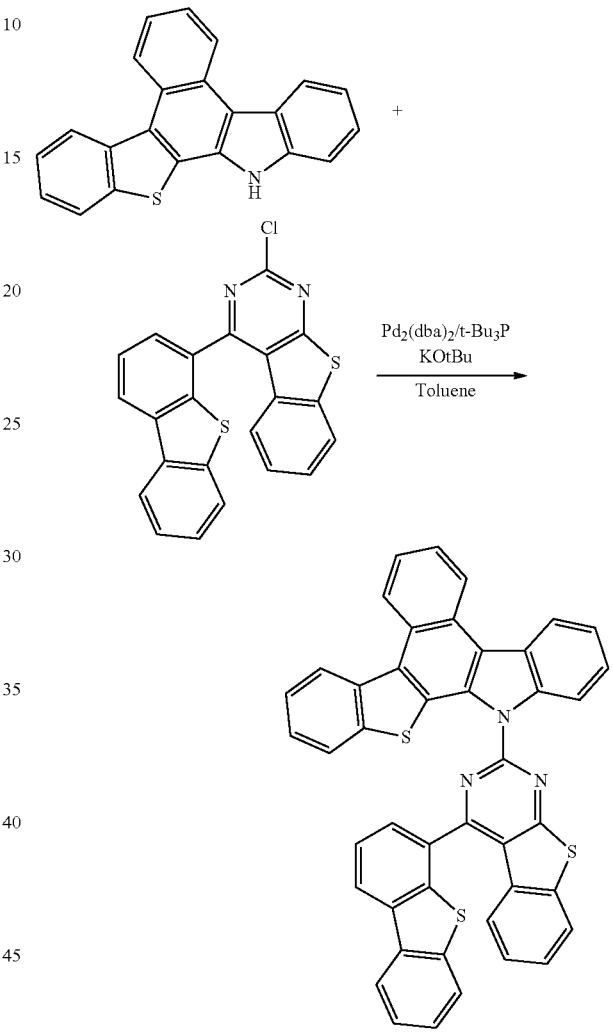

Compound 1-1-2-S-(18) (8.42 g, 79%) was obtained by using 3-1 Core (5 g, 15.46 mmol), Sub 4-2-S-(18) (7.47 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(4) Synthesis Example of 1-1-2-S-(19)

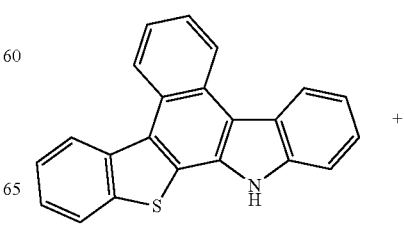

401

-continued

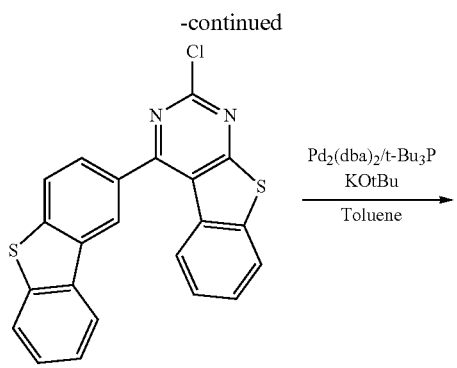

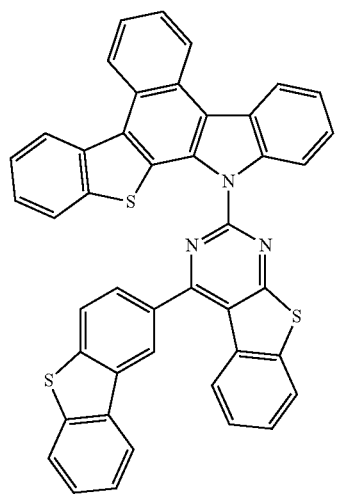

Compound 1-1-2-S-(19) (8.1 g, 76%) was obtained by using 3-1 Core (5 g, 15.46 mmol), Sub 4-2-S-(19) (7.47 g, 18.55 mmol), Pd₂(dba)₃ (0.56 g, 4 mol %), t-Bu₃P (0.25 g, 8 mol %), KOtBu (5.2 g, 46.38 mmol) and toluene in the same manner as described above for the synthesis example of the compound 1-1-1-O-(1).

(5) Synthesis Example of 1-1-2-S-(20)

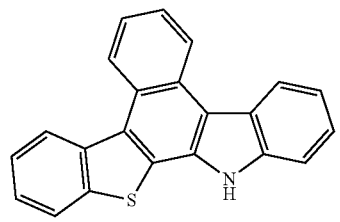

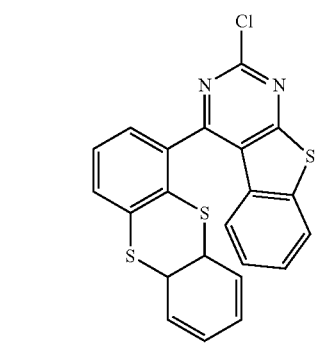

402

-continued

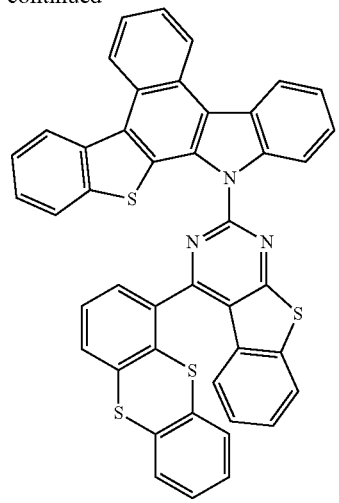

Compound 1-1-2-S-(20) (8.92 g, 80%) was obtained by using 3-1 Core (5 g, 15.46 mmol), Sub 4-2-S-(20) (8.06 g, 18.55 mmol), Pd₂(dba)₃ (0.56 g, 4 mol %), t-Bu₃P (0.25 g, 8 mol %), KOtBu (5.2 g, 46.38 mmol) and toluene in the same manner as described above for the synthesis example of the compound 1-1-1-O-(1).

5. Synthesis Example of 1-3-1-O 합성예

(1) Synthesis Example of 1-3-1-O-(11)

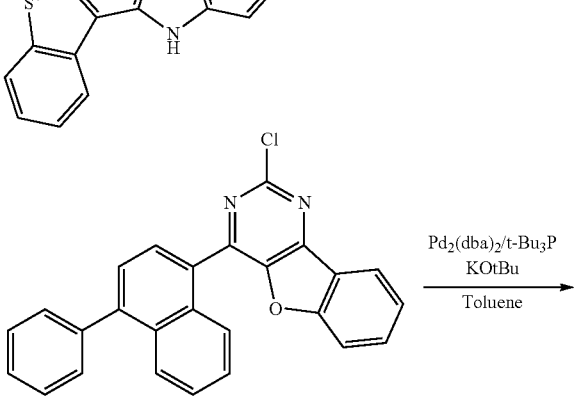

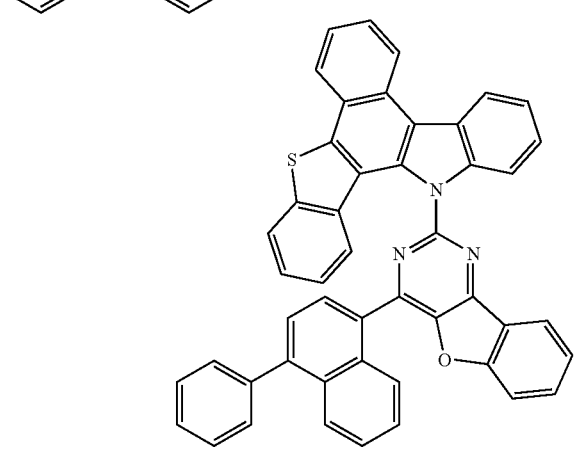

Compound 1-3-1-O-(11) (8.04 g, 75%) was obtained by using 3-2 Core (5 g, 15.46 mmol), Sub 4-1-O-(11) (7.54 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(2) Synthesis Example of 1-3-1-O-(12)

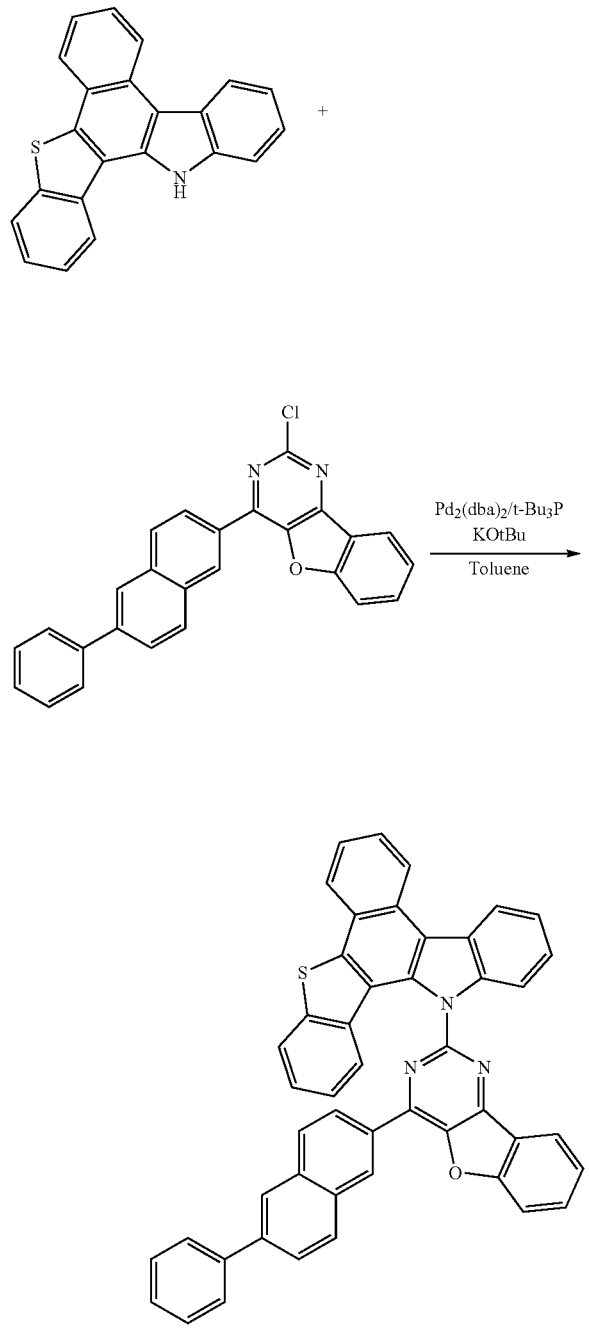

Compound 1-3-1-O-(12) (8.25 g, 77%) was obtained by using 3-2 Core (5 g, 15.46 mmol), Sub 4-1-O-(12) (7.54 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(3) Synthesis Example of 1-3-1-O-(13)

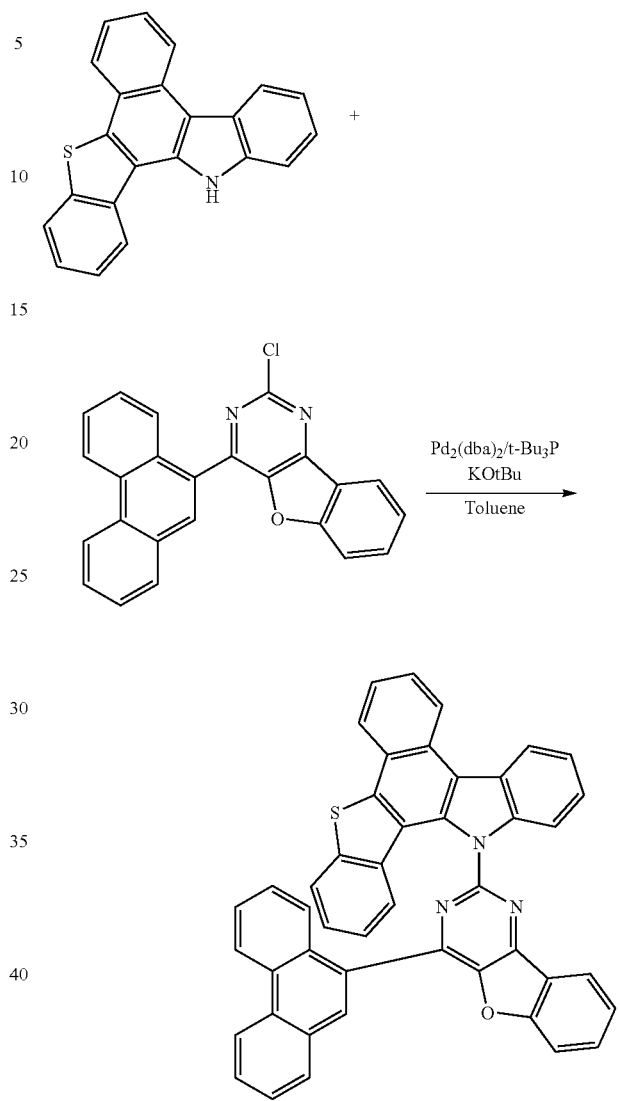

Compound 1-3-1-O-(13) (7.53 g, 73%) was obtained by using 3-2 Core (5 g, 15.46 mmol), Sub 4-1-O-(13) (7.06 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(4) Synthesis Example of 1-3-1-O-(14)

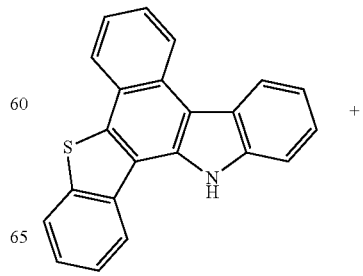

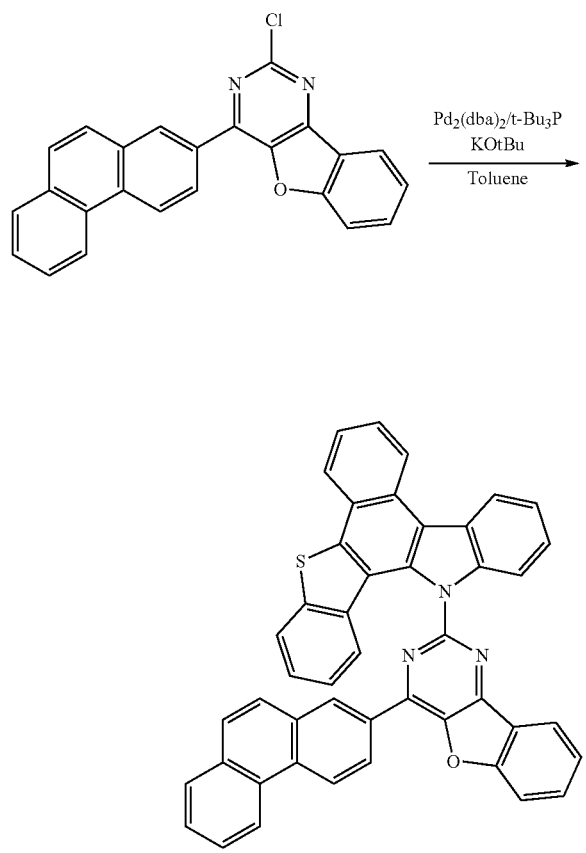

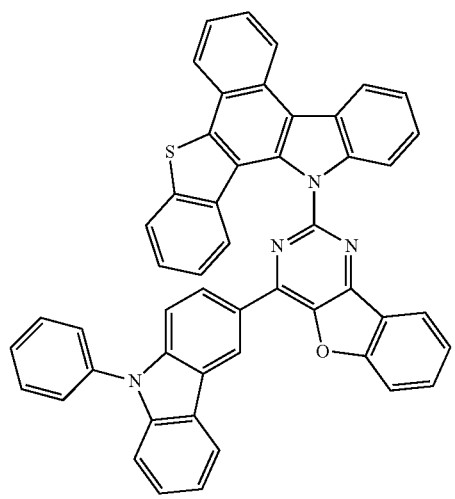

Compound 1-3-1-O-(14) (8.46 g, 82%) was obtained by using 3-2 Core (5 g, 15.46 mmol), Sub 4-1-O-(14) (7.06 g, 18.55 mmol), $Pd_2(dba)_3$ (0.56 g, 4 mol %), t-$Bu_3$P (0.25 g, 8 mol %), KOtBu (5.2 g, 46.38 mmol) and toluene in the same manner as described above for the synthesis example of the compound 1-1-1-O-(1).

(5) Synthesis Example of 1-3-1-O-(15)

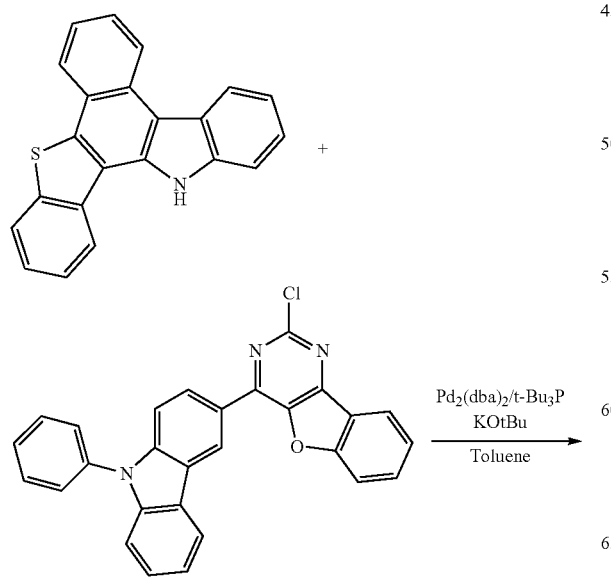

Compound 1-3-1-O-(15) (8.95 g, 79%) was obtained by using 3-2 Core (5 g, 15.46 mmol), Sub 4-1-O-(15) (8.27 g, 18.55 mmol), $Pd_2(dba)_3$ (0.56 g, 4 mol %), t-$Bu_3$P (0.25 g, 8 mol %), KOtBu (5.2 g, 46.38 mmol) and toluene in the same manner as described above for the synthesis example of the compound 1-1-1-O-(1).

6. Synthesis Example of 1-3-1-S (1) Synthesis Example of 1-3-1-S-(16)

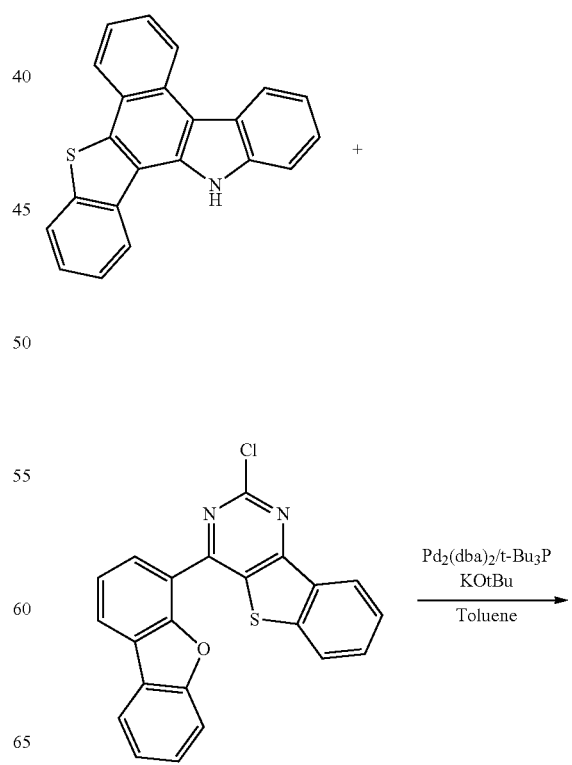

407
-continued

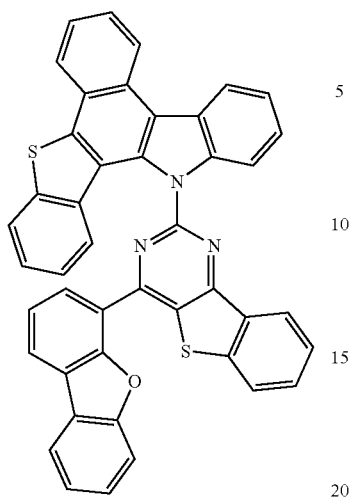

Compound 1-3-1-S-(16) (7.91 g, 76%) was obtained by using 3-2 Core (5 g, 15.46 mmol), Sub 4-1-S-(16) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(2) Synthesis Example of 1-3-1-S-(17)

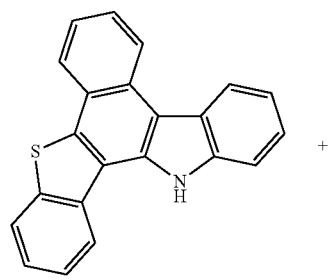

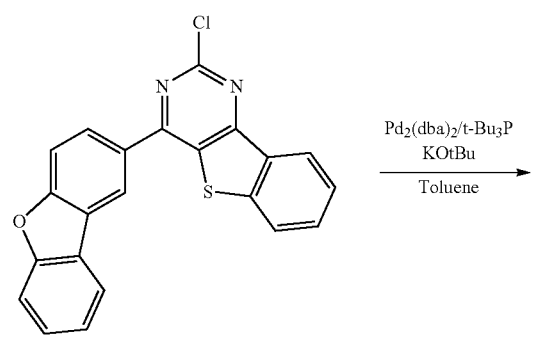

408
-continued

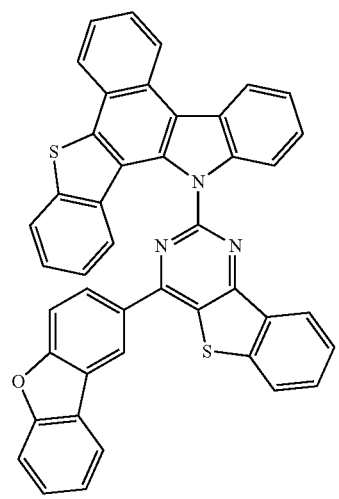

Compound 1-3-1-S-(17) (7.39 g, 71%) was obtained by using 3-2 Core (5 g, 15.46 mmol), Sub 4-1-S-(17) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(3) Synthesis Example of 1-3-1-S-(18)

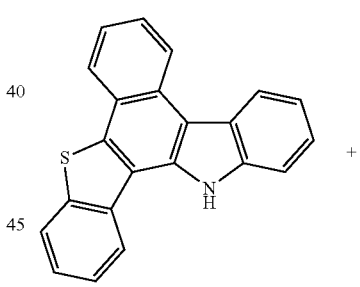

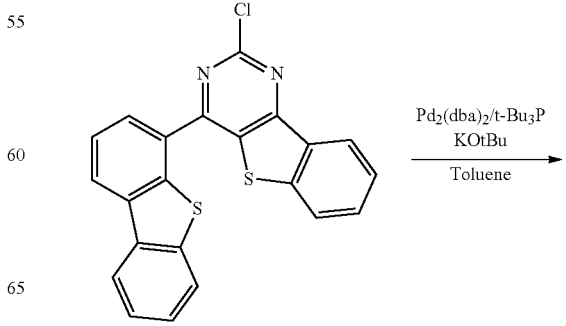

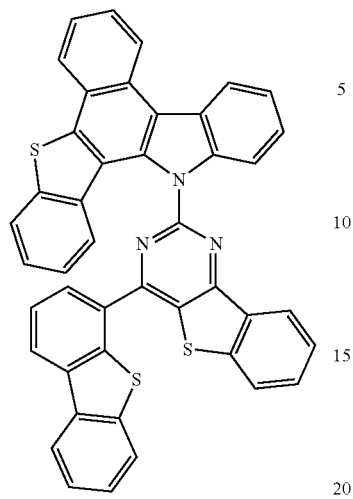

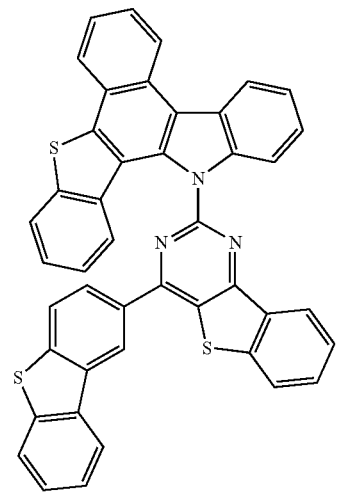

Compound 1-3-1-S-(18) (7.89 g, 74%) was obtained by using 3-2 Core (5 g, 15.46 mmol), Sub 4-1-S-(18) (7.47 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(4) Synthesis Example of 1-3-1-S-(19)

Compound 1-3-1-S-(19) (8.21 g, 77%) was obtained by using 3-2 Core (5 g, 15.46 mmol), Sub 4-1-S-(19) (7.47 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(5) Synthesis Example of 1-3-1-S-(20)

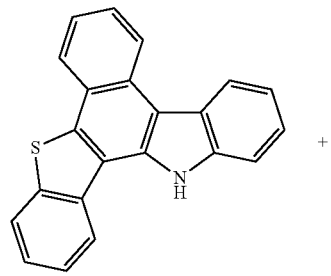 +

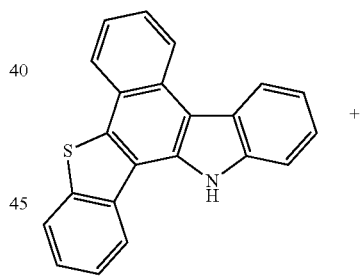 +

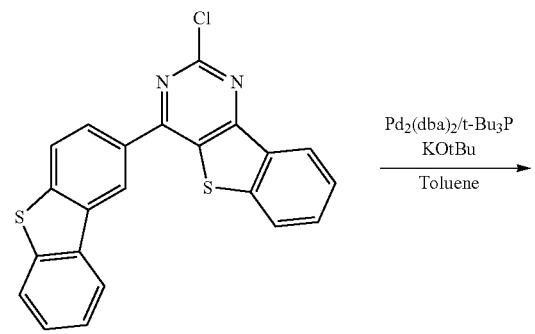

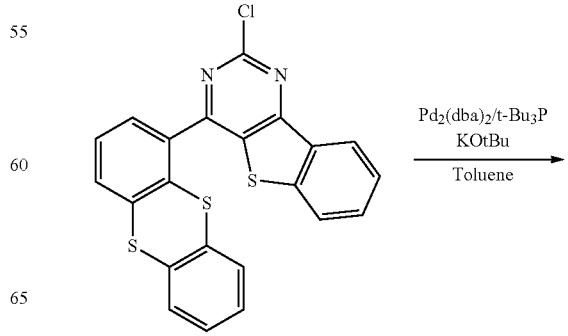

-continued

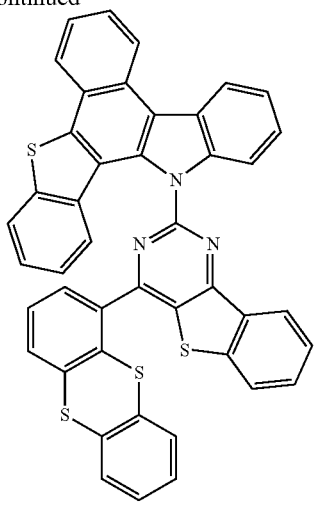

Compound 1-3-1-S-(20) (8.59 g, 77%) was obtained by using 3-2 Core (5 g, 15.46 mmol), Sub 4-1-S-(20) (8.06 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

7. Synthesis Example of 1-3-2-O
(1) Synthesis Example of 1-3-2-O-(1)

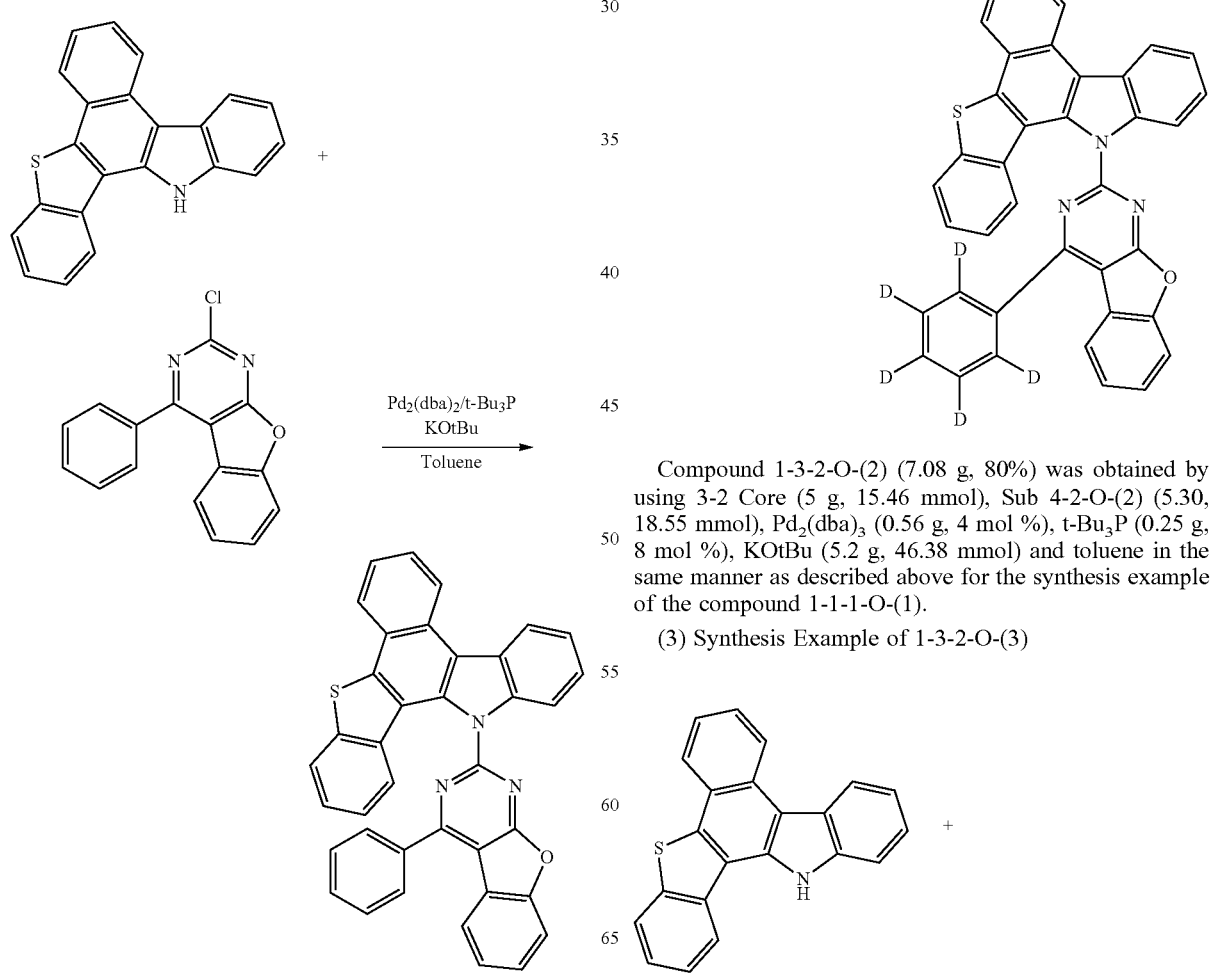

Compound 1-3-2-O-(1) (6.49 g, 74%) was obtained by using 3-2 Core (5 g, 15.46 mmol), Sub 4-2-O-(1) (5.20, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(2) Synthesis Example of 1-3-2-O-(2)

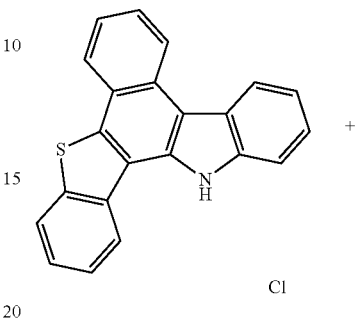

Compound 1-3-2-O-(2) (7.08 g, 80%) was obtained by using 3-2 Core (5 g, 15.46 mmol), Sub 4-2-O-(2) (5.30, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(3) Synthesis Example of 1-3-2-O-(3)

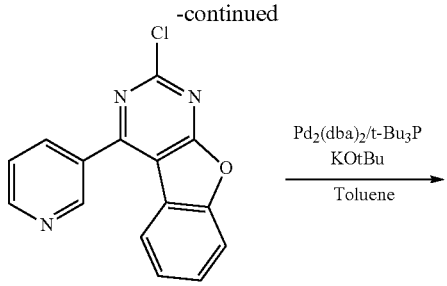

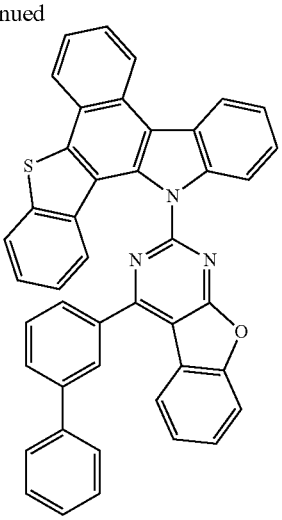

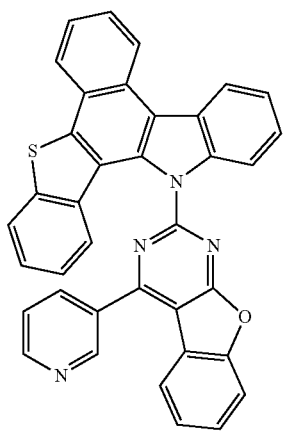

Compound 1-3-2-O-(3) (7.03 g, 80%) was obtained by using 3-2 Core (5 g, 15.46 mmol), Sub 4-2-O-(3) (5.22, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(4) Synthesis Example of 1-3-2-O-(4)

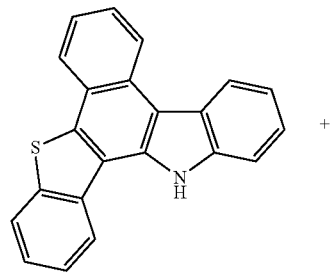

Compound 1-3-2-O-(4) (7.86 g, 79%) was obtained by using 3-2 Core (5 g, 15.46 mmol), Sub 4-2-O-(4) (6.61, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

(5) Synthesis Example of 1-3-2-O-(5)

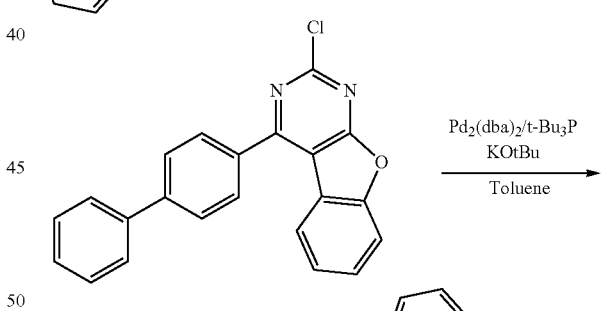

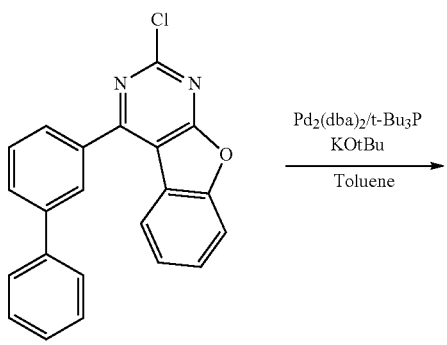

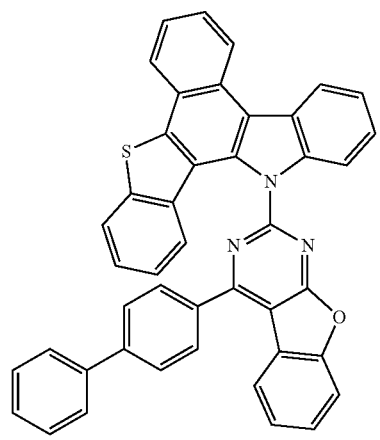

Compound 1-3-2-O-(5) (7.66 g, 77%) was obtained by using 3-2 Core (5 g, 15.46 mmol), Sub 4-2-O-(5) (6.61, 18.55 mmol), Pd₂(dba)₃ (0.56 g, 4 mol %), t-Bu₃P (0.25 g, 8 mol %), KOtBu (5.2 g, 46.38 mmol) and toluene in the same manner as described above for the synthesis example of the compound 1-1-1-O-(1).

8. Synthesis Example of 1-3-2-S
(1) Synthesis Example of 1-3-2-S-(6)

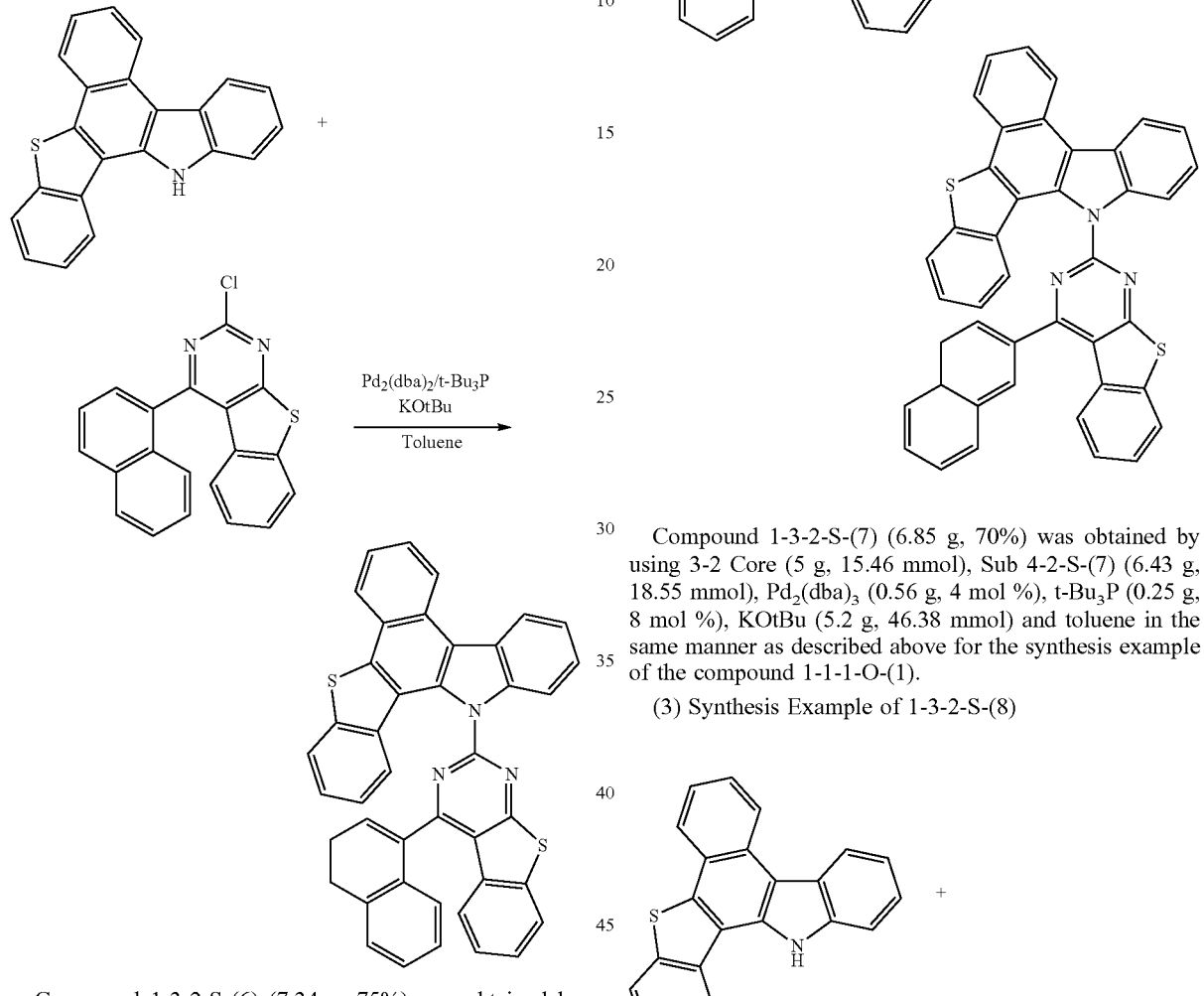

Compound 1-3-2-S-(6) (7.34 g, 75%) was obtained by using 3-2 Core (5 g, 15.46 mmol), Sub 4-2-S-(6) (6.43 g, 18.55 mmol), Pd₂(dba)₃ (0.56 g, 4 mol %), t-Bu₃P (0.25 g, 8 mol %), KOtBu (5.2 g, 46.38 mmol) and toluene in the same manner as described above for the synthesis example of the compound 1-1-1-O-(1).

(2) Synthesis Example of 1-3-2-S-(7)

Compound 1-3-2-S-(7) (6.85 g, 70%) was obtained by using 3-2 Core (5 g, 15.46 mmol), Sub 4-2-S-(7) (6.43 g, 18.55 mmol), Pd₂(dba)₃ (0.56 g, 4 mol %), t-Bu₃P (0.25 g, 8 mol %), KOtBu (5.2 g, 46.38 mmol) and toluene in the same manner as described above for the synthesis example of the compound 1-1-1-O-(1).

(3) Synthesis Example of 1-3-2-S-(8)

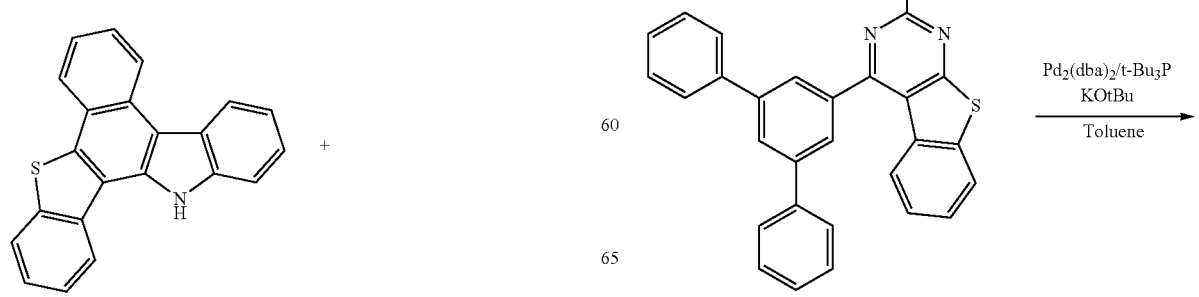

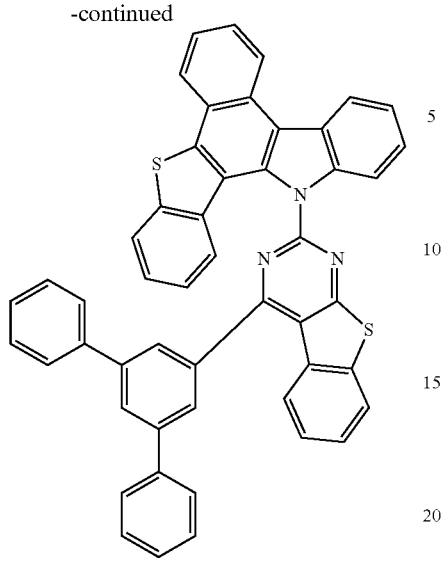
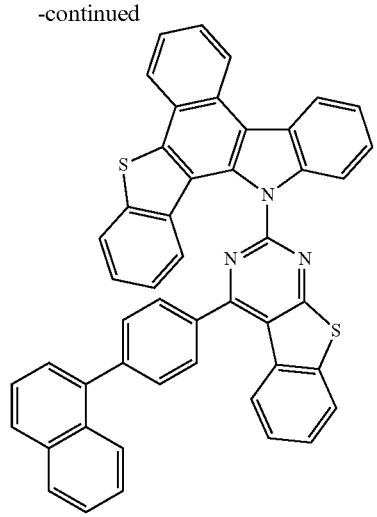

Compound 1-3-2-S-(8) (8.64 g, 76%) was obtained by using 3-2 Core (5 g, 15.46 mmol), Sub 4-2-S-(8) (8.32 g, 18.55 mmol), Pd₂(dba)₃ (0.56 g, 4 mol %), t-Bu₃P (0.25 g, 8 mol %), KOtBu (5.2 g, 46.38 mmol) and toluene in the same manner as described above for the synthesis example of the compound 1-1-1-O-(1).

(4) Synthesis Example of 1-3-2-S-(9)

Compound 1-3-2-S-(9) (8.34 g, 76%) was obtained by using 3-2 Core (5 g, 15.46 mmol), Sub 4-2-S-(9) (7.84 g, 18.55 mmol), Pd₂(dba)₃ (0.56 g, 4 mol %), t-Bu₃P (0.25 g, 8 mol %), KOtBu (5.2 g, 46.38 mmol) and toluene e in the same manner as described above for the synthesis example of the compound 1-1-1-O-(1).

(5) Synthesis Example of 1-3-2-S-(10)

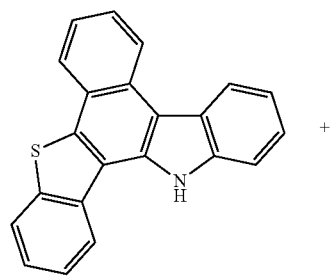
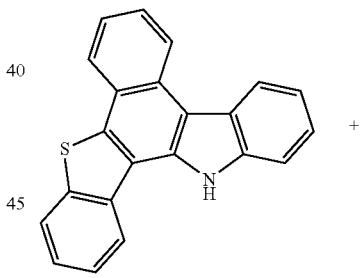
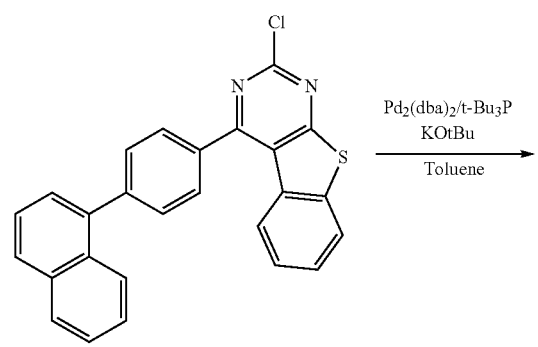
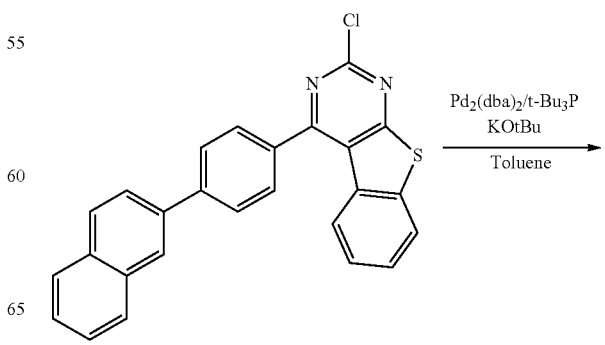

-continued

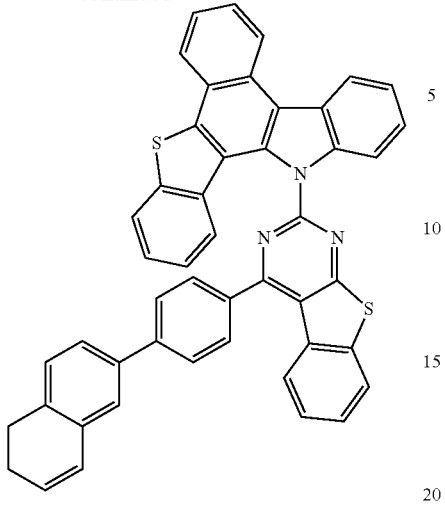

Compound 1-3-2-S-(10) (8.77 g, 80%) was obtained by using 3-2 Core (5 g, 15.46 mmol), Sub 4-2-S-(10) (7.84 g, 18.55 mmol), Pd$_2$(dba)$_3$ (0.56 g, 4 mol %), t-Bu$_3$P (0.25 g, 8 mol %), KOtBu (5.2 g, 46.38 mmol) and toluene in the same manner as described above for the synthesis example of the compound 1-1-1-O-(1).

On the other hand, the FD-MS values of compounds 1-1-1-O-(1) to 1-3-2-(23) synthesized according to the above synthesis examples are shown in Table 5 below.

TABLE 5

| compound | FD-MS | compound | FD-MS |
|---|---|---|---|
| 1-1-1-O-(1) | m/z = 567.14 (C$_{38}$H$_{21}$N$_3$OS = 567.66) | 1-1-1-O-(2) | m/z = 572.17 (C$_{38}$H$_{16}$D$_5$N$_3$OS = 572.69) |
| 1-1-1-O-(3) | m/z = 568.14 (C$_{32}$H$_{20}$N$_4$OS = 568.65) | 1-1-1-O-(4) | m/z = 643.17 (C$_{44}$H$_{25}$N$_3$S = 643.75) |
| 1-1-1-O-(5) | m/z = 643.17 (C$_{44}$H$_{25}$N$_3$OS = 643.75) | 1-1-1-O-(6) | m/z = 617.16 (C$_{42}$H$_{23}$N$_3$OS = 617.72) |
| 1-1-1-O-(7) | m/z = 617.16 (C$_{42}$H$_{23}$N$_3$OS = 617.72) | 1-1-1-O-(8) | m/z = 719.20 (C$_{50}$H$_{29}$N$_3$OS = 719.85) |
| 1-1-1-O-(9) | m/z = 693.19 (C$_{48}$H$_{27}$N$_3$OS = 693.81) | 1-1-1-O-(10) | m/z = 693.19 (C$_{48}$H$_{27}$N$_3$OS = 693.81) |
| 1-1-1-O-(11) | m/z = 693.19 (C$_{48}$H$_{27}$N$_3$OS = 693.81) | 1-1-1-O-(12) | m/z = 693.19 (C$_{48}$H$_{27}$N$_3$OS = 693.81) |
| 1-1-1-O-(13) | m/z = 667.17 (C$_{46}$H$_{25}$N$_3$OS = 667.78) | 1-1-1-O-(14) | m/z = 667.17 (C$_{46}$H$_{25}$N$_3$OS = 667.78) |
| 1-1-1-O-(15) | m/z = 732.20 (C$_{50}$H$_{28}$N$_4$OS = 732.85) | 1-1-1-O-(16) | m/z = 657.15 (C$_{44}$H$_{23}$N$_3$O$_2$S = 657.74) |
| 1-1-1-O-(17) | m/z = 657.15 (C$_{44}$H$_{23}$N$_3$O$_2$S = 657.74) | 1-1-1-O-(18) | m/z = 673.13 (C$_{44}$H$_{23}$N$_3$OS$_2$ = 673.80) |
| 1-1-1-O-(19) | m/z = 673.13 (C$_{44}$H$_{23}$N$_3$OS$_2$ = 673.80) | 1-1-1-O-(20) | m/z = 705.10 (C$_{44}$H$_{23}$N$_3$OS$_3$ = 705.87) |
| 1-1-1-O-(21) | m/z = 617.16 (C$_{42}$H$_{23}$N$_3$OS = 617.72) | 1-1-1-O-(22) | m/z = 693.19 (C$_{48}$H$_{27}$N$_3$OS = 693.81) |
| 1-1-1-S-(1) | m/z = 583.12 (C$_{38}$H$_{21}$N$_3$S$_2$ = 583.72) | 1-1-1-S-(2) | m/z = 588.15 (C$_{38}$H$_{16}$D$_5$N$_3$S$_2$ = 588.75) |
| 1-1-1-S-(3) | m/z = 584.11 (C$_{37}$H$_{20}$N$_1$S$_2$ = 584.71) | 1-1-1-S-(4) | m/z = 659.15 (C$_{44}$H$_{25}$N$_3$S$_2$ = 659.82) |
| 1-1-1-S-(5) | m/z = 659.15 (C$_{44}$H$_{25}$N$_3$S$_2$ = 659.82) | 1-1-1-S-(6) | m/z = 633.13 (C$_{42}$H$_{23}$N$_3$S$_2$ = 633.78) |
| 1-1-1-S-(7) | m/z = 633.13 (C$_{42}$H$_{23}$N$_3$S$_2$ = 633.78) | 1-1-1-S-(8) | m/z = 735.18 (C$_{50}$H$_{29}$N$_3$S$_2$ = 735.92) |
| 1-1-1-S-(9) | m/z = 709.16 (C$_{48}$H$_{27}$N$_3$S$_2$ = 709.88) | 1-1-1-S-(10) | m/z = 709.16 (C$_{48}$H$_{27}$N$_3$S$_2$ = 709.88) |
| 1-1-1-S-(11) | m/z = 709.16 (C$_{48}$H$_{27}$N$_3$S$_2$ = 709.88) | 1-1-1-S-(12) | m/z = 709.16 (C$_{48}$H$_{27}$N$_3$S$_2$ = 709.88) |
| 1-1-1-S-(13) | m/z = 683.15 (C$_{46}$H$_{25}$N$_3$S$_2$ = 683.84) | 1-1-1-S-(14) | m/z = 683.15 (C$_{46}$H$_{25}$N$_3$S$_2$ = 683.84) |
| 1-1-1-S-(15) | m/z = 748.18 (C$_{50}$H$_{28}$N$_4$S$_2$ = 748.91) | 1-1-1-S-(16) | m/z = 673.13 (C$_{44}$H$_{23}$N$_3$OS$_2$ = 673.80) |
| 1-1-1-S-(17) | m/z = 673.13 (C$_{54}$H$_{23}$N$_3$OS$_2$ = 673.80) | 1-1-1-S-(18) | m/z = 689.11 (C$_{44}$H$_{23}$N$_3$S$_3$ = 689.87) |
| 1-1-1-S-(19) | m/z = 689.11 (C$_{44}$H$_{23}$N$_3$S$_3$ = 689.87) | 1-1-1-S-(20) | m/z = 721.08 (C$_{44}$H$_{23}$N$_3$S$_4$ = 721.93) |
| 1-1-1-S-(21) | m/z = 683.15 (C$_{46}$H$_{25}$N$_3$S$_2$ = 683.84) | 1-1-1-S-(22) | m/z = 785.20 (C$_{54}$H$_{31}$N$_3$S$_2$ = 785.97) |
| 1-1-1-S-(23) | m/z = 739.12 (C$_{48}$H$_{25}$N$_3$S$_3$ = 739.93) | | |
| 1-1-2-O-(1) | m/z = 567.14 (C$_{38}$H$_{21}$N$_3$OS = 567.66) | 1-1-2-O-(2) | m/z = 572.17 (C$_{38}$H$_{16}$D$_5$N$_3$OS = 572.69) |
| 1-1-2-O-(3) | m/z = 568.14 (C$_{37}$H$_{20}$N$_4$OS = 568.65) | 1-1-2-O-(4) | m/z = 643.17 (C$_{44}$H$_{25}$N$_3$OS = 643.75) |
| 1-1-2-O-(5) | m/z = 643.17 (C$_{44}$H$_{25}$N$_3$OS = 643.75) | 1-1-2-O-(6) | m/z = 617.16 (C$_{42}$H$_{23}$N$_3$OS = 617.72) |
| 1-1-2-O-(7) | m/z = 617.16 (C$_{42}$H$_{23}$N$_3$OS = 617.72) | 1-1-2-O-(8) | m/z = 719.20 (C$_{50}$H$_{29}$N$_3$OS = 719.85) |
| 1-1-2-O-(9) | m/z = 693.19 (C$_{48}$H$_{27}$N$_3$OS = 693.81) | 1-1-2-O-(10) | m/z = 693.19 (C$_{48}$H$_{27}$N$_3$OS = 693.81) |
| 1-1-2-O-(11) | m/z = 693.19 (C$_{48}$H$_{27}$N$_3$OS = 693.81) | 1-1-2-O-(12) | m/z = 693.19 (C$_{48}$H$_{27}$N$_3$OS = 693.81) |
| 1-1-2-O-(13) | m/z = 667.17 (C$_{46}$H$_{25}$N$_3$OS = 667.78) | 1-1-2-O-(14) | m/z = 667.17 (C$_{46}$H$_{25}$N$_3$OS = 667.78) |
| 1-1-2-O-(15) | m/z = 732.20 (C$_{50}$H$_{28}$N$_4$OS = 732.85) | 1-1-2-O-(16) | m/z = 657.15 (C$_{44}$H$_{23}$N$_3$O$_2$S = 657.74) |
| 1-1-2-O-(17) | m/z = 657.15 (C$_{44}$H$_{23}$N$_3$O$_2$S = 657.74) | 1-1-2-O-(18) | m/z = 673.13 (C$_{44}$H$_{23}$N$_3$OS$_2$ = 673.80) |
| 1-1-2-O-(19) | m/z = 673.13 (C$_{44}$H$_{23}$N$_3$OS$_2$ = 673.80) | 1-1-2-O-(20) | m/z = 705.10 (C$_{44}$H$_{23}$N$_3$OS$_3$ = 705.87) |
| 1-1-2-O-(21) | m/z = 667.17 (C$_{46}$H$_{25}$N$_3$OS = 667.78) | 1-1-2-O-(22) | m/z = 667.17 (C$_{46}$H$_{25}$N$_3$OS = 667.78) |
| 1-1-2-S-(1) | m/z = 583.12 (C$_{38}$H$_{22}$N$_3$S$_2$ = 583.72) | 1-1-2-S-(2) | m/z = 588.15 (C$_{38}$H$_{16}$D$_5$N$_3$S$_2$ = 588.75) |
| 1-1-2-S-(3) | m/z = 584.11 (C$_{37}$H$_{20}$N$_4$S$_2$ = 584.71) | 1-1-2-S-(4) | m/z = 659.15 (C$_{44}$H$_{25}$N$_3$S$_2$ = 659.82) |
| 1-1-2-S-(5) | m/z = 659.15 (C$_{44}$H$_{25}$N$_3$S$_2$ = 659.82) | 1-1-2-S-(6) | m/z = 633.13 (C$_{42}$H$_{23}$N$_3$S$_2$ = 633.78) |
| 1-1-2-S-(7) | m/z = 633.13 (C$_{42}$H$_{23}$N$_3$S$_2$ = 633.78) | 1-1-2-S-(8) | m/z = 735.18 (C$_{50}$H$_{29}$N$_3$S$_2$ = 735.92) |
| 1-1-2-S-(9) | m/z = 709.16 (C$_{48}$H$_{27}$N$_3$S$_2$ = 709.88) | 1-1-2-S-(10) | m/z = 709.16 (C$_{48}$H$_{27}$N$_3$S$_2$ = 709.88) |
| 1-1-2-S-(11) | m/z = 709.16 (C$_{48}$H$_{27}$N$_3$S$_2$ = 709.88) | 1-1-2-S-(12) | m/z = 709.16 (C$_{48}$H$_{27}$N$_3$S$_2$ = 709.88) |
| 1-1-2-S-(13) | m/z = 683.15 (C$_{46}$H$_{25}$N$_3$S$_2$ = 683.84) | 1-1-2-S-(14) | m/z = 683.15 (C$_{45}$H$_{25}$N$_3$S$_2$ = 683.84) |

TABLE 5-continued

| compound | FD-MS | compound | FD-MS |
|---|---|---|---|
| 1-1-2-S-(15) | m/z = 748.18 ($C_{50}H_{28}N_4S_2$ = 748.91) | 1-1-2-S-(16) | m/z = 673.13 ($C_{44}H_{23}N_3OS_2$ = 673.80) |
| 1-1-2-S-(17) | m/z = 673.13 ($C_{44}H_{23}N_3OS_2$ = 673.80) | 1-1-2-S-(18) | m/z = 689.11 ($C_{44}H_{23}N_3S_3$ = 689.87) |
| 1-1-2-S-(19) | m/z = 689.11 ($C_{44}H_{23}N_3S_3$ = 689.87) | 1-1-2-S-(20) | m/z = 721.08 ($C_{44}H_{23}N_3S_4$ = 721.93) |
| 1-1-2-S-(21) | m/z = 683.15 ($C_{46}H_{25}N_3S_2$ = 683.84) | 1-1-2-S-(22) | m/z = 709.16 ($C_{48}H_{27}N_3S_2$ = 709.88) |
| 1-1-2-S-(23) | m/z = 826.22 ($C_{56}H_{34}N_4S_2$ = 827.03) | | |
| 1-3-1-O-(1) | m/z = 567.14 ($C_{38}H_{21}N_3OS$ = 567.66) | 1-3-1-O-(2) | m/z = 572.17 ($C_{38}H_{16}D_5N_3OS$ = 572.69) |
| 1-3-1-O-(3) | m/z = 568.14 ($C_{37}H_{20}N_4OS$ = 568.65) | 1-3-1-O-(4) | m/z = 643.17 ($C_{44}H_{25}N_3OS$ = 643.75) |
| 1-3-1-O-(5) | m/z = 643.17 ($C_{44}H_{25}N_3OS$ = 643.75) | 1-3-1-O-(6) | m/z = 617.16 ($C_{42}H_{23}N_3OS$ = 617.72) |
| 1-3-1-O-(7) | m/z = 617.16 ($C_{42}H_{23}N_3OS$ = 617.72) | 1-3-1-O-(8) | m/z = 719.20 ($C_{50}H_{29}N_3OS$ = 719.85) |
| 1-3-1-O-(9) | m/z = 693.19 ($C_{48}H_{27}N_3OS$ = 693.81) | 1-3-1-O-(10) | m/z = 693.19 ($C_{48}H_{27}N_3OS$ = 693.81) |
| 1-3-1-O-(11) | m/z = 693.19 ($C_{48}H_{27}N_3OS$ = 693.81) | 1-3-1-O-(12) | m/z = 693.19 ($C_{48}H_{27}N_3OS$ = 693.81) |
| 1-3-1-O-(13) | m/z = 667.17 ($C_{46}H_{25}N_3OS$ = 667.78) | 1-3-1-O-(14) | m/z = 667.17 ($C_{48}H_{25}N_3OS$ = 667.78) |
| 1-3-1-O-(15) | m/z = 732.20 ($C_{50}H_{28}N_4OS$ = 732.85) | 1-3-1-O-(16) | m/z = 657.15 ($C_{44}H_{23}N_3O_2S$ = 657.74) |
| 1-3-1-O-(17) | m/z = 657.15 ($C_{44}H_{23}N_3O_2S$ = 657.74) | 1-3-1-O-(18) | m/z = 673.13 ($C_{44}H_{23}N_3OS_2$ = 673.80) |
| 1-3-1-O-(19) | m/z = 673.13 ($C_{44}H_{23}N_3OS_2$ = 673.80) | 1-3-1-O-(20) | m/z = 705.10 ($C_{44}H_{23}N_3OS_3$ = 705.87) |
| 1-3-1-O-(21) | m/z = 617.16 ($C_{42}H_{23}N_3OS$ = 617.72) | 1-3-1-O-(22) | m/z = 693.19 ($C_{48}H_{27}N_3OS$ = 693.81) |
| 1-3-1-S-(1) | m/z = 583.12 ($C_{38}H_{21}N_3S_2$ = 583.72) | 1-3-1-S-(2) | m/z = 588.15 ($C_{38}H_{26}D_5N_3S_2$ = 588.75) |
| 1-3-1-S-(3) | m/z = 584.11 ($C_{37}H_{20}N_4S_2$ = 584.71) | 1-3-1-S-(4) | m/z = 659.15 ($C_{44}H_{25}N_3S_2$ = 659.82) |
| 1-3-1-S-(5) | m/z = 659.15 ($C_{44}H_{25}B_3S_2$ = 659.82) | 1-3-1-S-(6) | m/z = 633.13 ($C_{42}H_{23}N_3S_2$ = 633.78) |
| 1-3-1-S-(7) | m/z = 633.13 ($C_{42}H_{23}N_3S_2$ = 633.78) | 1-3-1-S-(8) | m/z = 735.18 ($C_{50}H_{29}N_3S_2$ = 735.92) |
| 1-3-1-S-(9) | m/z = 709.16 ($C_{48}H_{27}N_3S_2$ = 709.88) | 1-3-1-S-(10) | m/z = 709.16 ($C_{48}H_{27}N_3S_2$ = 709.88) |
| 1-3-1-S-(11) | m/z = 709.16 ($C_{48}H_{27}N_3S_2$ = 709.88) | 1-3-1-S-(12) | m/z = 709.16 ($C_{48}H_{27}N_3S_2$ = 709.88) |
| 1-3-1-S-(13) | m/z = 683.15 ($C_{46}H_{25}N_3S_2$ = 683.84) | 1-3-1-S-(14) | m/z = 683.15 ($C_{45}H_{25}N_3S_2$ = 683.84) |
| 1-3-1-S-(15) | m/z = 748.18 ($C_{50}H_{28}N_4S_2$ = 748.91) | 1-3-1-S-(16) | m/z = 673.13 ($C_{44}H_{23}N_3OS_2$ = 673.80) |
| 1-3-1-S-(17) | m/z = 673.13 ($C_{44}H_{23}N_3OS_2$ = 673.80) | 1-3-1-S-(18) | m/z = 689.11 ($C_{44}H_{23}N_3S_3$ = 689.87) |
| 1-3-1-S-(19) | m/z = 689.11 ($C_{44}H_{23}N_3S_3$ = 689.87) | 1-3-1-S-(20) | m/z = 721.08 ($C_{44}H_{23}N_3S_4$ = 721.93) |
| 1-3-1-S-(21) | m/z = 683.15 ($C_{46}H_{25}N_3S_2$ = 683.84) | 1-3-1-S-(22) | m/z = 709.16 ($C_{48}H_{27}N_3S_2$ = 709.88) |
| 1-3-1-S-(23) | m/z = 739.12 ($C_{48}H_{25}N_3S_3$ = 739.93) | | |
| 1-3-2-O-(1) | m/z = 567.14 ($C_{38}H_{21}N_3OS$ = 567.66) | 1-3-2-O-(2) | m/z = 572.17 ($C_{38}H_{16}D_5N_3OS$ = 572.69) |
| 1-3-2-O-(3) | m/z = 568.14 ($C_{37}H_{20}N_4OS$ = 568.65) | 1-3-2-O-(4) | m/z = 643.17 ($C_{44}H_{25}N_3OS$ = 643.75) |
| 1-3-2-O-(5) | m/z = 643.17 ($C_{44}H_{25}N_3OS$ = 643.75) | 1-3-2-O-(6) | m/z = 617.16 ($C_{42}H_{23}N_3OS$ = 617.72) |
| 1-3-2-O-(7) | m/z = 617.16 ($C_{42}H_{23}N_3OS$ = 617.72) | 1-3-2-O-(8) | m/z = 719.20 ($C_{50}H_{29}N_3S$ = 719.85) |
| 1-3-2-O-(9) | m/z = 693.19 ($C_{48}H_{27}N_3OS$ = 693.81) | 1-3-2-O-(10) | m/z = 693.19 ($C_{48}H_{27}N_3OS$ = 693.81) |
| 1-3-2-O-(11) | m/z = 693.19 ($C_{48}H_{27}N_3OS$ = 693.81) | 1-3-2-O-(12) | m/z = 693.19 ($C_{48}H_{27}N_3OS$ = 693.81) |
| 1-3-2-O-(13) | m/z = 667.17 ($C_{46}H_{25}N_3OS$ = 667.78) | 1-3-2-O-(14) | m/z = 667.17 ($C_{46}H_{25}N_3OS$ = 667.78) |
| 1-3-2-O-(15) | m/z = 732.20 ($C_{50}H_{28}N_4OS$ = 732.85) | 1-3-2-O-(16) | m/z = 657.15 ($C_{44}H_{23}N_3O_2S$ = 657.74) |
| 1-3-2-O-(17) | m/z = 657.15 ($C_{44}H_{23}N_3O_2S$ = 657.74) | 1-3-2-O-(18) | m/z = 673.13 ($C_{44}H_{23}N_3OS_2$ = 673.80) |
| 1-3-2-O-(19) | m/z = 673.13 ($C_{44}H_{23}N_3OS_2$ = 673.80) | 1-3-2-O-(20) | m/z = 705.10 ($C_{44}H_{23}N_3OS_3$ = 705.87) |
| 1-3-2-O-(21) | m/z = 667.17 ($C_{46}H_{25}N_3OS$ = 667.78) | 1-3-2-O-(2) | m/z = 572.17 ($C_{38}H_{16}D_5N_3OS$ = 572.69) |
| 1-3-2-S-(1) | m/z = 583.12 ($C_{38}H_{21}N_3S_2$ = 583.72) | 1-3-2-S-(2) | m/z = 588.15 ($C_{38}H_{16}D_5N_3S_2$ = 588.75) |
| 1-3-2-S-(3) | m/z = 584.11 ($C_{37}H_{20}N_4S_2$ = 584.71) | 1-3-2-S-(4) | m/z = 659.15 ($C_{44}H_{25}N_3S_2$ = 659.82) |
| 1-3-2-S-(5) | m/z = 659.15 ($C_{44}H_{25}N_3S_2$ = 659.82) | 1-3-2-S-(6) | m/z = 633.13 ($C_{42}H_{23}N_3S_2$ = 633.78) |
| 1-3-2-S-(7) | m/z = 633.13 ($C_{42}H_{23}N_3S_2$ = 633.78) | 1-3-2-S-(8) | m/z = 735.18 ($C_{50}H_{29}N_3S_2$ = 735.92) |
| 1-3-2-S-(9) | m/z = 709.16 ($C_{48}H_{27}N_3S_2$ = 709.88) | 1-3-2-S-(10) | m/z = 709.16 ($C_{48}H_{27}N_3S_2$ = 709.88) |
| 1-3-2-S-(11) | m/z = 709.16 ($C_{48}H_{27}N_3S_2$ = 709.88) | 1-3-2-S-(12) | m/z = 709.16 ($C_{48}H_{27}N_3S_2$ = 709.88) |
| 1-3-2-S-(13) | m/z = 683.15 ($C_{46}H_{25}N_3S_2$ = 683.84) | 1-3-2-S-(14) | m/z = 683.15 ($C_{46}H_{25}N_3S_2$ = 683.84) |
| 1-3-2-S-(15) | m/z = 748.18 ($C_{50}H_{25}N_4S_2$ = 748.91) | 1-3-2-S-(16) | m/z = 673.13 ($C_{44}H_{23}N_3OS_2$ = 673.80) |
| 1-3-2-S-(17) | m/z = 673.13 ($C_{44}H_{23}N_3OS_2$ = 673.80) | 1-3-2-S-(18) | m/z = 689.11 ($C_{44}H_{23}N_3S_3$ = 689.87) |
| 1-3-2-S-(19) | m/z = 689.11 ($C_{44}H_{23}N_3S_3$ = 689.87) | 1-3-2-S-(20) | m/z = 721.08 ($C_{44}H_{23}N_3S_4$ = 721.93) |
| 1-3-2-S-(21) | m/z = 683.15 ($C_{46}H_{25}N_3S_2$ = 683.84) | 1-3-2-S-(22) | m/z = 709.16 ($C_{48}H_{27}N_3S_2$ = 709.88) |
| 1-3-2-S-(23) | m/z = 826.22 ($C_{56}H_{34}N_4S_2$ = 827.03) | | |

Synthesis Example 3

Final products represented by Formula 8 according to the present invention are synthesized by reacting Sub 5 or Sub 6 and Sub 2 as shown in Reaction Scheme 2, but are not limited thereto.

<Reaction Scheme 66>

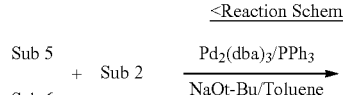

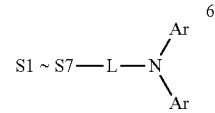

Final Product 3

(L is $L^2$ to $L^4$ defined in formulas 8-1, 8-2 and 8-3, Ar is $Ar^4$, $Ar^5$)

1. Synthesis Example of Sub 5

<Reaction Scheme 67>

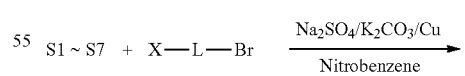

Here, S1 to S7 are as follows.

S1
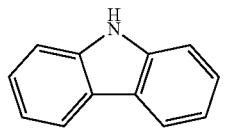

S2
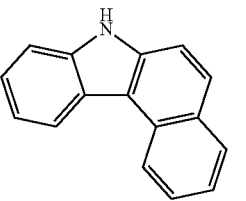

S3
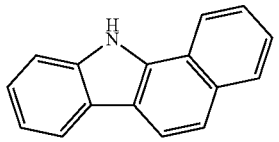

S4
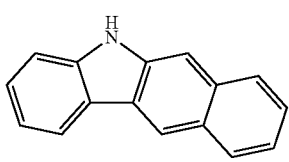

S5
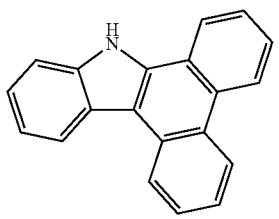

S6
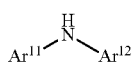

S7
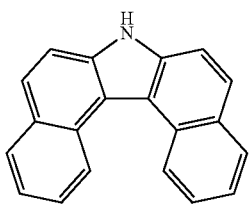

1) Synthesis Example of Sub 5-1-1 (L=biphenyl)

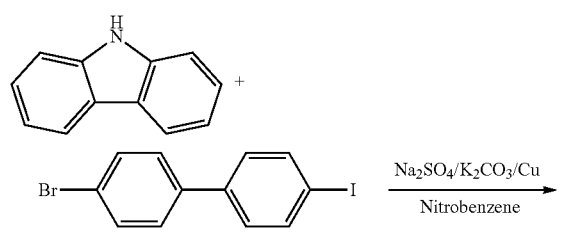

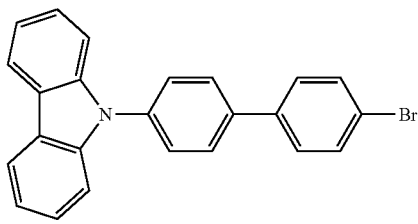

Sub 5-1-1

The starting material 9H-carbazole (50.16 g, 300 mmol) was dissolved in nitrobenzene (600 ml), and then, 4-bromo-4'-iodo-1,1'-biphenyl (129.2 g, 360 mmol), Na₂SO₄ (42.6 g, 300 mmol), K₂CO₃ (41.4 g, 300 mmol), Cu (5.72 g, 90 mmol) were added and stirred at 200° C. When the reaction was completed, nitrobenzene was removed by distillation, and then the reaction product was extracted with CH₂Cl₂ and water. Then, the organic layer was dried with MgSO₄ and concentrated, and the concentrate was passed through silica gel column and recrystallized to obtain 80.05 g (yield: 67%) of the product.

2) Synthesis Example of Sub 5-1-2 (L=9,9-dimethyl-9H-fluorene)

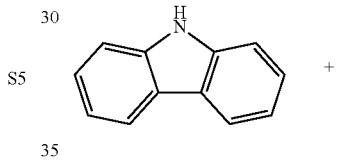

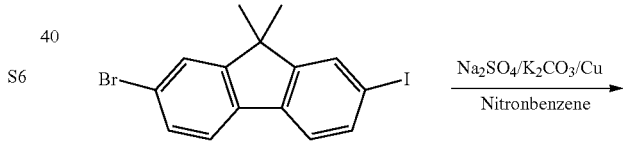

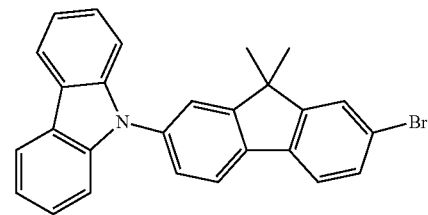

Sub 5-1-2

2-bromo-7-iodo-9,9-dimethyl-9H-fluorene (143.7 g, 360 mmol), Na₂SO₄ (42.6 g, 300 mmol), K₂CO₃ (41.4 g, 300 mmol), Cu (5.72 g, 90 mmol), nitrobenzene were added to the starting material 9H-carbazole (50.16 g, 300 mmol), and then 88.11 g (yield: 67%) of the product was obtained by using the same manner as described above for the synthesis of Sub 5-1-1.

3) Synthesis Example of Sub 5-1-3 (L=9,9-dimethyl-9H-fluorene)

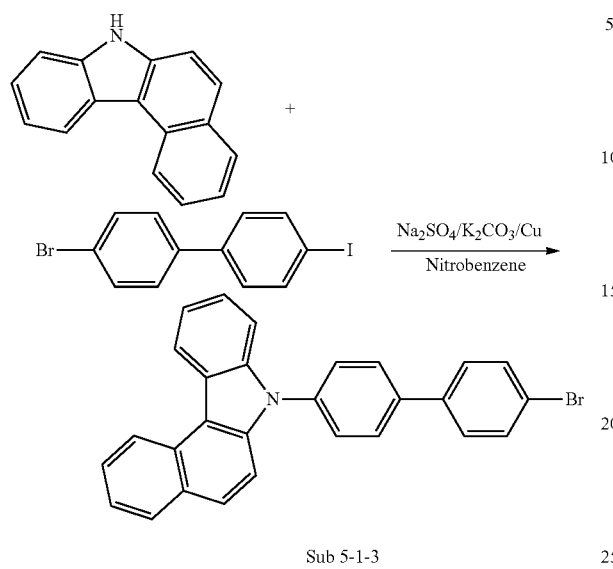

Sub 5-1-3

4-bromo-4'-iodo-1,1'-biphenyl (129.2 g, 360 mmol), Na₂SO₄ (42.6 g, 300 mmol), K₂CO₃ (41.4 g, 300 mmol), Cu (5.72 g, 90 mmol), nitrobenzene were added to the starting material 7H-benzo[c]carbazole (65.18 g, 300 mmol), and then 92.8 g (yield: 69%) of the product was obtained by using the same manner as described above for the synthesis of Sub 5-1-1.

4) Synthesis Example of Sub 5-1-4 (L=9,9-dimethyl-9H-fluorene)

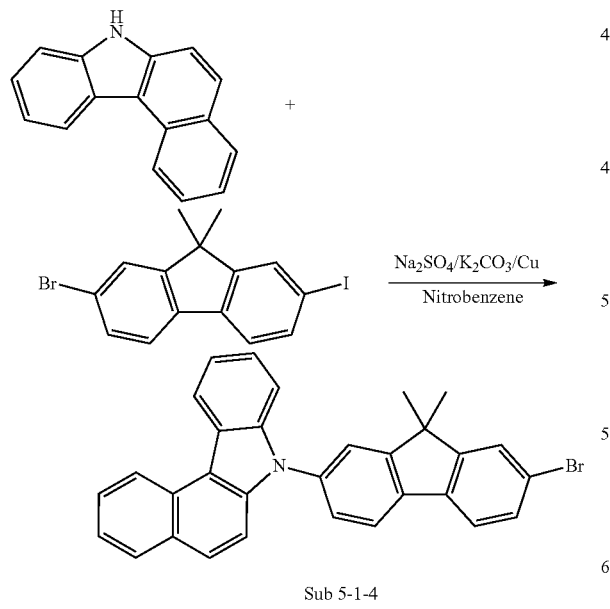

Sub 5-1-4

2-bromo-7-iodo-9,9-dimethyl-9H-fluorene (143.7 g, 360 mmol), Na₂SO₄ (42.6 g, 300 mmol), K₂CO₃ (41.4 g, 300 mmol), Cu (5.72 g, 90 mmol), nitrobenzene were added to the starting material 7H-benzo[c]carbazole (65.18 g, 300 mmol), and then 95.24 g (yield: 65%) of the product was obtained by using the same manner as described above for the synthesis of Sub 5-1-1.

5) Synthesis Example of Sub 5-1-5 (L=biphenyl)

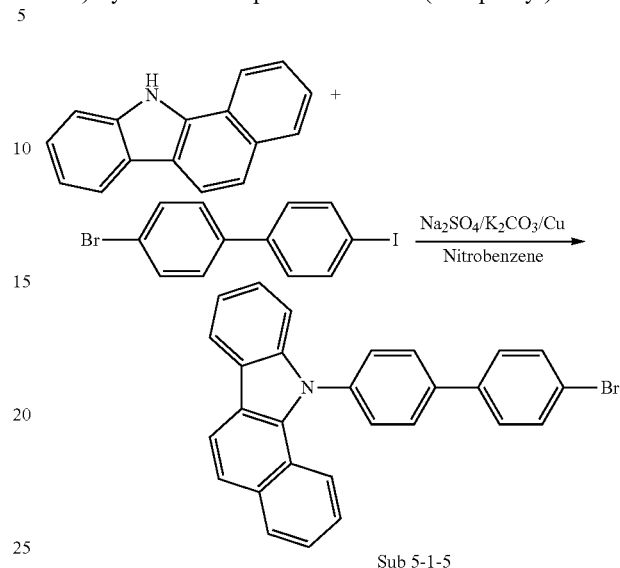

Sub 5-1-5

4-bromo-4'-iodo-1,1'-biphenyl (129.2 g, 360 mmol), Na₂SO₄ (42.6 g, 300 mmol), K₂CO₃ (41.4 g, 300 mmol), Cu (5.72 g, 90 mmol), nitrobenzene were added to the starting material 11H-benzo[a]carbazole (65.18 g, 300 mmol), and then 80.05 g (yield: 62%) of the product was obtained by using the same manner as described above for the synthesis of Sub 5-1-1.

6) Synthesis Example of Sub 5-1-6 (L=9,9-dimethyl-9H-fluorene)

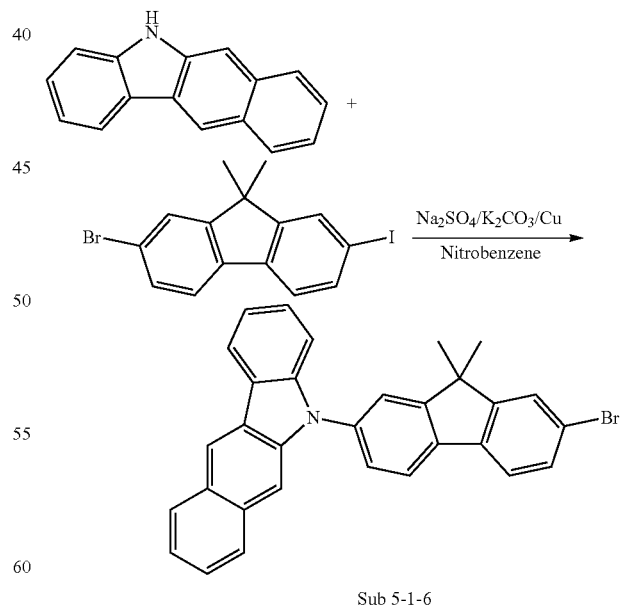

Sub 5-1-6

2-bromo-7-iodo-9,9-dimethyl-9H-fluorene (143.7 g, 360 mmol), Na₂SO₄ (42.6 g, 300 mmol), K₂CO₃ (41.4 g, 300 mmol), Cu (5.72 g, 90 mmol), nitrobenzene were added to the starting material 5H-benzo[b]carbazole (65.18 g, 300 mmol), and then 93.78 g (yield: 64%) of the product was obtained by using the same manner as described above for the synthesis of Sub 5-1-1.

7) Synthesis Example of Sub 5-1-7 (L=biphenyl)

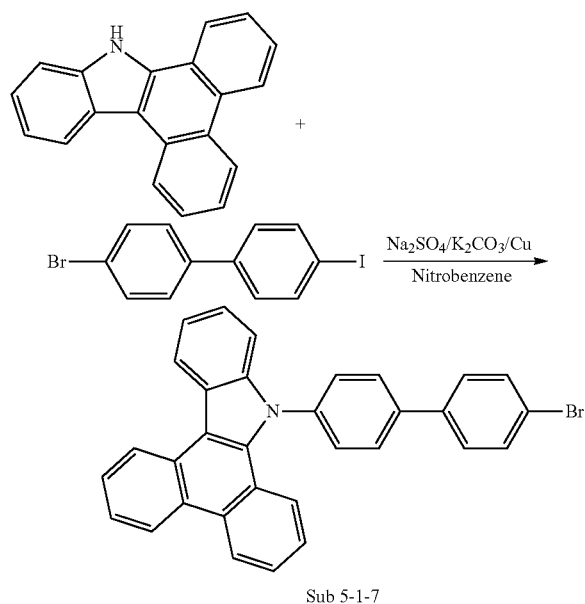

Sub 5-1-7

4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene were added to the starting material 9H-dibenzo[a,c]carbazole (80.2 g, 300 mmol), and then 98.7 g (yield: 66%) of the product was obtained by using the same manner as described above for the synthesis of Sub 5-1-1.

8) Synthesis Example of Sub 5-1-8 (L=biphenyl)

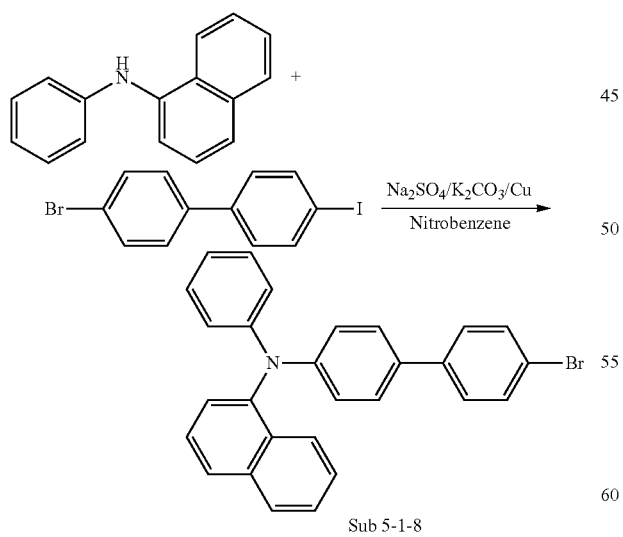

Sub 5-1-8

4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene were added to the starting material N-phenylnaphthalen-1-amine (65.8 g, 300 mmol), and then 89.2 g (yield: 66%) of the product was obtained by using the same manner as described above for the synthesis of Sub 5-1-1.

9) Synthesis Example of Sub 5-1-9 (L=9,9-dimethyl-9H-fluorene)

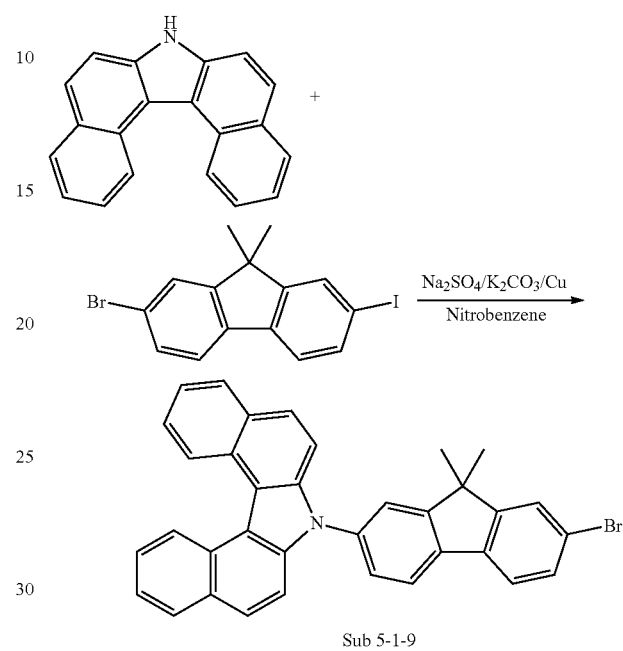

Sub 5-1-9

2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), nitrobenzene were added to the starting material 7H-dibenzo[c,g]carbazole (80.2 g, 300 mmol), and then 98.5 g (yield: 61%) of the product was obtained by using the same manner as described above for the synthesis of Sub 5-1-1.

2. Synthesis Example of Sub 6

<Reaction Scheme 68>

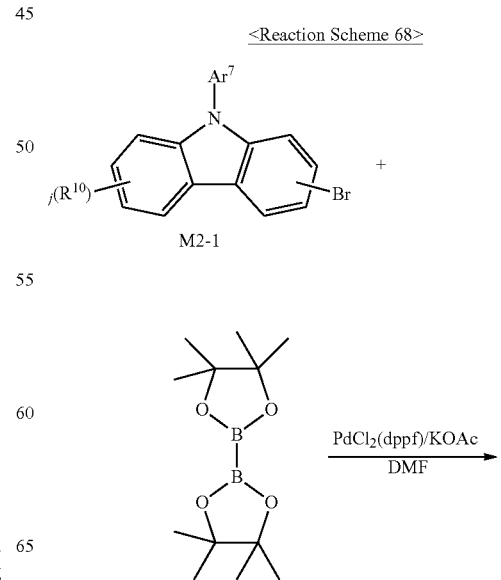

-continued

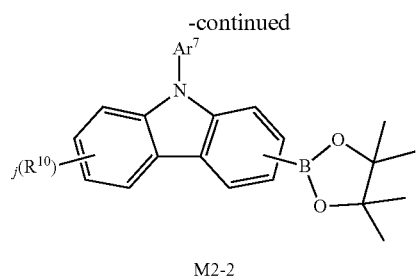

M2-2

I—L2—Br $\xrightarrow{\text{Pd(PPh}_3)_4/\text{NaOH}}{\text{THF/H}_2\text{O}}$

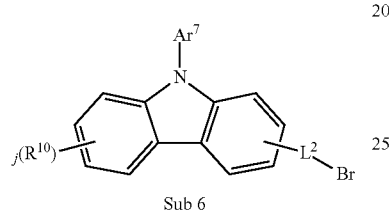

Sub 6

1) Synthesis Example of M2-2-1

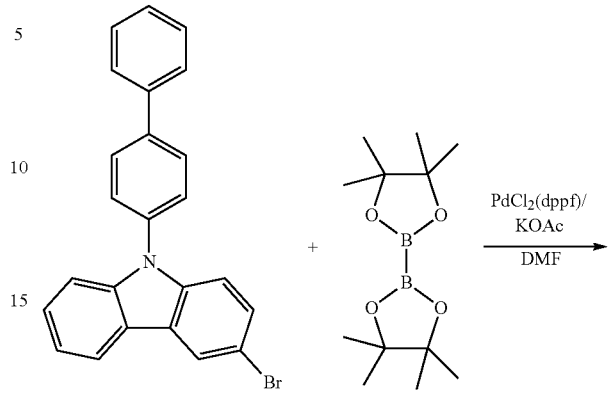

M2-2-1

3-bromo-9-phenyl-9H-carbazole (45.1 g, 140 mmol) was dissolved in DMF 980mL, and Bispinacolborate (39.1 g, 154 mmol), PdCl$_2$(dppf) catalyst (3.43 g, 4.2 mmol), KOAc (41.3 g, 420 mmol) were added in order, then, borate compound was synthesized after stirring for 24 hours. Then, the obtained compound was separated by silica gel column and recrystallization to obtain 35.2 g (68%) of borate compound.

2) Synthesis Example of M2-2-2

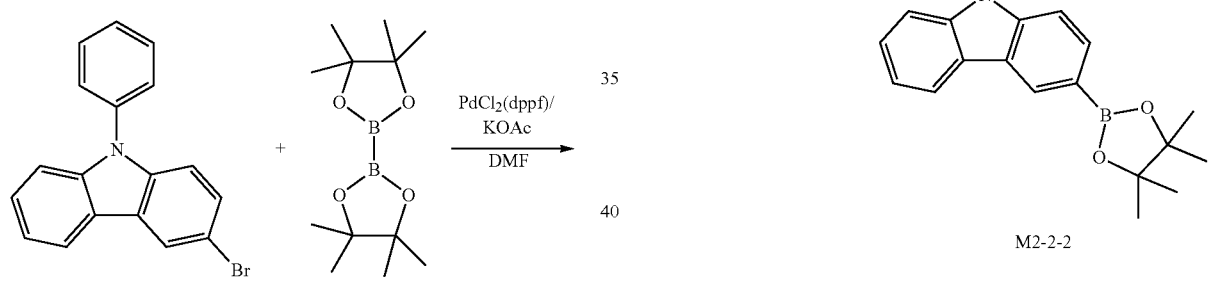

M2-2-2

40 g (64%) of the product was obtained by the same experimental procedure as M2-2-1.

3) Synthesis Example of Sub 6-1-1

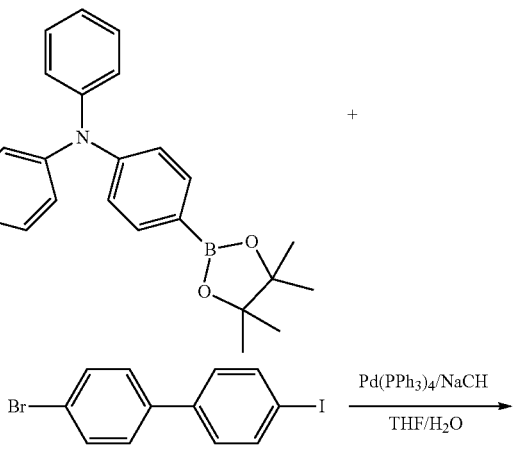

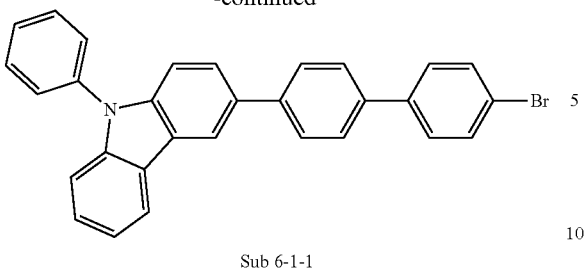

Sub 6-1-1

M2-2-1 (29.5 g, 80 mmol) was dissolved in THF 360 mL, and 4-bromo-4'-iodo-1,1'-biphenyl (30.16 g, 84 mmol), Pd(PPh$_3$)$_4$ (2.8 g, 2.4 mmol), NaOH (9.6 g, 240 mmol), water 180 mL were added, then, refluxing and stirring are followed. When the reaction was completed, the reaction product was extracted with ether and water, and then, the organic layer was dried with MgSO$_4$ and concentrated. Then, the concentrate was passed through silica gel column and recrystallized to obtain 26.56 g (70%) of the product.

4) Synthesis Example of Sub 6-1-2

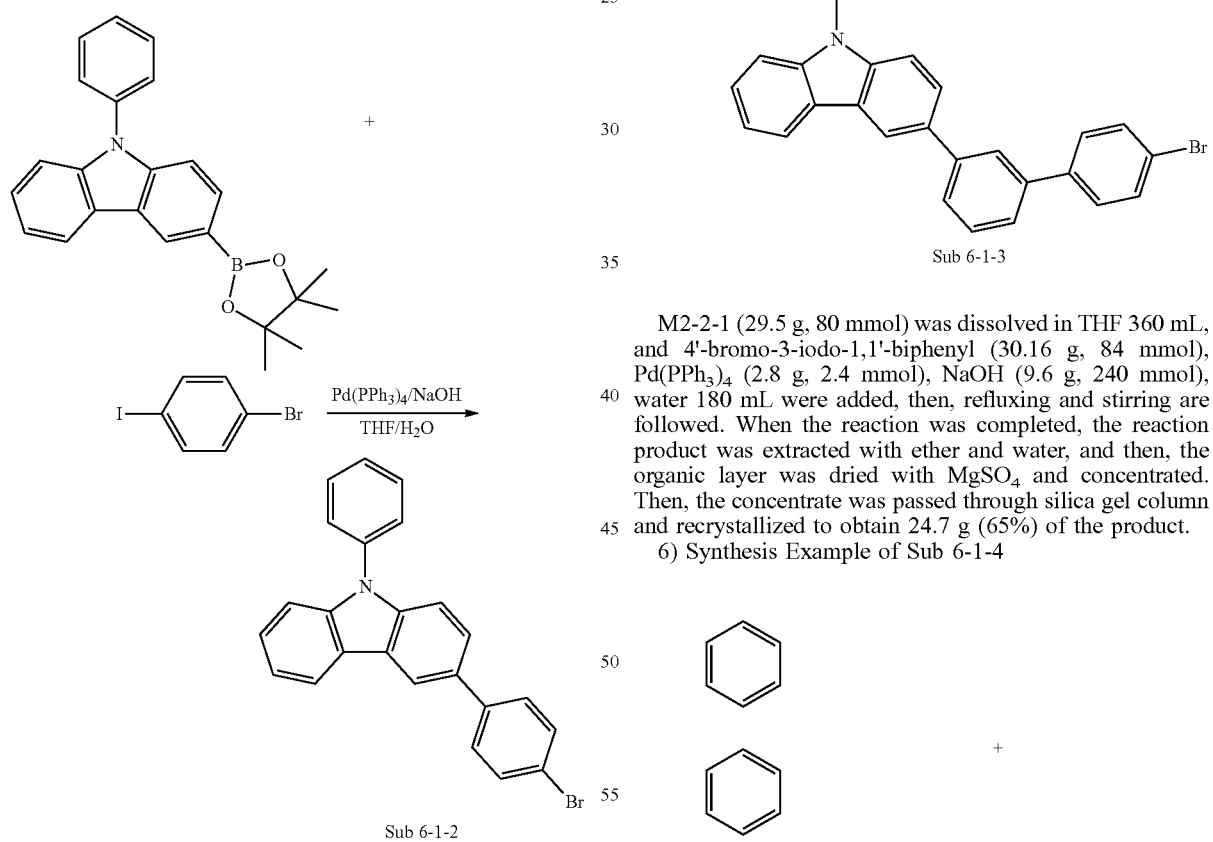

Sub 6-1-2

M2-2-1 (29.5 g, 80 mmol) was dissolved in THF 360 mL, and 1-bromo-4-iodobenzene (23.8 g, 84 mmol), Pd(PPh$_3$)$_4$ (2.8 g, 2.4 mmol), NaOH (9.6 g, 240 mmol), water 180 mL were added, then, refluxing and stirring are followed. When the reaction was completed, the reaction product was extracted with ether and water, and then, the organic layer was dried with MgSO$_4$ and concentrated. Then, the concentrate was passed through silica gel column and recrystallized to obtain 22.9 g (72%) of the product.

5) Synthesis Example of Sub 6-1-3

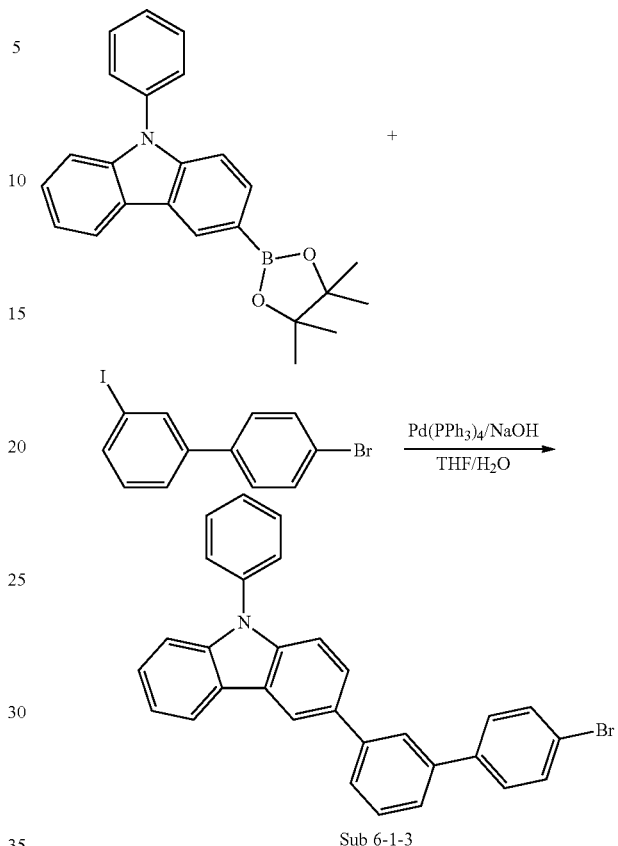

Sub 6-1-3

M2-2-1 (29.5 g, 80 mmol) was dissolved in THF 360 mL, and 4'-bromo-3-iodo-1,1'-biphenyl (30.16 g, 84 mmol), Pd(PPh$_3$)$_4$ (2.8 g, 2.4 mmol), NaOH (9.6 g, 240 mmol), water 180 mL were added, then, refluxing and stirring are followed. When the reaction was completed, the reaction product was extracted with ether and water, and then, the organic layer was dried with MgSO$_4$ and concentrated. Then, the concentrate was passed through silica gel column and recrystallized to obtain 24.7 g (65%) of the product.

6) Synthesis Example of Sub 6-1-4

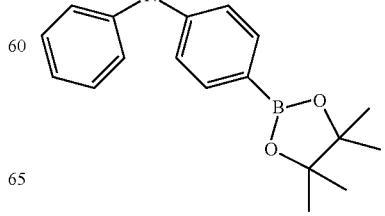

433
-continued

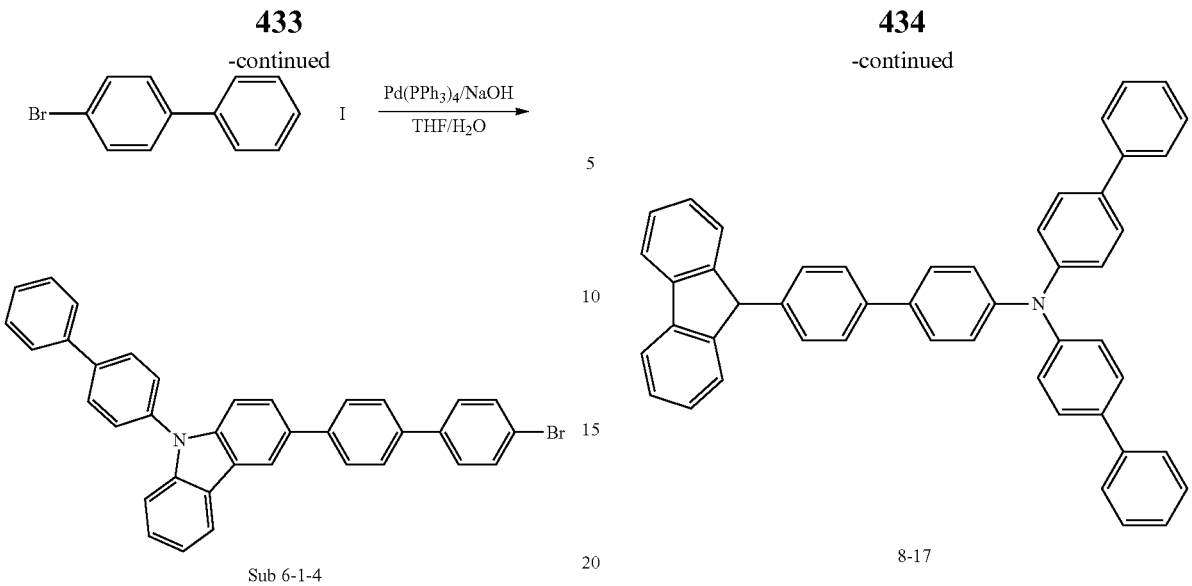

Sub 6-1-4

434
-continued

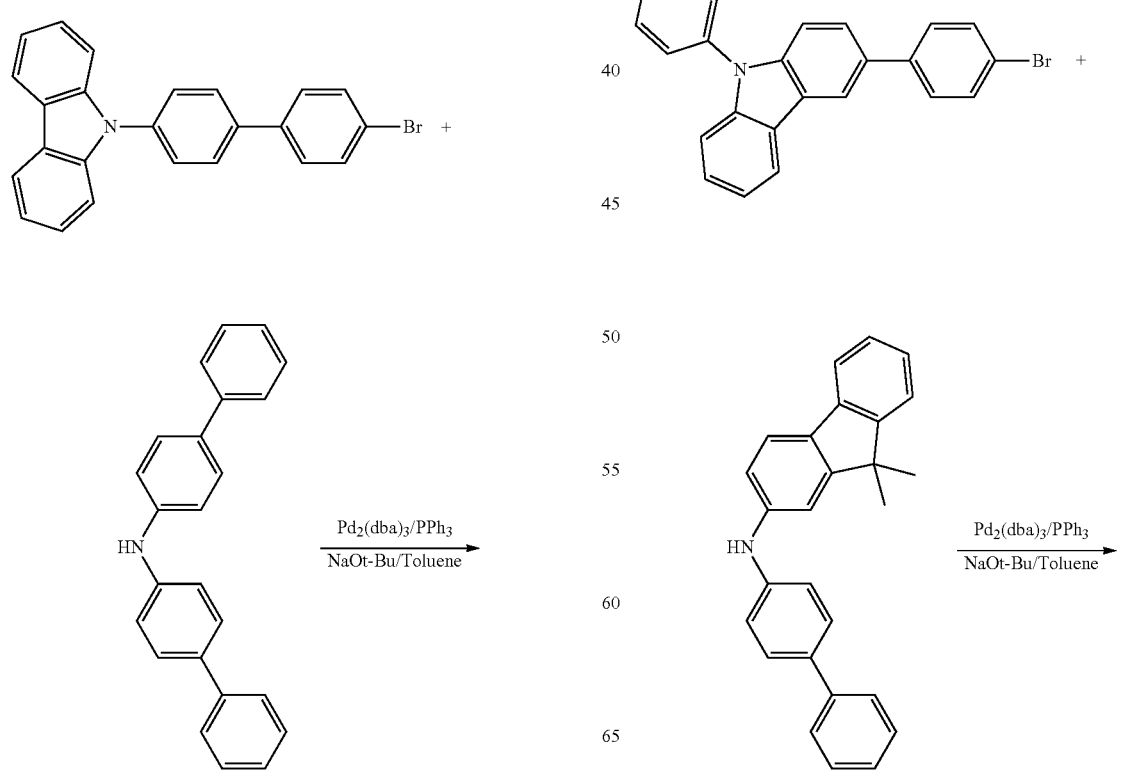

8-17

M2-2-2 (35.63 g, 80 mmol) obtained in the above synthesis was dissolved in THF 360 mL, and 4-bromo-4'-iodo-1,1'-biphenyl (30.16 g, 84 mmol), Pd(PPh$_3$)$_4$ (2.8 g, 2.4 mmol), NaOH (9.6 g, 240 mmol), water 180 mL were added, then, refluxing and stirring are followed. When the reaction was completed, the reaction product was extracted with ether and water, and then, the organic layer was dried with MgSO$_4$ and concentrated. Then, the concentrate was passed through silica gel column and recrystallized to obtain 29.51 g (67%) of the product.

3. Synthesis Example of Final Products (1) Synthesis Example of 8-17

9-(4'-bromo-[1,1'-biphenyl]-4-yl)-9H-carbazole(9.6 g, 24 mmol) was dissolved in toluene, and di([1,1'-biphenyl]-4-yl)amine(6.4 g, 20 mmol), Pd$_2$(dba)$_3$ (0.05 eq.), PPh$_3$ (0.1 eq.), NaOt-Bu (3 eq.) were added, then, refluxing and stirring are followed at 100° C. for 24 hours. When the reaction was completed, the reaction product was extracted with ether and water, and then, the organic layer was dried with MgSO$_4$ and concentrated. Then, the concentrate was passed through silica gel column and recrystallized to obtain 12.9 g (yield: 84%) of the product.

(2) Synthesis Example of 8-32

-continued

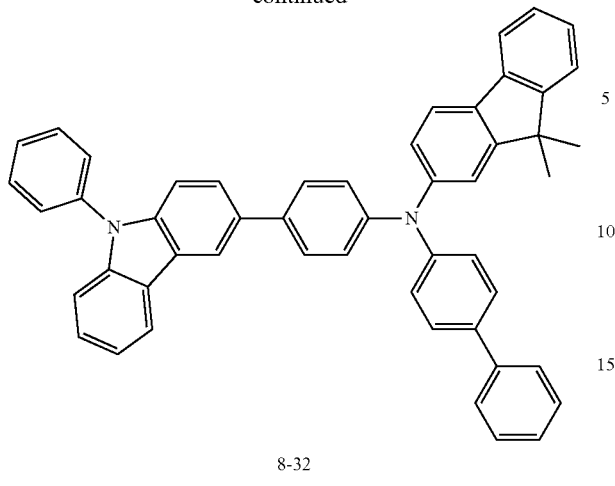

8-32

3-(4-bromophenyl)-9-phenyl-9H-carbazole (9.6 g, 24 mmol) was dissolved in toluene, and N-([1,1'-biphenyl]-4-yl)-9,9-dimethyl-9H-fluoren-2-amine (7.2 g, 20 mmol), Pd$_2$(dba)$_3$ (0.05 eq.), PPh$_3$ (0.1 eq.), NaOt-Bu (3 eq.) were added, then, refluxing and stirring are followed at 100° C. for 24 hours. When the reaction was completed, the reaction product was extracted with ether and water, and then, the organic layer was dried with MgSO$_4$ and concentrated. Then, the concentrate was passed through silica gel column and recrystallized to obtain 13.8 g (yield: 85%) of the product.

(3) Synthesis Example of 8-61

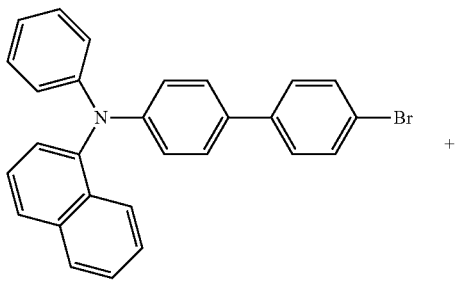

-continued

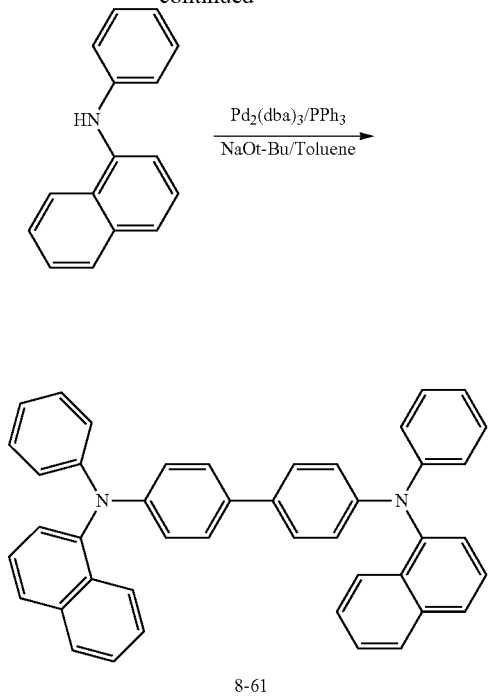

8-61

N-(4'-bromo-[1,1'-biphenyl]-4-yl)-N-phenylnaphthalen-1-amine (10.8 g, 24 mmol) was dissolved in toluene, and N-phenylnaphthalen-1-amine (4.4 g, 20 mmol), Pd$_2$(dba)$_3$ (0.05 eq.), PPh$_3$ (0.1 eq.), NaOt-Bu (3 eq.) were added, then, refluxing and stirring are followed at 100° C. for 24 hours. When the reaction was completed, the reaction product was extracted with ether and water, and then, the organic layer was dried with MgSO$_4$ and concentrated. Then, the concentrate was passed through silica gel column and recrystallized to obtain 11.4 g (yield: 81%) of the product.

On the other hand, the FD-MS values of compounds represented by formula 8 according to the above synthesis examples are shown in Table 6 below.

TABLE 6

| compound | FD-MS | compound | FD-MS |
|---|---|---|---|
| 8-17 | m/z = 638.27 ($C_{48}H_{34}N_2$ = 638.80) | 8-20 | m/z = 678.30 ($C_{51}H_{38}N_2$ = 678.86) |
| 8-21 | m/z = 802.33 ($C_{61}H_{42}N_2$ = 803.00) | 8-22 | m/z = 800.32 ($C_{61}H_{40}N_2$ = 800.98) |
| 8-32 | m/z = 678.30 ($C_{51}H_{38}N_2$ = 678.86) | 8-33 | m/z = 802.33 ($C_{61}H_{42}N_2$ = 803.00) |
| 8-34 | m/z = 800.32 ($C_{61}H_{40}N_2$ = 800.98) | 8-43 | m/z = 714.30 ($C_{54}H_{38}N_2$ = 714.89) |
| 8-44 | m/z = 754.33 ($C_{57}H_{42}N_2$ = 754.96) | 8-45 | m/z = 878.37 ($C_{67}H_{46}N_2$ = 879.10) |
| 8-46 | m/z = 876.35 ($C_{67}H_{44}N_2$ = 877.08) | 8-47 | m/z = 744.26 ($C_{54}H_{36}N_2S$ = 744.94) |
| 8-52 | m/z = 826.33 ($C_{63}H_{42}N_2$ = 827.02) | 8-53 | m/z = 824.32 ($C_{63}H_{40}N_2$ = 825.01) |
| 8-54 | m/z = 688.29 ($C_{52}H_{36}N_2$ = 688.86) | 8-55 | m/z = 728.32 ($C_{55}H_{40}N_2$ = 728.92) |
| 8-57 | m/z = 778.33 ($C_{59}H_{42}N_2$ = 778.98) | 8-58 | m/z = 902.37 ($C_{69}H_{46}N_2$ = 903.12) |
| 8-59 | m/z = 900.35 ($C_{59}H_{44}N_2$ = 901.10) | 8-60 | m/z = 538.24 ($C_{40}H_{30}N_2$ = 538.68) |
| 8-61 | m/z = 588.26 ($C_{44}H_{32}N_2$ = 588.74) | 8-62 | m/z = 588.26 ($C_{44}H_{32}N_2$ = 588.74) |
| 8-63 | m/z = 614.27 ($C_{46}H_{34}N_2$ = 614.78) | | |

Fabrication and Evaluation of Organic Electronic Element

Example 1

Red OLED (A Hole Transport Layer, Phosphorescent Host)

First, an ITO layer (anode) was formed on a glass substrate, and then $N^1$-(naphthalen-2-yl)-$N^4,N^4$-bis(4-(naphthalen-2-yl(phenyl)amino)phenyl)-$N^1$-phenylbenzene-1,4-diamine (hereinafter, "2-TNATA") was vacuum-deposited on the ITO layer to form a hole injection layer with a thickness of 60 nm. Subsequently, compound A1 of the present invention was vacuum-deposited with a thickness of 60 nm on the hole injection layer to form a hole transport layer. Then, a light emitting layer with a thickness of 30 nm was formed on the hole transport layer by using compound 1-1-1-S-(1) of the present invention as a host material and bis-(1-phenylisoquinolyl)iridium(III)acetylacetonate (hereinafter, "$(piq)_2Ir(acac)$") as a dopant material in a weight ratio of 95:5.

Subsequently, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "$Alq_3$") was formed with a thickness of 40 nm to form an electron transport layer. Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

Example 2 to Example 36

Red OLED (A Hole Transport Layer, Phosphorescent Host)

The OLEDs were fabricated in the same manner as described in Example 1 except that the compounds represented by formula 1 described in Table 7, instead of the compound A1 of the present invention, were used as hole transporting material and the compounds represented by formula 2 described in Table 7, instead of the compound 1-1-1-S-(1) of the present invention, were used as host material of a light emitting layer.

Comparative Example 1

The OLEDs were fabricated in the same manner as described in Example 1 except that the Comparative compound A instead of the compound A1 of the present invention was used as hole transporting material and the Comparative compound C instead of the compound 1-1-1-S-(1) of the present invention, was used as host material of a light emitting layer.

Comparative Example 2

The OLED were fabricated in the same manner as described in Example 1 except that the Comparative compound B instead of the compound A1 of the present invention was used as hole transporting material and the Comparative compound C instead of the compound 1-1-1-S-(1) of the present invention, was used as host material of a light emitting layer.

Comparative Example 3

The OLED were fabricated in the same manner as described in Example 1 except that the Comparative compound A instead of the compound A1 of the present invention was used as hole transporting material.

Comparative Example 4

The OLED were fabricated in the same manner as described in Example 1 except that the Comparative compound B instead of the compound A1 of the present invention was used as hole transporting material.

Comparative Example 5

The OLED were fabricated in the same manner as described in Example 1 except that the Comparative compound C instead of the compound 1-1-1-S-(1) of the present invention was used as host material of a light emitting layer.

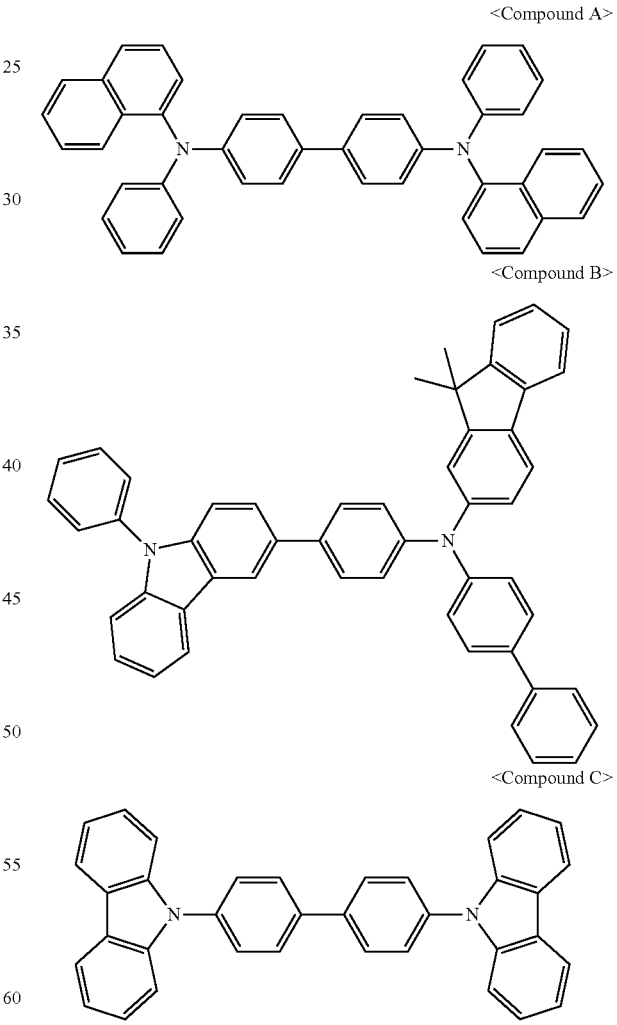

<Compound A>

<Compound B>

<Compound C>

Electroluminescence (EL) characteristics were measured with a PR-650(Photoresearch) by applying a forward bias DC voltage to the OLEDs prepared in Examples 1 to 36 of the present invention and Comparative Examples 1 to 5. And, the T95 life time was measured using a life time measuring apparatus manufactured by Macscience Inc. at reference brightness of 2500 cd/m². The measurement results are shown in Tables 7 below.

TABLE 7

| | HTL com. | Phosphorescent host com. | Voltage (V) | Current Density (mA/cm²) | Brightness (cd/m²) | Efficiency (cd/A) | Lifetime T(95) |
|---|---|---|---|---|---|---|---|
| comp. Ex. (1) | comp. Com. A | comp. Com. C | 6.8 | 32.9 | 2500.0 | 7.6 | 79.7 |
| comp. Ex. (2) | comp. Com. B | comp. Com. C | 6.6 | 31.6 | 2500.0 | 7.9 | 83.7 |
| comp. Ex. (3) | comp. Com. A | Com. 1-1-1-S-(1) | 6.6 | 30.1 | 2500.0 | 8.3 | 87.1 |
| comp. Ex. (4) | comp. Com. B | Com. 1-1-1-S-(1) | 6.4 | 28.1 | 2500.0 | 8.9 | 97.9 |
| comp. Ex. (5) | Com. (A258) | comp. Com. C | 6.5. | 29.4 | 2500.0 | 8.5 | 86.5 |
| Ex. (1) | Com. (A1) | Com. 1-1-1-S-(1) | 5.7 | 18.2 | 2500.0 | 13.7 | 113.6 |
| Ex. (2) | Com. (A1) | Com. 1-1-1-S-(7) | 5.8 | 19.0 | 2500.0 | 13.2 | 118.7 |
| Ex. (3) | Com. (A1) | Com. 1-1-2-O-(5) | 5.7 | 18.9 | 2500.0 | 13.2 | 119.3 |
| Ex. (4) | Com. (A1) | Com. 1-1-2-S-(17) | 5.8 | 18.0 | 2500.0 | 13.9 | 112.4 |
| Ex. (5) | Com. (A1) | Com. 1-1-3-O-(6) | 5.7 | 19.0 | 2500.0 | 13.2 | 105.8 |
| Ex. (6) | Com. (A1) | Com. 1-1-3-S-(1) | 5.7 | 18.3 | 2500.0 | 13.6 | 107.8 |
| Ex. (7) | Com. (A5) | Com. 1-1-1-S-(1) | 5.7 | 17.9 | 2500.0 | 14.0 | 111.3 |
| Ex. (8) | Com. (A5) | Com. 1-1-1-S-(7) | 5.8 | 18.2 | 2500.0 | 13.8 | 108.2 |
| Ex. (9) | Com. (A5) | Com. 1-1-2-O-(5) | 5.7 | 19.1 | 2500.0 | 13.1 | 118.4 |
| Ex. (10) | Com. (A5) | Com. 1-1-2-S-(17) | 5.8 | 18.5 | 2500.0 | 13.5 | 116.1 |
| Ex. (11) | Com. (A5) | Com. 1-1-3-O-(6) | 5.7 | 17.9 | 2500.0 | 14.0 | 113.1 |
| Ex. (12) | Com. (A5) | Com. 1-1-3-S-(1) | 5.7 | 18.6 | 2500.0 | 13.5 | 112.9 |
| Ex. (13) | Com. (A258) | Com. 1-1-1-S-(1) | 5.5 | 16.3 | 2500.0 | 15.4 | 115.3 |
| Ex. (14) | Com. (A258) | Com. 1-1-1-S-(7) | 5.5 | 15.6 | 2500.0 | 16.0 | 105.4 |
| Ex. (15) | Com. (A258) | Com. 1-1-2-O-(5) | 5.6 | 16.2 | 2500.0 | 15.4 | 117.6 |
| Ex. (16) | Com. (A258) | Com. 1-1-2-S-(17) | 5.5 | 15.7 | 2500.0 | 15.9 | 108.2 |
| Ex. (17) | Com. (A258) | Com. 1-1-3-O-(6) | 5.5 | 16.3 | 2500.0 | 15.4 | 116.0 |
| Ex. (18) | Com. (A258) | Com. 1-1-3-S-(1) | 5.5 | 15.9 | 2500.0 | 15.7 | 118.9 |
| Ex. (19) | Com. (A296) | Com. 1-1-1-S-(1) | 5.5 | 16.6 | 2500.0 | 15.0 | 117.6 |
| Ex. (20) | Com. (A296) | Com. 1-1-1-S-(7) | 5.5 | 15.7 | 2500.0 | 15.9 | 117.6 |
| Ex. (21) | Com. (A296) | Com. 1-1-2-O-(5) | 5.5 | 16.2 | 2500.0 | 15.4 | 113.0 |
| Ex. (22) | Com. (A296) | Com. 1-1-2-S-(17) | 5.5 | 15.8 | 2500.0 | 15.9 | 105.9 |
| Ex. (23) | Com. (A296) | Com. 1-1-3-O-(6) | 5.6 | 15.9 | 2500.0 | 15.7 | 105.8 |
| Ex. (24) | Com. (A296) | Com. 1-1-3-S-(1) | 5.6 | 16.0 | 2500.0 | 15.6 | 108.7 |
| Ex. (25) | Com. (A321) | Com. 1-1-1-S-(1) | 5.8 | 22.5 | 2500.0 | 11.1 | 112.4 |
| Ex. (26) | Com. (A321) | Com. 1-1-1-S-(7) | 5.8 | 23.6 | 2500.0 | 10.6 | 112.3 |
| Ex. (27) | Com. (A321) | Com. 1-1-2-O-(5) | 5.9 | 23.5 | 2500.0 | 10.6 | 112.2 |
| Ex. (28) | Com. (A321) | Com. 1-1-2-S-(17) | 5.9 | 21.8 | 2500.0 | 11.5 | 108.4 |
| Ex. (29) | Com. (A321) | Com. 1-1-3-O-(6) | 5.9 | 24.4 | 2500.0 | 10.3 | 114.7 |
| Ex. (30) | Com. (A321) | Com. 1-1-3-S-(1) | 5.9 | 23.2 | 2500.0 | 10.8 | 107.6 |
| Ex. (31) | Com. (A389) | Com. 1-1-1-S-(1) | 5.8 | 22.7 | 2500.0 | 11.0 | 109.6 |
| Ex. (32) | Com. (A389) | Com. 1-1-1-S-(7) | 6.0 | 22.6 | 2500.0 | 11.0 | 107.2 |
| Ex. (33) | Com. (A389) | Com. 1-1-2-O-(5) | 5.8 | 23.7 | 2500.0 | 10.5 | 107.2 |
| Ex. (34) | Com. (A389) | Com. 1-1-2-S-(17) | 5.9 | 22.8 | 2500.0 | 10.9 | 108.3 |
| Ex. (35) | Com. (A389) | Com. 1-1-3-O-(6) | 5.9 | 21.0 | 2500.0 | 11.9 | 106.4 |
| Ex. (36) | Com. (A389) | Com. 1-1-3-S-(1) | 5.9 | 23.3 | 2500.0 | 10.7 | 106.5 |

From the results of the above table, it is found that luminous efficiency and lifetime of OLED are remarkably improved when the compound of the present invention represented by Formula 1 is used as material of a hole transport layer and the compound of the present invention represented by Formula 2 is used as phosphorescent host material of a light emitting layer.

That is, the organic electroluminescent element of the present invention according to Examples 1 to 36 showed remarkably excellent results in terms of driving voltage, the efficiency and the lifetime, comparing to Comparative Examples 1 and 2, Comparative Examples 3 and 4, and Comparative Example 5. Here, the compound of the present invention represented by Formula 1 is used as material of a hole transport layer and the compound of the present invention represented by Formula 2 is used as phosphorescent host material in Example 1 to 36, any one of Comparative compounds A and B is used as material of a hole transport layer and Comparative compound C is used as phosphorescent host material in Comparative Examples 1 and 2, any one of Comparative compounds A and B is used as material of a hole transport layer and the compound represented by Formula 1 is used as phosphorescent host material in Comparative Examples 3 and 4, and the compound of the present invention represented by Formula 1 is used as material of a hole transport layer and Comparative compound C is used as phosphorescent host material in Comparative Example 5.

This is because the compound of the present invention represented by the formula 1 has a faster mobility and a broad band gap as compared with the Comparative compounds A and B, and the compound of the present invention represented by the formula 2 has high stability and T1 values for holes as well as electrons as compared with the Comparative compounds C. Therefore, thanks to the combination of the two, more holes can be quickly and easily transferred to the light emitting layer, and thus the charge balance in the light emitting layer of holes and electrons is increased, so that light emission is performed well inside the light emitting layer rather than at the interface of the hole transporting layer. As a result, the deterioration of the ITO and HTL interfaces is also reduced, and it is considered that the driving voltage, efficiency and lifetime of the entire element are maximized. That is, it is believed that the combination of the compound of the present invention represented by the formula 1 and the compound of the present invention represented by the formula 2 is electrochemically synergistic to improve the performance of the element as a whole.

Example 37

Red OLED (A Hole Transport Layer, an Emission-Auxiliary Layer, Phosphorescent Host)

First, an ITO layer (anode) was formed on a glass substrate, and a film of 2-TNATA was vacuum-deposited on the ITO layer to form a hole injection layer with a thickness of 60 nm. Subsequently, the compound 8-17 of the present invention was vacuum-deposited with a thickness of 60 nm on the hole injection layer to form a hole transport layer.

Subsequently, a film of the compound A1 of the present invention was vacuum-deposited on the hole transport layer to form an emission-auxiliary layer with a thickness of 60 nm. A light emitting layer with a thickness of 30 nm was deposited on the emission-auxiliary layer by using the compound 1-1-1-S-(1) of the present invention as a host material and $(piq)_2Ir(acac)$ as a dopant material in a weight ratio of 95:5.

Next, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "$Alq_3$") was formed with a thickness of 40 nm to form an electron transport layer.

Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

Example 38 to Example 54

Red OLED (A Hole Transport Layer, an Emission-Auxiliary Layer, Phosphorescent Host)

The OLEDs were fabricated in the same manner as described in Example 37 except that the compounds represented by formula 8 described in Table 8, instead of the compound 8-17 of the present invention, were used as hole transporting material, the compounds represented by formula 1 described in Table 8, instead of the compound A1 of the present invention, were used as material of an emission-auxiliary layer, and the compounds represented by formula 2 described in Table 8, instead of the compound 1-1-1-S-(1) of the present invention, were used as host material of a light emitting layer.

Comparative Example 6 to Comparative Example 8

The OLEDs were fabricated in the same manner as described in Example 37, 43, 49 except that the same material as hole transporting material, instead of the compound A1 of the present invention, were used as an emission-auxiliary layer material.

Comparative Example 9 to Comparative Example 11

The OLEDs were fabricated in the same manner as described in Example 37, 43, 49 except that Comparative compounds A, instead of the compound A1 of the present invention, was used as an emission-auxiliary layer material.

Comparative Example 12 to Comparative Example 14

The OLEDs were fabricated in the same manner as described in Example 37, 43, 49 except that Comparative compounds B, instead of the compound A1 of the present invention, was used as an emission-auxiliary layer material.

Comparative Example 15 to Comparative Example 17

The OLEDs were fabricated in the same manner as described in Example 39, 45, 51 except that Comparative compounds C, instead of the compound 1-1-1-S-(1) of the present invention, was used as phosphorescent host material of a light emitting layer.

Electroluminescence (EL) characteristics were measured with a PR-650(Photoresearch) by applying a forward bias DC voltage to the OLEDs prepared in Examples 37 to 54 of the present invention and Comparative Examples 6 to 17. And, the T95 life time was measured using a life time measuring apparatus manufactured by Macscience Inc. at reference brightness of 2500 $cd/m^2$. The measurement results are shown in Tables 8 below.

TABLE 8

| | HTL com. | EAL com. | Phosphorescent host com. | Voltage (V) | Current Density (mA/cm$^2$) | Brightness (cd/m$^2$) | Efficiency (cd/A) | Lifetime T(95) |
|---|---|---|---|---|---|---|---|---|
| comp. Ex. (6) | Com. (8-17) | Com. (8-17) | Com. 1-1-1-S-(1) | 6.9 | 22.1 | 2500.0 | 11.3 | 87.7 |
| comp. Ex. (7) | Com. (8-32) | Com. (8-32) | Com. 1-1-1-S-(1) | 6.8 | 19.2 | 2500.0 | 13.0 | 84.1 |
| comp. Ex. (8) | Com. (8-61) | Com. (8-61) | Com. 1-1-1-S-(1) | 6.9 | 20.0 | 2500.0 | 12.5 | 80.3 |
| comp. Ex. (9) | Com. (8-17) | comp. Com. A | Com. 1-1-1-S-(1) | 7.1 | 13.6 | 2500.0 | 18.4 | 114.5 |
| comp. Ex. (10) | Com. (8-32) | comp. Com. A | Com. 1-1-1-S-(1) | 6.9 | 12.8 | 2500.0 | 19.6 | 118.5 |
| comp. Ex. (11) | Com. (8-61) | comp. Com. A | Com. 1-1-1-S-(1) | 7.0 | 13.1 | 2500.0 | 19.1 | 112.2 |
| comp. Ex. (12) | Com. (8-17) | comp. Com. B | Com. 1-1-1-S-(1) | 7.0 | 14.3 | 2500.0 | 17.5 | 118.0 |
| comp. Ex. (13) | Com. (8-32) | comp. Com. B | Com. 1-1-1-S-(1) | 7.0 | 13.5 | 2500.0 | 18.5 | 117.1 |
| comp. Ex. (14) | Com. (8-61) | comp. Com. B | Com. 1-1-1-S-(1) | 7.2 | 13.7 | 2500.0 | 18.3 | 105.2 |
| comp. Ex. (15) | Com. (8-17) | Com. (A258) | comp. Com. C | 7.2 | 13.0 | 2500.0 | 19.2 | 119.5 |
| comp. Ex. (16) | Com. (8-32) | Com. (A258) | comp. Com. C | 7.0 | 11.5 | 2500.0 | 21.8 | 116.8 |
| comp. Ex. (17) | Com. (8-61) | Com. (A258) | comp. Com. C | 7.2 | 12.5 | 2500.0 | 20.0 | 110.4 |
| Ex. (37) | Com. (8-17) | Com. (A1) | Com. 1-1-1-S-(1) | 6.6 | 8.6 | 2500.0 | 29.0 | 127.9 |
| Ex. (38) | Com. (8-17) | Com. (A1) | Com. 1-1-1-S-(7) | 6.6 | 8.5 | 2500.0 | 29.4 | 123.9 |
| Ex. (39) | Com. (8-17) | Com. (A258) | Com. 1-1-1-S-(1) | 6.5 | 8.4 | 2500.0 | 29.8 | 129.4 |
| Ex. (40) | Com. (8-17) | Com. (A258) | Com. 1-1-1-S-(7) | 6.5 | 8.3 | 2500.0 | 30.1 | 129.8 |
| Ex. (41) | Com. (8-17) | Com. (A321) | Com. 1-1-1-S-(1) | 6.6 | 8.8 | 2500.0 | 28.3 | 128.7 |
| Ex. (42) | Com. (8-17) | Com. (A321) | Com. 1-1-1-S-(7) | 6.6 | 8.5 | 2500.0 | 29.3 | 124.2 |
| Ex. (43) | Com. (8-32) | Com. (A1) | Com. 1-1-1-S-(1) | 6.3 | 8.2 | 2500.0 | 30.5 | 129.0 |
| Ex. (44) | Com. (8-32) | Com. (A1) | Com. 1-1-1-S-(7) | 6.3 | 7.6 | 2500.0 | 33.1 | 125.9 |
| Ex. (45) | Com. (8-32) | Com. (A258) | Com. 1-1-1-S-(1) | 6.2 | 7.0 | 2500.0 | 35.6 | 132.8 |

TABLE 8-continued

|  | HTL com. | EAL com. | Phosphorescent host com. | Voltage (V) | Current Density (mA/cm$^2$) | Brightness (cd/m$^2$) | Efficiency (cd/A) | Lifetime T(95) |
|---|---|---|---|---|---|---|---|---|
| Ex. (46) | Com. (8-32) | Com. (A258) | Com. 1-1-1-S-(7) | 6.2 | 7.1 | 2500.0 | 35.2 | 131.5 |
| Ex. (47) | Com. (8-32) | Com. (A321) | Com. 1-1-1-S-(1) | 6.3 | 7.4 | 2500.0 | 33.8 | 125.9 |
| Ex. (48) | Com. (8-32) | Com. (A321) | Com. 1-1-1-S-(7) | 6.4 | 7.5 | 2500.0 | 33.3 | 123.9 |
| Ex. (49) | Com. (8-61) | Com. (A1) | Com. 1-1-1-S-(1) | 6.6 | 8.9 | 2500.0 | 28.2 | 128.8 |
| Ex. (50) | Com. (8-61) | Com. (A1) | Com. 1-1-1-S-(7) | 6.6 | 8.4 | 2500.0 | 29.7 | 129.2 |
| Ex. (51) | Com. (8-61) | Com. (A258) | Com. 1-1-1-S-(1) | 6.4 | 8.3 | 2500.0 | 30.1 | 130.0 |
| Ex. (52) | Com. (8-61) | Com. (A258) | Com. 1-1-1-S-(7) | 6.5 | 8.0 | 2500.0 | 31.1 | 129.7 |
| Ex. (53) | Com. (8-61) | Com. (A321) | Com. 1-1-1-S-(1) | 6.7 | 8.9 | 2500.0 | 28.1 | 126.5 |
| Ex. (54) | Com. (861) | Com. (A321) | Com. 1-1-1-S-(7) | 6.6 | 8.8 | 2500.0 | 28.4 | 127.9 |

From the results of the above table, it is found that the driving voltage is lowered and luminous efficiency and lifetime are improved according to Example of the present invention, compared with Comparative Examples 6 to 8 not forming an emission-auxiliary layer and Comparative Examples 9 to 14 in which Comparative compounds A and B are used as material of an emission-auxiliary layer, and Comparative Examples 15 to 17 Comparative compounds C is used as phosphorescent host material. Here, the compound of the present invention represented by Formula 8 is used as material of a hole transport layer, the compound of the present invention represented by Formula 2 is used as material of an emission-auxiliary layer, and the compound of the present invention represented by Formula 2 is used as phosphorescent host material in Example of the present invention. Further, an emission-auxiliary layer is not formed in Comparative Examples 6 to 8 of Table 8 in which the materials of an emission-auxiliary layer and the hole transport layer are indicated as being the same, but this is for comparison with element of the same thickness, actually, an emission-auxiliary layer was not formed, and the hole transport layer material is further stacked by the thickness of an emission-auxiliary layer.

When the compound of the present invention represented by Formula 1 is used alone as material of an emission-auxiliary layer, it has a high T1 energy level and a deep HOMO energy level. As a result, the holes and electrons form a charge balance and light emission occurs inside the light emitting layer rather than at the interface of the hole transport layer, thereby maximizing efficiency.

In addition, by using the compound of the present invention represented by the general formula 2 as a phosphorescent host, it is considered that the combination of these elements is electrochemically synergistic to improve the performance of the element as a whole. This can he easily seen by comparing Comparative Examples 13 to 15 in which the compound of the present invention represented by the formula 1 is used as material of an emission-auxiliary layer and Comparative compound C is used as the phosphorescent host.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. An organic electric element comprising a first electrode, a second electrode, and an organic material layer stacked in sequence, wherein the organic material layer comprises a hole transport layer, an emission-auxiliary layer and a light emitting layer, at least one of the hole transport layer and the emission-auxiliary layer comprises a compound represented by Formula 1 below, and the light emitting layer comprises a compound represented by Formula 2 below:

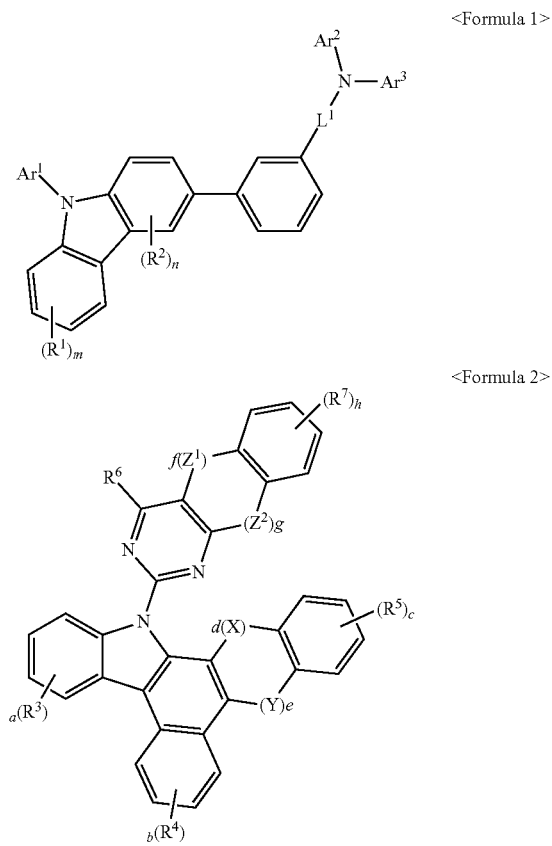

<Formula 1>

<Formula 2> wherein,

Ar$^1$ to Ar$^3$ are each independently selected from the group consisting of a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, and $Ar^2$ and $Ar^3$ are optionally linked to each other to form a ring, $L^1$ is selected from the group consisting of a $C_6$-$C_{60}$ arylene group, a fluorenylene group, a divalent $C_2$-$C_{60}$ heterocyclic group containing at least one heteroatom selected from the group consisting of O, N, S, Si, and P, a divalent fused ring formed by a $C_3$-$C_{60}$ aliphatic ring and a $C_6$-$C_{60}$ aromatic ring, and a divalent $C_2$-$C_{60}$ aliphatic hydrocarbon group, $R^1$, $R^2$, $R^3$ to $R^5$, and $R^7$ i) are each independently selected from the group consisting of deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and -L'-N($R^a$)($R^b$), or ii) any two adjacent groups of $R^1$, $R^2$, $R^3$ to $R^5$, and $R^7$ are optionally linked together to form at least one ring, and the remaining groups not forming the ring are defined as same as in i), m is an integer of 0 to 4, n is an integer of 0 to 3, a to c and h are each independently an integer of 0 to 4, wherein when m, n, a to c and h are each an integer of 2 or more, a plurality of $R^1$s, $R^2$s, $R^3$s to $R^5$s, and $R^7$s may be the same or different from each other, $R^6$ is selected from the group consisting of hydrogen, a $C_6$-$C_{60}$ aryl group, a fluorenyl group, and a $C_2$-$C_{60}$ heterocyclic group containing at least one heteroatom selected from the group consisting of O, N, S, Si, and P, X and Y are each independently selected from the group consisting of a single bond, S, O, N(R') and C(R')(R''), wherein R' and R'' are each independently selected from the group consisting of hydrogen, a $C_6$-$C_{60}$ aryl group, a fluorenyl group, a $C_2$-$C_{60}$ heterocyclic group containing at least one heteroatom selected from the group consisting of O, N, S, Si, and P, and a $C_1$-$C_{50}$ alkyl group, and R' and R'' are optionally linked to each other to form a ring, d and e are each independently an integer of 0 or 1, and d+e is an integer of 1 or 2, $Z^1$ and $Z^2$ are each independently a single bond, O or S, f and g are each independently an integer of 0 or 1, and f+g is an integer of 1 or 2, in -L'-N($R^a$)($R^b$) of $Ar^1$ to $Ar^3$, $R^1$ to $R^5$, and $R^7$, L' is selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and $R^a$ and $R^b$ are each independently selected from the group consisting of a $C_6$-$C_{60}$ aryl group, a fluorenyl group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and the aryl group, heterocyclic group, fluorenyl group, alkyl group, alkenyl group, fused ring group, alkoxyl group, aryloxly group, arylene group, fluorenylene group, aliphatic hydrocarbon group of $Ar^1$-$Ar^3$, $R^1$, $R^7$, R', R'', $L^1$, L', $R_a$ and $R^b$ may be each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

2. The organic electric element of claim 1, wherein Formula 1 is represented by one of Formulas 3-1 to 3-3:

<Formula 3-1>

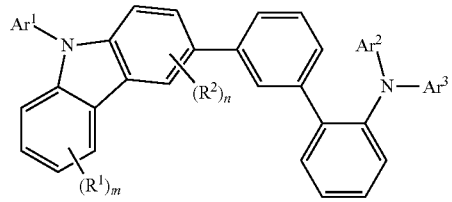

<Formula 3-2>

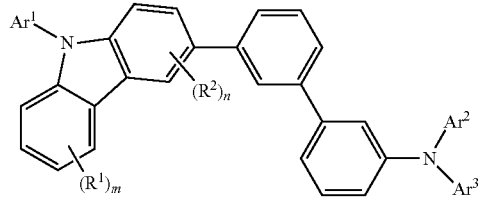

<Formula 3-3>

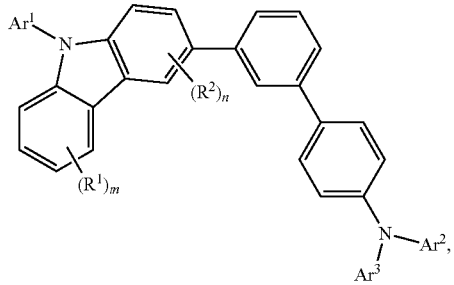

wherein $Ar^1$ to $Ar^3$, $R^1$, $R^2$, m and n are the same as defined in claim 1.

3. The organic electric element of claim 1, wherein Formula 2 is represented by one of Formulas 4 to 7:

<Formula 4>

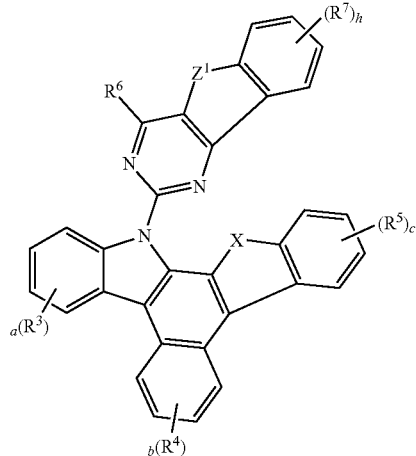

<Formula 5>
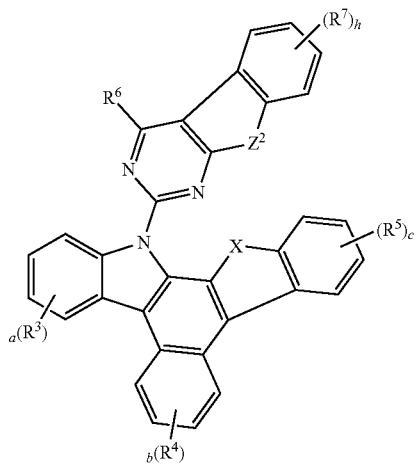
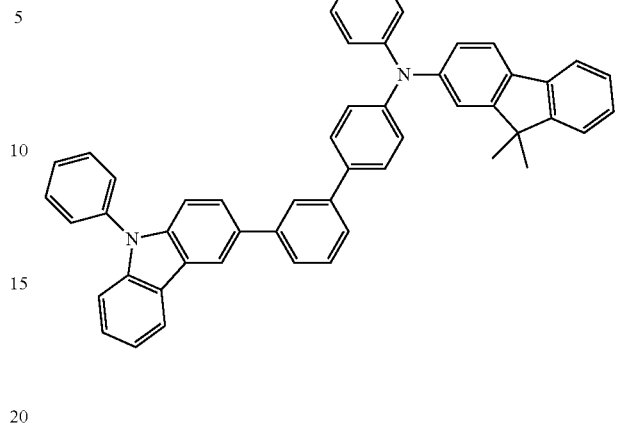
A1
<Formula 6>
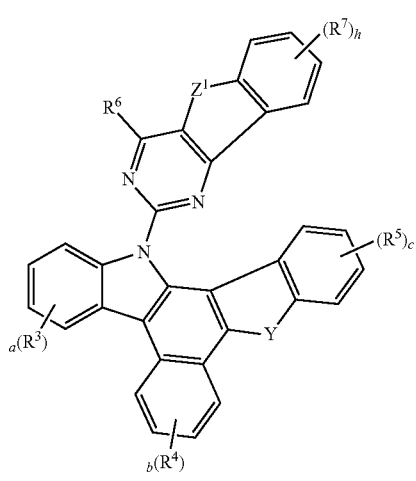
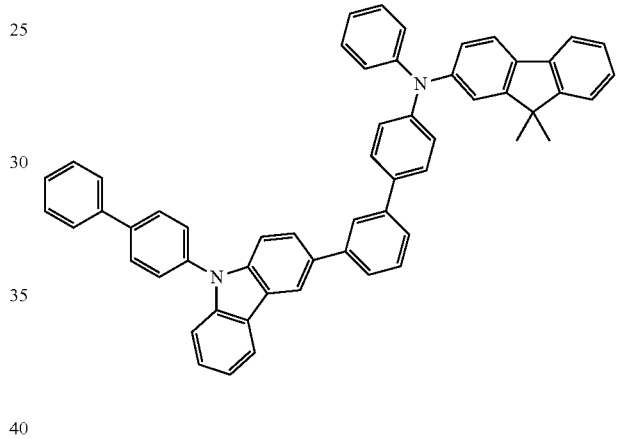
A2
<Formula 7>
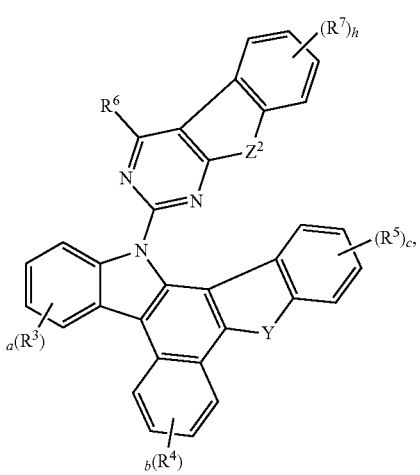
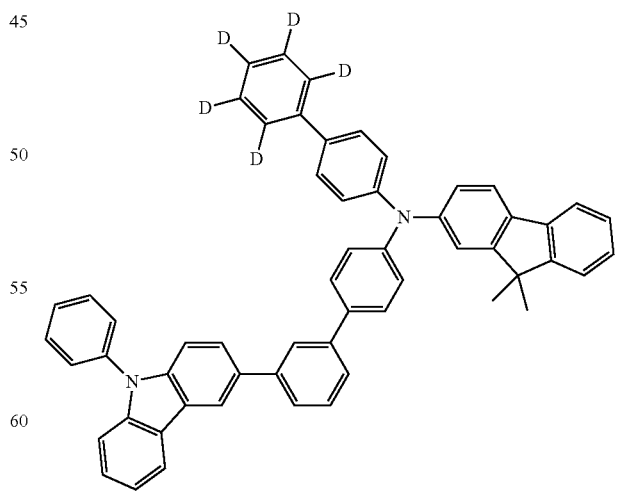
A6
wherein $R^3$ to $R^7$, X, Y, $Z^1$, $Z^2$, a, b, c and h are the same as defined in claim 1.
4. The organic electric element of claim 1, wherein Formula 1 is one of the following compounds:

-continued
A7
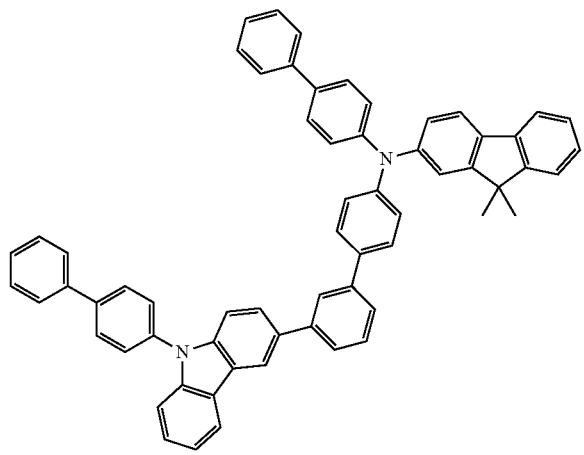
A11
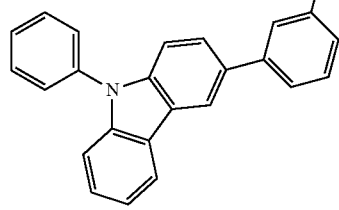
A12
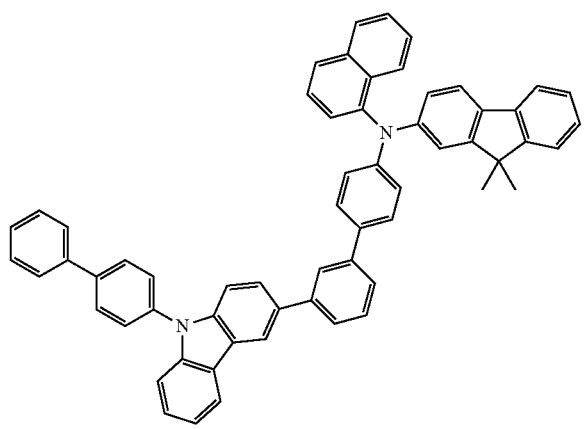
-continued
A16
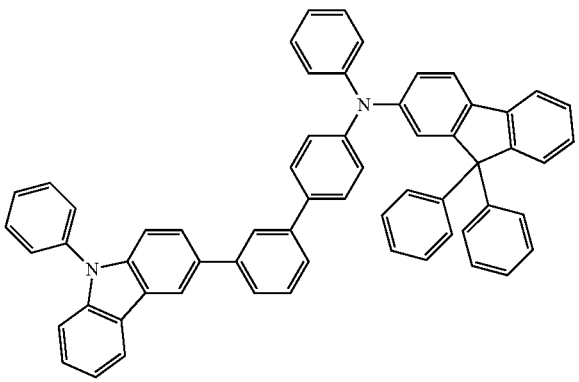
A17
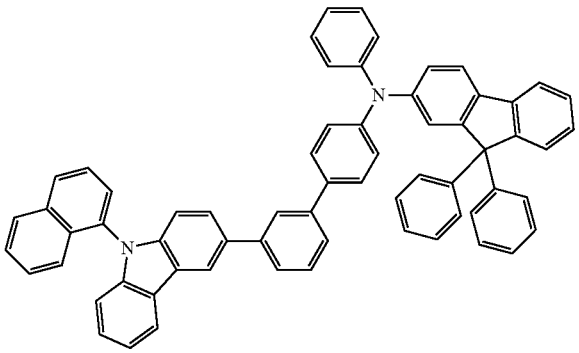
A19
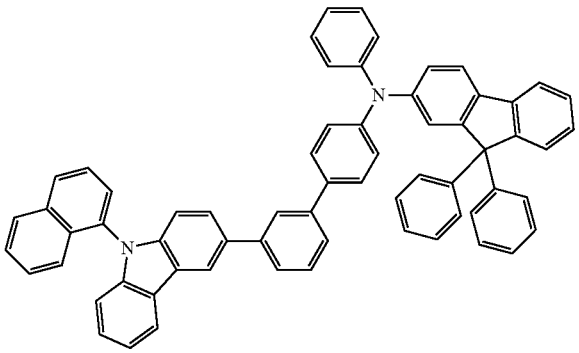
A21
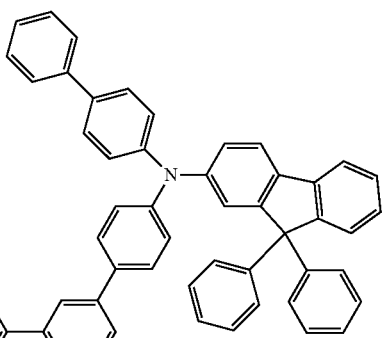

A22
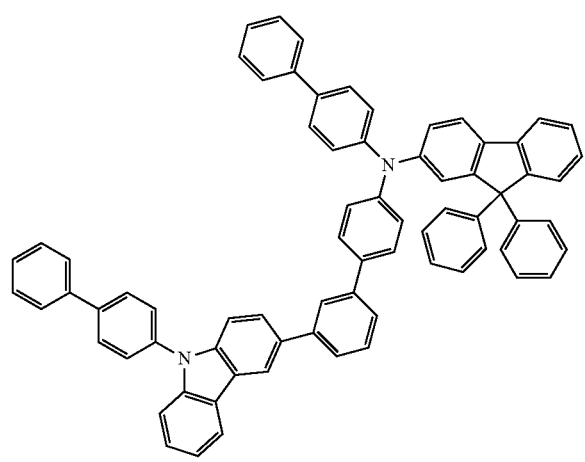
A23
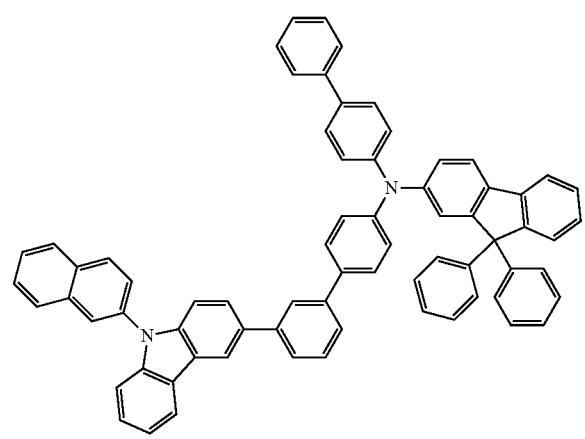
A24
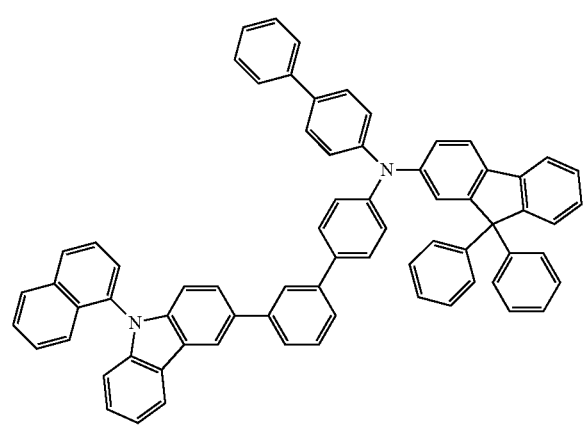
A25
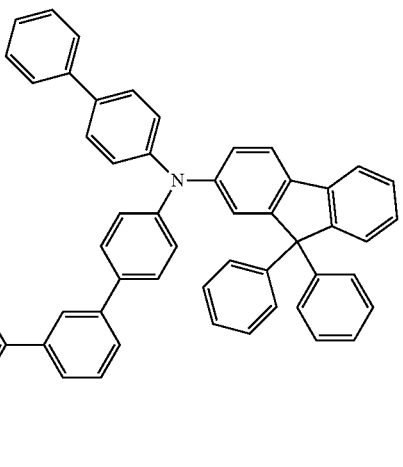
A26
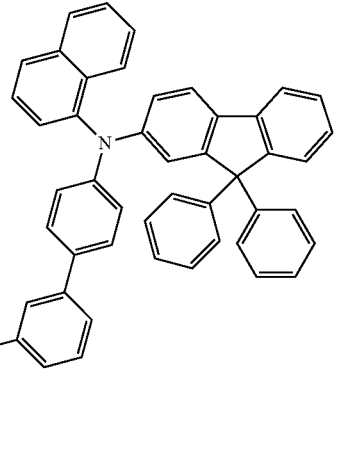
A27
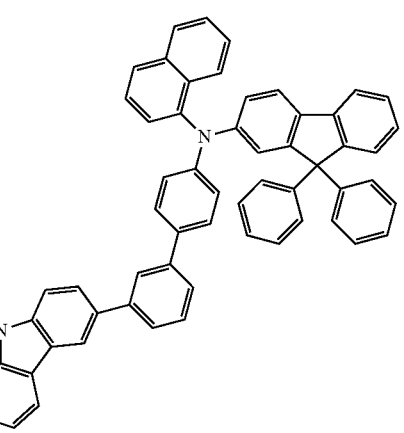

A31
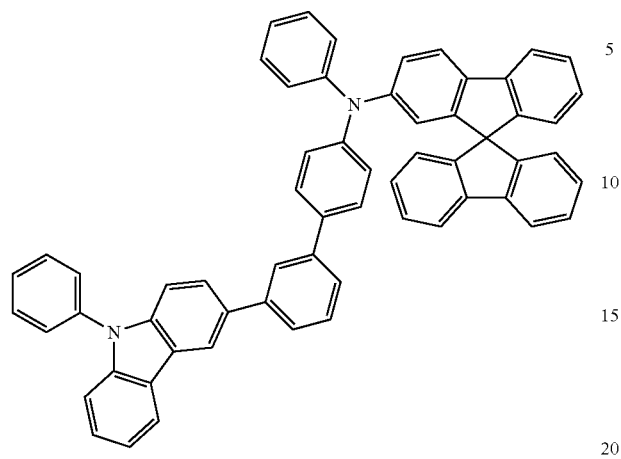
A36
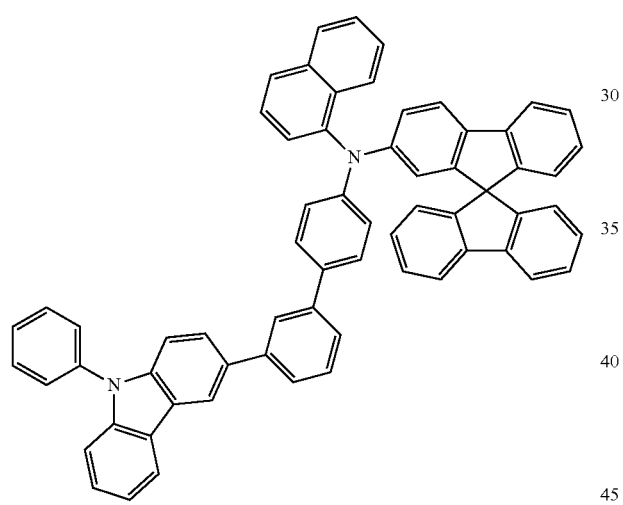
A47
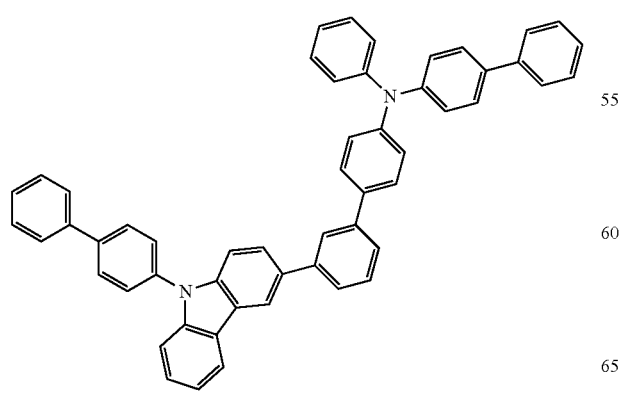
A51
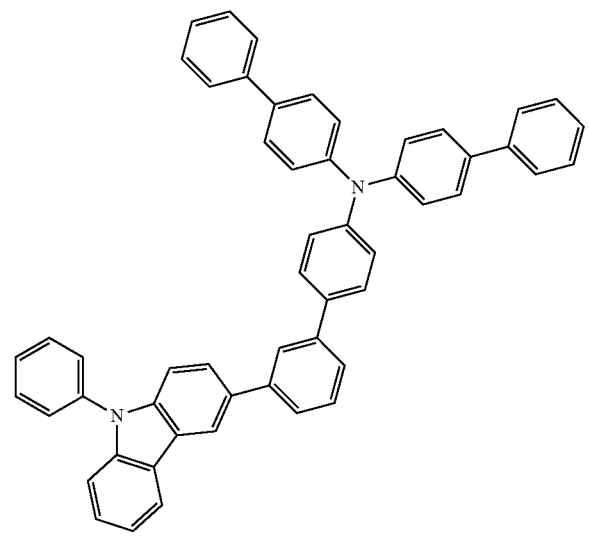
A56
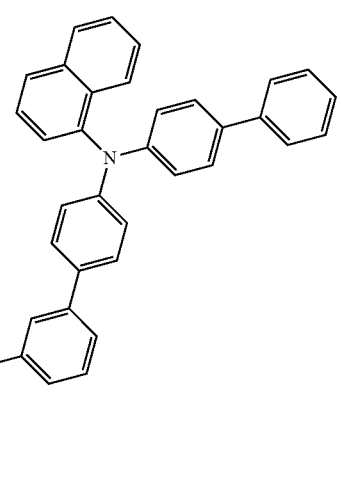
A62
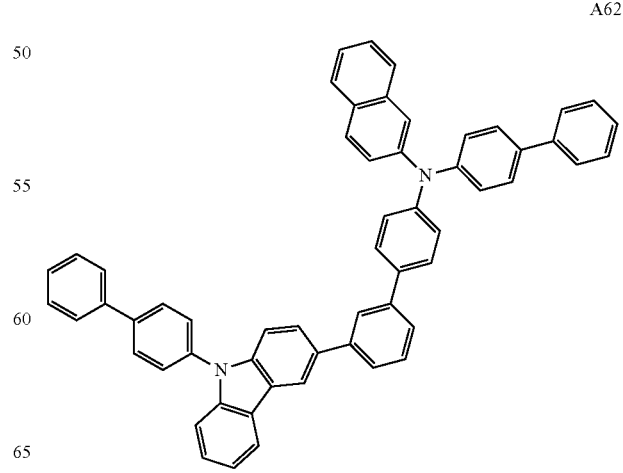

-continued
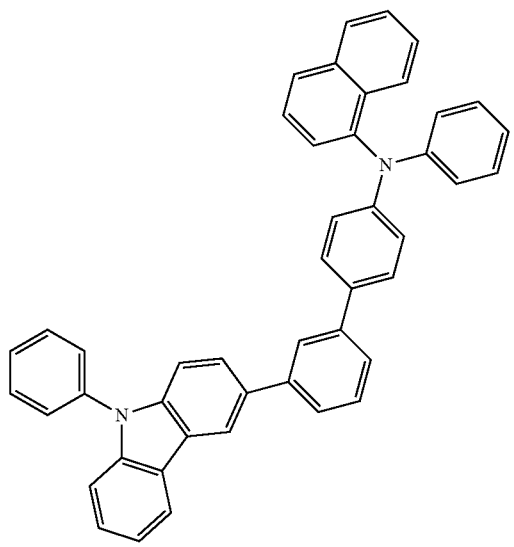
A66
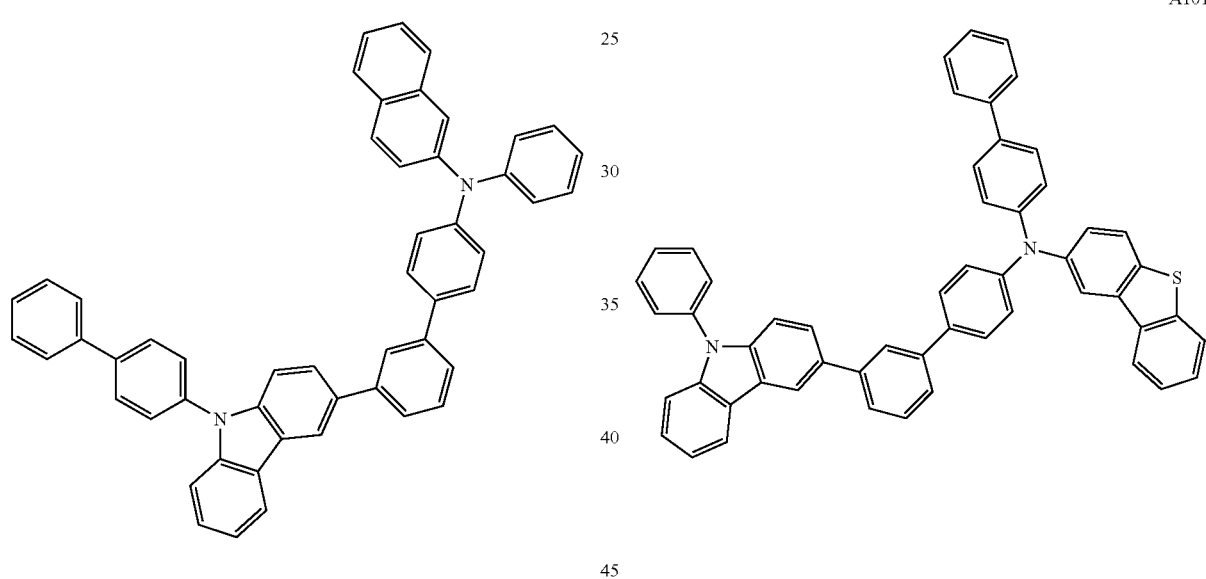
A72
A87
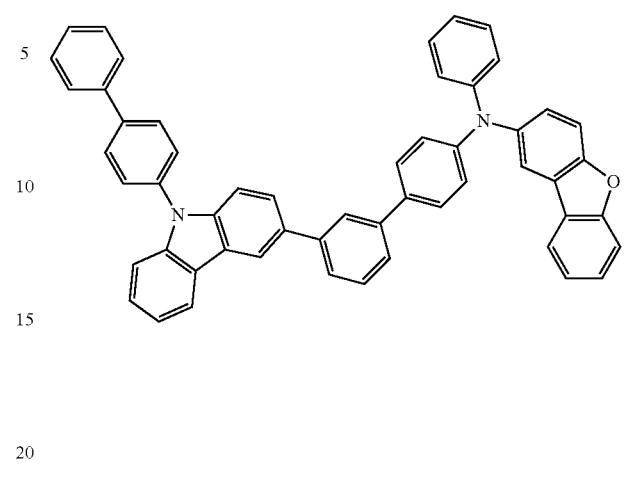
A97
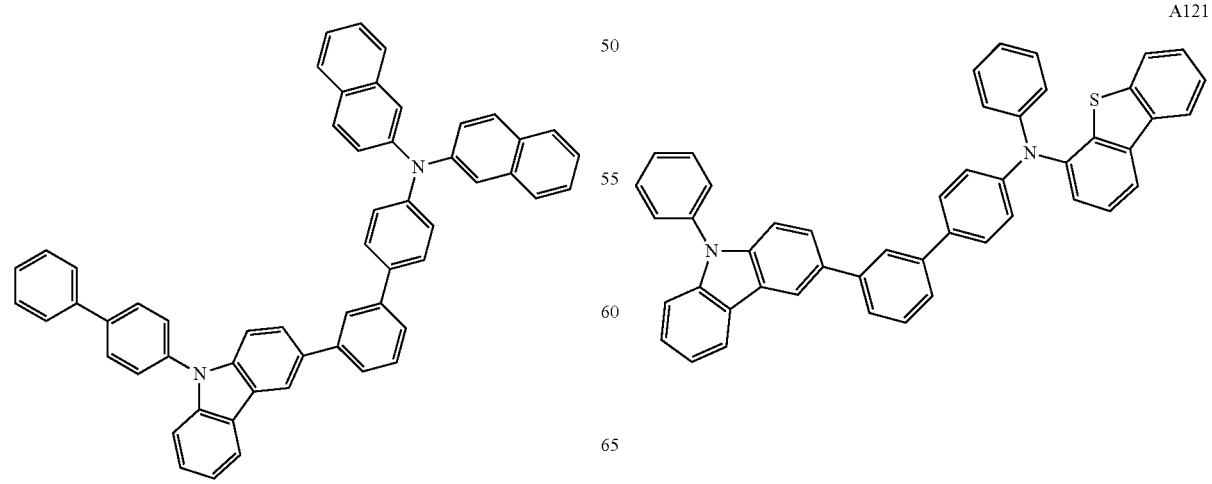
A101
A121

A123
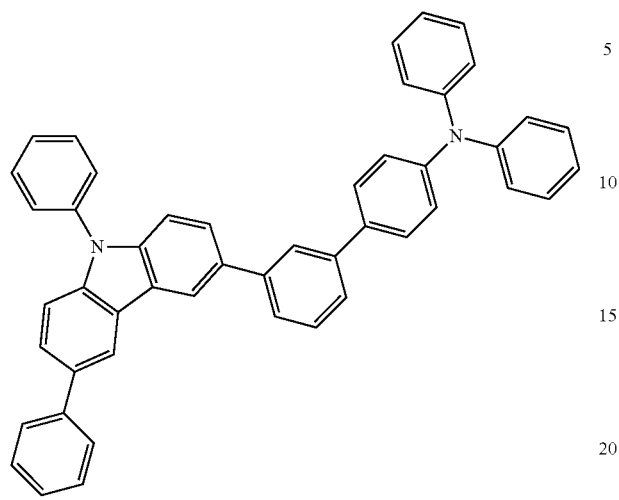
A124
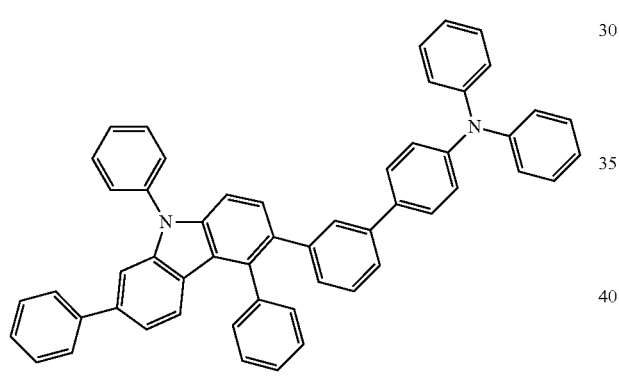
A125
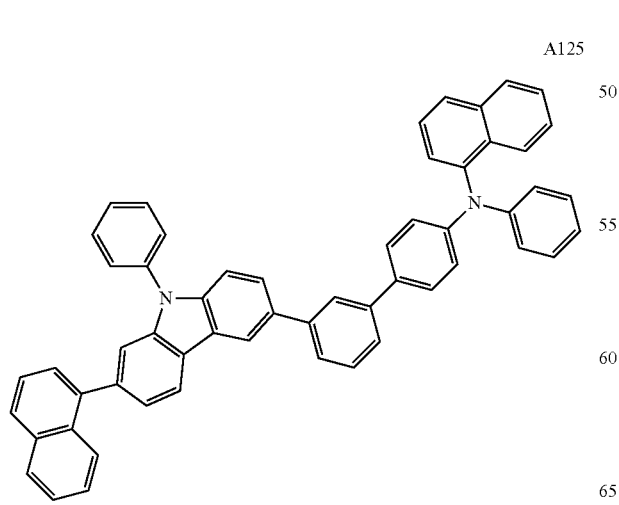
A127
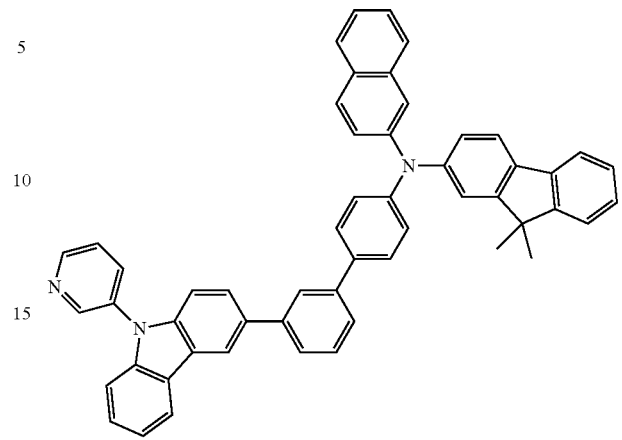
A128
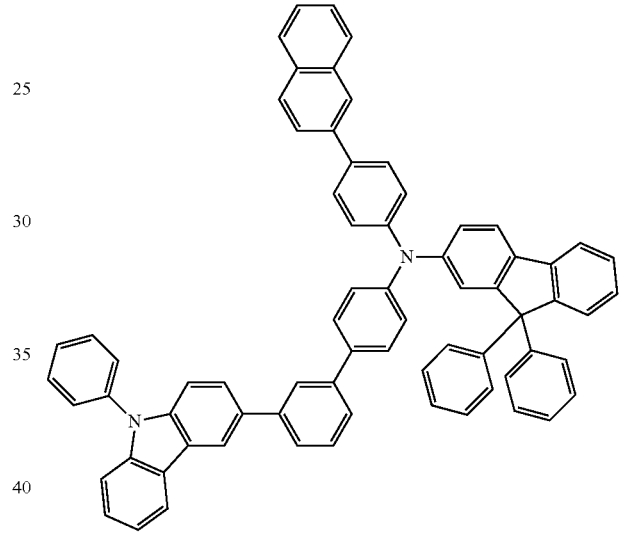
A129
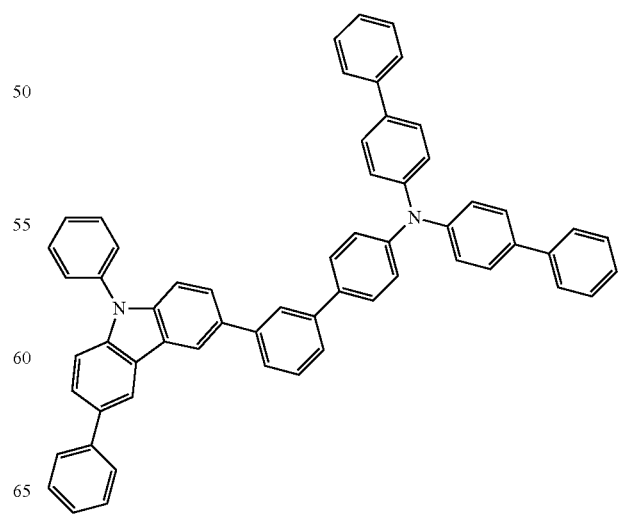

A130
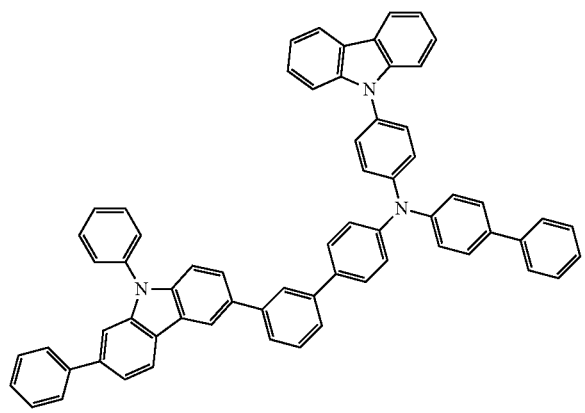
A135
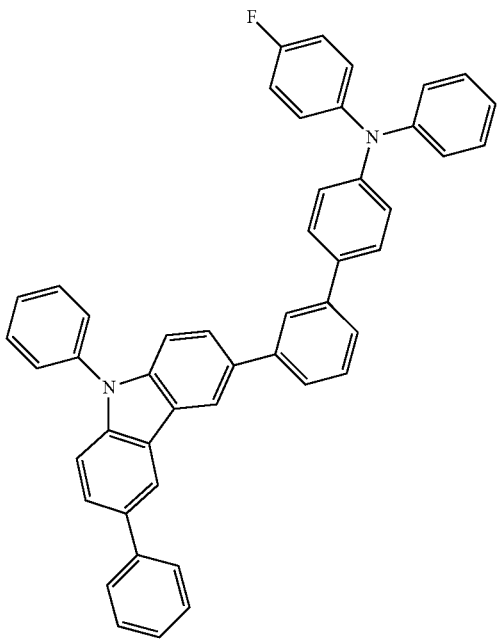
A131
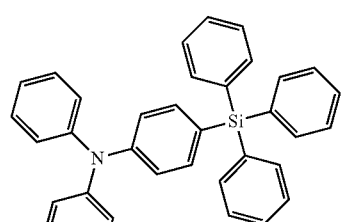
A142
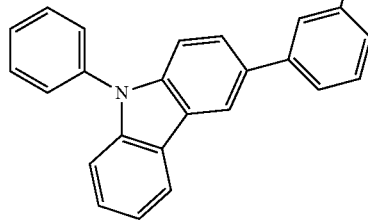
A134
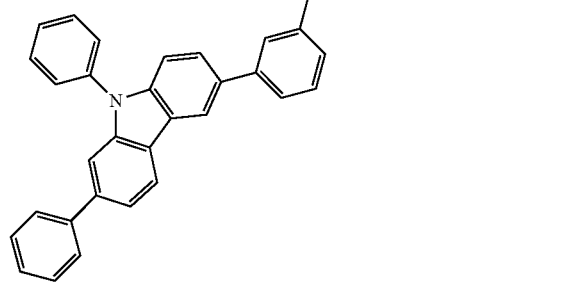
A146
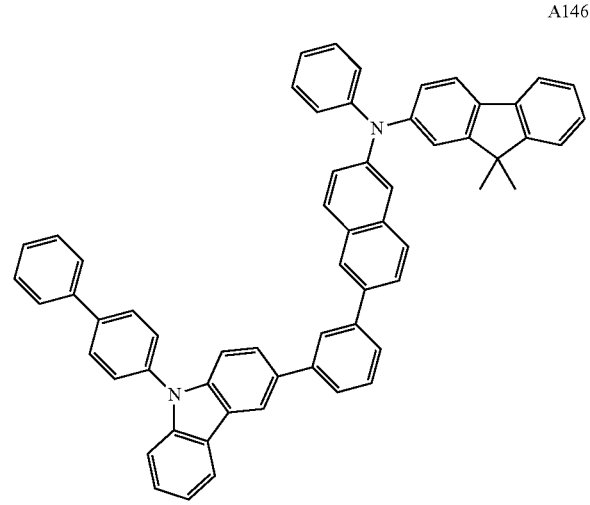
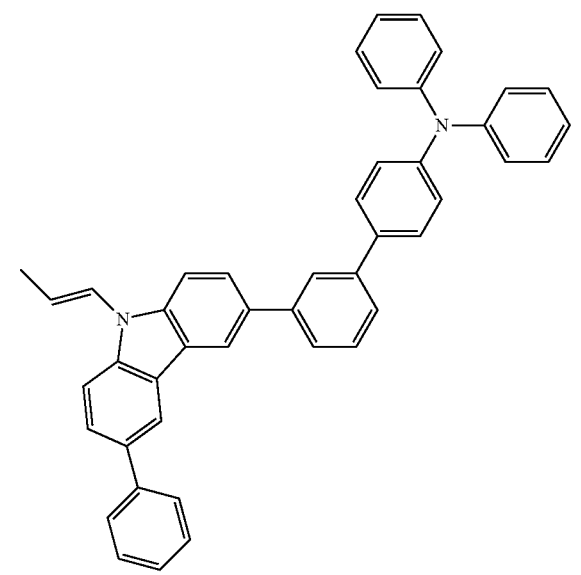

A161
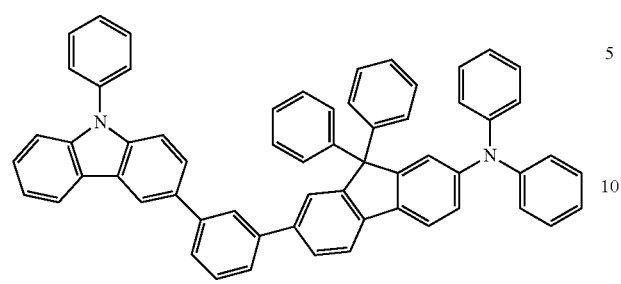
A162
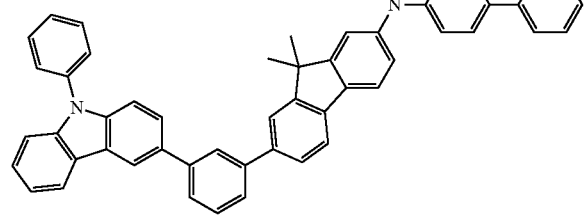
A165
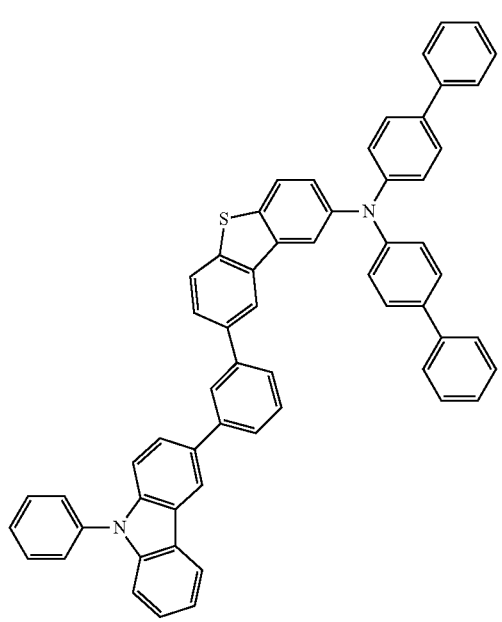
A168
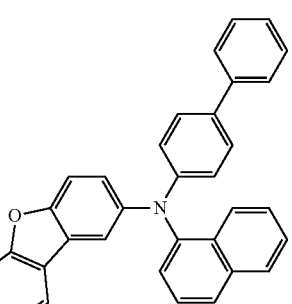
A169
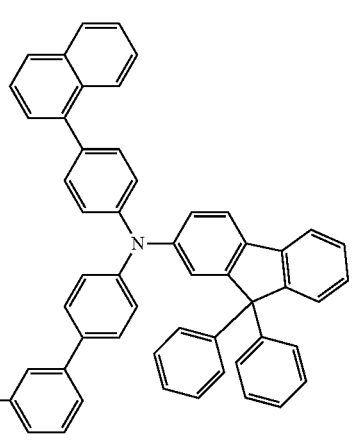

A170
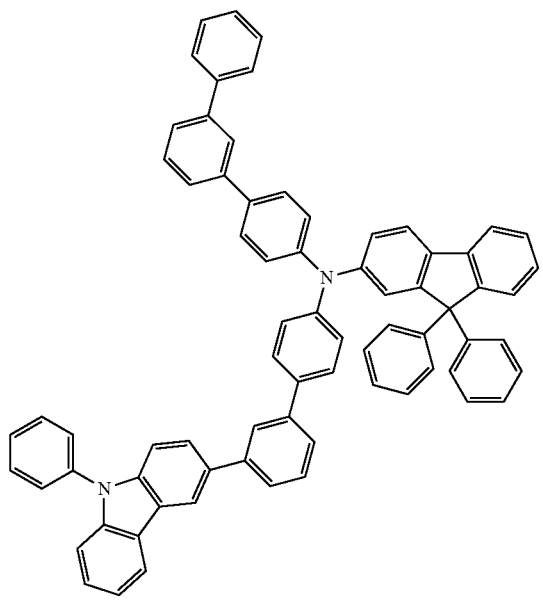
A173
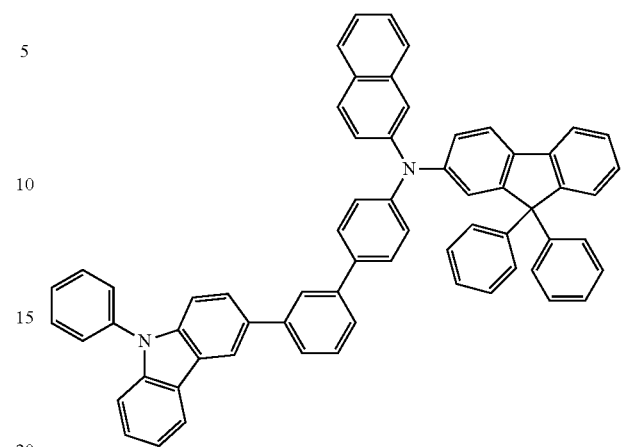
A171
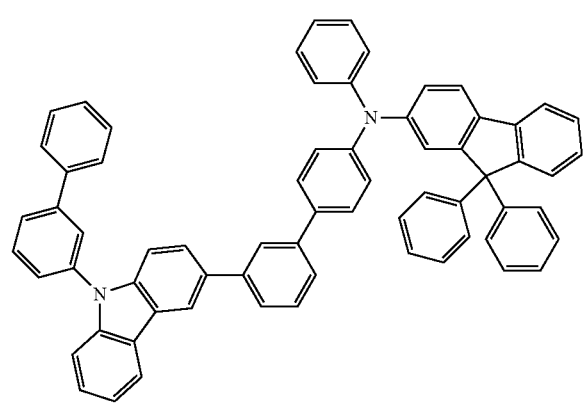
A174
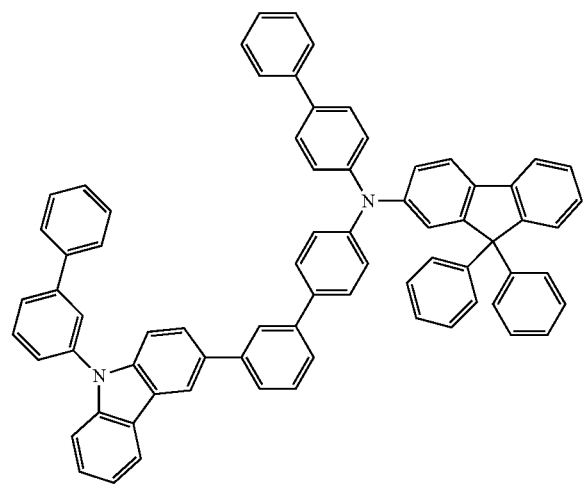
A172
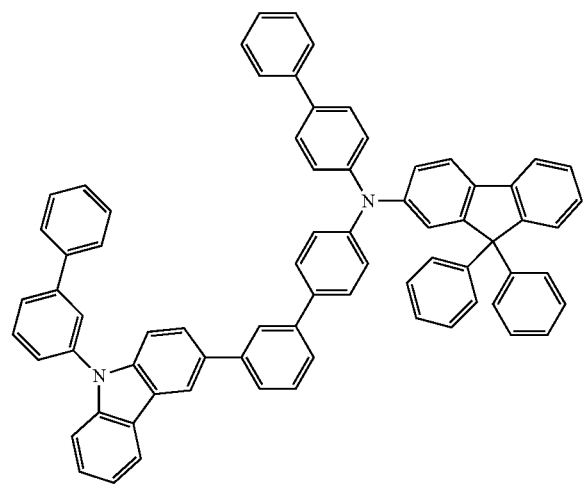
A175
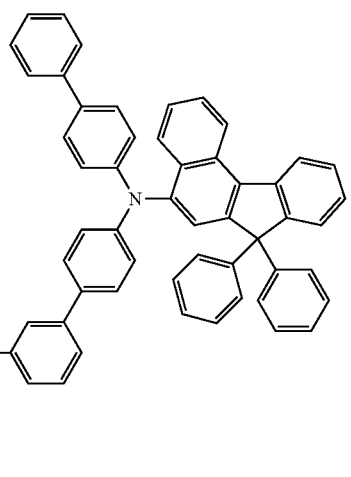

A176
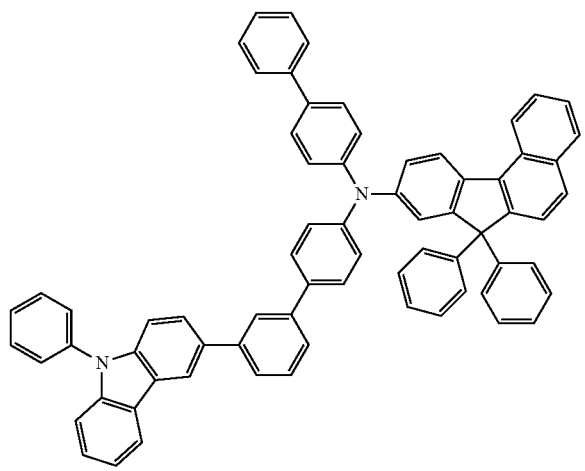
A177
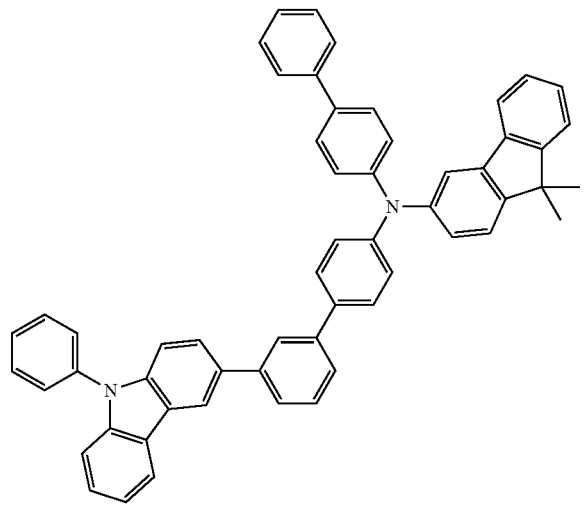
A178
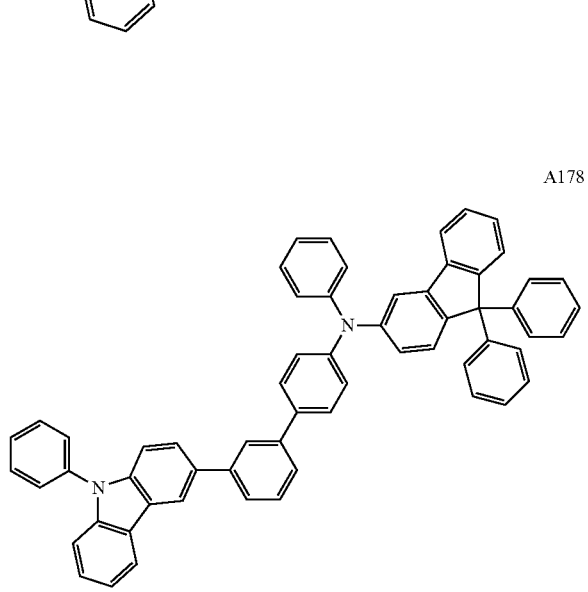
A179
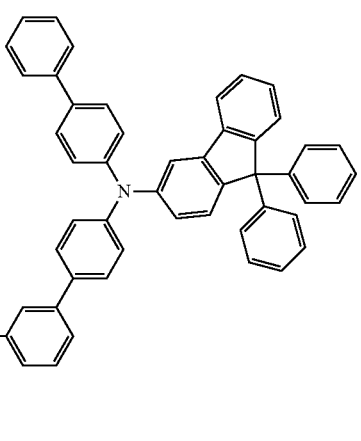
A180
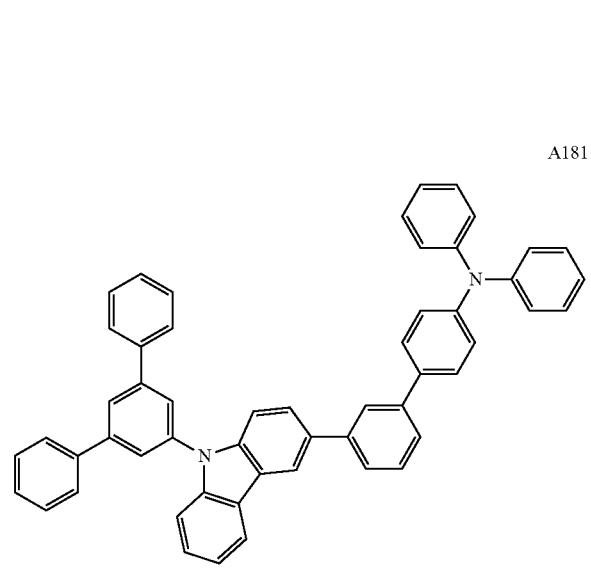
A181

-continued
A182
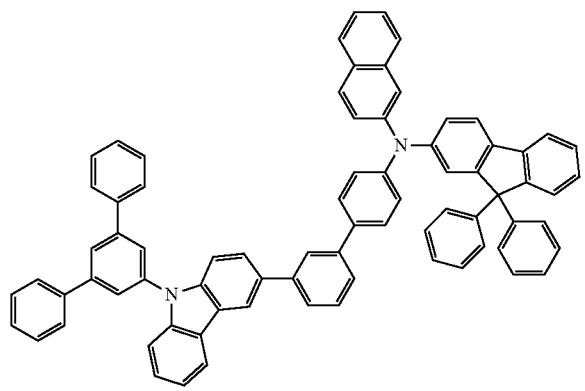
A183
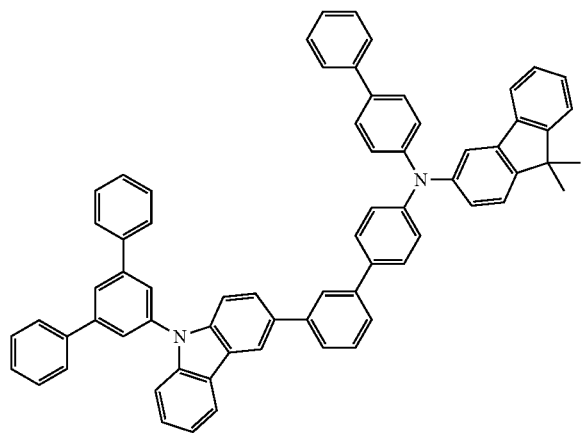
A184
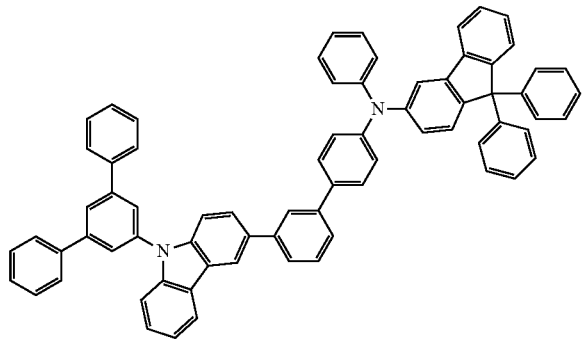
A185
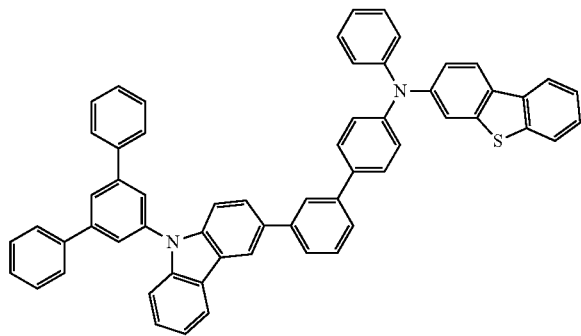
-continued
A186
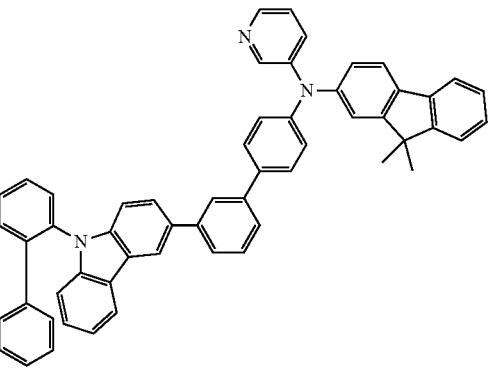
A187
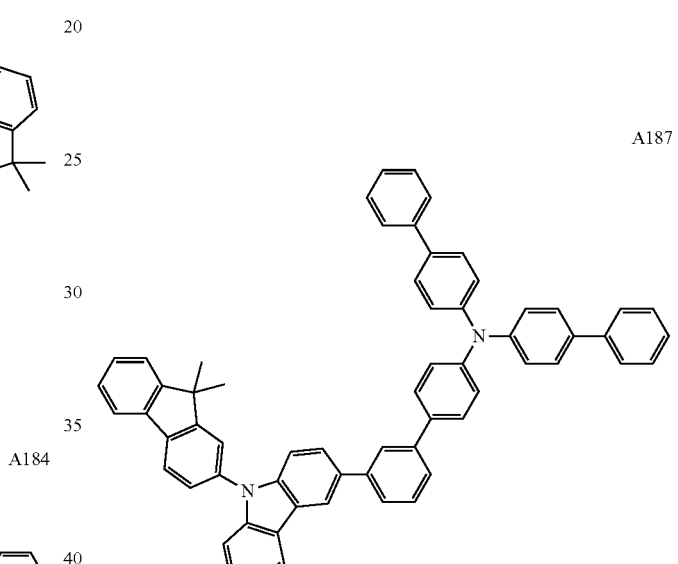
A188
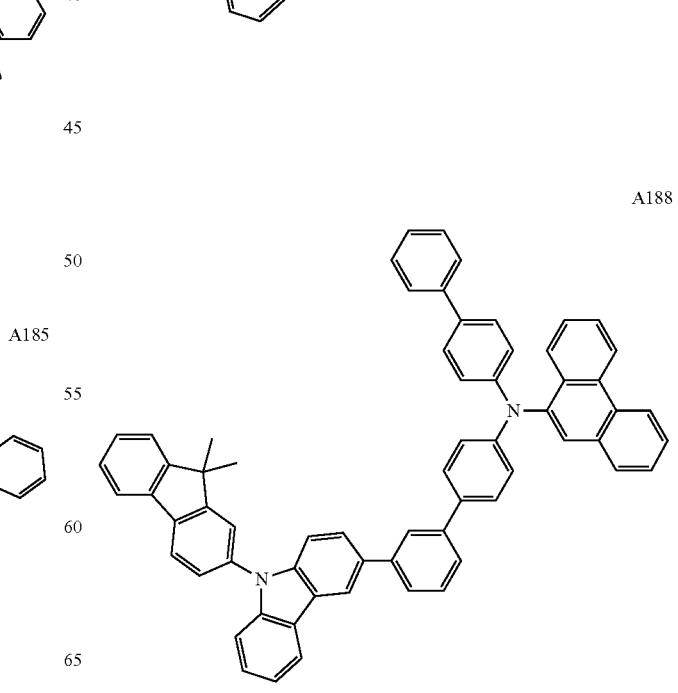

A189
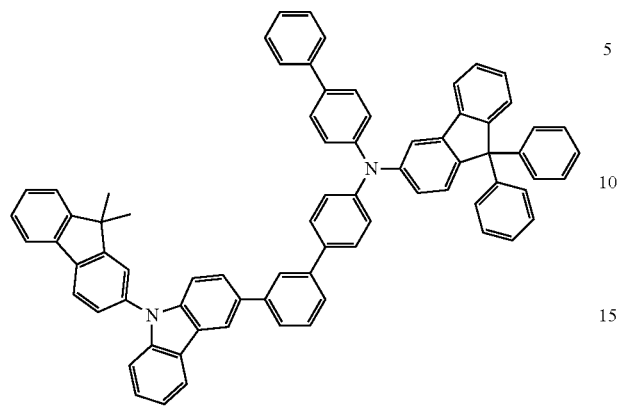
A190
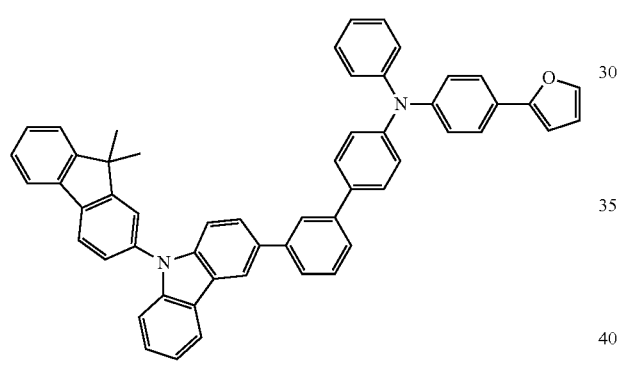
A191
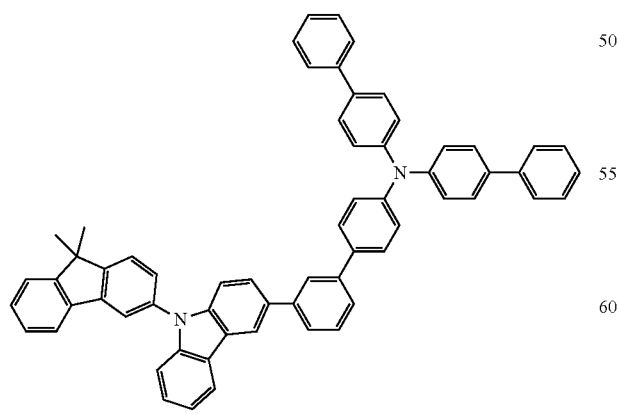
A192
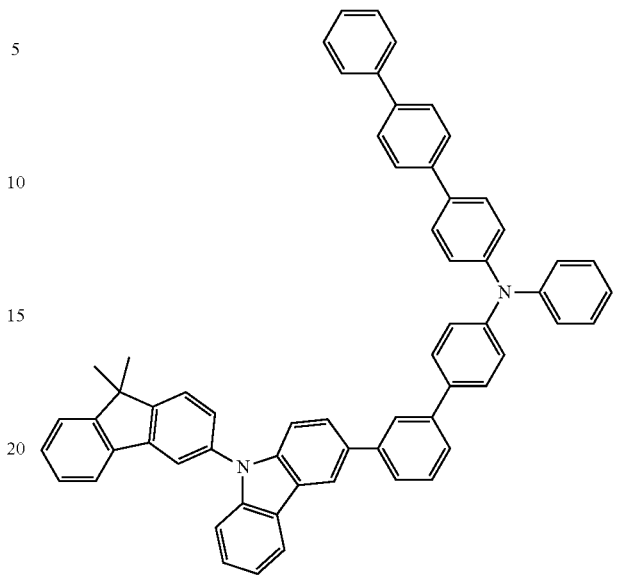
A193
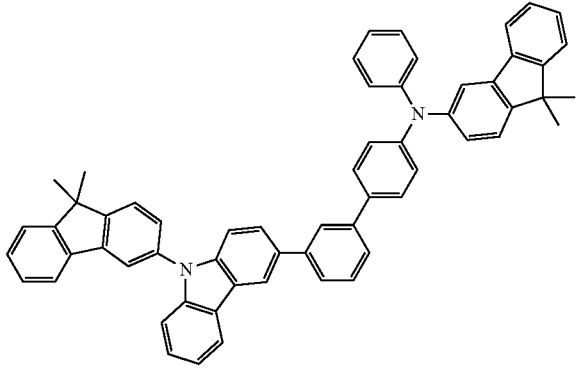
A194
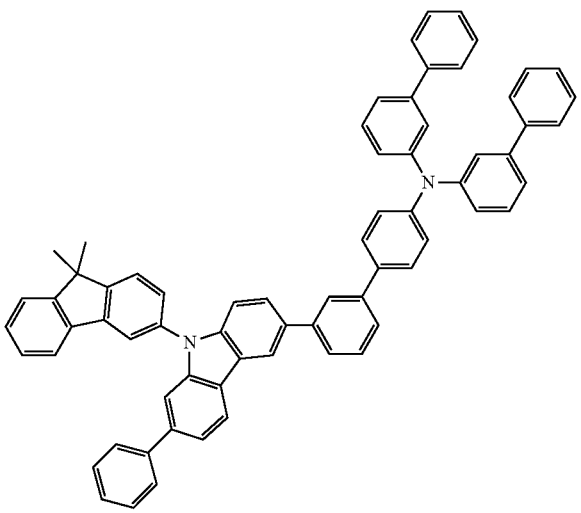

A195
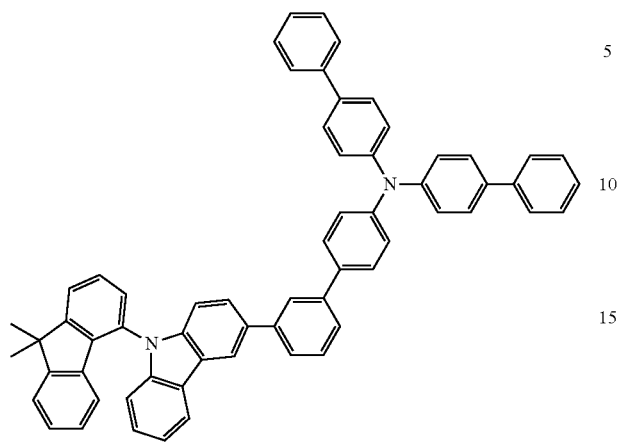
A196
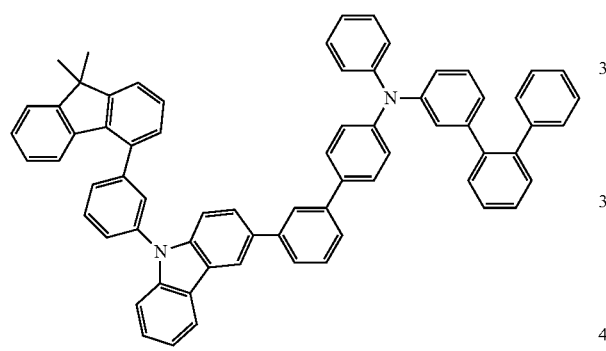
A197
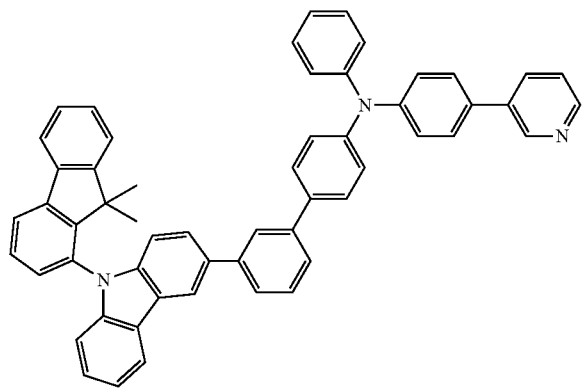
A198
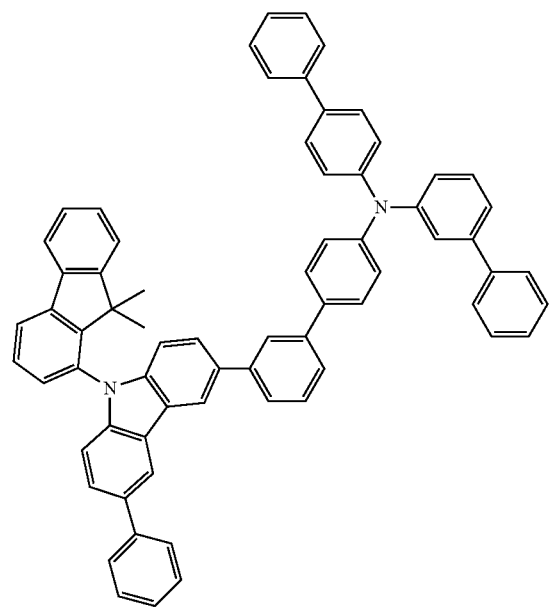
A199
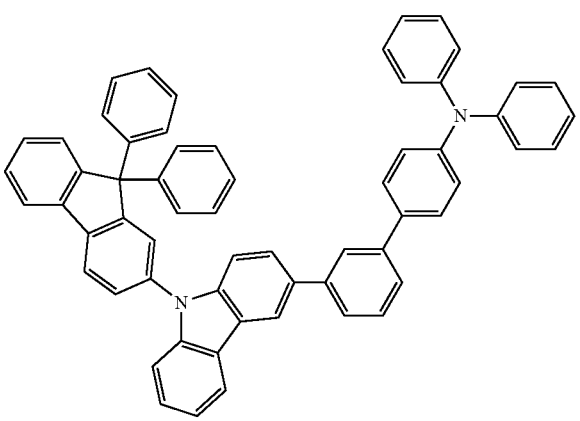
A200
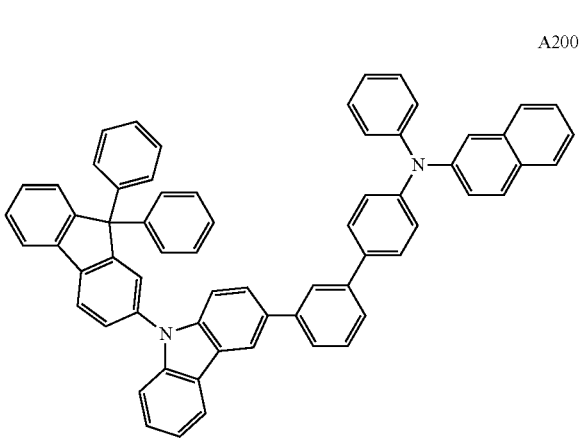

A201
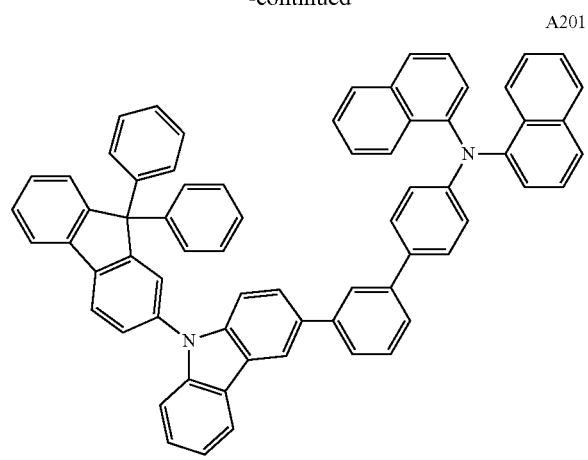
A205
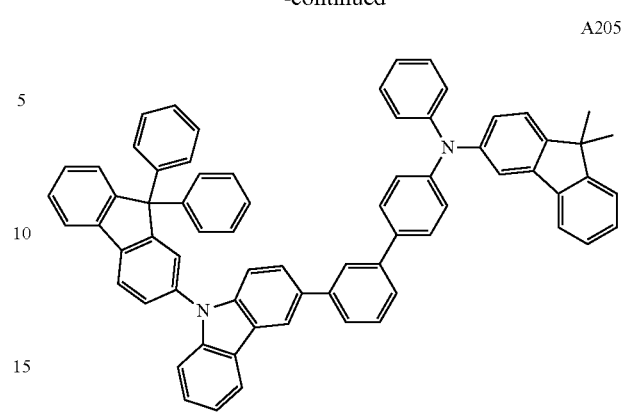
A202
A206
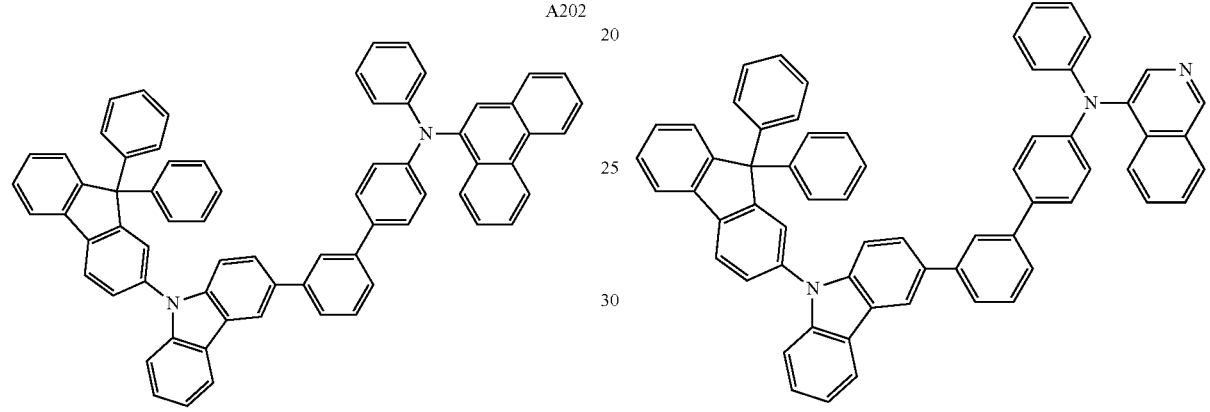
A203
A207
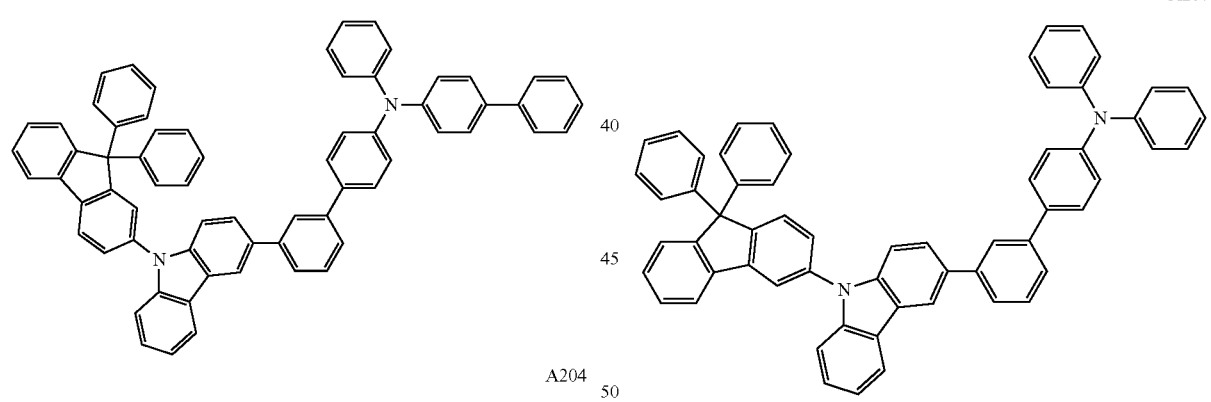
A204
A208
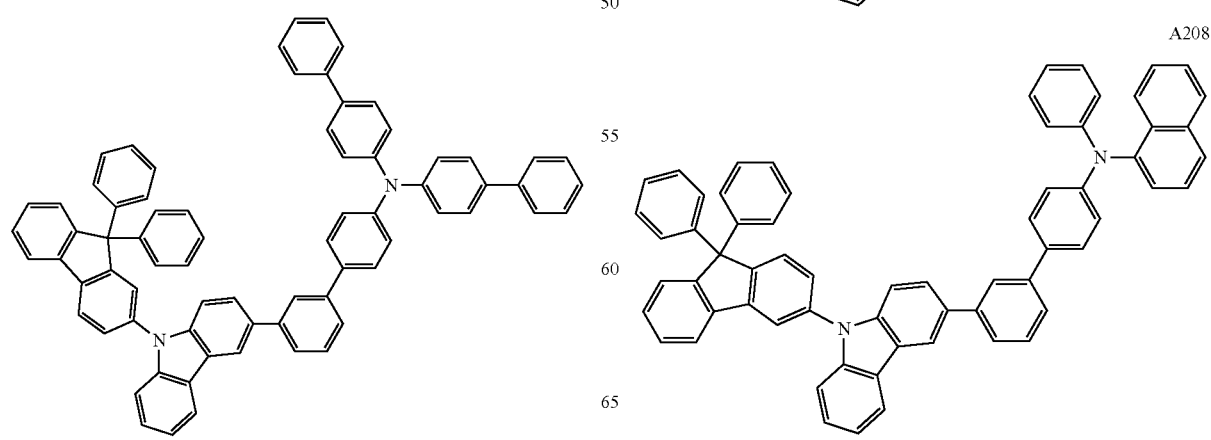

A209
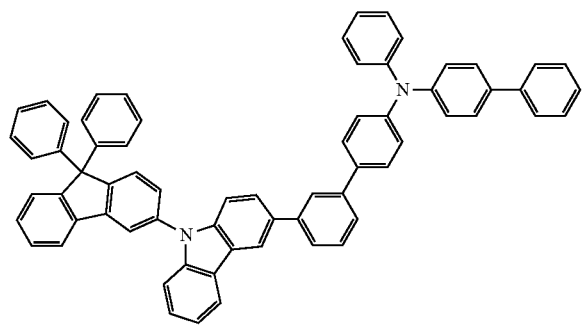
A210
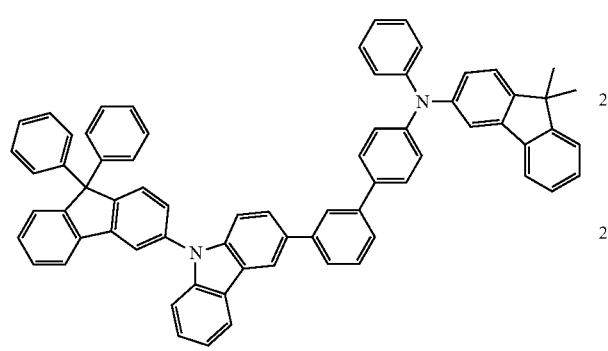
A211
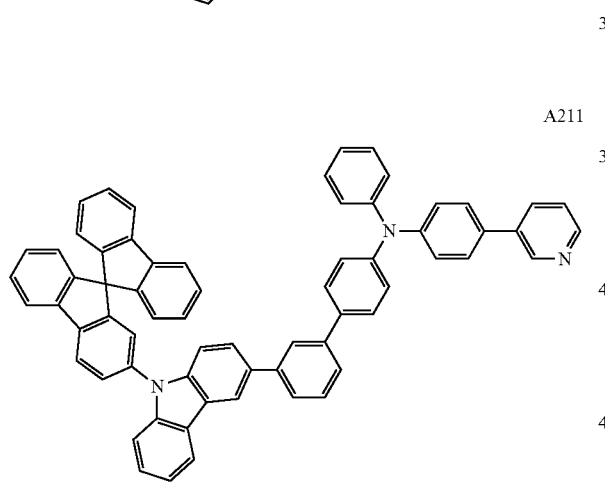
A212
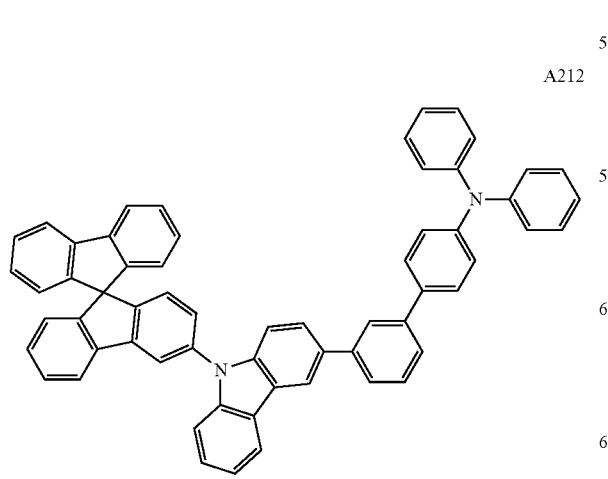
A213
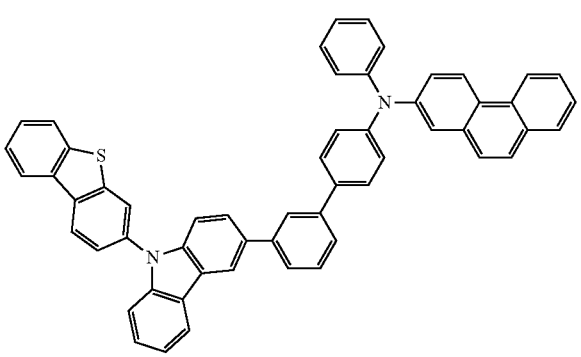
A214
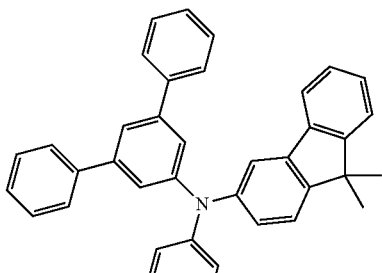
A215
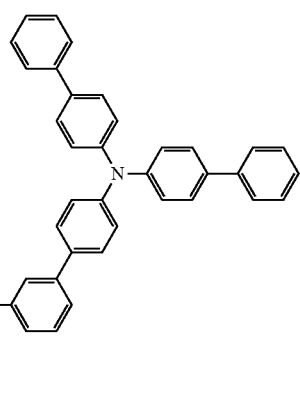

-continued
A216
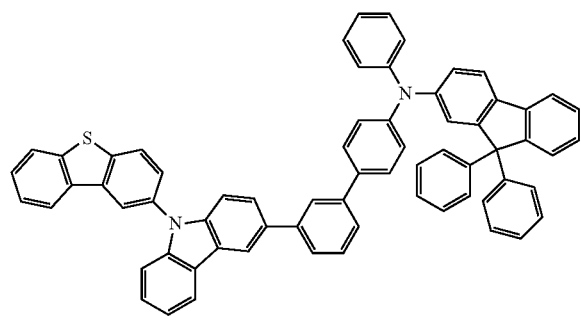
A217
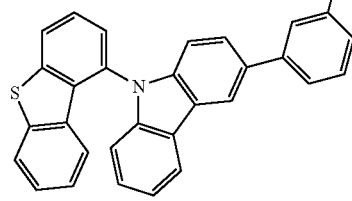
A218
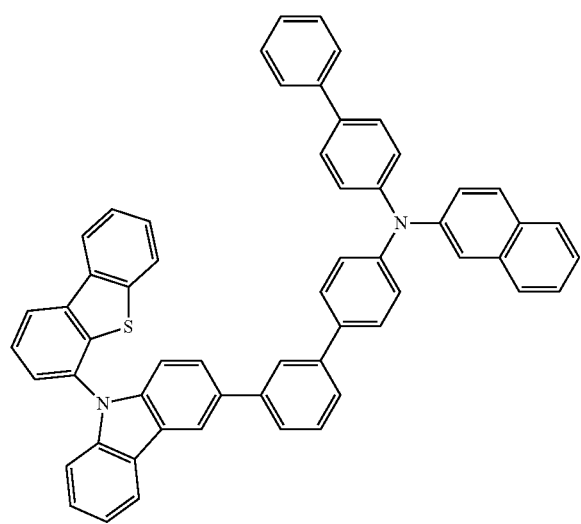
-continued
A219
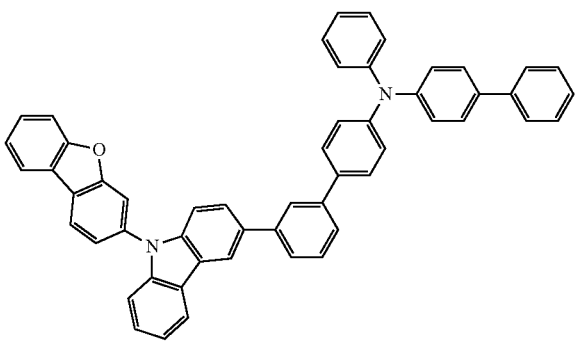
A220
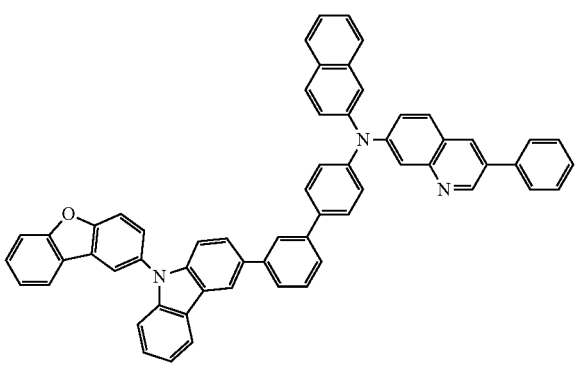
A221
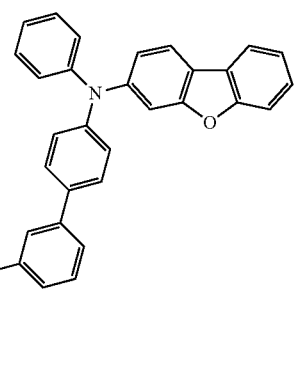
A222
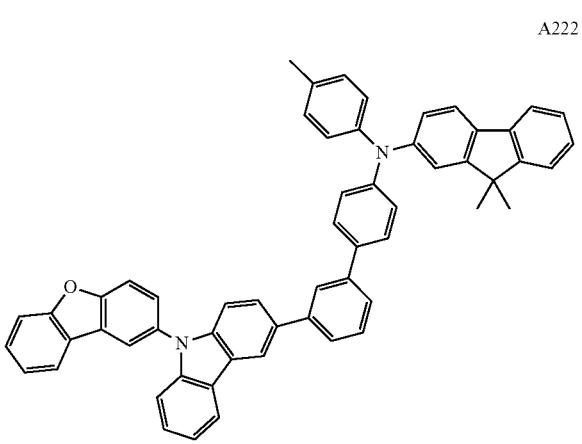

-continued
A223
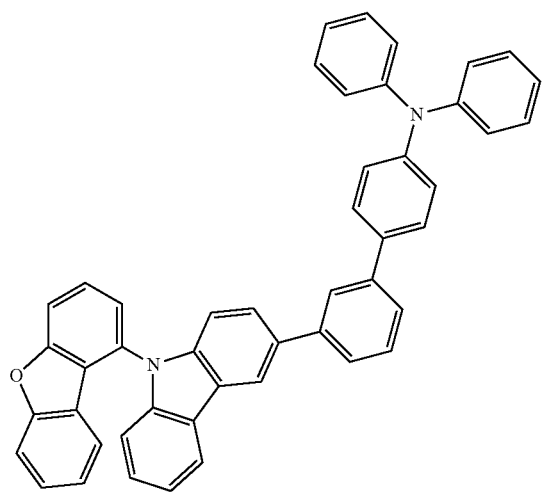
A224
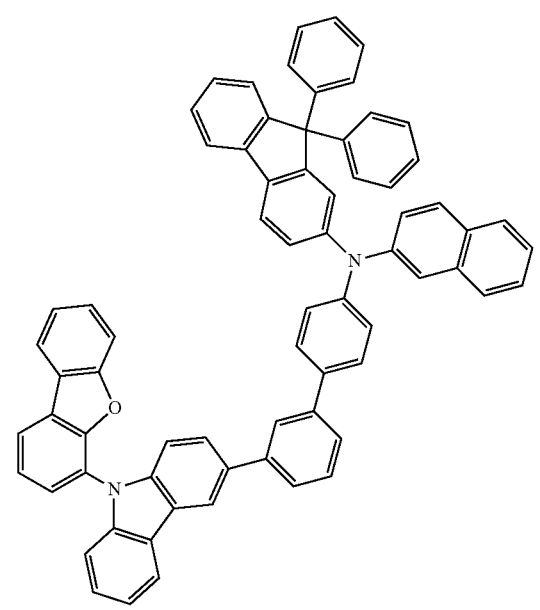
A225
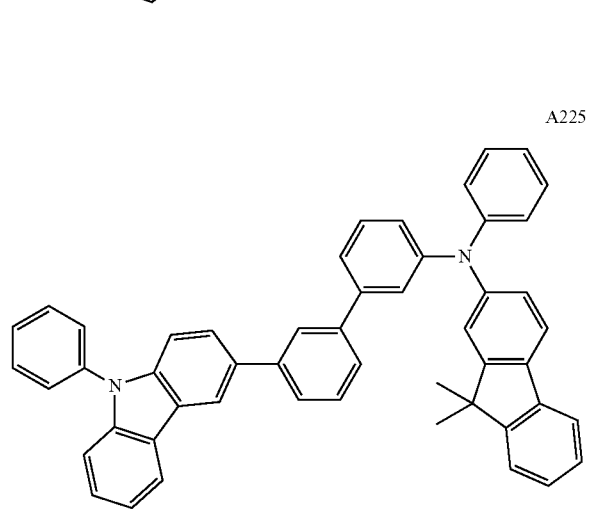
-continued
A226
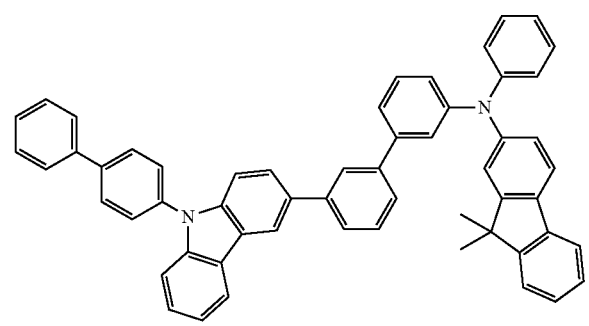
A227
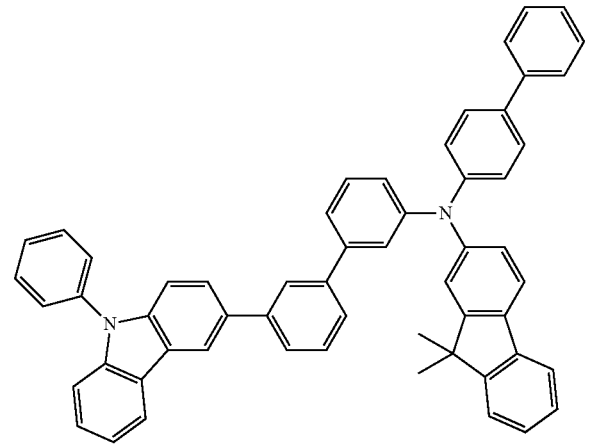
A228
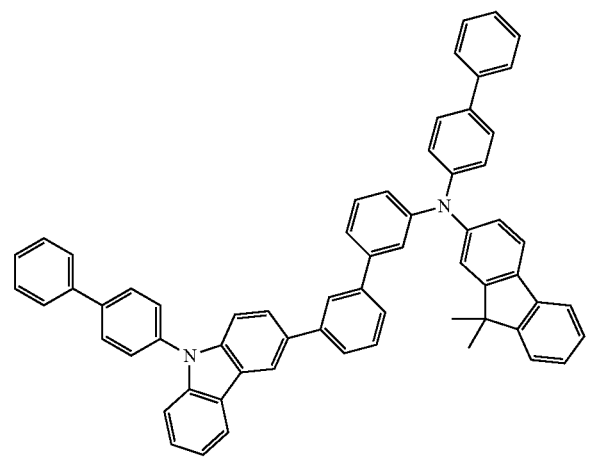

A229
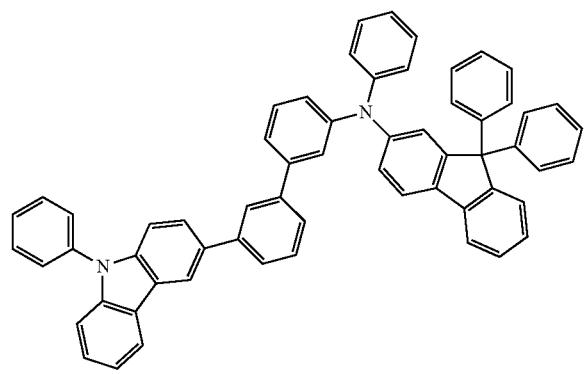
A230
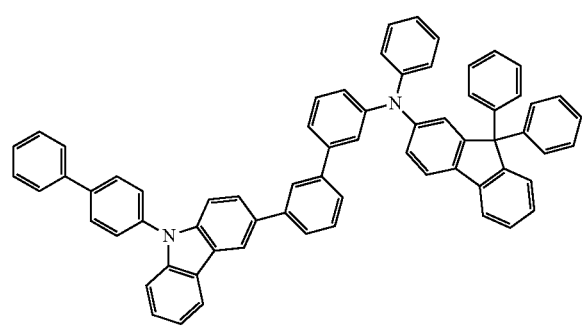
A231
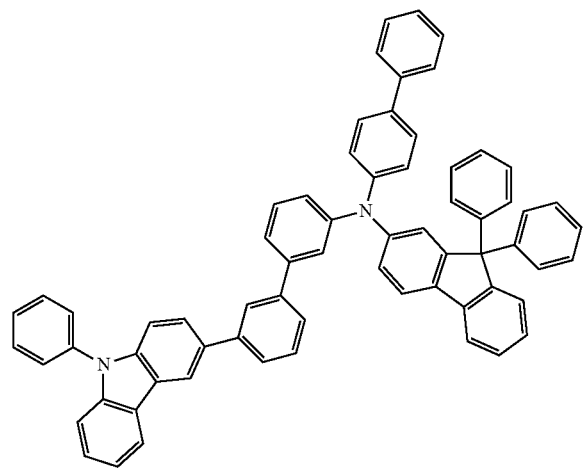
A232
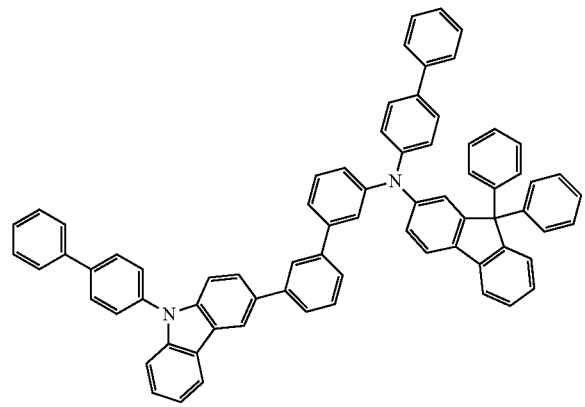
A233
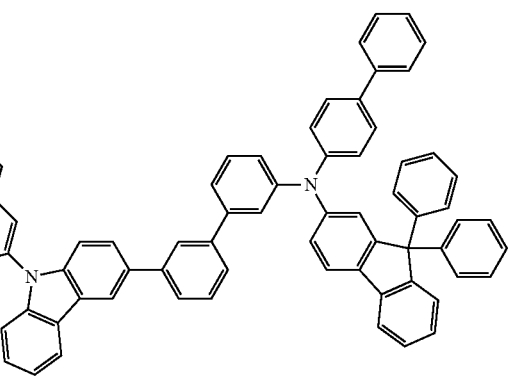
A234
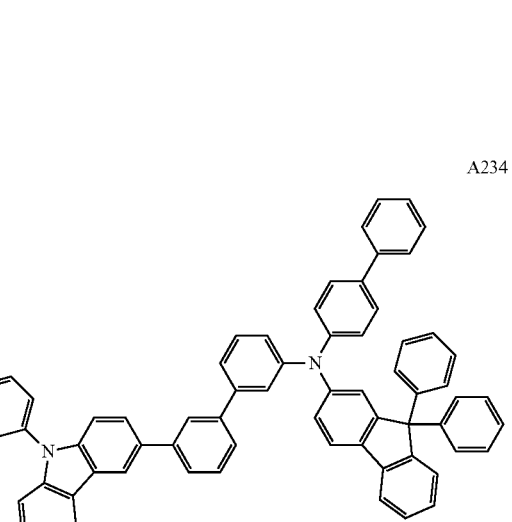
A235
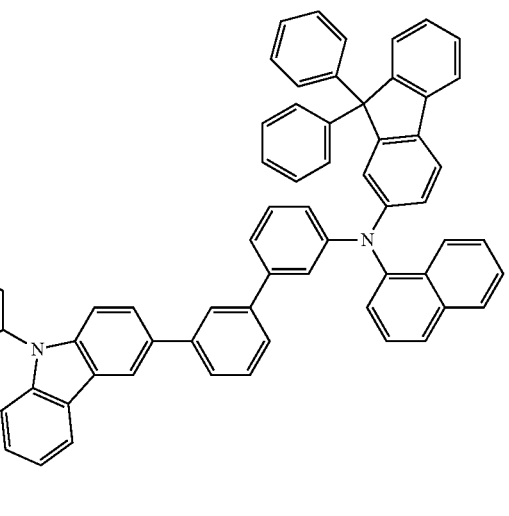

A236
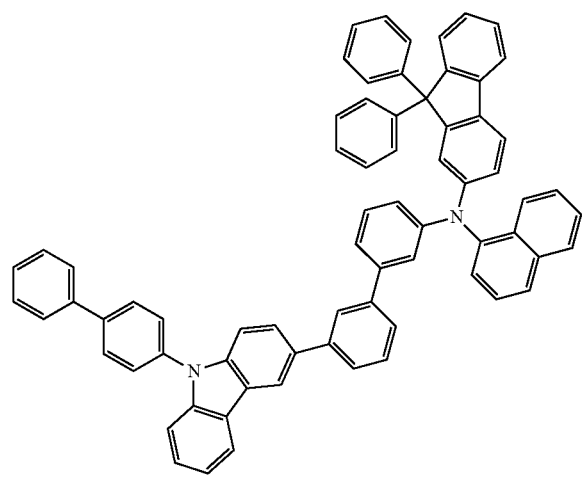
A237
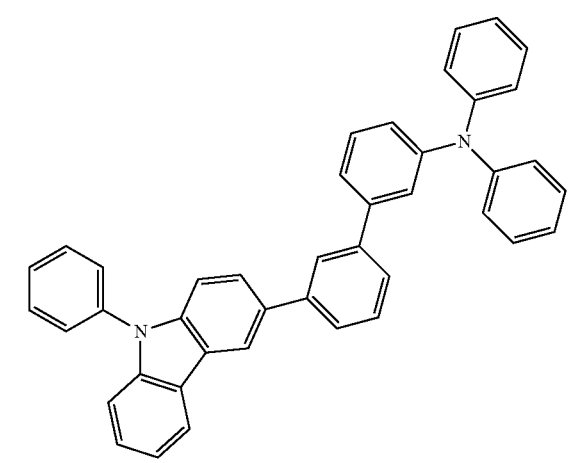
A238
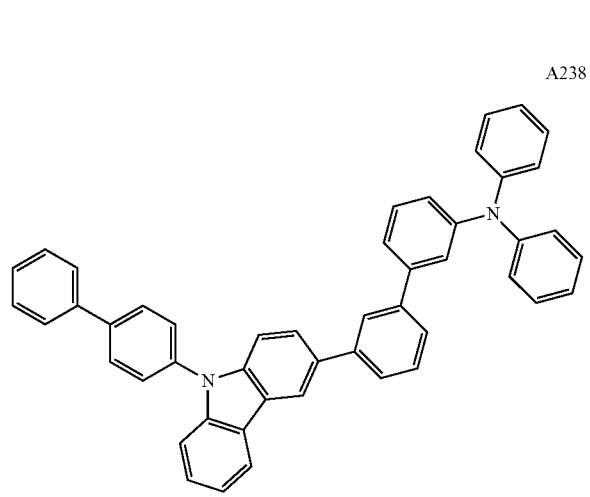
A239
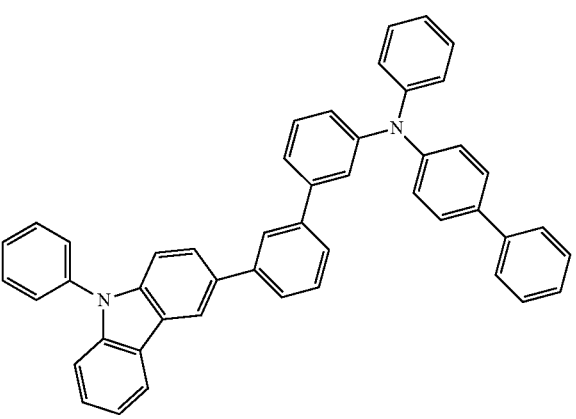
A240
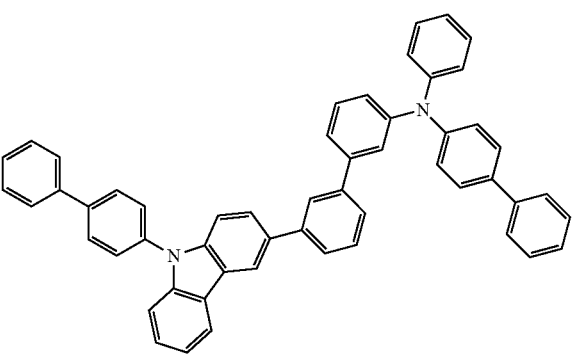
A241
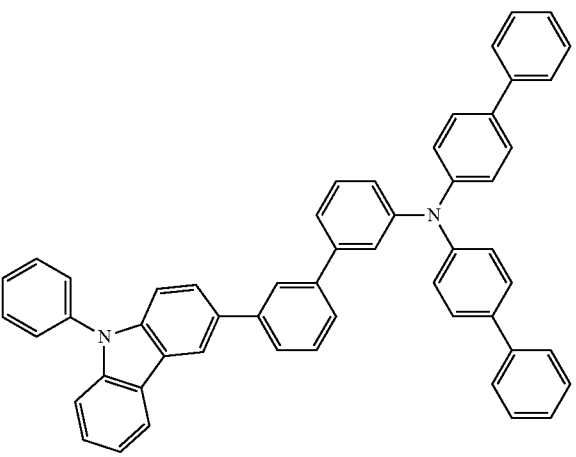

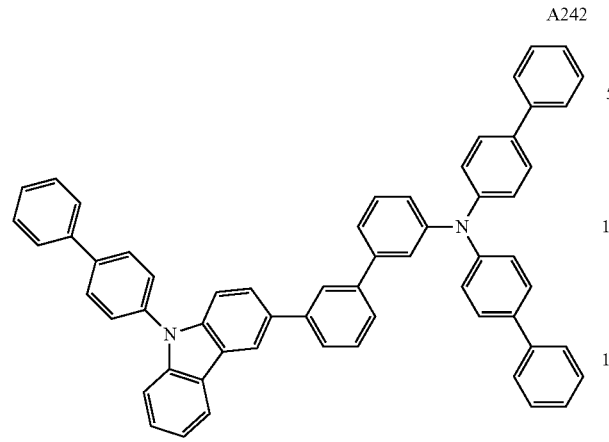
A242
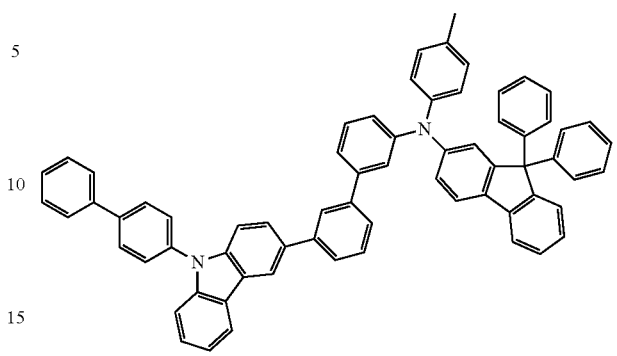
A246
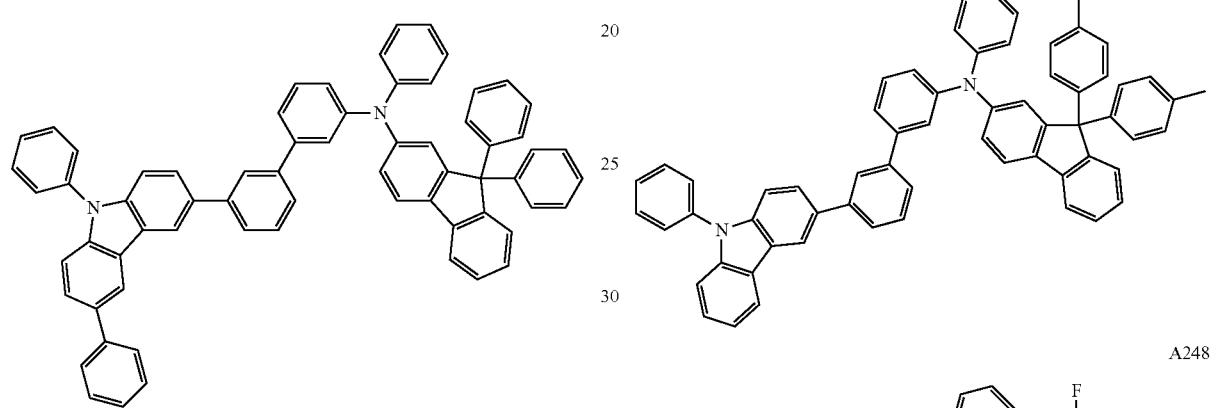
A243
A247
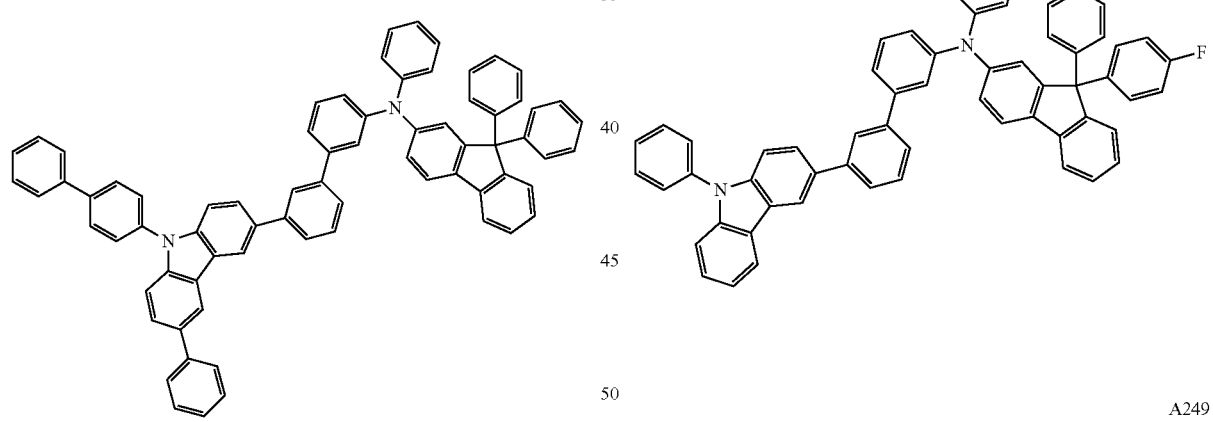
A244
A248
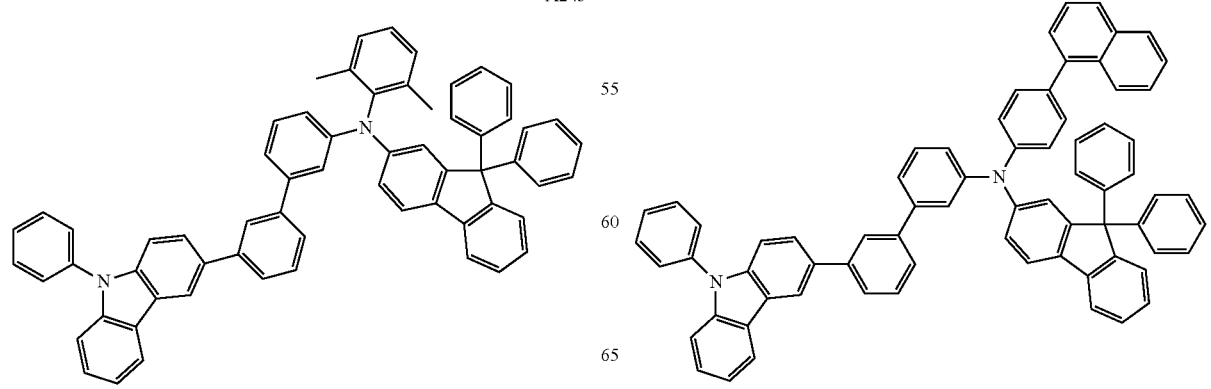
A245
A249

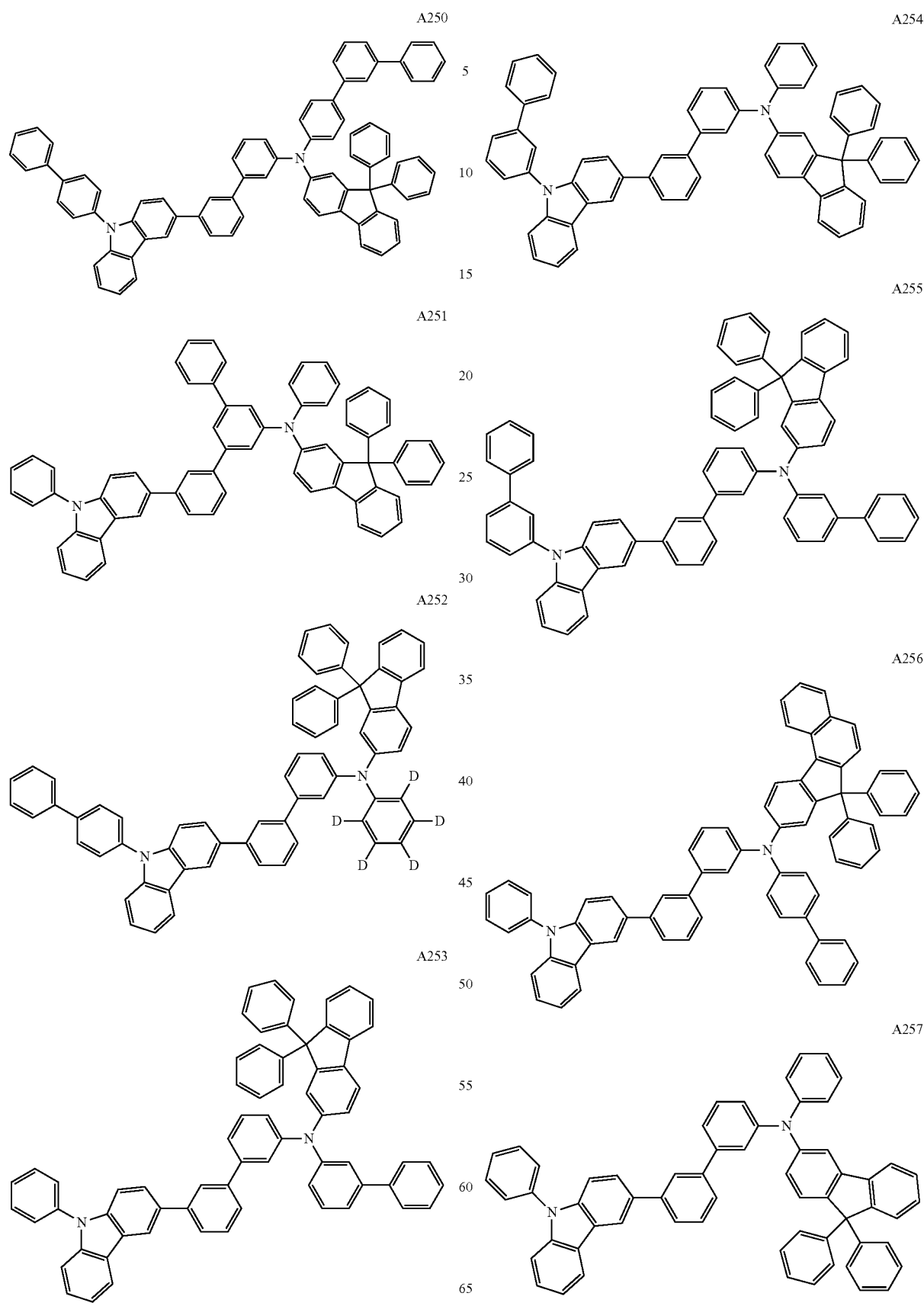

A258
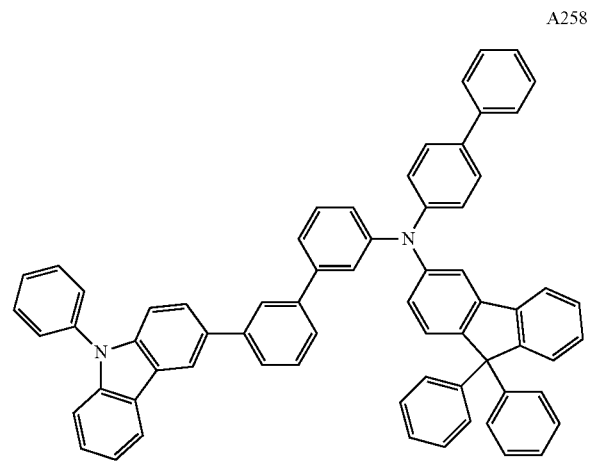
A259
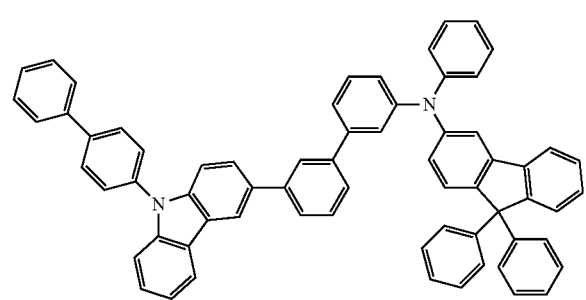
A260
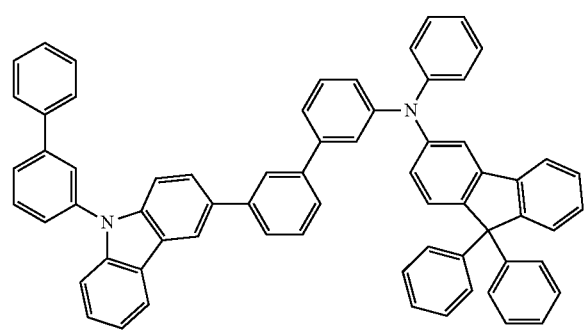
A261
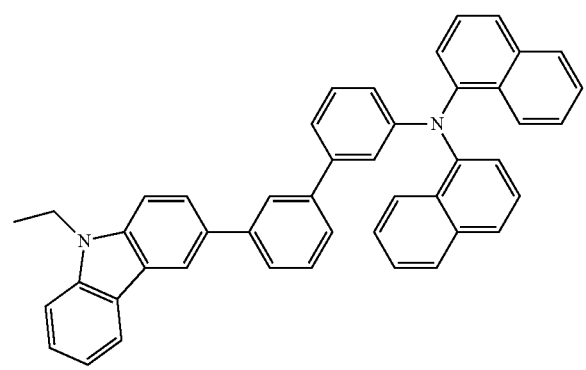
A262
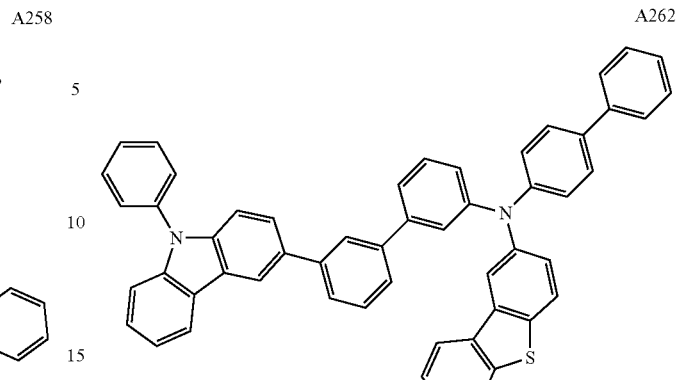
A263
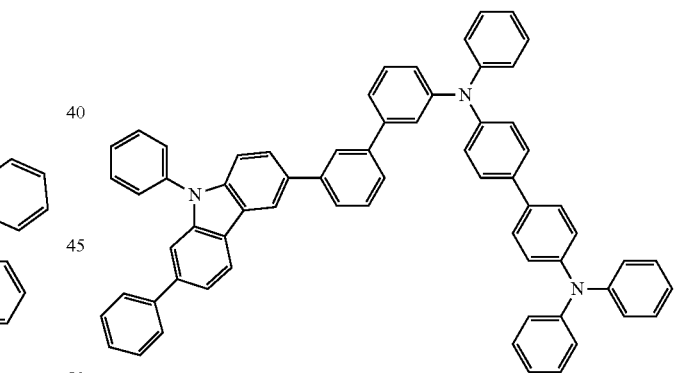
A264
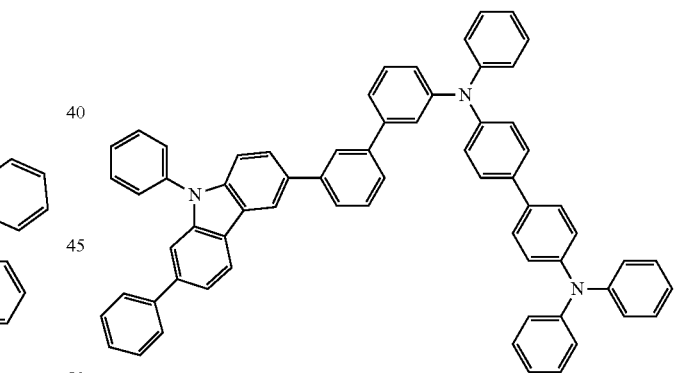
A265
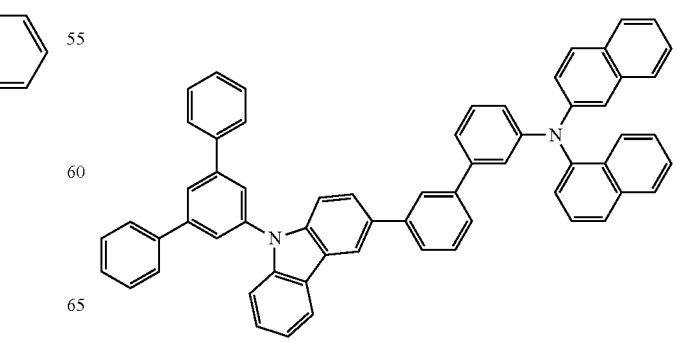

A266
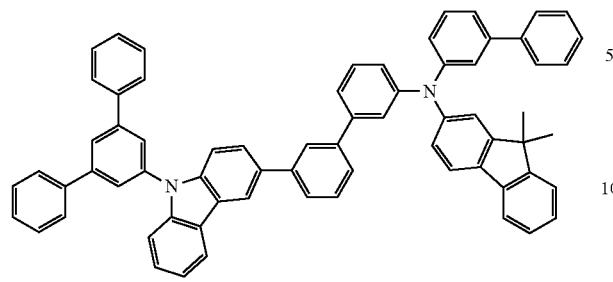
A267
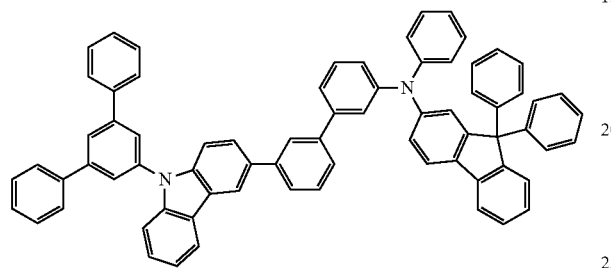
A268
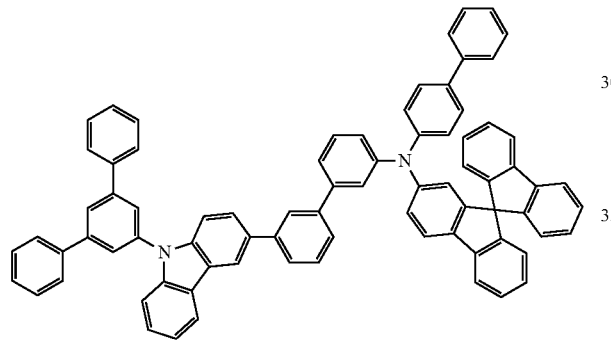
A269
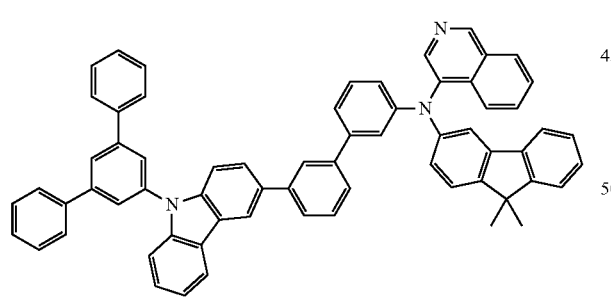
A270
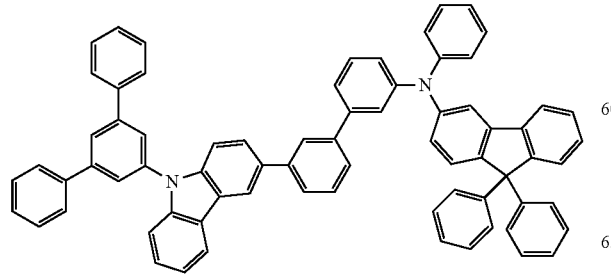
A271
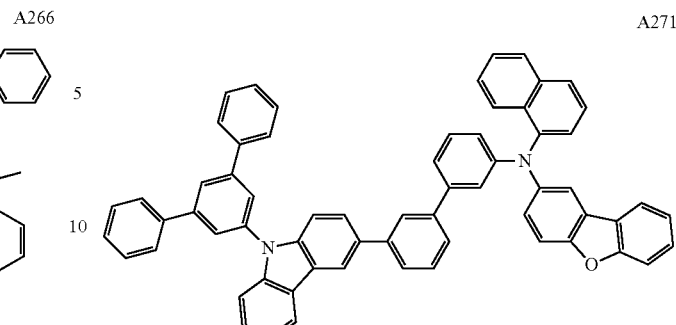
A272
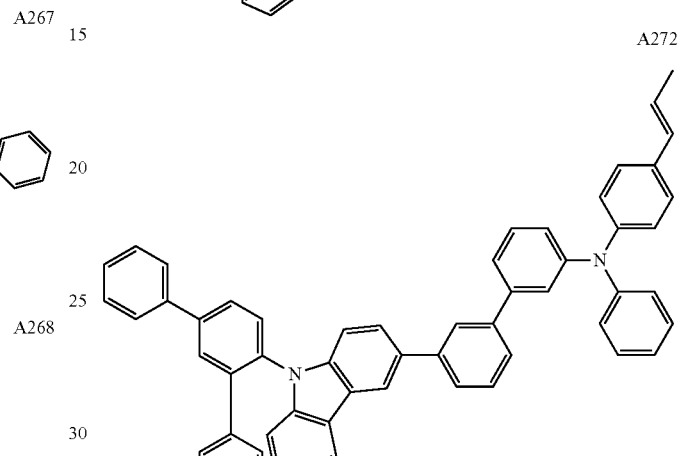
A273
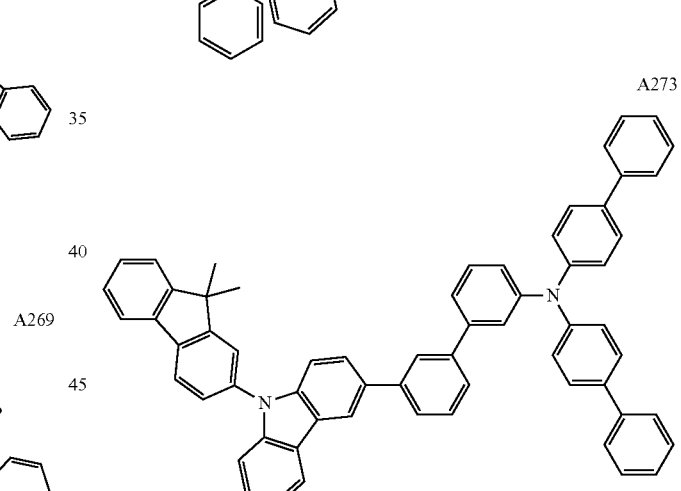
A274
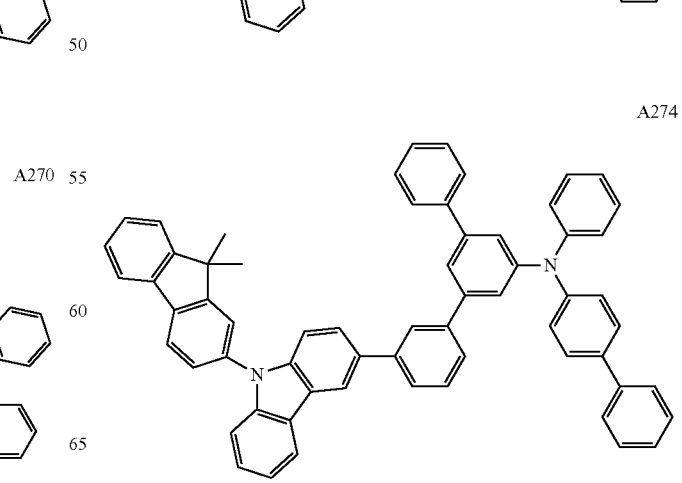

A275
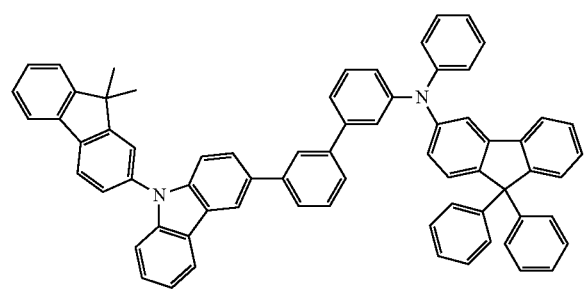
A276
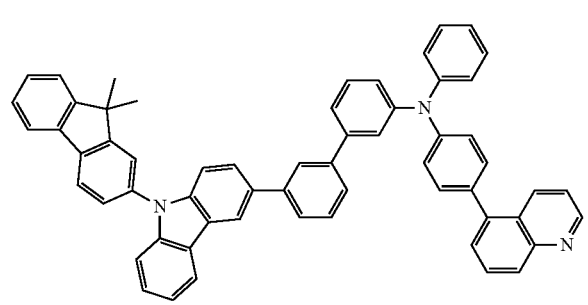
A277
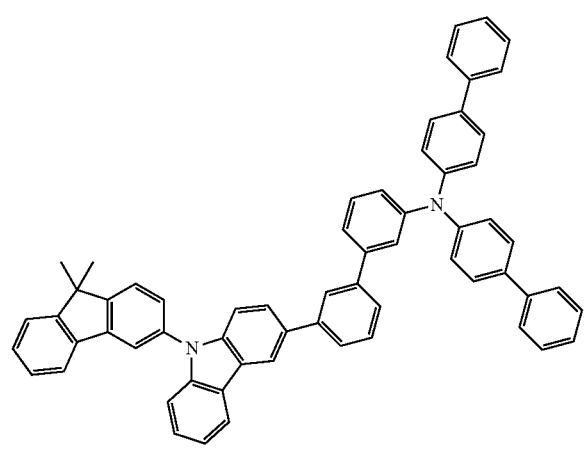
A278
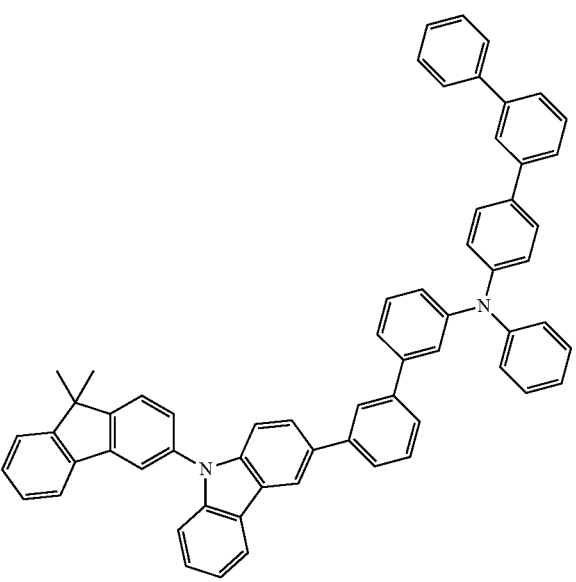
A279
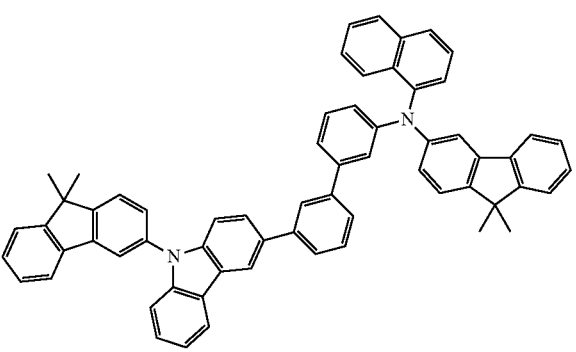
A280
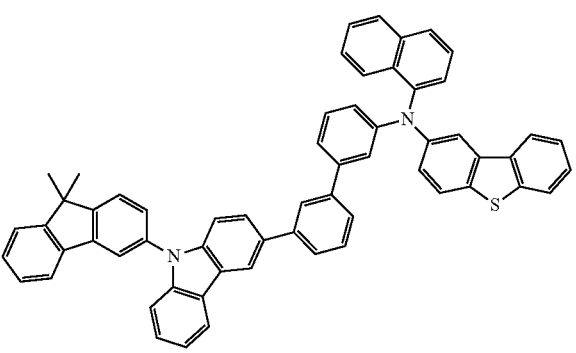

A281
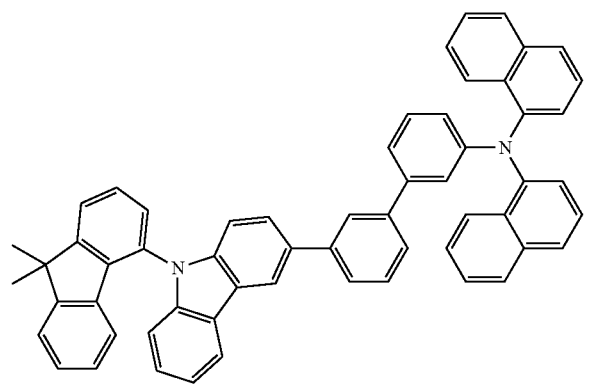
A282
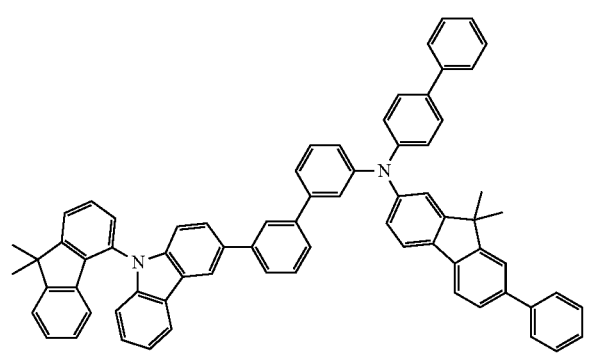
A283
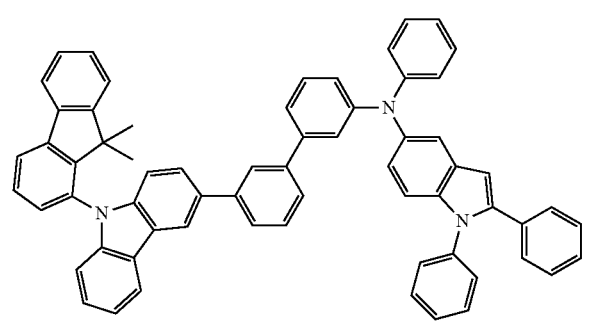
A284
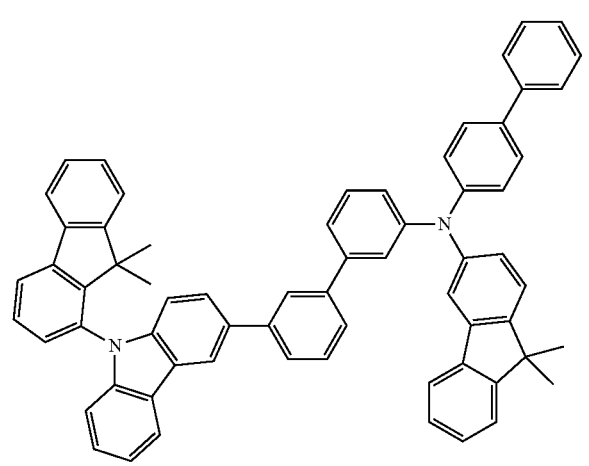
A285
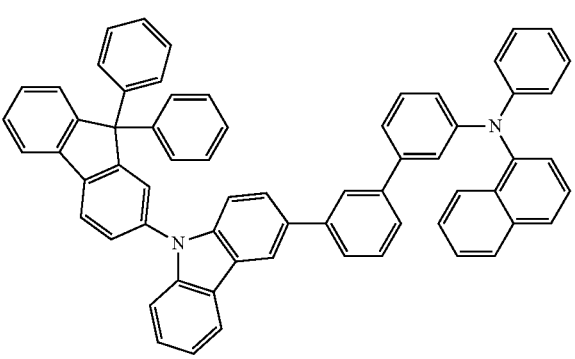
A286
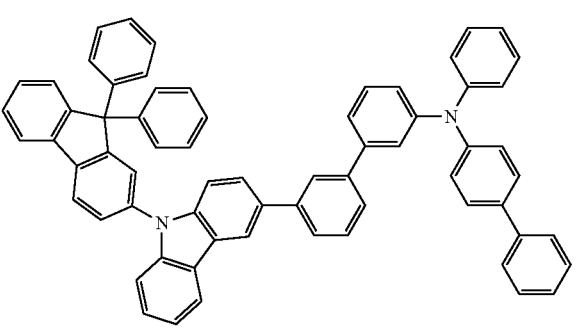
A287
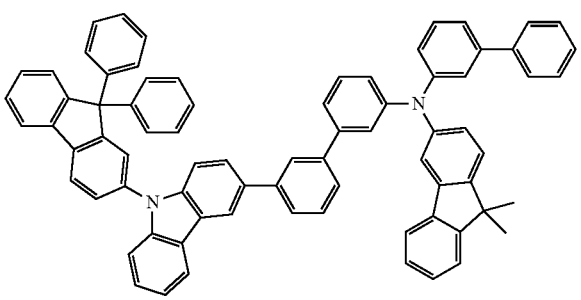
A288
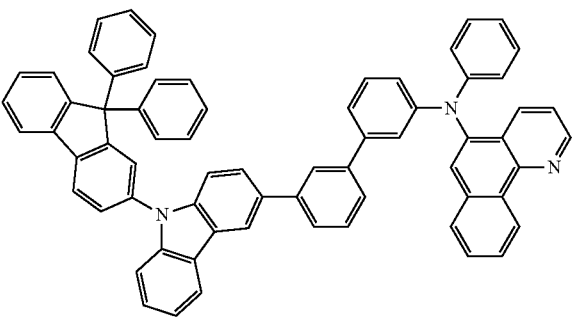

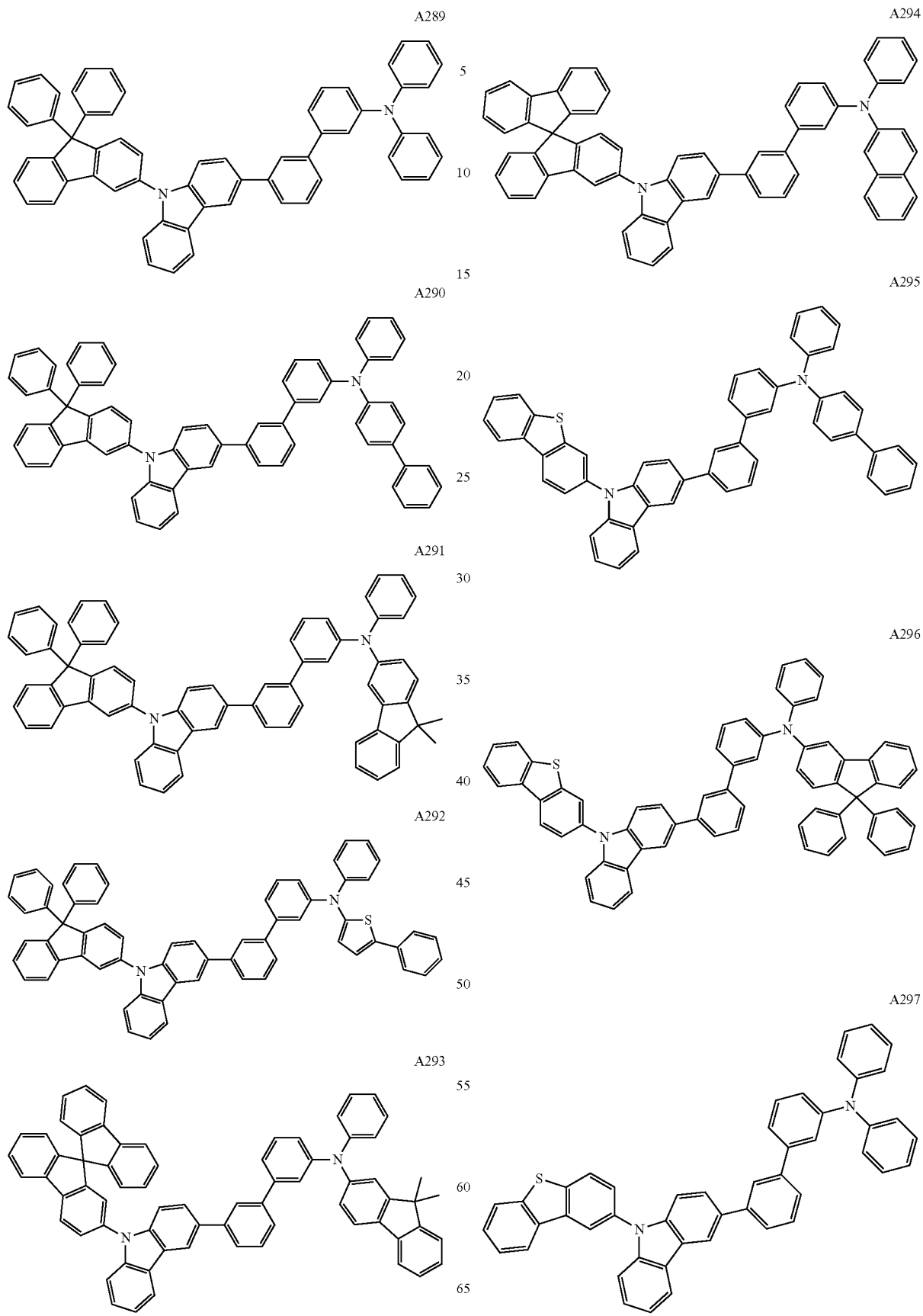

-continued
A298
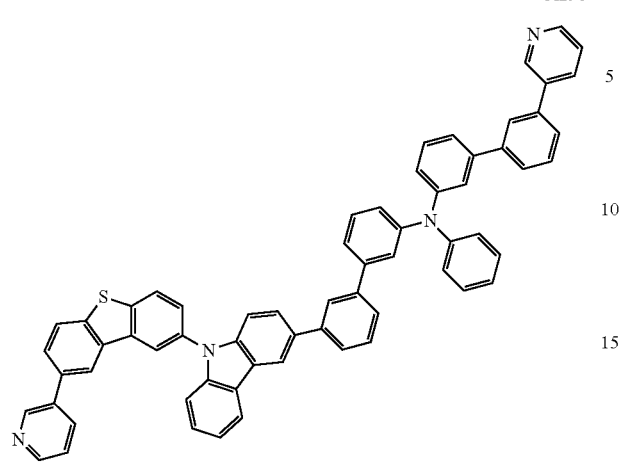
A299
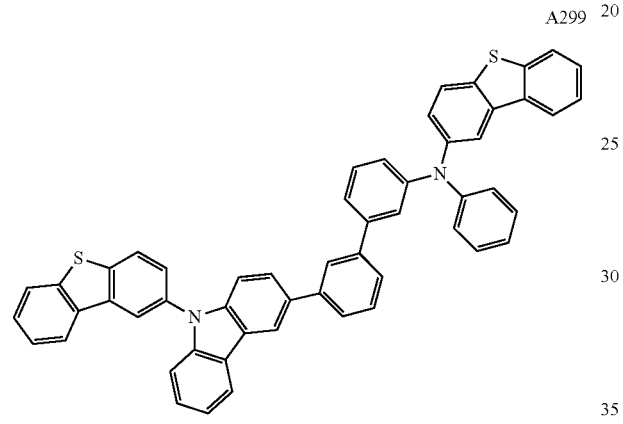
A300
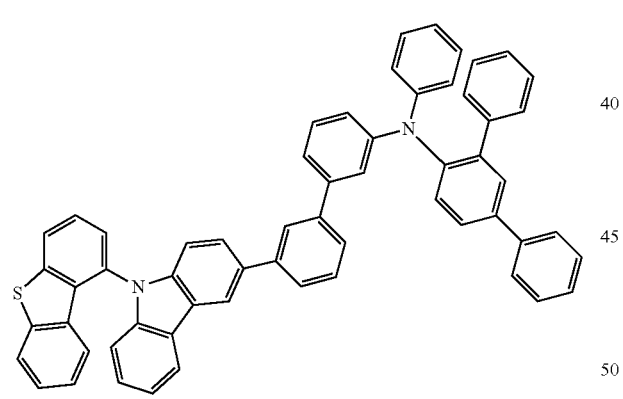
A301
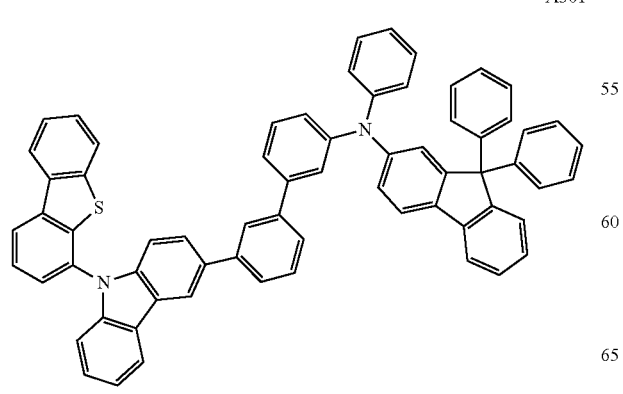
-continued
A302
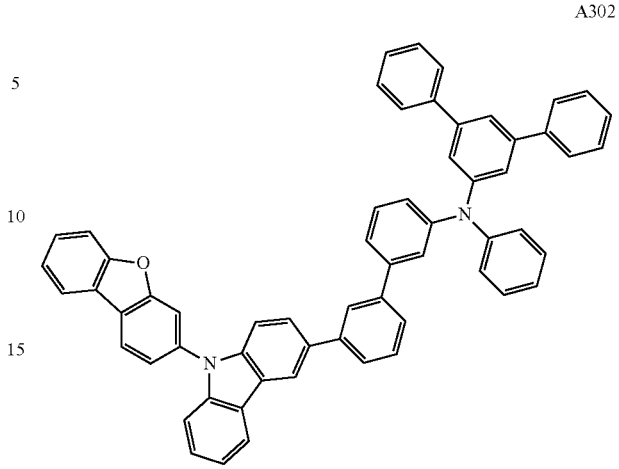
A303
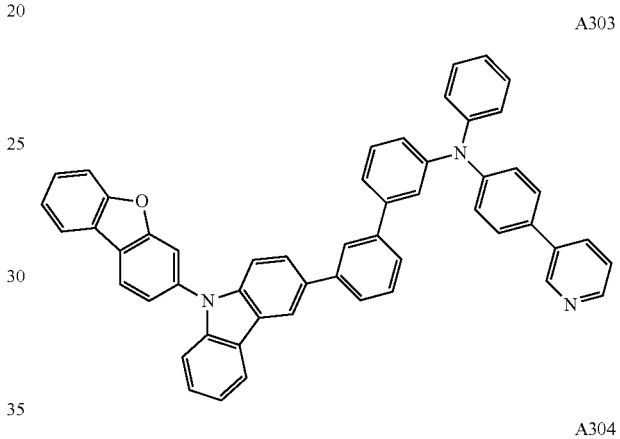
A304
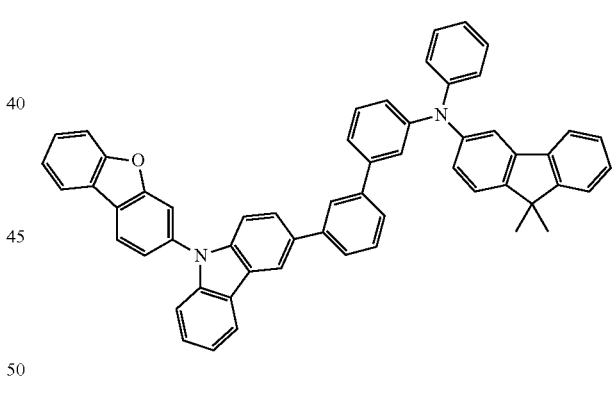
A305
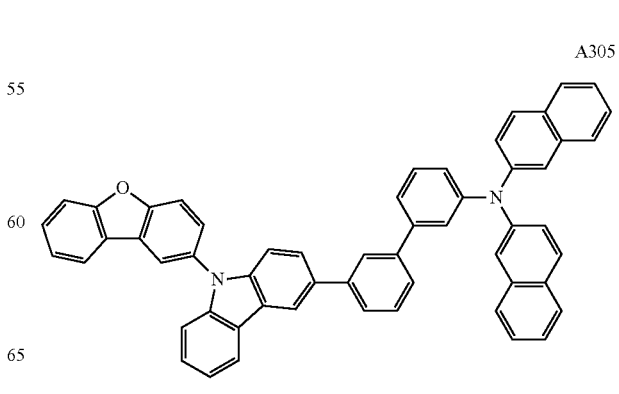

A306
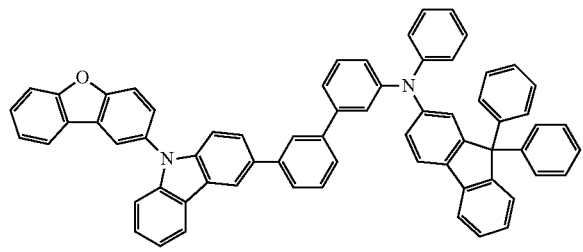
A307
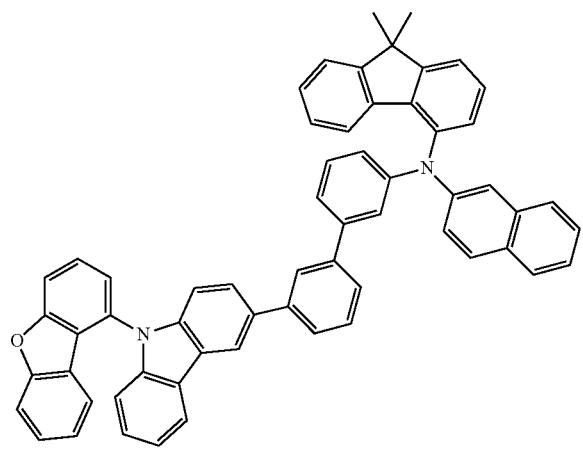
A308
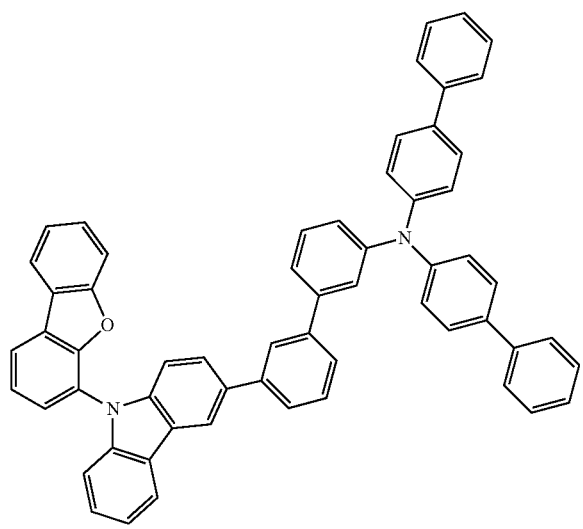
A309
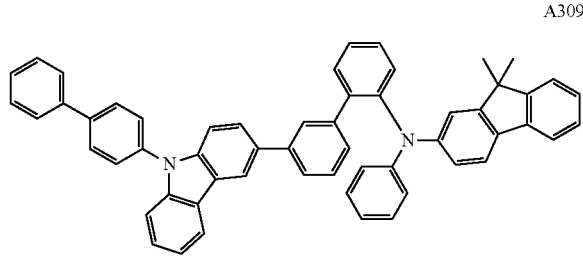
A310
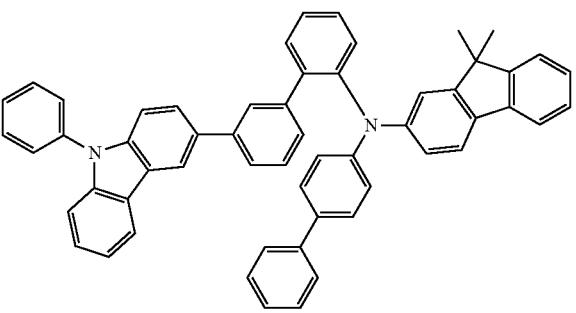
A311
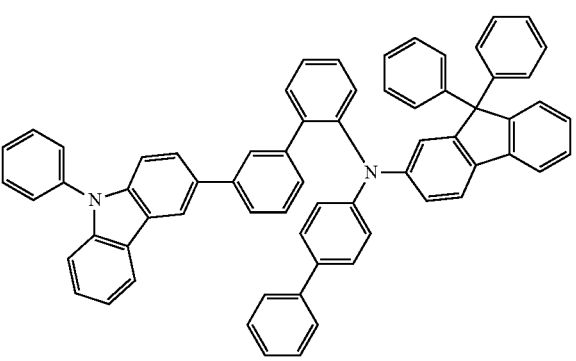
A312
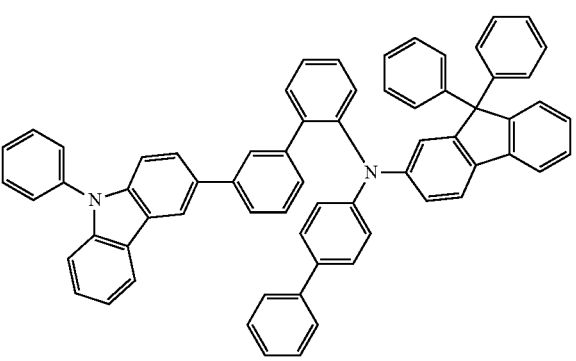
A313
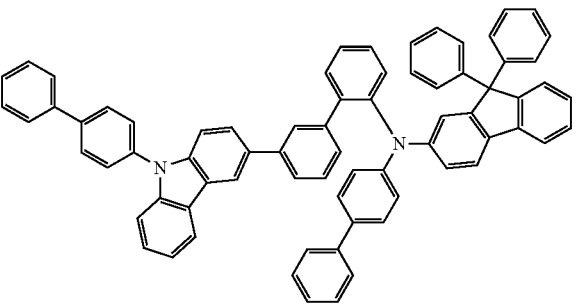

-continued
A314
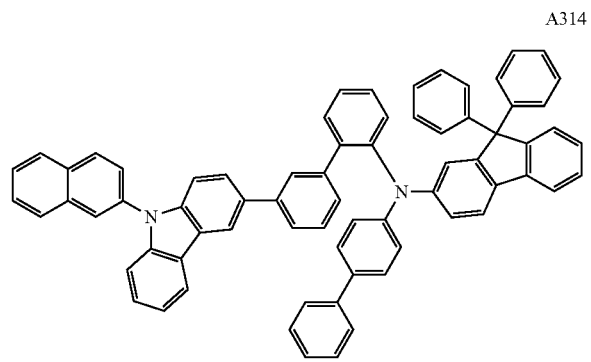
A315
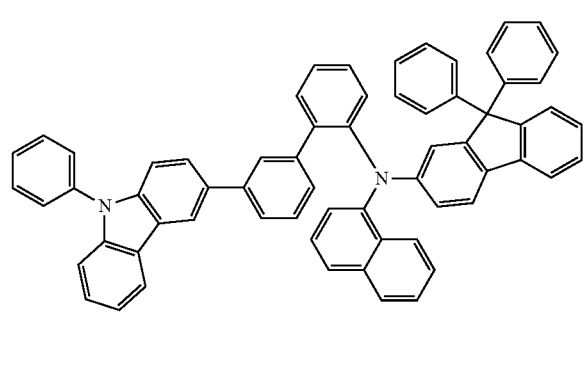
A316
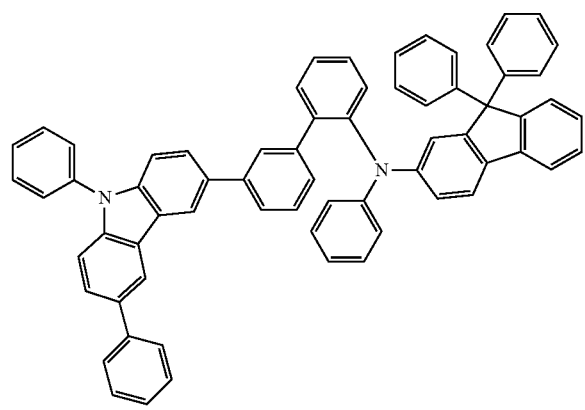
A317
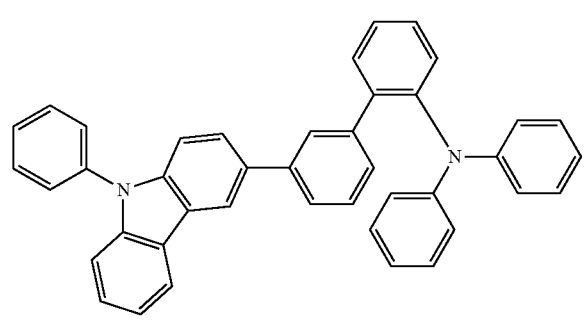
-continued
A318
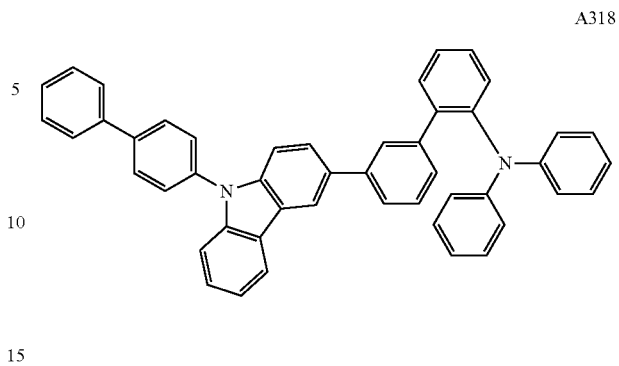
A319
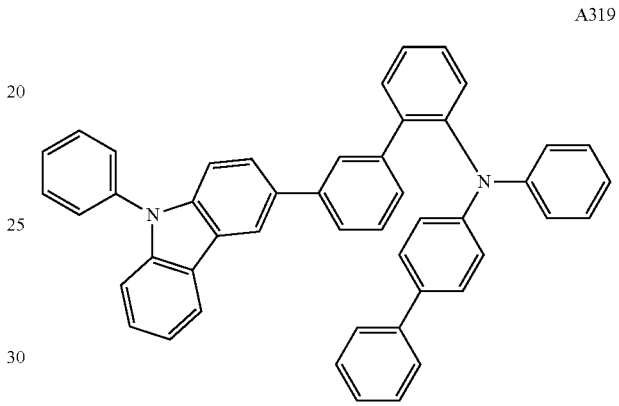
A320
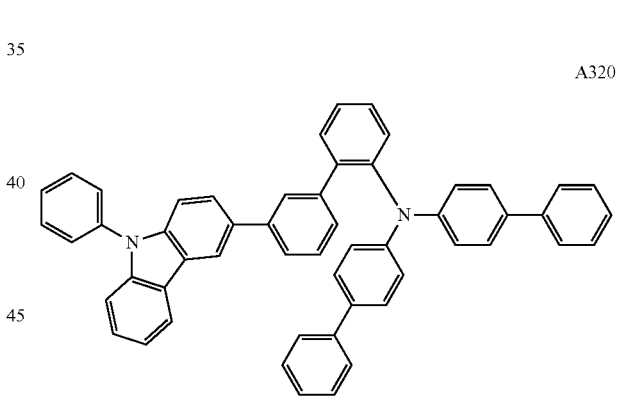
A321
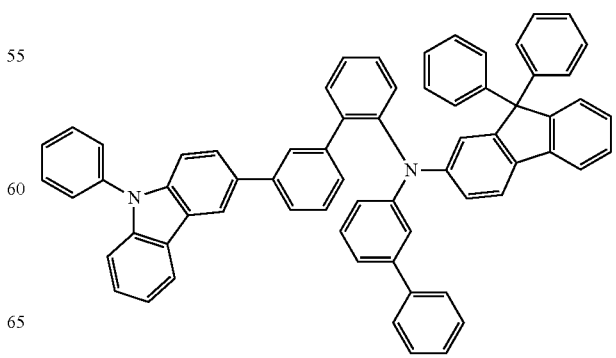

-continued
A322
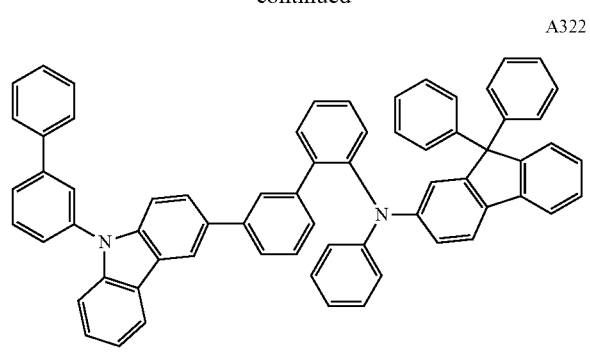
A326
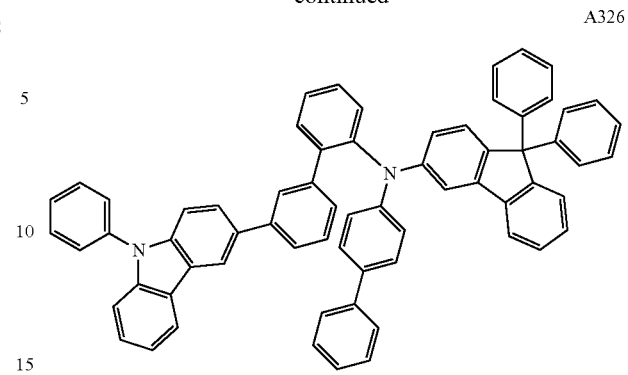
A323
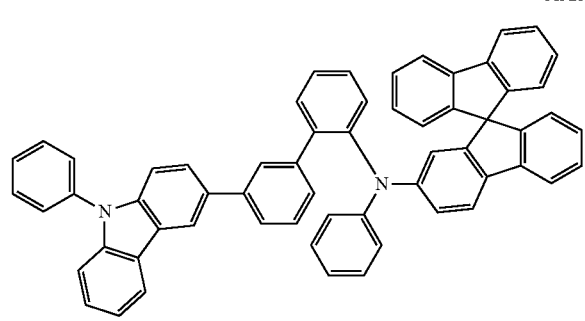
A327
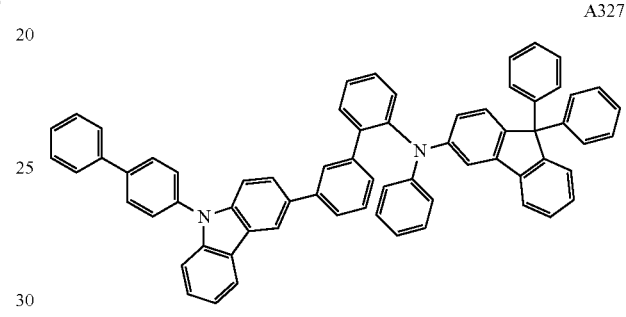
A324
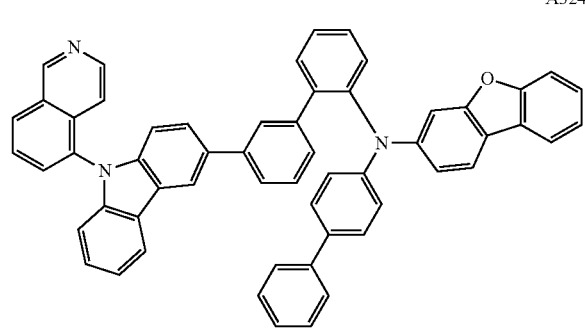
A328
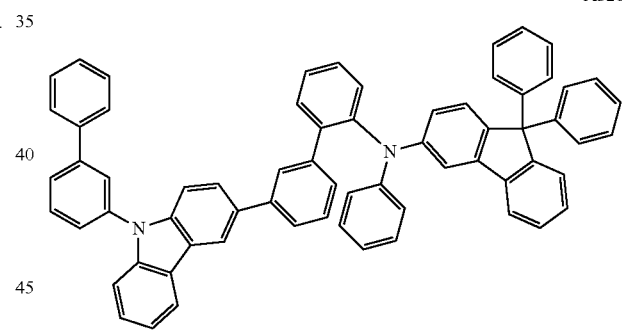
A325
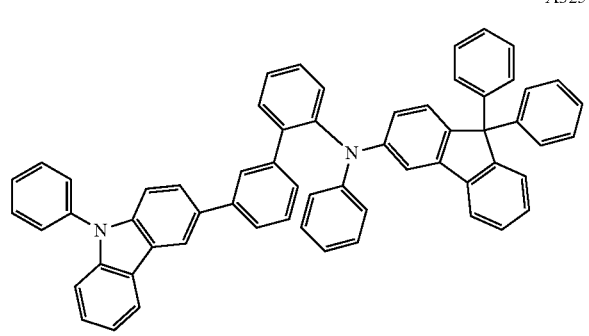
A329
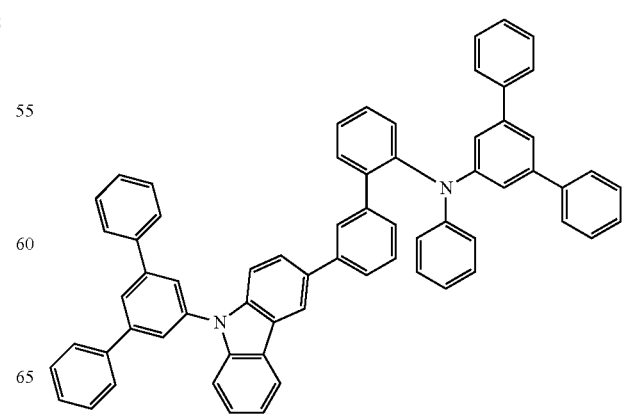

-continued
A330
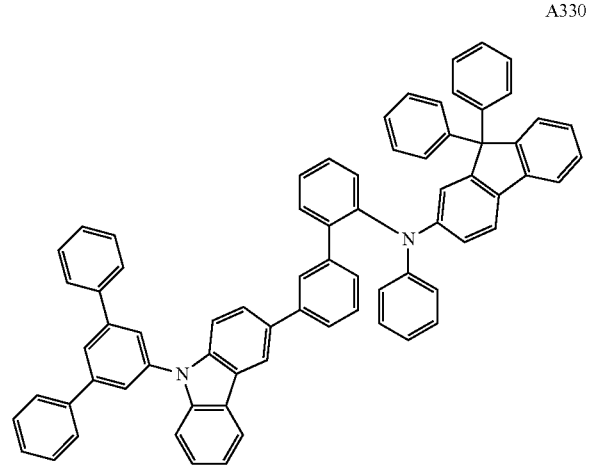
A331
A332
A333
A334
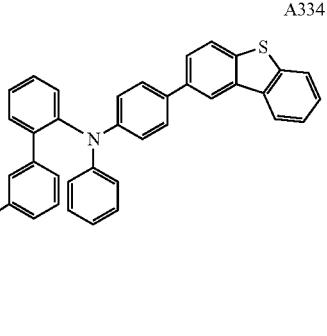
A335
A336
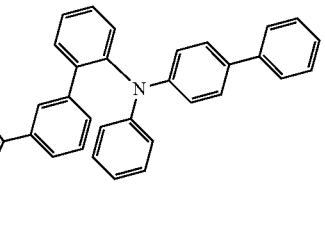
A337
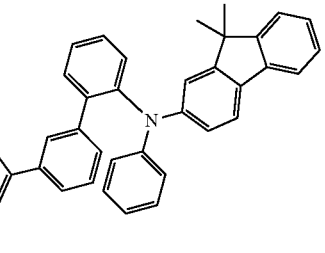
A338
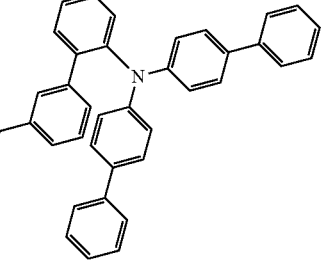

A339
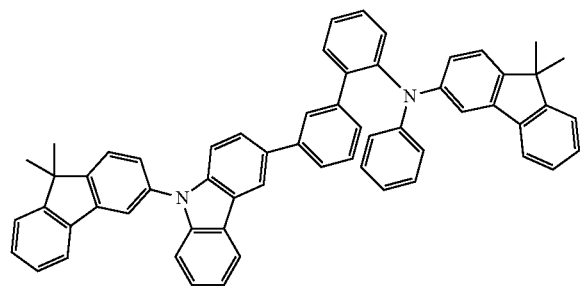
A340
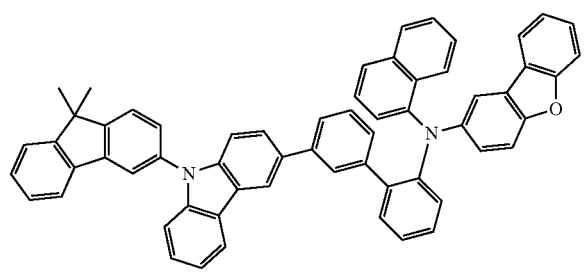
A341
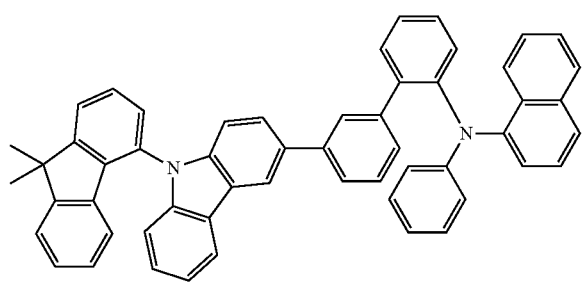
A342
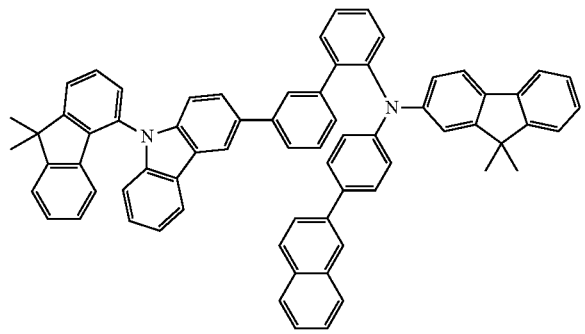
A343
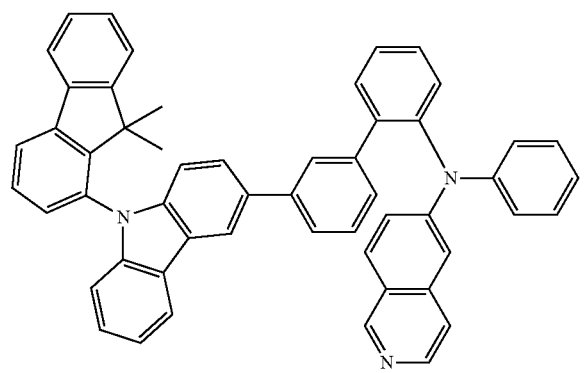
A344
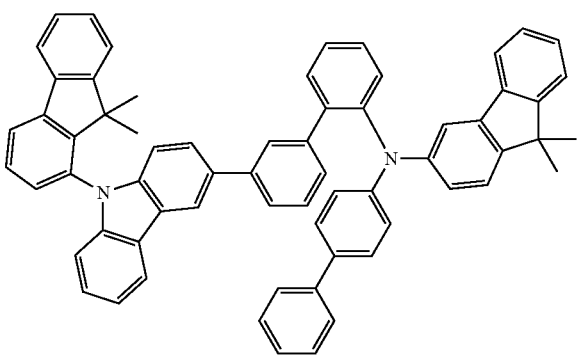
A345
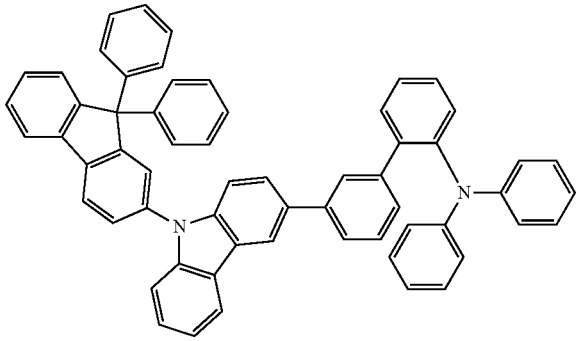
A346
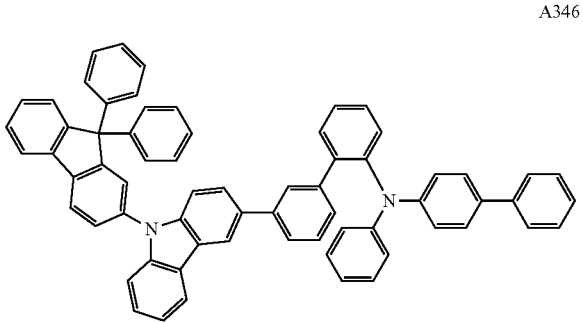
A347
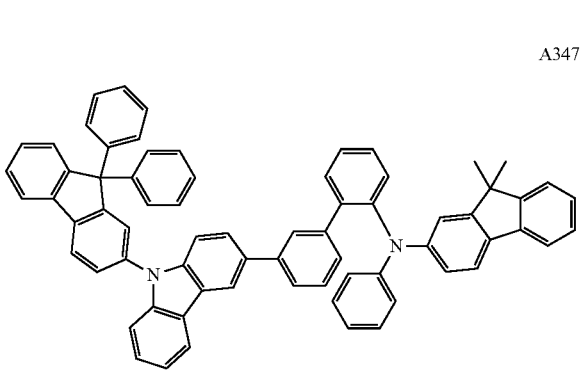

A348
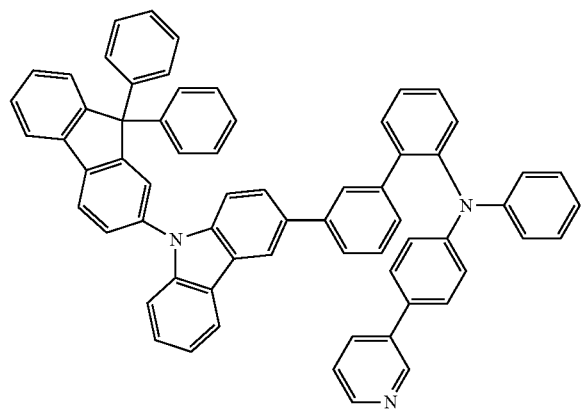
A349
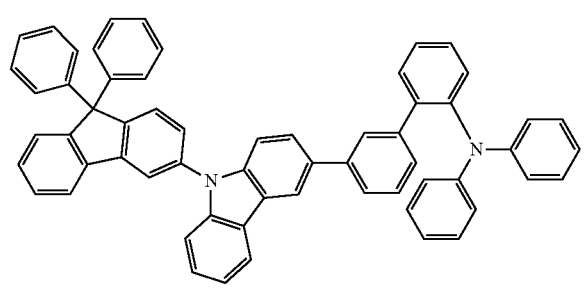
A350
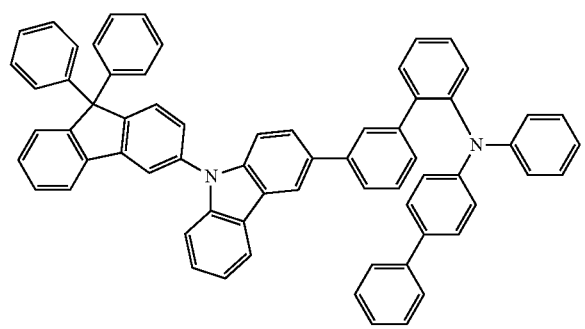
A351
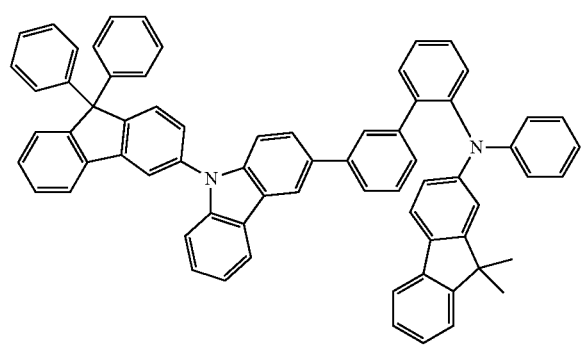
A352
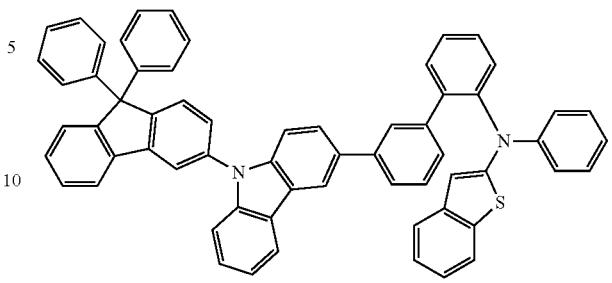
A353
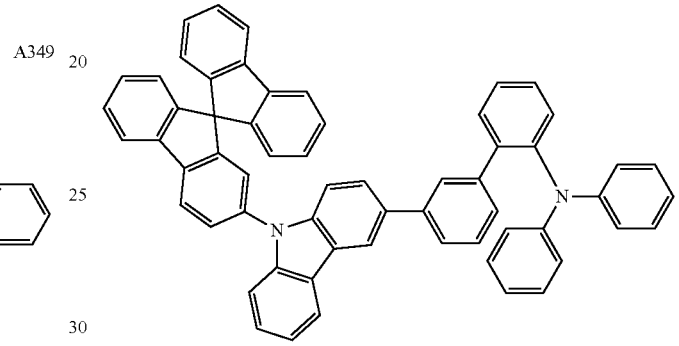
A354
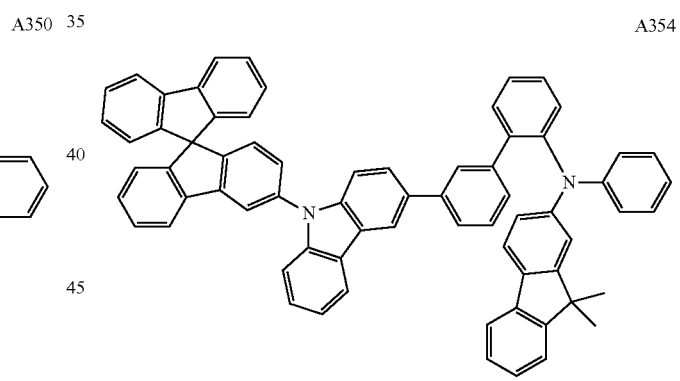
A355
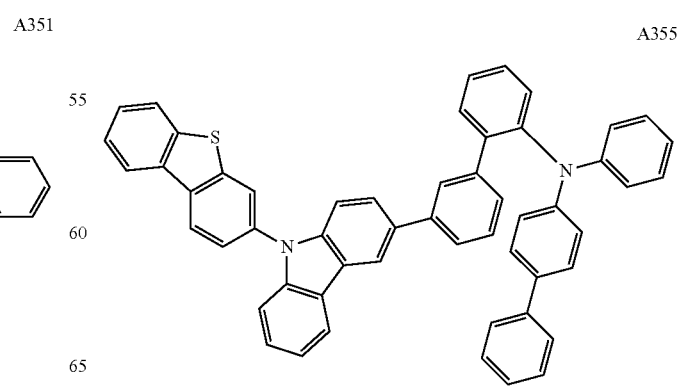

A356
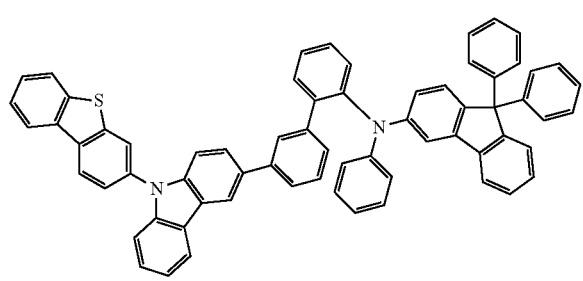
A357
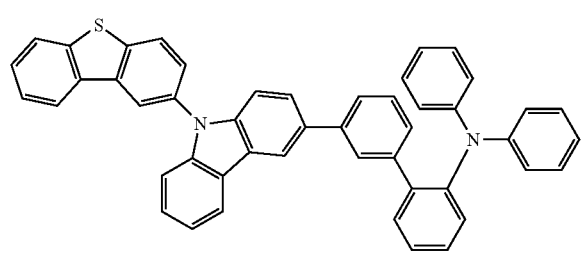
A358
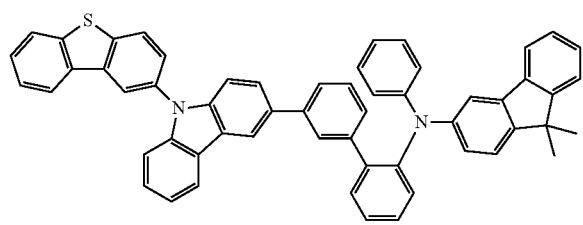
A359
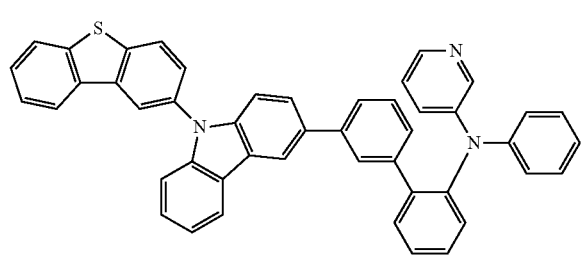
A360
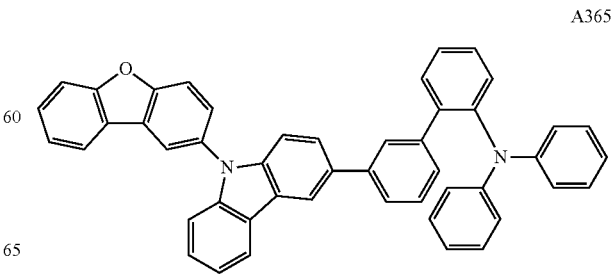
A361
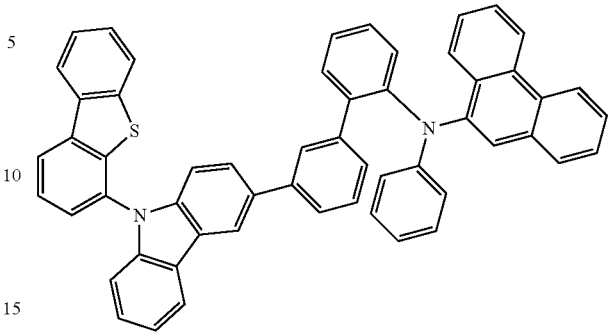
A362
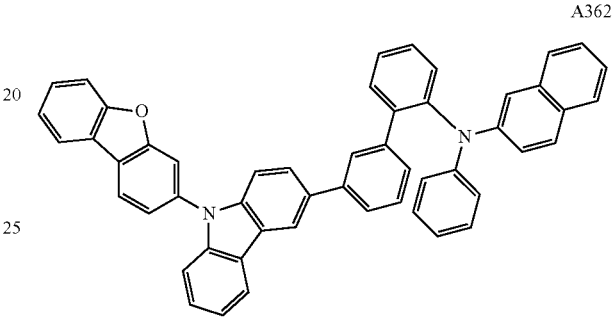
A363
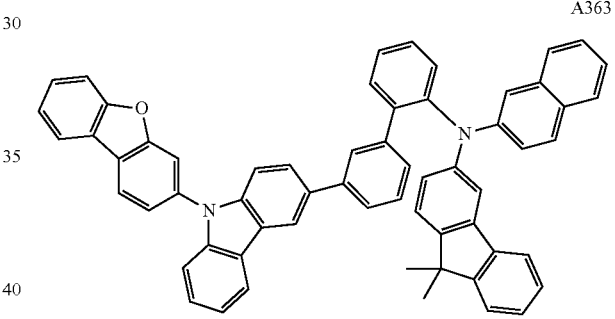
A364
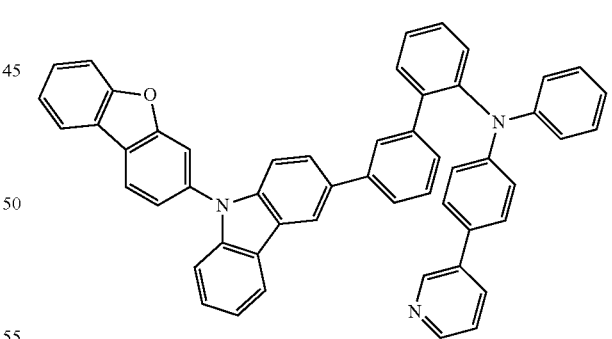
A365

A366
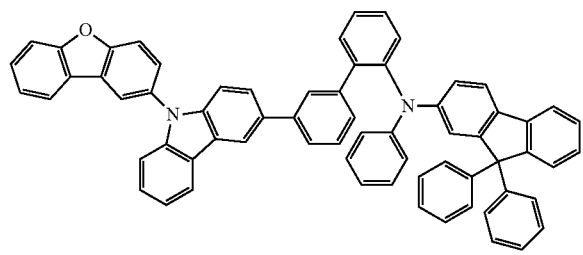
A367
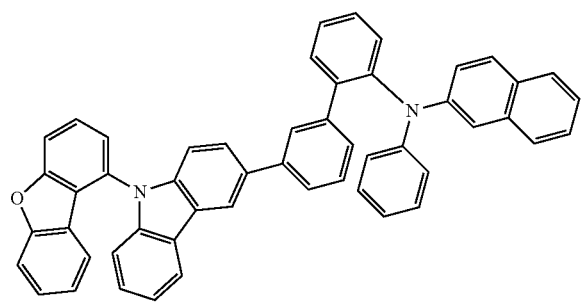
A368
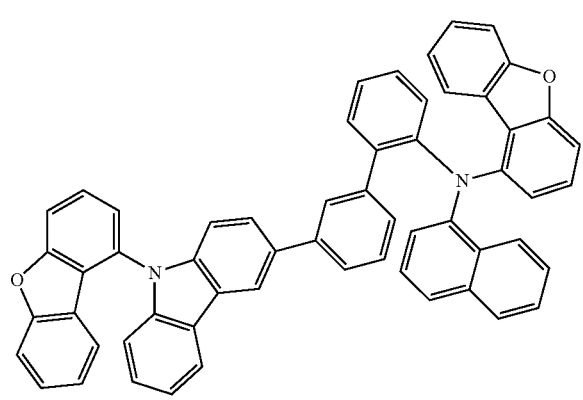
A369
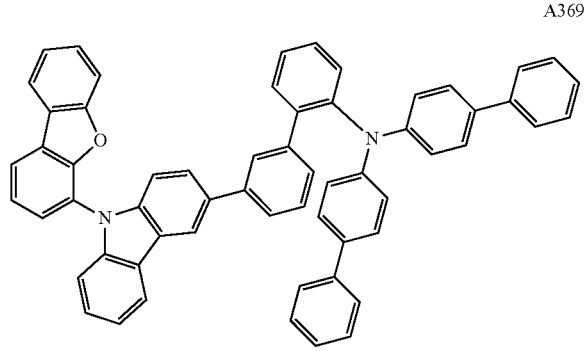
A370
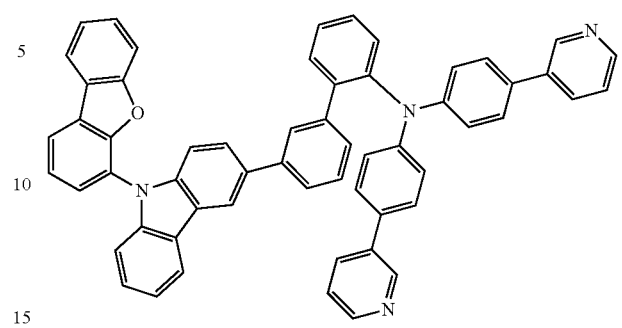
A371
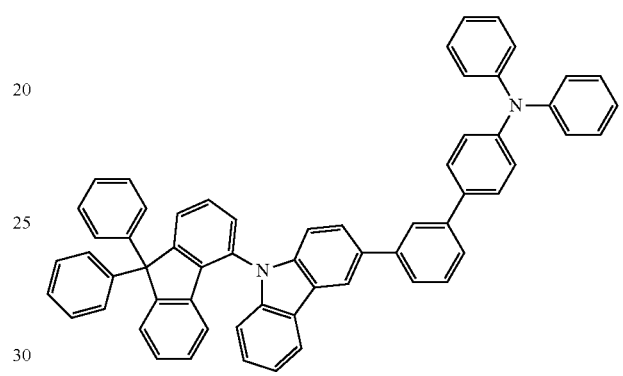
A372
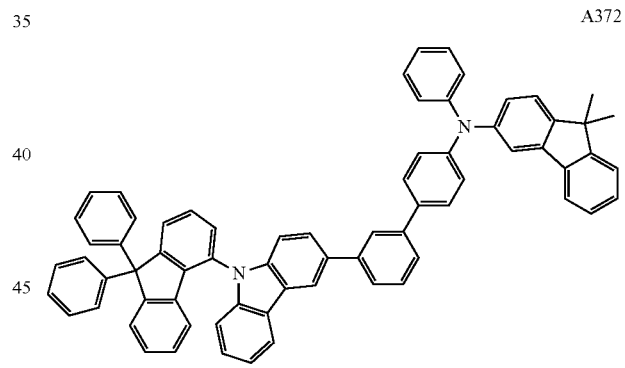
A373
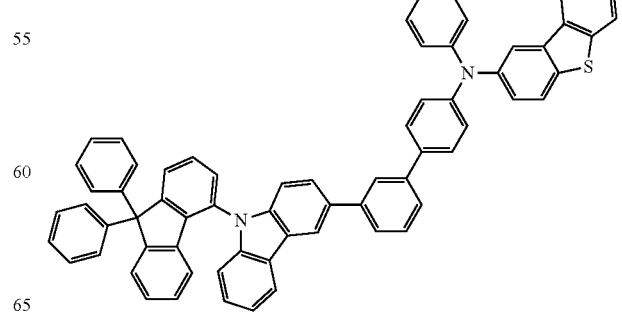

517
-continued
A374
A375
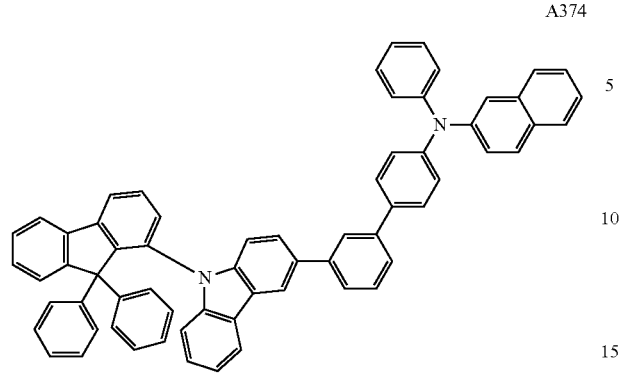
A376
A377
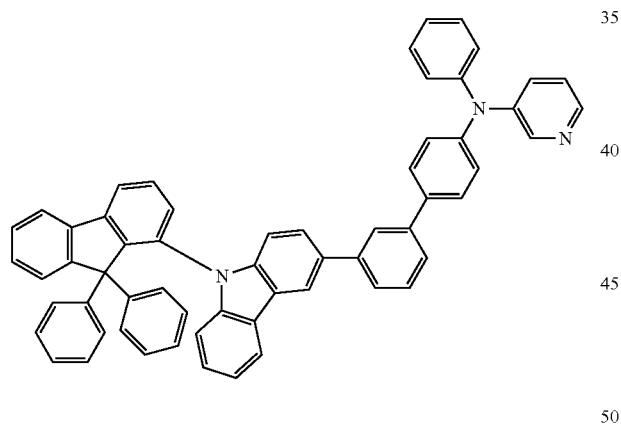
518
-continued
A378
A379
A380
A381
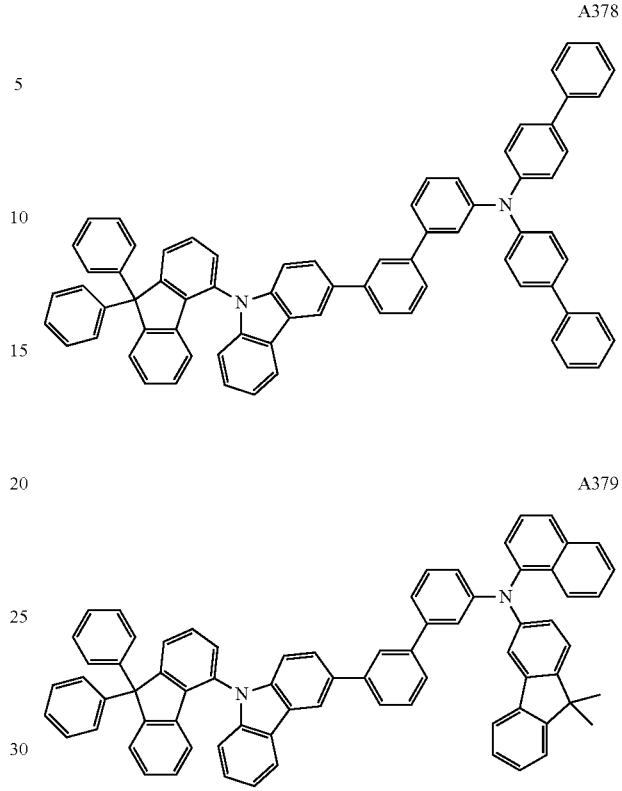
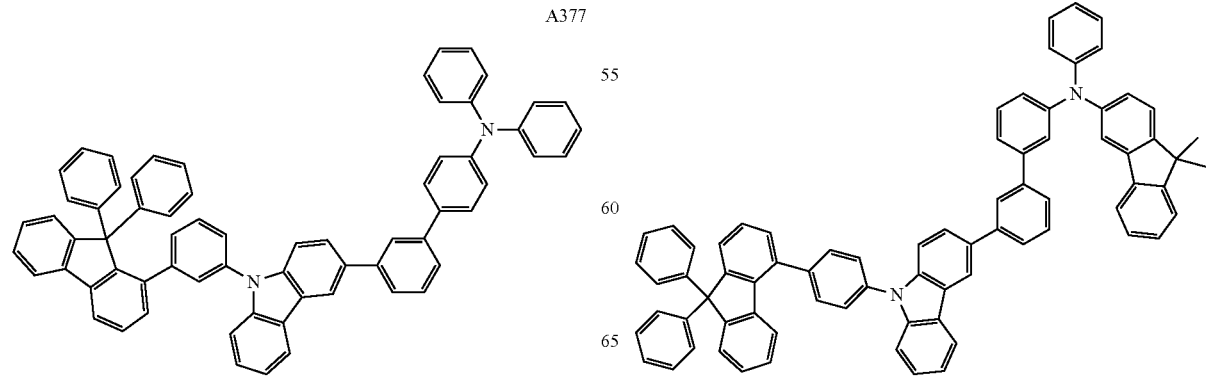

A382
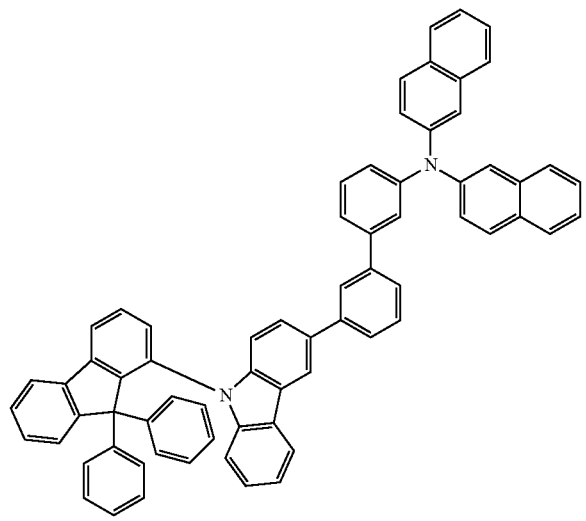
A383
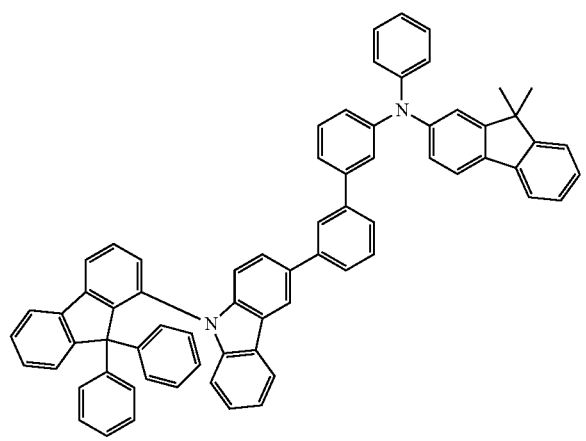
A384
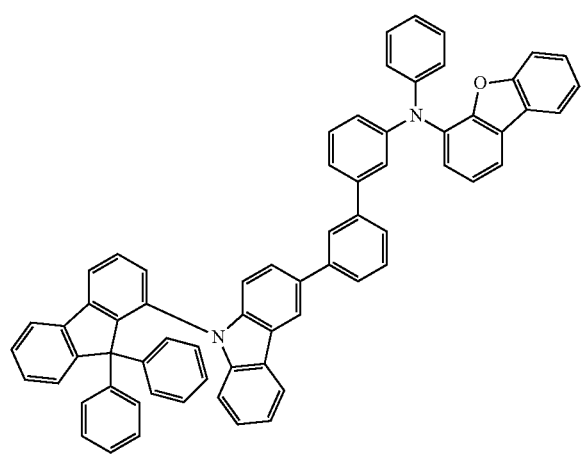
A385
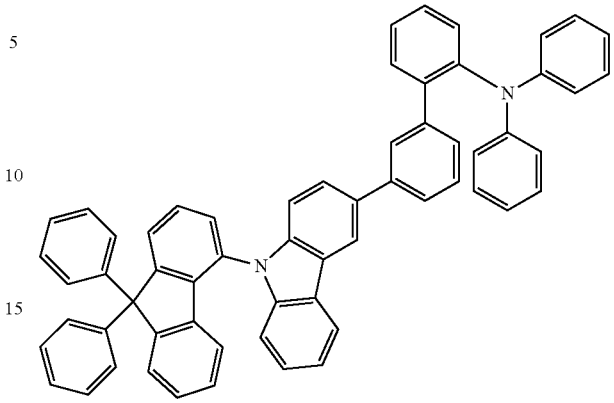
A386
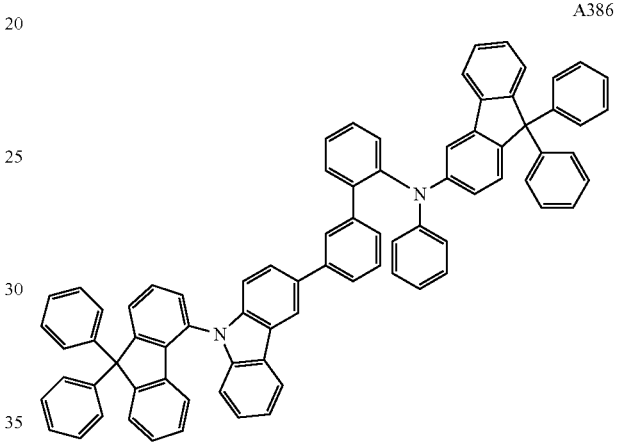
A387
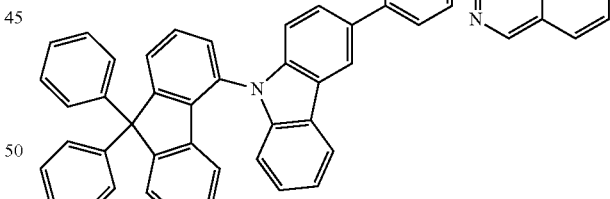
A388
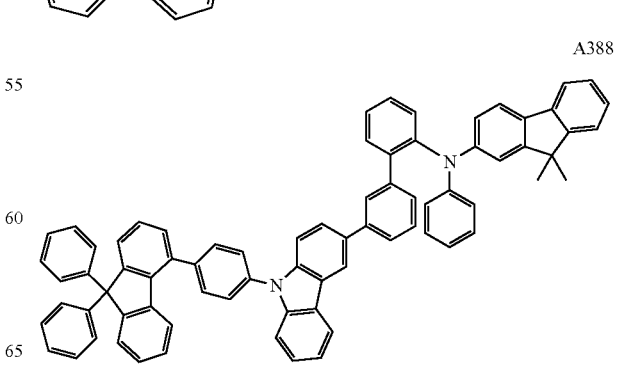

A389
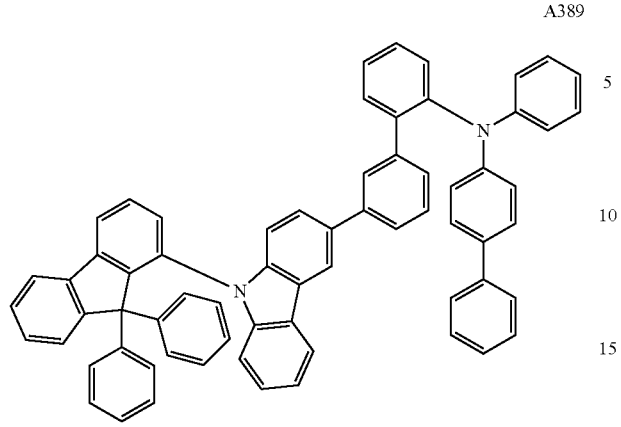
A392
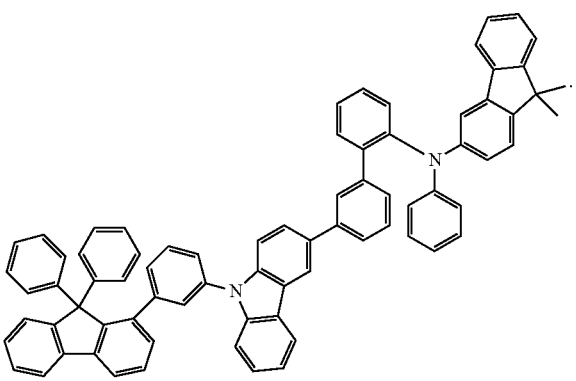
A390
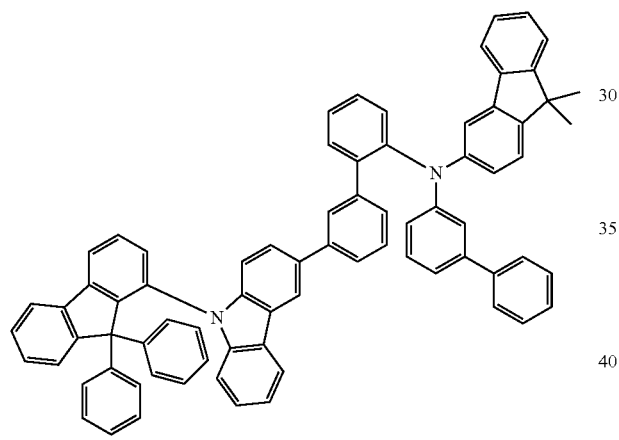
5. The organic electric element of claim 1, wherein Formula 2 is any one of the compounds below:
1-1-1-O-(1)
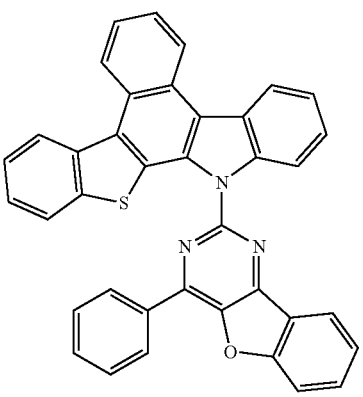
A391
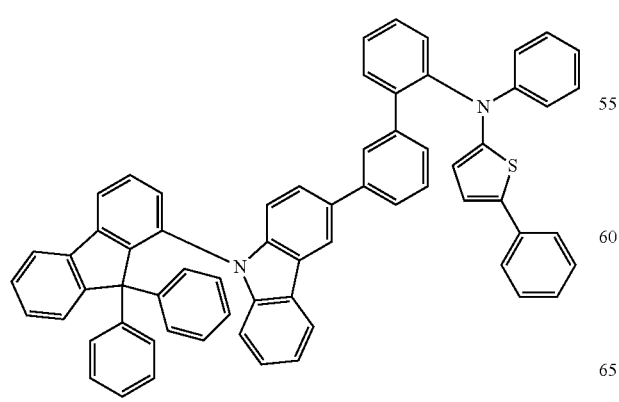
1-1-1-O-(2)
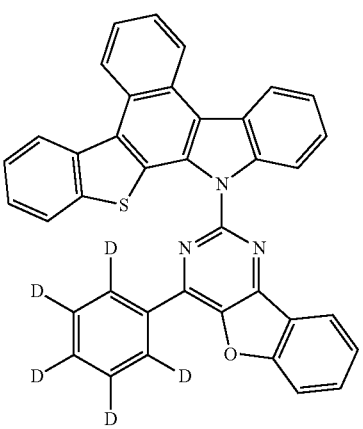

523
-continued
1-1-1-O-(3)
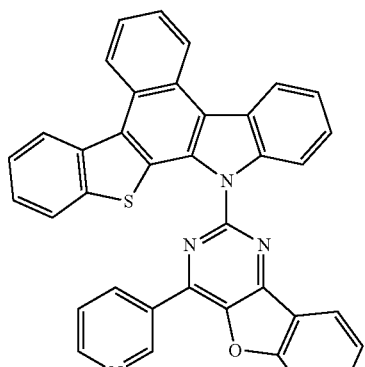
1-1-1-O-(4)
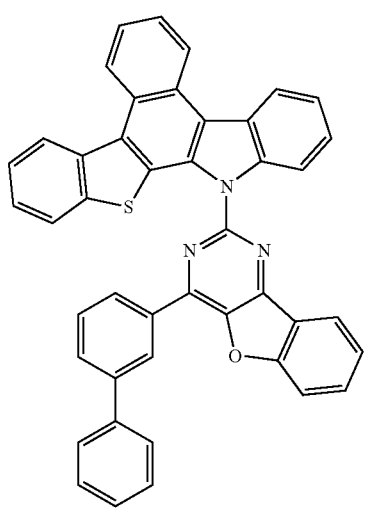
1-1-1-O-(5)
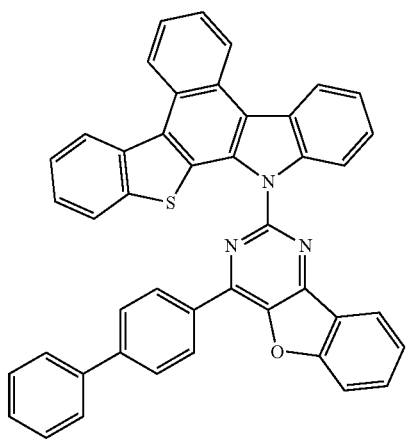
524
-continued
1-1-1-O-(6)
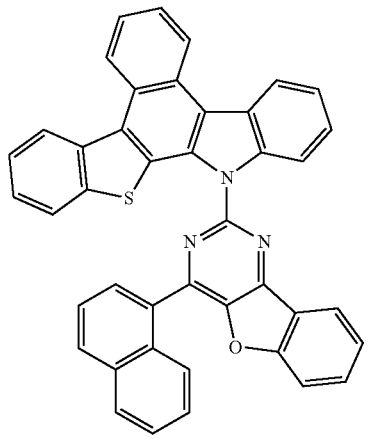
1-1-1-O-(7)
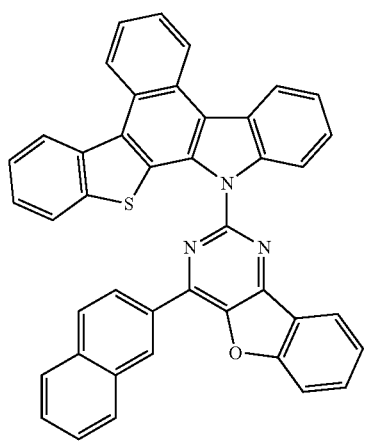
1-1-1-O-(8)
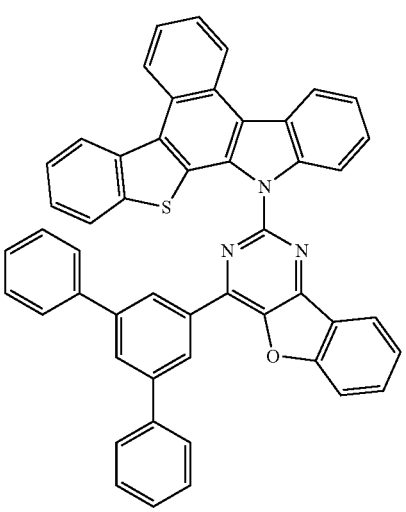

525
-continued
1-1-1-O-(9)
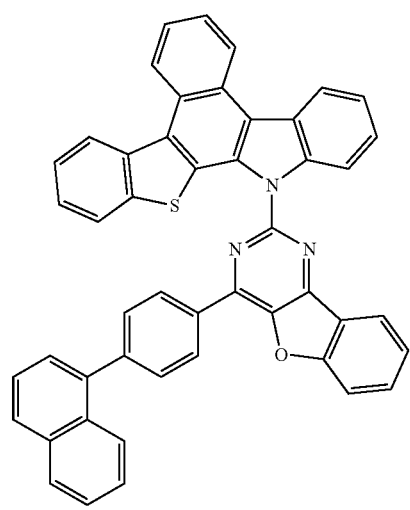
1-1-1-O-(10)
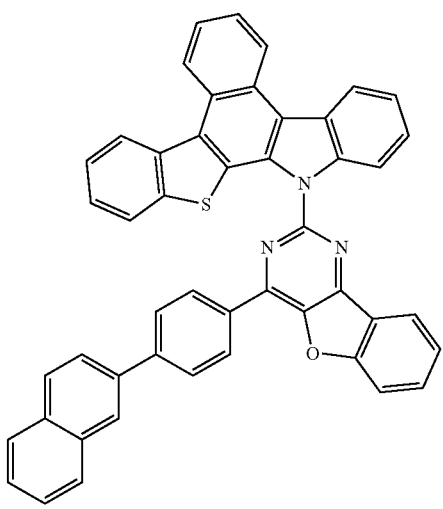
1-1-1-O-(11)
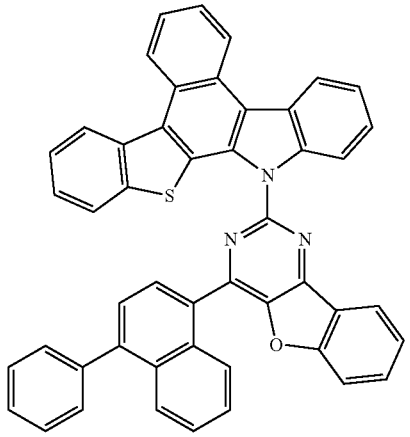
526
-continued
1-1-1-O-(12)
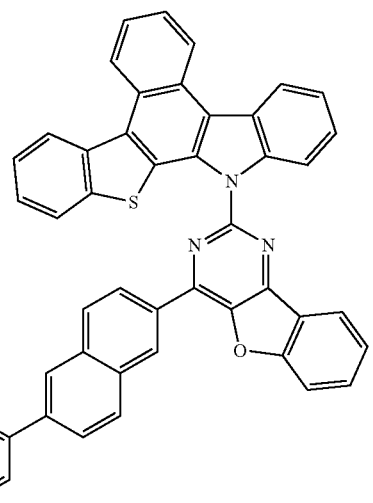
1-1-1-O-(13)
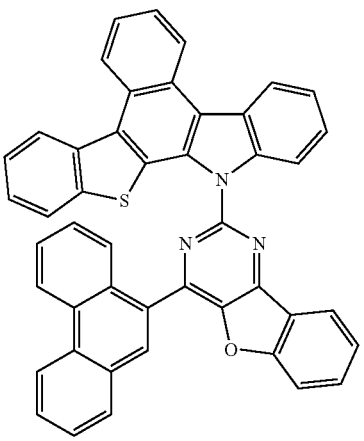
1-1-1-O-(14)
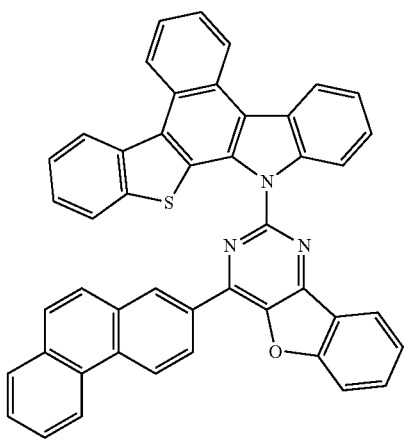

527
-continued
1-1-1-O-(15)
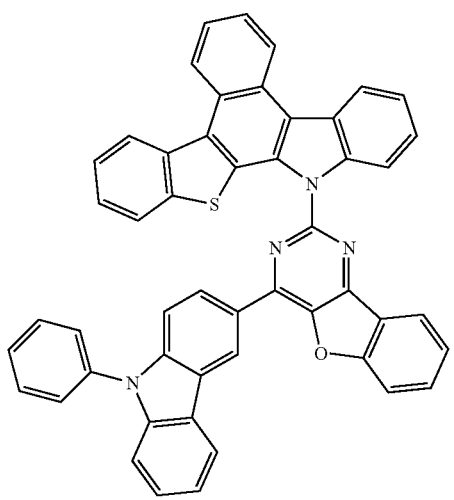
1-1-1-O-(16)
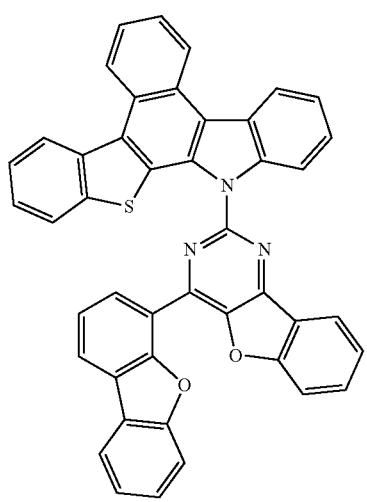
1-1-1-O-(17)
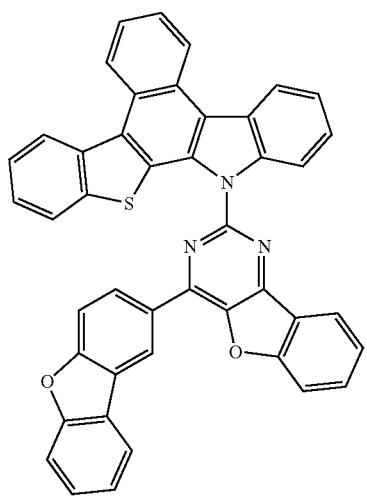
528
-continued
1-1-1-O-(18)
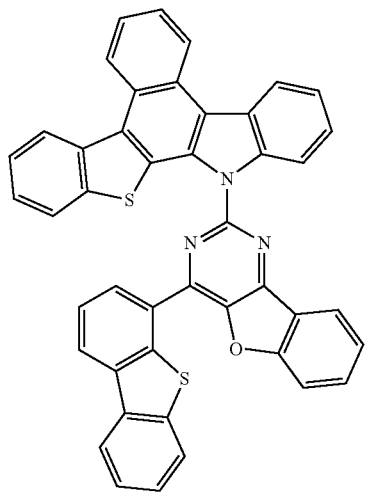
1-1-1-O-(19)
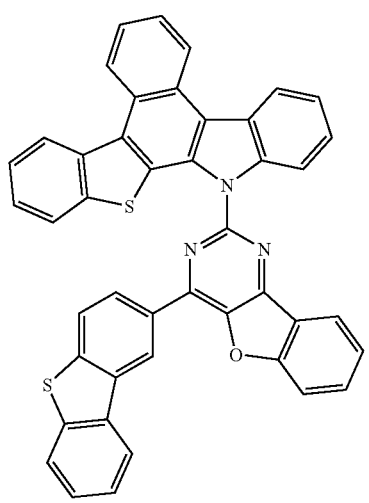
1-1-1-O-(20)
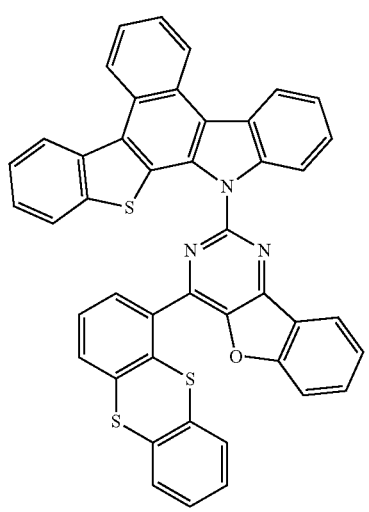

-continued
1-1-1-S-(1)
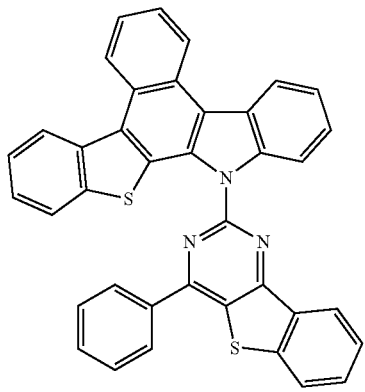
1-1-1-S-(2)
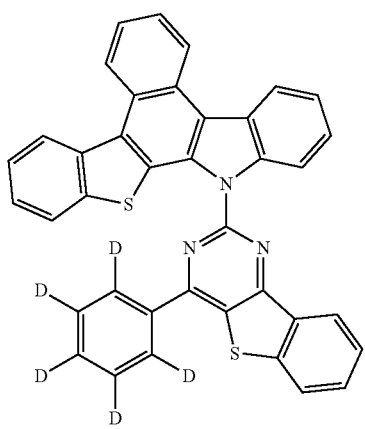
1-1-1-S-(3)
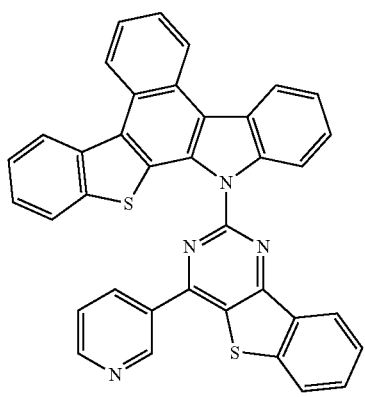
-continued
1-1-1-S-(4)
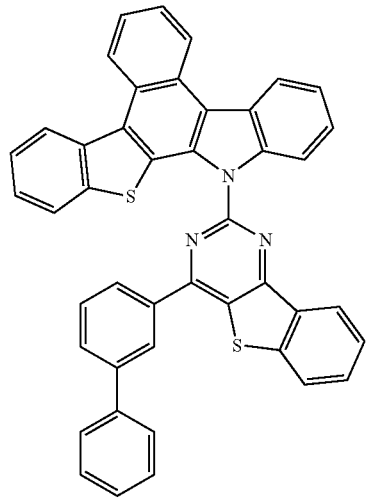
1-1-1-S-(5)
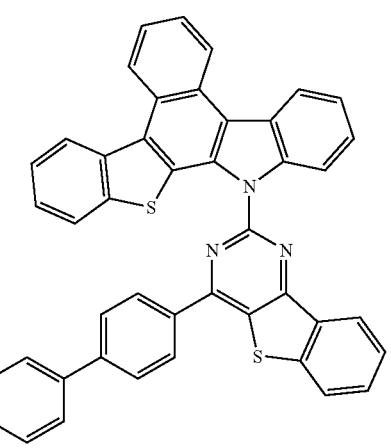
1-1-1-S-(6)
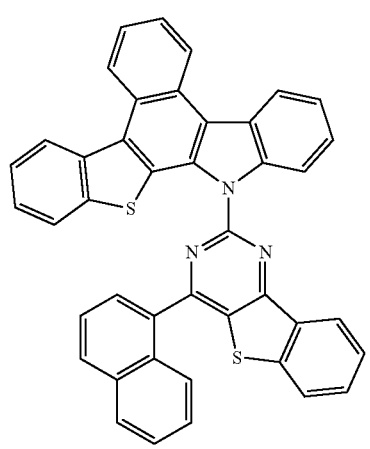

531
-continued
1-1-1-S-(7)
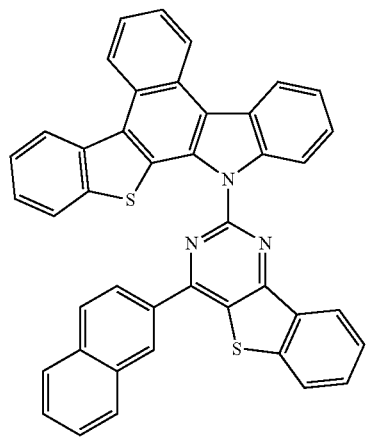
1-1-1-S-(8)
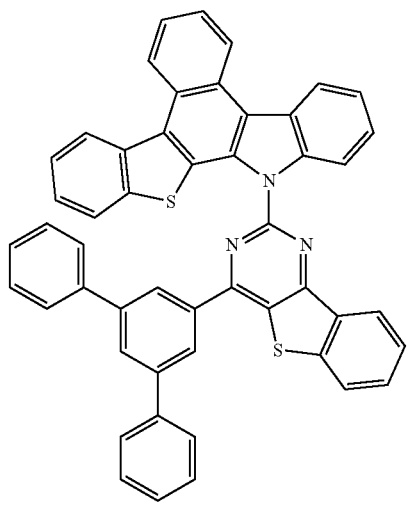
1-1-1-S-(9)
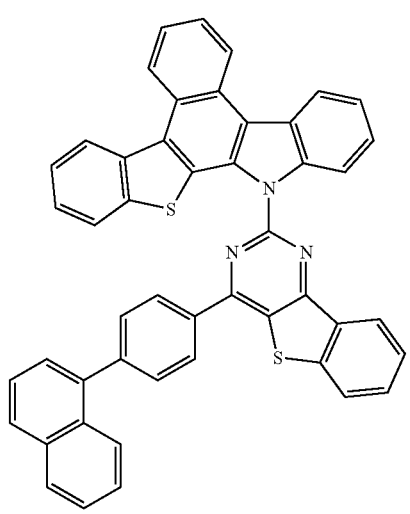
532
-continued
1-1-1-S-(10)
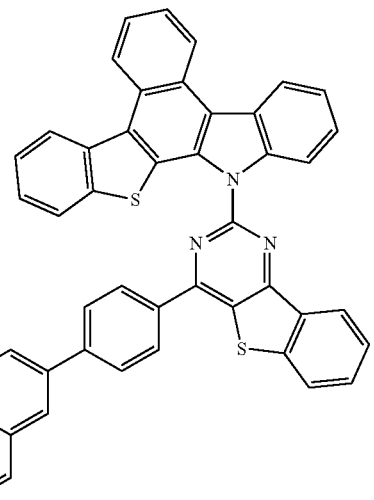
1-1-1-S-(11)
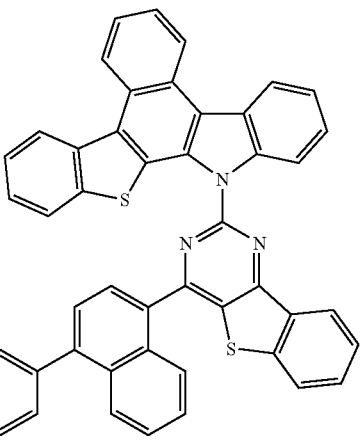
1-1-1-S-(12)
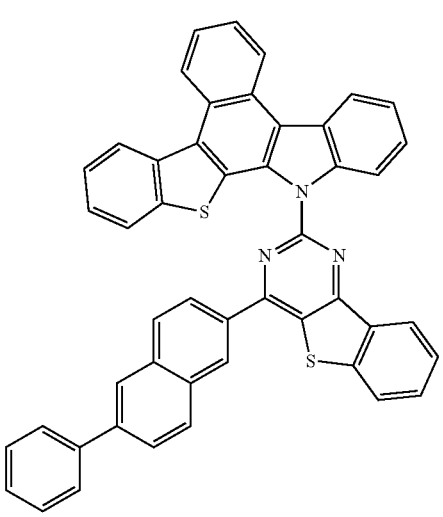

1-1-1-S-(13)
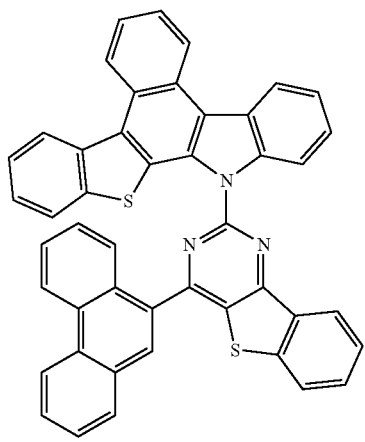
1-1-1-S-(14)
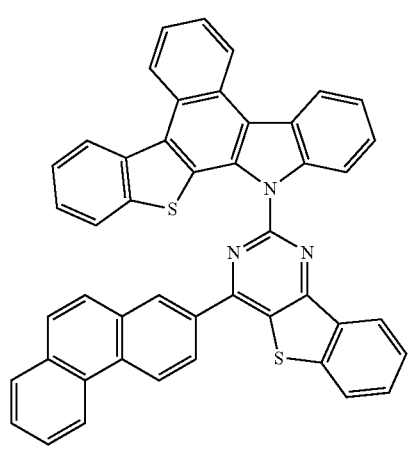
1-1-1-S-(15)
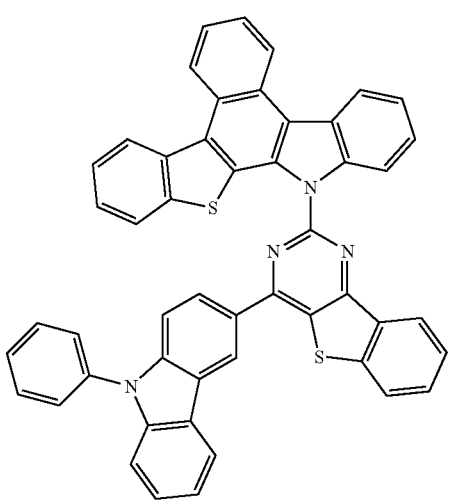
1-1-1-S-(16)
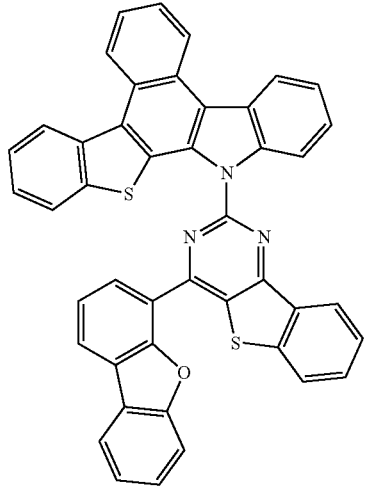
1-1-1-S-(17)
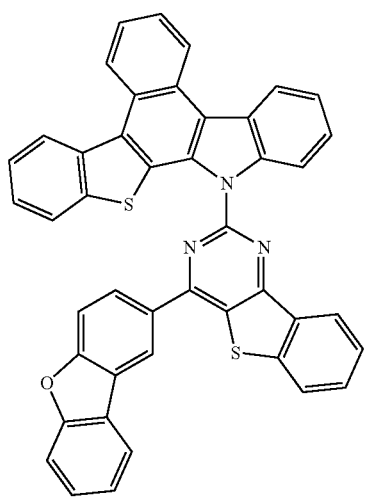
1-1-1-S-(18)
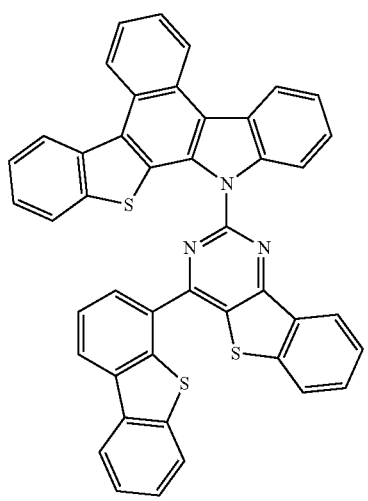

-continued
1-1-1-S-(19)
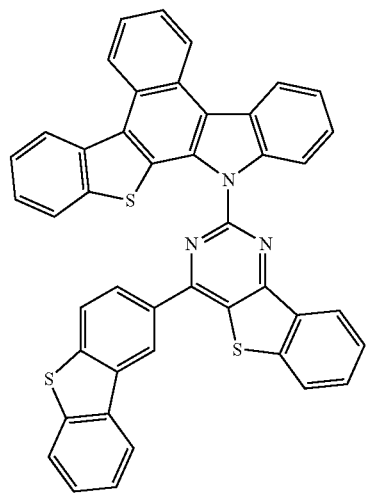
1-1-1-S-(20)
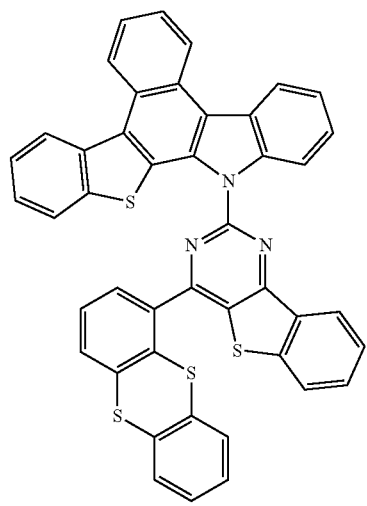
1-1-1-O-(21)
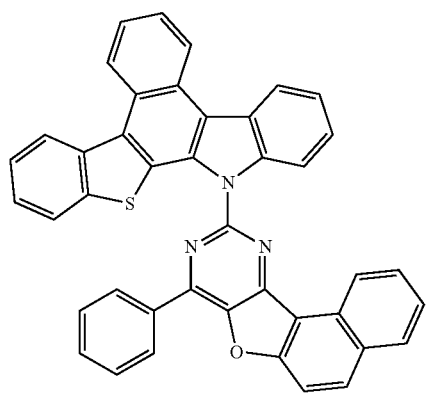
-continued
1-1-1-O-(22)
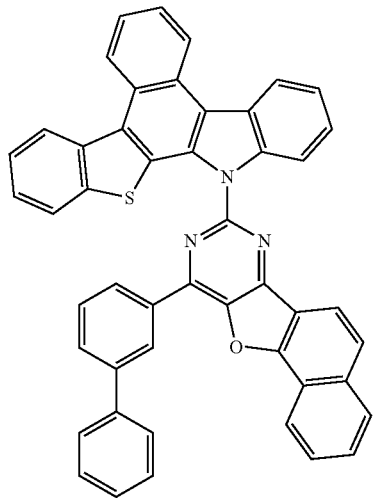
1-1-1-S-(21)
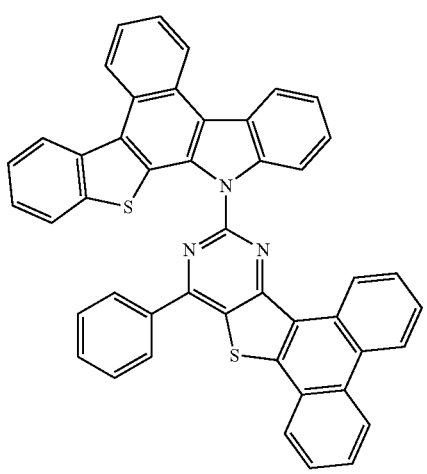
1-1-1-S-(22)
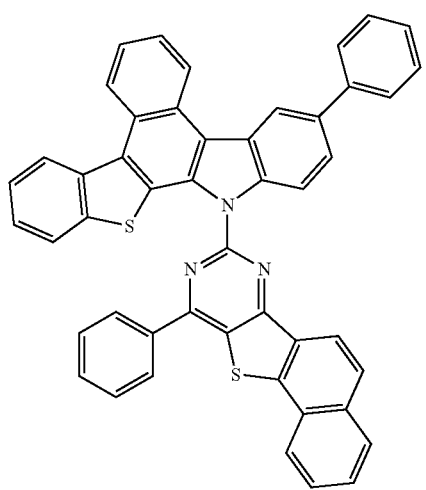

1-1-1-S-(23)
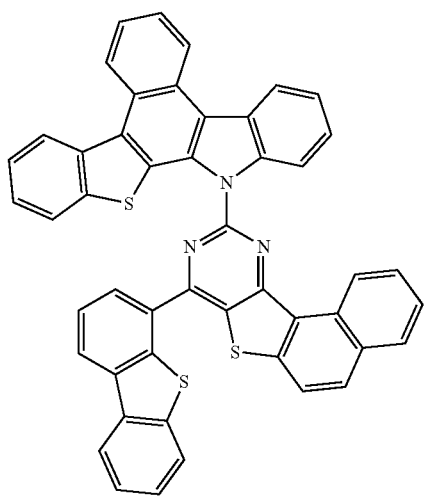
1-1-2-O-(1)
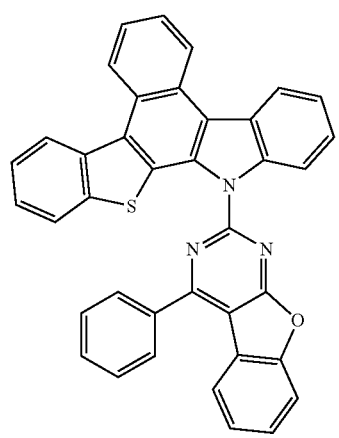
1-1-2-O-(2)
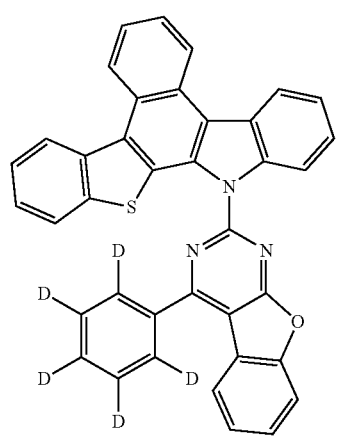
1-1-2-O-(3)
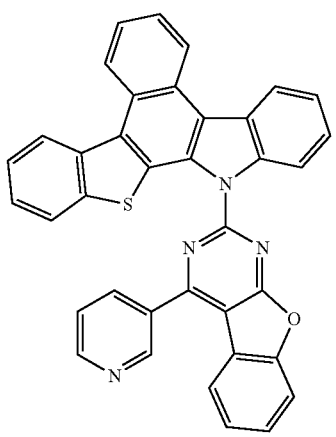
1-1-2-O-(4)
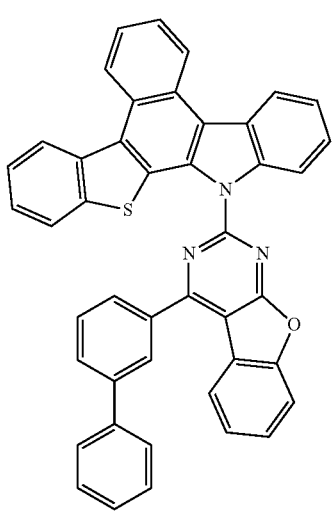
1-1-2-O-(5)
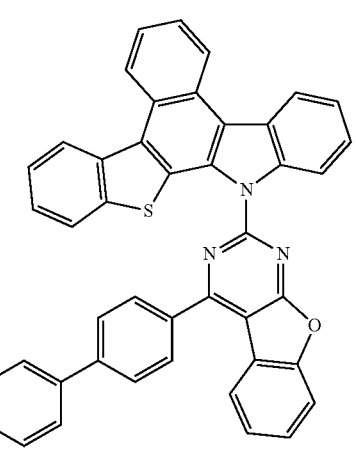

539 540
-continued -continued
1-1-2-O-(6)
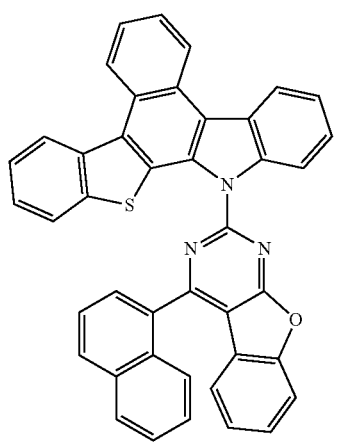
1-1-2-O-(9)
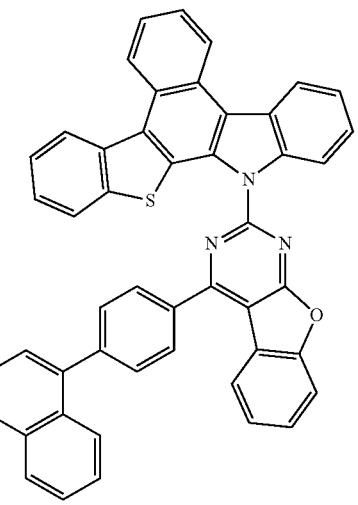
1-1-2-O-(7)
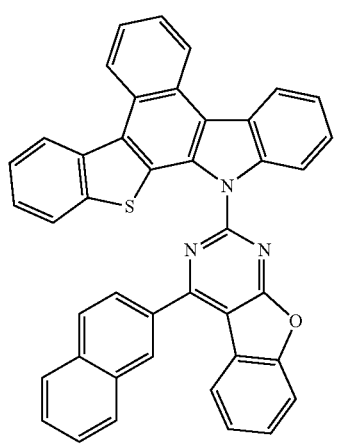
1-1-2-O-(10)
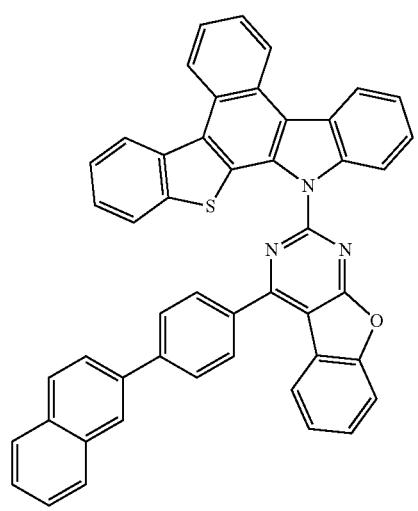
1-1-2-O-(8)
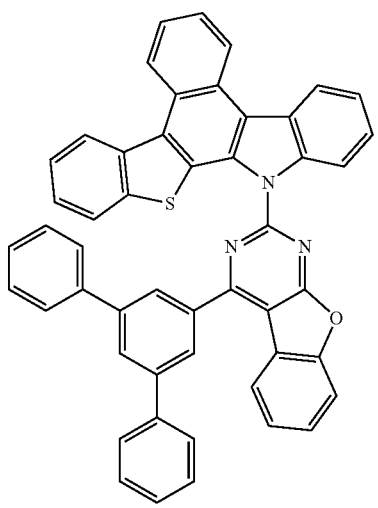
1-1-2-O-(11)
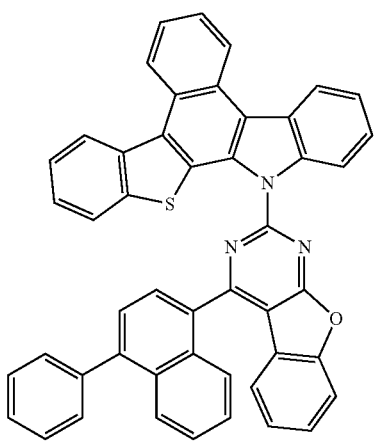

1-1-2-O-(12)
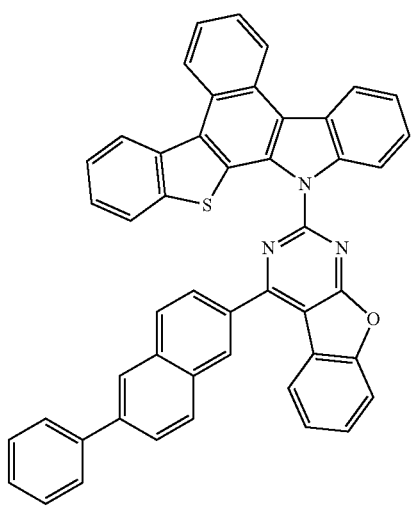
1-1-2-O-(13)
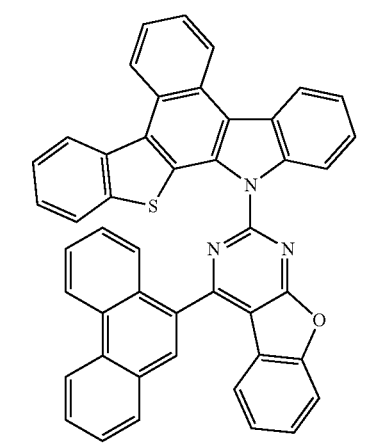
1-1-2-O-(14)
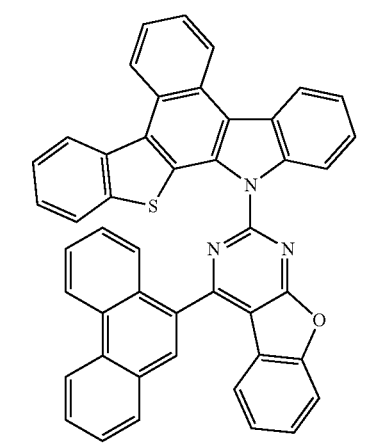
1-1-2-O-(15)
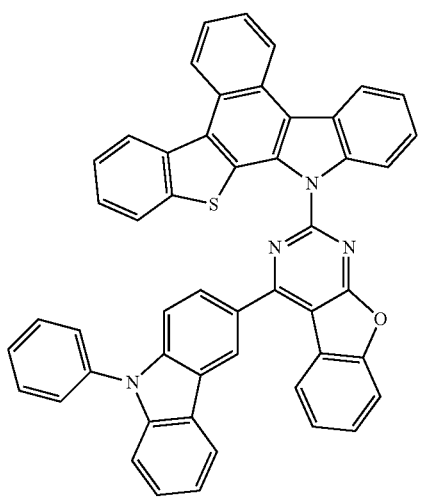
1-1-2-O-(16)
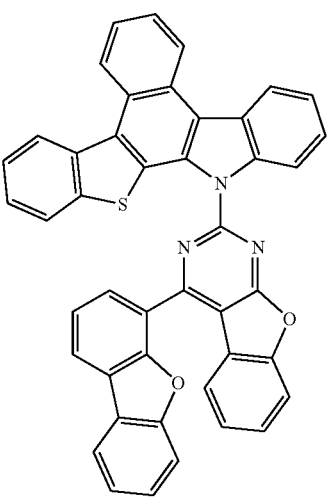
1-1-2-O-(17)
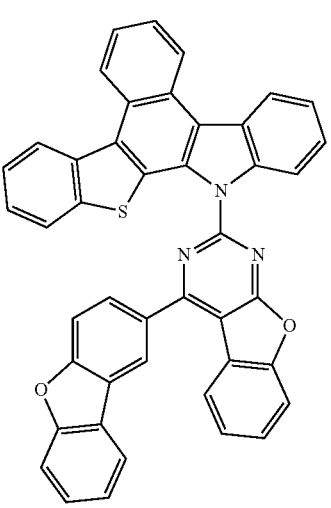

1-1-2-O-(18)
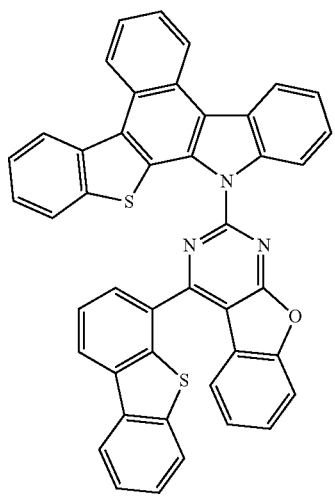
1-1-2-S-(1)
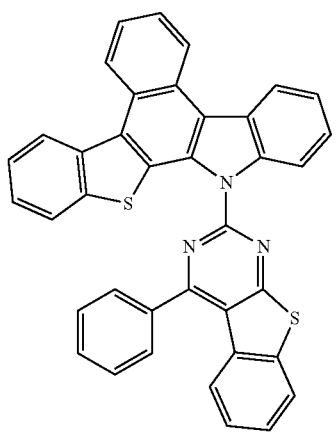
1-1-2-O-(19)
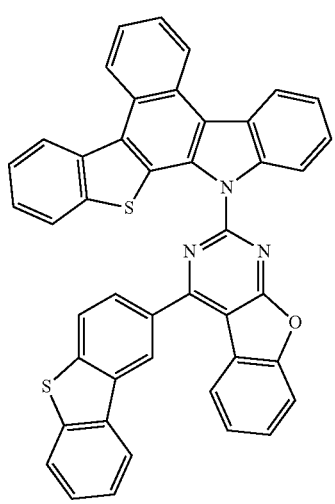
1-1-2-S-(2)
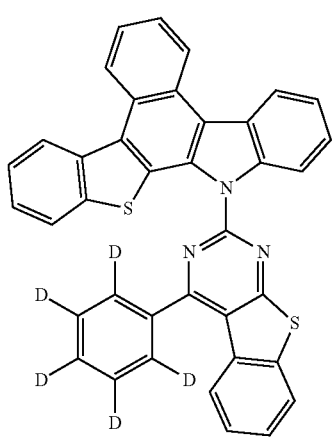
1-1-2-O-(20)
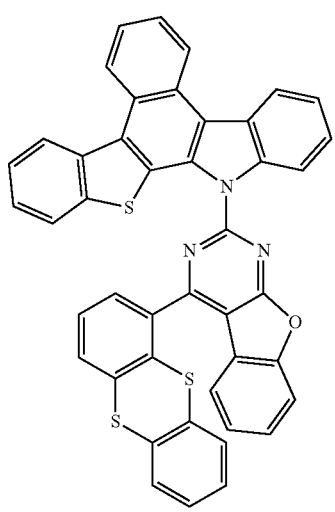
1-1-2-S-(3)
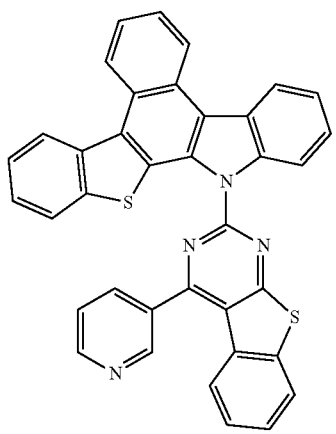

1-1-2-S-(4)
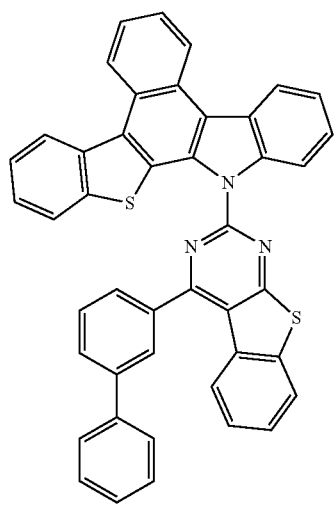
1-1-2-S-(5)
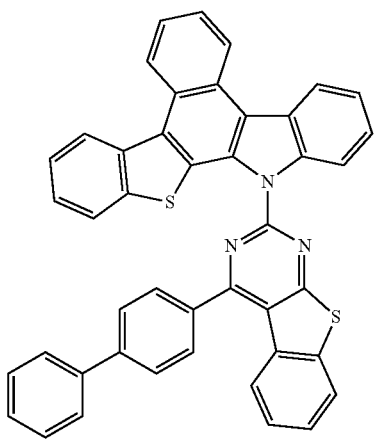
1-1-2-S-(6)
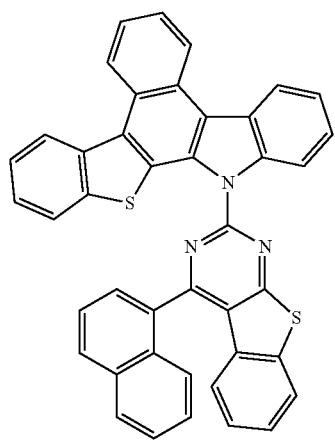
1-1-2-S-(7)
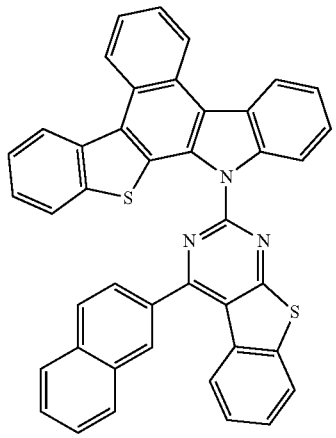
1-1-2-S-(8)
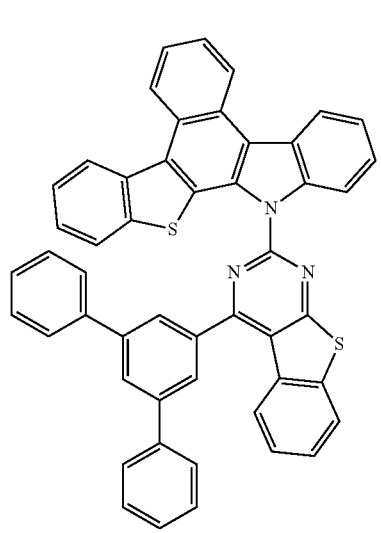
1-1-2-S-(9)
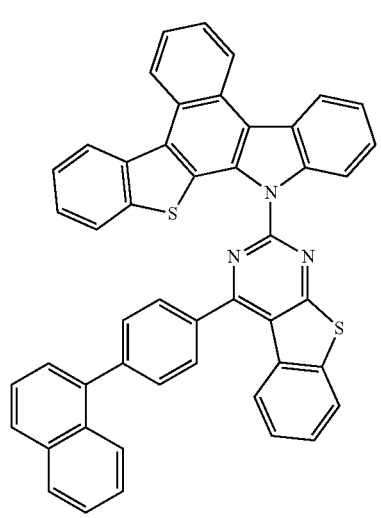

-continued
1-1-2-S-(10)
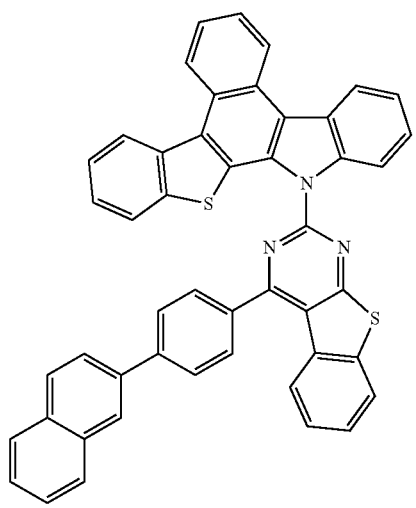
1-1-2-S-(11)
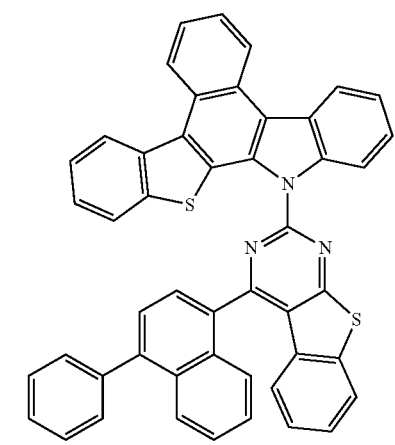
1-1-2-S-(12)
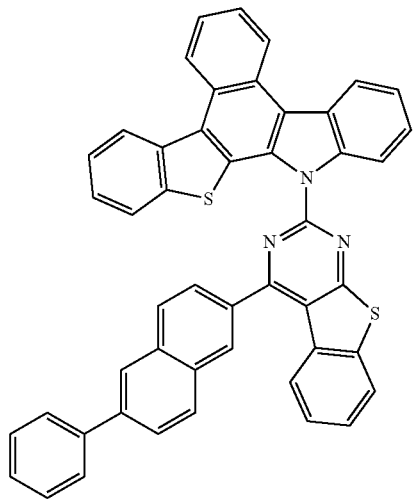
-continued
1-1-2-S-(13)
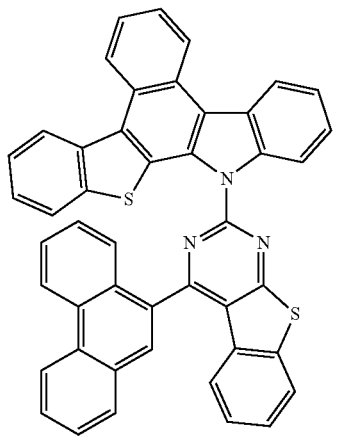
1-1-2-S-(14)
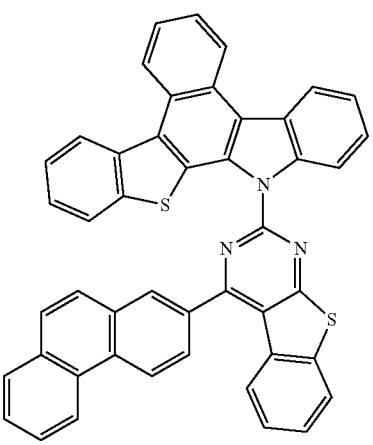
1-1-2-S-(15)
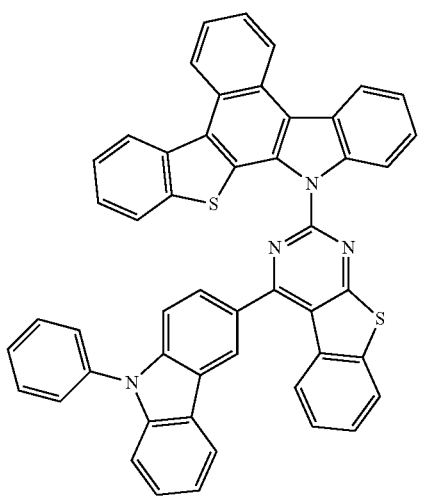

1-1-2-S-(16)
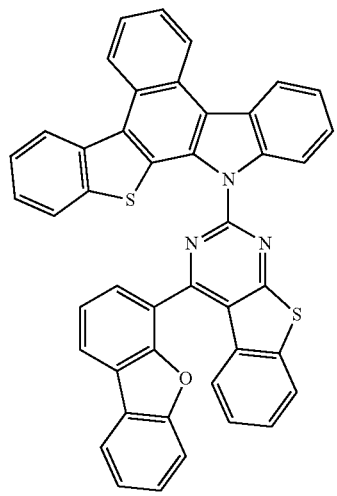
1-1-2-S-(17)
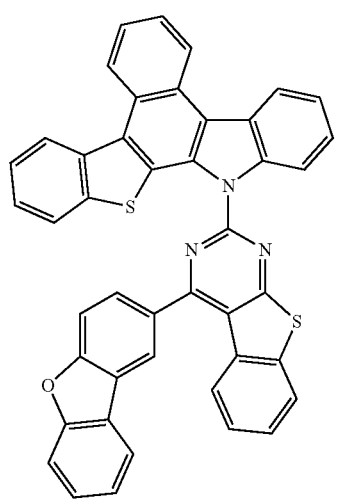
1-1-2-S-(18)
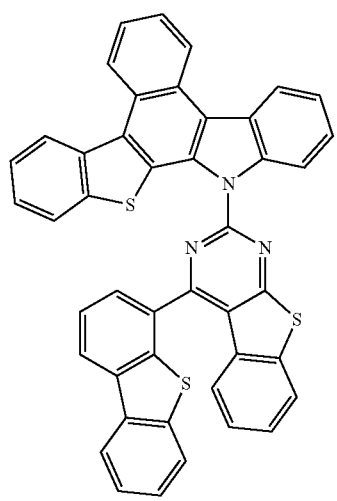
1-1-2-S-(19)
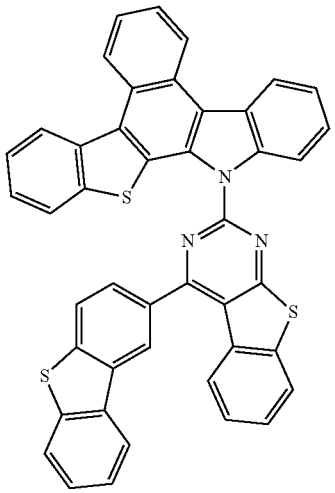
1-1-2-S-(20)
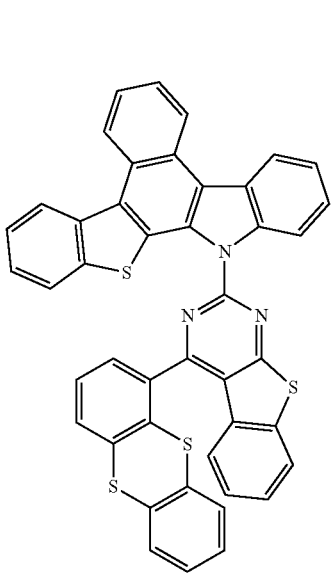
1-1-2-O-(21)
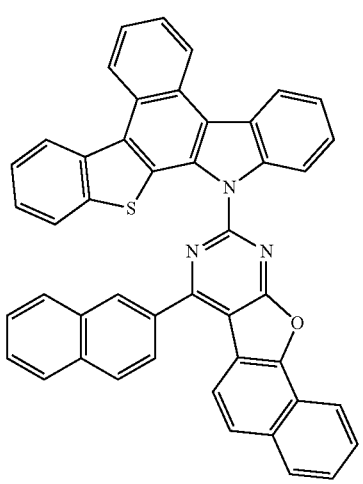

1-1-2-O-(21)
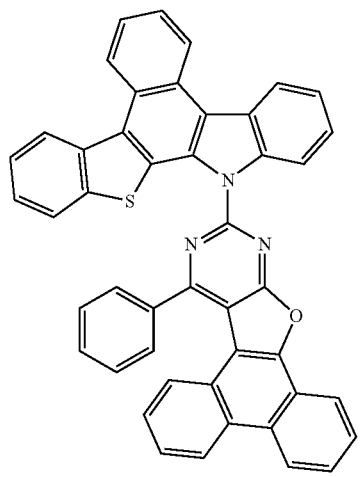
1-1-2-S-(23)
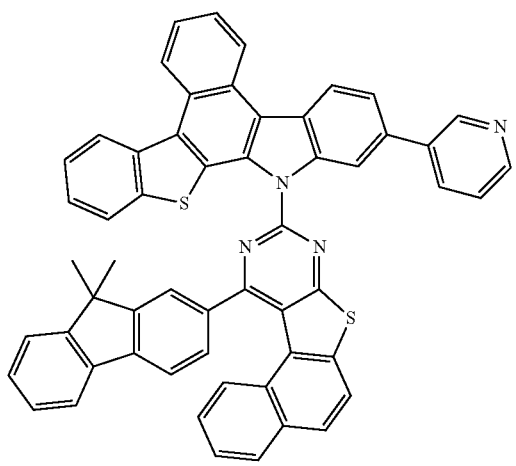
1-1-2-S-(21)
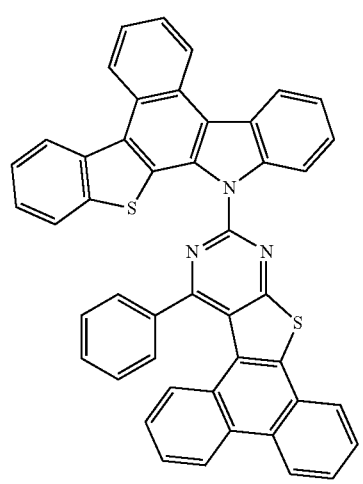
1-3-1-O-(1)
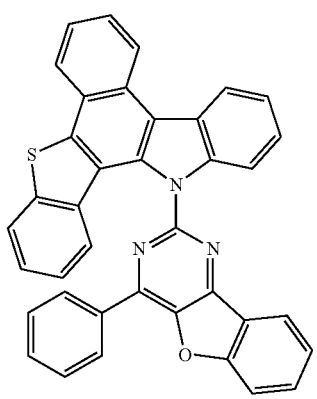
1-1-2-S-(22)
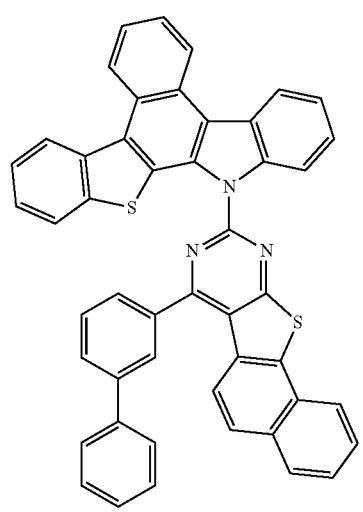
1-3-1-O-(2)
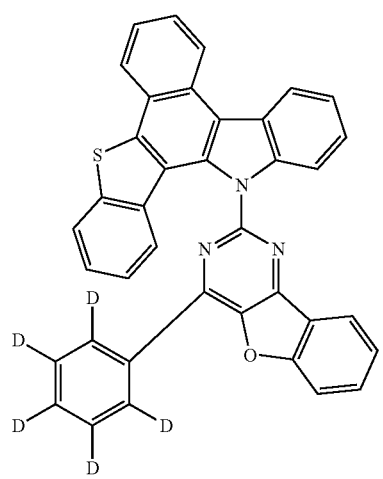

1-3-1-O-(3)
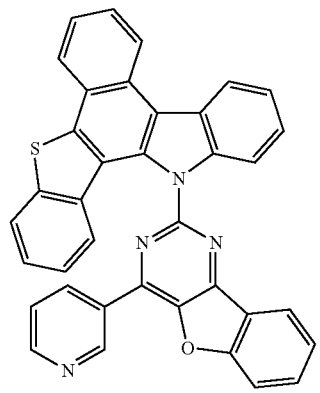
1-3-1-O-(4)
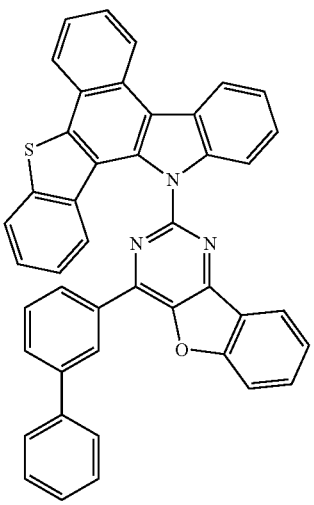
1-3-1-O-(5)
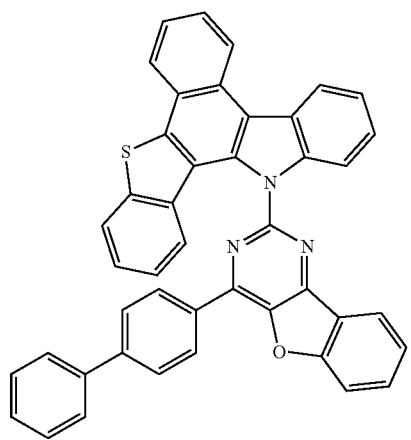
1-3-1-O-(6)
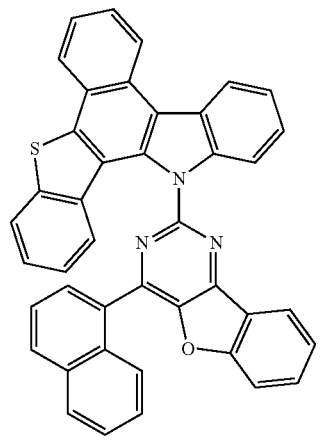
1-3-1-O-(7)
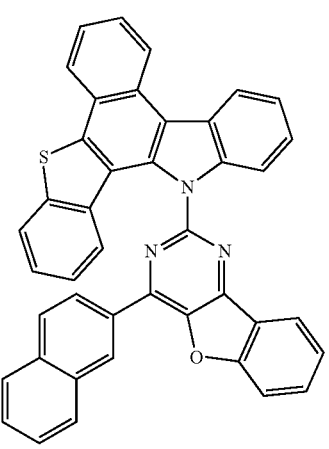
1-3-1-O-(8)
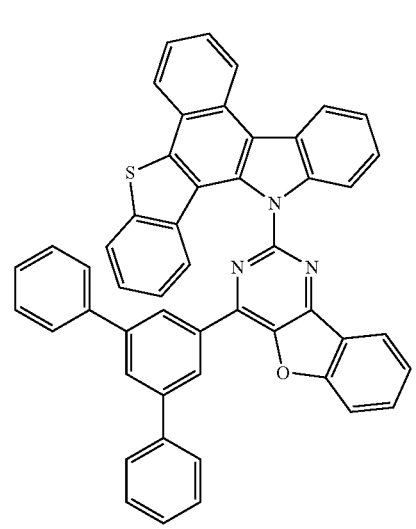

1-3-1-O-(9)
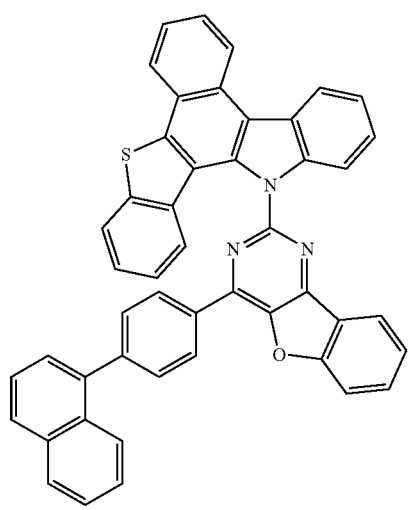
1-3-1-O-(10)
1-3-1-O-(11)
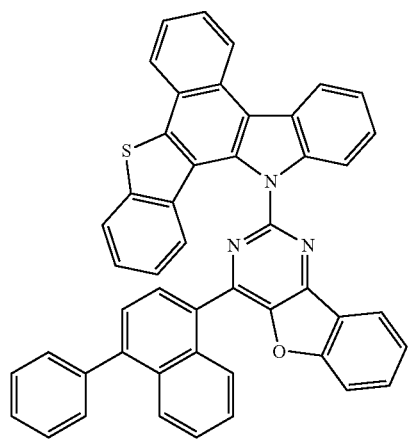
1-3-1-O-(12)
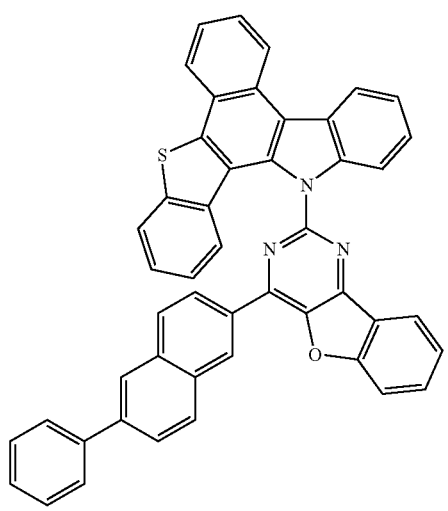
1-3-1-O-(13)
1-3-1-O-(14)
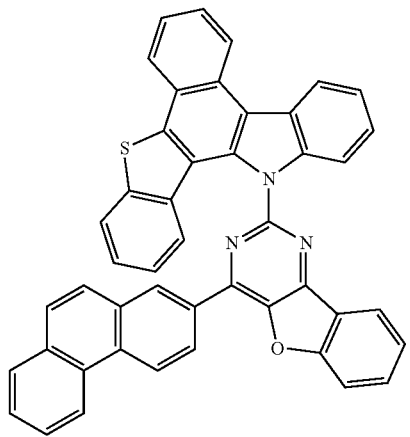

-continued
1-3-1-O-(15)
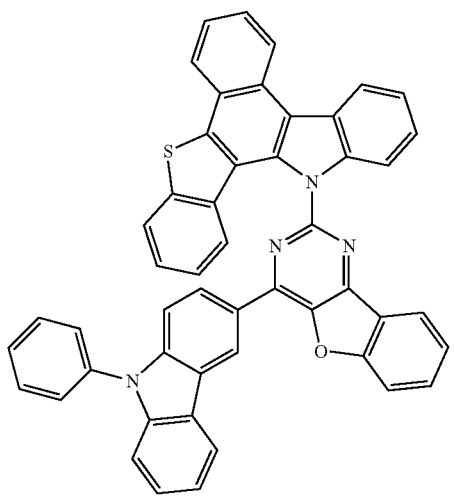
1-3-1-O-(16)
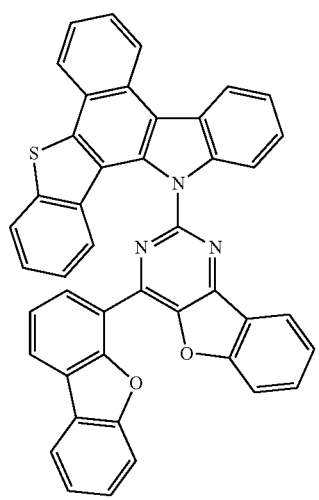
1-3-1-O-(17)
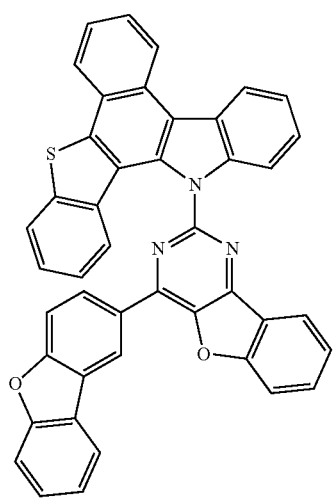
-continued
1-3-1-O-(18)
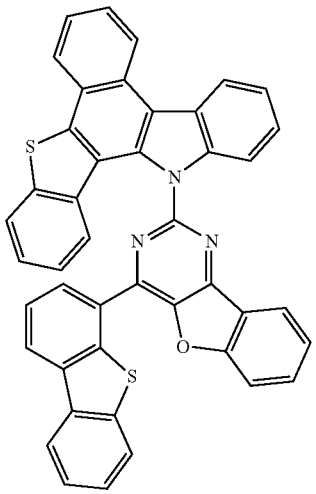
1-3-1-O-(19)
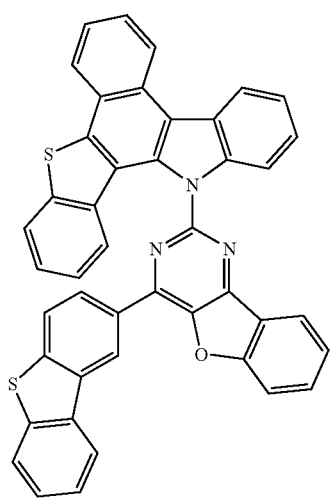
1-3-1-O-(20)
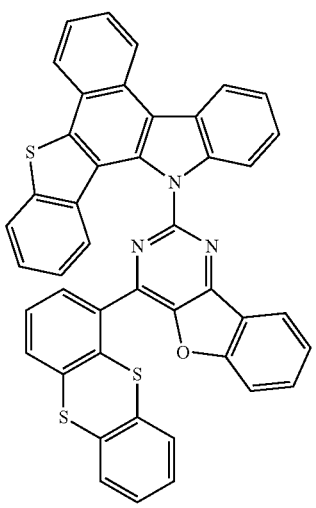

-continued
1-3-1-S-(1)
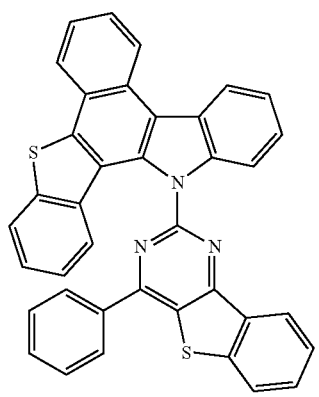
1-3-1-S-(2)
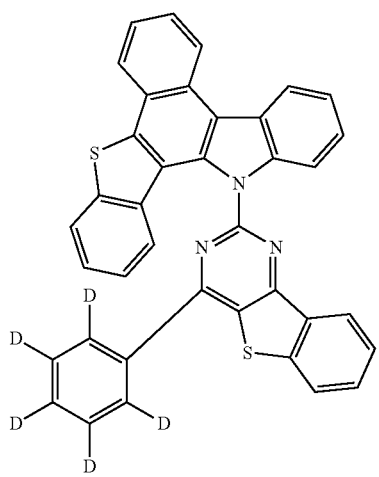
1-3-1-S-(3)
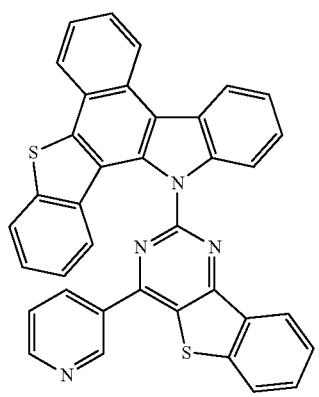
-continued
1-3-1-S-(4)
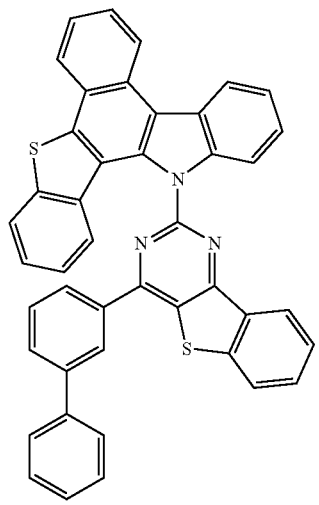
1-3-1-S-(5)
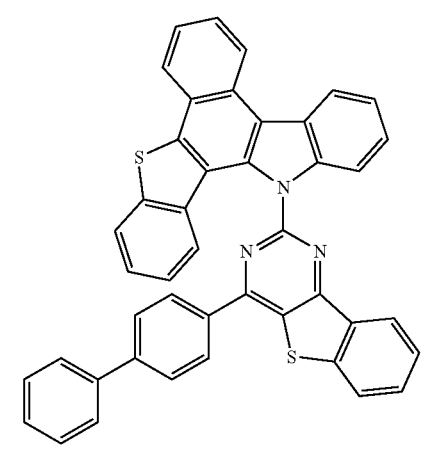
1-3-1-S-(6)
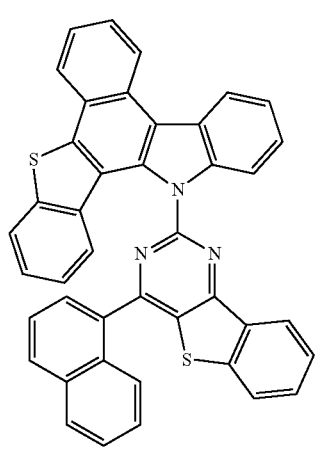

1-3-1-S-(7)
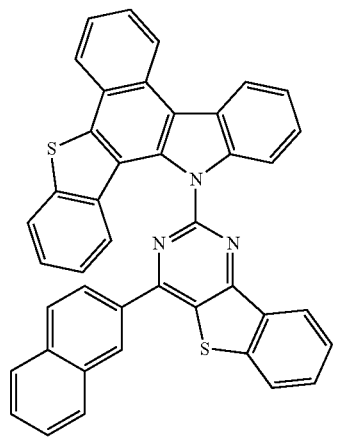
1-3-1-S-(8)
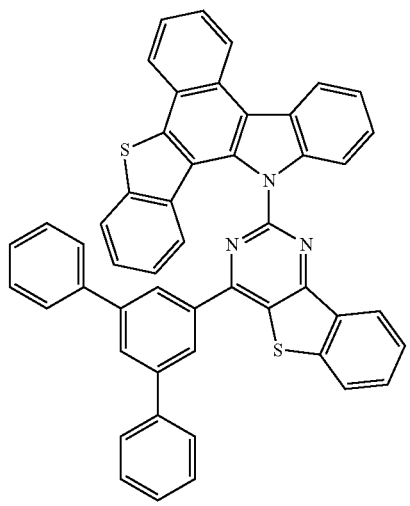
1-3-1-S-(9)
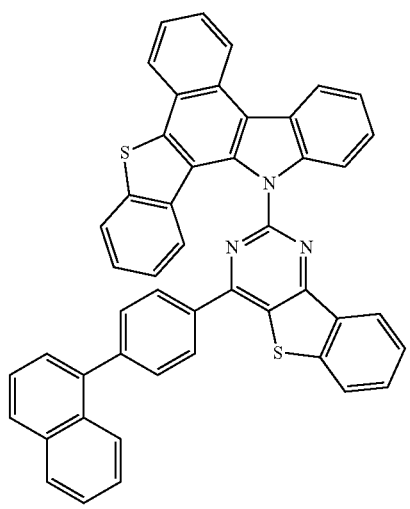
1-3-1-S-(10)
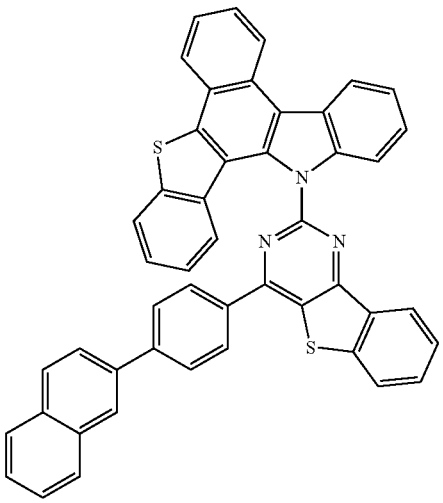
1-3-1-S-(11)
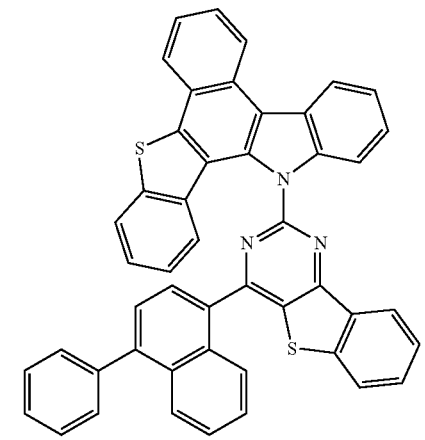
1-3-1-S-(12)
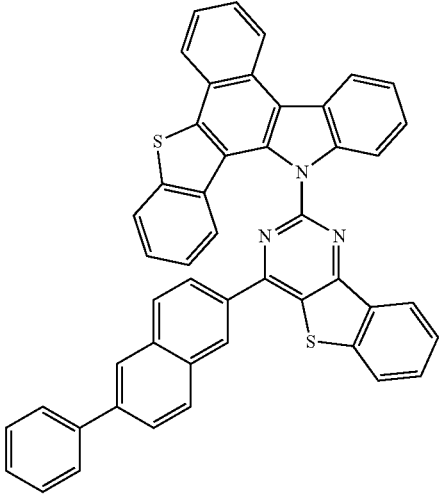

1-3-1-S-(13)
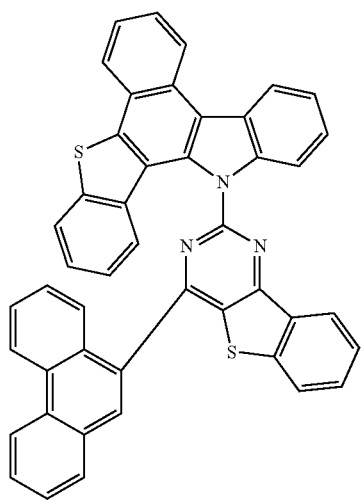
1-3-1-S-(14)
1-3-1-S-(15)
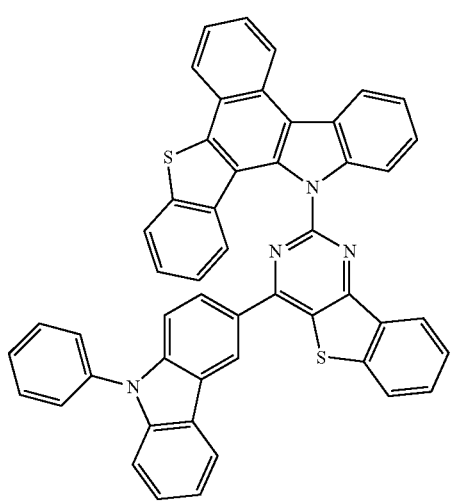
1-3-1-S-(16)
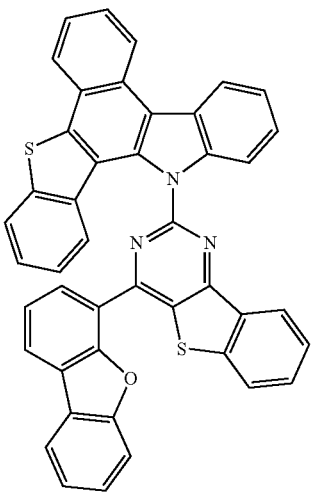
1-3-1-S-(17)
1-3-1-S-(18)
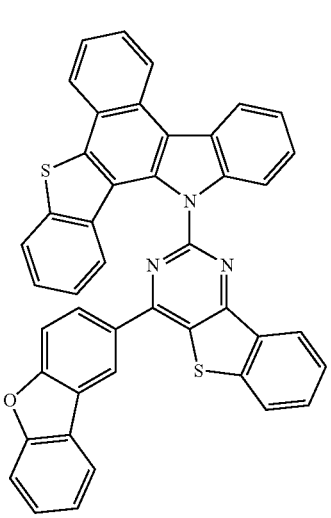

565
-continued
1-3-1-S-(19)
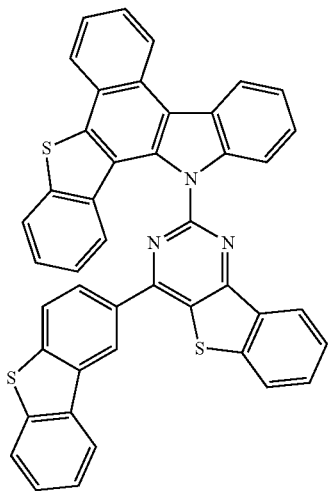
1-3-1-S-(20)
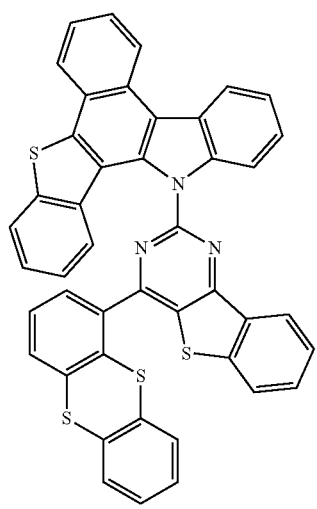
1-3-1-O-(21)
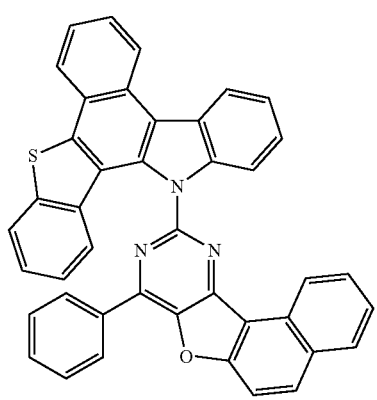
566
-continued
1-3-1-O-(22)
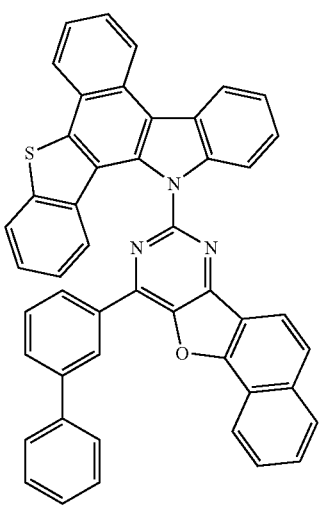
1-3-1-S-(21)
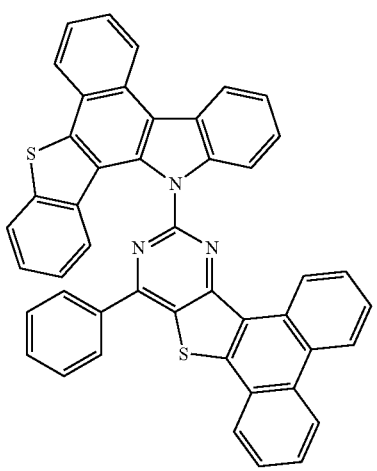
1-3-1-S-(22)
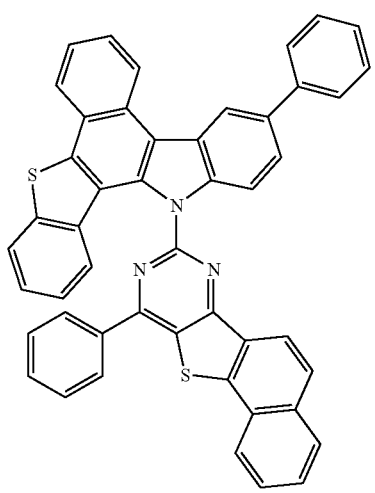

567
-continued
1-3-1-S-(23)
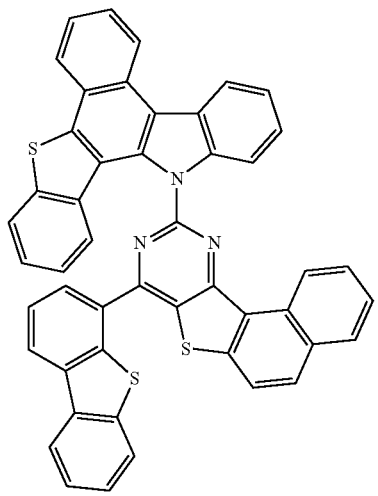
1-3-2-O-(1)
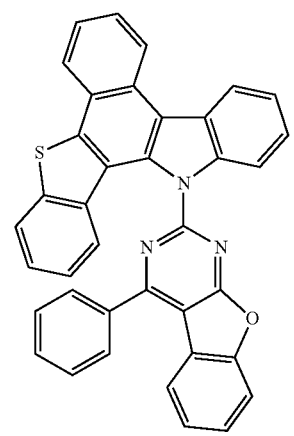
1-3-2-O-(2)
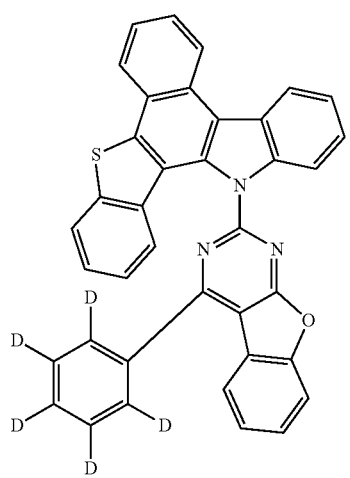
568
-continued
1-3-2-O-(3)
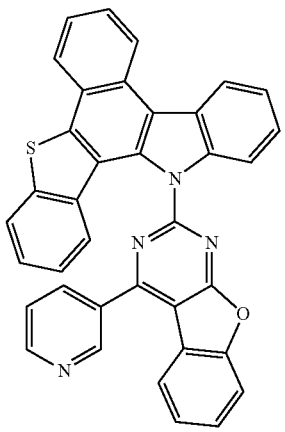
1-3-2-O-(4)
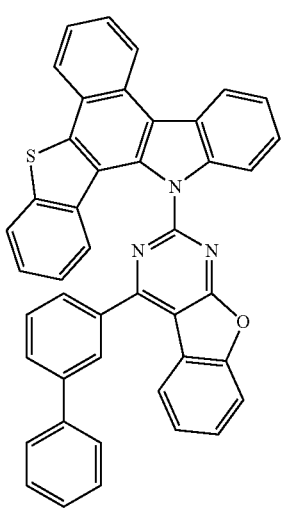
1-3-2-O-(5)
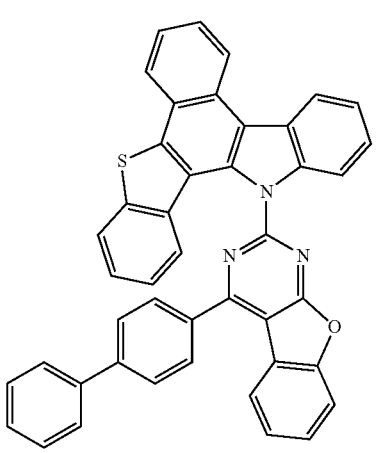

569
-continued
1-3-2-O-(6)
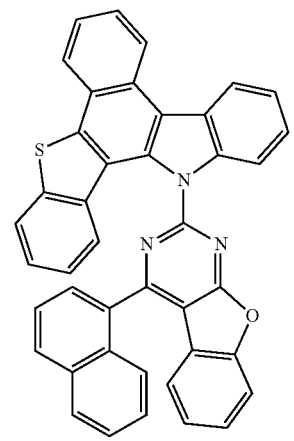
1-3-2-O-(7)
1-3-2-O-(8)
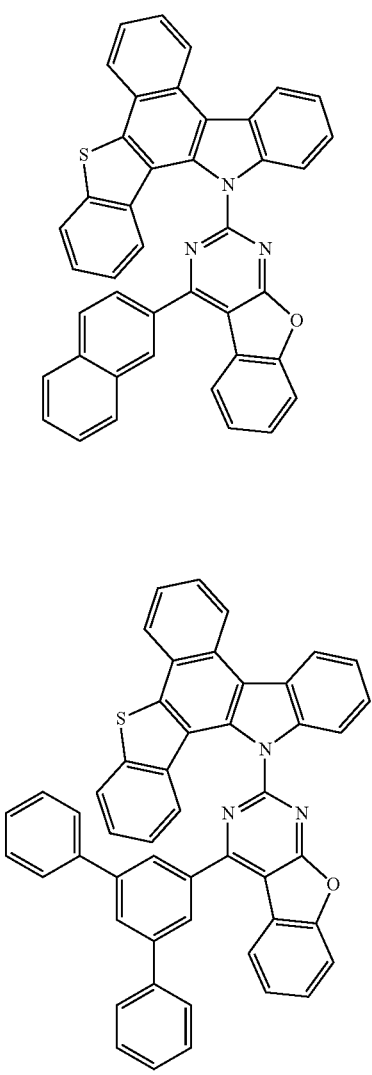
570
-continued
1-3-2-O-(9)
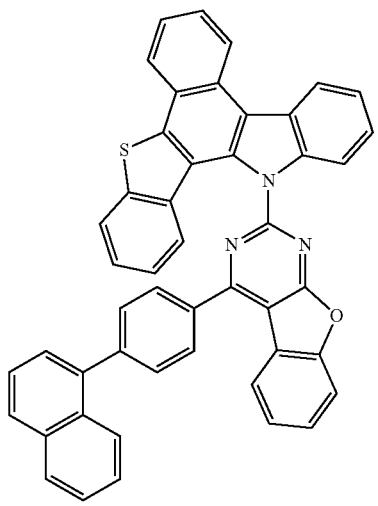
1-3-2-O-(10)
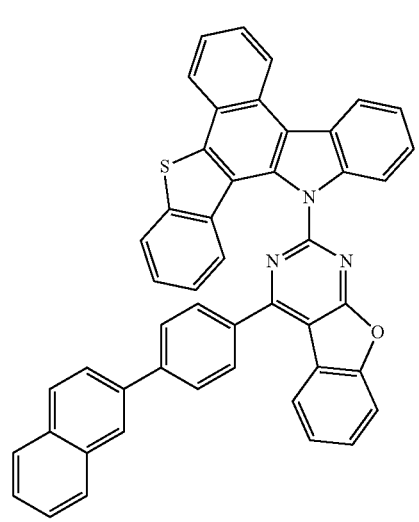
1-3-2-O-(11)
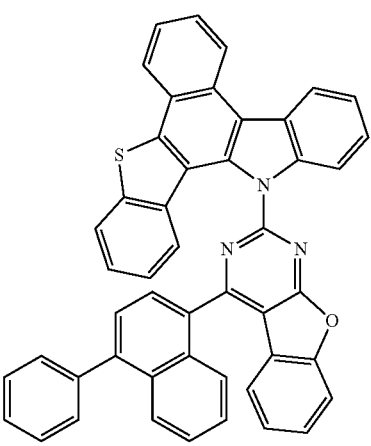

1-3-2-O-(12)
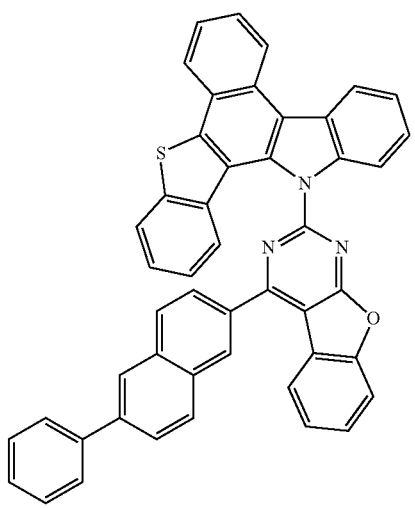
1-3-2-O-(15)
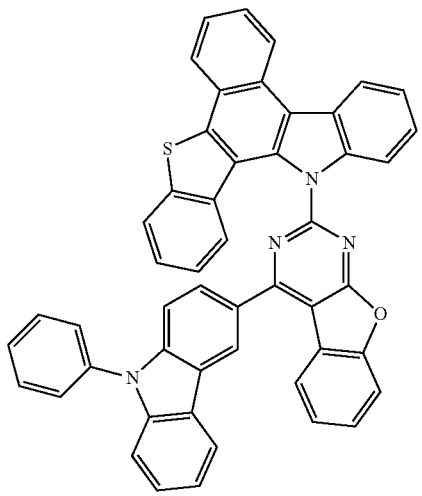
1-3-2-O-(13)
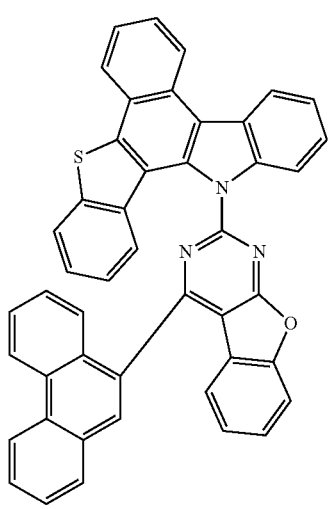
1-3-2-O-(16)
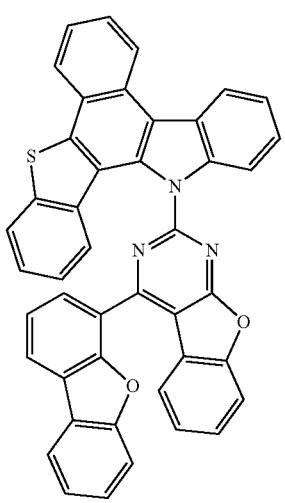
1-3-2-O-(14)
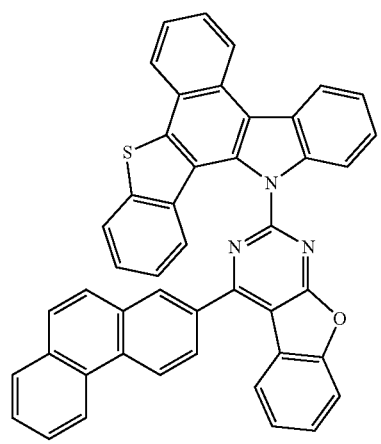
1-3-2-O-(17)
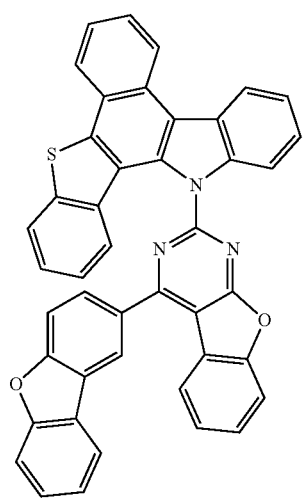

1-3-2-O-(18)
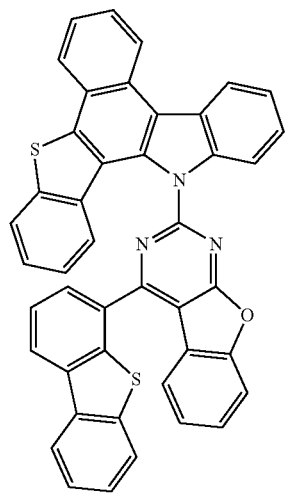
1-3-2-O-(19)
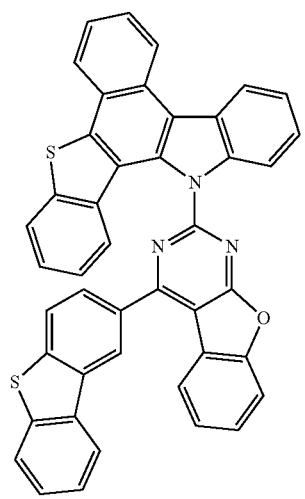
1-3-2-O-(20)
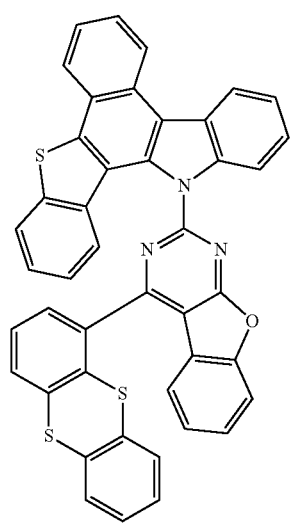
1-3-2-S-(1)
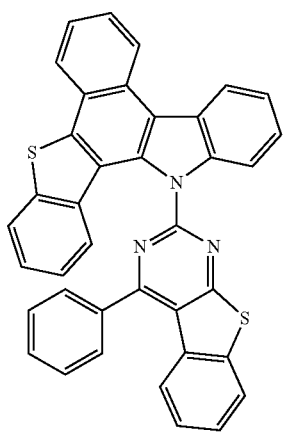
1-3-2-S-(2)
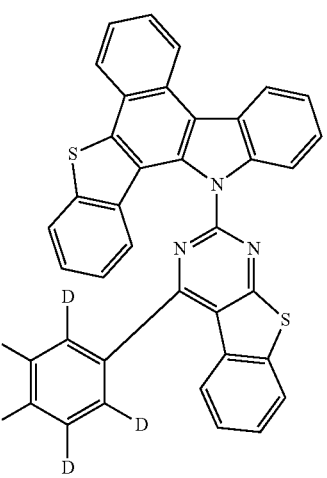
1-3-2-S-(3)
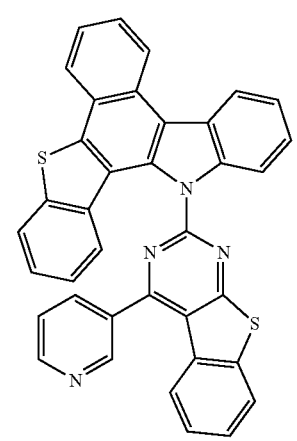

575
-continued
1-3-2-S-(4)
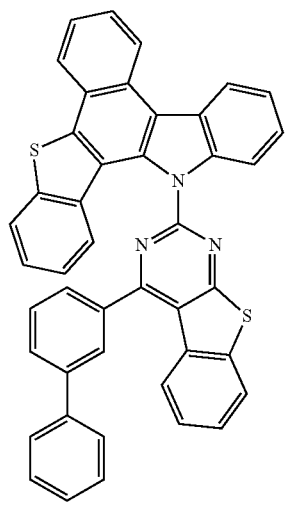
1-3-2-S-(5)
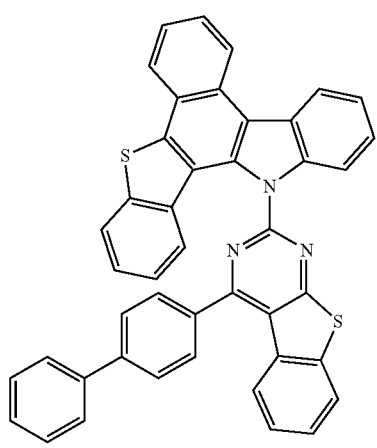
1-3-2-S-(6)
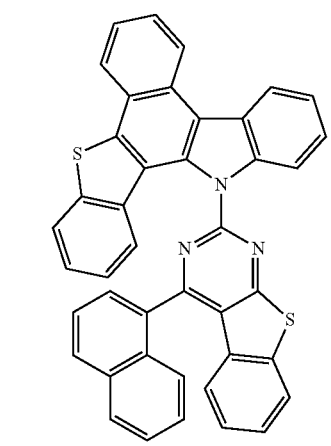
576
-continued
1-3-2-S-(7)
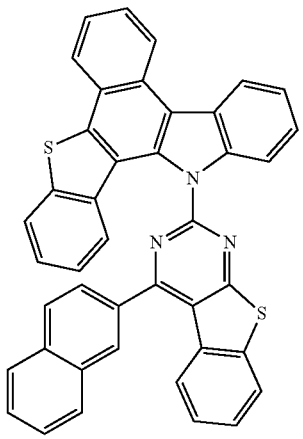
1-3-2-S-(8)
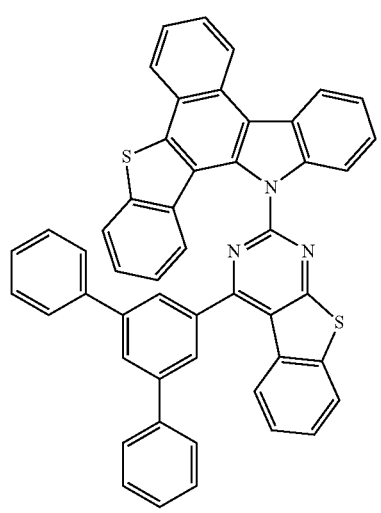
1-3-2-S-(9)
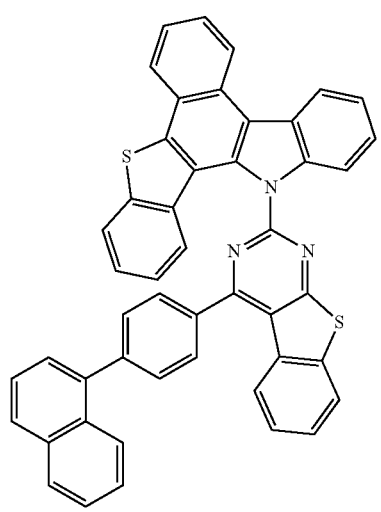

1-3-2-S-(10)
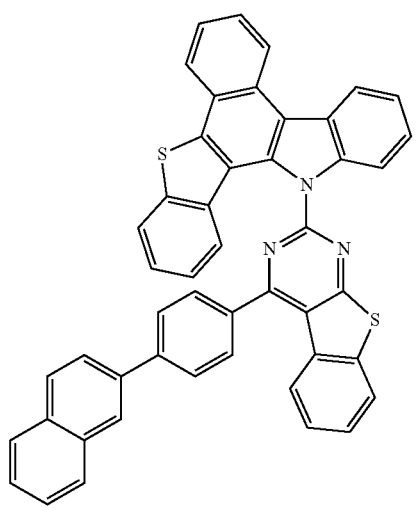
1-3-2-S-(11)
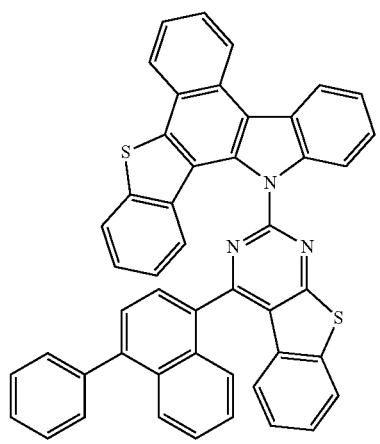
1-3-2-S-(12)
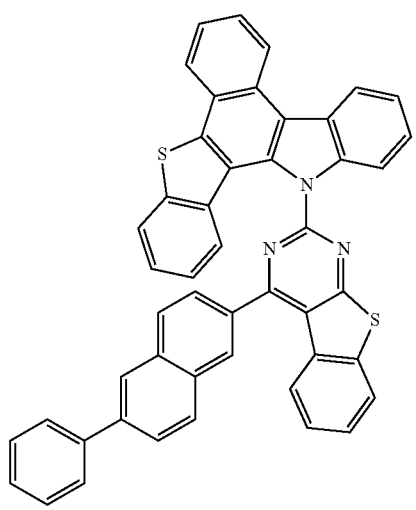
1-3-2-S-(13)
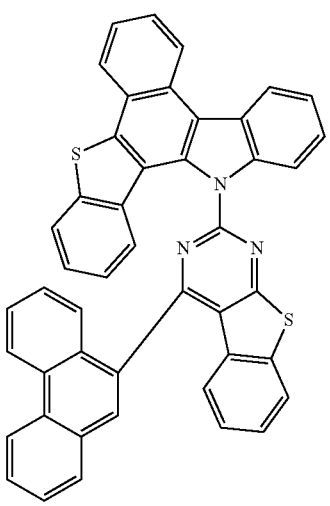
1-3-2-S-(14)
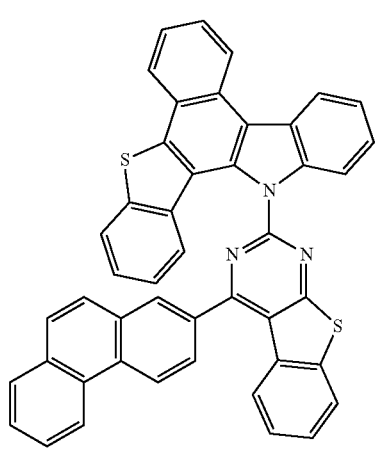
1-3-2-S-(15)
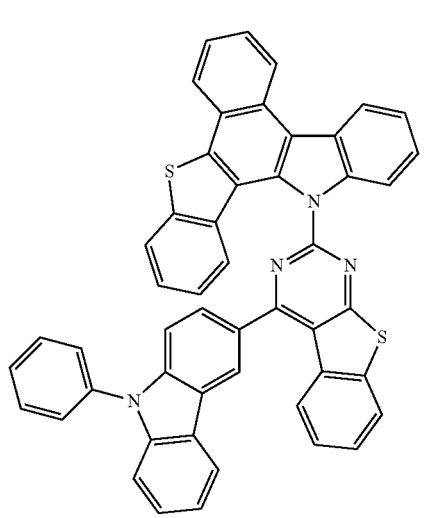

1-3-2-S-(16)
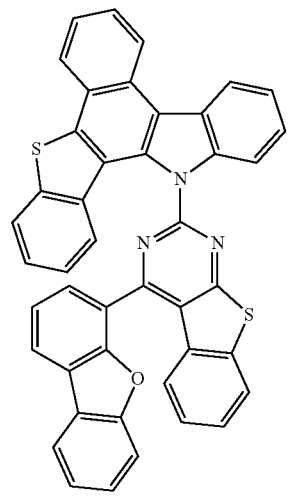
1-3-2-S-(17)
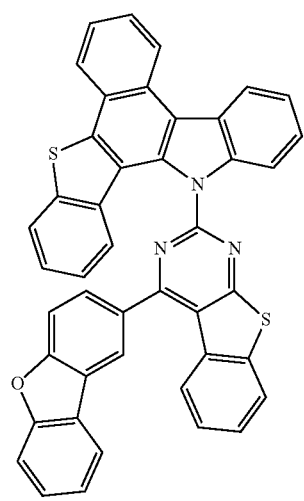
1-3-2-S-(18)
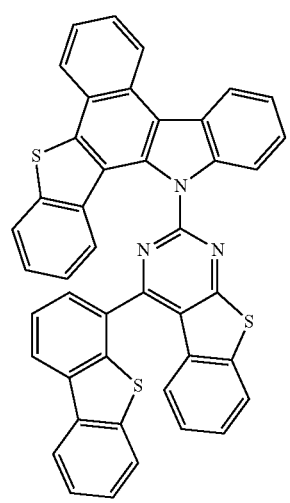
1-3-2-S-(19)
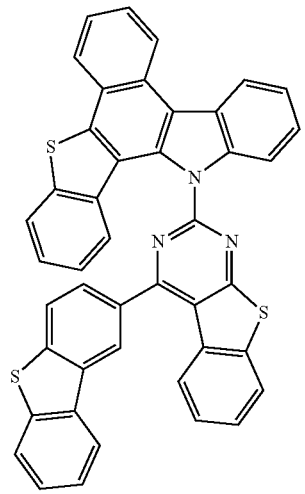
1-3-2-S-(20)
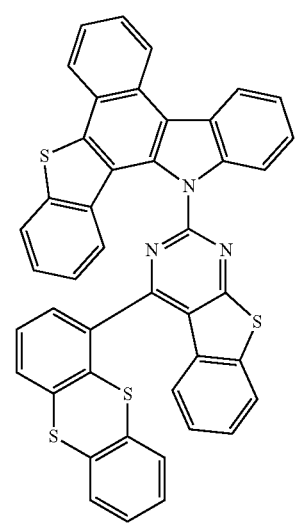
1-3-2-O-(21)
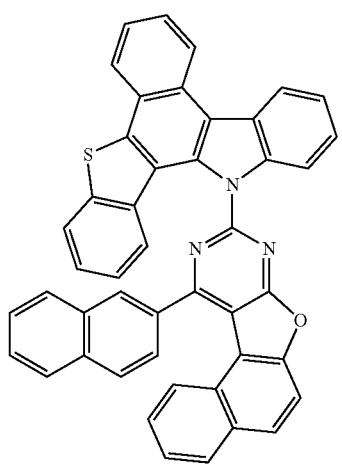

6. The organic electric element of claim 1, wherein the emission-auxiliary layer comprises a compound of Formula 1, the hole transport layer comprises a compound of the following Formula 8:

<Formula 8> wherein,

Ar⁴ and Ar⁵ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group and -L'-N($R^a$)($R^b$), Ar⁶ is one of the following 8-1, 8-2 and 8-3:

<Formula 8-1>

<Formula 8-2>

-continued

<Formula 8-3>

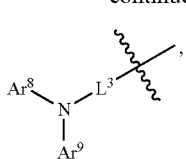

wherein, $Ar^7$, $Ar^8$ and $Ar^9$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group and -L'-N($R^a$)($R^b$), $R^8$ to $R^{10}$ i) are each independently selected from the group consisting of deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group, and -L'-N($R^a$)($R^b$), or ii) any two adjacent groups of $R^8$ to $R^{10}$ are optionally linked together to form at least one ring, and remaining groups not forming a ring are the same as defined in i), h, i and j are each independently an integer of 0 to 4, when h, i and j are each an integer of 2 or more, a plurality of $R^8$s to $R^{10}$s may be each the same or different from each other, $L^2$ to $L^4$ are each independently selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, with the proviso that a single bond is excluded from $L^3$ and $L^4$, in -L'-N($R^a$)($R^b$) of $Ar^4$, $Ar^5$, $Ar^7$ to $Ar^9$, $R^8$ to $R^{10}$, L' is selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and $R^a$ and $R^b$ are each independently selected from the group consisting of a $C_6$-$C_{60}$ aryl group, a fluorenyl group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and the aryl group, heterocyclic group, fluorenyl group, alkyl group, alkenyl group, fused ring group, alkoxyl group, aryloxly group, arylene group, fluorenylene group, aliphatic hydrocarbon group of $Ar^4$-$Ar^5$, $Ar^7$-$Ar^9$, $R^8$-$R^{10}$, R'R", $L^2$, $L^3$, L', $R^a$ and $R^b$ may be each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

7. The organic electric element of claim 6, wherein Formula 8 is one of the following compounds:

8-1

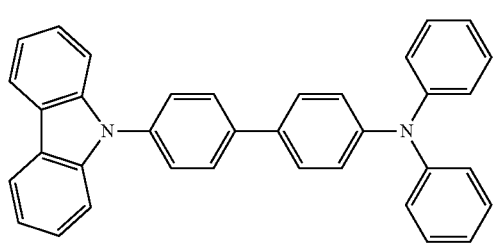

8-2

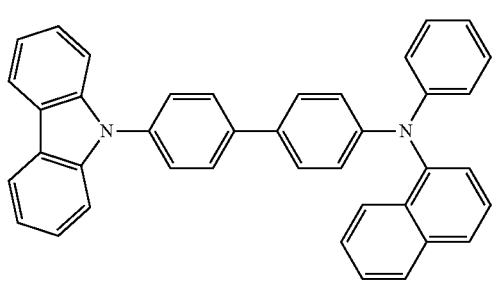

8-3

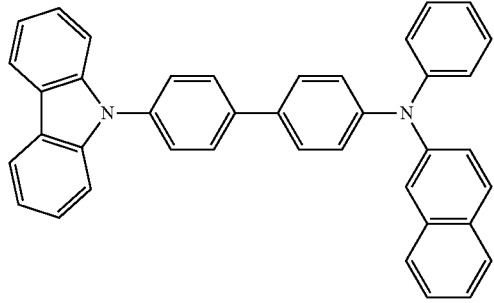

8-4

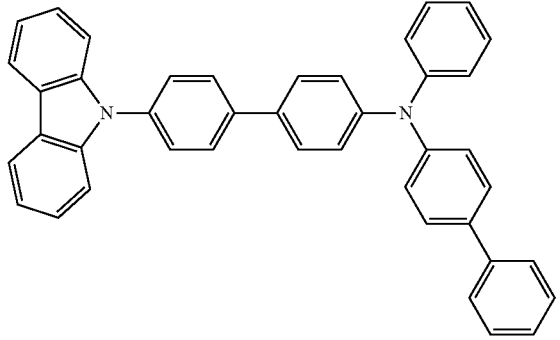

-continued
8-5
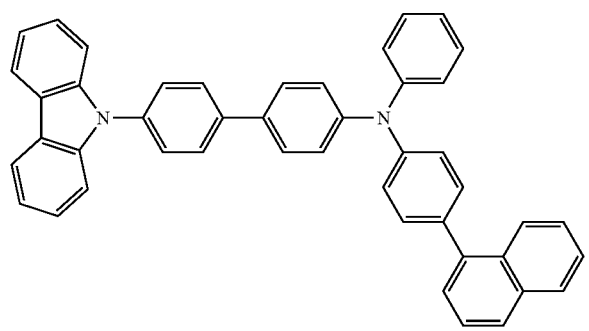
8-6
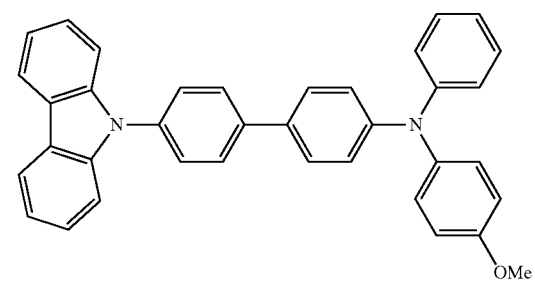
8-7
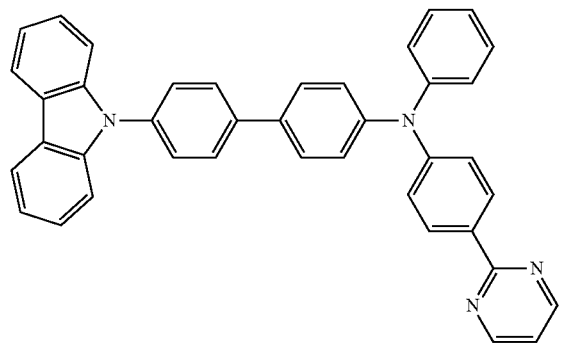
8-8
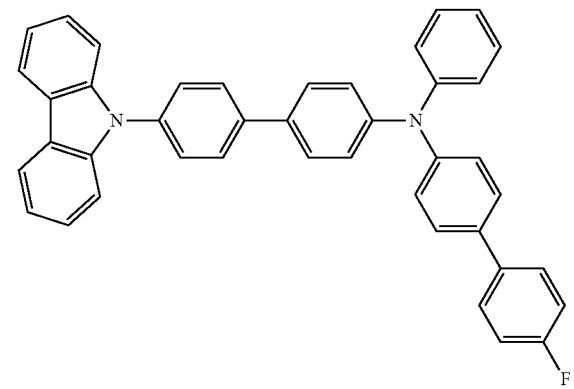
8-9
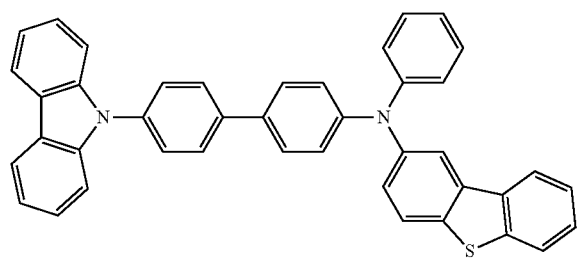
8-10
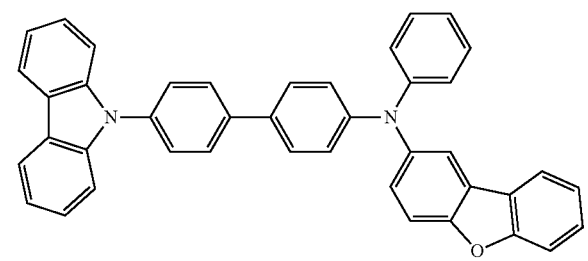
8-11
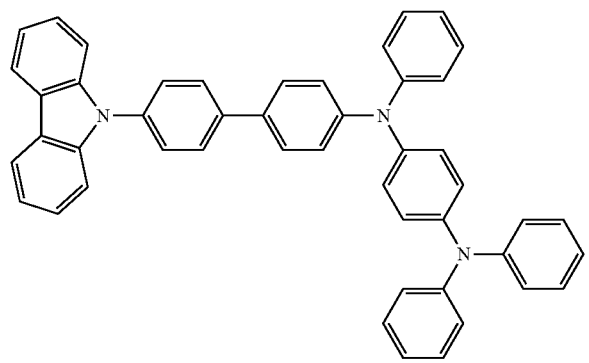
8-12
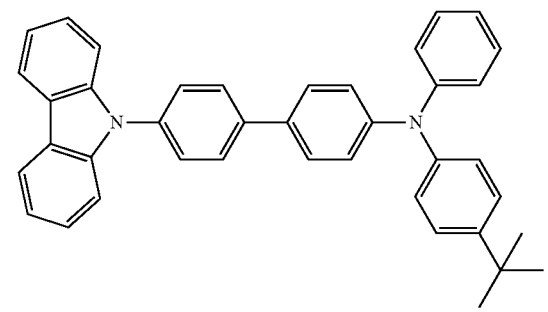

-continued
8-13
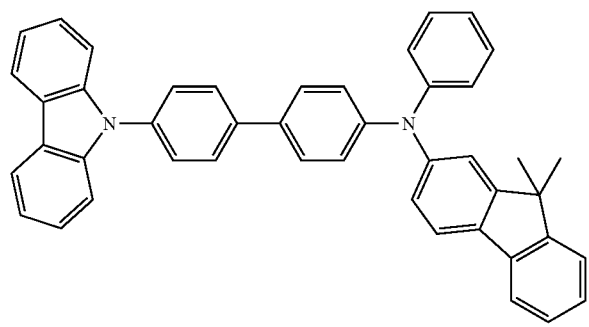
8-14
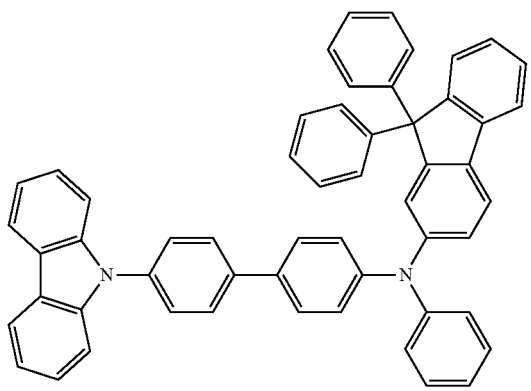
8-15
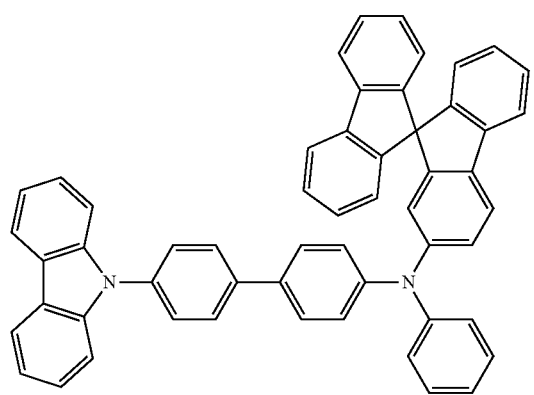
8-16
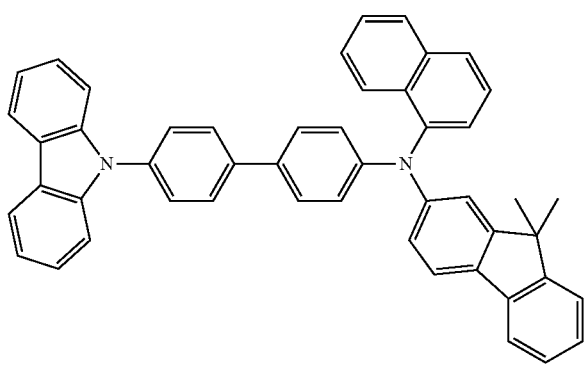
8-17
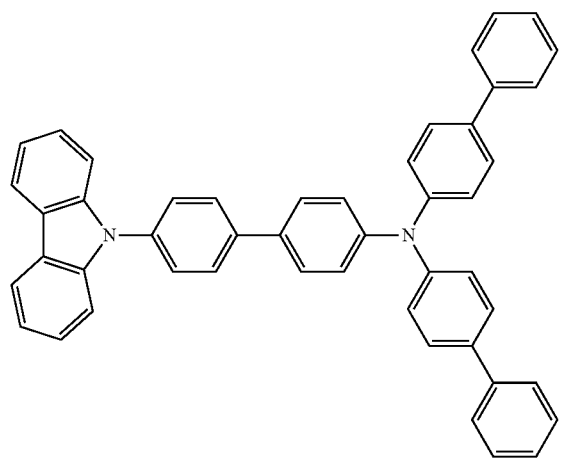
8-18
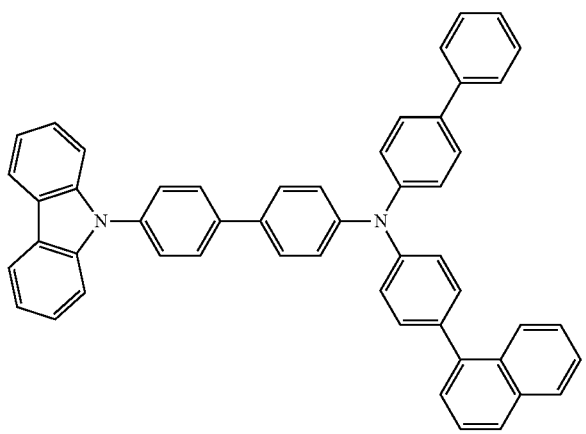

-continued
8-19
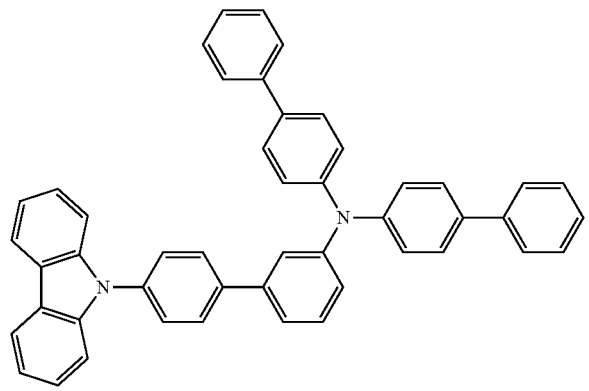
8-20
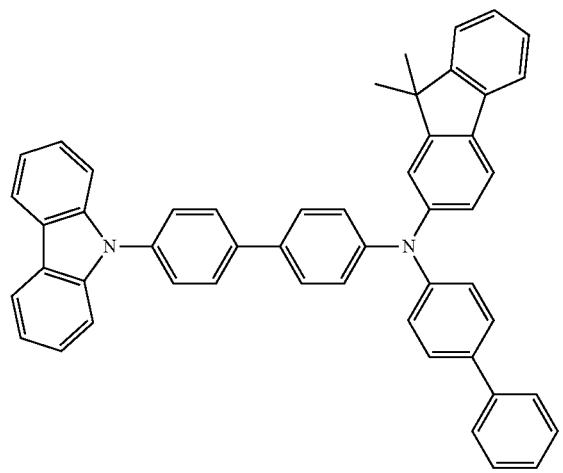
8-21
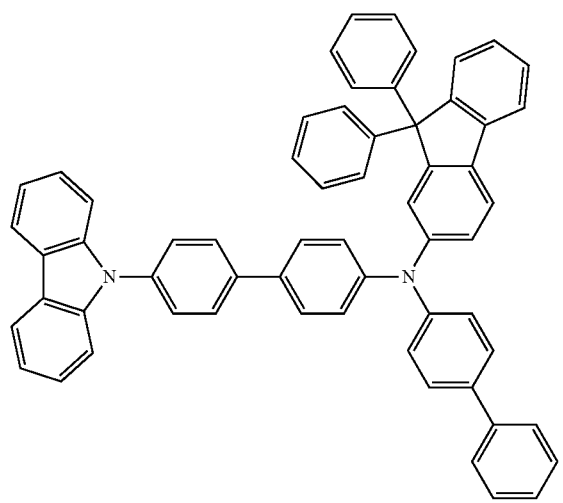
8-22
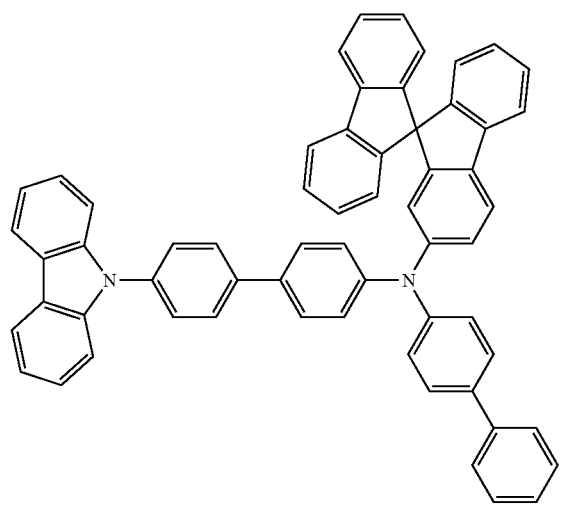
8-23
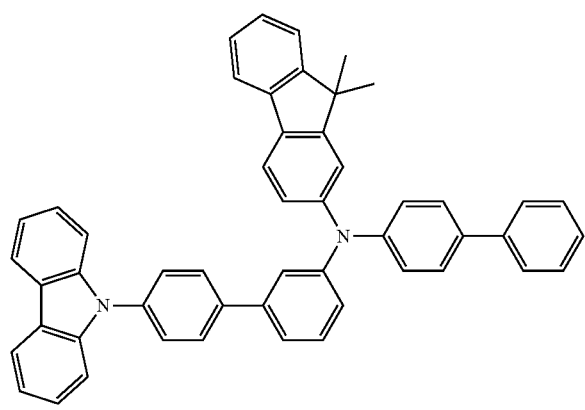
8-24
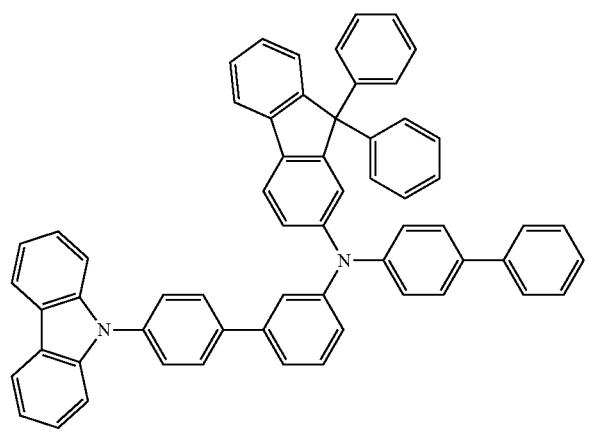

8-25
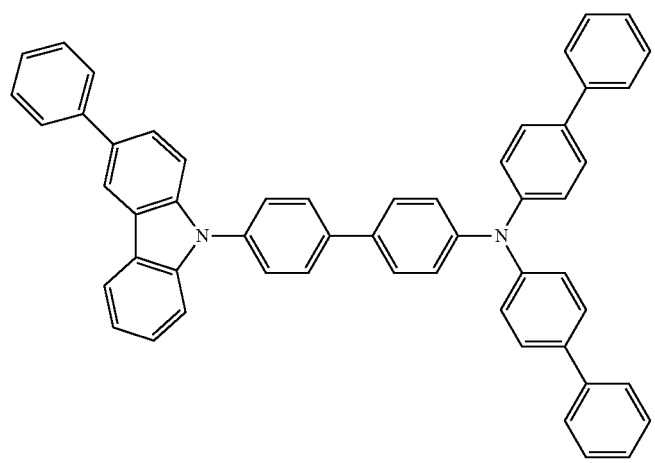
8-26
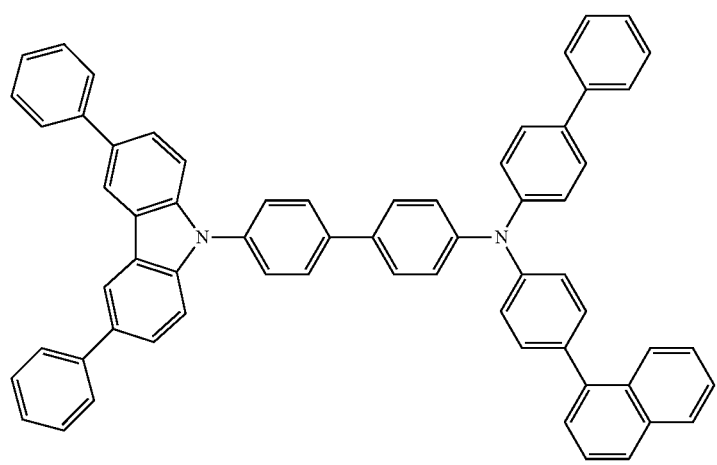
8-27
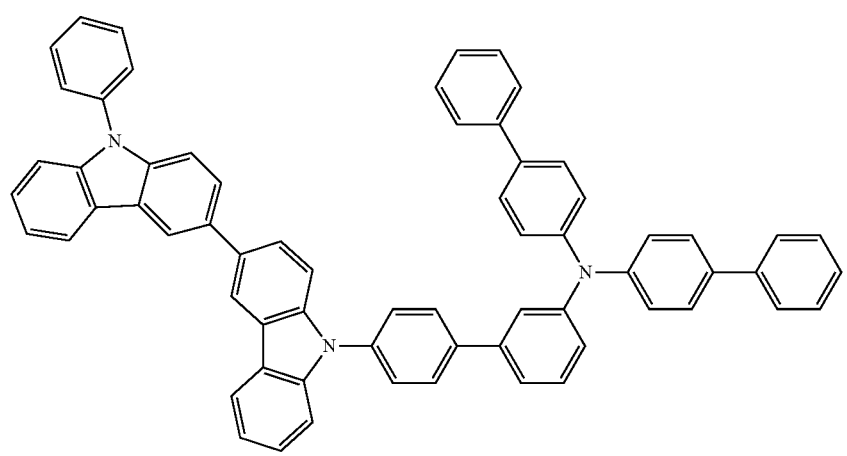

-continued
8-28
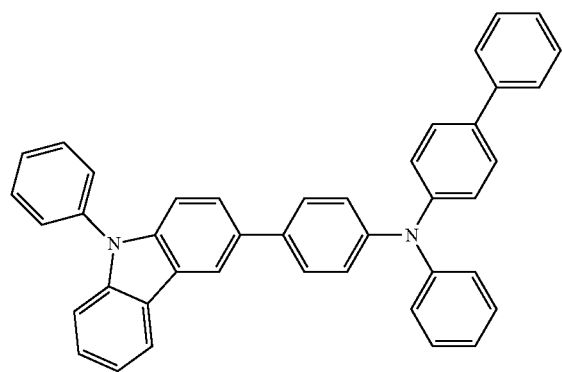
8-29
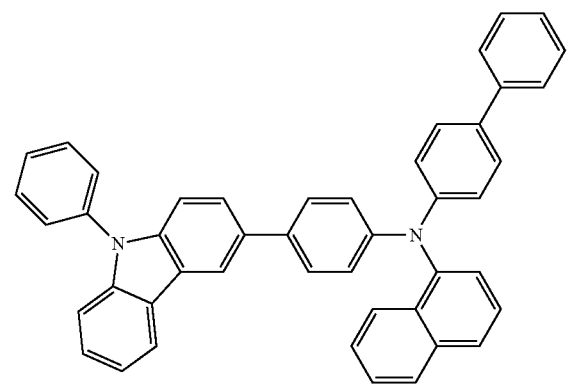
8-30
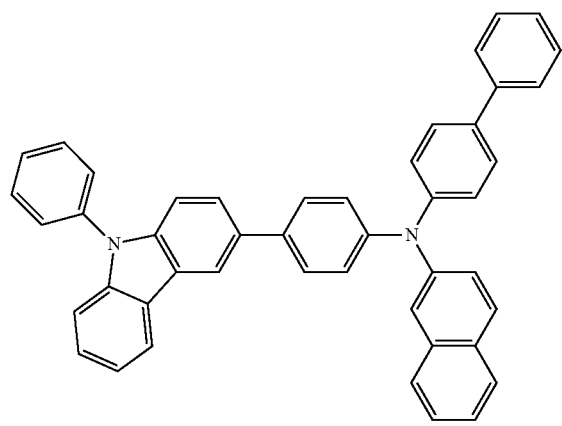
8-31
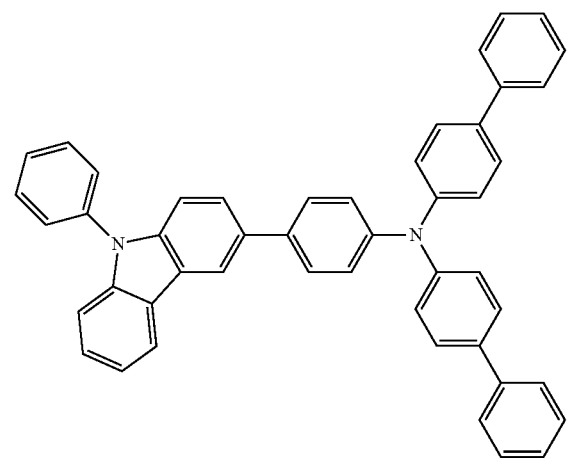
8-32
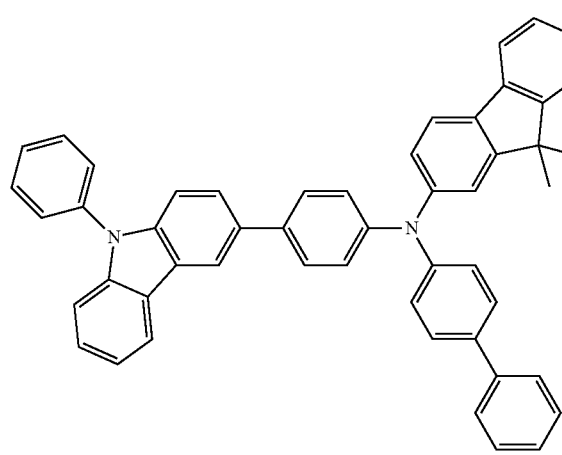
8-33
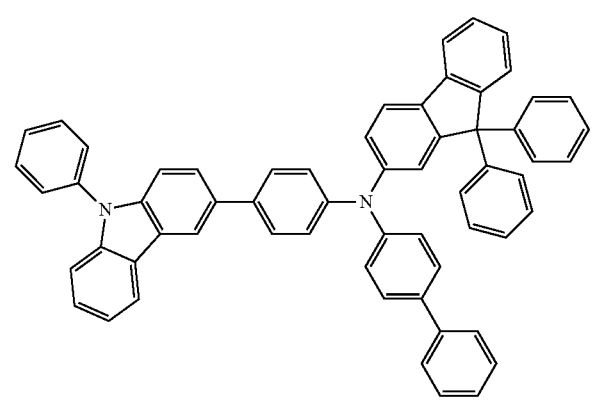

-continued
8-34
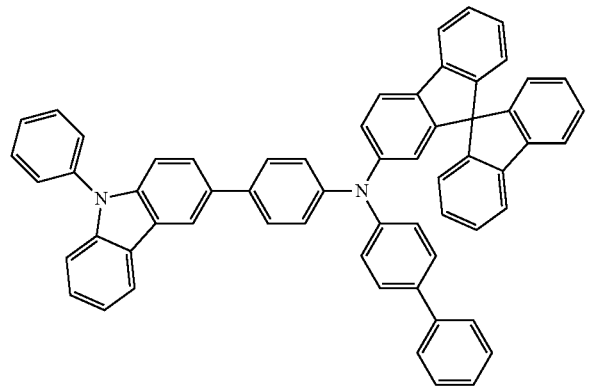
8-35
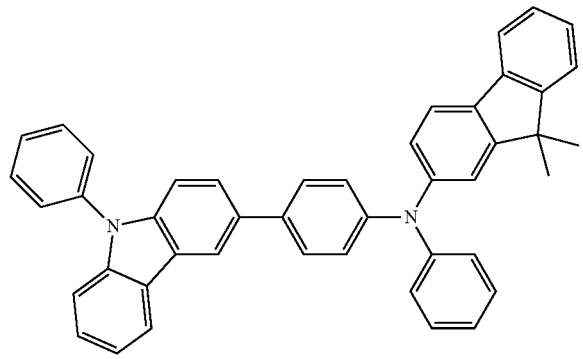
8-36
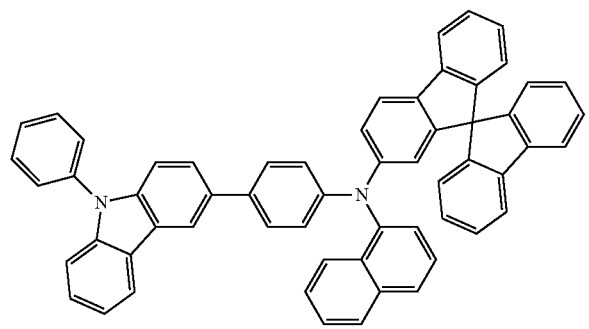
8-37
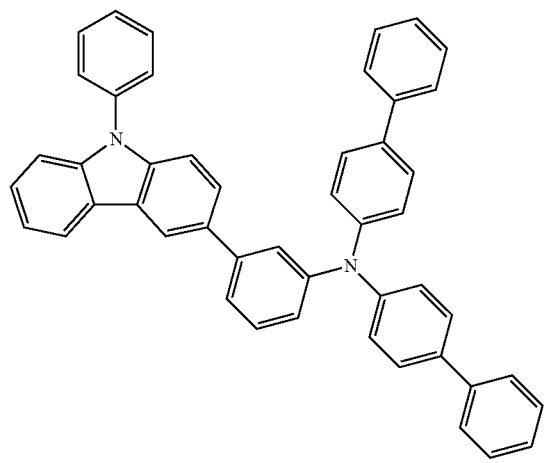
8-38
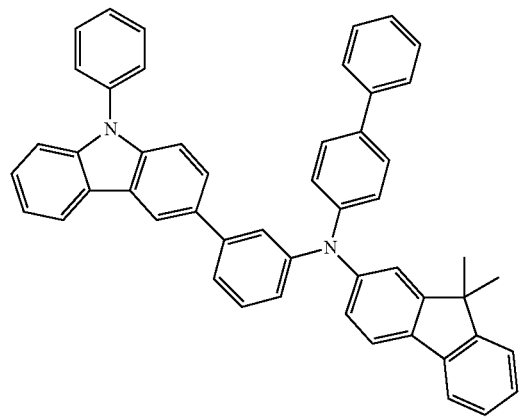
8-39
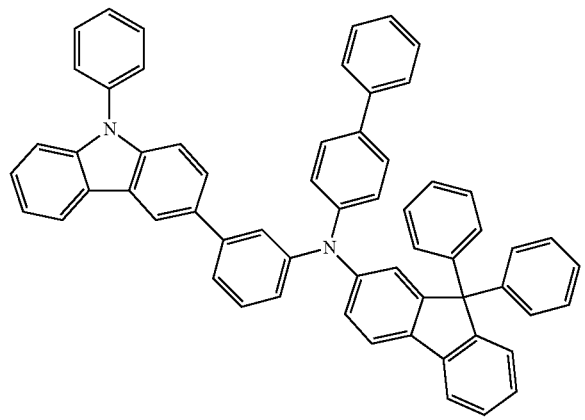

-continued
8-40
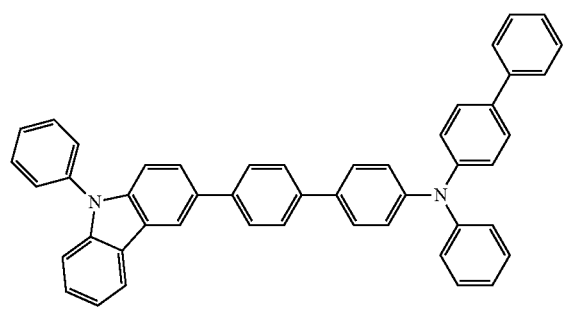
8-41
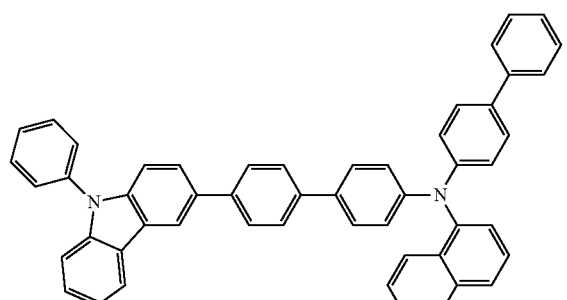
8-42
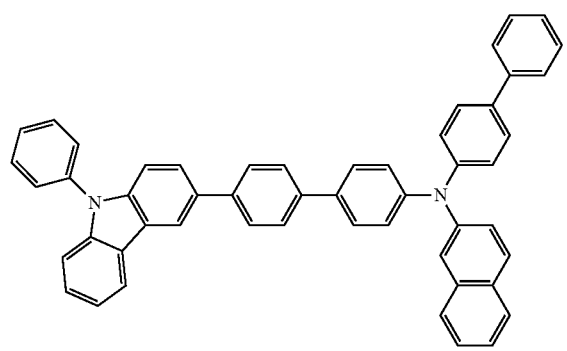
8-43
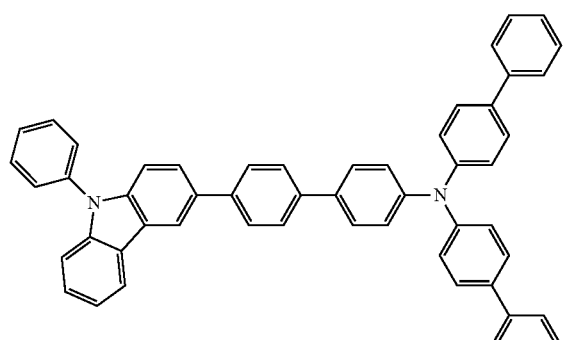
8-44
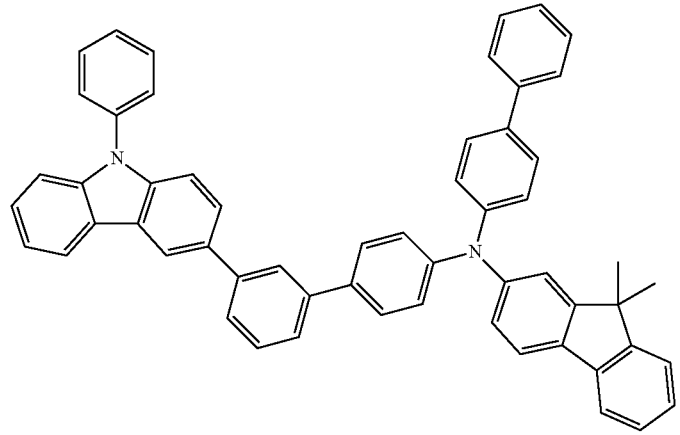
8-45
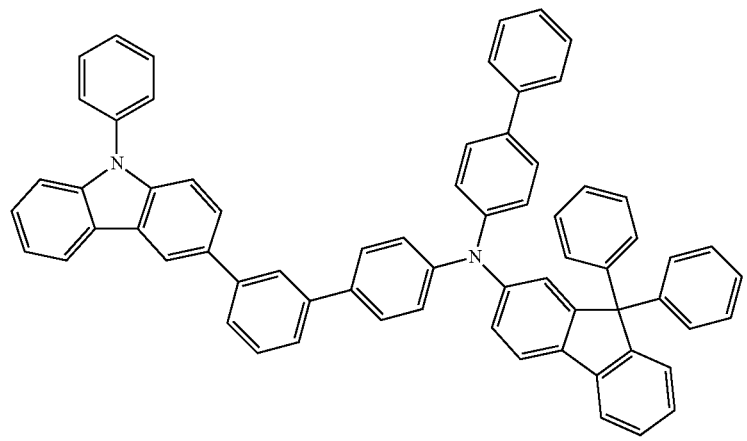

8-46
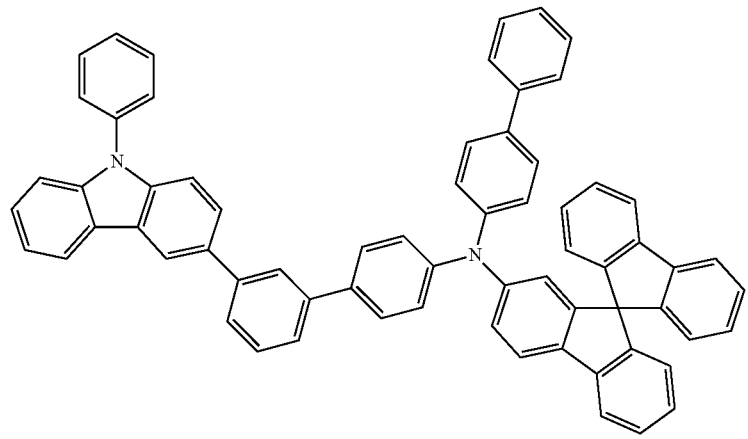
8-47
8-48
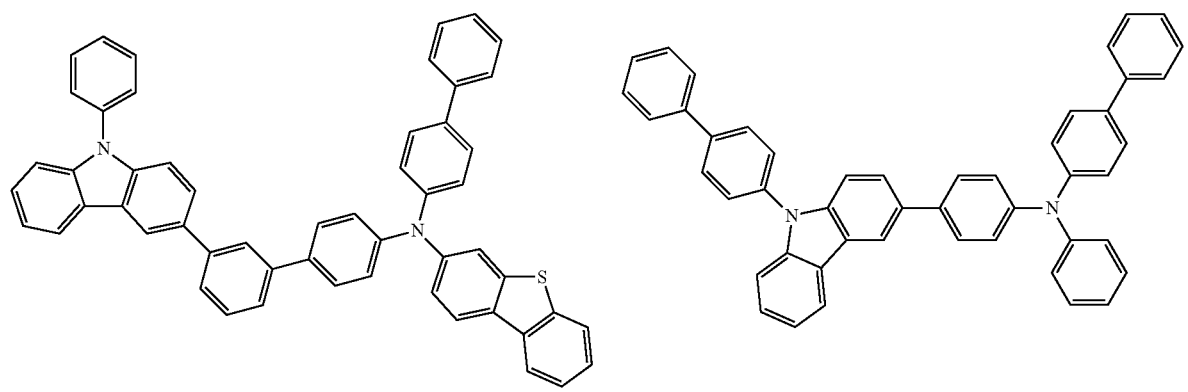
8-49
8-50
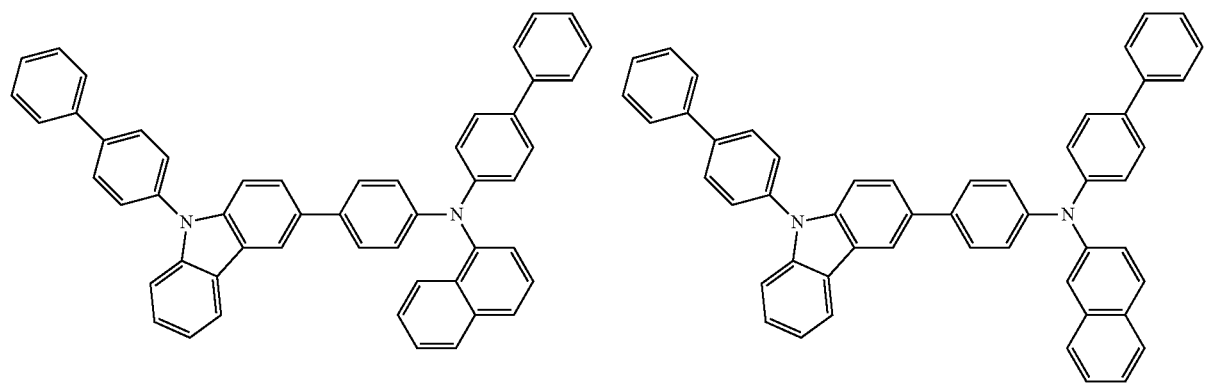

-continued
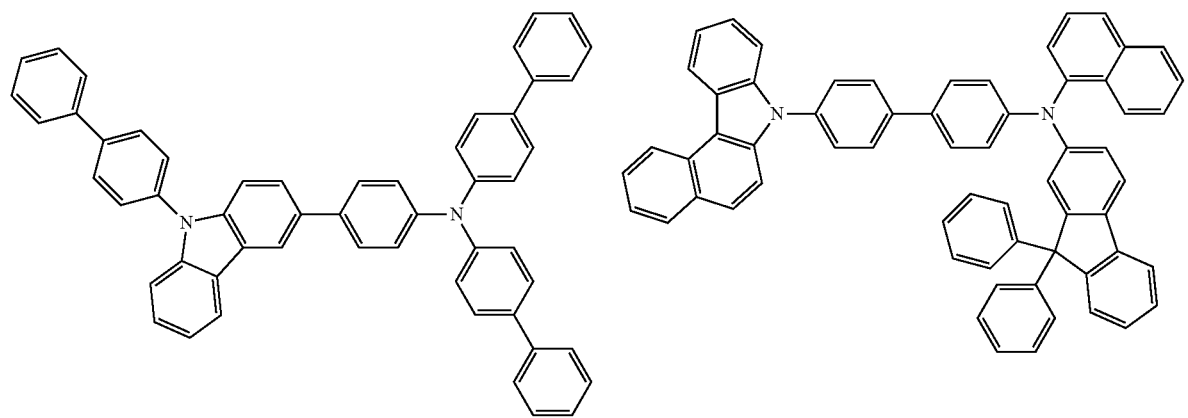
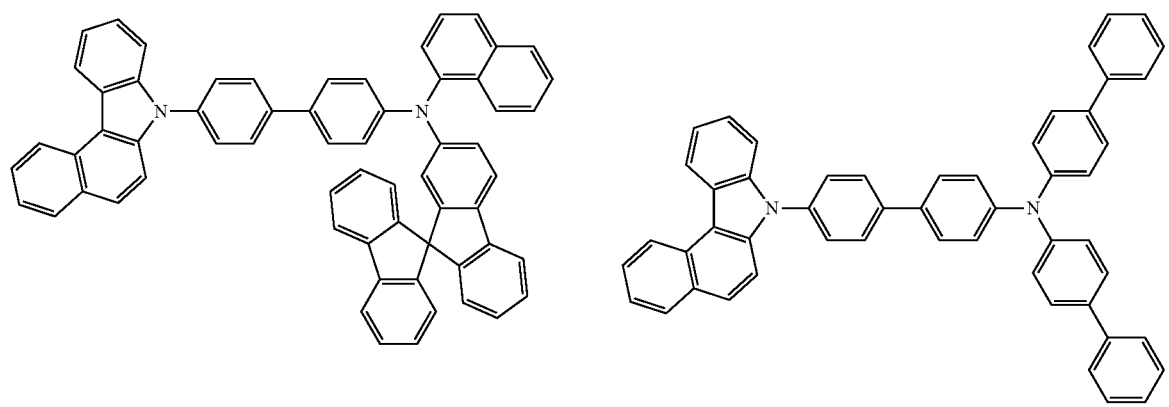
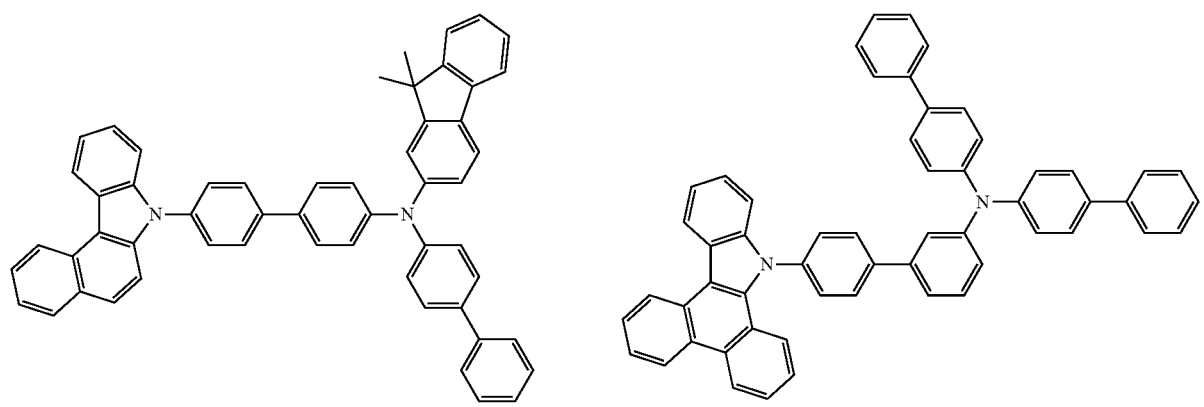

-continued
8-57
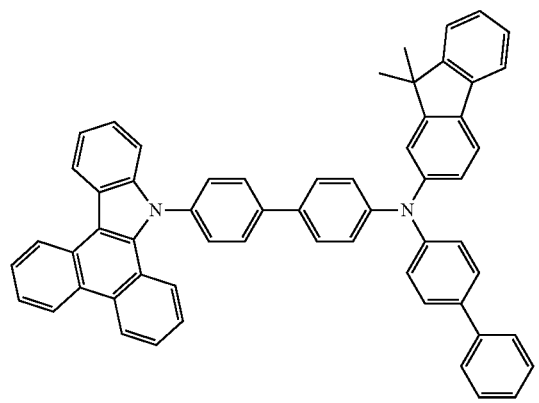
8-58
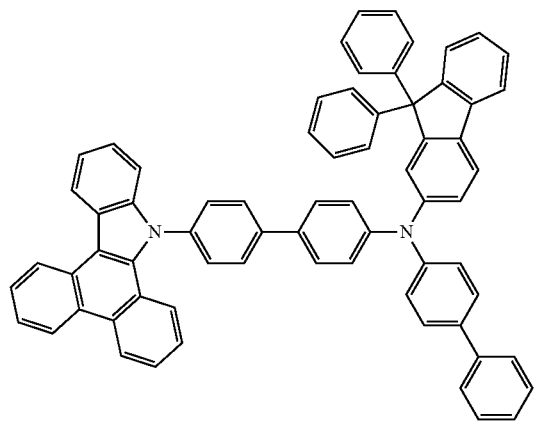
8-59
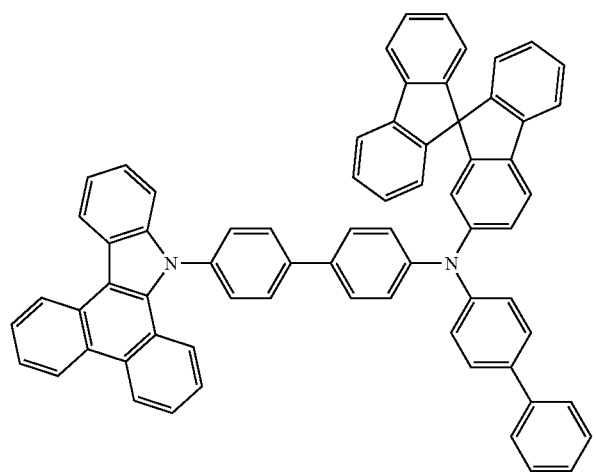
8-60
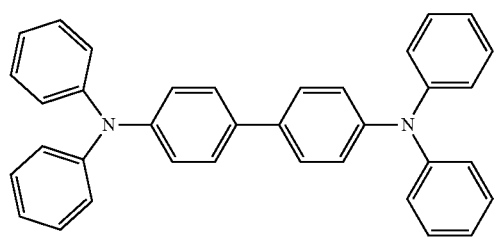
8-61
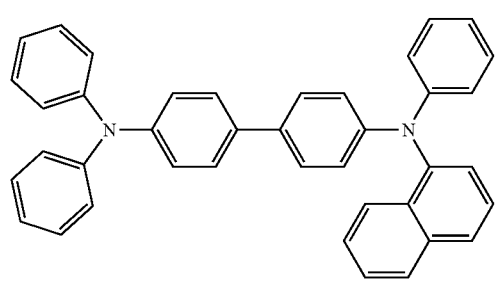
8-62
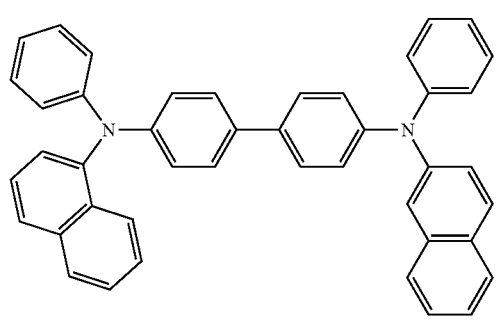

-continued
8-63
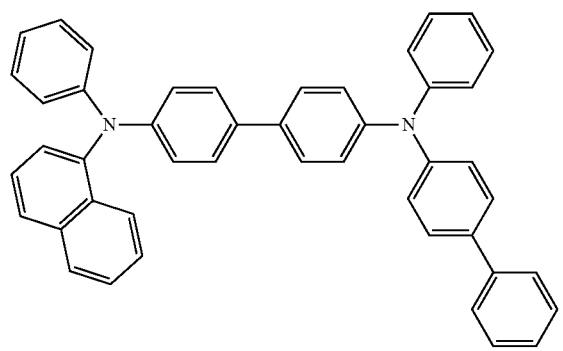
8-64
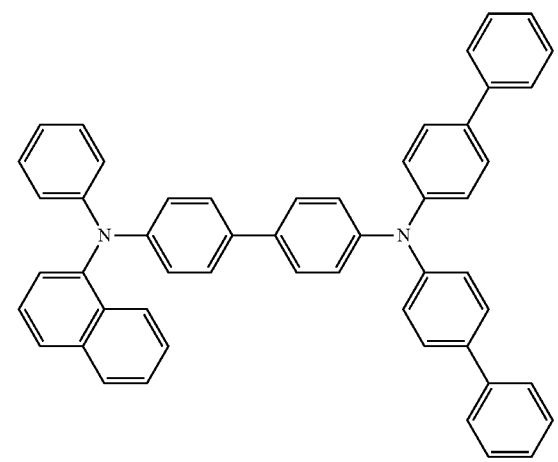
8-65
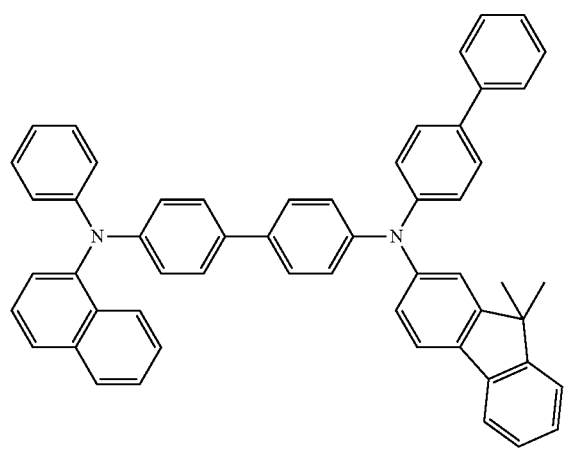
8-66
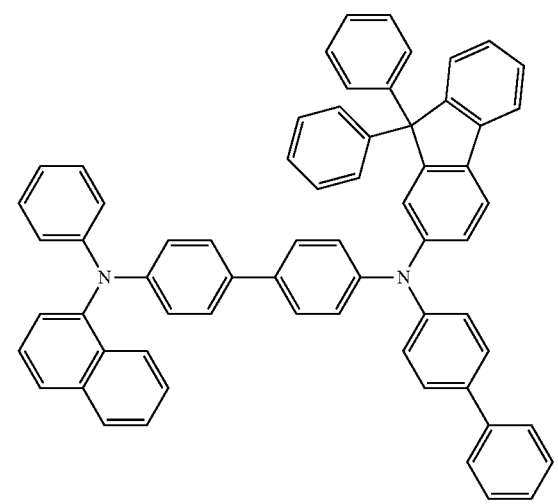
8-67
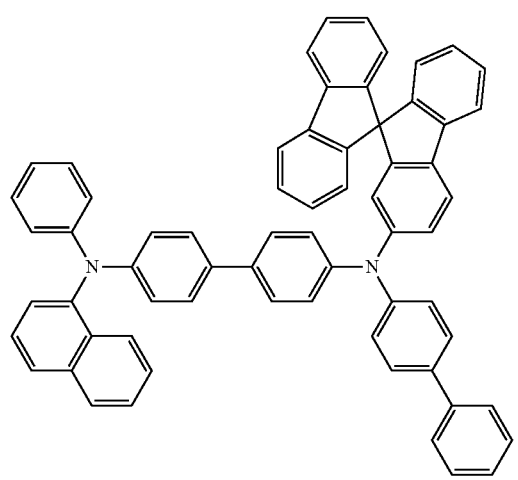
8-68
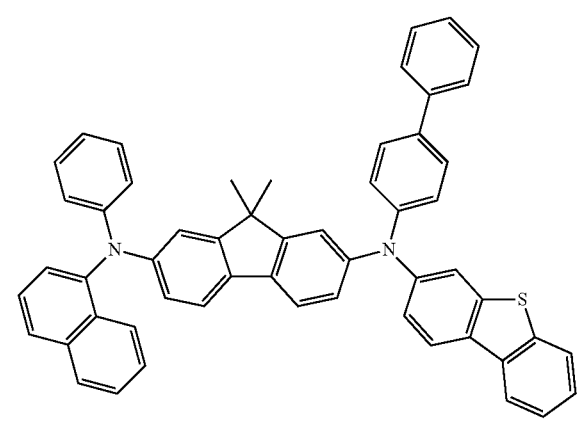

8-69

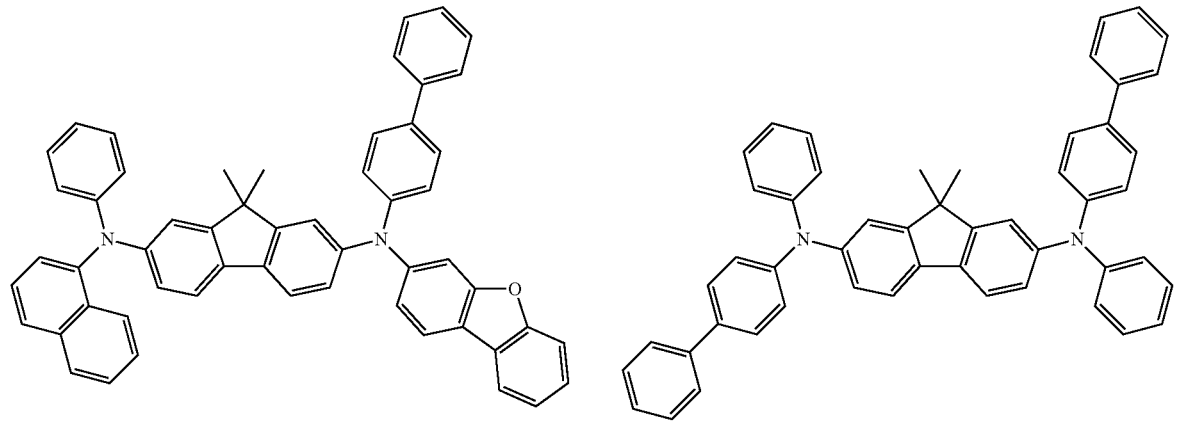

8-70

8-71

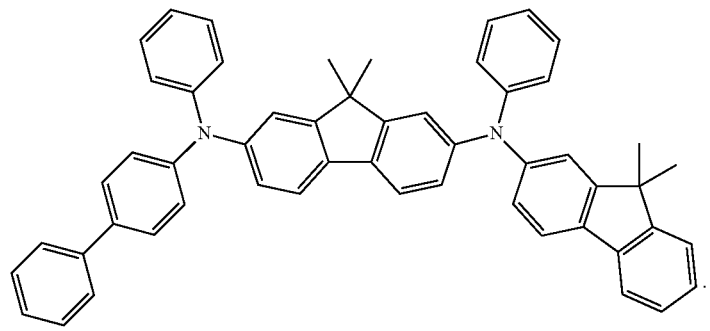

8. The organic electric element of claim 1, wherein the compound represented by Formula 1 is comprised in the hole transport layer or the emission-auxiliary layer in the form of a single compound or a mixture of two or more compounds.

9. The organic electric element of claim 1, wherein the compound represented by Formula 2 is comprised in the light emitting layer in the form of a single compound or a mixture of two or more compounds.

10. The organic electric element of claim 6, wherein the compound represented by Formula 1 is comprised in the emission-auxiliary layer in the form of a single compound or a mixture of two or more compounds, and the compound represented by Formula 8 is comprised in the hole transport layer in the form of a single compound or a mixture of two or more compounds.

11. The organic electric element of claim 1, further comprising a layer for improving luminous efficiency formed on one side of the first electrode and/or one side of the second electrode, the side facing the organic material layer.

12. The organic electric element of claim 1, wherein the organic material layer is formed by one of the processes of spin coating, nozzle printing, inkjet printing, slot coating, dip coating and roll-to-roll.

13. An electronic device comprising a display device and a control unit for driving the display device, wherein the display device comprises the organic electric element of claim 1.

14. The electronic device of claim 13, wherein the organic electric element is an organic light emitting diode, an organic solar cell, an organic photo conductor, an organic transistor, or an element for monochromatic or white illumination.

* * * * *